US008685897B2

(12) United States Patent
Bowers et al.

(10) Patent No.: US 8,685,897 B2
(45) **Date of Patent: *Apr. 1, 2014**

(54) METHODS OF GENERATING LIBRARIES AND USES THEREOF

(75) Inventors: Peter M. Bowers, Encinitas, CA (US); Andrew B. Cubitt, San Diego, CA (US); Robert A. Horlick, San Diego, CA (US)

(73) Assignee: Anaptysbio, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/109,106

(22) Filed: May 17, 2011

(65) Prior Publication Data

US 2011/0287485 A1 Nov. 24, 2011

Related U.S. Application Data

(63) Continuation of application No. 12/070,904, filed on Feb. 20, 2008.

(60) Provisional application No. 60/902,414, filed on Feb. 20, 2007, provisional application No. 60/904,622, filed on Mar. 1, 2007, provisional application No. 60/995,970, filed on Sep. 28, 2007, provisional application No. 61/020,124, filed on Jan. 9, 2008.

(51) Int. Cl.
*C40B 50/06* (2006.01)

(52) U.S. Cl.
USPC .......... 506/26

(58) Field of Classification Search
None
See application file for complete search history.

(56) References Cited

U.S. PATENT DOCUMENTS

| | | | |
|---|---|---|---|
| 3,773,919 | A | 11/1973 | Boswell et al. |
| 4,275,149 | A | 6/1981 | Litman et al. |
| 4,318,980 | A | 3/1982 | Boguslaski et al. |
| 4,356,270 | A | 10/1982 | Itakura |
| 4,683,195 | A | 7/1987 | Mullis et al. |
| 4,683,202 | A | 7/1987 | Mullis et al. |
| 4,737,456 | A | 4/1988 | Weng et al. |
| 4,816,397 | A | 3/1989 | Boss et al. |
| 4,816,567 | A | 3/1989 | Cabilly et al. |
| 4,937,190 | A | 6/1990 | Palmenberg et al. |
| 4,959,317 | A | 9/1990 | Sauer |
| 5,070,012 | A | 12/1991 | Nolan et al. |
| 5,122,464 | A | 6/1992 | Wilson et al. |

(Continued)

FOREIGN PATENT DOCUMENTS

| | | |
|---|---|---|
| EP | 0 404 097 A2 | 6/1990 |
| EP | 1 174 509 A1 | 1/2002 |

(Continued)

OTHER PUBLICATIONS

Rader et al. (Jul. 21, 1998) Proceedings of the National Academy of Sciences USA vol. 95 pp. 8910 to 8915.*

(Continued)

*Primary Examiner* — Christian Boesen
(74) *Attorney, Agent, or Firm* — Leydig, Voit & Mayer, Ltd.

(57) ABSTRACT

This invention relates to methods for the generation of humanized antibodies, particularly a humanized antibody heavy chain protein and a humanized antibody light chain protein. The method comprises using cells that express or can be induced to express Activation Induced Cytidine Deaminase (AID).

10 Claims, 79 Drawing Sheets

(56) References Cited

U.S. PATENT DOCUMENTS

| | | | |
|---|---|---|---|
| 5,221,623 | A | 6/1993 | Legocki et al. |
| 5,464,758 | A | 11/1995 | Gossen et al. |
| 5,514,548 | A | 5/1996 | Krebber et al. |
| 5,571,698 | A | 11/1996 | Ladner et al. |
| 5,650,289 | A | 7/1997 | Wood |
| 5,654,182 | A | 8/1997 | Wahl et al. |
| 5,674,713 | A | 10/1997 | McElroy et al. |
| 5,677,177 | A | 10/1997 | Wahl et al. |
| 5,683,888 | A | 11/1997 | Campbell |
| 5,698,417 | A | 12/1997 | Robinson et al. |
| 5,698,426 | A | 12/1997 | Huse |
| 5,723,323 | A | 3/1998 | Kauffman et al. |
| 5,741,657 | A | 4/1998 | Tsien et al. |
| 5,750,335 | A | 5/1998 | Gifford |
| 5,770,359 | A | 6/1998 | Wilson et al. |
| 5,770,428 | A | 6/1998 | Boris-Lawrie |
| 5,814,618 | A | 9/1998 | Bujard et al. |
| 5,827,739 | A | 10/1998 | Wilson et al. |
| 5,843,746 | A | 12/1998 | Tatsumi et al. |
| 5,843,757 | A | 12/1998 | Vogelstein et al. |
| 5,885,793 | A | 3/1999 | Griffiths et al. |
| 5,885,827 | A | 3/1999 | Wabl et al. |
| 5,955,604 | A | 9/1999 | Tsien et al. |
| 6,027,933 | A | 2/2000 | Huse |
| 6,083,719 | A | 7/2000 | Momparler et al. |
| 6,146,894 | A | 11/2000 | Nicolaides et al. |
| 6,291,158 | B1 | 9/2001 | Winter et al. |
| 6,291,159 | B1 | 9/2001 | Winter et al. |
| 6,291,160 | B1 | 9/2001 | Lemer et al. |
| 6,291,161 | B1 | 9/2001 | Lemer et al. |
| 6,294,353 | B1 | 9/2001 | Pack et al. |
| 6,300,064 | B1 | 10/2001 | Knappik et al. |
| 6,331,415 | B1 | 12/2001 | Cabilly et al. |
| 6,455,253 | B1 | 9/2002 | Patten et al. |
| 6,576,468 | B1 | 6/2003 | Nicolaides et al. |
| 6,610,477 | B1 | 8/2003 | Haseltine et al. |
| 6,645,492 | B2 | 11/2003 | Levitt et al. |
| 6,653,068 | B2 | 11/2003 | Frisch et al. |
| 6,656,736 | B2 | 12/2003 | Nicolaides et al. |
| 6,675,105 | B2 | 1/2004 | Hogarth et al. |
| 6,696,248 | B1 | 2/2004 | Knappik et al. |
| 6,699,658 | B1 | 3/2004 | Wittrup et al. |
| 6,706,484 | B1 | 3/2004 | Knappik et al. |
| 6,713,279 | B1 | 3/2004 | Short |
| 6,723,433 | B2 | 4/2004 | Bacon, Jr. |
| 6,737,268 | B1 | 5/2004 | Nicolaides et al. |
| 6,740,506 | B2 | 5/2004 | Short et al. |
| 6,806,079 | B1 | 10/2004 | McCafferty et al. |
| 6,808,894 | B1 | 10/2004 | Nicolaides et al. |
| 6,815,194 | B2 | 11/2004 | Honjo et al. |
| 6,825,038 | B2 | 11/2004 | Nicolaides et al. |
| 6,828,422 | B1 | 12/2004 | Achim et al. |
| 6,835,753 | B2 | 12/2004 | Baell et al. |
| 6,893,845 | B1 | 5/2005 | Huse |
| 6,900,370 | B2 | 5/2005 | Nicolaides et al. |
| 6,919,183 | B2 | 7/2005 | Fandl et al. |
| 6,921,666 | B2 | 7/2005 | Nicolaides et al. |
| 6,969,586 | B1 | 11/2005 | Lerner et al. |
| 7,083,966 | B2 | 8/2006 | Honjo |
| 7,112,715 | B2 | 9/2006 | Chamboa et al. |
| 7,122,339 | B2 | 10/2006 | Sale et al. |
| 7,314,621 | B2 | 1/2008 | Honjo et al. |
| 2002/0051976 | A1 | 5/2002 | Patten et al. |
| 2002/0155453 | A1 | 10/2002 | Sale et al. |
| 2002/0164743 | A1 | 11/2002 | Honjo et al. |
| 2003/0087236 | A1 | 5/2003 | Sale et al. |
| 2003/0096401 | A1 | 5/2003 | Huse et al. |
| 2003/0108889 | A1 | 6/2003 | Sale et al. |
| 2003/0119190 | A1 | 6/2003 | Wang et al. |
| 2003/0153038 | A1 | 8/2003 | Ohlin et al. |
| 2003/0198971 | A1 | 10/2003 | Balint et al. |
| 2004/0038317 | A1 | 2/2004 | Balint |
| 2004/0115695 | A1 | 6/2004 | Grasso et al. |
| 2004/0132066 | A1 | 7/2004 | Balint |
| 2004/0158886 | A1 | 8/2004 | Nicolaides et al. |
| 2004/0175756 | A1 | 9/2004 | Kolkman et al. |
| 2004/0219144 | A1 | 11/2004 | Shelton et al. |
| 2004/0228862 | A1 | 11/2004 | Shelton et al. |
| 2004/0237124 | A1 | 11/2004 | Pons et al. |
| 2004/0242517 | A1 | 12/2004 | Cascalho et al. |
| 2004/0253244 | A1 | 12/2004 | Shelton et al. |
| 2005/0008625 | A1 | 1/2005 | Balint et al. |
| 2005/0014761 | A1 | 1/2005 | Hoffinann et al. |
| 2005/0022686 | A1 | 2/2005 | Wessells et al. |
| 2005/0026246 | A1 | 2/2005 | Sale et al. |
| 2005/0037421 | A1 | 2/2005 | Honda et al. |
| 2005/0048051 | A1 | 3/2005 | Reynaud et al. |
| 2005/0048512 | A1 | 3/2005 | Kolkman et al. |
| 2005/0048578 | A1 | 3/2005 | Zhang |
| 2005/0048621 | A1 | 3/2005 | Grasso et al. |
| 2005/0053973 | A1 | 3/2005 | Kolkman et al. |
| 2005/0054073 | A1 | 3/2005 | Honjo et al. |
| 2005/0074821 | A1 | 4/2005 | Wild et al. |
| 2005/0089932 | A1 | 4/2005 | Kolkman et al. |
| 2005/0095712 | A1 | 5/2005 | Martin et al. |
| 2005/0106667 | A1 | 5/2005 | Fellouse et al. |
| 2005/0119455 | A1 | 6/2005 | Fuh et al. |
| 2005/0142106 | A1 | 6/2005 | Wittrup et al. |
| 2005/0164301 | A1 | 7/2005 | Kolkman et al. |
| 2005/0188428 | A1 | 8/2005 | Nicolaides et al. |
| 2005/0220795 | A1 | 10/2005 | Wittrup et al. |
| 2005/0221384 | A1 | 10/2005 | Kolkman et al. |
| 2005/0255552 | A1 | 11/2005 | Flynn et al. |
| 2005/0255555 | A1 | 11/2005 | Johns et al. |
| 2005/0265994 | A1 | 12/2005 | Shelton et al. |
| 2005/0266000 | A1 | 12/2005 | Bond et al. |
| 2006/0003334 | A1 | 1/2006 | Achim et al. |
| 2006/0003387 | A1 | 1/2006 | Peelle et al. |
| 2006/0019262 | A1 | 1/2006 | Petersen-Mahrt et al. |
| 2006/0052585 | A1 | 3/2006 | Grawunder et al. |
| 2006/0080745 | A1 | 4/2006 | Bergsagel et al. |
| 2006/0088884 | A1 | 4/2006 | Seifer et al. |
| 2006/0099679 | A1 | 5/2006 | Tsien et al. |
| 2006/0134098 | A1 | 6/2006 | Bebbington et al. |
| 2006/0147450 | A1 | 7/2006 | Shelton |
| 2007/0111260 | A1 | 5/2007 | Gao et al. |
| 2007/0186292 | A1 | 8/2007 | Buerstedde et al. |

FOREIGN PATENT DOCUMENTS

| | | | |
|---|---|---|---|
| EP | 1 345 495 | A4 | 9/2003 |
| EP | 1 556 508 | A2 | 7/2005 |
| EP | 1 572 935 | A1 | 9/2005 |
| EP | 1 572 971 | A2 | 9/2005 |
| WO | WO 92/08796 | A1 | 5/1992 |
| WO | WO 93/11161 | A1 | 6/1993 |
| WO | WO 93/12228 | A1 | 6/1993 |
| WO | WO 94/028143 | A1 | 12/1994 |
| WO | WO 95/12689 | A1 | 5/1995 |
| WO | WO 00/22111 | A1 | 4/2000 |
| WO | WO 02/100998 | A2 | 12/2002 |
| WO | WO 03/095636 | A3 | 11/2003 |
| WO | WO 2004/055182 | A1 | 7/2004 |
| WO | WO 2005/011735 | A1 | 2/2005 |
| WO | WO 2005/014642 | A1 | 2/2005 |
| WO | 2005023865 | | 3/2005 |
| WO | WO 2005/023865 | A2 | 3/2005 |
| WO | WO 2005/023865 | A3 | 3/2005 |
| WO | WO 2005/056599 | A2 | 6/2005 |
| WO | WO 2005/056599 | A3 | 6/2005 |
| WO | WO 2005/080431 | A2 | 9/2005 |
| WO | WO 2006/053021 | A2 | 5/2006 |

OTHER PUBLICATIONS

Martin et al. (Feb. 14, 2002) Nature vol. 415 pp. 802 to 806.*

Adetugbo et al., "Molecular analysis of spontaneous somatic mutants," *Nature* 265:299-304 (1977).

Aggarwal et al., "Synthesis and Screening of a Random Dimeric Peptide Library Using the One-Bead-One-Dimer Combinatorial Approach," *Bioconj. Chem.*, 17:335-340 (2006).

Akamatsu et al., "Construction of a Human Ig Combinatorial Library from Genomic V Segments and Synthetic CDR3 Fragments," *J. Immunol.*, 151:4651-4659 (1993).

(56) References Cited

OTHER PUBLICATIONS

Akamatsu et al., "Whole IgG surface display on mammalian cells: Application to isolation of neutralizing chicken monoclonal anti-IL-12 antibodies," *J. Immunol. Methods*, 327:40-52 (2007).
Akselband et al., "Isolation of Rare Isotype Switch Variants in Hybridoma Cell Lines Using an Agarose Gel Microdrop-Based Protein Secretion Assay," *Assay and Drug Development Technologies*, 1(5):619-626 (2003).
Alla et al., "Extracellular Domains of the Bradykinin B2 Receptor Involved in Ligand Binding and Agonist Sensing Defined by Anti-peptide Antibodies," *J. Biol. Chem.*, 271 (3):1748-1755 (1996).
Alt et al., "Immunoglobulin heavy-chain expression and class switching in a murine leukaemia cell line," *Nature*, 296(5855):325-331 (1982).
Amit et al., "Three-Dimensional Structure of an Antigen-Antibody Complex at 2.8 A Resolution," *Science*, 233:747-753 (1986).
Anaptys Presentation at Bio-Europe Nov. 12 -14, 2007, Congress Center Hamburg (CCH) Germany, 29 pages.
Andersen et al., "Screening for Epitope Specificity Directly on Culture Supernatants in the Early Phase of Monoclonal Antibody Production by an ELISA with Biotin-Labeled Antigen," *J. Immunoassay & Immunochemistry*, 25(2):147-157 (2004).
Andersson et al., "Affinity selection and repertoire shift: paradoxes as a consequence of somatic mutation?" *Immunological Reviews*, 162:173-182 (1998).
Arakawa et al., "Requirement of the Activation-induced Deaminase (AID) Gene for Immunoglobuin Gene Conversion," *Science*, 295:1301-1306 (2002).
Atanasiu et al., "ORC binding to TRF2 stimulates OriP replication," *EMBO Reports*, 7(7):716-721 (2006).
Atochina et al., "Comparison of results using the gel microdrop cytokine secretion assay with ELISPOT and intracellular cytokine staining assay," *Cytokine*, 27:120-128 (2004).
Ayriss et al., "High-Throughput Screening of Single-Chain Antibodies Using Multiplexed Flow Cytometry," *J. Proteome Res.*, 6:1072-1082 (2007).
Azuma, "Somatic hypermutation in mouse λ chains," *Immunological Reviews*, 162:97-105 (1998).
Babcock et al., "Ligand Binding Characteristics of CXCR4 Incorporated into Paramagnetic Proteoliposomes," *J. Biol. Chem.*, 276(2):38433-38440 (2001).
Bachl et al., "Increased transcription levels induce higher mutation rates in a hypermutating cell line," *J. Immunol.*, 166(8):5051-5057 (2001).
Bahler et al., "Clonal evolution of a follicular lymphoma: Evidence for antigen selections," *PNAS USA*, 89:6770-6774 (1992).
Barbas et al., "In vitro Evolution of a Neutralizing Human Antibody to Human Immunodeficiency Virus Type I to Enhance Affinity and Broaden Strain Cross-Reactivity," *PNAS*, 91:3809-3813 (1994).
Bass et al., "Hormone Phage: An Enrichment Method for Variant Proteins With Altered Binding Properties," *Proteins*, 8:309-314 (1990).
Batista et al., "Affinity Dependence of the B Cell Response to Antigen: A Threshold, a Ceiling, and the Importance of Off-Rate," *Immunity*, 9:751-759 (1998).
Becker et al., "Ultra-high-throughput screening based on cell-surface display and fluorescence-activated cell sorting for the indentification of novel biocatalysts." *Curr. Op. Biotech.*, 15(4):323-329 (2004).
Becker et al., "A Three-Hybrid Approach to Scanning the Proteome for Targets of Small Molecule Kinase Inhibitors," *Chem. Biol.*, 11:211-223 (2004).
Bemark et al., "The c-MYC allele that is translocated into the *IgH* locus undergoes constitutive hypermutation in a Burkitt's lymphoma line," *Oncogene*, 19(30):3404-3410 (2000).
Berek et al., "The dynamic nature of the antibody repertorie," *Immunol. Rev.*, 105:5-26 (1988).
Berger et al., "Secreted placental alkaline phosphatase: a powerful new quantitative indicator of gene expression in eukaryotic cells," *Gene*, 66: 1-10 (1988).
Besmer et al., "The transcription elongation complex directs activation-induced cytidine deaminase-mediated DNA deamination," *Mol. Cell. Biol.*, 26(11):4378-85 (2006).
Betz et al., "Discriminating intrinsic and antigen-selected mutational hotspots in immunoglobulin V genes," *Immunol. Today*, 14:405-411 (1993).
Betz et al., "Elements Regulating Somatic Hypermutation of an Immunoglobulin K Gene: Critical Role for the Intron Enhancer/Matrix Attachment Region," *Cell*, 77:239-248 (1994).
Bezzubova et al., "Reduced X-ray resistance and homologous recombination frequencies in a RAD54-I-mutant of the chicken DT40 cell line," *Cell*, 89:185-193 (1997).
Bichet et al., "The 'Bringer' Strategy," *Applied Biochem & Biotech.*, 117:115-122 (2004).
Bird et al., "Single-Chain Antigen-Binding Proteins," *Science*, 242:423-426 (1988).
Blanden et al., "The signature of somatic hypermutation appears to be written into the germline IgV segment repertoire," *Immunological Reviews*, 162:117-132 (1998).
Boder et al., "Yeast surface display for screening combinatorial polypeptide libraries" *Nat. Biotech.*, 15:553-557 (1997).
Boder et al., "Optimal Screening of Surface-Displayed Polypeptide Libraries," *Biotechnol. Prog.*, 14:55-62 (1998).
Boder et al., "Directed evolution of antibody fragments with monovalent femtomolar antigen-binding affinity," *PNAS*, 97:10701-10705 (2000).
Boder et al., "Yeast Surface Display for Directed Evolution of Protein Expression, Affinity, and Stability," *Meth. Enzymol.*, 328:430-444 (2000).
Bonfield et al., "A new DNA-sequence assembly program," *Nucleic Acids Res.* 23:4992-4999 (1995).
Borth et al., "Efficient Selection of High-Producing Subclones During Gene Amplification of Recombinant Chinese Hamster Ovary Cells by Flow Cytometry and Cell Sorting," *Biotech. Bioeng.*, 71(4):266-273 (2000-2001).
Bouvet et al., "From natural polvreactive autoantibodies to a la carte monoreactive antibodies to infectious agents: is it a small world after all?" *Infect. Immun.*, 66:1-4 (1998).
Boyle, "Harnessing Somatic Hypermutation," Anaptys Biosciences, Inc., Dec. 13, 2007 Presentation, 27 pages.
Braeuninger et al., "Hodgkin and Reed-Sternberg cells in lymphocyte predominant Hodgkin disease represent clonal populations of germinal center-derived tumor B cells," *PNAS USA*, 94:9337-9342 (1997).
Bransteiter et al., "Activation-induced cytidine deaminase deaminates deoxycytidine on single-stranded DNA but requires the action of RNase," *PNAS*, 100(7):4102-4107 (2003).
Brar et al., "Activation-induced Cytosine Deaminase (AID) Is Actively Exported out of the Nucleus but Retained by the Induction of DNA Breaks," *J. Biol. Chem.*, 279(25):26395-26401 (2004).
Brenneman et al., "XRCC3 is required for efficient repair of chromosome breaks by homologous recombination," *Mutat. Res.*, 459:89-97 (2000).
Bross et al., "DNA double-strand breaks in immunoglobulin genes undergoing somatic hypermutaion," *Immunity*, 13:589-597 (2000).
Bruggemann et al., "Immunoglobulin V region variants in hybridoma cells. 1. Isolation of a variant with altered idiotypic and antigen binding specificity," *EMBO J.*, 1:629-634 (1982).
Buerstedde et al., "Light chain gene conversion continues at high rate in an ALV-induced cell line," *EMBO J.*, 9:921-927 (1990).
Canfield et al., "The Binding Affinity of Human IgG for its High Affinity Fe Receptor Is Determined by Multiple Amino Acids in the Ch2 Domain and Is Modulated by the Hinge Region," *J. Exp. Med.*, 173:1483-1491 (1991).
Capizzi et al., "A table for the estimation of the spontaneous mutation rate of cells in culture," *Mutat. Res.*, 17:147-148 (1973).
Carpentier et al., "Limiting factors governing protein expression following polyethylenimine-mediated gene transfer in HEK293-EBNA1 cells," *J. Biotech.*, 128:268-280 (2007).
Casali et al., "Structure and function of natural antibodies," *Curr. Top. Microbiol. Immunol.*, 10:167-179 (1996).

(56) References Cited

OTHER PUBLICATIONS

Ceccarelli et al., "Functional Analyses of the EBNA1 Origin DNA Binding Protein of Epstein-Barr Virus," *J. Virol.*, 74(11):4939-4948 (2000).
Chang et al., "A Sequence Analysis of Human Germline Ig $V_h$ and $V_L$ Genes," *Ann. N.Y. Acad. Sci.*, 170-179 (1994) Elsevier Science Ltd. 0167-699/94/507.00.
Chang et al., "The CDR1 sequences of a major proportion of human germline Ig VH genes are inherently susceptible to amino acid replacement," *Imm. Today Jeanette Greenspan Laboratory for Cancer Research* (1994).
Chapman et al., "In vitro selection of catalytic RNAs," *Curr. Op. Struct. Biol.*, 4:618-622 (1994).
Chapman et al. "Analysis of VH genes used by neoplastic B cells in endemic Burkitt's lymphoma shows somatic hypermutation and intraclonal heterogeneity," *Blood*, 85:2176-2181 (1995).
Chao et al., "Isolating and engineering human antibodies using yeast surface display," *Nature Protocols*, 1(2):755-768 (2006).
Chappel et al., "Identification of the Fcγ receptor class I binding site in human IgG through the use ofrecombinant IgGIIIgG2 hybrid and point-mutated antibodies," *PNAS USA*, 88:9036-9040 (1991).
Chau et al., "Dynamic Chromatin Boundaries Delineate a Latency Control Region of Epstein-Barr Virus," *J. Virol.*, 78(22):12308-12319 (2004).
Chen et al., "Identification of Key Amino Acid Residues in a Thyrotropin Receptor Monoclonal Antibody Epitope Provides Insight Into Its Inverse Agonist and Antagonist Properties," *Endocrinology*, published ahead of print Apr. 3, 2008 doi: 10.1210/en.2008-0207.
Chothia et al., "Canonical Structures for the Hypervariable Regions of Immunoglobulins," *J. Mol. Biol.*, 196:901-917 (1987).
Chothia et al., "Structural Repertoire of the Human VH Segments," *J. Mol. Biol.*, 227:799-817 (1992).
Chui et al., ."A reporter gene to analyse the hypermutation of immunoglobulin genes," *J. Mol. Biol.*, 249:555-563 (1995).
Clackson et al., "Making antibody fragments using phase display libraries," *Nature*, 352:624-628 (1991).
Clackson et al., "In vitro selection from protein and peptide libraries," *Trends Biotechnol.*, 12:173-184 (1994).
Coffino et al., "Rate of somatic mutation in immunoglobulin production by mouse myeloma cells," *PNAS USA*, 68(1):219-223 (1971).
Cohen et al., "Generation of a Monoclonal Antibody Agonist to Toll-Like Receptor 4," *Hybridoma*, 24(1):27-35 (2005).
Colby et al., "Engineering Antibody Affinity by Yeast Surface Display," *Hereditary Disease Foundation NIH CA96504 grant* (2004).
Coker et al., "Genetic and In Vitro Assays of DNA Deamination," *Meth. Enzymol.*, 408:156-170 (2006).
Conese et al., "Gene Therapy Progress and Prospects: Episomally maintained selfreplicating systems," *Gene Therapy*, 11:1735-1741 (2004).
Conticello et al., "Evolution of the AID/APOBEC family of polynucleotide (deoxy)cytidine deaminases," *Mol. Biol. Evol.*, 22(2):367-377 (2005).
Craenenbroeck et al, "Orientation-dependent gene expression with Epstein-Barr virus-derived vectors," *FEBS Lett.*, 555:489-494 (2003).
Cui et al., "The XRCC2 and XRCC3 repair genes are required for chromosome stability in mammalian cells," *Mutat. Res.*, 434:75-88 (1999).
Cull et al, "Screening for receptor ligands using large libraries of peptides linked to the C terminus of the *lac* repressor," *PNAS USA*, 89:1865-1869 (1992).
Cumbers et al., "Generation and iterative affinity maturation of antibodies in vitro using hypermutating B-cell lines," *Nat. Biotech.*, 20(11):1129-1134 (2002).
Daugherty et al, "Flow cytometric screening of cell-based libraries," *J. Immunol. Methods*, 243(1-2):211-227 (2000).
Davidson et al, "Apolipoprotein B: mRNA Editing, Lipoprotein Assembly, and Presecretory Degradation," *Ann. Rev. Nutr.*, 20:169-193 (2000).
Davies et al., "Interactions of protein antigens with antibodies," *PNAS USA*, 93:7-12 (1996).
Deans et al., Xrcc2 is required for genetic stability, embryonic neurogenesis and viability in mice, *EMBO J.*, 19:6675-6685 (2000).
Denepoux et al., "Induction of somatic mutation in a human B cell line in vitro," *Immunity*, 6:35-46 (1997).
Deng et al., "Telomere Repeat Binding Factors TRFI, TRF2, and hRAP1 Modulate Replication of Epstein-Barr Virus OriP," *J. Virol.*, 77(22):11992-12001 (2003).
Deng et al., "Inhibition of Epstein-Barr Virus OriP Function by Tankyrase, a Telomere-Associated Poly-ADP Ribose Polymerase That Binds and Modifies EBNAI ," *J. Virol.*, 79(8):4640-4650 (2005).
Diaz et al., "Evolution of somatic hypermutation and gene conversion in adaptive immunity," *Immunological Reviews*, 162:13-24 (1998).
Diaz et al., "Evolution lind the molecular basis of somatic hypennutation of antigen receptor genes," *Philos. Trans. R. Soc. Lond. B Biol. Sci.*, 356:67-72 (2001).
Di Scala et al., "Conformational state of human cardiac 5-HT4(g) receptors influences the functional effects of polyclonal anti-5-HT4 receptor antibodies," *Biochem. Pharmacol.*, 73:964-971 (2007).
Dmitriev et al., "Analysis of Bispecific Monoclonal Antibody Binding to Immobilized Antigens Using an Optical Biosensor," *Biochem*, 67(12):1356-1365 (2002).
Dorner et al., "Analysis of the targeting of the hypermutational machinery and the impact of subsequent selection on the distribution of nucleotide changes in human $V_HDJ_H$ rearrangements," *Immunological Reviews*, 162:161-171 (1998).
Drake et al., "Rates of spontaneous mutation," *Genetics*, 148:1667-1686 (1998).
Drummond et al., "Why High-error-rate Random Mutagenesis Libraries are Enriched in Functional and Improved Proteins," *J. Mol. Biol.*, 350:806-816 (2005).
Duquette et al., "AID binds to transcription-induced structures in c-MYC that map to regions associated with translocation and hypermutation," *Oncogene*, 24:5791-5798 (2005).
Durandy et al., "Activation-Induced Cytidine Deaminase: Structure-Function Relationship as Based on the Study of Mutants," *Hum. Mut.*, 0:1-7 (2006).
Durandy et al., *Hum. Mutat.*, 27(12):1185-1191 (2006) [previously provided].
Eglin, "An Overview of High Throughput Screening at G Protein Coupled Receptors," *Frontiers Drug Design Disc.*, 1:97-111 (2005).
Elies et al., "Immunochemical and functional characterization of an agonist-like monoclonal antibody against the M2 acetylcholine receptor," *Eur. J. Biochem.*, 251:659-666 (1998).
Ellington et al., "In vitro selection of RNA molecules that bind specific ligands," *Nature*, 346:818-822 (1990).
Ewert, *Methods*, 34:184-1999 (2004).
Farinas et al., "Fluoescence Activated Cell Sorting for Enzymatic Activity," *Comb.Chem. High Throughput Screen*, 9(4):321-328 (2006).
Feldhaus et al., "Flow-cytometric isolation of human antibodies from a nonimmune *Saccharomyces cerevisiae* surface display library," *Nature Biotech.*, 21(2):163-170 (2003).
Fellouse et al., "Synthetic antibodies from a four-amino-acid code: a dominant role for tyrosine in antigen recognition," *PNAS USA*, 101:12467-12472 (2004).
Fellouse et al., "Molecular recognition by a binary code," *J. Mol. Biol.*, 348:1153-1162 (2005).
Foote et al., "Breaking the affinity ceiling for antibodies and T cell receptors," *PNAS*, 97(20):10679-10681 (2000).
Fruton et al., "IUPAC-IUB Commission on Biochemical Nomenclature Symbols for Amino-Acid Derivatives and Peptides Recommendations," *Biochem.*, 11(9):1726-1732 (1972).
Fuhrmann-Benzakein, "Inducible and irreversible control of gene expression using a single transgene," *Nucl. Acid Res.*, 28(23):e99 (2000).
Gearhart et al., "Emerging Links Between Hypermutation of Antibody Genes and DNA Polymerases," *Nature Rev. Immunol.*, (12):187-192 (2001).
Gearhart, "Antibody Wars: Extreme Diversity," *J. Immunol.*, 177:4235-4236 (2006).

(56) References Cited

OTHER PUBLICATIONS

Geddie et al., "High Throughput Microplate Screens for Directed Protein Evolution," *Meth. Enzymol.*, 388:134-145 (2004).
Ghosh et al., "Design, synthesis, and progress toward optimization of potent small molecule antagonists of CC chemokine receptor 8 (CCR8)," *J. Med. Chem.*, 49(9):2669-2672 (2006).
Gift et al., "FACS-based isolation of slowly growing cells: Double encapsulation of yeast in gel microdrops," *Nature Biotechnol.*, 14(7):884-887 (1996).
Giordano et al., "Biopanning and rapid analysis of selective interactive ligands," *Nat. Med.*, 7(11):1249-1253 (2001).
Gold et al., "Diversity of Oligonucleotide Functions," *Annual Rev. Biochem.*, 64:763-797 (1995).
Gomez-Gonzalez et al., "Activation-induced cytidine deaminase action is strongly stimulated by mutations of the THO complex," *PNAS*, 104(20):8409-8414 (2007).
Gonzalez-Fernandez et al., "Analysis of somatic hypermutation in mouse Peyer's patches using immunoglobulin *K* light-chain transgenes," *PNAS USA*, 90:9862-9866 (1993).
Goodman et al., "Identifying protein-protein interactions in somatic hypermutation," *JEM*, 201(4):493-496 (2005).
Goossens et al., "Frequent occurrence of deletions and duplications during somatic hypermutation: Implications for oncogene translocations and heavy chain disease," *PNAS USA*, 95:2463-2468 (1998).
Goshorn et al., "Common Structural Features among Monoclonal Antibodies Binding the Same Antigenic Region of Cytochrome C*," *J. Biol. Chem.*, 266(4):2134-2142 (1991).
Goyenechea et al., "Cells strongly expressing Igk transgenes show clonal recruitment of hypermutation: a role for both MAR and the enhancers," *EMBO J.*, 16(13):3987-3994 (1997).
Graff et al., "Directed evolution of an anti-carcinoembryonic antigen scFv with a 4-day monovalent dissociation half-time at 370 C," *Protein Eng. Des. Selection*, 17(4):293-304 (2004).
Green et al., "Selection of a Ribozyrne That Functions as a Superior Template in a Self-Copying Reaction," *Science*, 258(5090):1910-1915 (1992).
Green et al., "IG V Region Hypermutation in B Cell Hybrids Mimics In Vivo Mutation and Allows for Isolation of Clonal Variants," *Mol. Immunol.*, 34(15):1095-1103 (1997).
Green et al., "Immunoglobulin hypermutation in cultured cells," *Immunological Reviews*, 162:77-87 (1998).
Gribskov et al., "The codon preference plot: graphic analysis of protein coding sequences and prediction of gene expression," *Nucl. Acids Res.*, 12(1):539-549 (1984).
Griffin et al., "Mammalian recombination-repair genes XRCC2 and XRCC3 promote correct chromosome segregation," *Nat. Cell Biol.*, 2:757-761 (2000).
Gronowicz et al., "Surface Ig isotypes on cells responding to lipopolysaccharide by IgM and IgG secretion," *J. Immunol.*, 123(5):2049-2056 (1979).
Gunneriusson et al., "Surface Display of a Functional Single-Chain Fv Antibody on Staphylococci," *J. Bacteriol.*, 78(5):1341-1346 (1996).
Gupta et al., "Conformation State-Sensitive Antibodies to G-protein-coupled Receptors," *J. Biol. Chem.*, 282(8):5116-5124 (2007).
Gupta et al., "Post-activation-mediated Changes in Opioid Receptors Detected by N-terminal Antibodies," *J. Biol. Chem.*, 283(16):10735-10744 (2008).
Gustafsson et al., "Codon bias and heterologous protein expression," *Trends Biotech.*, 22(7):346-353 (2004).
Haas et al., "Continuous Autotropic Signaling by Membrane-expressed Tumor Necrosis Factor," *J. Biol. Chem.*, 274(25):18107-18112 (1999).
Harris et al., "AID is Essential for Immunoglobulin V Gene Conversion in a Cultured B Cell Line," *Curr. Biol.*, 12:493-503 (2001).
Hawkins et al., "The Contribution of Contact and Non-contact Residues of Antibody in the Affinity of Binding to Antigen," *J. Mol. Biol.*, 234:958-964 (1993).
Hebner et al., "The spacing between adjacent binding sites in the family of repeats affects the functions of Epstein-Barr nuclear antigen 1 in transcription activation and stable plasmid maintenance," *Virology*, 311:263-274 (2003).
Heinzel et al., "Use of Simian Virus 40 Replication to Amplify Epstein-Barr Virus Shuttle Vectors in Human Cells," *J. Virol.*, 62(10):3738-3746 (1988).
Hershberg et al., "Differences in potential for amino acid change after mutation reveals distinct strategies for K and Alight-chain variation," *PNAS*, 103(43):15963-15968 (2006).
Hirai et al., "Replication Licensing of the EBV oriP Minichromosome," *Curr. Top. Microbiol. Immunol.*, 258:13-33 (2001).
Hoffmann et al., "Rapid translation system: A novel cell-free way from gene to protein," *Biotechnol. Annu. Rev.*, 10:1-30 (2004).
Ho et al., "Genetically Engineered *Saccharomyces* Yeast Capable of Effective Cofermentation of Glucose and Xylose," *Appl. Environ. Microbiol.*, 64(5):1852-1859 (1998).
Holliger et al., Diabodies: Small bivalent and bispecific antibody fragments, PNAS USA 90:6444-6448 (1993).
Holliger et al., "Engineered antibody fragments and the rise of single domains," *Nature Biotech.*, 23(9):1126-1136 (2005).
Holowaty et al., "Protein Profiling with Epstein-Barr Nuclear Antigen-I Reveals an Interaction with the Herpesvirus-associated Ubiquitin-specific Protease HAUSPIUSP7," *J. Biol. Chem.*, 278(32):29987-29994 (2003).
Holmes et al., "Improved cell line development by a high throughput affinity capture surface display technique to select for high secretors," *J. Immunol. Methods*, 230:141-147 (1999).
Hoogenboom, "Selecting and screening recombinant antibody libraries," *Nature Biotech.*, 23 (9):1105-1116 (2005).
Hsu, "Mutation, selection, and memory in B lymphocytes of exothermic vertebrates," *Immunological Reviews*, 162:25-36 (1998).
Huang et al., "Notch-Induced E2A Degradation Requires CHIP and Hsc70 as Novel Facilitators of Ubiquitination," *Mol. Cell Biol.*, 24(20):8951-8962 (2004).
Huston et al., "Protein engineering of antibody binding sites: Recovery of specific activity in an anti-digoxin single-chain Fv analogue produced in *Escherichia coli," PNAS USA*, 85:5879-5883 (1988).
Iglesias-Ussel et al., "Forced expression of AID facilitates the isolation of class switch variants from hybridoma cells," *J. Immunol. Methods*, 316:59-66 (2006).
Indra et al., "Temporally-controlled site-specific mutagenesis in the basal layer of the epidermis: comparison of the recombinase activity of the tamoxifen-inducible Cre-$ER^{T2}$ recombinases," *Nuc. Acid Res.*, 27(22):4324-4327 (1999).
Ito et al., "Activation-induced cytidine deaminase shuttles between nucleus and cytoplasm like apoliprotein B mRNA editing catalytic polypeptide 1," *PNAS*, 101(7):1975-1980 (2004).
Jacobs et al., "Hypermutation of Immunoglobulin Genes in Memory B Cells of DNA Repair-deficient Mice," *J. Exp. Med.*, 187(11):1735-1743 (1998).
Jain et al., "A potential role for antigen selection in the clonal evolution of Burkitt's lymphoma," *J. Immunol.*, 153:45-52 (1994).
Jankelevich et al., "A nuclear matrix attachment region organizes the Epstein-Barr viral plasmid in Raji cells into a single DNA domain," *EMBO J.*, 11(3):1165-1176 (1992).
Johnson et al., "Mammalian XRCC2 promotes the repair of DNA double-strand breaks by homologous recombination," *Nature*, 401:397-399 (1999).
Jolly et al., "The targeting of somatic hypermutation," *Semin. Immunol.*, 8:159-168 (1996).
Jolly et al., "Rapid methods for the analysis of immunoglobulin gene hypermutation: application to transgenic and gene targeted mice," *Nucleic Acids Research*, 25(10)1913-1919 (1997).
Jones et al., "Replacing the complementarity-determining regions in a human antibody with those from a mouse," *Nature*, 321:522-525 (1986).
Jones et al., "Regulation of cancer cell migration and bone metastasis by RANKL," *Nature*, 440:692-696 (2006).
Joyce, "In vitro evolution of nucleic acids," *Curr. Op. Struct., Biol.*, 4:331-336 (1994).
Jung et al., "Selection for Improved Protein Stability by Phage Display," *J. Mol. Biol.*, 294:163-180 (1999).

(56) References Cited

OTHER PUBLICATIONS

Kabat et al., "Attempts to locate complementarity-determining residues in-the variable positions of light and heavy chains," *Ann. NY Acad. Sci.*, 190:382-393 (1971).
Kabat et al., "Unusual distributions of amino acids in complementarity-determining (hypervariable) segments of heavy and light chains of immunoglobulins and their possible roles in specificity of antibody combining sites," *J. Biol. Chem.*, 252(19):6609-6616 (1977).
Kabat, "Antibody Diversity Versus Antibody Complementarity," *Pharmacol. Rev.*, 34(1):23-38 (1982).
Kallberg et al., "Somatic mutation of immunoglobulin V genes in vitro," *Science*, 271(5253):1285-1289 (1996).
Kapoor et al., "Reconstitution of Epstein-Barr virus-based plasmid partitioning in budding yeast," *EMBO J.*, 20(1-2):222-230 (2001).
Kapoor et al., "Methods for measuring the replication and segregation of Epstein-Barr virus-based plasmids," *Methods Mol. Biol.*, 292:247-266 (2005).
Kavli et al., "Uracil in DNA—General mutagen, but normal intermediate in acquired immunity," *DNA Repair:*.doi.10-1016/j.dnarep.2006.10.014, 12 pages (2006).
Kawahara et al., "A Growth Signal with an Artificially Induced Erythropoietin Receptor-gp130 Cytoplasmic Domain Heterodimer," *J. Biochem.*, 130(i):305-312 (2001).
Kawahara et al., "Bypassing antibiotic selection: positive screening of genetically modified cells with an antigen-dependent proliferation switch," *Nucl. Acids Res.*, 31(7):e32 (2003).
Kawahara et al., "Improved growth response of aiHibooy/receptor chimera attained by the engineering of transmembrane domain," *Protein Eng. Des. Sel.*, 17(10):715-719 (2004).
Kawamura et al., "DNA polymerase theta is preferentially expressed in lymphoid tissues and upregulated in human cancers," Int. 1. Cancer 109(1):9-16 (2004).
Keitel et al., "Crystallographic Analysis of Anti-p24 (HIV-I) Monoclonal Antibody Cross-Reactivity and Polyspecificity," *Cell*, 91:811-820 (1997).
Kim et al., "Ongoing diversification of the rearranged immunoglobulin light-chain gene in a bursal lymphoma cell line," *Mol. Cell Biol.*, 10(6):3224-3231 (1990).
Kinoshita et al., Linking Class-Switch Recombination with Somatic Hypermutation, *Mol. Cell Biol.*, 2:493-503 (2001).
Kirchmaier et al.Plasmid Maintenance of Derivatives of oriP of Epstein-Barr Virus, *J. Virol.*, 69(2):1280-1283 (1995).
Kitamura et al., "Nuclear Import of Epstein-Barr Virus Nuclear Antigen 1 Mediated by NP-I (Importin as) Is Up-and Down-Regulated by Phosphorylation of the Nuclear Localization Signal for Which Lys379 and Arg380 Are Essential," *J. Virol.*, 80(4):1979-1991 (2006).
Klein et al., "An EBV-genome-negative cell line established from Ii American Burkitt lymphoma; receptor characteristics, EBV infectibility and permanent conversion into EBV-positive sublines by in vitro infection," *Intervirology*, 5:319-334 (1975).
Klein et al., "Somatic hypermutation in normal and transformed human B cells," *Immunological Reviews*, 162:261-280 (1998).
Klionsky et al.,"A Polyclonal Antibody to the Prepore Loop of Transient Receptor Potential Vanilloid Type I Blocks Channel Activation," *J. Pharmacol. Exp. Ther.*, 319(1): 192-198 (2006).
Klix et al., "Multiple sequences from downstream of the Jx cluster can combine to recruit somatic hypermutation to a heterologous, upstream mutation domain," *Eur. J. Immunol.*, 28:317-326 (1998).
Knappik, *J. Mol. Biol.*, 296:57-86 (2000).
Knight et al., "Somatic diversifictaion of IgH genes in rabbit," *Immunological Reviews*, 162:37-47 (1998).
Kobrin et al., The Somatic Instability of Immunoglobulin Genes in Cultured cells, pp. 11-28 in Ch. 2 of *Somatic hypermutation in V regions* (ed. Steele, EJ.), CRC Press, Boca Raton, FL (1990).
Komori et al. "Biased dA/dT somatic hypermutation as regulated by the heavy chain intronic iEu enhancer and 3' E alpha enhancers in human lymphoblastoid B cells," *Mol. Immunol.*, 43:1817-1826 (2006).
Kong et al., "Recombination-based mechanisms for somatic hypermutation," *Immunological Reviews*, 162:67-76 (1998).
Kosmas et al, "Somatic hypermutation of immunoglobulin variable region genes: focus on follicular lymphoma and multiple myeloma," *Immunological Reviews*, 162:281-292 (1998).
Kou et al., "Expression of activation-induced cytidine deaminase in human hepatocytes during hepatocarcinogenesis," *Int. J. Cancer*, published online Oct. 25, 2006 http://www3.interscience.wiley.com.revproxy.brown.edu/cgi-bin/fulltext/113441207/main.html.journal.
Kramer, "Transgene Control Engineering in Mammalian Cells," *Methods Mol. Biol.*, 308: 123-144 (2005).
Krause et al., "The cytidine deaminases AID and APOBEC-1 exhibit distinct functional properties in a novel yeast selectable system," *Mol. Immunol.*, 43(4):295-307 (2006).
Kronick, "The use of phycobiliproteins as fluorescent labels in immunoassay," *J. Immunol. Methods*, 92:1-13 (1986).
Kunaparaju et al., "Epi-CHO, an Episomal Expression System for Recombinant Protein Production in CHO Cells," *Biotechnol. Bioeng.*, 91(6):670-677 (2005).
Kuppers et al., "Mechanisms of chromosomal translocations in B cell lymphomas," *Oncogene*, 20:5580-5594 (2001).
Kuriyan, "Allostery and Coupled Sequence Variation in Nuclear Hormone Receptors," *Cell*, 1 16(3):354-356 (2004).
Lagerstrom et al., "Structural diversity of G protein-coupled receptors and significance for drug discovery," *Nature Reviews/Drug Discovery*, 7:339-357 (2008).
Langle-Rouault et al., "Up to 100-fold Increase of Apparent Gene Expression in the Presence of Epstein-Barr Virus oriP Sequences and EBNA1: Implications of the Nuclear Import of Plasmids," *J. Virol.*, 72(7):6181-6185 (1998).
Lantto et al., "Uneven distribution of Repetitive Trinucleotide Motifs in Human Immunoglobulin Heavy Variable Genes," *J. Mol. Evol.*, 54:346-353 (2002).
Larijani et al., "Methylation protects cytidines from AID-mediated deamination," *Mol. Immunol.*, 42:599-604 (2005).
Larijani et al.; "AID Associates with Single-Stranded DNA with High Affinity and a Long Complex Half-Life in a Sequence-Independent Manner," *Mol. Cell Biol.*, 27(1):20-30 (2007).
Lazorchak et al., "E2A and IRF-4/Pip Promote Chromatin Modification and Transcription of the Immunoglobulin K Locus in Pre-B Cells," *Mol. Cell Biol.*, 26(3):810-821 (2006).
Leight et al., "Establishment of an oriP Replicon Is Dependent upon an Infrequent,. Epigenetic Event," *Mol. Cell. Biol.*, 21(13):4149-4161 (2001).
Leight et al., "The cis-Acting Family of Repeats Can Inhibit as well as Stimulate Establishment of an oriP Replicon," *J. Virol.*, 75(22):10709-10720 (2001).
Li et al., "Rad51 expression and localization in B cells carrying out class switch recombination," *PNAS USA*, 93:10222-10227 (1996).
Li et al., "The generation of antibody diversity through somatic hypermutation and class switch recombination," *Genes & Dev.*, 18:1-11 (2004).
Lin et al., "Sequence dependent hypermutation of the immunoglobulin heavy chain in cultured B cells," *PNAS USA*, 94(10):5284-5289 (1997).
Lin et al., "The effects of E-mu, 3'-alpha (hs 1,2) and 3'-kappa: enhancers on mutation of an Ig-VDJ-C-gamma-2a Ig immunoglobulin heavy gene in cultured B cells,", *Intl. Immunol.*, 10(8):1121-1129 (1998).
Lindner et al., "The plasmid replicon of Epstein-Barr virus: Mechanistic insights into efficient, licensed, extrachromosomal replication in human cells," *Plasmid*, 58:1-12 (2007).
Lingbeck et al., "E12 and E47 modulate cellular localization and proteasome-mediated degradation of MyoD and Idl," *Oncogene*, 24:6376-6384 (2005).
Lipovsek et al., "Selection of Horseradish Peroxidase Variants with Enhanced Enantioselectivity by Yeast Surface Display," *Chem. Biol.*, 14:1176-1185 (2007).
Lippow et al., "Computational design of antibody-affinity improvement beyond in vivo maturation," *Nature Biotech.*, 25(10):1171-1176 (2007).

(56) References Cited

OTHER PUBLICATIONS

Liu et al., "XRCC2 and XRCC3, new human Rad51-family members, promote chromosome stability and protect against DNA cross-links and other damages," *Mol. Cell*, 1:783-793 (1998).
Lopez et al., "A single $V_H$ family and long CDR3s are the targets for hypennutation in bovine immunoglobulin heavy chains," *Immunological Reviews*, 162:55-66 (1998).
Lluis et al., "E47 phosphorylation by p38 MAPK promotes MyoD/E47 association and muscle-specific gene transcription," *EMBO J.*, 24:974-984 (2005).
Lundberg et al., "High-fidelity amplification using a thermostable DNA polymerase isolated from *Pyrococcus furiosus," Gene*, 108:1-6 (1991).
Luria et al., "Mutations of bacteria from virus sensitivity to virus resistance," *Genetics*, 28:491-511 (1943).
Mage, "Diversification of rabbit $V_H$ genes by gene-conversion-like and hypermutation mechanisms," *Immunological Reviews*, 162:49-54 (1998).
Maelicke et al., "Epitope Mapping Employing Antibodies Raised against Short Synthetic Peptides: A Study of the Nicotinic Acetylcholine Receptor," *Biochem.*, 28:1396-1405 (1989).
Maizels, "Somatic hypermutation: how many mechanisms diversify V region sequences?" *Cell*, 83:9-12 (1995).
Manser et al., "The roles of antibody variable region hypermutation and selection in the development of the memory B-cell compartment," *Immunological Reviews*, 162:182-196 (1998).
Mantyh et al., "Rapid endocytosis of a G protein-coupled receptor: Substance P-evoked internalization of its receptor in the rat striatum in vivo," *PNAS*, 92:2622-2626 (1995).
Manz et al., "Analysis and sorting of live cells according to secreted molecules, relocated to a cell-surface affinity matrix," *PNAS USA*, 92:1921-1925 (1995).
Marchalonis et al., "Exquisite specificity and peptide epitope recognition promiscuity, properties shared by antibodies from sharks to humans," *J. Mol. Recognition*, 14:110-121 (2001).
Margolskee et al., "Epstein-Barr Virus Shuttle Vector for Stable Episomal Replication of cDNA Expression Libraries in Human Cells," *Mol. Cell. Biol.*, 8(7):2837-2847 (1988).
Marks et al., "By-Passing Immunization Human Antibodies from V-gene Libraries Displayed on Phage," *J. Mol. Biol.*, 222:581-597 (1991).
Martin et al., "AID and mismatch repair in antibody diversification," *Nat. Rev. Immunol.*, 2(8):605-614 (2002).
Martin et al., "Activation-induced cytidine deaminase turns on somatic hypermutation in hybridomas," *Nature*, 415:802-806 (2002).
Martin et al., "Somatic hypermutation of the AID transgene in B and non-B cells," *PNAS*, 99(19):12304-12308 (2002).
Mason et al., "The Kinetics of Antibody Binding to Membrane Antigens in Solution and at the Cell Surface," Biochem. J. 187: 1-20 (1980).
Mastrobattista et al., "High-Throughput Screening of Enzyme Libraries: In Vitro Evolution of a β-Galactosidase by Fluorescence-Activated Sorting of Double Emulsions," *Chem. Biol.*, 12(12)1291-1300 (2005).
Masuda et al., "Absence of DNA polymerase 0 results in decreased somatic hypennutation frequency and altered mutation patterns in Ig genes," DNA repair doi: 10: 1016/j.dnarep.2006.06.006, 8 pages (2006).
Mattheakis et al., "An in vitro polysome display system for identifying ligands from very large peptide libraries," *PNAS USA*, 91:9022-9026 (1994).
Matthias et al., "Eukaryotic expression vectors for the analysis of mutant proteins," *NAR*, 17:6418 (1989).
Mattes, "Binding parameters of antibodies reacting with multivalent antigens: functional affinity or pseudo-affinity," *J. Immunol. Methods*, 202:97-101 (1997).
Max et al., "The Nucleotide Sequence of a 5.5-kilobase DNA Segment Containing the Mouse k Immunoglobulin J and C Region Genes," *J. Biol. Chem.*, 256:5116-5120 (1981).
Mazor et al., "Isolation of engineered, full-length antibodies from libraries expressed in *Escherichia coli," Nat. Biotech.*, 25(5):563-565 (2007).
McBride et al., "Somatic hypermutation is limited by CRM1-dependent nuclear export of activation-induced deaminase," *J. Exp. Med.*, 199(9):1235-1244 (2004).
McBride et al., "Regulation of hypermutation by activation-induced cytidine deaminase phosphorylation," *PNAS*, 103(23):8798-8803 (2006).
McCafferty et al., "Phage antibodies: filamentous phage displaying antibody variable domains," *Nature*, 348:552-554 (1990).
McCormack et al., "Germ line maintenance of the pseudogene donor pool for somatic immunoglobulin gene conversion in chickens," *Mol. Cell Biol.*, 13(2):821-830 (1993).
McIntosh et al., "Somatic hypermutation in autoimmune thyroid disease," *Immunological Reviews*, 162:219-231 (1998).
McKean et al., "Generation of antibody diversity in the immune response of BALB/c mice to influenza virus hemagglutinin," *PNAS USA*, 81:3180-3184 (1984).
Meyer et al., "The immunoglobulin x locus contains a second, stronger B-cell-specific enhancer which is located downstream of the constant region," *EMBO J.*, 8(7): 1959-1964 (1989).
Mian et al., "Structure, Function and Properties of Antibody Binding Sites," *J. Mol. Biol.*, 217:133-151 (1991).
Midlefort et al., "Context-dependent mutations predominate in an engineered high-affinity single chain antibody fragment," *Protein Science*, 15:324-334 (2006).
Monteiro et al., "Molecular methods for the detection of mutations," *Teratog. Carcinog. Mutagen.*, 20(6):357-386 (2000).
Moore, "Exploration by lamp light," Nature 374:766-767 (1995).
Morino et al., "Antibody fusions with fluorescent proteins: a versatile reagent for profiling protein expression," *J. Immunol. Methods*, 257:175-184 (2001).
Moza et al., "Long-range cooperative binding effects in a T cell receptor variable domain," *PNAS*, 103(26):9867-9872 (2006).
Muramatsu et al. "Class Switch Recombination and Hypermutation Require Activation-Induced Cytidine Deaminase (Alb), Potential RNA Editing Enzyme," *Cell*, 102:553-563(2000).
Muschen et al., "Somatic Mutation of the CD95 Gene in Human B Cells as a Side-Effect of the Germinal Center Reaction," *J. Exp. Med.*, 192(12):1833-1839 (2000).
Muto et al., "Negative regulation of activation-induced cytidine deaminase in B cells," *PNAS*, 103(8):2752-2757 (2006).
Muyldermans et al., "Sequence and structure of VH domain from naturally occurring camel heavy chain immunoglobulins lacking light chains," *Protein Eng.*, 7(9):1129-1135 (1994).
Nakamura et al., Codon usage tabulated from international DNA sequence databases: status for the year 2000, *Nucl. Acid Res.*, 28(1):292 (2000).
Nakayama et al., "A limited nurnber of genes are involved in the differentiation of germinal center B cells," *J. Cell. Biol.*, Published online Jun. 22, 2006 DOI: 10.1 002/jcb.20952.
Navaratnam et al., "An Overview of Cytidine Deaminases," *Intl. J. Hematol.*, 83:195-200 (2006).
Neuberger et al., "Somatic hypermutation," *Curr. Op. Immunol.*, 7:248-254 (1995).
Neuberger et al., "Monitoring and interpreting the intrinsic features of somatic hypermutation," *Immunological Reviews*, 162:107-116 (1998).
Neuberger et al., "Somatic hypermutation at A T pairs: polymerase error versus dUTP incorporation," *Nature Rev. Immunol.*, 5(2):171-178 (2005).
Ng et al., "The immunology of AIDS-associated lymphomas," *Immunological Reviews*, 162:293-298 (1998).
Nie et al., "Notch-induced E2A ubiquitination arid degradation are controlled by MAP kinase activities," *EMBO J.*, 22(21):5780-5792(2003).
Nussinov, "Eukaryotic Dinucleotide Preference Ruels and Their Implications for Degenerate Codon Usage," *J. Mol. Biol.*, 149:125-131 (1981).
Odegard et al. Histone modifications associated With somatic hypermutation, *Immunity*, 23:101-110 (2005).

(56) References Cited

OTHER PUBLICATIONS

Odegard et al., "Targeting of somatic hypermutation," *Nature Rev. Imm.*, 6:573-583 (2006).
Ohki et al., "Telomere-bound TRF1 and TRF2 stall the replication fork at telomeric repeats," *Nucl. Acids Res.*, 32(5):1627-1637 (2004).
Okragly et al., "Elevated Tryptase, Nerve Growth Factor, Neurotrophin-3 and Glial Cell Line-Derived Neurotrophic Factor Levels in the Urine of Interstitial Cystitis and Bladder Cancer Patients," *J. Urol.*, 161:438-442 (1991).
Olsen et al., "High-Throughput FACS Method for Directed Evolution of Substrate Specificity," *Meth. Mol. Biol.*, 230:329-342 (2003).
Omori et al., "Regulation of Class-Switch Recombination and Plasma Cell Differentiation by Phosphatidylinositol 3-Kinase Signaling," *Immunity*, 25:1-13 (2006).
Osbourn et al., "Directed selection of MIP-1α neutralizing CCR5 antibodies from a phage display human antibody library," *Nat. Biotechnol.*, 16:778-781 (1998).
Otte et al., "Molecular basis for the binding polyspecificity of an anti-cholera toxin peptide 3 monoclonal antibody," *J. Mol. Recognition*, 19:49-59 (2006).
Okazaki et al., "The AID enzyme induces class switch recombination in fibroblasts," *Nature*, 416:340-345 (2002).
Papavasiliou et al., "Cell-cycle-regulated DNA double-stranded breaks in somatic hypermutation of immunoglobulin genes," *Nature*, 408:116-221 (2000).
Papavasiliou et al., "Somatic hypermutation of immunoglobulin genes: merging mechanisms for genetic diversity," *Cell*, 109(Suppl.):S35-S44 (2002).
Parham, ed., *Immunol. Reviews*, "Somatic hypermutation of immunoglobulin genes," vol. 162, Apr. 1998 (Copenhagen, Denmark: Munksgaard).
Pasqualucci et al., "BCL-6 mutations in normal germinal center B cells: Evidence of somatic hypermutation acting outside Ig loci," *Immunol.*, 95:11816-11821 (1998).
Pasqualucci et al., "Hypermutation of multiple proto-oncogenes in B-cell diffuse large-cell lymphomas," *Nature*, 412:341-346 (2001).
Pasqualucci et al., "PKA-mediated phosphorylation regulates the function of activation-induced deaminase (AID) in B cells," *PNAS*, 103(2):395-400 (2006).
Perini et al., "In vivo transcriptional regulation of N-Myc target genes is controlled by E-box methylation," *PNAS*, 102 (34):12117-12122 (2005).
Persson, *J. Mol. Biol.*, 357:607-620 (2006).
Peter et al., "Antibodies against the melanocortin-4 receptor act as inverse agonists in vitro and in vivo," *Am. J. Physiol. Regul. Integr. Compo Physiol.*, 292:R2151-R2158 (2007).
Peters et al., "Somatic Hypermutation of Immunoglobulin Genes is Linked to Transcription Initiation," *Immunity*, 4:57-65 (1996).
Petersen-Mart et al., "AID mutates *E. coli* suggesting a DNA deamination mechanism for antibody diversification," *Nature*, 418:99-104 (2002).
Pham et al., "Impact of Phosphorylation and Phosphorylation-null Mutants on the Activity and Deamination Specificity of Activation-induced Cytidine Deaminase," JBC Papers in Press published Apr. 16, 2008, Manuscript M802121200:doi/10/1074/3bc.M802-121200.
Phung et al., "Hypermutation in Ig V genes from mice deficient in the MLH1 mismatch repair protein," *J.Immunol.*, 162(6):3121-3124(1999).
Pierce et al., "XRCC3 promotes homology-directed repair of DNA damage in mammalian cells," *Genes Dev.*, 13:2633-2638 (1999).
Pioszak et al., "Molecular recognition of parathyroid hormone by its G protein-coUpled receptor," *PNAS*, 105(13):5034-5039 (2008).
Pluckthun, "Antibody Engineering: Advances from the Use of *Escherichia coli* Expression Systems," *Biotechnology*, 9:545-551 (1991).
Polonskaya et al., "Role for a region of helically unstable DNA within the Epstein-Barr virus latent cycle origin of DNA replication oriP in origin function," *Virology*, 328:282-291 (2004).
Poltoratsky et al., "Error-prone Candidates Vie for Somatic Mutation," *J. Exp. Med.*, 192(10):F27-F30 (2000).
Poltoratsky, "Down regulation of DNA polymerase beta accompanies somatic hypermutation in human BL2 cell lines," *DNA Repair*, 6(7):244-253 (2007).
Poltoratsky et al., "Negligible impact of pol *L* expression on the alkylation sensitivity of poll β-deficient mouse fibroblast cells," *DNA Repair*, 7:830-833 (2008).
Pons et al., "Energetic analysis of an antigen/antibody interface: alanine scanning mutagenesis and double mutant cycles on the HyHEL-10/lysozyme interaction," *Protein Science*, 8:958-968 (1999).
Presta, "Antibody Engineering," *Curr. Op. Struct. Biol.*, 2:593-596 (1992).
Rada et al., "Hot spot focusing of somatic hypermutation in MSH2-deficient mice suggests two stages of mutational targeting," *Immunity*, 9:135-141 (1998).
Rada et al. "The intrinsic hypermutability of antibody heavy and light chain genes decays exponentially," *EMBO J.*, 20(16):4570-4576 (2001).
Rakestraw et al., "A Flow Cytometric Assay for Screening Improved Heterologous Protein Secretion in Yeast," *Biotechnol. Prog.*, 22:1200-1208 (2006).
Ratech, "Rapid cloning of rearranged immunoglobulin heavy chain genes from human B-cell lines using anchored polymerase chain reaction," *Biochem. Biophys. Res. Commun.*, 182(3):1260-1263 (1992).
Reason et al., "Codon insertion and deletion functions as a somatic diversification mechanism in human antibody repertoires," *Biol. Direct.*, 1:24-45 (2006).
Ren et al., "Establishment and Applications of Epstein-Barr Virus-Based Episomal Vectors in Human Embryonic Stem Cells," *Stem Cells*, 24:1338-1347 (2006).
Revy et al., "Activation-Induced Cytidine Dearninase (AID) Deficiency Causes the Autosomal Recessive Form of the Hyper-IgM Syndrome (HIGM2)," *Cell*, 102(5):565-575 (2000).
Reynaud et al., "A hyperconversion mechanism generates the chicken light chain preimmune repertoire," *Cell*, 48:379-388 (1987).
Reynaud et al., "Somatic hyperconversion diversifies the single VH gene ofthe chicken with a high incidence in the D region," *Cell*, 59:171-183 (1989).
Robey et al., "Specificity mapping of human anti-T cell receptor monoclonal natural antibodies: defining the properties of epitope recognition promiscuity," *FASEB J.*, 16:642-652 (2002).
Rogozin et al., "Somatic hypermutagenesis of immunoglobulin genes. II. Influence of neighbouring base sequences on mutagenesis," *Biochem. Biophys. Acta*, 1171:11-18 (1992).
Rogozin et al., "Cutting Edge: DGYW/WRCH Is a Better Predictor of Mutability at G:C Bases in Ig Hypermutation Than the Widely Accepted RGYW/WRCY Motif and Probably Reflects a Two-Step Activation -induced Cytidine DeaminaseTriffered Process," *J. Immunol.*, 172:3382-3384 (2004).
Rogozin et al., "The cytidine deaminase AID exhibits similar functional properties in yeast and mammals," *Mol. Immunol.*, 43:1481-1484 (2006).
Romanow et al., "E2A and EBF Act in Synergy with the V(D)J Recombinase to Generate a Diverse Immunoglobulin Repertoire in Nonlymphoid Cells," *Mol. Cell*, 5:343-353 (2000).
Ronai et al., "Complex regulation of somatic hypermutation by cis-acting sequences in the endogenous IgH gene in hybridoma cells," *PNAS USA*, 102(33):11829-11834 (2005).
Rooney et al., "Paired Epstein-Barr virus-carrying lymphoma and lymphoblastoid cell lines from Burkitt's lymphoma patients: comparative sensitivity to non-specific and to allo-specific cytotoxic responses in vitro," *Int. J. Cancer*, 34:339-348 (1984).
Rowe et al., "Differences in B cell growth phenotype reflect novel patterns of Epstein-Barr virus latent gene expression in Burkitt's lymphoma cells," *EMBO J.*, 6(9):2743-2751 (1987).
Rucci et al. "Tissue-specific sensitivity to AID expression in transgenic mouse models," *Gene*, 377:150-158 (2006).
Ruckerl et al., "Activation induced cytidine deaminase fails to induce a mutator phenotype in the human pre-B cell line Nalm6," *Eur. J. Immunol.*, 35:290-298 (2005).
Ruckerl et al., "Episomal vectors to monitor and induce somatic hypermutation in human Burkitt-Lymphoma cell lines," *Mol. Immunol.*, 43(10):1645-1652 (2006).
Sagawa et al., "Thermodynamic and kinetic aspects of antibody evolution during the immune response to hapten," *Mol. Immunol.*, 39:801-808 (2003).

(56) References Cited

OTHER PUBLICATIONS

Saini et al., "Exceptionally long CDR3H region with multiple cysteine residues in functional bovine IgM antibodies," *Eur. J. Immunol.*, 29:2420-2426 (1999).
Salazar et al., "Evaluating a Screen and Analysis of Mutant Libraries," *Methods Mol. Biol.*, 230:85-97 (2003).
Sale et al., "TdT-accessible breaks are scattered over the immunoglobulin V domain in a constitutively hypermutating B cell line," *Immunity*, 9:859-869 (1998).
Sale et al., "Ablation of XRCC2/3 transforms immunoglobulin V gene conversion into somatic hypermutation," *Nature*, 412(6850):921-926 (2001).
Santa-Marta et al., "HIV-1 vifprotein blocks the cytidine deaminase activity of B-cell specific AID in the *E. coli* by a similar mechanism of action," *Mol. Imm.*, 44:583-590 (2006).
Schoetz et al. "E2A Expression Stimulates Ig Hypermutation," *J. Immunol.*, 177:395-400 (2006).
Schoonbroodt et al., "Oligonucleotide-assisted cleavage and ligation: a novel directional DNA cloning technology to capture cDNAs. Application in the construction of a human immune antibody phage-display library," *Nucl. Acids Res.*, 33(9):e81 (2005).
Sciammas et al., "Graded Expression of Interferon Regulatory Factor-4 Coordinates Isotype Switching with Plasma Cell Differentiation," *Immunity*, 25:225-236 (2006).
Sears et al., "Metaphase Chromosome Tethering Is Necessary for the DNA Synthesis and Maintenance of oriP Plasmids but Is Insufficient for Transcription Activation by Epstein-Barr Nuclear Antigen 1," *J. Virol.*, 77(21):11767-11780 (2003).
Sharpe et al., "Somatic hypermutation of immunoglobulin *K* may depend on sequences 3' of CK and occurs on passenger transgenes," *EMBO J.*, 10(8):2139-2145 (1991).
Shen et al., Mutation ofBCL-6 Gene in Normal B Cells by the Process of Somatic Hypermutation of Ig Genes, *Science*, 280:1750-1752 (1998).
Shen et al., The TATA binding protein, c-Myc and survivin genes are not somatically hypermutated, while Ig and BCL6 genes are hypermutated in human memory B cells, *Intl. Immunol.*, 12(7):1085-1093 (2000).
Shen et al., "Somatic hypermutation and class switch recombination in Msh6-/-Ung-/-double-knockout mice," *J. Immunol.*, 177:5386-6392 (2006).
Shinkura et al., "Separate domains of AID are required for somatic hypermutation and class-switch recombination," *Nat. Immunol.*, 5(7):707-712 (2004).
Shire et al., EBP2, a Human Protein That Interacts with Sequences of the Epstein-Barr Virus Nuclear Antigen 1 Important for Plasmid Maintenance, *J. Virol.*, 73(4):2587-2595 (1999).
Shire et al., "Regulation of the EBNAI Epstein-Barr Virus Protein by Serine Phosphorylation and Arginine Methylation," *J. Virol.*, 80(11):5261-5272 (2006).
Siehler, "Cell-based assays in GPCR drug discovery," *Biotech. J.*, 3: 1-13 (2008).
Silverman, "Multivalent avimer proteins evolved by exon shuffiing of a family of human receptor domains," *Nature Biotech.*, 23:1493-1494 (2005).
Sitaraman et al., "A novel cell-free protein synthesis system," *J. Biotechnol.*, 110(3):257-263 (2004).
Storb et al., "Cis-acting sequences that affect somatic hypermutation of Ig genes," *Immunological Reviews*, 162:153-160 (1998).
Smit et al., "Antigen receptors and somatic hypermutation in B-cell chronic lymphocytic leukemia with Richter's transformation," *Haematologica*, 91(7):903-911 (2006).
Smith, "Filamentous Fusion Phage: Novel Expression Vectors that Display Cloned Antigens on the Virion Surface," *Science*, 228(4705):1315-1317 (1985).
Smith-Gill et al., "$V_LV_H$ Expression by Monoclonal Antibodies Recognizing Avian Lysozyme," *J. Immunol.*, 132(2):963-967 (1984).
Sonderegger et al., "Evolutionary Engineering of *Saccharomyces cerevisiae* for Anaerobic Growth on Xylose," *Appl. Environ. Microbiol.*, 69(14):1990-1998 (2003).
Song et al., "Antibody feedback and somatic mutation in B cells: regulation of mutation by immune complexes with IgG antibody," *Immunological Reviews*, 162:211-218 (1998).
Spencer et al., "Characteristics of Sequences Around Individual Nucleotide Substitutions in IgVH Genes Suggest Different GC and AT Mutators," *J. Immunol.*, 162:6596-6601 (1999).
Spillmann et al., "Endogenous Expression of Activation-Induced Cytidine Deaminase in Cell Line WEHI-231," *J. Immunol.*, 173:1858-1867 (2004).
Stevenson et al., "Insight into the origin and clonal history of B-cell tumors as revealed by analysis of immunoglobulin variable region genes," *Immunological Reviews*, 162:247-259 (1998).
Storb, "Progress in understanding the mechanism and consequences of somatic hypermutation," *Immunological Reviews*, 162:5-11 (1998).
Storb et al., "Somatic hypermutation of immunoglobulin arid non-immunoglobulin genes," *Phil. Trans. R. Soc.*, Lond. B 356:13-19 (2001).
Storb et al., "The E Box Motif CAGGTG Enhances Somatic Hypermutation without Enhancing Transcription," *Immunity*, 19:235-242 (2003).
Steele et al. "Computational analyses show A-to-G mutations correlate with nascent mRNA hairpins at somatic hypermutation hotspots," *DNA Repair* doi:10.1016/j.dnarep.2006.06.002 (2006).
Stemmer, "DNA shuffiing by random fragmentation and reassembly: In vitro recombination for molecular evolution," *PNAS USA*, 91(22):10747-10751 (1994).
Taddei et al., "Role of mutator alleles in adaptive evolution," *Nature*, 387:700-702 (1997).
Takata et al., "Homologous recombination and non-homologous end-joining pathways of DNA double-strand break repair have overlapping roles in the maintenance of chromosomal integrity in vertebrate cells," *Embo J.*, 17(18):5497-5508 (1998).
Takata et al., "The Rad51 paralog Rad51B promotes homologous recombinational repair," *Mol. Cell Biol.*, 20(17):6476-6482 (2000).
Takata et al., "Chromosome Instability and Defective Recombinational Repair in Knockout Mutants of the Five Rad51 Paralogs," *Mol. Cell Biol.*, 21(8):2858-2866 (2001).
Tam, "Synthetic peptide vaccine design: Synthesis and properties of a high-density multiple antigenic peptide system," *PNAS USA*, 85:5409-5413 (1988).
Teh et al, "The 1.48 A Resolution Crystal Structure of the Homotetrameric Cytidine Deaminase from Mouse," *Biochem.*, 45:7825-7833 (2006).
Teng et al., "MicroRNA-155 Is a Negative Regulator of Activation-Induced Cytidine Deaminase," *Immunity*, 28:621-629 (2008).
Terskikh et al., "Peptabody: A new type of high avidity binding protein," *PNAS*, 94:1663-1668 (1997).
Tomlinson, (1997) "V Base database of human antibody genes;" Medical Research Council, Centre for Protein Engineering, UK Confirmation No. 149990 http://www.mrc-cpe.cam.ac.uk/.
Tuerk et al., "Systematic Evolution of Ligands by Exponential Enrichment: RNA Ligands to Bacteriophage T4 DNA Polymerase," *Science*, 249(4968):505-510 (1990).
Tumas-Brundage et al., "The Transcriptional Promoter Regulates Hypermutation of the Antibody Heavy Chain Locus," *J. Exp. Med.*, 185(2):239-250 (1997).
Turner, "Directed evolution of enzymes for applied biocatalysis," *Trends Biotech.*, 21(11):474-478 (2003).
Unniraman et al., "Strand-Biased Spreading of Mutations During Somatic Hypermutation," *Science*, 317:1227-1230 (2007).
Vanantwerp et al., "Fine Affinity Discrimination by Yeast Surface Display and Flor Cytometry," *Biotechnol. Prog.*, 16:31-37 (2000).
Wabl et al., "Hypermutation at the immunoglobulin heavy chain locus in a pre-B-cell line," *PNAS USA*, 82:479-482 (1985).
Wagner et al., "Codon bias targets mutation," *Nature*, 376:732 (1995).
Wang et al., "Enhancement of scFv fragment reactivity with target antigens in binding assays following mixing with anti-tag monoclonal antibodies," *J. Immunol. Meth.*, 294:23-35 (2004).
Wang et al., "Evolution of new nonantibody proteins via iterative somatic hypermutation," *PNAS USA*, 101(19):16745-16749 (2004).

(56) References Cited

OTHER PUBLICATIONS

Wang et al., "Genome-wide somatic hypermutation," *PNAS USA*, 101(19):7352-7356 (2004).
Wang et al., "Hypermutation Rate Normalized by Chronological Time," *J. Immunol.*, 174(9):5650-5654 (2005).
Wang et al., "Mutant Library Construction in Directed Molecular Evolution," *Mol. Biotech.*, 34:55-68 (2006).
Ward et al., "Binding activities of a repertoire of single immunoglobulin variable domains secreted from *Escherichia coli*," *Nature*, 341:544-546 (1989).
Watanabe et al., "Rad18 guides pol eta to replication stalling sites through physical interaction and PCNA monobuquitination," *EMBO J.*, 23(19):3886-3896 (2004).
Weaver et al., "Gel microdrop technology for rapid isolation ofrare and high producer cells," *Nature Medicine*, 3(5):583-585 (1997).
Weill et al., "Rearrangement/hypermutaitonlgene conversion: when, where and why?" *Immunol. Today*, 17(2):92-97 (1996).
Wendelburg et al., "An enhanced EBNA1 variant with reduced IR3 domain for long-term episomal maintenance and transgene expression of oriP-based plasmids in human cells," *Gene Therapy*, 5:1389-1399 (1998).
Werthen et al., "Cooperativity in the antibody binding to surface-adsorbed antigen," *BBA*, 1162:326-332 (1993).
White et al., "Sequences Adjacent to oriP Improve the Persistence of Epstein-Barr Virus-Based Episomes in B Cells," *J. Virol.*, 75(22):11249-11252 (2001).
Wiens et al., "Harmful somatic mutations: lessons from the dark side," *Immunological Reviews*, 162:197-209 (1998).
Wilson et al., "Amino acid insertions and deletions contribute to diversify the human Ig repertoire," *Immunological Reviews*, 162: 143-151 (1998).
Wilson et al., "Somatic hypermutation introduces insertions and deletions into immunoglobulin V genes," *J. Exp. Med.*, 187:59-70 (1998).
Wilson et al., "MSH2-MSH6 stimulates DNA polymerase eta, suggesting a role for A:T mutations in antibody genes," *J. Exp. Med.*, 201(4):637-645 (2005).
Winter et al. Making Antibodies by Phage Display Technology, *Ann. Rev. Immunol.*, 12:433-455 (1994).
Winter et al., "Dual enigma of somatic hypermutation of immunoglobulin variable genes: targeting and mechanism," *Immunological Reviews*, 162:89-96 (1998).
Wolfe et al., "Beyond the 'Recognition Code': Structures of Two Cys2His2 Zinc Finger/TATA Box Complexes," *Structure*, 9(8):717-723 (2001).
Wu et al., "An Analysis of the Sequences of the Variable Regions of Bence Jones Proteins and Myeloma Light Chains and Their Implications for Antibody Complementarity," *J. Exp. Med.*, 132:211-250 (1970).
Wu et al., "A human follicular lymphoma B cell line hypermutates its functional immunoglobulin genes in vitro," *Eur. J. Immunol.*, 25:3263-3269 (1995).
Wu et al., "The Somatic Hypermutation Activity of Follicular Lymphoma Links to Large Insertions and Deletions of Immunoglobulin Genes," *Scand. J. Immunol.*, 42:52-59 (1995).
Wu et al., "Separation of the DNA Replication, Segregation, and Transcriptional Activation Functions of Epstein-Barr Nuclear Antigen 1," *J. Viral.*, 76(5):2480-2490 (2002).
Wysocki et al., "Somatic origin of T-cell epitopes within antibody variable regions: significance to monoclonal therapy and genesis of systemic autoimmune disease," *Immunological Reviews*, 162:233-246 (1998).
Xie et al., "The structure of a yeast RNA-editing deaminase provides insight into the fold and function of activation-induced deaminase and APOBEC-1," *PNAS*, 101(21):8114-8119 (2004).
Xu et al., "Two monoclonal antibodies to precisely the same epitope of type II collagen select non-crossreactive phage clones by phage display: implications for autoimmunity and molecular mimicry," *Mol. Immunol.*, 41:411-419 (2004).
Yamaguchi-Iwai et al., "Homologous recombination, but not DNA repair, is reduced in vertebrate cells deficient in RAD52," *Mol. Cell Biol.*, 18(11):6430-6435 (1998).
Yang et al., "Activation-Induced Cytidine Deaminase (AID)-Mediated Sequence Diversification Is Transiently Targeted to Newly Integrated DNA Substrates," *JBC Papers in Press*, published Jul. 5, 2007 Manuscript M704231200.
Yang et al., "Targeting of AID-Mediated Sequence Diversification by cis-Acting Determinants," *Advances in Immunol.*, 94:109-125 (2007).
Yates et al., "The Minimal Replicator of Epstein-Barr Virus oriP," *J. Viral.*, 74(10):4512-4522 (2000).
Yelamos et al., "Targeting of non-Ig sequences in place of V segment by somatic hypermutation," *Nature*, 376:225-229 (1995).
Yoshikawa et al., "AID Enzyme-Induced Hypermutation in an Actively Transcribed Gene in Fibroblasts," *Science*, 296(5574):2033-2036 (2002).
Zan et al., "Induction of Ig Somatic Hypermutation and Class Switching in a Human Monoclonal IgM+ IgD+ B Cell Line in Vitro:Definition of the Requirements and Modalities of Hypermutation," *J. Immunol.*, 162:3437-3447 (1999).
Zan et al., "B Cell Receptor Engagement and T Cell Contact Induce bcl-6 Somatic Hypermutation in Human B Cells: Identity with Ig Hypermutation," *J. Immunol.*, 165(2):830-839 (2000).
Zan et al., "The translesion DNA polymerase 0 plays a dominant role in immunoglobulin gene somatic hypermutation," *EMBO J.*, 24:3757-3769 (2005).
Zemlin et al., "Expressed Murine and Human CDR-H3 Intervals of Equal Length Exhibit Distinct Repertoires that Differ in their Amino Acid Composition and Predicted Range.of Structures," *J. Mol. Biol.*, 334:733-749 (2003).
Zeng et al., "DNA polymerase eta is an A-T mutator in somatic hypermutation of immunoglobulin variable genes," *Nat. Immunol.*, 2(6):537-541 (2001).
Zhao et al., "Directed evolution of enzymes and pathways for industrial biocatalysis," *Curr. Op. Biotechnol.*, 13(2):104-110 (2002).
Zhang et al., "Clonal instability of V region hypermutation in the Ramos Burkitt's lymphoma cell line," *Int. Immunol.*, 13(9):1175-1184 (2001).
Zhang et al., "Broadly cross-reactive HIV neutralizing human monoclonal antibody Fab selected by sequential antigen panning of a phage display library," *J. Immunol. Methods*, 283:17-.25 (2003).
Zhang et al., "Identification and Characterization of a New Cross-Reactive Human Immunodeficiency Virus Type 1-Neutralizing Human Monoclonal Antibody," *J. Virology*, 78(17):9233-9242 (2004).
Zhang et al., "The development of anti-CD79 monoclonal antibodies for treatment of B-cell neoplastic disease," *Ther. Immunol.*, 2:191-202 (1995).
Zheng et al., "Immunoglobulin gene hypermutation in germinal centers is independent of the RAG-I V(D)J recombinase," *Immunological Reviews*, 162:133-141 (1998).
Zheng et al., "Intricate targeting of immunoglobulin somatic hypermutation maximizes the efficiency of affinity maturation," *JEM*, 201(9):1467-1478 (2005).
Zhou et al., "Cell cycle regulation of chromatin at an origin of DNA replication," *EMBO J.*, 24(7):1406-1417 (2005).
Zhu et al., "A well-differentiated B cell line is permissive for somatic mutation of a transfected immunoglobuin heavy-chain gene," *PNAS USA*, 92:2810-2814 (1995).
Zou et al., "Subtle differences in antibody responses and hypermutation of λ light chains in mice with a disrupted $_{\chi}$constant region," *Eur. J. Immunol.*, 25:2154-2162 (1995).
International Search Report issued in International Patent Application No. PCT/US08/02397, dated Jun. 16, 2008.
International Search Report issued in International Patent Application No. PCT/US08/02396, dated Jun. 26, 2008.

* cited by examiner

FIG. 8

Native Blasticidin

A. Input Amino Acid Sequence (SEQ ID NO: 2)

```
M A K P L S Q E E S T L I E R A T A T I N S I P I S E
D Y S V A S A A L S S D G R I F T G V N V Y H F T G G
P C A E L V V L G T A A A A A A G N L T C I V A I G N
E N R G I L S P C G R C R Q V L L D L H P G I K A I V
K D S D G Q P T A V G I R E L L P S G Y V W E G X
```

B. Input polynucleotide sequence (SEQ ID NO: 3)

```
1                                                                            80
ATGGCCAAGCCTTTGTCTCAAGAAGAATCCACCCTCATTGAAAGAGCAACGGCTACAATCAACAGCATCCCCATCTCTG
AAGACTACAGCGTCGCCAGCGCAGCTCTCTCTAGCGACGGCCGCATCTTCACTGGTGTCAATGTATATCATTTTACTGG
GGGACCTTGCGCAGAACTCGTGGTGCTGGGCACTGCTGCTGCTGCGGCAGCTGGCAACCTGACTTGTATCGTCGCGATC
GGAAATGAGAACAGGGGCATCTTGAGCCCCTGCGGACGGTGCCGACAGGTTCTTCTCGATCTGCATCCTGGGATCAAAG
CCATAGTGAAGGACAGTGATGGACAGCCGACGGCAGTTGGGATTCGTGAATTGCTGCCCTCTGGTTATGTGTGGGAGGG
CTAA
```

C. Initial analysis of hot spots (35 Hot spots)

```
1                                                                            80
hhhhhhhhHhhhhhhhhhhhhhhhhhhhhhhhhhhhhhhhhhhHhhhhhhHhhHhhhhhHhhHhhhhhhhhhhhhhh
hhhhhHhhhhhhhhhhhhhhhhHhhhhhhhhhhhhhhhhhhhhhhhhhhhhhhhhhhhhhhHhhhhhhhhhhHhhhhh
hhhhhhhhhhhhhhHhhhhhhhhHhhhhHhhhhHhhHhhHhhhhhHhhHhhhHhhHhhhhhhhhHhhhhhhhhhhhhh
hhhhhhhhhHhhhhhHhhhhhhhhHhhhhhhhhhhhhhHhhhhhhhHhhhhhhhhhhhhhHhhhhhhhhhhhhhhhHh
hhhhhhhhhhhhhhhhhhhhhhhhHhhhhhhHhhHhhhhhhhhhhhhhhhhhHhhHhhhhhhHhhhhhhhhhhhhhhHh
hhhh
```

D. Initial analysis of cold spots (60 Cold spots)

```
1                                                                            80
cccCcccccCcccccCcCcccccccccccccccCcCcccccccccCccccccCcccccccccccccccCCcccccCccc
ccCccccccccCccCcccccccccCcCcCccccccCcCccccccccccccccccccCccccccccccccccccccccCC
CcCcccccccccccccCcccccccccccccCCcccccccccccccCccccccCcccccccCcccccccccCcccccccc
ccccccCccccccCCCcccccccCcCCCccccccCccccccCcCccccccccccCccccccccccccccCccccccccC
cccccccccccCcccccccccCcccCccCccCccccccCcccccccccccccccccCCccccccccccccccCcCcCCc
cccc
```

E. Initial analysis of CpGs (21)

```
mmmmmmmmmmmmmmmmmmmmmmmmmmmmmmmmmmmmmmmmmmmmmmmmmMmmmmmmmmmmmmmmmmmmmmmmmmmmmmm
mmmmmmmmmmMmmMmmmmmMmmmmmmmmmmmmmmMmmMmmmMmmmmmmmmmmmmmmmmmmmmmmmmmmmmmmmmmmmmm
mmmmmmmmmMmmmmmmmmMmmmmmmmmmmmmmmmmmmmmmmmmmMmmmmmmmmmmmmmmmmmmmmmmmMmmMmMmmmM
mmmmmmmmmmmmmmmmmmmmmmmmmmmmmmmmMmmmMmmmmmMmmmmmmmmmmmmmMmmmmmmmmmmmmmmmmmmmmmm
mmmmmmmmmmmmmmmmmmmmmmmmmmmMmmMmmmmmmmmmmmmmMmmmmmmmmmmmmmmmmmmmmmmmmmmmmmmmmm
mmmm
```

FIG. 9

Optimization of SHM-resistant Blasticidin

A Amino Acid Sequence (SEQ ID NO: 2)

```
M A K P L S Q E E S T L I E R A T A T I N S I P I S E
D Y S V A S A A L S S D G R I F T G V N V Y H F T G G
P C A E L V V L G T A A A A A A G N L T C I V A I G N
E N R G I L S P C G R C R Q V L L D L H P G I K A I V
K D S D G Q P T A V G I R E L L P S G Y V W E G X
```

B. Output Polynucleotide Sequence SHM resistant (SEQ ID NO: 4)

```
1                                                                             80
ATGGCCAAGCCCCTCTCTCAAGAGGAGTCCACCCTCATTGAGAGAGCCACTGCCACAATCAACTCCATCCCCATCTCTG
AGGACTACTCCGTCGCCTCCGCCGCCCTCTCGTCAGACGGGAGAATCTTCACTGGGGTCAATGTCTATCATTTACTGG
GGGGCCCTGTGCCGAGCTCGTCGTCCTCGGGACAGCCGCCGCCGCCGCCGGGAACCTCACTTGTATCGTCGCCATA
GGGAATGAGAACAGGGGGATCCTCTCCCCCTGCGGGAGATGCCGACAGGTCCTCCTCGACCTCCACCCCGGGATCAAAG
CCATAGTCAAGGACTCAGACGGGCAGCCCACAGCCGTCGGGATTCGAGAGCTCCTCCCCTCTGGGTATGTCTGGGAGGG
GTAA
```

C. Analysis of hot spots (20 Hot spots)

```
hhhhhhhHhhhhhhhhhhhhhhhhhhhhhhhhhhhhhhhhhhhhhHhhhhhhHhhhhhhhhHhhhhhhhhhhhhhhhhhh
hhhhHhhhhhhhhhhhhhhhhhhhhhhhhhhhhhhhhhhhhhhhhhhhhhhhhhhhhhhhhhhhhhhhhhhhhHhhhhhh
hhhhhhhhHhhhhhHhhhhhhhhhhhhhhhhhhHhhhhhhhhhhhhhhhhhhhhhHhhhhhhhhHhhhhhhhhhhhhhhh
hhhhhhhhHhhhhhhhhhhhhhhhhhhhhhhhhhhhhhHhhhhhhhhhhhhhhhhhhhhhhhhhhhhhhhhhhhhhhHhh
hhhhhhhhhhhhhhhhhhhhHhhhHhhhhhhHhhhhhhhhhhhhhhhHhhhhhhhhhhhhhhHhhhhhhhhhhhhhhhHh
hhhh
```

D. Analysis of cold spots (113 Cold spots)

```
ccCCcccccCCCcCcCcCcccccCccCcCcccccCcCcccccCcCcCcCcccccCcccccccccccCcccccCCcccccCccccC
ccCcccccCcccCcccCcCccccCccCCcCcCccCcccCcccCcCccccccccccccccCCcCccccccCcccccccccccccccCC
CCCCCccccccCccCccCccCccCccCccCcCccccCccCccCccCccCccCccCccCccccccCcccccccccccCccCcccccc
CccccccCcccccccCCcccccccCcCcCCcccccCcCcccccCccCcccccCccCccCccCccCccccCCccCcccccccccC
cccccCccccccCcCccccCccCCccccCCcccccccCccCccCcccccccCcCccCccCcCCcCcccCccccccCccccCcCcCCc
cccc
```

E. Analysis of CpGs (26)

```
mmmmmmmmmmmmmmmmmmmmmmmmmmmmmmmmmmmmmmmmmmmmmmmmmmmmmmmmmmmmmmmmmmmmmmmmmmmmmmmm
mmmmmmmmmmMmmMmmmmmMmmMmmmmmmMmmmmmMmmmmmmmmmmmmmmmmmmmmmmmmmmmmmmmmmmmmmmmmmmmm
mmmmmmmmmmmmMmmmmmMmmMmmmmmmmmmmmmmmmMmmMmmMmmMmmMmmMmmmmmmmmmmmmmmmmmmMmmMmmmmmmm
mmmmmmmmmmmmmmmmmmmmmmmmmmmmmmmmMmmmmmmmmMmmmmmmmmmmmmmMmmmmmmmmmmmMmmmmmmmmmmm
mmmmmmmmmmmmmmmmmmMmmmmmmmmmmmmmMmmMmmmmmMmmmmmmmmmmmmmmmmmmmmmmmmmmmmmmmmmmmmmm
mmmm
```

FIG. 10

Optimization of SHM-susceptible Blasticidin

A. Amino Acid Sequence (SEQ ID NO: 2)

M A K P L S Q E E S T L I E R A T A T I N S I P I S E
D Y S V A S A A L S S D G R I F T G V N V Y H F T G G
P C A E L V V L G T A A A A A G N L T C I V A I G N
E N R G I L S P C G R C R Q V L L D L H P G I K A I V
K D S D G Q P T A V G I R E L L P S G Y V W E G X

B. Output Polynucleotide Sequence SHM Susceptible (SEQ ID NO: 5)

ATGGCTAAACCTCTTAGCCAGGAAGAAAGTACCTTGATTGAACGTGCAACTGCTACAATCAACAGCATACCCATATCTG
AAGACTACTCTGTTGCCAGTGCAGCTTTAAGTTCAGACGGTAGGATTTTTACAGGTGTGAATGTTTACCACTTTACTGG
GGGACCTTGTGCAGAGTTGGTAGTACTAGGTACAGCTGCAGCTGCAGCAGCTGGCAACCTAACCTGTATTGTAGCAATC
GGTAATGAAAACAGGGGCATACTAAGCCCCTGCGGTAGATGCAGGCAAGTACTGTTAGATCTGCATCCTGGCATCAAAG
CAATAGTTAAGGACAGTGATGGGCAGCCAACTGCAGTTGGTATTAGGGAACTACTGCCCTCTGGTTATGTATGGGAGGG
CTAA

C. Analysis of hot spots (69 Hot spots)

hhHhhhhHhhhhhhhhHhhhhhhhhhhhhHhHhhhhhhhhhhhhHhhHhhHhhHhhhhhhHhhHhhhHhhhhhhhhhhh
hhhhhHhhhhhHhhHhhhhhhHhhHhhhhhhhHhhhhhhhhHhhhhhhhhhhHhhhhhhhhHhhhHhhhhhHhhhhhh
hhhhhhhhhHhhhhhHhhhhHhhhHhHhhhhhhHhHhhhHhhhHhhhHhhhhHhhHhhhhHhhhHhhhHhhhHhhhhhh
HhhhhhhhhHhhhhhhHhhhhHhhhhhHhhhhhhhhhhHhhhhHhHhhHhhhhhhhhhhHhhhhhhhhHhhhhhhhhHh
hhhhHhhhhhhhhhhhhhhhhhhHhhhHhhhhHhhHhhhHhhhhhHhhhHhhhhhhhhhHhhhhhHhhhhhhhhhhhHh
hhhh D. Analysis of cold spots (34 Cold spots)

ccCcccccccCcccccCccccccccccccccccccccccccccccccccccccccccccccccccccccCccccccccc
ccCccccCcccccccCccccccccccccccccccCccccccccccccccccccccccccccccccccccccccccccCC
CcCcccccccccccCccccccccccccccccccccccccccccccccccccCcccccccccccccccccccccccccc
cccccccccccccCCCcccccccccccCCCccccccccccccccccCcccccccccccccccccccccCcccccccccc
ccccccccccccCcccccccccCCccccCcccccccccccccccCccccccccccCCcCcccccccccccccCcCcCCc
cccc E. Analysis of CpGs (4)

mmmmmmmmmmmmmmmmmmmmmmmmmmmmmmmmmmmmmmmmmmMmmmmmmmmmmmmmmmmmmmmmmmmmmmmmmmmmmm
mmmmmmmmmmmmmmmmmmmmmmmmmmmmmmmmmmmmmMmmmmmmmmmmmmmmmmmmmmmmmmmmmmmmmmmmmmmmmmm
mmmmmmmmmmmmmmmmmmmmmmmmmmmmmmmmmmmmmmmmmmmmmmmmmmmmmmmmmmmmmmmmmmmmmmmmmmmmmmM
mmmmmmmmmmmmmmmmmmmmmmmmmmmmmmmmMmmmmmmmmmmmmmmmmmmmmmmmmmmmmmmmmmmmmmmmmmmmmmm
mmmmmmmmmmmmmmmmmmmmmmmmmmmmmmmmmmmmmmmmmmmmmmmmmmmmmmmmmmmmmmmmmmmmmmmmmmmmmmm
mmmm

FIG. 11

Sequence Comparison of Mammalian Activation-Induced Cytidine Deaminases

| | | |
|---|---|---|
| *Homo sapiens* / 1-198 | MDSLLMNRRKFLYQFKNVRWAKGRRETYLCYVVKRRDSATSFSLDFGYLRN | 51 |
| *Mus musculus* / 1-198 | MDSLLMKQKKFLYHFKNVRWAKGRHETYLCYVVKRRDSATSFSLDFGYLRN | 51 |
| *Canis familiaris* / 1-198 | MDSLLMKQKKFLYHFKNVRWAKGRHETYLCYVVKRRDSATSFSLDFGYLRN | 51 |
| *Rattus norv* / 1-199 | MDSLLMKQKKFLYHFKNVRWAKGRHETYLCYVVKRRDSATSFSLDFGYLRN | 51 |
| *Pan troglodytes* / 1-199 | MDSLLMNRRKFLYQFKNVRWAKGRRETYLCYVVKRRDSATSFSLDFGYLRN | 51 |
| *Homo sapiens* / 1-198 | KNGCHVELLFLRYISDWDLDPGRCYRVTWFTSWSPCYDCARHVADFLRGNP | 102 |
| *Mus musculus* / 1-198 | KSGCHVELLFLRYISDWDLDPGRCYRVTWFTSWSPCYDCARHVAEFLRWNP | 102 |
| *Canis familiaris* / 1-198 | KSGCHVELLFLRYISDWDLDPGRCYRVTWFTSWSPCYDCARHVADFLRGYP | 102 |
| *Rattus norv* / 1-199 | KSGCHVELLFLRYISDWDLDPGRCYRVTWFTSWSPCYDCARHVAEFLRWNP | 102 |
| *Pan troglodytes* / 1-199 | KNGCHVELLFLRYISDWDLDPGRCYRVTWFTSWSPCYDCARHVADFLRGNP | 102 |
| *Homo sapiens* / 1-198 | NLSLRIFTARLYFCEDRKAEPEGLRRLHRAGVQIVIMTFKDYFYCWNTFVE | 153 |
| *Mus musculus* / 1-198 | NLSLRIFTARLYFCEDRKAEPEGLRRLHRAGVQIGIMTFKDYFYCWNTFVE | 153 |
| *Canis familiaris* / 1-198 | NLSLRIFAARLYFCEDRKAEPEGLRRLHRAGVQIAIMTFKDYFYCWNTFVE | 153 |
| *Rattus norv* / 1-199 | NLSLRIFTARLYFCEDRKAEPEGLRRLHRAGVQIGIMTFKDYFYCWNTFVE | 153 |
| *Pan troglodytes* / 1-199 | NLSLRIFTARLYFCEDRKAEPEGLRRLHRAGVQIAIMTFKDYFYCWNTFVE | 153 |
| *Homo sapiens* / 1-198 | NHERTFKAWEGLHENSVRLSRQLRRILLPLYEVDDLRDAFRTLGL | 198 |
| *Mus musculus* / 1-198 | NRERTFKAWEGLHENSVRLSRQLRRILLPLYEVDDLRDAFRMLGL | 198 |
| *Canis familiaris* / 1-198 | NRERTFKAWEGLHENSVRLSRQLRRILLPLYEVDDLRDAFRTLGL | 198 |
| *Rattus norv* / 1-199 | NHERTFKAWEGLHENSVRLSRQLRRILLPLYEVDDLRDAFRILGL | 198 |
| *Pan troglodytes* / 1-199 | NHERTFKAWEGLHENSVRLSRQLRRILLPLYEVDDLRDAFRTLGL | 198 |

| | |
|---|---|
| *Homo sapiens* | SEQ ID NO: 6 |
| *Mus musculus* | SEQ ID NO: 7 |
| *Canis familiaris* | SEQ ID NO: 8 |
| *Rattus norv* | SEQ ID NO: 9 |
| *Pan troglodytes* | SEQ ID NO: 10 |

FIG. 12

Native AID (Canine)

A Input Amino Acid Sequence (SEQ ID NO: 11)

MDSLLMKQRKFLYHFKNVRWAKGRHETYLCYVVKRRDSATSFSLDFGHLRNKSGCHVELLFLRYISDWDLDPGRCYRVTWFTSWSPCYDCARHVADFLRGYPNLSLR
IFAARLYFCEDRKAEPEGLRRLHRAGVQIAIMTFKDYFYCWNTFVENREKTFKAWEGLHENSVRLSRQLRRILLPLYEVDDLRDAFRTLGL

B Input DNA Sequence: (SEQ ID NO: 12)

ATGGACAGTTTACTGATGAAACAGCGCAAATTCTTATATCACTTTAAGAACGTCCGCTGGGCCAAAGGTAGACATGAGACCTACCTGTGTTATGTTGTGAAGAGGCG
GGATAGTGCAACATCTTTTTCCCTGGACTTCGGCCACCTCCGTAATAAGTCCGGGTGCCACGTGGAACTGCTGTTCTTGCGTTATATTAGCGACTGGGACCTGGACC
CAGGGCGGTGTTATCGGGTGACTTGGTTTACCTCTTGGTCCCCCTGCTATGATTGTGCACGCCATGTGGCTGATTTTCTTCGCGGCTATCCAAATCTAAGTCTACGT
ATCTTTGCAGCACGGTTATACTTTTGTGAGGATCGCAAGGCAGAGCCCGAGGGTCTGCGGCGCCTACATAGGGCTGGGGTCCAGATCGCTATTATGACCTTCAAGGA
TTACTTTTATTGCTGGAATACATTTGTCGAGAACAGGGAGAAAACCTTCAAGGCCTGGGAGGGCCTGCATGAAAACTCCGTGAGACTGAGCAGACAACTGCGAAGAA
TCCTGTTGCCTCTGTATGAGGTCGACGACCTAAGGGACGCTTTCCGCACCCTAGGCTTA

C. Analysis of hot spots (41 Hot spots)

hhhhhhHhhhhHhhhhhhhhhHhhhhhhhhhhhhhhhhhhhhhhhhhhhhhhhhhhhhhhhhhhhhhhhhhHhhhhhhhhhhhhhhHhhhhhHhhhhHhhhhhhhhhhhhh
hhhhhhHhhHhhhhhhhhhhhhhhhhhhhhhhhhhhhhhhhhhhhhhhhhHhhhhhhhhhHhhHhhHhhhhhhhhhhhhhhhhhhhhhhhhhhhhhhhhhhhhhhhh
hhhhhhhhHhhhhhhhhhhhhhhHhhhHhhhhhhhhhhhhhhhHhhhhhhhhhHhhhhhhhhhhhHhhhhhhhhhhhhhhhHhhhhhhhhhhhhhhhhhhhhhhhh
hhhhhHhhHhhhhHhhhhHhhhhhhhhhhhhhhhhhhhhHhhhhHhhhhhhhhhhhhhhhhhhhHhhhhhhHhhhhhhhhhhhhhhhhhhhhhhhhhhhhhhhhhhhhh
hHhhhhhhhhHhhhhhhhHhhhhhhhhhhhhhHhhhhhhhhhhHhhhhhhhhhhhhhhhhhhhhhhhhhhHhhhhhhhHhhhhhhhhhhhhhhhHhhhhhhHhhhhhhhhhh
hhhHhhHhhhhhHhhhhhhhhhhhhhhhhhhhhhhhhhhhhhhhhhhhhHhhhhh D. Analysis of cold spots (79 Cold spots)

cccCccccccccccccccccccccccccccccccccccccccccccccCcccccccCCcccccccccccCcccccCcCccccccccccccccccccccccccCcCccC
ccccccccccccccccccccCcccccCccccccCCccccCcccccccccccCccccCcccCcccccccccccccccccccccccccccccccccccccCccccCcCccccccCcCc
ccCCccccccccccccCccccCccccccccccccCcccccCcCCccccccccccccccccccccCccccccCcccccccccccccccCccccccccccccccccCccccccc
ccccccccccccccccccccccccccccCccccccccccCccccCcCCcccCcCcCccccccCcccCccccccccccCCccccCCcCcccccccccccccccccCccccccccccc
cccccccccccccccccccccccccccCcccCcccccccCcCcccccccccccccccCCcccCcCcCCcccccccccccccccCccccccCcCccccCcccccCcccccccccccccccc
cccccccCcCccccccccCcccCccCcccCccccccCcCcccccccccccccCcccccCccccc E. Analysis of CpGs (29)

mmmmmmmmmmmmmmmmmmmmmmmmmmmmmmmMmmmmmmmmmmmmmmmmmmmmmmmmmmmmmmmmmMmmmMmmmmmmmmmmmmmmmmmmmmmmmmmmmmmmmmmmmmmmmmmMm
mmmmmmmmmmmmmmmmmmmmmmmmmmmmmmmmmmmmmMmmmmmmmmmmmMmmmmmmmmmmmMmmmmmmmmmMmmmmmmmmmmmmmmmmmmmmmmMmmmmmmmmmmMmmmmmmmmmmmmmmmmmm
mmmmmMmmmmmmmmmMmmmmmmmmmmmmmmmmmmmmmmmmmmmmmmmmmmmmmmmmmmmmmmmmmMmmmmmmmmmmmmmmmmmmmmmmmmMmMmmmmmmmmmmmmmmmmmmmmmmmMmm
mmmmmmmmmmmmmMmmmmmmmmmmmmmmmmmmmmmmMmmmmmmmmmmmmmmmMmmmmmmmmmmMmmMmmmmmmmmmmmmmmmmmmmmmmmmmmmmMmmmmmmmmmmmmmmmmmmmmmmm
mmmmmmmmmmmmmmmmmmmmmmmmmmmmmmmmmMmmmmmmmmmmmmmmmmmmmmmmmmmmmmmmmmmmmmmmmmmmmmmmmmmmmmmmmmmMmmmmmmmmmmmmmmmmmmmmMmmmmmmm
mmmmmmmmmmmmmmmmmmmmmmmmmmmmmmmMmmMmmmmmmmmmmmmMmmmmmmmMmmmmmmmmmmmmmmmm

FIG. 13

Hot AID (Canine)

A Output Polynucleotide Sequence: SHM Susceptible (SEQ ID NO: 13)

ATGGACAGTTTACTGATGAAACAGCGCAAGTTCCTGTACCACTTTAAGAATGTTCGGTGGGCAAAAGGTAGGCATGAAACCTACCTGTGTTATGTAGTTAAAAGGCG
GGATAGTGCAACAAGCTTTAGCTTGGACTTCGGGCACCTTCGTAACAAAAGCGGCTGCCATGTTGAACTGCTGTTCTTGAGGTACATTAGCGACTGGGACCTGGACC
CAGGTAGATGCTACCGAGTAACTTGGTTTACTAGTTGGAGCCCATGCTATGATTGTGCAAGGCATGTAGCAGATTTTCTTCGCGGCTATCCAAACCTAAGCCTTAGA
ATCTTTGCAGCAAGGTTGTACTTTTGTGAGGATCGCAAGGCAGAGCCCGAGGGGCTACGCCGGCTGCATAGGGCTGGAGTACAAATAGCTATTATGACCTTCAAGGA
TTACTTTTACTGTTGGAATACATTTGTTGAGAACAGGGAGAAAACCTTCAAAGCCTGGGAGGGTTTGCATGAAAACTCAGTAAGGTTAAGCAGGCAACTGCGAAGAA
TACTACTACCTCTGTATGAGGTTGACGACCTAAGGGATGCCTTCCGTACCCTAGGCTTA

B. Analysis of hot spots (84 Hot spots)

hhhhhhHhhhHhhhhhhhhhHhhhhhhhhhHhhhhhHhHhhhhhhhhhhhhhHhhhhhhhhhHhhhhhhhHhhhHhhhhhhHhhhhHhhhhhHhhhhHhhHhhhhhhhhhhh
hhhhhhHhhHhhhHhhhhhhHhhhhhhhhhhhhhHhhhhhhhhhhHhhhhhhhhHhhHhhhhHhhhhHhhHhhHhhhhhhhhhHhHhhhhhhhhhhhhhhhhhhhhhhhh
hhHhhhhhhHhhHhhhhhHhhHhhhhhHhhhHhhhhHhhhhhHhhhhhHhhhhhhhhhhHhhhhHhhhhHhhHhhhhhhhhhhhhhhhHhhhhhhhhHhhhhhHhhhhhhhh
hhhhhHhhHhhhhhHhhHhHhhhhhhhhhhhhhhhhhhhhHhhhhHhhhhhhhhHhhhhhhhhHhhHhhhhhhHhhhhhHhHhhhhhhHhhhhhhhhhhhhhhhhhhhhh
hHhhhhhhHhhHhhhhhhhhHhhhhhhHhhhhhhHhhhhhhhhhhhHhhhhhhhhHhhhhhhhhHhhhhHhhhhhhhHhhhhHhhhhHhhhhHhhhhHhhHhhhhhhhhhhh
HhhHhhHhhhhhhHhhhhhhHhhhhhhhhhhhhhhhhhhHhhhhhhhhHhhhhhhHhhhhh C. Analysis of cold spots (56 Cold spots)

cccCcccccccccccccccccccccccccccccccccccccccccccccccccCCccccccccccCcccccccccccccccccccccccccccccccCccC
ccccccccccccccccccccccccCccccccCCccccccccccccccccccccccCccccCcccccccccccccccccccccccCcccccccccccccCcccCcCccccccCcCc
cccccccccccccccCcccccccccccccccccccccccCcCCcccccccccccccccccccccCcccccccccccccccccccccccccCcccccccccccccccCccccccc
ccccccccccccccccccccccccccCcccccccccccCcccCcCCccCcCCCccccccCccCcccccccccCCcccccCccccccccccccccccccccCcccccccccccc
ccccccccccccccccccccccccccccCcccccccCcCcccccccccccccccCcccCcCcCccccccccccccccCcccccccccccccccCcccccccccccccccc
ccccccccCcccccccCccccccCccCcccccccCcccccCccccccccccCcccccCccccc D. Analysis of CpGs (17)

mmmmmmmmmmmmmmmmmmmmmmmmmMmmmmmmmmmmmmmmmmmmmmmmmmmmmMmmmmmmmmmmmmmmmmmmmmmmmmmmmmmmmmmmmmmmmmmmmmmmMm
mmmmmmmmmmmmmmmmmmmmmmmmmmmmmmMmmmmmmmmmMmmmmmmmmmmMmmmmmmmmmmmmmmmmmmmmmmmmmmmmmmmmmMmmmmmmmmmmmmmmm
mmmmmmmmmmmmmMmmmmmmmmmmmmmmmmmmmmmmmmmmmmmmmmmmmmmmmmmmmmmmmmmmmmmmmmmmmmmmmMmMmmmmmmmmmmmmmmmmmmmmmm
mmmmmmmmmmmmmmmmmmmmmmmmmmmmmMmmmmmmmmmmmmmMmmmmmmmmmmMmmMmmmmmmmmmmmmmmmmmmmmmmmmmmmmmmmmmmmmmmmmmmmm
mmmmmmmmmmmmmmmmmmmmmmmmmmmmmmmmmmmmmmmmmmmmmmmmmmmmmmmmmmmmmmmmmmmmmmmmmmmmmmmmmmmmmmmmmmmmmmmMmmmmmm
mmmmmmmmmmmmmmmmmmmmmmmmmmMmmmmmmmmmmmmmmmmmmmMmmmmmmmmmmmmmmmmmm

FIG. 14
Cold AID (Canine)

A Output Polynucleotide Sequence: SHM Resistant (SEQ ID NO: 14)

ATGGACTCCCTCCTCATGAAACAGAGGAAGTTTCTCTACCATTTCAAAAATGTCAGGTGGGCCAAGGGGAGACATGAGACTTATCTCTGTTATGTCGTCAAGAGACG
GGACTCAGCCACGAGTTTCTCCCTCGACTTTGGGCATCTCAGAAACAAGTCGGGGTGCCATGTCGAGCTCCTCTTCCTCAGATACATCTCAGACTGGGACCTCGACC
CCGGGAGGTGCTATAGAGTCACCTGGTTTACCTCCTGGTCCCCCTGCTACGACTGTGCCCGACATGTCGCCGACTTCCTCAGGGGGTACCCCAATCTCTCCCTCAGA
ATATTCGCCGCCAGACTCTATTTCTGTGAGGACAGGAAGGCCGAGCCCGAGGGGCTCAGGAGACTCCACAGGGCCGGGGTCCAGATCGCCATTATGACATTCAAAGA
CTACTTCTACTGCTGGAACACATTTGTCGAGAATAGGGAGAAGACTTTTAAGGCCTGGGAGGGGCTCCATGAGAATTCGGTCAGACTCTCTCGCCAACTCAGGAGAA
TTCTCCTCCCCCTCTATGAGGTCGACGACCTCAGGGACGCCTTCAGGACCCTCGGGCTC

B. Analysis of hot spots (27 Hot spots)

hhhhhhhhhhhhhhhhhhhHhhhhhhhhHhhhhhhhHhhhhhhhhhhhhhhhhhhhhhhhhhhhhhhhhhhhhhhhhhhhhhhhhhhhHhhhhhhhhhhhhhhhhhhh
hhhhhhHhhhhhhHhhhhhhhhhhhhhhhhhhHhhhhhhhhhHhhhhhhhhhhHhhhhhhhhhHhhhhhhhhhhhhhhhHhhhhhhhhhhhhhhhhhhhhhhhh
hhhhhhhhHhhhhhhhhhhhhhhHhhhHhhhhhhhhhhhhhhhHhhhhhhhhhhHhhhhhhhhhhhhhhhhhhhhhhhhhhhHhHhhhhhhhhhhhhhhhhhhh
hhhhhhhhhhhhhhhhhhhhhhhhhhhhhhhhhhhhhhhhhhhHhhhhhhhhHhhhhhhhhhhhhhhhhhhhhhhhhhhhhhhhhhhhhhhhhhhhhhhhhhhhh
hHhhhhhHhhHhhhhhHhhhhhhhhhhhhhhhhhhhhhhhhhhhhhhhhhhhhhhhhhhhhHhhhhhhhhhhhhhhhhhhhhhhhhhhhhhhhhHhhhhhhhhhh
hhhhhhhhhhhhhhhhhhhhhhhhhhhhhhhhhhhhhhhhhhhhhhhhhhhhhhHhhhh

C. Analysis of cold spots (147 Cold spots)

cccCcCcCcCccCccccccccccCcccccccccCcccccccccccccccccCccccccCCCccccCCcCcCccccCcCccccccCccccccccCccCccccCcCccC
cCcCcccCccccCcccccCcCcCccCcccccCCccccCccccccccccCccCCcccCccccCccCccCccCcccccCccccccccccCcccCcccCcCccCccCcCC
ccCcCccccccccccCcCcccccccccccccCcccccCcCCCccccccccCcccccCCccCccccCccCccCcccccCcccCCCccccCCcccccCcCcCcCccccc
ccccccCccCcccCcCcccccccccccCccCcccccccCCccCcCCccCcCCCcCccccCcCcCccccccCCCccCCcCccccccccCcccccccCcccccccccCc
cccccccccccccccccccccccccCccCccccccCcCccccCccccccccCCcccCcCcCCCcCcccccCccccccccCcccCcCcCcCccCccccCccccCcccc
ccCccCcCCCcCcccccCccCccCccCccCcccCcCccCcccccccCcCcCccCCcCcc

D. Analysis of CpGs (25)

mmmmmmmmmmmmmmmmmmmmmmmmmmmmmmmmmmmmmmmmmmmmmmmmmmmmmmmmmmmmmmmmmmmmmmmmmmmmmmmmmmmmmmmmmmmmmMmmmmmmmmmMm
mmmmmmmmmmmMmmmmmmmmmmmmMmmmmmmmmmmmmmmmmmmmmmmmmMmmmmmmmmmmmMmmmmmmmmmmmmmmmmmmmmmmmmmmmmmmmmmmmmmmmmmMmmmm
mMmmmmmmmmmmmmmmmmmmmmmmmmmmmmmmmmmmmmmmmmmmmmmmMmmmmmmmmmMmmmmmmmMmmMmmmmmmmmmmmmmmmmmmmmmmmmmmmmmmmmmmmm
mmmmmMmmMmmmmmmmmmmmmmmmmmmmmmmmmmmmmmmmmMmmmmmMmmmmmmmmmmmmmmmmmmmmmmmmmMmmmmmmmmmmMmmmmmmmmmmmmmmmmmmmm
mmmmmmmmmmmmmmmmmmmmmmmmmmmMmmmmmmmmmmmmmmmmmmmmmmmmmmmmmmmmmmmmmmmmmmmmmmmmMmmmmmmmmmmmmMmmmmmmmmmmmmmm
mmmmmmmmmmmmmmmmmmmmmmMmmMmmmmmmmmmmMmmmmmmmmmmmmmMmmmmmm

FIG. 15

Genomic Mouse, Human, Dog and Cold Canine AID Sequences

| | |
|---|---|
| *C. familiaris* | ATGGACAGCCTCCTGATGAAGCAGAGGAAGTTTCTTTACCATTTCAAGAATGTCCGCTGGGCGAAGGGTCGCCATGAGACTTACTT |
| Cold *C. familiaris* | ATGGACAGCCTCCTGATGAAGCAGAGGAAGTTTCTTTACCATTTCAAGAATGTCCGCTGGGCCAAGGGGAGACATGAGACTTACTT |
| *Homo sapiens* | ATGGACAGCCTCTTGATGAACCGGAGGAAGTTTCTTTACCAATTCAAAAATGTCCGCTGGGCTAAGGGTCGCCGTGAGACCTACCT |
| *Mus musculus* mRNA | ATGGACAGCCTTCTGATGAAGCAAAAGAAGTTTCTTTACCATTTCAAAAATGTCCGCTGGGCCAAGGGACGCCATGAGACCTACCT |
| | |
| *Canis familiaris* | GTGCTACGTGGTGAAGCGGCGGGATAGTGCCACCTCCTTTTCTCTGGACTTTGGTCACCTTCGAAACAAGTCGGGCTGCCACGTGG |
| Cold *C. familiaris* | GTGCTATGTGGTCAAGAGAAGGGATAGTGCCACCTCCTTTTCTCTGGACTTTGGTCACTTGAGGAATAAGTCGGGCTGTCATGTCG |
| *Homo sapiens* | GTGCTACGTAGTGAAGAGGCGTGACAGTGCTACATCCTTTTCACTGGACTTTGGTTATCTTCGCAATAAGAACGGCTGCCACGTGG |
| *Mus musculus* mRNA | CTGCTACGTGGTGAAGAGGAGAGATAGTGCCACCTCCTGCTCACTGGACTTCGGCCACCTTCGCAACAAGTCTGGCTGCCACGTGG |
| | |
| *Canis familiaris* | AGCTGCTCTTCCTCCGCTACATCTCCGACTGGGACCTGGACCCCGGCCGGTGCTACCGCGTCACCTGGTTCACGTCCTGGAGCCCC |
| Cold *C. familiaris* | AGCTGCTCTTCCTCCGCTACATCTCCGACTGGGACCTGGACCCCGGGAGATGCTATAGAGTCACCTGGTTCACGTCCTGGAGCCCC |
| *Homo sapiens* | AATTGCTCTTCCTCCGCTACATCTCGGACTGGGACCTAGACCCTGGCCGCTGCTACCGCGTCACCTGGTTCACCTCCTGGAGCCCC |
| *Mus musculus* mRNA | AATTGTTGTTCCTACGCTACATCTCAGACTGGGACCTGGACCCGGGCCGGTGTTACCGCGTCACCTGGTTCACCTCCTGGAGCCCG |
| | |
| *Canis familiaris* | TGCTACGACTGCGCGCGGCACGTGGCGGACTTCCTGCGCGGGTACCCCAACCTCAGCCTCAGGATCTTCGCCGCGCGCCTCTACTT |
| Cold *C. familiaris* | TGCTACGACTGCGCCAGACATGTCGCCGACTTCCTGAGGGGGTATCCCAACCTCAGCCTCAGGATCTTCGCCGCCCGTCTCTACTT |
| *Homo sapiens* | TGCTACGACTGTGCCCGACATGTGGCCGACTTTCTGCGAGGGAACCCCAACCTCAGTCTGAGGATCTTCACCGCGCGCCTCTACTT |
| *Mus musculus* mRNA | TGCTATGACTGTGCCCGGCACGTGGCTGAGTTTCTGAGATGGAACCCTAACCTCAGCCTGAGGATTTTCACCGCGCGCCTCTACTT |
| | |
| *Canis familiaris* | CTGCGAGGACCGCAAGGCGGAGCCCGAGGGGCTGCGGCGGCTGCACCGGGCGGGCGTCCAGATCGCCATCATGACCTTCAAGGATT |
| Cold *C. familiaris* | CTGCGAGGACCGTAAGGCCGAGCCCGAGGGGCTGAGGAGACTCCACAGGGCCGGAGTCCAGATCGCCATCATGACCTTCAAGGATT |
| *Homo sapiens* | CTGTGAGGACCGCAAGGCTGAGCCCGAGGGGCTGCGGCGGCTGCACCGCGCCGGGGTGCAAATAGCCATCATGACCTTCAAAGATT |
| *Mus musculus* mRNA | CTGTGAAGACCGCAAGGCTGAGCCTGAGGGGCTGCGGAGACTGCACCGCGCTGGGGTCCAGATCGGGATCATGACCTTCAAAGACT |
| | |
| *Canis familiaris* | ATTTTTATTGCTGGAATACTTTTGTGGAAAATCGTGAAAAAACTTTCAAAGCCTGGGAGGGGTTGCACGAAAATTCCGTTCGACTA |
| Cold *C. familiaris* | ATTTTTATTGCTGGAATACTTTTGTGGAGAATAGGGAAAAAACTTTCAAAGCCTGGGAGGGGCTCCATGAGAATTCTGTCAGACTC |
| *Homo sapiens* | ATTTTTACTGCTGGAATACTTTTGTAGAAAACCATGAAAGAACTTTCAAAGCCTGGGAAGGGCTGCATGAAAATTCAGTTCGTCTC |
| *Mus musculus* mRNA | ATTTTTACTGCTGGAATACATTTGTAGAAAATCGTGAAAGAACTTTCAAAGCCTGGGAAGGGCTACATGAAAATTCTGTCCGGCTA |
| | |
| *Canis familiaris* | TCCAGACAGCTTCGACGCATTCTTTTGCCCCTGTATGAGGTTGATGACTTACGAGATGCATTTCGTACTTTGGGACTTTGA |
| Cold *C. familiaris* | AGTAGACAGCTCAGGAGAATTCTTTTGCCCCTGTATGAGGTTGATGACCTTAGAGACGCATTTAGGACACTGGGACTTTGA |
| *Homo sapiens* | TCCAGACAGCTTCGACGCATCCTTTTGCCCCTGTATGAGGTTGATGACTTACGAGACGCATTTCGTACTTTGGGACTTTGA |
| *Mus musculus* mRNA | ACCAGACAACTTCGACGCATCCTTTTGCCCTTGTACGAAGTCGATGACTTGCGAGATGCATTTCGTATGTTGGGATTTTGA |

FIGURE 16
Analysis of AID activity
A
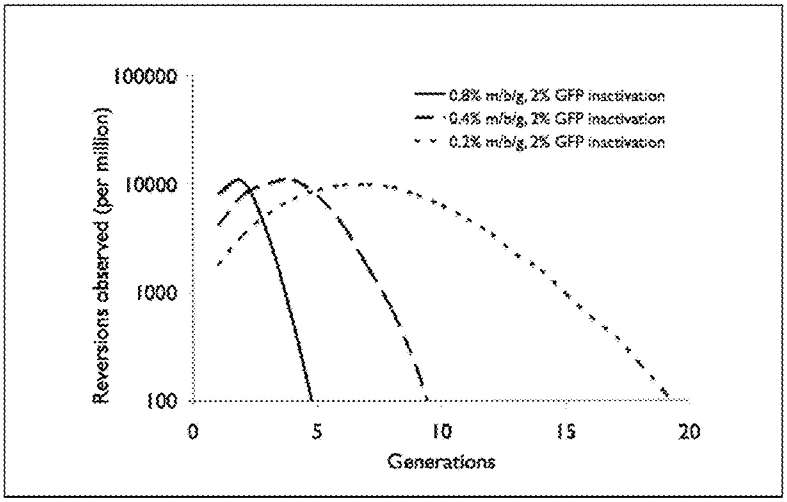
B
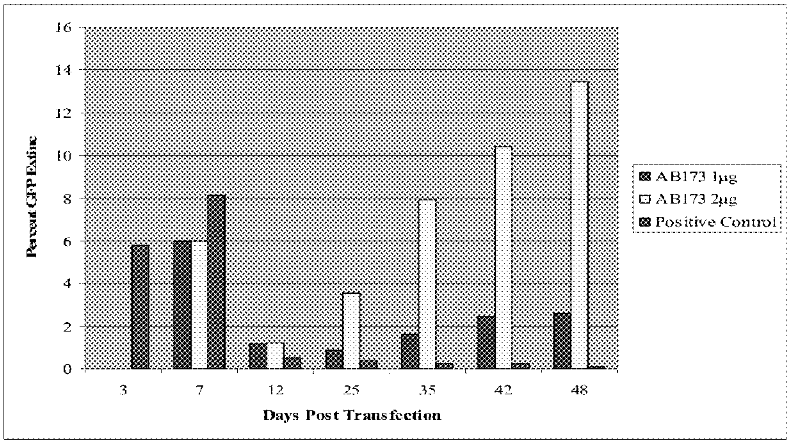
C
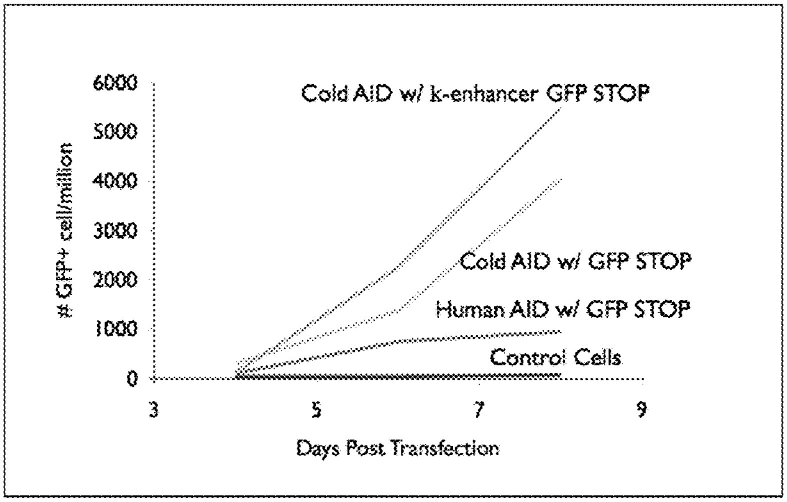

FIG. 17
A. Expression Vector Format 1
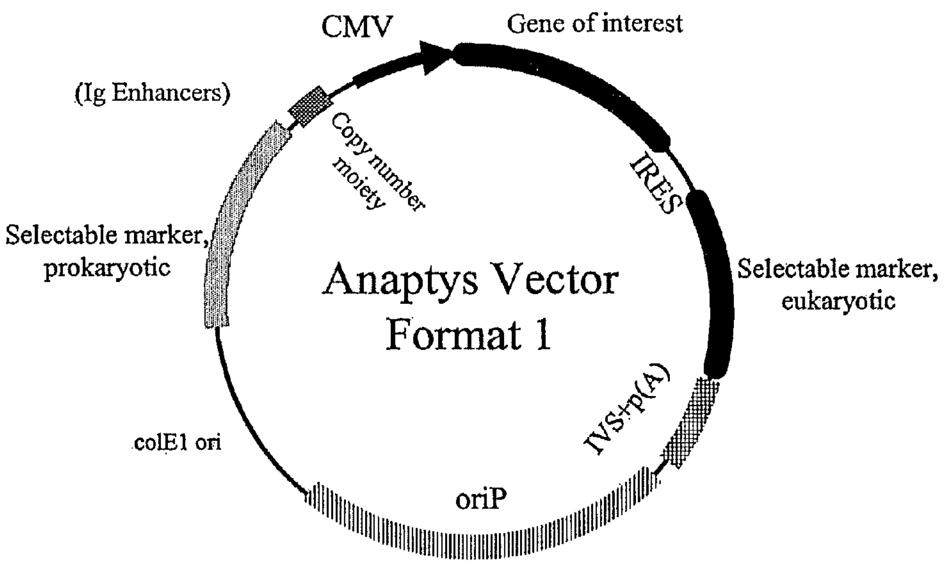
B. Expression Vector Format 2
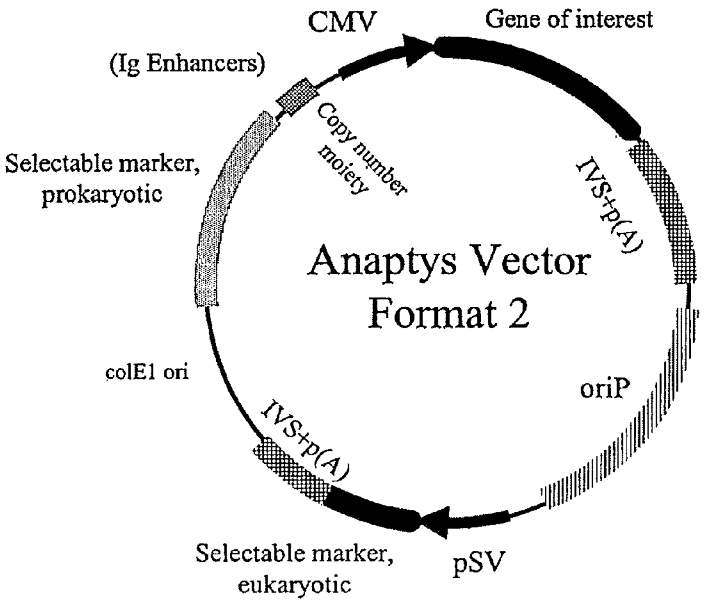

FIGURE 18
A. Expression Vector Format 3
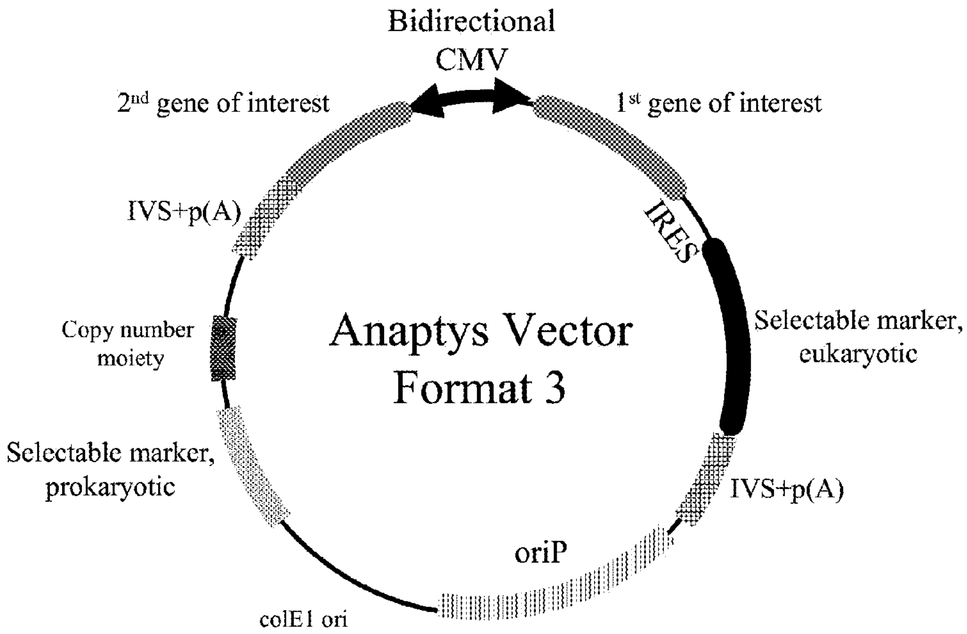
B. Expression Vector Format 4
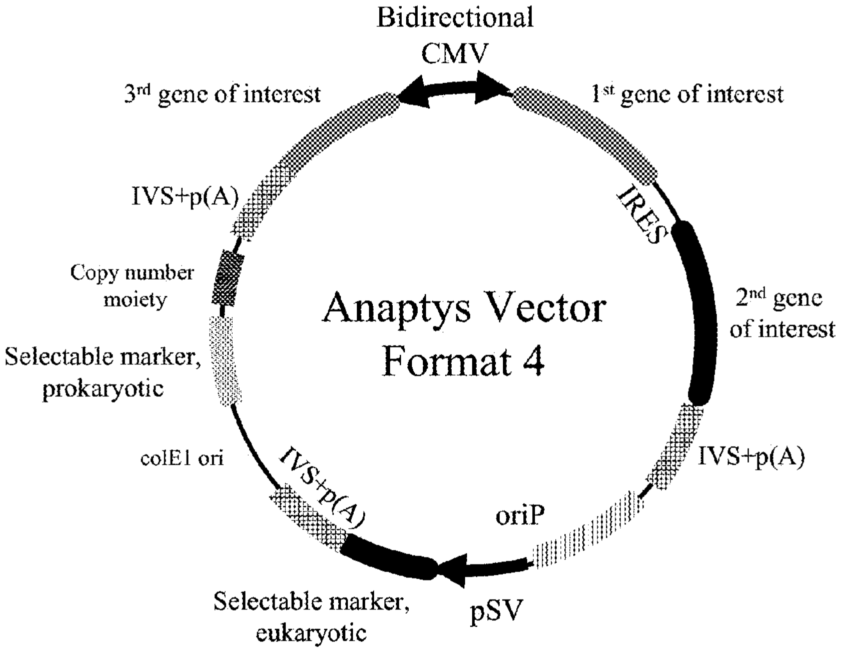

FIGURE 19
Expression Vector Format 5
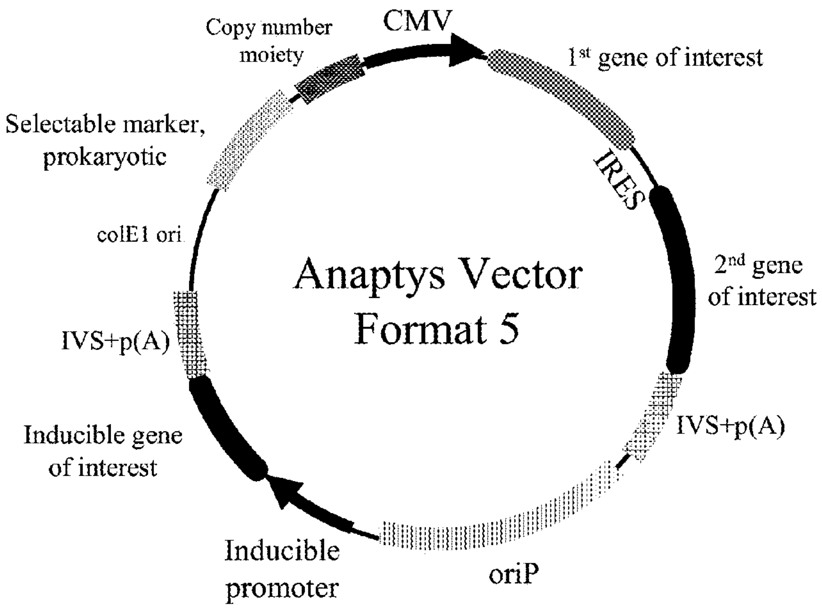
AAB184, restriction sites and elements
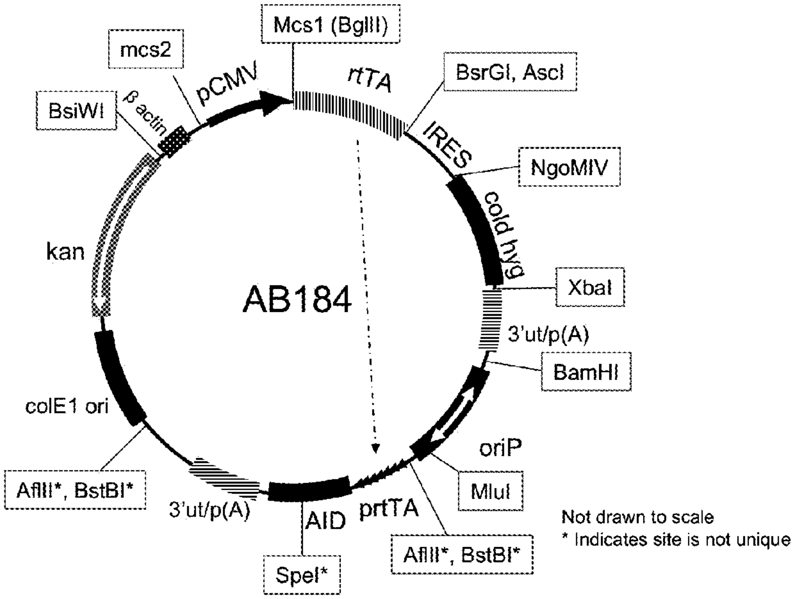

FIG. 21A
1. Steps to Generating Heavy Chain Library
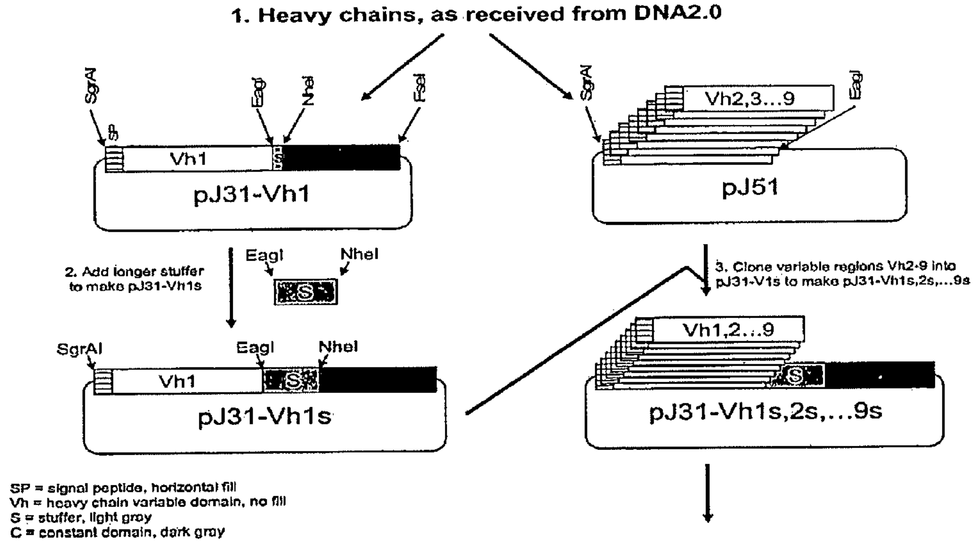
2. Steps to Generating Heavy Chain Library
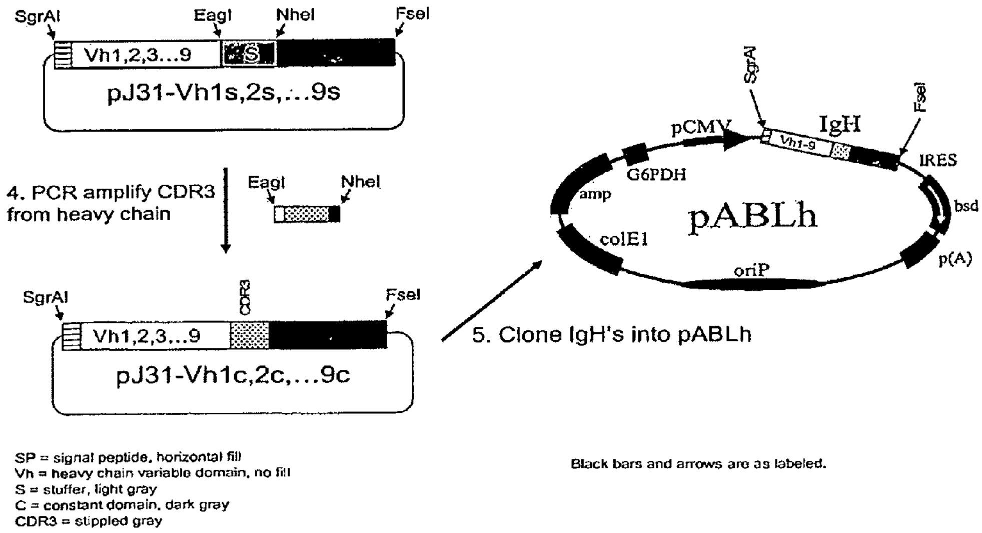

FIG. 21B
3. Steps to Generating κ Light Chain Library
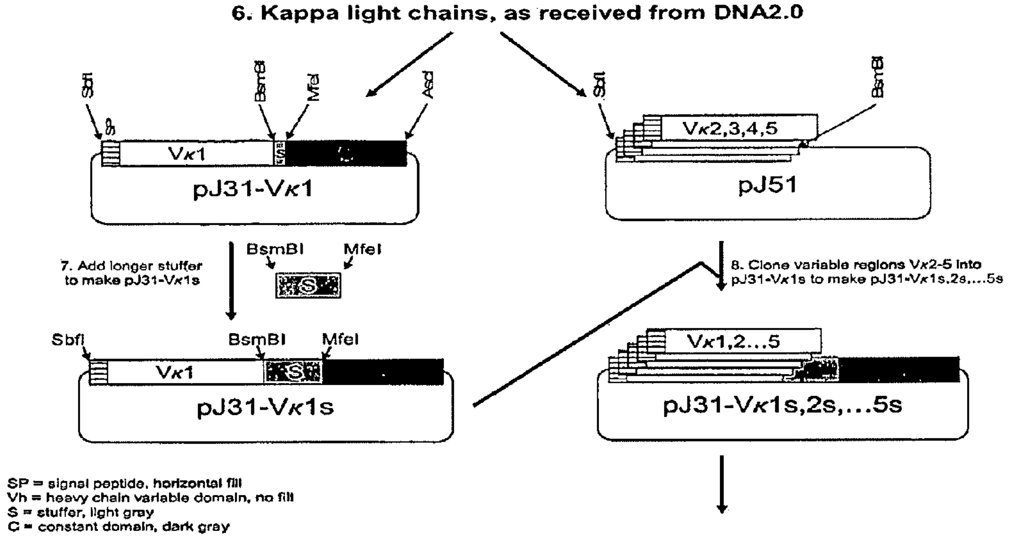
4. Steps to Generating κ Light Chain Library
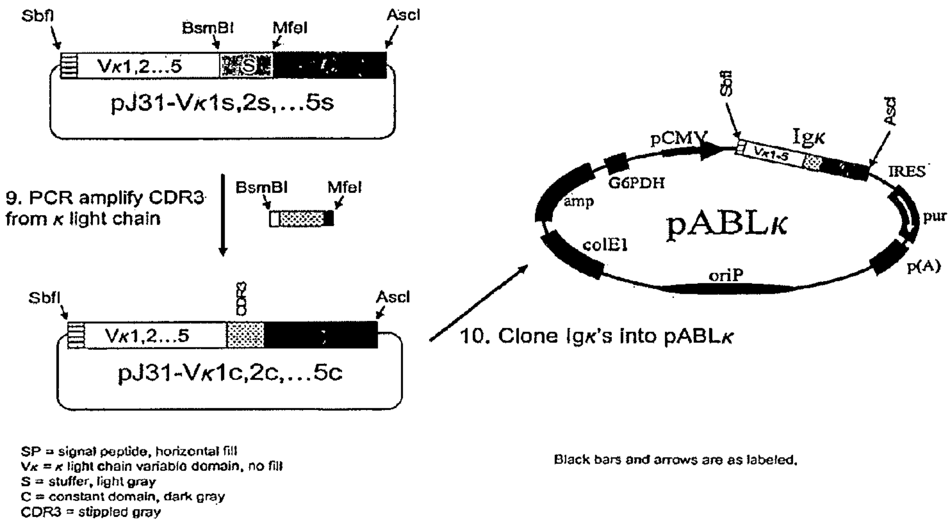

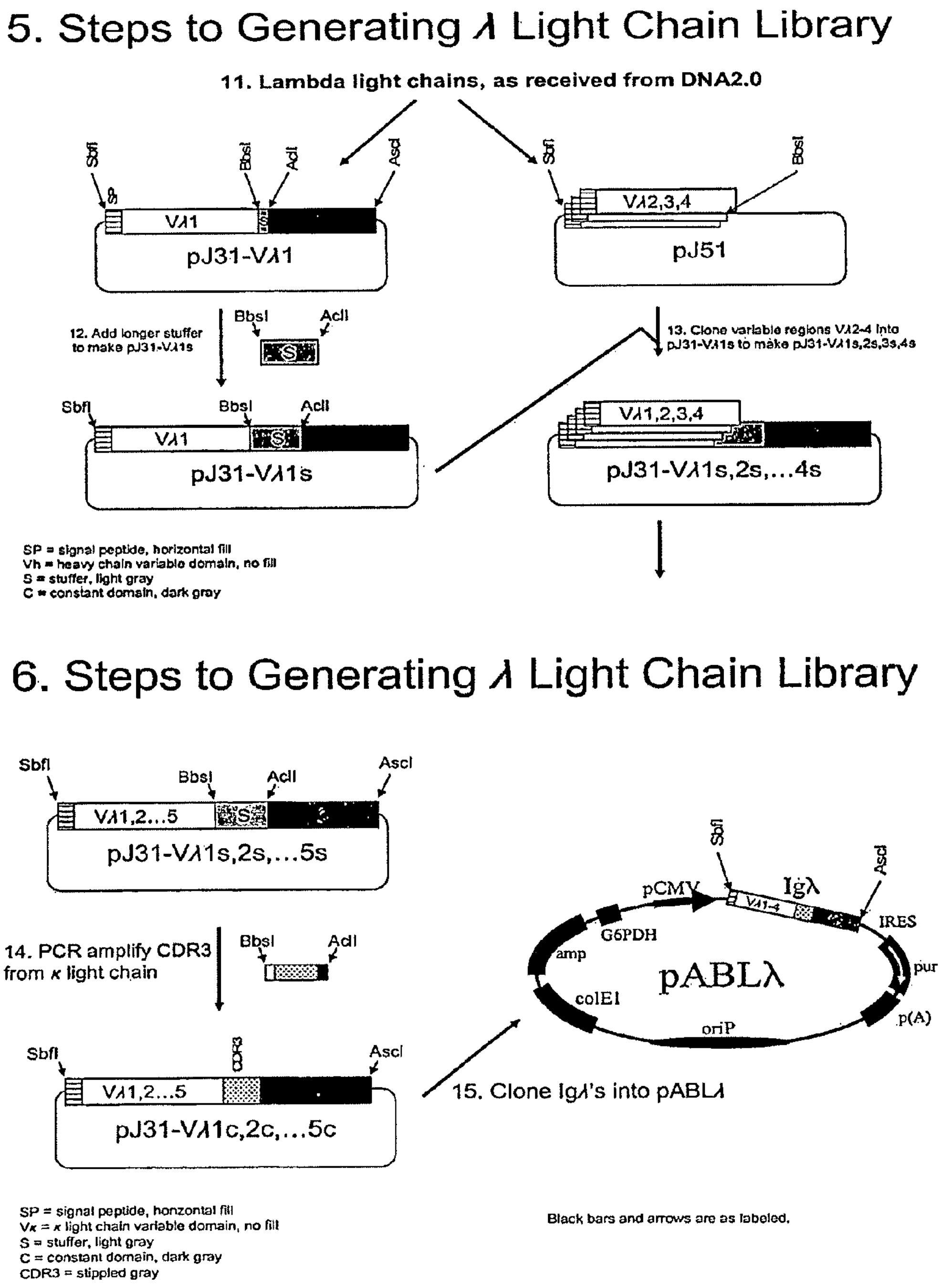

FIG. 21C

5. Steps to Generating λ Light Chain Library

SP = signal peptide, horizontal fill
Vh = heavy chain variable domain, no fill
S = stuffer, light gray
C = constant domain, dark gray

6. Steps to Generating λ Light Chain Library

SP = signal peptide, horizontal fill
Vκ = κ light chain variable domain, no fill
S = stuffer, light gray
C = constant domain, dark gray
CDR3 = stippled gray Black bars and arrows are as labeled.

FIG. 22

```
FR3 FR3 FR3 FR3 FR3 FR3   CDR3 CDR3 CDR3 CDR3 CDR3 CDR3 CDR3 CDR3    FR4 FR4 FR4 FR4 FR4 FR4 FR4 FR4 FR4 FR4 FR4 Constant Constant Constant Constant
VVVVVVVVVVVVVVVVVVVVVVVV DDDDDDDDDDDDDDDDDDDDDDDDDDDDDD JJJJJJJJJJJJJJJJJJJJJJJJJJJJJJJJJJJJJJJJJJJJJJJJJJJJCCCCCCCCCCCCCCCCCCCCCCCCCCCCCCCCCCCC
acggccgtgtattactgtgcgaga GTCGTCGTC AGCTACAGCTAC GTCGTCGTC GCTGAATACTTCCAGCACTGGGGCCAGGGCACCCTGGTCACCGTCTCCTCAGcctccaccaagggcccatcggtcttcccgctagcac
                         GTCGTCGTC CAGCTACAGCTA GTCGTCGTC
                         GTCGTCGTC ACAGCTACAGCT GTCGTCGTC

T A V Y Y C A R   V V V   S Y S Y   V V V   A E Y F Q H W G Q G T L V T V S S A S T K G P S V F P L A
                  V V V   Q L Q L   V V V
                  V V V   T A T A   V V V
```

FIG. 24

Native NisB Polynucleotide sequence

ATGATTAAGTCATCATTTAAAGCTCAGCCTTTCCTCGTGCGAAATACCATCCTGTCCCCTAATGATAAAAGGTCCTTCACAGAGTACACTCAGGTGATCGAGACGGT
ATCAAAGAATAAGGTCTTTCTTGAACAGCTGCTGCTCGCCAACCCCAAATTATACAACGTTATGCAGAAGTATAATGCTGGCTTGCTGAAAAAAAAGCGCGTTAAAA
AATTGTTCGAATCTATATACAAGTATTACAAGCGTTCTTACCTGCGGAGCACCCCGTTTGGCTTGTTTTCTGAAACCTCGATCGGCGTATTCTCAAAGTCATCTCAG
TATAAACTGATGGGGAAGACCACCAAAGGTATCCGCCTGGACACCCAATGGCTGATCAGGCTGGTGCATAAGATGGAGGTCGATTTCTCTAAAAAGCTAAGCTTCAC
GCGTAATAATGCCAACTATAAATTCGGCGACAGGGTGTTTCAGGTCTACACCATCAACAGCAGCGAGCTTGAGGAGGTGAATATCAAATACACTAACGTGTATCAGA
TCATTTCAGAGTTCTGTGAAAATGACTACCAGAAATACGAAGACATTTGCGAAACTGTGACTCTGTGCTACGGGGACGAATACAGAGAACTGTCAGAGCAGTACTTA
GGCTCGCTGATTGTGAACCATTATCTGATCTCTAACCTTCAGAAAGACCTGCTTTCAGATTTCTCGTGGGACACATTCCTCACTAAGGTCGAGGCTATCGATGAGGA
TAAGAAGTATATAATCCCCCTGAAGAAGGTGCAGAAATTCATTCAGGAGTACTCCGAGATTGAAATCGGCGAAGGCATTGAAAAATTGAAGGAGATTTACCAAGAAA
TGTCTCAGATTTTAGAAAACGATAACTATATTCAGATAGACCTGATAAGCGATTCCGAAATCAACTTTGACGTAAAGCAAAAGCAACAGCTGGAGCACCTTGCCGAA
TTTCTCGGGAACACCACCAAGTCCGTGAGAAGGACCTATCTTGATGATTATAAGGACAAATTTATCGAAAAATACGGTGTCGATCAGGAAGTCCAGATTACCGAGCT
TTTTGATAGTACTTTCGGCATTGGCGCGCCTTATAATTACAACCATCCTCGCAATGACTTTTACGAGAGTGAACCTTCTACTCTTTACTACTCCGAGGAAGAGAGGG
AAAAGTACCTGTCCATGTACGTGGAAGCAGTGAAAAATCACAATGTGATTAATTTGGATGATCTGGAGTCTCACTATCAGAAGATGGACTTAGAGAAAAAGAGCGAA
TTGCAGGGTCTGGAACTGTTCCTAAACCTCGCAAAGGAGTACGAGAAAGATATTTTTATTCTGGGCGATATAGTGGGCAATAACAACCTGGGCGGCGCTAGCGGTCG
TTTTAGCGCCCTAAGCCCCGAGCTGACTAGCTATCACAGAACCATCGTCGACTCCGTGGAGAGAGAGAACGAGAATAAGGAGATAACAAGCTGCGAAATTGTGTTCC
TGCCTGAGAACATTAGGCACGCCAACGTGATGCATACAAGCATCATGCGGCGGAAAGTCCTTCCATTCTTCACTTCCACCTCACACAATGAGGTGCAGCTAACCAAC
ATCTACATCGGCATCGACGAAAAGGAGAAATTTTATGCCAGAGACATCTCCACCCAAGAAGTGCTGAAGTTTTATATCACCTCTATGTATAACAAGACACTATTCAG
TAACGAACTCAGATTTCTTTACGAGATATCTTTAGACGACAAGTTCGGAAATCTACCCTGGGAGCTGATATACAGAGACTTCGATTACATTCCACGCCTGGTGTTTG
ATGAGATTGTGATAAGCCCAGCCAAGTGGAAAATCTGGGGGCGAGACGTGAACAATAAAATGACGATTCGGGAGTTGATTCAGTCAAAGGAAATACCTAAGGAATTT
TACATTGTGAATGGGGACAACAAAGTGTATTTGAGTCAGGAAAACCCGCTCGACATGGAAATCCTGGAAAGTGCCATTAAGAAGTCATCTAAGAGAAAGGATTTCAT
CGAACTGCAGGAGTACTTTGAGGATGAGAACATCATCAATAAGGGTCAGAAAGGCAGGGTTGCTGACGTGGTCGTGCCCTTCATTCGAACACGAGCACTGGGCAACG
AGGGGCGCGCCTTTATCAGGGAGAAGCGTGTGTCAGTCGAGCGCCGCGAGAAACTGCCCTTTAATGAGTGGCTATATTTGAAGTTGTACATCTCTATTAATAGGCAG
AATGAATTTTTACTGAGTTACCTTCCAGACATACAGAAGATTGTTGCCAACCTGGGCGGGAAGTTGTTTTTTCTCAGATATACAGATCCGAAGCCACATATACGGCT
GCGCATCAAGTGCTCCGATCTCTTTCTGGCCTATGGATCAATACTGGAAATCCTGAAGAGGTCTCAGAAAAATCGTATCATGTCTACATTTGATATTTCCATTTATG
ACCAGGAGGTCGAAAGATACGGTGGCTTCGACACTCTTGAACTGTCCGAAGCTATTTTTTGTGCTGACTCCAAAATTATACCTAACTTATTGACTCTGATCAAGGAC
ACAAATAATGACTGGAAGGTCGACGATGTCTCCATACTGGTCAACTACCTTTATTTGAAGTGTTTCTTTCAAAACGACAACAAAAAAATCCTCAATTTTCTGAACCT
GGTGTCTCCCAAGAAGGTCAAGGAGAACGTAAACGAAAAGATCGAGCACTACCTGAAGTTGCTCAAGGTGGATAATCTGGGAGACCAGATCTTTTATGACAAAAACT
TCAAGGAACTGAAGCATGCAATCAAGAATCTCTTTCTCAAAATGATTGCCCAGGATTTTGAGCTCCAGAAAGTGTATTCGATCATTGACAGTATCATCCACGTGCAT
AATAACCGCTTGATAGGCATCGAAAGGGATAAGGAGAAGCTGATCTATTACACGCTCCAGCGCCTGTTTGTCTCTGAGGAGTACATGAAG (SEQ ID NO : 31)

203 hot spots
291 cold spots
121 CpGs

FIG. 25

SHM Resistant NisB Polynucleotide sequence

ATGATTAAGTCCTCTTTCAAAGCCCAGCCCTTCCTCGTCCGAAATACTATTCTCTCCCCCAATGACAAGAGGAGCTTCACAGAGTACACTCAAGTCATCGAGACAGT
CTCAAAGAATAAGGTCTTCCTCGAGCAGCTCCTCCTCGCCAACCCCAAACTCTATAATGTCATGCAGAAGTATAATGCCGGGCTCCTCAAAAAAAAGAGGGTCAAGA
AGCTCTTCGAGAGCATATACAAGTATTACAAGAGGTCTTACCTCAGGTCGACCCCCTTTGGGCTCTTCTCCGAGACGAGCATCGGGGTCTTCTCCAAGTCCTCCCAA
TATAAACTCATGGGGAAGACCACCAAGGGGATTAGACTCGACACCCAGTGGCTCATAAGACTCGTCCATAAAATGGAGGTCGACTTCTCTAAAAAGCTCTCTTTTAC
CCGAAATAATGCCAACTATAAATTTGGGGACAGGGTCTTTCAGGTCTACACCATCAACTCCTCTGAGCTCGAGGAGGTCAATATCAAATACACTAATGTCTATCAGA
TCATCTCTGAGTTCTGTGAGAATGACTACCAGAAATATGAGGACATTTGCGAGACGGTCACTCTCTGTTATGGGGACGAGTATAGGGAGCTCTCTGAGCAATATCTC
GGGTCTCTCATTGTCAATCACTATCTCATCTCTAACCTCCAGAAGGACCTCCTCTCTGACTTCTCGTGGGACACATTCCTCACTAAGGTCGAGGCCATCGACGAGGA
CAAAAAATATATAATCCCCCTCAAGAAGGTCCAGAAGTTCATTCAGGAGTACTCCGAGATTGAGATAGGGGAGGGGATTGAGAAACTCAAAGAGATTTACCAGGAGA
TGTCTCAGATCCTCGAGAATGACAATTATATTCAGATAGACCTCATCTCTGACTCGGAGATAAACTTTGACGTCAAGCAAAAGCAGCAACTCGAGCATCTCGCCGAG
TTTCTCGGGAACACCACCAAGAGTGTCAGGAGGACCTATCTCGACGACTATAAGGACAAATTCATCGAGAAATACGGGGTCGACCAAGAGGTCCAGATTACCGAGCT
CTTTGACTCTACCTTCGGGATTGGGGCCCCCTACAATTACAACCACCCCCGGAATGACTTTTACGAGTCTGAGCCCTCCACCCTCTACTACTCCGAGGAGGAGAGGG
AGAAATACCTCTCCATGTATGTCGAGGCCGTCAAAAATCACAATGTCATAAATCTCGACGACCTCGAGTCTCACTATCAGAAGATGGACCTCGAGAAAAAGAGCGAG
CTCCAGGGGCTCGAGCTCTTCCTCAATCTCGCCAAGGAGTACGAGAAAGACATTTTCATCCTCGGGGACATAGTCGGGAATAATAACCTCGGGGGGGCCTCGGGGAG
ATTCTCTGCCCTCTCCCCCGAGCTCACCTCCTATCACAGGACCATAGTCGACTCAGTCGAGAGAGAGAACGAGAATAAGGAGATCACCTCATGCGAGATAGTCTTCC
TCCCCGAGAACATTAGACATGCCAATGTCATGCATACCTCCATAATGAGACGCAAGGTCCTCCCCTTCTTTACCTCCACCTCCCACAATGAGGTCCAACTCACCAAC
ATCTACATAGGGATCGACGAGAAGGAGAAATTTTATGCCAGAGACATCTCCACCCAAGAGGTCCTCAAGTTTTATATCACCTCTATGTATAACAAGACCCTCTTCTC
CAATGAGCTCAGGTTCCTCTACGAGATCTCCCTCGACGACAAGTTCGGGAATCTCCCCTGGGAGCTCATATACAGAGACTTTGACTACATCCCCAGACTCGTCTTTG
ACGAGATTGTCATCTCCCCCGCCAAGTGGAAAATCTGGGGGAGAGACGTCAACAATAAAATGACGATTCGGGAGCTCATTCAGTCAAAGGAGATCCCCAAGGAGTTT
TATATAGTCAATGGGGACAACAAAGTCTATCTCTCCCAGGAGAATCCCCTCGACATGGAGATCCTCGAGAGTGCCATTAAGAAGTCCTCAAAGAGAAAAGACTTTAT
CGAGCTCCAAGAGTACTTTGAGGACGAGAACATCATCAATAAGGGGCAGAAGGGGAGAGTCGCCGACGTCGTCGTCCCCTTCATTCGGACGAGGGCCCTCGGGAACG
AGGGGAGGGCCTTCATCAGGGAGAAGAGGGTCTCAGTCGAGAGGAGAGAGAAGCTCCCCTTTAATGAGTGGCTCTACCTCAAGCTCTACATCTCTATTAATAGACAG
AATGAGTTTCTCCTCTCTTATCTCCCCGACATACAGAAAATTGTCGCCAACCTCGGGGGAAACTCTTTTTTCTCAGATATACAGACCCCAAGCCCCACATAAGACT
CCGCATCAAGTGCTCGGACCTCTTCCTCGCCTATGGGTCTATTCTCGAGATCCTCAAGAGGTCTCAGAAAAATCGTATCATGTCTACTTTTGACATCTCCATATATG
ACCAGGAGGTCGAGAGATACGGGGGGTTTGACACCCTCGAGCTCTCTGAGGCCATTTTCTGTGCCGACTCCAAAATCATCCCCAATCTCCTCACTCTCATCAAGGAC
ACAAATAATGACTGGAAGGTCGACGACGTCTCCATTCTCGTCAATTACCTCTATCTCAAGTGTTTCTTTCAAAACGACAACAAAAAAATCCTCAATTTTCTCAATCT
CGTCTCCCCCAAGAAGGTCAAGGAGAACGTCAACGAGAAGATCGAGCACTATCTCAAACTCCTCAAGGTCGACAACCTCGGGGACCAAATCTTTTATGACAAAAACT
TCAAAGAGCTCAAACATGCCATCAAGAATCTCTTTCTCAAAATGATTGCCCAAGACTTTGAGCTCCAAAAAGTCTATTCGATCATTGACTCCATAATCCACGTCCAT
AATAACCGTCTCATTGGGATTGAGAGGGACAAGGAGAAGCTCATCTATTACACTCTCCAGAGACTCTTTGTCTCTGAGGAGTACATGAAG (SEQ ID NO: 32)

131 hot spots
609 cold spots
115 CpGs

FIG. 26

NisP, native polynucleotide sequence

Native
ATGAAGAAGATCCTCGGATTTCTATTCATCGTGTGTTCTCTGGGCCTGTCCGCTACCGTGCATGGCGAAACAACTAATTCCCAGCAACTTCTGTCCAACAACATCAA
CACAGAGCTTATAAATCACAATTCTAATGCAATTCTCTCCAGTACTGAGGGGTCGACCACCGACTCAATCAATCTCGGCGCACAGAGTCCCGCTGTAAAGTCCACTA
CACGTACGGAGCTCGATGTAACCGGGGCCGCGAAGACTCTCCTCCAGACATCAGCTGTGCAGAAGGAAATGAAAGTCTCGTTACAAGAGACCCAGGTGTCCAGTGAA
TTTTCCAAGCGCGATTCAGTGACCAATAAAGAGGCAGTTCCCGTGAGCAAGGATGAACTGCTGGAGCAGTCCGAGGTGGTTGTGAGTACCAGTTCTATCCAGAAAAA
TAAGATTCTCGACAACAAGAAGAAAAGAGCAAACTTCGTCACAAGCTCCCCACTAATCAAAGAGAAACCAAGCAACTCTAAAGATGCCTCTGGGGTCATTGACAACT
CTGCCAGTCCTCTTTCGTATAGGAAGGCTAAGGAGGTGGTCTCCCTTCGGCAGCCCCTAAAGAACCAGAAAGTTGAAGCTCAGCCTCTTCTGATCTCGAATTCTTCG
GAAAAGAAGGCCTCAGTGTACACTAATTCCCACGACTTTTGGGATTACCAATGGGATATGAAGTATGTCACTAACAACGGCGAGAGCTATGCCCTGTACCAACCCAG
TAAGAAAATCAGTGTGGGGATAATCGATTCTGGTATTATGGAGGAGCACCCCGACCTGTCTAACTCCTTAGGCAACTATTTTAAGAACCTGGTGCCTAAGGGTGGAT
TTGATAACGAGGAGCCAGACGAAACGGGTAATCCCAGCGATATCGTGGACAAAATGGGCCACGGGACTGAAGTTGCTGGGCAGATCACCGCCAACGGTAACATTCTG
GGTGTGGCCCCCGGTATCACTGTGAATATTTATCGAGTTTTCGGGGAAAACCTCAGCAAGAGTGAATGGGTCGCGCGTGCAATCAGGAGGGCAGCGGATGACGGCAA
CAAAGTGATCAATATCTCTGCGGGGCAATATCTCATGATCTCCGGCTCATACGACGACGGCACGAATGACTATCAGGAATACCTGAACTACAAGTCTGCGATCAATT
ATGCTACAGCCAAGGGATCCATTGTAGTCGCGGCACTGGGCAACGACTCCCTAAACATTCAGGACAATCAGACGATGATTAACTTCCTCAAACGGTTCAGGAGTATT
AAGGTCCCCGGTAAAGTCGTCGATGCCCCCTCAGTGTTCGAGGACGTCATTGCCGTCGGGGGCATTGATGGTTATGGTAATATAAGTGATTTTAGTAACATCGGCGC
TGACGCAATATACGCACCGGCCGGCACCACTGCCAACTTCAAGAAGTACGGCCAGGACAAATTTGTCTCTCAGGGCTACTACCTAAAGGACTGGCTGTTTACAACCG
CCAATACTGGCTGGTATCAATACGTGTATGGCAACAGCTTTGCGACTCCTAAAGTTAGCGGTGCCCTCGCACTTGTCGTTGACAAATACGGCATTAAGAATCCCAAT
CAGCTTAAGCGGTTTCTCCTGATGAACAGTCCTGAAGTTAACGGCAATCGCGTTTTAAATATTGTGGACCTGCTCAATGGTAAAAACAAGGCCTTCAGCCTCGACAC
GGACAAAGGACAGGACGATGCTATAAATCATAAGTCTATGGAAAACCTTAAGGAGTCAAGAGATACCATGAAACAGGAACAGGACAAAGAGATACAGCGGAATACCA
ATAACAACTTCAGCATAAAGAACGACTTCCACAATATCAGCAAAGAGGTTATCAGTGTAGACTACAATATCAACCAGAAAATGGCCAATAATAGGAACAGCCGCGGT
GCTGTTTCTGTCCGGTCCCAGGAGATCCTGCCAGTGACCGGCGACGGCGAAGACTTCCTGCCTGCTCTGGGGATCGTGTGCATCTCCATTCTCGGTATCTTGAAAAG
AAAGACAAAAAAC (SEQ ID NO: 33)

161 hot spots
257 cold spots
99 CpGs

FIG. 27

NisP, SHM resistant polynucleotide sequence

ATGAAGAAGATTCTCGGGTTTCTCTTTATCGTCTGCTCCCTCGGGCTCTCGGCCACTGTCCATGGGGAGACGACTAATTCCCAGCAGCTCCTCTCAAACAACATCAA
CACTGAGCTCATAAATCACAATTCTAATGCCATTCTCTCCTCTACAGAGGGGTCGACGACAGACTCAATCAATCTCGGGGCCCAGTCCCCCGCCGTCAAGTCGACCA
CAAGGACTGAGCTCGACGTCACGGGGGCCGCCAAGACTCTCCTCCAGACCTCTGCCGTCCAAAAGGAGATGAAAGTCTCTCTCCAAGAGACTCAAGTCTCCTCTGAG
TTCTCCAAGAGGGACTCTGTCACCAATAAGGAGGCCGTCCCCGTCTCAAAGGACGAGCTCCTCGAGCAGTCCGAGGTCGTCGTCTCCACCTCCTCAATCCAGAAAAA
TAAGATTCTCGACAACAAGAAGAAGAGGGCCAACTTCGTCACCTCCTCCCCCCTCATCAAAGAGAAGCCCTCAAACTCAAAGGACGCCTCTGGGGTCATTGACAACT
CTGCCTCCCCCCTCTCATATAGGAAGGCCAAGGAGGTCGTCTCTCTCCGCCAGCCCCTCAAGAACCAAAAAGTCGAGGCCCAGCCCCTCCTCATCTCGAATTCCTCC
GAGAAGAAGGCCTCAGTCTACACCAATTCCCACGACTTTTGGGACTATCAGTGGGACATGAAGTATGTCACTAACAACGGGGAGAGCTATGCCCTCTATCAGCCCTC
CAAAAAAATCTCAGTCGGGATAATCGACTCTGGGATAATGGAGGAGCACCCCGACCTCTCTAACTCTCTCGGGAATTATTTTAAGAACCTCGTCCCCAAGGGGGGT
TTGACAACGAGGAGCCCGACGAGACAGGGAATCCCTCCGACATAGTCGACAAAATGGGGCACGGGACAGAGGTCGCCGGGCAGATCACCGCCAACGGGAATATCCTC
GGGGTCGCCCCCGGGATTACAGTCAATATCTATCGAGTCTTTGGGGAGAATCTCTCAAAGAGTGAGTGGGTCGCCCGGGCCATCAGGAGGGCCGCCGACGACGGGAA
CAAAGTCATCAATATCTCCGCCGGGCAATATCTCATGATCTCGGGGTCATACGACGACGGGACAAATGACTATCAGGAGTATCTCAATTACAAGTCGGCCATCAATT
ATGCCACTGCCAAGGGGTCCATTGTCGTCGCCGCCCTCGGGAACGACTCTCTCAATATTCAGGACAATCAGACGATGATTAACTTCCTCAAGAGATTTAGGAGTATT
AAGGTCCCCGGGAAAGTCGTCGACGCCCCCTCTGTCTTTGAGGACGTCATTGCCGTCGGGGGGATTGACGGGTATGGGAATATCTCAGACTTCTCAAACATTGGGGC
CGACGCCATATACGCCCCCGCCGGGACGACAGCCAACTTCAAGAAATACGGGCAGGACAAATTTGTCTCTCAGGGGTACTATCTCAAGGACTGGCTCTTTACGACAG
CCAATACTGGGTGGTATCAATACGTCTATGGGAACTCGTTTGCCACCCCCAAGGTCTCGGGGGCCCTCGCCCTCGTCGTCGACAAATACGGGATAAAGAATCCCAAT
CAGCTCAAGAGATTTCTCCTCATGAATTCCCCCGAGGTCAACGGGAATAGAGTCCTCAATATTGTCGACCTCCTCAACGGGAAAAACAAGGCCTTCTCTCTCGACAC
GGACAAGGGGCAAGACGACGCCATAAATCATAAGTCTATGGAGAATCTCAAGGAGTCAAGGGACACCATGAAACAAGAGCAGGACAAAGAGATACAGAGGAACACCA
ATAACAACTTCTCCATCAAGAACGACTTCCACAATATCTCAAAAGAGGTCATCTCTGTCGACTACAATATCAACCAGAAAATGGCCAATAATAGGAACTCCCGGGGG
GCCGTCTCTGTCCGGTCCCAGGAGATCCTCCCCGTCACAGGGGACGGGGAGGACTTCCTCCCCGCCCTCGGGATCGTCTGTATCTCCATACTCGGGATCCTCAAGAG
AAAGACAAAAAAC (SEQ ID NO: 34)

75 hot spots
491 cold spots
114 CpGs

FIG. 28

NisT, Native and SHM Resistant Polynucleotide sequences

A. Native (SEQ ID NO: 35)

ATGGACGAGGTAAAAGAGTTTACGAGCAAGCAGTTCTTCTATACACTGCTAACGCTCCCATCAACTCTGAAACTGATCTTTCAGCTGGAAAAGAGGTACGCCATTTA
TCTGATTGTGCTTAACGCTATAACCGCCTTCGTCCCGCTGGCATCCCTCTTTATCTATCAGGACCTGATTAACAGTGTGCTGGGCTCTGGTCGCCATCTTATAAATA
TTATCATCATATACTTCATTGTGCAGGTGATTACTACCGTGTTGGGCCAGTTAGAGTCCTACGTATCGGGCAAATTTGACATGCGGCTCAGCTATTCAATCAATATG
CGGCTTATGAGGACGACGTCTAGCCTGGAATTATCCGACTACGAACAGGCTGATATGTACAATATCATAGAGAAAGTGACCCAGGATTCCACCTACAAGCCTTTCCA
GTTATTCAATGCCATCATTGTCGAGTTGTCATCATTTATCTCTTTGCTGTCAAGTCTTTTCTTCATAGGCACGTGGAACATTGGAGTGGCCATCCTGTTGCTGATTG
TCCCTGTTTTGTCACTAGTTCTTTTCCTCAGGGTGGGGCAACTGGAATTCCTCATTCAGTGGCAAAGAGCATCATCGGAGCGAGAAACCTGGTACATCGTTTACCTG
CTGACTCATGATTTCAGCTTCAAGGAGATCAAACTGAATAACATCAGTAACTATTTTATCCACAAGTTTGGCAAACTTAAGAAAGGGTTCATCAACCAGGATTTGGC
TATCGCTCGGAAGAAGACATATTTTAATATCTTTCTTGATTTCATTTTAAACCTAATCAATATTCTGACCATCTTCGCCATGATTCTCTCTGTTCGGGCAGGTAAGC
TTCTGATTGGCAATCTCGTGTCTCTCATTCAGGCCATATCAAAAATTAATACATATTCTCAGACCATGATCCAGAACATCTACATTATCTACAACACCTCATTGTTT
ATGGAGCAACTGTTCGAGTTTCTTAAGAGAGAATCAGTAGTTCATAAGAAGATTGAGGACACCGAAATTTGCAATCAGCACATCGGCACTGTGAAGGTTATCAACCT
GTCATATGTATATCCTAACTCTAATGCCTTCGCACTCAAAAATATCAATCTGAGCTTCGAAAAAGGGGAACTGACTGCCATCGTCGGTAAAAATGGCTCCGGCAAAT
CTACACTTGTAAAAATAATTAGCGGCCTGTATCAGCCCACCATGGGCATAATCCAGTACGACAAGATGCGCTCCTCCCTCATGCCAGAGGAATTCTATCAGAAGAAC
ATCTCCGTCCTGTTTCAGGATTTTGTCAAATACGAACTCACTATTCGGGAGAATATAGGCCTATCGGACCTTAGTTCACAGTGGGAGGATGAGAAGATAATCAAGGT
ACTCGATAATCTGGGGCTCGACTTTTTGAAGACCAATAACCAATACGTCCTGGATACACAGCTGGGAAACTGGTTCCAGGAAGGCCACCAGCTGAGTGGCGGTCAGT
GGCAGAAGATTGCTCTCGCCAGGACATTTTTTAAAAAGGCCTCAATCTACATTCTTGACGAGCCAAGCGCTGCCCTGGACCCCGTGGCGGAGAAAGAAATTTTTGAC
TATTTTGTCGCCCTGAGCGAGAACAACATCTCTATATTCATCTCTCATAGCCTGAATGCTGCTCGTAAGGCCAACAAGATCGTCGTGATGAAGGATGGACAGGTTGA
GGACGTCGGGAGCCATGACGTGCTTCTTAGACGGTGCCAGTACTATCAGGAGCTGTATTACAGCGAGCAGTATGAAGATAATGATGAG

B. SHM Resistant (SEQ ID NO: 36)

ATGGACGAGGTCAAAGAGTTTACGAGCAAGCAGTTCTTCTATACTCTCCTCACTCTCCCCTCAACTCTCAAGCTCATCTTCCAGCTCGAGAAGAGATACGCCATTTA
TCTCATTGTCCTCAACGCCATCACTGCCTTCGTCCCCCTCGCCTCTCTCTTTATCTATCAGGACCTCATTAACTCTGTCCTCGGGTCGGGGAGACATCTCATAAACA
TTATCATCATATACTTCATAGTCCAAGTCATTACTACAGTCCTCGGGCAGCTCGAGTCCTATGTCTCTGGGAAGTTTGACATGAGACTCTCTTACTCAATCAATATG
AGACTCATGAGGACGACCTCCTCCCTCGAGCTCTCTGACTACGAGCAAGCCGACATGTACAATATCATAGAGAAGGTCACCCAAGACTCCACCTATAAGCCCTTCCA
GCTCTTCAATGCCATCATTGTCGAGCTCTCCTCTTTCATCTCTCTCCTCTCCTCCCTCTTCTTCATCGGGACTTGGAACATAGGGGTCGCCATCCTCCTCCTCATAG
TCCCCGTCCTCTCCCTCGTCCTCTTCCTCAGAGTCGGGCAGCTCGAGTTCCTCATTCAGTGGCAGAGGGCCTCGTCTGAGAGAGAGACCTGGTATATAGTCTATCTC
CTCACTCATGACTTCTCATTCAAGGAGATCAAGCTCAATAATATCTCAAACTATTTTATCCACAAGTTTGGGAAACTCAAGAAGGGGTTCATCAACCAGGACCTCGC
CATCGCCCGGAAGAAGACATATTTTAATATCTTCCTCGACTTCATCCTCAACCTCATAAACATCCTCACCATCTTCGCCATGATTCTCTCTGTCAGAGCCGGGAAGC
TCCTCATCGGGAATCTCGTCTCTCTCATTCAGGCCATCTCCAAAATTAATACATATTCTCAGACCATGATCCAGAACATCTACATTATCTACAACACCTCTCTCTTT
ATGGAGCAACTCTTCGAGTTCCTCAAGAGAGAGTCAGTCGTCCATAAAAAGATTGAGGACACTGAGATTTGCAATCAGCACATCGGGACAGTCAAAGTCATCAATCT
CTCATATGTCTACCCCAACTCTAATGCCTTCGCCCTCAAAAATATAAATCTCTCTTTTGAGAAGGGGGAGCTCACTGCCATCGTCGGGAAAAACGGGAGTGGGAAGT
CCACTCTCGTCAAAATAATCTCGGGGCTCTATCAGCCCACCATGGGGATCATCCAGTACGACAAGATGAGGTCCTCCCTCATGCCCGAGGAGTTCTATCAGAAGAAC
ATCTCCGTCCTCTTCCAGGACTTCGTCAAATATGAGCTCACTATTCGGGAGAATATTGGGCTCTCGGACCTCTCCTCTCAGTGGGAGGACGAGAAGATAATCAAGGT
CCTCGACAATCTCGGGCTCGACTTCCTCAAGACCAATAACCAATACGTCCTCGACACCCAGCTCGGGAACTGGTTTCAGGAGGGGCACCAGCTCTCTGGGGGGCAGT
GGCAGAAAATTGCCCTCGCCAGGACATTTTTTAAAAAGGCCTCAATCTACATTCTCGACGAGCCCTCAGCCGCCCTCGACCCCGTCGCCGAGAAAGAGATATTCGAC
TATTTTGTCGCCCTCTCAGAGAACAACATCTCTATATTCATCTCTCACTCTCTCAATGCCGCCCGAAAGGCCAACAAGATCGTCGTCATGAAAGACGGGCAAGTCGA
GGACGTCGGGAGCCATGACGTCCTCCTCAGACGGTGCCAGTACTATCAGGAGCTCTATTACTCCGAGCAGTATGAGGACAATGACGAG

Native 138 hot spots; 195 cold spots, 62 CpGs. SHM resistant 92 hot spots; 372 cold spots, 75 CpGs

FIG. 29

NisA

A. Input DNA Sequence (SEQ ID NO: 37):

ATGTCTACTAAAGACTTCAACCTGGACCTCGTGAGTGTGAGCAAAAAGGATTCCGGGGCTAGCCCAAGGATAACCTCCATTTCTCTGTGTACACCTGG
ATGCAAAACTGGGGCCCTCATGGGGTGTAATATGAAGACGGCGACATGCCATTGTTCCATCCACGTTTCCAAG

B. Initial Analysis of hot spots:

hhhhhHhhhhhhhhhhhhHhhhhhhhhhhhhhhhhhhhhHhhhhhhhhhhhhhhhhHhhhHhhhhhhhhhHhhhhhhhhhhhhhhhHhHhhhhhhhhh
hHhhhhHhhhhhhhhhhhhhhhhhHhhhhhhhhhhhhhhhhhhhHhhhhhHhhhhhhhhhhhhhhhhhhh

C. Initial Analysis of cold spots:

ccCccccccccccCccccccccccCccCccccCcccccCcccccccccccccccCCCccccCCccccccccccccCccccccccCccccccccccccccc
ccccccccccCCCCCcCccccCCcccccccccccccCccCccCccccCcccccccccccccccccccccccc

D. Output polynucleotide Sequence; Underlined: SHM resistant / Non underlined: SHM susceptible (SEQ ID NO: 38)

ATGTCTACTAAAGACTTCAATCTCGACCTCGTCTCAGTCTCCAAAAAGGACTCGGGGGCCTCCCCCAGAATAACCAGCATAAGCCTGTGTACACCTGG
CTGTAAAACTGGGGCTCTCATGGGCTGTAACATGAAGACAGCCACATGCCATTGTAGTATACATGTCTCCAAG

E. Analysis of hot spots:

hhhhhHhhhhhhhhhhhhhhhhhhhhhhhhhhhhhhhhhhhhhhhhhhhhhhhhhhhhhhhhhhhhhhhhhHhhhHhhhhhHhhhhhHhHhhhhhhhHh
hHhhhhHhhhhhHhhhhhhhhhHhhHhhHhhhhhhhhhhHhhhhhhHhhhhhHhhHhhhHhhhhhhhhhhhh

F. Analysis of cold spots:

ccCccccccccccCcccccccccCccCccCccCcCcccCcCccccccccccCcCccCCCCCcCcCCCcccccccccccccccccccCcccccccccccccccCc
ccccccccccCCCcCcCccccCCcccccccccccccCcccCcccccccCccccccccccccccccCcCccccccc

FIG. 30

NisC

A. Input DNA Sequence (SEQ ID NO: 39):

ATGCGCATCATGATGAATAAGAAGAATATTAAAAGGAATGTGGAAAAGATTATCGCTCAGTGGGACGAGAGGACTCGGAAGAACAAAGAGAACTTTGACTTCGGGGA
GCTGACTCTCTCTACCGGCCTTCCTGGTATTATCTTAATGCTGGCAGAGCTGAAAAATAAAGATAACAGTAAGATTTACCAAAAGAAGATCGATAACTATATAGAGT
ACATTGTTTCGAAACTGTCAACCTACGGTCTCTTAACCGGCAGTCTCTATTCCGGGGCCGCGGGCATAGCCTTAAGCATTCTGCACCTGCGCGAGGATGACGAAAAG
TATAAAAATCTCTTAGACTCTCTAAACCGGTACATCGAGTATTTCGTGAGGGAAAAGATTGAGGGCTTTAATCTGGAGAATATCACCCCCCCCGATTACGATGTCAT
CGAGGGCCTCAGCGGTATCCTTTCCTACCTGTTGCTGATAAATGATGAACAGTATGATGATCTGAAGATTTTGATCATCAACTTCTTGTCAAATTTAACTAAAGAGA
ACAATGGTCTCATTTCTTTGTACATCAAGAGCGAGAATCAGATGTCCCAGTCAGAGTCCGAAATGTACCCTCTTGGGTGTCTGAACATGGGTCTCGCCCACGGACTG
GCCGGAGTGGGCTGCATACTGGCTTACGCCCATATCAAAGGGTACAGTAATGAGGCCTCTCTATCCGCACTGCAGAAAATCATCTTTATTTACGAGAAGTTCGAGTT
GGAGCGAAAAAAACAGTTCCTGTGGAAAGATGGCCTGGTGGCTGACGAACTCAAAAAGGAGAAGGTCATCAGGGAGGCCTCTTTTATTAGAGACGCGTGGTGCTATG
GGGGCCCTGGTATTTCTCTCCTCTACCTATACGGTGGGTTAGCCCTGGACAACGACTACTTTGTTGATAAAGCCGAGAAAATCCTTGAATCAGCCATGCAGCGCAAA
TTGGGAATCGATAGTTATATGATCTGCCATGGATACAGTGGCCTAATCGAGATATGCAGTCTATTTAAGCGGCTGCTGAATACAAAGAAATTCGATAGTTACATGGA
GGAGTTCAATGTCAATAGCGAACAGATCCTGGAAGAATACGGGGATGAGAGTGGGACCGGATTCCTGGAGGGCATCTCCGGCTGTATCCTGGTCTTAAGTAAGTTCG
AATACTCCATCAACTTTACATACTGGCGGCAGGCCTTGCTACTTTTCGACGATTTTCTCAAGGGAGGGAAGAGGAAA

B. Initial Analysis of hot spots:

hhhhhhhhhhhhhhhhhhhhhhhhhhhhhhhhhhhhhhhhhhhhhhhhhhhhhhhhhhhhhhhhhhhhhhhhhhhhhhhhhhhhhhHhhhhhhhhHhhhhhhhhhhhhhhH
hhhhhhhhhhhhHhhhhhhhhhhhhHhhhhhhhhhhhHhhhHhhhhHhhhhhhhhhhhhhhhhhhHhhHhhhhhhhhHhhhhhhhhhhhhhhhhhHhhhhhhhhhHhH
hhhhHhhhhhhhHhhhhhhhHhhhhhhhhhhhhhhHhhhhHhhhhhhhhhhhhhhhhhhhhhhhhHhhhhHhhhhhhHhhhhhhHhhhhhhhhhhhhhhhhhhhhhhhHh
hhhhhhhhhhhhhhhhhhhhhhhhHhhhHhHhhhhhhHhhhhhhhhhhhhhhhhhhhhhhhhhhhhhhHhhhhhhhhhhhhhhhhhhhhhhhhhhhhhhhhhhhhhhhh
hhhhhhhhhhhhhHhhhhhhhhhhhHhhhHhhHhhhhhhhhhhhhhhhhHhhHhhhhhhhhhhhhhhhhhhhhhhhhhhHhhhhhhhhhhhhhhhhHhhhhhhhhhhH
hhhhhhhhhhhhhhhhhhHhHhhhhhhhhhhhhhhhhhhhhhhhhhhhhhhhhhhhhhhhhhhhHhHhhhhhhhhhhhhhhhhhhHhhhhhhhhhhhhhhhhhhhhhhh
hhhhhhhhhHhhHhhhHhhhHhhhhhhhhhhhhhhhhhhhhHhHhhHhhhhhhhhhhhhhhhhhhhhhhhhhhHhhhhhhhhhhhhhhhhhhhhhhhhhhHhhhhhHhhh
hhhhhhhhhhhHhhHhhhhhhhhhhhhhhhhhhhhhhhHhhhhhhhHhhhhhhhhhhhhhhhhhhhhhhhhhhhhhhhhhhhhhhhhhhhhhhhhhhhHhhhhhh
hhhhhhhhHhhhhhhhhhhhhhHhhhhhhhhhhhhhHhhhHhhhhhhhhhhhhhhhHhhhhhHhhhhhHhhhhhhhhhhHhhhhhhhhhhhhhhhhhhhhhhHhhhhhHhhhhhhhhhh
hhhhhhhhhhhhHhhhhhhhhhhhHhhhhhhhhHhhhhhhhhhhhhhhhhhhhHhhhhhHhhhhhhhhhhhhhhhhhhhHhhHhhhhhhHhhhhhhhhhhhhhhhHhhHhhhhhhh
hhHhhhhhhhhhhhhhhhhhhHhhhhhhhhhhhhhhhhhhhhhhhhhhhhhhhhhhhhhHhhhhhhhhhhhhhhhhhhhhhhhhhHhhhhhhhhhHhhHhhhhhhhhhhhhhhHhhhhHhhhhh
hhHhhhhhhhhhHhhhhHhhhHhhhhhhHhhhhhhhhhHhhHhhhhhhhhhhhhhhhhhhhhhhhhhhhhhhhhhhhh

C. Initial Analysis of cold spots:

cccccccccccccccccccccccccccccccccccccccccccccccccccccCcccccCcCccCcCccCcCccccccccccccCcccccccccCccccccCCcCc
cccCcCcCcCcccccccCCcccccccccccccccccccccccccCcccCccccccccccccccccccccccccccccccccccccccccccccccccccccCccc
ccccccccccccccccCcccccccccccCcCccccccccCccccCcCcccccccccCCCCcccccCCcccccCcccccccccccccccccccccCccccccCcccccccc
ccccccccccCccccccCcCcCccccccccccccccccccCcccccccccccCcCccccccccccCcCCcccccccccccCcccccccccCCCCCcccccccccccccCcccc
cCcCCCcCccccccccccccccccccccccccccccccccccccccccccccccccccccccccccccccccccccccccccCccccccccccccccccCccc
ccccccCcCcccccccccccccccccccCccccCcccccccccccCcCccccCccccCcCccccccccccccCcCcccccCccccCcccccccccCcCcCccCCccccccCccccC
CccccCccccCCcccccccccccCcccccccCCcccccccccccCcccccccccccCcCCcCcCcccccccccccccccccccccccccccccccccccCcccccccccCcccc
cCcccccccccccccccccccccccccccCCcccccccCccccCcccccCccccccccCcccccccCcCcCCcCcccccccccccCcCcccccccccccccccC
CCCCCccccccccccccCcCccCcccccccccccccccccCcccccCCccccCcccccCcccccccccccccccccCccCcccccccccccccccCcccccccccccccccc
ccCccccccccccccccccccccccccCcccccccccccccccCCcccccccCcccccccccccccccCcccccccccccccCcccccccccccccccccccccccccccccCc
cCccccccccCcccccccccccccccccccccccccccccCCcccccCcCccccCcCccCcCccccccccccccCcCccccccCccccCccccccccccccCccccccccccccccc
ccccCcccccccccccccccccccCcccCccccCCccccccccccccccCccccccccCcccccCcCcCcccccCcccccc

FIG. 31

NisC

A. Output polynucleotide Sequence (SEQ ID NO: 40)

ATGAGAATAATGATGAATAAGAAGAATATTAAGAGGAATGTCGAGAAGATTATCGCCCAGTGGGACGAGAGGACTCGGAAGAACAAAGAGAACTTTGACTTCGGGGA
GCTCACTCTGAGTACCGGTCTCCCCGGGATTATCCTCATGCTCGCCGAGCTCAAGAATAAAGACAACTCAAAAATTTACCAAAAGAAGATCGACAACTATATAGAGT
ACATCGTCTCTAAGCTCTCTACCTATGGGCTCCTCACGGGGTCTTTGTACTCGGGGGCCGCCGGGATAGCCCTCTCAATACTCCATCTCCGAGAGGACGACGAGAAA
TACAAAAATCTCCTCGACTCTCTCAACCGGTACATCGAGTATTTCGTCAGGGAGAAGATTGAGGGGTTCAATCTCGAGAATATCACCCCCCCCGACTATGATGTAAT
TGAGGGACTCTCAGGGATACTCTCATATCTCCTCCTCATCAATGACGAGCAGTATGACGACCTCAAGATTCTCATCATCAACTTTCTCTCCAATCTCACTAAAGAGA
ATAATGGGCTCATCTCCCTCTACATCAAGAGCGAGAATCAGATGTCCCAGTCAGAGTCTGAGATGTACCCCCTCGGGTGTCTCAATATGGGGCTGGCTCATGGTCTC
GCCGGGGTCGGGTGCATCCTCGCCTACGCCCATATAAAGGGGTACTCCAACGAGGCCTCCCTCTCGGCCCTCCAGAAGATCATCTTTATTTACGAGAAGTTCGAGCT
CGAGAGAAAAAAACAGTTCCTCTGGAAAGATGGTTTGGTCGCCGACGAGCTCAAGAAGGAGAAGGTCATCAGGGAGGCCTCTTTTATTAGAGATGCCTGGTGCTATG
GGGGGCCCGGGATCTCTCTCCTCTACCTCTATGGGGGGCTCGCCCTCGACAACGACTATTTTGTCGACAAGGCCGAGAAGATCCTCGAGAGCGCCATGCAGAGGAAA
CTGGGTATAGATAGTTACATGATTTGCCATGGTTACAGTGGGCTCATAGAGATATGCTCCCTCTTCAAGAGACTCCTCAACACAAAGAAATTTGACTCGTACATGGA
GGAGTTCAATGTCAATTCGGAGCAGATCCTCGAGGAGTACGGGGACGAGTCGGGGACAGGGTTTCTCGAGGGGATCTCGGGGTGCATCCTCGTCCTCTCCAAGTTTG
AGTACTCCATCAACTTTACATACTGGAGACAGGCCCTCCTCCTCTTCGACGACTTCCTCAAGGGGGGGAAGAGGAAA

B. Initial Analysis of hot spots hhhhhhhhhhhhhhhhhhhhhhhhhhhhhhhhhhhhhhhhhhhhhhhhhhhhhhhhhhhhhhhhhhhhhhhhhhhhhhhhHhhhhhhhhhHhhhhhhhhhhhhhhhHh
hhhhhhhhhHhHhhhhhhhhhhhhhhhhhhhhhhhhhHhhhhhhhhhHhhhhhhhhhhhhhhhhhhhhHhhhhhhhhhhhHhhhhhhhhhhhhhhhhHhhhhhhhhhhHhHh
hhhhhhhhhhhHhhhhhhHhhhhhhhHhhhhhhhhhhhhhhhhhhHhHhhhhhhhhhhhhhhhhhhhhhHhhhhhhhhhhHhhhhhhhhhhhhhhhhhhhhhhhhhhhhhhhhH
hhhhhhhhhhhhhhhhhhhhhhhHhhhhHhHhhhhhhhHhhhhhhhhhhhhhhhhhhhhhhhhhhhhhHhhhhhhhhhhhhhhhhhhhhhhhhhhhhhhhhhhhhhhhhhhHhhhhhh
hhhhhhhhhhhhhhhhHhhhhhhhhhhhhhhhhhhhhhhhhhhhhhhHhhHhhhhhhhhhhhhhhhhhhhhhhhhhhhhhhhhhhhhhHhhhhhhhhhhhhhhhhhhhhhhhhhhhhhh
hhhhhHhhhhhhhhhhhhhhHhhhhhhhhhhhhhhhhhhhhhhhhhhhhhhhhhhhhhhhhhhhhhHhHhhhhhhhhhhhhhhhhhhhhhhhhhhhhHhhhHhhhhhhhhhhhhhh
hhhhhhhhhhhHhhhhhhhhhhhhhhhhhhhhhhhhhhhhHhHhhhhhhhhhhhhhhhhhhhhhhhhhhhhhhhhhhhhhhhhhhhhhhhhhhhhhhhhhhhhhhHhhhhhHhhhhh
hhhhhhhhhhHhhHhhhhhhhhhhhhhhhhhhHhhhhhhhhhhhhhhhhHhhhhhhhhhhhhhhhhhhhhhhhhhhhhhhhhhhhhhhhhhhhhhhhhHhhhhhhHhhhhhhh
hhhhhhhhhhhhhhhhhhhhhhhhHhhhhhhhhhhhhHhhhhhhhhhhhhhhhhhhhhhhhhhhhhhhhhhhhhhhhhhhhhhhhhhhhhhhhhhhhhhhhhhHhhhhhhhhhHhh
hhHhhhhhhhhhHhhHhhhhhhhhhHhhhhhhHhhHhhhhhhhhHhhhhhhhhhhhhhHhhhhhhhhhhhhhhhhhhhhhhhhhhHhhhhhhhhhhhhhhhhhhhhhhhHhhhhhhhh
hHhhhhhhhhhhhhhhhhhHhhhhhhhhhhhhhhHhhhhhhhhhhhhhhhhhhhhhhhhhhHhhhhhhhhhhhhhhhhhhhhhhhhhhHhhhhhhhhhhhhhhhhhhhhhhHhhhhhhH
hHhhhhhhhhHhhhhHhhhHhhhhhhhhhhhhhhhhhhhhhhhhhhhhhhhhhhhhhhhhhhhhhhhhhhhhhhhh

C. Initial Analysis of cold spots:

ccCcccccccccccccccccccccccccccccCccccccCccCcccccccccccCCcccccCcCcccCcCcccCcCcccccccccccccccCcccccccccCccccccCCcCc
cCcccCccccCcccccccCcCcCCcccCcccccccccCccccccCccCccCccCccccccccccccccccCccccCcccccccccccccccccccccccCcccccccccccccCccc
cccccCcCccccccCcCccccccccccCCcCccCcccccCCcCcccccccccCcccCCCCCcccCccCccccccCCcCcCccccccCcccccccCccccCcCccCccCccCcccccc
cccccccccCccCcçCcCcCcCcccccccccccccccccCccccccccCcccCcCccccccccCcCCcccccccccCccCcccccccccccCCCCCccCcccccccccccccc
cCcCcCcCcCccccCccccccCcCcccccccCccCccCccccccccccCccCccccccccCccCccccccCccCccCcccccccccCccccccccccccccccCcCcccccccCccccccccCccc
cccccCCcCcccccCcCcCccccccccccccCcccCccccccccccCcCccccCccccCcCccccCcCccccCccccccccCCCcCccCcccCcCcccccccCCCccccCcCccccccCcCcc
CccCCcCccCccccccccCccCccccccCCcccccccccCCccccCcccccccCcCCcCcCcCcCccCCCcCccccccccccccccccccccccccCcccccccccCccCc
cCcCcccccccccccccCcccccccccccccccCccCccCccCcccccccCccccccccCcccccCcCcCCcCcccccccccCccccCccccccccccccC
CCCCCCccCccccCcCcCccCccccccCcccccCCCCcCccCCcCccCcccccCccccCcccccccccCccCccccCCcccCcccccccccCccCcCccccCcccccccCcccccc
ccCccccccccccccccccccccCcccccccccccccCCcCcccccCccccccCcCcCcccccccccCcCcCccCccccccccccccccccCcCcccccccccCc
cCccccccccCccccccccCccccccccCccCccCccccccCCcCccCcCccCCcCccccCcccccCccccCcCCccccCccCCcccccccccCccCccCcCccccccccccC
ccccCccccccccccccccccccCcCccccCCCcCccCccCccccccCccCccccccCcccccCCCCCcccccCcccccc

SEQ ID NO: 43

| V C | z-score | Rank |
|---|---|---|
| GTATGC | -14.69 | 2845 |
| GTATGT | -22.60 | 3194 |
| GTCTGC | -34.86 | 3594 |
| GTCTGT | -45.61 | 3844 |
| *GTGTGC* | *-66.96* | *4060* |
| GTGTGT | -60.05 | 4022 |
| GTTTGC | -36.16 | 3623 |
| GTTTGT | -45.26 | 3838 |

| E H | z-score | Rank |
|---|---|---|
| GAACAC | 35.48 | 979 |
| GAACAT | 32.45 | 1065 |
| GAGCAC | 63.17 | 488 |
| GAGCAT | 35.02 | 992 |

| ORF | NAME | AAA | AAC | AAG | AAT | ACA | ACC | ACG |
|---|---|---|---|---|---|---|---|---|
| AAA | AAA | 0.99613734 | 9.72E-05 | 0.00066958 | 0.000108 | 0.00024119 | 0 | 0 |
| AAC | AAC | 0.00088197 | 0.98219866 | 0.00100436 | 0.00311029 | 0 | 0.00072717 | 0 |
| AAG | AAG | 0.00165594 | 0.00119156 | 0.99696891 | 0.00023759 | 0 | 0 | 0.00058318 |
| AAT | AAT | 0.00029519 | 0.00151194 | 0.00024479 | 0.99279667 | 0 | 0 | 0 |
| ACA | ACA | 0.000144 | 0 | 0 | 0 | 0.994467 | 0.00020519 | 0.00051478 |
| ACC | ACC | 0 | 0.00091077 | 0 | 0 | 0.00033839 | 0.9865221 | 0.00104396 |
| ACG | ACG | 0 | 0 | 0.0001296 | 0 | 0.00249471 | 0.00099716 | 0.99694011 |
| ACT | ACT | 0 | 0 | 0 | 0.0001008 | 7.56E-05 | 0.0001476 | 4.32E-05 |
| AGA | AGA | 0.00070557 | 0 | 0 | 0 | 0.00079557 | 0 | 0 |
| AGC | AGC | 0 | 0.01245554 | 0 | 0 | 0 | 0.00968364 | 0 |
| AGG | AGG | 0 | 0 | 0.00026999 | 0 | 0 | 0 | 0.00025559 |
| AGT | AGT | 0 | 0 | 0 | 0.0026459 | 0 | 0 | 0 |
| ATA | ATA | 5.76E-05 | 0 | 0 | 0 | 0.00022319 | 0 | 0 |
| ATC | ATC | 0 | 6.12E-05 | 0 | 0 | 0 | 0.00051478 | 0 |
| ATG | ATG | 0 | 0 | 0.00016199 | 0 | 0 | 0 | 0.00020879 |
| ATT | ATT | 0 | 0 | 0 | 2.88E-05 | 0 | 0 | 0 |
| CAA | CAA | 6.12E-05 | 0 | 0 | 0 | 0 | 0 | 0 |
| CAC | CAC | 0 | 0.000108 | 0 | 0 | 0 | 0 | 0 |
| CAG | CAG | 0 | 0 | 0.00029879 | 0 | 0 | 0 | 0 |
| CAT | CAT | 0 | 0 | 0 | 7.20E-06 | 0 | 0 | 0 |
| CCA | CCA | 0 | 0 | 0 | 0 | 5.04E-05 | 0 | 0 |
| CCC | CCC | 0 | 0 | 0 | 0 | 0 | 8.64E-05 | 0 |
| CCG | CCG | 0 | 0 | 0 | 0 | 0 | 0 | 2.16E-05 |
| CCT | CCT | 0 | 0 | 0 | 0 | 0 | 0 | 0 |
| CGA | CGA | 0 | 0 | 0 | 0 | 0 | 0 | 0 |
| CGC | CGC | 0 | 0 | 0 | 0 | 0 | 0 | 0 |
| CGG | CGG | 0 | 0 | 0 | 0 | 0 | 0 | 0 |
| CGT | CGT | 0 | 0 | 0 | 0 | 0 | 0 | 0 |
| CTA | CTA | 0 | 0 | 0 | 0 | 0 | 0 | 0 |
| CTC | CTC | 0 | 0 | 0 | 0 | 0 | 0 | 0 |
| CTG | CTG | 0 | 0 | 0 | 0 | 0 | 0 | 0 |
| CTT | CTT | 0 | 0 | 0 | 0 | 0 | 0 | 0 |

FIG. 36A-1

| ACT | AGA | AGC | AGG | AGT | ATA | ATC | ATG | ATT |
|---|---|---|---|---|---|---|---|---|
| 0 | 0.00105116 | 0 | 0 | 0 | 7.92E-05 | 0 | 0 | 0 |
| 0 | 0 | 0.00243711 | 0 | 0 | 0 | 0.00023039 | 0 | 0 |
| 0 | 0 | 0 | 0.00417945 | 0 | 0 | 0 | 0.00043198 | 0 |
| 0.00039239 | 0 | 0 | 0 | 0.00064078 | 0 | 0 | 0 | 0.00028079 |
| 0.00027359 | 0.00018359 | 0 | 0 | 0 | 0.00048598 | 0 | 0 | 0 |
| 0.00136435 | 0 | 0.00210952 | 0 | 0 | 0 | 0.00178913 | 0 | 0 |
| 0.00061918 | 0 | 0 | 0.0001296 | 0 | 0 | 0 | 0.00059038 | 0 |
| 0.9892364 | 0 | 0 | 0 | 0.00028799 | 0 | 0 | 0 | 0.00023039 |
| 0 | 0.99555416 | 0.00030599 | 0.00070197 | 8.28E-05 | 0.000108 | 0 | 0 | 0 |
| 0 | 0.00137875 | 0.99292266 | 0.00205192 | 0.00923726 | 0 | 0.00113756 | 0 | 0 |
| 0 | 0.00062278 | 0.00015839 | 0.99172391 | 6.12E-05 | 0 | 0 | 2.16E-05 | 0 |
| 0.00359267 | 0.00076317 | 0.00161634 | 0.00063358 | 0.98752286 | 0 | 0 | 0 | 0.00059038 |
| 0 | 5.40E-05 | 0 | 0 | 0 | 0.99552537 | 0.00023759 | 0.00096117 | 0.00034559 |
| 0 | 0 | 0.0001116 | 0 | 0 | 0.00017279 | 0.99413942 | 0.00059758 | 0.00106916 |
| 0 | 0 | 0 | 7.92E-05 | 0 | 0.00116276 | 0.00046078 | 0.99531657 | 0.00038879 |
| 0.00029879 | 0 | 0 | 0 | 0.00017999 | 0.00038519 | 0.00091077 | 0.00022679 | 0.99629934 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0.0001008 | 0 | 0 | 0 | 0 | 0 | 0 | 0 | 0 |
| 0 | 1.08E-05 | 0 | 0 | 0 | 0 | 0 | 0 | 0 |
| 0 | 0 | 5.40E-05 | 0 | 0 | 0 | 0 | 0 | 0 |
| 0 | 0 | 0 | 1.44E-05 | 0 | 0 | 0 | 0 | 0 |
| 0 | 0 | 0 | 0 | 0.0001008 | 0 | 0 | 0 | 0 |
| 0 | 0 | 0 | 0 | 0 | 1.08E-05 | 0 | 0 | 0 |
| 0 | 0 | 0 | 0 | 0 | 0 | 6.48E-05 | 0 | 0 |
| 0 | 0 | 0 | 0 | 0 | 0 | 0 | 0.00062998 | 0 |
| 0 | 0 | 0 | 0 | 0 | 0 | 0 | 0 | 0.0001476 |

FIG. 36A-2

| | | | | | | | | |
|---|---|---|---|---|---|---|---|---|
| GAA | GAA | 6.12E-05 | 0 | 0 | 0 | 0 | 0 | 0 |
| GAC | GAC | 0 | 0.00030959 | 0 | 0 | 0 | 0 | 0 |
| GAG | GAG | 0 | 0 | 0.00025199 | 0 | 0 | 0 | 0 |
| GAT | GAT | 0 | 0 | 0 | 0.00025199 | 0 | 0 | 0 |
| GCA | GCA | 0 | 0 | 0 | 0 | 0.00124195 | 0 | 0 |
| GCC | GCC | 0 | 0 | 0 | 0 | 0 | 0.00087117 | 0 |
| GCG | GCG | 0 | 0 | 0 | 0 | 0 | 0 | 0.00034919 |
| GCT | GCT | 0 | 0 | 0 | 0 | 0 | 0 | 0 |
| GGA | GGA | 0 | 0 | 0 | 0 | 0 | 0 | 0 |
| GGC | GGC | 0 | 0 | 0 | 0 | 0 | 0 | 0 |
| GGG | GGG | 0 | 0 | 0 | 0 | 0 | 0 | 0 |
| GGT | GGT | 0 | 0 | 0 | 0 | 0 | 0 | 0 |
| GTA | GTA | 0 | 0 | 0 | 0 | 0 | 0 | 0 |
| GTC | GTC | 0 | 0 | 0 | 0 | 0 | 0 | 0 |
| GTG | GTG | 0 | 0 | 0 | 0 | 0 | 0 | 0 |
| GTT | GTT | 0 | 0 | 0 | 0 | 0 | 0 | 0 |
| TAA | TAA | 0 | 0 | 0 | 0 | 0 | 0 | 0 |
| TAC | TAC | 0 | 0.00115556 | 0 | 0 | 0 | 0 | 0 |
| TAG | TAG | 0 | 0 | 0 | 0 | 0 | 0 | 0 |
| TAT | TAT | 0 | 0 | 0 | 0.00071277 | 0 | 0 | 0 |
| TCA | TCA | 0 | 0 | 0 | 0 | 7.20E-05 | 0 | 0 |
| TCC | TCC | 0 | 0 | 0 | 0 | 0 | 0.00024479 | 0 |
| TCG | TCG | 0 | 0 | 0 | 0 | 0 | 0 | 3.96E-05 |
| TCT | TCT | 0 | 0 | 0 | 0 | 0 | 0 | 0 |
| TGA | TGA | 0 | 0 | 0 | 0 | 0 | 0 | 0 |
| TGC | TGC | 0 | 0 | 0 | 0 | 0 | 0 | 0 |
| TGG | TGG | 0 | 0 | 0 | 0 | 0 | 0 | 0 |
| TGT | TGT | 0 | 0 | 0 | 0 | 0 | 0 | 0 |
| TTA | TTA | 0 | 0 | 0 | 0 | 0 | 0 | 0 |
| TTC | TTC | 0 | 0 | 0 | 0 | 0 | 0 | 0 |
| TTG | TTG | 0 | 0 | 0 | 0 | 0 | 0 | 0 |
| TTT | TTT | 0 | 0 | 0 | 0 | 0 | 0 | 0 |

FIG. 36A-3

| | | | | | | | | |
|---|---|---|---|---|---|---|---|---|
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0.00393826 | 0 | 0 | 0 | 0 | 0 | 0 | 0 | 0 |
| 0 | 0.00038159 | 0 | 0 | 0 | 0 | 0 | 0 | 0 |
| 0 | 0 | 0.00024479 | 0 | 0 | 0 | 0 | 0 | 0 |
| 0 | 0 | 0 | 0.00037079 | 0 | 0 | 0 | 0 | 0 |
| 0 | 0 | 0 | 0 | 0.00183233 | 0 | 0 | 0 | 0 |
| 0 | 0 | 0 | 0 | 0 | 0.00201233 | 0 | 0 | 0 |
| 0 | 0 | 0 | 0 | 0 | 0 | 0.00072357 | 0 | 0 |
| 0 | 0 | 0 | 0 | 0 | 0 | 0 | 0.00117356 | 0 |
| 0 | 0 | 0 | 0 | 0 | 0 | 0 | 0 | 0.00058678 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0.00018359 | 0 | 0 | 0 | 0 | 0 | 0 | 0 | 0 |
| 0 | 0 | 0 | 0 | 0 | 0 | 0 | 0 | 0 |
| 0 | 0 | 3.96E-05 | 0 | 0 | 0 | 0 | 0 | 0 |
| 0 | 0 | 0 | 0.0001152 | 0 | 0 | 0 | 0 | 0 |
| 0 | 0 | 0 | 0 | 5.40E-05 | 0 | 0 | 0 | 0 |
| 0 | 0 | 0 | 0 | 0 | 5.76E-05 | 0 | 0 | 0 |
| 0 | 0 | 0 | 0 | 0 | 0 | 0.00030599 | 0 | 0 |
| 0 | 0 | 0 | 0 | 0 | 0 | 0 | 5.04E-05 | 0 |
| 0 | 0 | 0 | 0 | 0 | 0 | 0 | 0 | 6.12E-05 |

FIG. 36A-4

| ORF | NAME | CAA | CAC | CAG | CAT | CCA | CCC | CCG |
|---|---|---|---|---|---|---|---|---|
| AAA | AAA | 0.000255591 | 0 | 0 | 0 | 0 | 0 | 0 |
| AAC | AAC | 0 | 0.000673175 | 0 | 0 | 0 | 0 | 0 |
| AAG | AAG | 0 | 0 | 0.001418348 | 0 | 0 | 0 | 0 |
| AAT | AAT | 0 | 0 | 0 | 0.000183593 | 0 | 0 | 0 |
| ACA | ACA | 0 | 0 | 0 | 0 | 0.000169194 | 0 | 0 |
| ACC | ACC | 0 | 0 | 0 | 0 | 0 | 0.000482382 | 0 |
| ACG | ACG | 0 | 0 | 0 | 0 | 0 | 0 | 3.96E-05 |
| ACT | ACT | 0 | 0 | 0 | 0 | 0 | 0 | 0 |
| AGA | AGA | 0 | 0 | 0 | 0 | 0 | 0 | 0 |
| AGC | AGC | 0 | 0 | 0 | 0 | 0 | 0 | 0 |
| AGG | AGG | 0 | 0 | 0 | 0 | 0 | 0 | 0 |
| AGT | AGT | 0 | 0 | 0 | 0 | 0 | 0 | 0 |
| ATA | ATA | 0 | 0 | 0 | 0 | 0 | 0 | 0 |
| ATC | ATC | 0 | 0 | 0 | 0 | 0 | 0 | 0 |
| ATG | ATG | 0 | 0 | 0 | 0 | 0 | 0 | 0 |
| ATT | ATT | 0 | 0 | 0 | 0 | 0 | 0 | 0 |
| CAA | CAA | 0.996626924 | 0.000302389 | 0.000969964 | 0.000111596 | 0.000104396 | 0 | 0 |
| CAC | CAC | 1.44E-05 | 0.995154578 | 0.000100796 | 0.000255591 | 0 | 0.000104396 | 0 |
| CAG | CAG | 0.002753699 | 0.001166357 | 0.995222976 | 0.00026999 | 0 | 0 | 0.000233991 |
| CAT | CAT | 7.92E-05 | 0.000316788 | 3.60E-05 | 0.997235302 | 0 | 0 | 0 |
| CCA | CCA | 1.08E-05 | 0 | 0 | 0 | 0.999049635 | 0.00028079 | 0.000392362 |
| CCC | CCC | 0 | 1.44E-05 | 0 | 0 | 3.96E-05 | 0.997174104 | 8.28E-05 |
| CCG | CCG | 0 | 0 | 0 | 0 | 3.24E-05 | 5.04E-05 | 0.995975346 |
| CCT | CCT | 0 | 0 | 0 | 2.18E-05 | 0.000133195 | 0.000457183 | 0.002401112 |
| CGA | CGA | 0.000118796 | 0 | 0 | 0 | 1.08E-05 | 0 | 0 |
| CGC | CGC | 0 | 7.92E-05 | 0 | 0 | 0 | 3.80E-05 | 0 |
| CGG | CGG | 0 | 0 | 0.000133195 | 0 | 0 | 0 | 1.8E-05 |
| CGT | CGT | 0 | 0 | 0 | 0.000118796 | 0 | 0 | 0 |
| CTA | CTA | 8.64E-05 | 0 | 0 | 0 | 7.56E-05 | 0 | 0 |
| CTC | CTC | 0 | 1.44E-05 | 0 | 0 | 0 | 0.000158394 | 0 |
| CTG | CTG | 0 | 0 | 0.000187193 | 0 | 0 | 0 | 0.000748772 |

FIG. 36B-1

| CCT | CGA | CGC | CGG | CGT | CTA | CTC | CTG | CTT |
|---|---|---|---|---|---|---|---|---|
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 7.20E-05 | 0 | 0 | 0 | 0 | 0 | 0 | 0 | 0 |
| 0 | 0.000597578 | 0 | 0 | 0 | 0 | 0 | 0 | 0 |
| 0 | 0 | 0.000482382 | 0 | 0 | 0 | 0 | 0 | 0 |
| 0 | 0 | 0 | 0.000104396 | 0 | 0 | 0 | 0 | 0 |
| 0 | 0 | 0 | 0 | 0.000719974 | 0 | 0 | 0 | 0 |
| 0 | 0 | 0 | 0 | 0 | 8.64E-05 | 0 | 0 | 0 |
| 0 | 0 | 0 | 0 | 0 | 0 | 0.000435584 | 0 | 0 |
| 0 | 0 | 0 | 0 | 0 | 0 | 0 | 0.000680375 | 0 |
| 0 | 0 | 0 | 0 | 0 | 0 | 0 | 0 | 0.000622777 |
| 0 | 0.000338388 | 0 | 0 | 0 | 0.000104396 | 0 | 0 | 0 |
| 0 | 0 | 0.000111596 | 0 | 0 | 0 | 3.24E-05 | 0 | 0 |
| 0 | 0 | 0 | 0.000993503 | 0 | 0 | 0 | 0.000399585 | 0 |
| 5.76E-05 | 0 | 0 | 0 | 6.12E-05 | 0 | 0 | 0 | 2.02E-05 |
| 0.000190793 | 1.08E-05 | 0 | 0 | 0 | 7.20E-05 | 0 | 0 | 0 |
| 6.12E-05 | 0 | 1.80E-05 | 0 | 0 | 0 | 0.000471583 | 0 | 0 |
| 3.60E-06 | 0 | 0 | 7.20E-06 | 0 | 0 | 0 | 1.44E-05 | 0 |
| 0.998228865 | 0 | 0 | 0 | 3.60E-05 | 0 | 0 | 0 | 0.000111696 |
| 0 | 0.996264884 | 0.000115196 | 0.000331188 | 3.96E-05 | 1.08E-05 | 0 | 0 | 0 |
| 0 | 5.04E-05 | 0.998434058 | 0.000125995 | 0.00226792 | 0 | 3.60E-05 | 0 | 0 |
| 0 | 0.000611977 | 0.00055078 | 0.997800481 | 0.000100796 | 0 | 0 | 3.6E-06 | 0 |
| 1.08E-05 | 1.44E-05 | 8.64E-06 | 1.80E-05 | 0.998268464 | 0 | 0 | 0 | 1.80E-5 |
| 0 | 7.20E-06 | 0 | 0 | 0 | 0.995420969 | 6.12E-05 | 0.000251991 | 0.000100796 |
| 0 | 0 | 5.40E-05 | 0 | 0 | 9.72E-05 | 0.99510418 | 0.000244791 | 0.000208792 |
| 0 | 0 | 0 | 9.72E-05 | 0 | 0.002951891 | 0.001738736 | 0.996486529 | 0.000863968 |

FIG. 36B-2

| | | | | | | | | |
|---|---|---|---|---|---|---|---|---|
| CTT | CTT | 0 | 0 | 0 | 7.20E-06 | 0 | 0 | 0 |
| GAA | GAA | 5.40E-05 | 0 | 0 | 0 | 0 | 0 | 0 |
| GAC | GAC | 0 | 0.000115196 | 0 | 0 | 0 | 0 | 0 |
| GAG | GAG | 0 | 0 | 0.001871931 | 0 | 0 | 0 | 0 |
| GAT | GAT | 0 | 0 | 0 | 9.00E-05 | 0 | 0 | 0 |
| GCA | GCA | 0 | 0 | 0 | 0 | 0.000305969 | 0 | 0 |
| GCC | GCC | 0 | 0 | 0 | 0 | 0 | 0.000338388 | 0 |
| GCG | GCG | 0 | 0 | 0 | 0 | 0 | 0 | 2.18E-05 |
| GCT | GCT | 0 | 0 | 0 | 0 | 0 | 0 | 0 |
| GGA | GGA | 0 | 0 | 0 | 0 | 0 | 0 | 0 |
| GGC | GGC | 0 | 0 | 0 | 0 | 0 | 0 | 0 |
| GGG | GGG | 0 | 0 | 0 | 0 | 0 | 0 | 0 |
| GGT | GGT | 0 | 0 | 0 | 0 | 0 | 0 | 0 |
| GTA | GTA | 0 | 0 | 0 | 0 | 0 | 0 | 0 |
| GTC | GTC | 0 | 0 | 0 | 0 | 0 | 0 | 0 |
| GTG | GTG | 0 | 0 | 0 | 0 | 0 | 0 | 0 |
| GTT | GTT | 0 | 0 | 0 | 0 | 0 | 0 | 0 |
| TAA | TAA | 0 | 0 | 0 | 0 | 0 | 0 | 0 |
| TAC | TAC | 0 | 0.00216352 | 0 | 0 | 0 | 0 | 0 |
| TAG | TAG | 0 | 0 | 3.96E-05 | 0 | 0 | 0 | 0 |
| TAT | TAT | 0 | 0 | 0 | 0.001708337 | 0 | 0 | 0 |
| TCA | TCA | 0 | 0 | 0 | 0 | 7.92E-05 | 0 | 0 |
| TCC | TCC | 0 | 0 | 0 | 0 | 0 | 0.000917968 | 0 |
| TCG | TCG | 0 | 0 | 0 | 0 | 0 | 0 | 8.64E-05 |
| TCT | TCT | 0 | 0 | 0 | 0 | 0 | 0 | 0 |
| TGA | TGA | 0 | 0 | 0 | 0 | 0 | 0 | 0 |
| TGC | TGC | 0 | 0 | 0 | 0 | 0 | 0 | 0 |
| TGG | TGG | 0 | 0 | 0 | 0 | 0 | 0 | 0 |
| TGT | TGT | 0 | 0 | 0 | 0 | 0 | 0 | 0 |
| TTA | TTA | 0 | 0 | 0 | 0 | 0 | 0 | 0 |
| TTC | TTC | 0 | 0 | 0 | 0 | 0 | 0 | 0 |
| TTG | TTG | 0 | 0 | 0 | 0 | 0 | 0 | 0 |
| TTT | TTT | 0 | 0 | 0 | 0 | 0 | 0 | 0 |

FIG. 36B-3

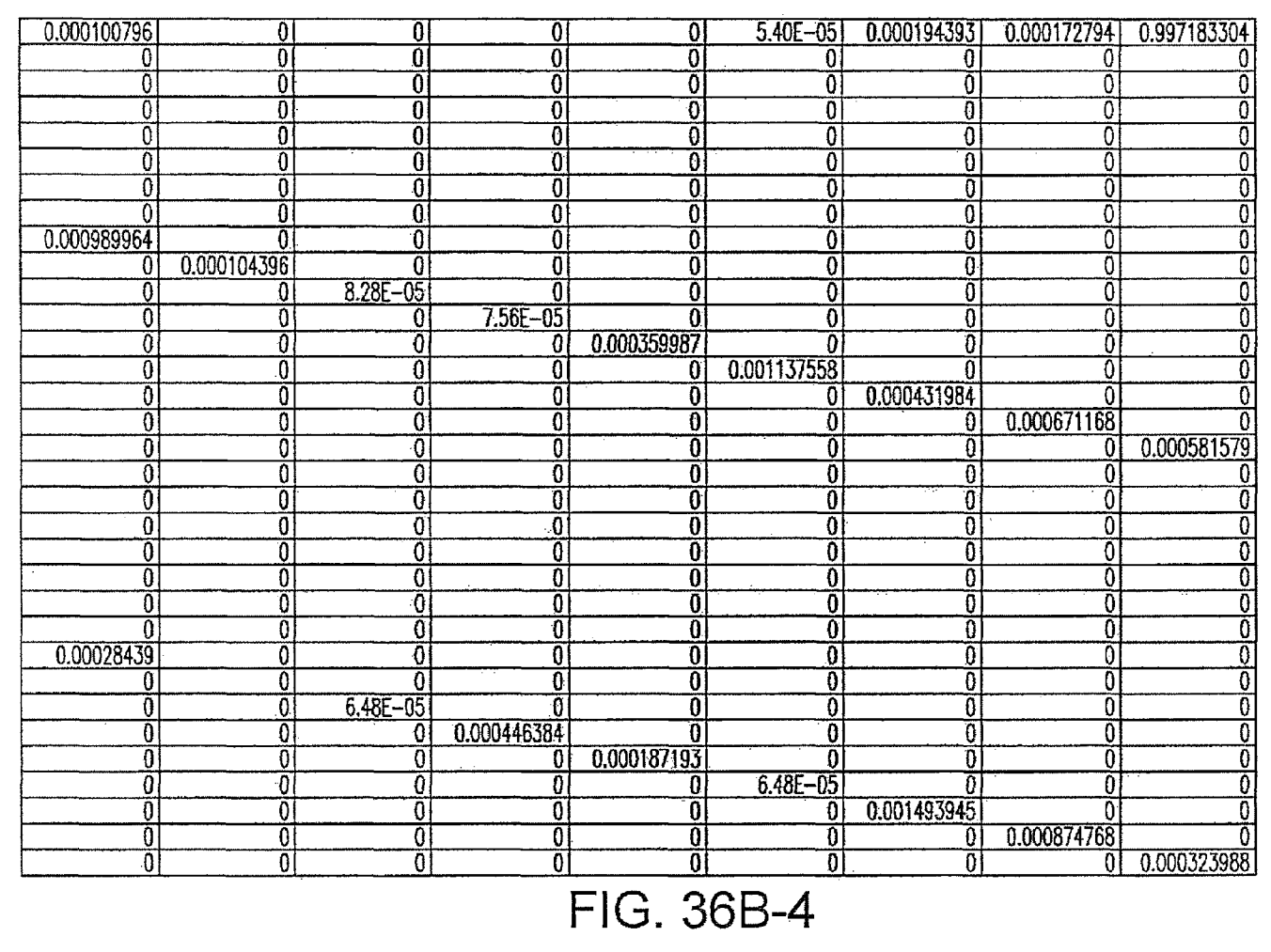

| | | | | | | | | |
|---|---|---|---|---|---|---|---|---|
| 0.000100796 | 0 | 0 | 0 | 0 | 5.40E-05 | 0.000194393 | 0.000172794 | 0.997183304 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0.000989964 | 0 | 0 | 0 | 0 | 0 | 0 | 0 | 0 |
| 0 | 0.000104396 | 0 | 0 | 0 | 0 | 0 | 0 | 0 |
| 0 | 0 | 8.28E-05 | 0 | 0 | 0 | 0 | 0 | 0 |
| 0 | 0 | 0 | 7.56E-05 | 0 | 0 | 0 | 0 | 0 |
| 0 | 0 | 0 | 0 | 0.000359987 | 0 | 0 | 0 | 0 |
| 0 | 0 | 0 | 0 | 0 | 0.001137558 | 0 | 0 | 0 |
| 0 | 0 | 0 | 0 | 0 | 0 | 0.000431984 | 0 | 0 |
| 0 | 0 | 0 | 0 | 0 | 0 | 0 | 0.000671168 | 0 |
| 0 | 0 | 0 | 0 | 0 | 0 | 0 | 0 | 0.000581579 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0.00028439 | 0 | 0 | 0 | 0 | 0 | 0 | 0 | 0 |
| 0 | 0 | 0 | 0 | 0 | 0 | 0 | 0 | 0 |
| 0 | 0 | 6.48E-05 | 0 | 0 | 0 | 0 | 0 | 0 |
| 0 | 0 | 0 | 0.000446384 | 0 | 0 | 0 | 0 | 0 |
| 0 | 0 | 0 | 0 | 0.000187193 | 0 | 0 | 0 | 0 |
| 0 | 0 | 0 | 0 | 0 | 6.48E-05 | 0 | 0 | 0 |
| 0 | 0 | 0 | 0 | 0 | 0 | 0.001493945 | 0 | 0 |
| 0 | 0 | 0 | 0 | 0 | 0 | 0 | 0.000874768 | 0 |
| 0 | 0 | 0 | 0 | 0 | 0 | 0 | 0 | 0.000323988 |

FIG. 36B-4

| ORF | NAME | GAA | GAC | GAG | GAT | GCA | GCC | GCG |
|---|---|---|---|---|---|---|---|---|
| AAA | AAA | 0.000565179 | 0 | 0 | 0 | 0 | 0 | 0 |
| AAC | AAC | 0 | 0.001994327 | 0 | 0 | 0 | 0 | 0 |
| AAG | AAG | 0 | 0 | 0.001789134 | 0 | 0 | 0 | 0 |
| AAT | AAT | 0 | 0 | 0 | 0.000669575 | 0 | 0 | 0 |
| ACA | ACA | 0 | 0 | 0 | 0 | 0.000644376 | 0 | 0 |
| ACC | ACC | 0 | 0 | 0 | 0 | 0 | 0.001472346 | 0 |
| ACG | ACG | 0 | 0 | 0 | 0 | 0 | 0 | 0.000608378 |
| ACT | ACT | 0 | 0 | 0 | 0 | 0 | 0 | 0 |
| AGA | AGA | 0 | 0 | 0 | 0 | 0 | 0 | 0 |
| AGC | AGC | 0 | 0 | 0 | 0 | 0 | 0 | 0 |
| AGG | AGG | 0 | 0 | 0 | 0 | 0 | 0 | 0 |
| AGT | AGT | 0 | 0 | 0 | 0 | 0 | 0 | 0 |
| ATA | ATA | 0 | 0 | 0 | 0 | 0 | 0 | 0 |
| ATC | ATC | 0 | 0 | 0 | 0 | 0 | 0 | 0 |
| ATG | ATG | 0 | 0 | 0 | 0 | 0 | 0 | 0 |
| ATT | ATT | 0 | 0 | 0 | 0 | 0 | 0 | 0 |
| CAA | CAA | 0.000590378 | 0 | 0 | 0 | 0 | 0 | 0 |
| CAC | CAC | 0 | 5.40E-05 | 0 | 0 | 0 | 0 | 0 |
| CAG | CAG | 0 | 0 | 0.001306752 | 0 | 0 | 0 | 0 |
| CAT | CAT | 0 | 0 | 0 | 7.20E-05 | 0 | 0 | 0 |
| CCA | CCA | 0 | 0 | 0 | 0 | 0.000230392 | 0 | 0 |
| CCC | CCC | 0 | 0 | 0 | 0 | 0 | 0.000255591 | 0 |
| CCG | CCG | 0 | 0 | 0 | 0 | 0 | 0 | 2.16E-05 |
| CCT | CCT | 0 | 0 | 0 | 0 | 0 | 0 | 0 |
| CGA | CGA | 0 | 0 | 0 | 0 | 0 | 0 | 0 |
| CGC | CGC | 0 | 0 | 0 | 0 | 0 | 0 | 0 |
| CGG | CGG | 0 | 0 | 0 | 0 | 0 | 0 | 0 |
| CGT | CGT | 0 | 0 | 0 | 0 | 0 | 0 | 0 |
| CTA | CTA | 0 | 0 | 0 | 0 | 0 | 0 | 0 |
| CTC | CTC | 0 | 0 | 0 | 0 | 0 | 0 | 0 |
| CTG | CTG | 0 | 0 | 0 | 0 | 0 | 0 | 0 |
| CTT | CTT | 0 | 0 | 0 | 0 | 0 | 0 | 0 |

FIG. 36C-1

| GCT | GGA | GGC | GGG | GGT | GTA | GTC | GTG | GTT |
|---|---|---|---|---|---|---|---|---|
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0.00028439 | 0 | 0 | 0 | 0 | 0 | 0 | 0 | 0 |
| 0 | 0.000640776 | 0 | 0 | 0 | 0 | 0 | 0 | 0 |
| 0 | 0 | 0.002768298 | 0 | 0 | 0 | 0 | 0 | 0 |
| 0 | 0 | 0 | 0.000298789 | 0 | 0 | 0 | 0 | 0 |
| 0 | 0 | 0 | 0 | 0.003063487 | 0 | 0 | 0 | 0 |
| 0 | 0 | 0 | 0 | 0 | 0.000179993 | 0 | 0 | 0 |
| 0 | 0 | 0 | 0 | 0 | 0 | 0.00217792 | 0 | 0 |
| 0 | 0 | 0 | 0 | 0 | 0 | 0 | 0.001177157 | 0 |
| 0 | 0 | 0 | 0 | 0 | 0 | 0 | 0 | 0.000701974 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0.000122395 | 0 | 0 | 0 | 0 | 0 | 0 | 0 | 0 |
| 0 | 2.16E-05 | 0 | 0 | 0 | 0 | 0 | 0 | 0 |
| 0 | 0 | 7.20E-06 | 0 | 0 | 0 | 0 | 0 | 0 |
| 0 | 0 | 0 | 7.20E-6 | 0 | 0 | 0 | 0 | 0 |
| 0 | 0 | 0 | 0 | 2.88E-05 | 0 | 0 | 0 | 0 |
| 0 | 0 | 0 | 0 | 0 | 3.24E-05 | 0 | 0 | 0 |
| 0 | 0 | 0 | 0 | 0 | 0 | 0.000377986 | 0 | 0 |
| 0 | 0 | 0 | 0 | 0 | 0 | 0 | 0.002545106 | 0 |
| 0 | 0 | 0 | 0 | 0 | 0 | 0 | 0 | 2.68E-05 |

FIG. 36C-2

| | | | | | | | | |
|---|---|---|---|---|---|---|---|---|
| GAA | GAA | 0.993790229 | 7.92E-05 | 0.000356387 | 7.92E-05 | 3.60E-05 | 0 | 0 |
| GAC | GAC | 0.000122395 | 0.99075554 | 0.000442784 | 0.000585179 | 0 | 0.000223192 | 0 |
| GAG | GAG | 0.003337077 | 0.002775498 | 0.994722594 | 0.000338388 | 0 | 0 | 0.000296789 |
| GAT | GAT | 0.000237591 | 0.000496782 | 9.72E-05 | 0.99374703 | 0 | 0 | 0 |
| GCA | GCA | 0.000496782 | 0 | 0 | 0 | 0.99673132 | 0.000313188 | 0.001004363 |
| GCC | GCC | 0 | 0.000691175 | 0 | 0 | 0.12E-05 | 0.992681469 | 0.000230392 |
| GCG | GCG | 0 | 0 | 2.16E-05 | 0 | 0.000485982 | 0.000748772 | 0.996558527 |
| GCT | GCT | 0 | 0 | 0 | 0.000302389 | 0.000435584 | 0.001767535 | 0.000201593 |
| GGA | GGA | 0.000568779 | 0 | 0 | 0 | 0.000496782 | 0 | 0 |
| GGC | GGC | 0 | 0.002141921 | 0 | 0 | 0 | 0.001231155 | 0 |
| GGG | GGG | 0 | 0 | 0.000874768 | 0 | 0 | 0 | 0.000359987 |
| GGT | GGT | 0 | 0 | 0 | 0.003668265 | 0 | 0 | 0 |
| GTA | GTA | 0.000291589 | 0 | 0 | 0 | 0.000460783 | 0 | 0 |
| GTC | GTC | 0 | 3.96E-05 | 0 | 0 | 0 | 0.000691175 | 0 |
| GTG | GTG | 0 | 0 | 0.000388786 | 0 | 0 | 0 | 0.000683975 |
| GTT | GTT | 0 | 0 | 0 | 4.68E-05 | 0 | 0 | 0 |
| TAA | TAA | 0 | 0 | 0 | 0 | 0 | 0 | 0 |
| TAC | TAC | 0 | 0.000971964 | 0 | 0 | 0 | 0 | 0 |
| TAG | TAG | 0 | 0 | 0 | 0 | 0 | 0 | 0 |
| TAT | TAT | 0 | 0 | 0 | 0.000511181 | 0 | 0 | 0 |
| TCA | TCA | 0 | 0 | 0 | 0 | 0.000417585 | 0 | 0 |
| TCC | TCC | 0 | 0 | 0 | 0 | 0 | 0.000615577 | 0 |
| TCG | TCG | 0 | 0 | 0 | 0 | 0 | 0 | 3.24E-05 |
| TCT | TCT | 0 | 0 | 0 | 0 | 0 | 0 | 0 |
| TGA | TGA | 0 | 0 | 0 | 0 | 0 | 0 | 0 |
| TGC | TGC | 0 | 0 | 0 | 0 | 0 | 0 | 0 |
| TGG | TGG | 0 | 0 | 0 | 0 | 0 | 0 | 0 |
| TGT | TGT | 0 | 0 | 0 | 0 | 0 | 0 | 0 |
| TTA | TTA | 0 | 0 | 0 | 0 | 0 | 0 | 0 |
| TTC | TTC | 0 | 0 | 0 | 0 | 0 | 0 | 0 |
| TTG | TTG | 0 | 0 | 0 | 0 | 0 | 0 | 0 |
| TTT | TTT | 0 | 0 | 0 | 0 | 0 | 0 | 0 |

FIG. 36C-3

| | | | | | | | | |
|---|---|---|---|---|---|---|---|---|
| 0 | 4.68E-05 | 0 | 0 | 0 | 3.60E-06 | 0 | 0 | 0 |
| 0 | 0 | 0.000709174 | 0 | 0 | 0 | 0.000104396 | 0 | 0 |
| 0 | 0 | 0 | 0.00053638 | 0 | 0 | 0 | 0.000115196 | 0 |
| 9.00E-5 | 0 | 0 | 0 | 0.000223192 | 0 | 0 | 0 | 1.44E-05 |
| 0.000482382 | 0.000428384 | 0 | 0 | 0 | 0.001529944 | 0 | 0 | 0 |
| 0.001033162 | 0 | 0.001799934 | 0 | 0 | 0 | 0.003394675 | 0 | 0 |
| 4.68E-05 | 0 | 0 | 0.000136795 | 0 | 0 | 0 | 0.0006277 | 0 |
| 0.995258974 | 0 | 0 | 0 | 0.004139848 | 0 | 0 | 0 | 0.002350713 |
| 0 | 0.99436607 | 0.000352787 | 0.001717137 | 0.000233991 | 2.88E-05 | 0 | 0 | 0 |
| 0 | 0.000107996 | 0.991664306 | 0.000367186 | 0.000471583 | 0 | 0.000244791 | 0 | 0 |
| 0 | 0.002879894 | 0.000878368 | 0.995894558 | 0.000525581 | 0 | 0 | 6.48E-05 | 0 |
| 0.002253517 | 0.00134995 | 0.001702737 | 0.000925166 | 0.991189525 | 0 | 0 | 0 | 0.000716374 |
| 0 | 0.000161994 | 0 | 0 | 0 | 0.996215776 | 0.000939565 | 0.001558743 | 0.001205956 |
| 0 | 0 | 9.00E-5 | 0 | 0 | 0.000298789 | 0.969923971 | 0.00027719 | 0.00061717 |
| 0 | 0 | 0 | 0.000205192 | 0 | 0.002609904 | 0.001727936 | 0.991601509 | 0.001108759 |
| .000176394 | 0 | 0 | 0 | 0.000100796 | 9.36E-05 | 0.000475183 | 0.000489582 | 0.992983858 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0.000251991 | 0 | 0 | 0 | 0 | 0 | 0 | 0 | 0 |
| 0 | 0 | 0 | 0 | 0 | 0 | 0 | 0 | 0 |
| 0 | 0 | 7.20E-06 | 0 | 0 | 0 | 0 | 0 | 0 |
| 0 | 0 | 0 | 0.000111596 | 0 | 0 | 0 | 0 | 0 |
| 0 | 0 | 0 | 0 | 4.32E-05 | 0 | 0 | 0 | 0 |
| 0 | 0 | 0 | 0 | 0 | 7.20E-06 | 0 | 0 | 0 |
| 0 | 0 | 0 | 0 | 0 | 0 | 0.000633577 | 0 | 0 |
| 0 | 0 | 0 | 0 | 0 | 0 | 0 | 0.00136795 | 0 |
| 0 | 0 | 0 | 0 | 0 | 0 | 0 | 0 | 7.20E-05 |

FIG. 36C-4

| ORF | NAME | TAA | TAC | TAG | TAT | TCA | TCC | TCG |
|---|---|---|---|---|---|---|---|---|
| AAA | AAA | 7.20E−06 | 0 | 0 | 0 | 0 | 0 | 0 |
| AAC | AAC | 0 | 0.000485982 | 0 | 0 | 0 | 0 | 0 |
| AAG | AAG | 0 | 0 | 2.88E−05 | 0 | 0 | 0 | 0 |
| AAT | AAT | 0 | 0 | 0 | 0.000298789 | 0 | 0 | 0 |
| ACA | ACA | 0 | 0 | 0 | 0 | 0.00027359 | 0 | 0 |
| ACC | ACC | 0 | 0 | 0 | 0 | 0 | 0.000907167 | 0 |
| ACG | ACG | 0 | 0 | 0 | 0 | 0 | 0 | 0.000331188 |
| ACT | ACT | 0 | 0 | 0 | 0 | 0 | 0 | 0 |
| AGA | AGA | 0 | 0 | 0 | 0 | 0 | 0 | 0 |
| AGC | AGC | 0 | 0 | 0 | 0 | 0 | 0 | 0 |
| AGG | AGG | 0 | 0 | 0 | 0 | 0 | 0 | 0 |
| AGT | AGT | 0 | 0 | 0 | 0 | 0 | 0 | 0 |
| ATA | ATA | 0 | 0 | 0 | 0 | 0 | 0 | 0 |
| ATC | ATC | 0 | 0 | 0 | 0 | 0 | 0 | 0 |
| ATG | ATG | 0 | 0 | 0 | 0 | 0 | 0 | 0 |
| ATT | ATT | 0 | 0 | 0 | 0 | 0 | 0 | 0 |
| CAA | CAA | 7.56E−05 | 0 | 0 | 0 | 0 | 0 | 0 |
| CAC | CAC | 0 | 0.00302389 | 0 | 0 | 0 | 0 | 0 |
| CAG | CAG | 0 | 0 | 0.000118796 | 0 | 0 | 0 | 0 |
| CAT | CAT | 0 | 0 | 0 | 9.00E−05 | 0 | 0 | 0 |
| CCA | CCA | 0 | 0 | 0 | 0 | 0.000140395 | 0 | 0 |
| CCC | CCC | 0 | 0 | 0 | 0 | 0 | 0.0647976 | 0 |
| CCG | CCG | 0 | 0 | 0 | 0 | 0 | 0 | 0.000129595 |
| CCT | CCT | 0 | 0 | 0 | 0 | 0 | 0 | 0 |
| CGA | CGA | 0 | 0 | 0 | 0 | 0 | 0 | 0 |
| CGC | CGC | 0 | 0 | 0 | 0 | 0 | 0 | 0 |
| CGG | CGG | 0 | 0 | 0 | 0 | 0 | 0 | 0 |
| CGT | CGT | 0 | 0 | 0 | 0 | 0 | 0 | 0 |
| CTA | CTA | 0 | 0 | 0 | 0 | 0 | 0 | 0 |
| CTC | CTC | 0 | 0 | 0 | 0 | 0 | 0 | 0 |
| CTG | CTG | 0 | 0 | 0 | 0 | 0 | 0 | 0 |
| CTT | CTT | 0 | 0 | 0 | 0 | 0 | 0 | 0 |

FIG. 36D-1

| TCT | TGA | TGC | TGG | TGT | TTA | TTC | TTG | TTT |
|---|---|---|---|---|---|---|---|---|
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0.000194393 | 0 | 0 | 0 | 0 | 0 | 0 | 0 | 0 |
| 0 | 5.76E-05 | 0 | 0 | 0 | 0 | 0 | 0 | 0 |
| 0 | 0 | 0.000118796 | 0 | 0 | 0 | 0 | 0 | 0 |
| 0 | 0 | 0 | 5.04E-05 | 0 | 0 | 0 | 0 | 0 |
| 0 | 0 | 0 | 0 | 6.84E-05 | 0 | 0 | 0 | 0 |
| 0 | 0 | 0 | 0 | 0 | 6.12E-05 | 0 | 0 | 0 |
| 0 | 0 | 0 | 0 | 0 | 0 | 0.000503981 | 0 | 0 |
| 0 | 0 | 0 | 0 | 0 | 0 | 0 | 0.000629977 | 0 |
| 0 | 0 | 0 | 0 | 0 | 0 | 0 | 0 | 0.000345587 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0.000449983 | 0 | 0 | 0 | 0 | 0 | 0 | 0 | 0 |
| 0 | 2.52E-05 | 0 | 0 | 0 | 0 | 0 | 0 | 0 |
| 0 | 0 | 0.000100796 | 0 | 0 | 0 | 0 | 0 | 0 |
| 0 | 0 | 0 | 2.16E-05 | 0 | 0 | 0 | 0 | 0 |
| 0 | 0 | 0 | 0 | 6.12E-05 | 0 | 0 | 0 | 0 |
| 0 | 0 | 0 | 0 | 0 | 0.000241191 | 0 | 0 | 0 |
| 0 | 0 | 0 | 0 | 0 | 0 | 0.000572379 | 0 | 0 |
| 0 | 0 | 0 | 0 | 0 | 0 | 0 | 0.005655392 | 0 |
| 0 | 0 | 0 | 0 | 0 | 0 | 0 | 0 | 9.36E-05 |

FIG. 36D-2

| | | | | | | | | |
|---|---|---|---|---|---|---|---|---|
| GAA | GAA | 0.000143995 | 0 | 0 | 0 | 0 | 0 | 0 |
| GAC | GAC | 0 | 5.40E-05 | 0 | 0 | 0 | 0 | 0 |
| GAG | GAG | 0 | 0 | 7.20E-06 | 0 | 0 | 0 | 0 |
| GAT | GAT | 0 | 0 | 0 | 4.32E-05 | 0 | 0 | 0 |
| GCA | GCA | 0 | 0 | 0 | 0 | 0.000457183 | 0 | 0 |
| GCC | GCC | 0 | 0 | 0 | 0 | 0 | 0.000341967 | 0 |
| GCG | GCG | 0 | 0 | 0 | 0 | 0 | 0 | 9.36E-05 |
| GCT | GCT | 0 | 0 | 0 | 0 | 0 | 0 | 0 |
| GGA | GGA | 0 | 0 | 0 | 0 | 0 | 0 | 0 |
| GGC | GGC | 0 | 0 | 0 | 0 | 0 | 0 | 0 |
| GGG | GGG | 0 | 0 | 0 | 0 | 0 | 0 | 0 |
| GGT | GGT | 0 | 0 | 0 | 0 | 0 | 0 | 0 |
| GTA | GTA | 0 | 0 | 0 | 0 | 0 | 0 | 0 |
| GTC | GTC | 0 | 0 | 0 | 0 | 0 | 0 | 0 |
| GTG | GTG | 0 | 0 | 0 | 0 | 0 | 0 | 0 |
| GTT | GTT | 0 | 0 | 0 | 0 | 0 | 0 | 0 |
| TAA | TAA | 0.999640013 | 0 | 0 | 0 | 0 | 0 | 0 |
| TAC | TAC | 7.56E-05 | 0.995892551 | 0.000133195 | 0.005885783 | 0 | 0.001385949 | 0 |
| TAG | TAG | 1.05E-05 | 5.76E-05 | 0.999521218 | 1.08E-05 | 0 | 0 | 7.20E-06 |
| TAT | TAT | 3.24E-05 | 0.002768298 | 2.52E-05 | 0.993390643 | 0 | 0 | 0 |
| TCA | TCA | 3.60E-05 | 0 | 0 | 0 | 0.997804081 | 0.000883975 | 0.000766772 |
| TCC | TCC | 0 | 0.000287969 | 0 | 0 | 0.000424784 | 0.99483779 | 0.000529181 |
| TCG | TCG | 0 | 0 | 1.44E-05 | 0 | 0.000305889 | 7.58E-05 | 0.996853716 |
| TCT | TCT | 0 | 0 | 0 | 0.000118796 | 0.000529181 | 0.000878368 | 0.000914366 |
| TGA | TGA | 0 | 0 | 0 | 0 | 0 | 0 | 0 |
| TGC | TGC | 0 | 1.80E-05 | 0 | 0 | 0 | 7.20E-06 | 0 |
| TGG | TGG | 0 | 0 | 0.000147595 | 0 | 0 | 0 | 0.000107996 |
| TGT | TGT | 0 | 0 | 0 | 0.000107996 | 0 | 0 | 0 |
| TTA | TTA | 1.08E-05 | 0 | 0 | 0 | 6.48E-05 | 0 | 0 |
| TTC | TTC | 0 | 0.000133195 | 0 | 0 | 0 | 0.000233991 | 0 |
| TTG | TTG | 0 | 0 | 3.60E-06 | 0 | 0 | 0 | 0.00026639 |
| TTT | TTT | 0 | 0 | 0 | 5.40E-05 | 0 | 0 | 0 |

FIG. 36D-3

| | | | | | | | | |
|---|---|---|---|---|---|---|---|---|
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0 | 0 | 0 | 0 | 0 | 0 | 0 | 0 | 0 |
| 0.001144758 | 0 | 0 | 0 | 0 | 0 | 0 | 0 | 0 |
| 0 | 1.80E-05 | 0 | 0 | 0 | 0 | 0 | 0 | 0 |
| 0 | 0 | 3.60E-06 | 0 | 0 | 0 | 0 | 0 | 0 |
| 0 | 0 | 0 | 3.96E-05 | 0 | 0 | 0 | 0 | 0 |
| 0 | 0 | 0 | 0 | 3.24E-05 | 0 | 0 | 0 | 0 |
| 0 | 0 | 0 | 0 | 0 | 0.000475183 | 0 | 0 | 0 |
| 0 | 0 | 0 | 0 | 0 | 0 | 0.00129595 | 0 | 0 |
| 0 | 0 | 0 | 0 | 0 | 0 | 0 | 0.000629977 | 0 |
| 0 | 0 | 0 | 0 | 0 | 0 | 0 | 0 | 0.000187193 |
| 0 | 0 | 0 | 0 | 0 | 0 | 0 | 0 | 0 |
| 0 | 0 | 0.000377986 | 0 | 0 | 0 | 0.003311878 | 0 | 0 |
| 0 | 0 | 0 | 2.52E-05 | 0 | 0 | 0 | 0 | 0 |
| 0.001537143 | 0 | 0 | 0 | 0.00053998 | 0 | 0 | 0 | 0.0003769061 |
| 0.000464383 | 7.20E-06 | 0 | 0 | 0 | 0.000215992 | 0 | 0 | 0 |
| 0.001407548 | 0 | 0.000115196 | 0 | 0 | 0 | 0.000712774 | 0 | 0 |
| 0.000140395 | 0 | 0 | 0.000115196 | 0 | 0 | 0 | 2.88E-05 | 0 |
| 0.994474203 | 0 | 0 | 0 | 3.96E-05 | 0 | 0 | 0 | 0.000406785 |
| 0 | 0.99965813 | 0 | 0 | 0 | 0 | 0 | 0 | 0 |
| 0 | 1.06E-05 | 0.998225265 | 2.52E-05 | 0.000215992 | 0 | 1.44E-05 | 0 | 0 |
| 0 | 0.000215992 | 0.00026639 | 0.999546417 | 9.72E-05 | 0 | 0 | 0.000241191 | 0 |
| 6.12E-05 | 1.08E-05 | 0.000701974 | 2.88E-06 | 0.998941639 | 0 | 0 | 0 | 4.32E-05 |
| 0 | 3.60E-06 | 0 | 0 | 0 | 0.998052472 | 1.08E-05 | 1.44E-05 | 6.12E-05 |
| 0 | 0 | 9.00E-05 | 0 | 0 | 0.000205192 | 0.99374703 | 0.000197993 | 0.000699967 |
| 0 | 0 | 0 | 0.000147595 | 0 | 0.000637177 | 0.00194393 | 0.992530275 | 0.000125995 |
| 0.000125995 | 0 | 0 | 0 | 3.60E-06 | 0.000111596 | 0.00080277 | 7.20E-05 | 0.994067418 |

SLSCRASQSI GDNLHWYQQK
SLSCRASQSI GDNLHWYQQK
SLSCRASQSI GDNLHWYQQK
SLSCRASQSI GDNLHWYQQK
SLSCRASQSI GNNLHWYQQK
SLSCRASQSI GDNLHWYQQK
SLSCRASQSI GDNLHWYQQK
SLSCRASQSI GDNLHWYQQK
SLSCRASQSI GDNLHWYQQK
SLSCRASQSI GGNLHWYQQK
SLSCRASQSI GGNLHWYQQK
SLSCRASQSI GGNLHWYQQK
SLSCRASQSI GGNLHWYQQK
SLSCRASQSI GGNLHWYQQK
SLSCRASQSI GGNLHWYQQK

B.

CCAAAGTATT GGCGATAACC
CCAAAGTATT GGCGATAACC
CCAAAGTATT GGCGATAACC
CCAAAGTATT GGCGATAACC
CCAAAGTATT GGCAATAACC
CCAAAGTATT GGCGATAACC
CCAAAGTATT GGCGATAACC
CCAAAGTATT GGCGATAACC
CCAAAGTATT GGCGATAACC
CCAAAGTATT GGCGGTAACC
CCAAAGTATT GGCGGTAACC
CCAAAGTATT GGCGGTAACC

C.

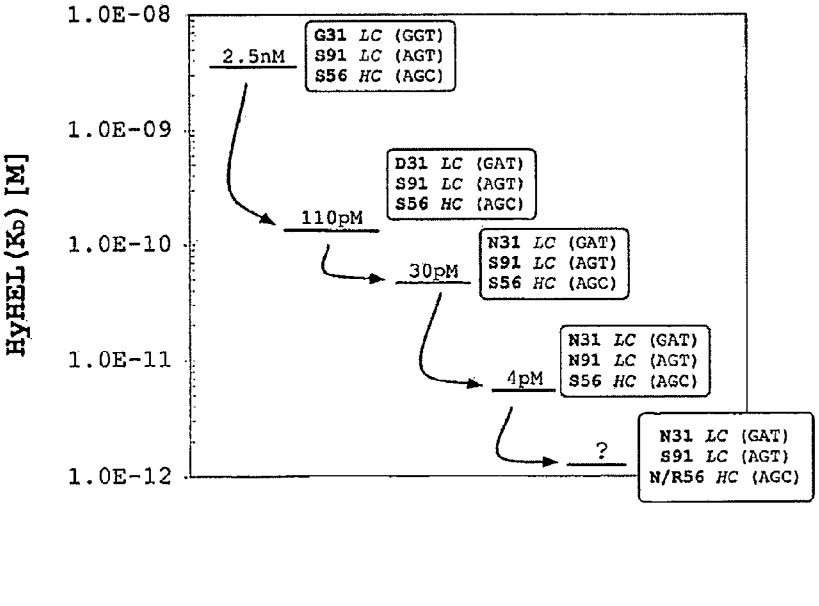

FIG. 51

Unmodified Teal Fluorescent Protein

A. Input DNA Sequence (SEQ ID NO: 458)

ATGGTCTCTAAGGGCGAAGAGACCACTATGGGCGTGATCAAGCCCGACATGAAAATTAAACTGAAGATGGAAGGTAACGTGAACGGCCACGCCTTTGTGATA
GAGGGCGAGGGGGAAGGGAAACCATCGATGGTACCAATACAATCAATCTGGAGGTGAAGGAAGGTGCTCCCCTTCCCTTTTCCTACGACATCCTGACAACAG
CTTTTGCCTATGGTAACCGGGCCTTCACCAAGTACCCGGACGACATCCCCAATTACTCAAGCAGTCATTCCCGGAGGGGTATAGTTGGGAACGCACTATGAC
CTTCGAGGATAAGGGGATTGTCAAGGTCAAGAGCGACATAAGCATGGAGGAAGATTCGTTTATCTATGAGATACACCTGAAGGGTGAAATTTCCCCCCCAAC
GGCCCCGTTATGCAGAAAAAGACCACCGGGTGGACGCCTCCACGGAGCGAATGTACGTCCGCGATGGGGTGCTCAAGGGCGACGTAAAACACAAACTGCTG
CTGGAAGGCGGCGGGCCCACCGTGTTGACTTCAAGACGATTTATCGTGCCAAGAAGGCCGTCAAACTTCCCGACTACCACTTCGTAGATCACAGAATCGAGA
TACTCAACCATGACAAGGATTACAACAAGGTGACCGTCTATGAGAGCCCGTGGCTAGAAACTCCACCGATGGGATGGACGAGTTATATAAA

B. Analysis of hot spots (40 Hot spots)

hhhhhhhhhhhhhhhhhhhhhhhhhhhhhhhhhhhhhhhhHhhhhhhhhhhhhhhhhHhhhhhhhhhhhhHhhhhhhhhhhhhhhhhhhhhhhhhhhhhh
hhhhhhhhhhhhhhhhhhhHhhhhhhhhhHhHhhhhhHhhhhhhhhhhhhhhhhhhhhhhhhhhHhhhhhhhhhhhhhhhhhhhhhhhhhhhhhhhhHhhHh
hhhhHhhhhhhHhhHhhhhhhhhhhhhhhhHhHhhhhhhhhhhhhhhhhhhhhHhhhhhHhhhhhhhhhhhhhhhhhHhhhhHhhhhhhhhhhhhhhhhhhh
hhhhhhhhhhhhhhhhhhhhhhhhhhhhhhhhhhhhhhhhHhhhhhhhhhhhhhhhhhhhhhhhhhhhhhHhhhhhhhhhhhhhhhhhhhhhhhhhhhhhh
hhhhhhhhhhHhhhhhhhhhhhhhhhhhhhhhhhhhhhhhhhhhhhhhhhhhHhhhhhhhhhhhhhhhhHhhhhhhhhhhhhhhhhhHhhhhhHhhHhhHh
hhhhhhhhhhhhhHhhhhhhhhHhhhhhhhhhhhhhhhhhhhhhhhHhhhhhhhhhhhhhhhhHhhhhhhhhhHhhhhhhhhhhhhhhhhhhhhhhhhhhh
HhhhhHhhhhhhhhhhhhhhHhhHhhhhhhhhhhhhhhhhhhhhhhhhhhHhhhhhhHhhhhhhhhhhhhhhhhhhhhhHhhhhhhhhhh C. Analysis of cold spots (103 Cold spots)

cccCcCcccccCCcccccCcCccccccccCCccccccccccCCccCccccccccccccccccccccccccccccccccccccccCCccccCccccccccccc
CcCCccCcCCCccccCccccccccccccccccccccccccccccccccccCcccccccccccccccCcCCccccCcccccccccccCcccccccCccccccc
cccccCccccccccccccCCCcccccccccccccCcccCccCccccCCcccccccccccccccCcccccCcccCcCCcccccccccCccccccccccccCcc
ccccCcccccccCCcccccCcccccCccccCcccCcccccccccccCccccccccccccccccccccCcccccccccccccCccccccccccCCCCCccccc
CCCCccccccccccccccccCccccccCcccCcCccCcCccccccCcccccccccccCccccccccCCccccCccccCCccCcccccccccccccccccccc
ccccccCccCccCCccccccccccccCcccccccCccccccccccccCcccccccCCccCccccccccCccCccccccccccccccccccccccccccCccc
ccCccccccccCcccccccccccccccccccCcccCcccccCcCcccccccCccccccccCcccccccccCcccccCccCccccccccccc

FIG. 52

Hot Teal Fluorescent Protein

A. Output Polynucleotide Sequence: SHM Susceptible (SEQ ID NO: 459)

ATGGTTTCCAAAGGGGAGGAAACAACAATGGGTGTTATAAAACCGGACATGAAGATTAAGCTGAAAATGGAAGGCAATGTTAATGGGCATGCTTTTGTGATA
GAGGGGGAAGGTGAGGGTAAGCCCTCGATGGTACAAACACTATCAACCTAGAGGTGAAGGAAGGTGCACCGCTGCCATTTTCCTATGATATCCTCACCACTG
CCTTTGCATACGGCAACAGGGCCTTTACCAAGTACCCTGATGACATTCCCAACTACTCAAGCAGAGTTTTCCTGAGGGGTATAGCTGGGAGAGAACCATGAC
GTTTGAGGATAAAGGGATTGTTAAGGTCAAGTCTGACATCAGCATGGAAGAGGATAGCTTTATATACGAAATCCACCTGAAGGGGGAAATTTCCCTCCTAAC
GGCCCTGTGATGCAGAAAAAAACTACCGGTTGGGATGCCAGTACAGAACGAATGTATGTACGTGACGGAGTACTCAAAGGCGATGTAAAGCATAAACTGCTG
CTTGAAGGTGGGGGCCCCATAGAGTTGACTTTAAGACAATTTATAGGGCCAAAAAAGCTGTAAAATTGCCCGACTACCATTTTGTAGATCATCGGATCGAAA
TTCTTAACCATGACAAGGACTATAACAAAGTGACTGTATATGAGAGTCAGTTGCTCGCAACAGTACTGATGGAATGGATGAATTGTACAAG

B. Analysis of hot spots (68 Hot spots)

hhHhhhhhhhhhhhhhhhhhHhhHhhhhhhhhhHhhhhhhhHhhhhhhhhhhhhhhhhHhhhhhhhhhhhhhHhhhhHhhhhhhhHhhhHhhhhhhhhhhhh
hhhhhhhhhhhhhhHhhhHhhhhhhhhhHhHhhhhHhhhhhhhhHhhhhhhhhhhhhhhhhhhhHhhhhhhhHhhhhhhhhhhhhhhhhhhhhhhhhhhhHh
hhhhHhhhhhhHhhHhhhhhhhhhhHhhhhHhHhhhhhhhhhhhhhhhhHhhHhhhhhHhhhHhhhhhhhhhhhhHhhhhHhhhhhhhhhHhhhhhhh
hhhhhhhhhhhhhhhhhHhhhhhhhhhhhhhhhhhhhhhHhhhhhhhhhhhhhhHhhhhhhhhhhhhhhhhhhhhhhhhhhhhhhhhhhhhhhhhhhhhh
hhhhhhhhhHhhhhhhhhhHhhHhhhHhhhhhhhHhhhHhHhhhhhhhhhhHhhhhHhhhhhhhhhhhHhHhhhhhhhhhhhhhHhhhhHhhhhhHhhHhhHh
hhhhhhhhhhhhhhhhhhhhhhHhhhhhhhhhhhhhhhhhhhhhhhhhhhhhhhHhhHhhhhhhhHhhhhhhhHhhhhhhhHhhhhhhhhhhhhhhhhhh
hhhhhHhhhhhhhhhhhhhhhhhHhhhhhhhhhhhHhhhhhhhhhhhhHhHhhHhHhhhhhHhhHhHhhhhhhhhhhhhhhhhhhhhhhhhHhHhhhhh C. Analysis of cold spots (76 Cold spots)

ccccccccccccCCcCccccccccccccccCcccccccccccccccCccccccccccccccccccccccccccCcccccccccccCCcccccccccccccccc
CcCCCccccccccCcCccccccCCcccccccccccccccccccccccccccccCcccccccccccccccccccccccCccccccccccccccccccCcccccccccC
cccccccccccCcccccccCCCccccccccccccccCcccccccCcccccCcccccccccccccccCcccccccccCcCCcccccccccCcCcCccccccccCcc
ccccCcccccccccCccccccccccccCcccccCccccCcccccccccccccccCcccccccccccccccccccccccccccccccccCCCcCcccccccCcCcccccccc
CCCccccccccccccccccccccccccccccCccccCcccccccccccccccccccccccccCccccCccccCcccccCccccccccccccccccccccccccc
cccccccccCCCCCcccccccCccccCccccccccCccccccccccCCCccccccccccccccccccccCCccCccccccccccccccccccccccccccccccc
cccccccccccCccccccCccccccccccccccCcccccccccCcCcccccccccCcccccccccccccccccccccccccccccccccccc

FIG. 53

Cold Teal Fluorescent Protein

A. Output Polynucleotide Sequence: SHM Resistant (SEQ ID NO:460)

ATGGTCTCTAAGGGAGAAGAGACCACTATGGGAGTCATCAAGCCCGACATGAAAATTAAACTGAAGATGGAAGGTAATGTCAATGGCCACGCCTTTGTGATA
GAGGGAGAGGGGGAAGGGAAACCATTGATGGGACCAATACAATCAATCTGGAGGTGAAGGAAGGTGCTCCCCTTCCCTTTTCCTACGACATCCTGACAACAG
CTTTTGCCTATGGGAACAGGGCCTTCACCAAGTACCCCGACGACATCCCCAATTACTCAAGCAGTCCTTCCCCGAGGGGTATAGTTGGGAAAGGACTATGAC
CTTTGAGGACAAGGGGATTGTCAAGGTCAAGAGCGACATAAGCATGGAGGAAGACTCTTTTATCTATGAGATACACCTGAAGGGTGAAATTTCCCCCCCAAT
GGGCCCGTTATGCAGAAAAAGACCACCGGGTGGGACGCCTCCACGGAGAGAATGTACGTCAGGGACGGGGTGCTCAAGGGAGATGTCAAACACAAACTGCTG
CTGGAAGGTGGGGGGCCCACAGAGTCGACTTCAAGACGATTTATAGAGCCAAGAAGGCCGTCAAACTCCCAGACTACCACTTTGTGGACCACAGAATCGAGA
TACTCAACCATGACAAGGATTACAACAAGGTGACCGTCTATGAGAGCCCGTGGCTAGAAACTCCACTGACGGGATGGACGAGTTATATAAA

B. Analysis of hot spots (36 Hot spots)

hhhhhhhhhhhhhhhhhhhhhhhhhhhhhhhhhhhhhhhhHhhhhhhhhhhhhhhhhhHhhhhhhhhhhhhhHhhhhhhhhhhhhhhhhhhhhhhhhhhhhh
hhhhhhhhhhhhhhhhhhhHhhhhhhhhhhhhhhhhhHhhhhhhhhhhhhhhhhhhhhhhhhhhHhhhhhhhhhhhhhhhhhhhhhhhhhhhhhhhHhhHh
hhhhHhhhhhhhhhHhhhhhhhhhhhhhhhhHhHhhhhhhhhhhhhhhhhhhhHhhhhhHhhhhhhhhhhhhhhhhhHhhhhHhhhhhhhhhhhhhhhhhhh
hhhhhhhhhhhhhhhhhhhhhhhhhhhhhhhhhhhhhhhhHhhhhhhhhhhhhhhhhhhhhhhhhhhhhhHhhhhhhhhhhhhhhhhhhhhhhhhhhhhhh
hhhhhhhhhhHhhhhhhhhhhhhhhhhhhhhhhhhhhhhhhhhhhhhhhhhhHhhhhhhhhhhhhhhhhHhhhhhhhhhhhhhhhhHhhhhhHhhHhhHh
hhhhhhhhhhhhhHhhhhhhhhhhhhhhhhhhhhhhhhhhhhhhhhHhhhhhhhhhhhhhhhhHhhhhhhhhhhHhhhhhhhhhhhhhhhhhhhhhhhhhhh
HhhhhHhhhhhhhhhhhhhhHhhHhhhhhhhhhhhhhhhhhhhhhhhhhhHhhhhhhHhhhhhhhhhhhhhhhhhhhhhHhhhhhhhhhh C. Analysis of cold spots (124 Cold spots)

cccCcCcccccCcCccccCcCccccccccCcCcCcccccccCCccCccccccccccccccccccccccccccccccccCcccccCCccccCccccccccccc
CcCcCcCcCCCccccCcccccccccccccCcCccccccccccccccccccCcccccccccccccccCcCCccccCcccccccccccCcccccccCccccccc
cccccCcccccCccccccCCCcccccccccccccCCccCccCccccCCcccccccccccccccCcccccCCccCcCCcccccccccCccccccCcccccCcc
ccccCccCccccCCcccccCcccccCcccccCccCcccccccccccCcccccCcCccccccccccccCcccccccccccccCccccccccccCCCCCccccc
CCCCccccccccccccccccCccccccCcccCcCccCcCccccccCcCcccccccccCcccCcCccCCccccCccccCcCccccCccccccccccccccccc
cccccccccCCCCCcccccccCcCccCcccccccCccccccccccCcCcccccccCCccCcccccCcCcccCccccccccccccccCcccccccccccCccc
ccCccccccccCcccccccccccccccccccCcccCcccccCcCcccccccCccccccccCccccccCccCcccccCccCccccccccccc

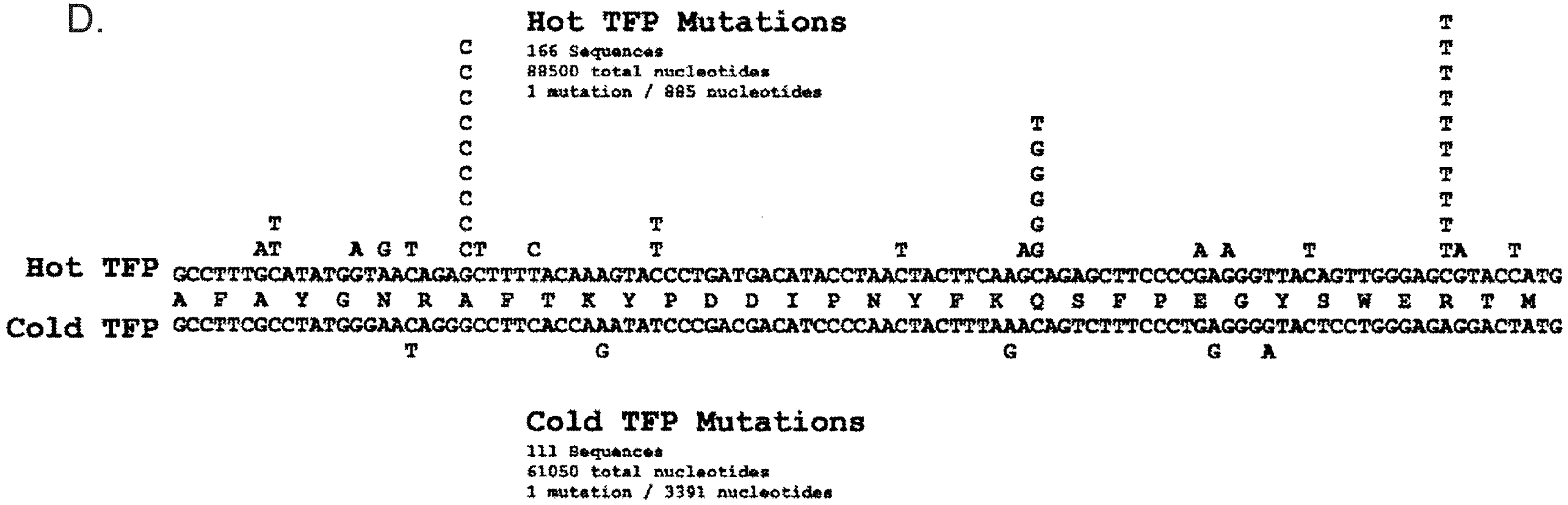

Hot TFP Mutations
166 Sequences
88500 total nucleotides
1 mutation / 885 nucleotides Hot TFP GCCTTCGCATATGGTAACAGAGCTTTTACAAAGTACCCTGATGACTACTTCAAGCAGAGCTTCCCCGAGGGTTACAGTTGGGAGCGTACCATG
         A F A Y G N R A F T K Y P D D I P N Y F K Q S F P E G Y S W E R T M Cold TFP GCCTTCGCCTATGGGAACAGGGCCTTCACCAAATATCCCGACGACATCCCCAACTACTTTAAACAGTCTTTCCCTGAGGGTTACTCCTGGGAGAGGACTATG Cold TFP Mutations
111 Sequences
61050 total nucleotides
1 mutation / 3391 nucleotides FIG. 53 (continued)
E.
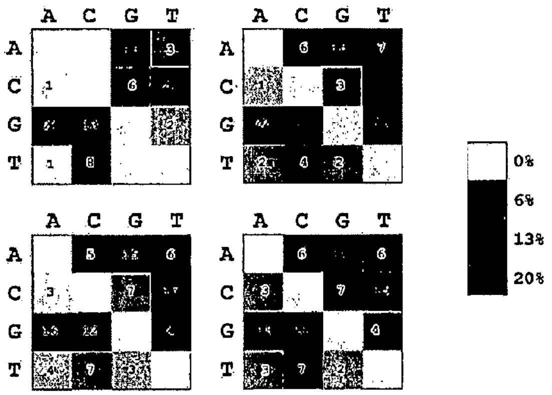
G.
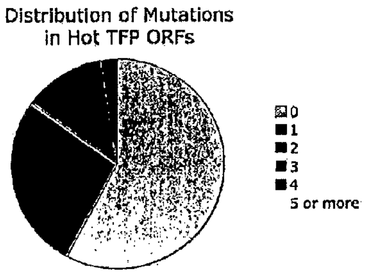
H.
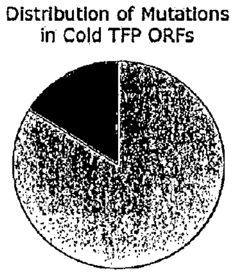

F.

METHODS OF GENERATING LIBRARIES AND USES THEREOF

CROSS-REFERENCE TO RELATED APPLICATIONS

This application is a continuation of co-pending U.S. patent application Ser. No. 12/070,904, filed Feb. 20, 2008, which claims the benefit of U.S. Provisional Application No. 60/902,414, filed Feb. 20, 2007, U.S. Provisional Application No. 60/904,622, filed Mar. 1, 2007, U.S. Provisional Application No. 60/995,970, filed Sep. 28, 2007, and U.S. Provisional Application No. 61/020,124, filed Jan. 9, 2008, each of which applications is incorporated herein by reference in its entirety.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 235,481 Byte ASCII (Text) file named "SEQUENCELISTING.TXT," created on May 12, 2011.

FIELD OF THE INVENTION

This invention relates to methods for the generation of polynucleotide seed libraries and the use of these libraries in generating novel mutants of recombinant proteins and, more particularly, for generating focused libraries of recombinant human antibodies and screening for their affinity binding with target antigens.

BACKGROUND OF THE INVENTION

The market for the use of recombinant protein therapeutics has increased steadily for the last quarter century. In 2005, six of the top 20 drugs were proteins, and overall, biopharmaceutical drugs accounted for revenues of approximately $40 billion, of which approximately $17 billion was based on the sales of monoclonal antibodies.

Monoclonal antibodies represent a distinct class of biotherapeutics with a great deal of promise. The antibody scaffold is well tolerated in the clinic, and glycosylated IgG molecules have favorable pharmacokinetic and pharmacodynamic properties. Comparison of the sequences of the approved antibody drugs, as well as those in development, demonstrates that some of the individual drug molecules are strikingly similar to each other, differing only by a few variations of amino acid residues located in the variable region of the immunoglobulin.

Typical monoclonal antibodies, like naturally occurring antibodies, have the appearance of a "Y"-shaped structure and the antigen binding portion being located at the end of both short arms of the Y. The typical antibody molecule consists of four polypeptides—two identical copies of a heavy (H) chain and two copies of a light (L) chain, forming a general formula $H_2$ $L_2$. It is known that each of the heavy chains contains one N-terminal variable ($V_H$) plus three C-terminal constant ($C_{H1}$, $C_{H2}$ and $C_{H3}$) regions and light chains contain one N-terminal variable ($V_L$) and one C-terminal constant ($C_L$) region each. The different variable and constant regions of either heavy or light chains are of roughly equal length (about 110 amino residues per region). Each light chain is linked to a heavy chain by disulphide bonds and the two heavy chains are linked to each other by disulphide bonds. Each heavy chain has at one end a variable domain followed by a number of constant domains, and each light chain has a variable domain at one end and a constant domain at the other end. The light chain variable domain is aligned with the variable domain of the heavy chain. The light chain constant domain is aligned with the first constant domain of the heavy chain. The remaining constant domains of the heavy chains are aligned with each other. The constant domains in the light and heavy chains are not involved directly in binding the antibody to the antigen.

Antibodies are typically divided into different classes on the basis of the structure of the constant region. In humans for example, five major structural classes can be identified immunoglobulin G or IgG, IgM, IgA, IgD and IgE. Each class is distinguished on the basis of its physical and biological characteristics which relate to the function of the immunoglobulin in the immune system. IgGs can be further divided into four subclasses: IgG1, IgG2, IgG3 and IgG4, based on differences in the heavy chain amino acid composition and in disulphide bridging, giving rise to differences in biological behavior. A description of the classes and subclasses is set out in "Essential Immunology" by Ivan Roitt, Blackwell Scientific Publications.

The variable domains of each pair of light and heavy chains form the antigen binding site. They have the same general structure with each domain comprising a framework of four regions, whose sequences are relatively conserved, connected by three complementarity determining regions (CDRs). The four framework regions (FWs or FRs) largely adopt a beta-sheet conformation and the CDRs form loops connecting, and in some cases comprising part of, the beta-sheet structure. The CDRs are held in close proximity by the framework regions and, with the CDRs from the other domain, contribute to the formation of the antigen binding site.

The vertebrate immune system has evolved unique genetic mechanisms that enable it to generate an almost unlimited number of different light and heavy chains in a remarkably economical way by joining separate gene segments together before they are transcribed. The antibody chains are encoded by genes at three separate loci on different chromosomes. One locus encodes the heavy chain isotypes and there are separate loci for the kappa (κ) and lambda (λ) light isotypic chains, although a B-lymphocyte only transcribes from one of these light chain loci. For each type of Ig chain—heavy chains, lambda (λ) light chains, and kappa (κ) light chain—there is a separate pool of gene segments from which a single peptide chain is eventually synthesized. Each pool is on a different chromosome and usually contains a large number of gene segments encoding the V region of an Ig chain and a smaller number of gene segments encoding the C region. More specifically, the variable region of an H-chain comprises three gene fragments, i.e., V, D and J gene fragments, while the variable region of an L-chain comprises two gene fragments, i.e., J and V gene fragments, regardless of whether the L-chain belongs to a lambda (λ) or kappa (κ) chain. During B cell development a complete coding sequence for each of the two Ig chains to be synthesized is assembled by site-specific genetic recombination, bringing together the entire coding sequences for a V region and the coding sequence for a C region.

The large number of inherited V, J and D gene segments available for encoding Ig chains makes a substantial contribution on its own to antibody diversity, but the combinatorial joining of these segments greatly increases this contribution. Further, imprecise joining of gene segments and somatic mutations introduced during the V-D-J segment joining at the pre-B cell stage greatly increases the diversity of the V regions In addition to these structural characteristics, analyses of natural antibody sequences together with structural studies have been instrumental in revealing how antibodies work (Chothia et al., 1992, J. Mol. Biol., 227: 799-817; Kabat, 1982, Pharmacological Rev., 34: 23-38; Kabat, 1987, Sequences of Proteins of Immunological Interest (National Institutes of Health, Bethesda, Md.)). These studies have shown that antigen recognition is primarily mediated by complementarity determining regions (CDRs) that are located at one end of the antibody variable domain and are connected by a β-sheet framework (Wu & Kabat, 1970, J. Exp. Med., 132: 211-250; Kabat & Wu, 1971, Annals New York Acad. Sci., 190: 382-393).

The sequence diversity of natural antibodies shows that the CDRs are hypervariable in comparison with the framework, and it is the CDR sequences that determine the antigen specificity of a particular antibody (Jones et al., 1986, Nature, 321: 522-5; Amit et al., 1986, Science, 233: 747-53). These studies have also revealed that the natural sequence diversity at most CDR positions is not completely random, as biases for particular amino acids occur in both a site-specific manner and in terms of overall CDR composition (Davies & Cohen, 1996, Proc. Natl. Acad. Sci. USA, 93: 7-12; Kabat et al., 1977, J. Biol. Chem., 252: 6609-16; Zemlin et al., 2003, J. Mol. Biol., 334: 733-49; Mian et al., 1991, J. Mol. Biol., 217: 133-51; Padlan, 1994, Mol. Immunol, 31: 169-217).

In contrast to traditional small molecule based approaches, therapeutic antibodies have significant advantages, including (i) their ability to be generated and validated quickly; (ii) therapeutic antibodies exhibit fewer side effects and have improved safety profiles, (iii) therapeutic antibodies have well understood pharmacokinetic characteristics, and they can be optimized to create long half-life products with reduced dosing frequency; iv) therapeutic antibodies are versatile and exhibit flexibility in drug function; v) therapeutic antibody scale-up and manufacturing processes are robust and well-understood; and vi) they have a proven track record of clinical and regulatory success.

Even given the success of monoclonal antibodies, the antibody-as-drug modality is continuing to evolve, and subject to inefficiency. Further, intrinsic biological bias within the native immune system often works against the more rapid development of improved therapeutics. These limitations include, i) the long development time for the isolation of biologically active antibodies with affinity constants of therapeutic caliber, ii) the inability to raise antibodies to certain classes of protein targets (intractable targets), and iii) the intrinsic affinity ceiling inherent in immune system based affinity selection.

Specifically there is a need for methods to more rapidly develop antibodies with improved pharmacokinetics, cross-reactivity, safety profiles and superior dosing regimens. Central to this need is the development of methods that enable the systematic analysis of potential epitopes with a protein, and enable the selective development of antibodies with the desired selectivity profiles.

An approach used by a number of companies includes the use of random or semi random mutagenesis (for example the use of error prone PCR), in conjunction with in vitro molecular evolution. This approach is based on the creation of random changes in protein structure and the generation of huge libraries of mutant polynucleotides that are subsequently screened for improved variants, usually through the expression of the encoded proteins within a living cell. From these libraries a few improved proteins may be selected for further optimization.

Such in vitro mutation approaches are generally limited by the inability to systematically search a significant fraction of sequence space, and by the relative difficulty of detecting very rare improvement mutants at heavy mutagenesis loads. This fundamental problem arises because the total number of possible mutants for a reasonably sized protein is massive. For example, a 100 amino acid protein has a potential diversity of $20^{100}$ different sequences of amino acids, while existing high throughput screening methodologies are typically limited to a maximum screening capacity of $10^7$-$10^8$ samples per week. Additionally such approaches are relatively inefficient because of redundant codon usage, in which up to around $3^{100}$ of the nucleotide sequences possible for a 100 amino acid residue protein actually encode for the same amino acids and protein, (Gustafsson et al. (2004) Codon Bias and heterologous protein expression Trends. Biotech. 22 (7) 346-353).

A more sophisticated approach uses a mixture of random mutagenesis with recombination between protein domains in order to select for improved proteins (Stemmer Proc. Natl. Acad. Sci. (1994) 91 (22) 10747-51). This approach exploits natural design concepts inherent in protein structures across families of proteins, but again requires significant recombinant DNA manipulation and screening capacity of a large number of sequences to identify rare improvements. Both approaches require extensive follow-up mutagenesis and analysis to understand the significance of each mutation, and to identify the best combination of the many thousands or millions of mutants identified.

SUMMARY OF THE INVENTION

The present invention meets the foregoing and related needs by providing methods for the generation of polynucleotide libraries, including synthetic, semi-synthetic and/or seed libraries, and the use of these libraries in generating novel mutants of recombinant proteins. In certain embodiments, the methods provided herein are useful for generating focused libraries of recombinant human antibodies and screening for their affinity binding with target antigens. In one aspect, a synthetic gene is one that does naturally undergo SHM when expressed in a B cell (i.e., an antibody gene). In another aspect, a synthetic gene is one that does not naturally undergo SHM when expressed in a B cell (i.e., a non-antibody gene). In certain embodiments, the methods provided herein herein are useful for generating focused libraries of recombinant non-antibody proteins and screening for enhanced function or reduced susceptibility to somatic hypermutation.

In certain aspects of the present invention, provided herein are compositions of matter comprising a seed library of polynucleotides encoding a plurality of one or more polypeptide species of interest that have at least one region of interest of a protein of interest, wherein the seed library of polynucleotides comprise at least one synthetic nucleic acid sequence that encodes said at least one region of interest and has been modified to act as a substrate for AID mediated somatic hypermutation.

In certain aspects of the present invention, provided herein are compositions of matter comprising a seed library of polynucleotides encoding one or more proteins, wherein said seed library of polynucleotides comprises at least one synthetic polynucleotide that has been optimized for SHM by insertion of one or more preferred SHM codons. In other aspects, at least one synthetic polynucleotide has been optimized for SHM by reducing the density of non-preferred codons. Synthetic polynucleotides can be made resistant to SHM or made susceptible to SHM using the methods described herein.

In certain aspects, the compositions of the present invention can comprise a synthetic nucleic acid sequence has been modified to act as a substrate for AID mediated somatic hypermutation by the insertion of somatic hypermutation motifs. In one embodiment, the synthetic nucleic acid sequence has been modified to act as a substrate for AID mediated somatic hypermutation by the insertion of one or more preferred SHM codons. In another embodiment, the synthetic nucleic acid sequence has been modified to act as a substrate for AID mediated somatic hypermutation by the insertion of one or more WAC motif, WRC motif or a combination thereof.

In certain other aspects, the compositions of the present invention comprise a seed library of polynucleotides encoding a protein of interest that is an antibody. In one embodiment, the protein of interest is an antibody heavy chain or fragment thereof. In another embodiment, the antibody heavy chain comprises a variable region selected from those set forth in FIG. 20A. In still another embodiment, the antibody heavy chain comprises a variable region selected from the group consisting of IGHV6-1, IGHV4-34, IGHV4-59, IGHV3-30-3, IGHV3-7, IGHV3-23, IGHV5-51, IGHV1-2, or IGHV1-69.

In other embodiments, the protein of interest is an antibody light chain or fragment thereof. In one embodiment, the antibody light chain comprises a variable region selected from set forth in FIG. 20B. In still another embodiment, the antibody light chain comprises a κ light chain variable region selected from the group consisting of IGKV2D-30, IGKV4-1, IGKV1-33, IGKV1D-39, or IGKV3-20. In yet another embodiment, the antibody light chain comprises a variable region selected from set forth in FIG. 20C. In yet still another embodiment, antibody light chain comprises a λ light chain variable region selected from the group consisting of IGKLV7-43, IGLV1-40, IGLV2-11, or IGLV3-21.

In certain embodiments, the compositions of the present invention comprise at least one region of interest comprising an antibody heavy or light chain CDR1, CDR2 or CDR3 domain. In other embodiments, the compositions comprise at least one said region of interest comprising an antibody heavy or light chain CDR3.

In certain other aspects, the compositions of the present invention comprise a protein of interest that is a receptor. In other aspects, the protein of interest is an enzyme. In still other aspects, the protein of interest is a co-factor. In yet other aspects, the protein of interest is a transcription factor.

The present invention also provides a method of making a protein of interest with a desired property, the method comprising the steps of: a. synthesizing a seed library of polynucleotides encoding a plurality of one or more polypeptide species of interest that have at least one region of interest of a protein of interest, wherein the seed library of polynucleotides comprise at least one synthetic nucleic acid sequence that encodes at least one region of interest and has been modified to act as a substrate for AID mediated somatic hypermutation; b. joining in operable combination a seed library of polynucleotides encoding a plurality of one or more polypeptide species of interest of a protein of interest into an expression vector; c. transforming a host cell with the expression vector, so that the protein of interest is produced by expression of the seed library of polynucleotides encoding a plurality of one or more polypeptide species of interest of a protein of interest; and wherein the host cell expresses AID, or can be induced to express AID via the addition of an inducing agent; d. optionally inducing AID activity, or allowing AID mediated mutagenesis to occur on the seed library; e. identifying a cell or cells within the population of cells which expresses a mutated protein having a desired property, and f. establishing one or more clonal populations of cells from the cell or cells identified in step (e).

In other embodiments, provided herein is a method of making a protein of interest with a desired or identified property, said method comprising the steps of: (a) synthesizing a seed library of polynucleotides encoding one or more proteins, wherein said seed library of polynucleotides comprises at least one synthetic polynucleotide that has been optimized for SHM; (b) joining in operable combination said seed library of polynucleotides into an expression vector; (c) transforming a host cell with said expression vector, so that said one or more proteins is produced by expression of said seed library of polynucleotides; and wherein said host cell expresses AID activity or can be induced to express AID activity via the addition of an inducing agent; (d) if needed, inducing AID activity; (e) identifying a cell or cells within the population of cells which express(es) one or more mutated proteins having said desired or identified property, and (f) establishing one or more clonal populations of cells from the cell or cells identified in step (e).

In other embodiments, provided herein is a method of making an antibody or antigen-binding fragment thereof with a desired property, the method comprising the steps of: a. synthesizing a seed library of polynucleotides encoding a plurality of one or more antibody heavy chain proteins or fragments that have at least one CDR, wherein the polynucleotides comprise at least one synthetic nucleic acid sequence that encodes the at least one CDR and has been modified to act as a substrate for AID mediated somatic hypermutation; b. synthesizing a seed library of polynucleotides encoding a plurality of one or more antibody light chain proteins or fragments that have at least one CDR, wherein the seed library of polynucleotides comprise at least one synthetic nucleic acid sequence that encodes the at least one CDR and has been modified to act as a substrate for AID mediated somatic hypermutation; c. joining in operable combination the seed library of polynucleotides encoding the plurality of antibody heavy chain proteins or fragments thereof and the seed library of polynucleotides encoding the plurality of antibody light chain proteins or fragments thereof into expression vectors; d. transforming a host cell with the expression vectors, so that an antibody or an antigen-binding fragment thereof is produced by coexpression of a heavy chain sequence from the seed library of polynucleotides encoding a plurality of antibody heavy chain proteins or fragments thereof and a light chain sequence from the seed library of polynucleotides encoding a plurality of antibody light chain proteins or fragments thereof, either on the same or different expression vectors; and wherein the host cell expresses AID, or can be induced to express AID via the addition of an inducing agent; e. optionally inducing AID activity, or allowing AID mediated mutagenesis to occur on the seed libraries of polynucleotides; f. identifying a cell or cells within the population of cells which expresses a mutated antibody or an antigen-binding fragment thereof having the desired property, and g. establishing one or more clonal populations of cells from the cell or cells identified in step (f).

In other embodiments, provided herein is a method of making an antibody or antigen-binding fragment thereof with a desired or identified property, said method comprising the steps of: (a) synthesizing a first seed library of first polynucleotides encoding a plurality of one or more antibody heavy chain proteins or fragments thereof that have at least one heavy chain CDR, wherein said first seed library of polynucleotides comprises at least one first synthetic polynucleotide that has been optimized for SHM; (b) synthesizing a second seed library of second polynucleotides encoding said plurality of one or more antibody light chain proteins or fragments thereof that have at least one light chain CDR, wherein said second seed library of polynucleotides comprises at least one second synthetic polynucleotide that has been optimized for SHM; (c) joining in operable combination said first and second seed libraries of polynucleotides into expression vectors; (d) transforming a host cell with said expression vectors, so that an antibody or an antigen-binding fragment thereof is produced by coexpression of a heavy chain sequence from said first seed library of polynucleotides and a light chain sequence from said second seed library of polynucleotides (either on the same or different expression vectors); and wherein said host cell expresses AID activity or can be induced to express AID activity via the addition of an inducing agent; (e) if needed, inducing AID activity; (f) identifying a cell or cells within the population of cells which expresses one or more mutated antibodies or antigen-binding fragments thereof having the desired or identified property, and (g) establishing one or more clonal populations of cells from the cell or cells identified in step (f).

In still other embodiments, provided herein is a method of co-evolving a plurality of proteins, the method comprising the steps of: a. synthesizing a first seed library of polynucleotides encoding a plurality of one or more polypeptide species of interest that have at least one region of interest of a first protein of interest, wherein the seed library of polynucleotides comprise at least one synthetic nucleic acid sequence that encodes the at least one region of interest and has been modified to act as a substrate for AID mediated somatic hypermutation; b. synthesizing a second seed library of polynucleotides encoding a plurality of one or more polypeptide species of interest that have at least one region of interest of a second protein of interest, wherein the seed library of polynucleotides comprise at least one synthetic nucleic acid sequence that encodes the at least one region of interest and has been modified to act as a substrate for AID mediated somatic hypermutation; c. joining in operable combination the seed library of polynucleotides encoding the plurality of polypeptide species of interest of the first protein of interest and the seed library of polynucleotides encoding the plurality of polypeptide species of interest of the second protein of interest into expression vectors; d. transforming a host cell with the expression vectors, so that the first and second proteins of interest are produced by coexpression of the first and second seed libraries of polynucleotides, either on the same or different expression vectors; and wherein the host cell expresses AID, or can be induced to express AID via the addition of an inducing agent; e. optionally inducing AID activity, or allowing AID mediated mutagenesis to occur on the seed libraries of polynucleotides; f. identifying a cell or cells within the population of cells which expresses a mutated first or second protein of interest having the desired property, and g. establishing one or more clonal populations of cells from the cell or cells identified in step (f).

In one aspect, provided herein is a method of co-evolving a plurality of proteins, said method comprising the steps of: (a) synthesizing a first seed library of polynucleotides encoding one or more proteins, wherein said first seed library of polynucleotides comprise at least one first synthetic polynucleotide that has been optimized for SHM; (b) synthesizing a second seed library of polynucleotides encoding one or more proteins, wherein said second seed library of polynucleotides comprise at least one second synthetic polynucleotide that has been optimized for SHM; (c) joining in operable combination said first and second seed libraries of polynucleotides into expression vectors; (d) transforming a host cell with said expression vectors, so that said one or more first and second proteins are produced by coexpression of said first and second seed libraries of polynucleotides, either on the same or different expression vectors; and wherein said host cell expresses AID activity or can be induced to express AID activity via the addition of an inducing agent; (e) if needed, inducing AID activity; (f) identifying a cell or cells within the population of cells which expresses one or more mutated proteins having the desired or identified property, and (g) establishing one or more clonal populations of cells from the cell or cells identified in step (f).

In certain aspects, the methods described herein comprise at least one synthetic nucleic acid sequence that has been modified to act as a substrate for AID mediated somatic hypermutation by the insertion of somatic hypermutation motifs. In certain embodiments, the at least one synthetic nucleic acid sequence has been modified to act as a substrate for AID mediated somatic hypermutation by the insertion of one or more preferred SHM codons. In other embodiments, the at least one synthetic nucleic acid sequence has been modified to act as a substrate for AID mediated somatic hypermutation by the insertion of one or more WAC motif, WRC motif, or a combination thereof.

In one embodiment of any of these methods, the identified codon may be replaced with a preferred (canonical) SHM codon or preferred (canonical) hot spot SHM codon which introduces a conservative amino acid substitution, compared to either the wild-type or AID modified codon. In another embodiment of any of these methods, the identified codon may be replaced with a preferred SHM codon or preferred hot spot SHM codon which introduces a semi-conservative mutation at the amino acid level, compared to either the wild-type or AID modified codon. In another embodiment of any of these methods, the identified codon may be replaced with a preferred SHM codon or preferred hot spot SHM codon which introduces a non-conservative mutation at the amino acid level compared to either the wild-type or AID modified codon. In one embodiment, insertion of one or more preferred SHM codons is by insertion of one or more amino acids substitutions in said region of interest, said amino acid substitutions being silent, conservative, semi-conservative, non-conservative or a combination thereof. Modifications to polynucleotides made using the methods described herein can render at least one polynucleotide sequence susceptible or resistant to SHM.

In certain embodiments, the methods described herein comprise a host cell that is a prokaryotic cell. In one embodiment, the prokaryotic cell is an *E. coli* cell.

In certain other embodiments, the methods described herein comprise a host cell that is a eukaryotic cell. In one embodiment, the eukaryotic cell is a mammalian cell. In another embodiment, the host is a mammalian cell that is a Chinese hamster ovary cell (CHO), a human embryonic kidney (HEK) 293 cell, 3T3 cell, a HEK 293T cell, a PER.C6TM cell, or a lymphoid derived cell. In still other embodiments, the host cell is a lymphoid derived cell that is a RAMOS (CRL-1596) cell, a Daudi (CCL-213) cell, an EB-3 (CCL-85) cell, a DT40 (CRL-2111) cell, an 18-81 cell, a Raji (CCL-86), or derivatives thereof.

In another embodiment, the methods described herein comprise a host cell that is a eukaryotic cell that is a yeast cell.

The present invention further provides a method for humanizing a non human antibody, the method comprising the steps of: a. determining the sequence of the heavy and light chains of the non human antibody to be humanized; b. synthesizing a seed library of polynucleotides encoding a plurality of one or more human antibody heavy chain protein scaffolds comprising at least one synthetic nucleic acid sequence which encodes at least one CDR, or a portion thereof, derived from the non human antibody heavy chain protein, wherein the nucleic acid sequence has been modified to act as a substrate for AID mediated somatic hypermutation; c. synthesizing a seed library of polynucleotides encoding a plurality of one or more human antibody light chain protein scaffolds comprising at least one synthetic nucleic acid sequence which encodes at least one CDR, or a portion thereof, derived from the non human antibody light chain protein, wherein the nucleic acid sequence has been modified to act as a substrate for AID mediated somatic hypermutation; d. joining in operable combination the seed library of polynucleotides encoding the plurality of antibody heavy chain protein scaffolds and the seed library of polynucleotides encoding the plurality of antibody light chain protein scaffolds into expression vectors; e. transforming a host cell with the expression vectors, so that an antibody or an antigen-binding fragment thereof is produced by coexpression of a heavy chain sequence from the seed library of polynucleotides encoding the plurality of antibody heavy chain protein scaffolds and a light chain sequence from the seed library of polynucleotides encoding the plurality of antibody light chain protein scaffolds, either on the same or different expression vectors; and wherein the host cell expresses AID, or can be induced to express AID via the addition of an inducing agent; f. optionally inducing AID activity, or allowing AID mediated mutagenesis to occur on the seed libraries; g. identifying a cell or cells within the population of cells which expresses a humanized antibody having binding characteristic of the non-human antibody, and h. establishing one or more clonal populations of cells from the cell or cells identified in step (g).

In certain embodiments, the method for humanizing a non-human antibody comprises human antibody heavy chain protein scaffolds comprising a variable region selected from FIG. 20A. In other embodiments, the human antibody heavy chain protein scaffolds comprise a variable region selected from FIG. 20A, wherein said selected variable region exhibits the highest amino acid homology to said non human antibody. In still other embodiments, the antibody heavy chain protein scaffolds comprise a variable region selected from the group consisting of IGHV6-1, IGHV4-34, IGHV4-59, IGHV3-30-3, IGHV3-7, IGHV3-23, IGHV5-51, IGHV1-2 or IGHV1-69.

In certain other embodiments, the method for humanizing a non-human antibody comprises human antibody light chain protein scaffolds comprise a variable region selected from FIG. 20B. In other embodiments, the human antibody light chain protein scaffolds comprise a variable region selected from FIG. 20B, wherein said selected variable region exhibits the highest amino acid homology to said non human antibody. In still other embodiments, the antibody light chain protein scaffolds comprise a variable region selected from the group consisting of IGKV2D-30, IGKV4-1, IGKV1-33, IGKV1D-39, or IGKV3-20.

In certain other embodiments, the method for humanizing a non-human antibody comprises human antibody light chain protein scaffolds comprise a variable region selected from FIG. 20C. In other embodiments, the human antibody light chain protein scaffolds comprise a variable region selected from FIG. 20C, wherein said selected variable region exhibits the highest amino acid homology to said non human antibody. In still other embodiments, the antibody light chain protein scaffolds comprise a variable region selected from the group consisting of IGKLV7-43, IGLV1-40, IGLV2-11, or IGLV3-21.

In other aspects, the method for humanizing a non-human antibody described herein comprise at least one synthetic nucleic acid sequence has been modified to act as a substrate for AID mediated somatic hypermutation by the insertion of somatic hypermutation motifs. In other aspects, the at least one synthetic nucleic acid sequence has been modified to act as a substrate for AID mediated somatic hypermutation by the insertion of one or more preferred SHM codons. In still other aspects, the at least one synthetic nucleic acid sequence has been modified to act as a substrate for AID mediated somatic hypermutation by the insertion of one or more WAC motif, WRC motif, or a combination thereof.

In other embodiments, the method for humanizing a non-human antibody described herein comprise a plurality of one or more human antibody heavy chain protein scaffolds comprise a synthetic nucleic acid sequence which encodes a CDR3 domain derived from said non human antibody heavy chain protein, wherein said nucleic acid sequence has been modified to act as a substrate for AID mediated somatic hypermutation.

In still other embodiments, the method for humanizing a non-human antibody described herein comprise a plurality of one or more human antibody light chain protein scaffolds comprise a synthetic nucleic acid sequence which encodes a CDR3 domain derived from said non human antibody light chain protein, wherein said nucleic acid sequence has been modified to act as a substrate for AID mediated somatic hypermutation.

In yet other embodiments, the method for humanizing a non-human antibody described herein comprise a plurality of one or more human antibody heavy chain protein scaffolds comprise a synthetic nucleic acid sequence which encodes a portion of a CDR3 domain derived from said non human antibody heavy chain protein, wherein said nucleic acid sequence has been modified to act as a substrate for AID mediated somatic hypermutation.

In still yet other embodiments, the method for humanizing a non-human antibody described herein comprise a plurality of one or more human antibody light chain protein scaffolds comprise a synthetic nucleic acid sequence which encodes a portion of a CDR3 domain derived from said non human antibody light chain protein, wherein said nucleic acid sequence has been modified to act as a substrate for AID mediated somatic hypermutation.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

A better understanding of the features and advantages of the present invention will be obtained by reference to the following detailed description that sets forth illustrative embodiments, in which the principles of the invention are utilized, and the accompanying drawings of which:

FIG. 1—Shows that within CDRs, (the codons AGC, TAT, and TAC (encoding tyrosine and serine amino acids), feed a directed flow of primary, secondary and tertiary SHM events generating amino acid diversity. Within CDRs, the most common codon transition observed is AGC to AAC (785 instances), leading to a serine to asparagine conversion. While that transitions are also common in framework regions (354 instances), a simple frame shift of the same mutation in the same hotspot motif (..TACAGCTAT..; SEQ ID NO: 1) context leads to a CAG to CAA silent mutation that is common in framework regions (288 instances) but not commonly observed in CDRs.

FIG. 2—In contrast to FIG. 1, the most commonly observed codon (amino acid) transition events in frame work regions generate silent mutations (FIG. 2).

FIG. 8—Provides the amino acid (A; SEQ ID NO: 2), and polynucleotide sequence (B; SEQ ID NO: 3) of native blasticidin gene. Also shown is the initial analysis of hot spots (C), cold spots (D) and occurrences of CpGs (E).

FIG. 9—Provides the amino acid (A; SEQ ID NO: 2), and polynucleotide sequence (B; SEQ ID NO: 4) of a synthetic, SHM resistant version of the blasticidin gene. Also shown is the analysis of hot spots (C), cold spots (D) and occurrences of CpGs (E) in the synthetic sequence.

FIG. 10—Provides the amino acid (A; SEQ ID NO: 2), and polynucleotide sequence (B; SEQ ID NO: 5) of a synthetic, SHM susceptible version of the blasticidin gene. Also shown is the analysis of hot spots (C), cold spots (D) and occurrences of CpGs (E) in the synthetic sequence.

FIG. 11—Provides a sequence comparison of activation-induced cytidine deaminase (AID) from *Homo sapiens* (human; SEQ ID NO: 6), *Mus musculus* (mouse; SEQ ID NO: 7), *Canis familiaris* (dog; SEQ ID NO: 8), *Rattus norvegicus* (norv-) (rat; SEQ ID NO: 9) and *Pan troglodytes* (chimpanzee; SEQ ID NO: 10). Variations between the species are represented by bold amino acids.

FIG. 12—Provides the amino acid (A; SEQ ID NO: 11), and polynucleotide sequence (B; SEQ ID NO: 12) of native canine cytidine deaminase (AID) (L198A). Also shown is the analysis of hot spots (C), cold spots (D) and occurrences of CpGs (E) in the native sequence.

FIG. 13—Provides the polynucleotide sequence (A; SEQ ID NO: 13) of a synthetic SHM susceptible form of canine AID. Also shown is the analysis of hot spots (B), cold spots (C) and occurrences of CpGs (D).

FIG. 14—Provides the polynucleotide sequence (A; SEQ ID NO: 14) of a synthetic SHM resistant form of canine AID. Also shown is the analysis of hot spots (B), cold spots (C) and occurrences of CpGs (D).

FIG. 15—Provides a comparison of cDNA sequences of *Canis familiaris* (dog; SEQ ID NO: 15) and SHM-optimized (cold) *Canis familiaris* (dog; SEQ ID NO: 16), *Homo sapiens* (human; SEQ ID NO: 17) and *Mus musculus* (mouse; SEQ ID NO: 18) mRNA activation-induced cytidine deaminase (AID) sequences. GAG sequences are illustrated by bold, underlining. Variations between the sequences are illustrated by bold amino acid residues.

FIG. 16—Shows the predicted effect of AID activity on reversion frequency using a protein containing a mutable stop codon such as a fluorescent protein (16A). FIG. 16B shows the actual rates of loss of fluorescence achieved (shown as GFP extinction) with cells transfected with two different concentrations of an expression vector capable of expressing AID, and stably expressing GFP. FIG. 16C shows the initial rates of GFP reversion mediated by wild type human AID, and cold canine AID. Also shown is the effect of Ig enhancers on reversion rate.

FIG. 17—Provide schematics of Vector Formats 1 (17A) and 2 (17B).

FIG. 18—Provide schematics of Vector Format 3 (18A) and 4 (18B).

FIG. 19—Provide schematics of Vector Format 5 (19A) and AB184 (19B).

FIG. 21—Illustrates the steps for generating the (A) heavy chain, (B) kappa and (C) lambda light chain libraries.

FIG. 22—Shown is a synthetic CDR3 that contains two circularly permuted ideal hot spots (AGCTAC; SEQ ID NO:

19) contained between 2 nonameric ideal cold spots (GTCGTCGTC; SEQ ID NO: 20). Here 'V' represents variable domain derived sequences, "D" represents the synthetic polynucleotide sequence that has been optimized for SHM, but are naturally derived from CDR3 in the corresponding wild type antibody, "J" represents junction domain derived sequences, and "C" represents constant domain derived sequences. The synthetic CDR3 is placed within the context of the human IGHV4-34, IGHJ1, IgG1 germline sequence as more fully described in Examples 4-7. The nucleotide and amino acid sequences of FR3, CDR3, FR4 and a portion of the constant region are set forth in SEQ ID NO: 21 and 24, respectively. Alternate CDR3 nucleotide sequences are set forth as SEQ ID NOS: 22 and 23. Hot spots are underlined and are contained within 2 nonameric ideal cold spots (italics). Alternate amino acid sequences are set forth as SEQ ID NOS: 25 and 26.

Figure 23:
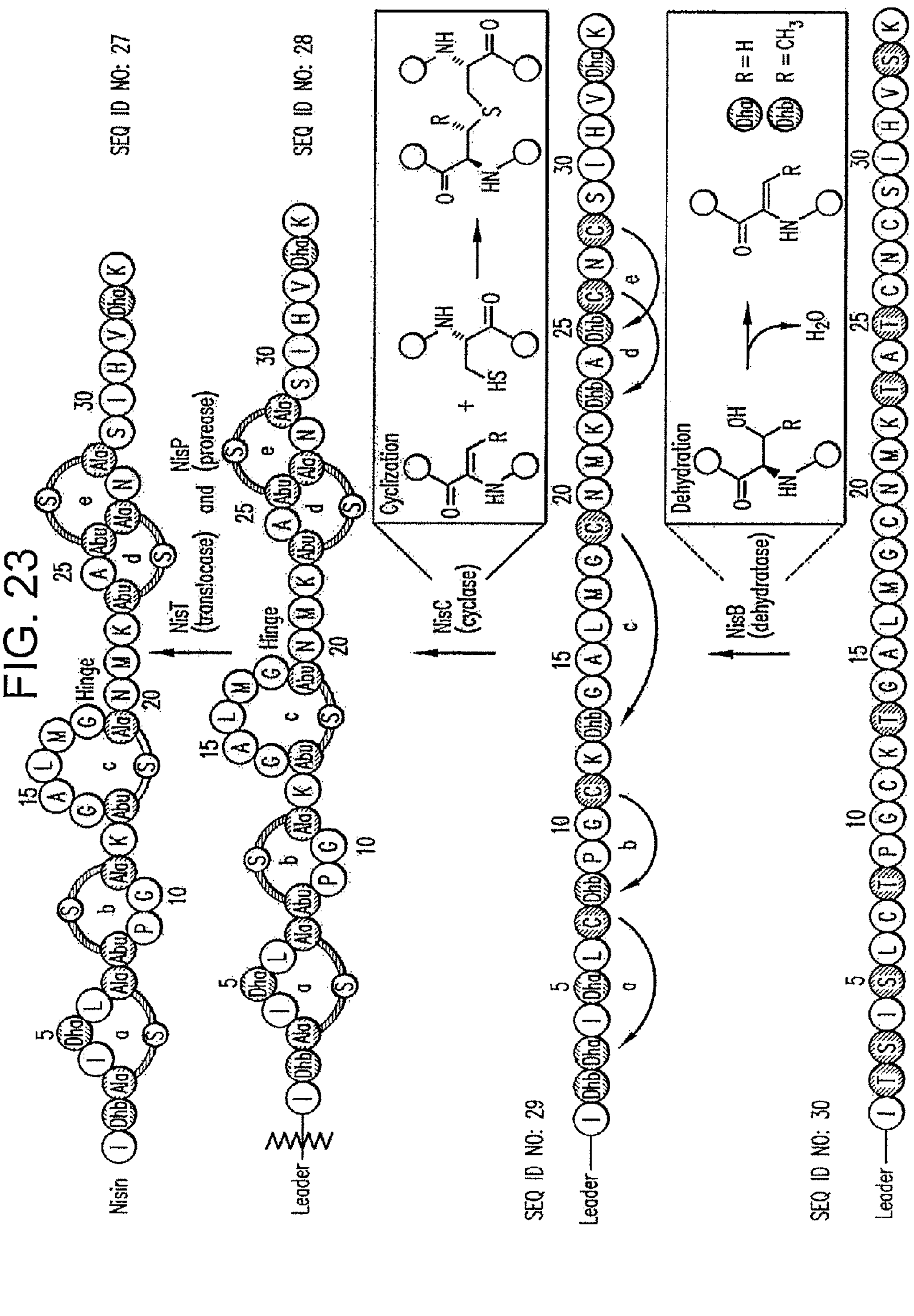

FIG. 23—Provides a diagram of the synthesis and maturation of Nisin (23A) illustrating amino acid sequences set forth as SEQ ID NOS: 27-30.

FIG. 24—Provide the polynucleotide sequence of native NisB (SEQ ID NO: 31). Also shown is the analysis of hot spots, cold spots and occurrences of CpGs in the native sequence.

FIG. 25—Provides the polynucleotide sequence of a SHM resistant form of NisB (SEQ ID NO: 32). Also shown is the analysis of hot spots, cold spots and occurrences of CpGs in the synthetic sequence.

FIG. 26—Provides the polynucleotide sequence of native NisP (SEQ ID NO: 33). Also shown is the analysis of hot spots, cold spots and occurrences of CpGs in the native sequence.

FIG. 27—Provides the polynucleotide sequence of a SHM resistant form of NisP (SEQ ID NO: 34). Also shown is the analysis of hot spots, cold spots and occurrences of CpGs in the synthetic sequence.

FIG. 28—Provides the polynucleotide sequence of native NisT (28A; SEQ ID NO: 35), and SHM resistant form of NisT (28B; SEQ ID NO: 36).

FIG. 29—Provides the polynucleotide sequence of native NisA (29A; SEQ ID NO: 37), as well as the initial analysis of hot spots (29B), and cold spots (29C). Also shown is a synthetic form of NisA (29D; SEQ ID NO: 38) showing areas of SHM resistant sequence (underlined) and SHM susceptible sequence, and the analysis of hot (29E) and cold spots (29F).

FIG. 30—Provides the polynucleotide sequence of native NisC (SEQ ID NO: 39), as well as the initial analysis of hot spots (30B) and cold spots (30C).

FIG. 31—Shows a synthetic form of NisC (31A; SEQ ID NO: 40) showing the analysis of hot (31B) and cold spots (31C).

Figure 32:
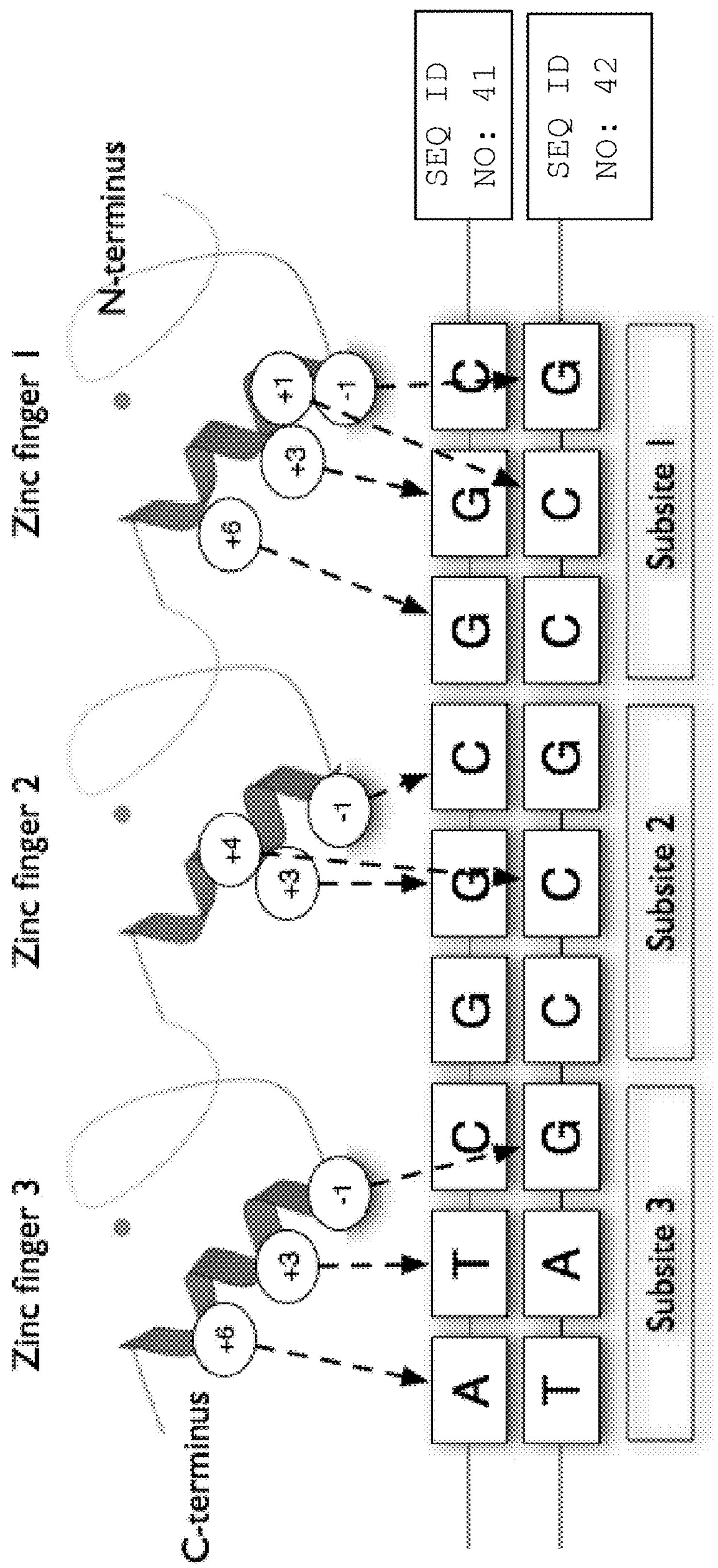

FIG. 32—Provides a schematic of a three zinc-finger protein making contacts to a DNA sequence. Each finger is composed of a small beta sheet and alpha helix that coordinate a zinc metal ion. While two histidines and two cysteines bind the zinc, the sidechains of key amino acids emanate from the beginning of the alpha helix to make base specific contacts. These positions may be targeted as SHM hotspots where mutations creating amino acid diversity are desirable. Structural and zinc binding positions of the finger should correspondingly be made cold. ATCGGCGGC (SEQ ID NO:41); TAGCCGCCG (SEQ ID NO: 42).

Figure 33:
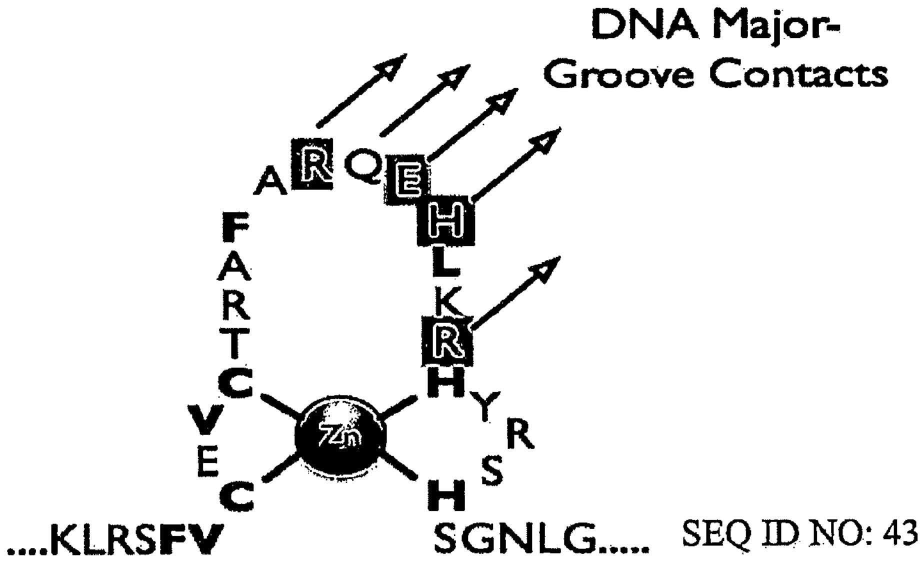

FIG. 33—Provides a schematic of an individual finger with structurally conserved positions shown in bold, and residues contacting DNA shown with a gray background (SEQ ID NO: 43). Portions of the amino acid sequence to be made hot or cold are shown, along with all possible corresponding nucleic acid sequences.

| V C | SEQ ID NO | E H | SEQ ID NO |
|---|---|---|---|
| GTATGC | 44 | GAACAC | 52 |
| GTATGT | 45 | GAACAT | 53 |
| GTCTGC | 46 | GAGCAC | 54 |
| GTCTGT | 47 | GAGCAT | 55 |
| GTGTGC | 48 | | |
| GTGTGT | 49 | | |
| GTTTGC | 50 | | |
| GTTTGT | 51 | | |

The accompanying z-score for each nucleotide sequence indicates the degree to which that sequence recruits or repels SHM machinery to that site. Individual sequences from these lists may be chosen to enhance or limit SHM-mediated mutations at each site.

Figure 34:
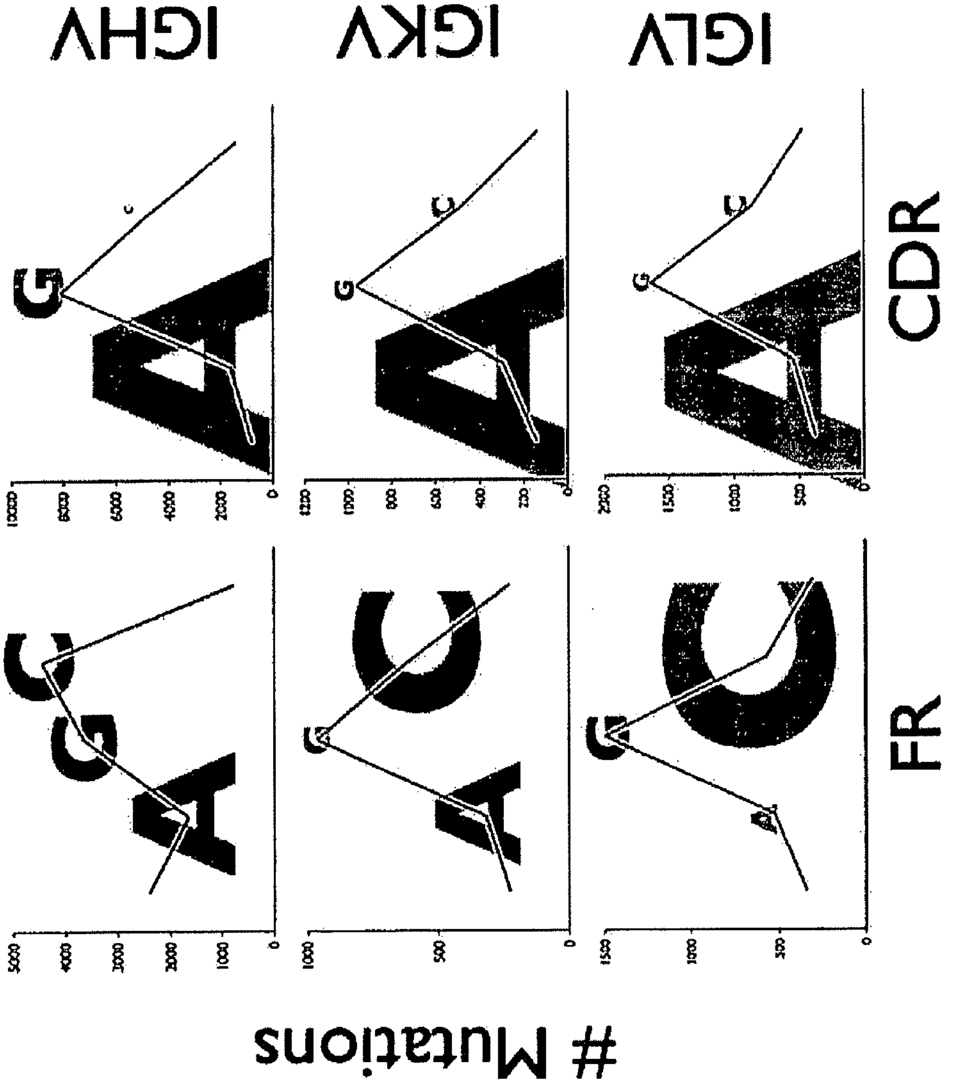

FIG. 34 The 3-mer nucleotide motif AGC represents a preferred site for somatic hypermutation events. In the Figure, we see the number of mutations observed in our analysis (line graph) at each position of the AGC motif found in framework (FR) and complementarity-determining regions (CDR) for the heavy and light chains of antibodies. The font size for each nucleotide position of the motif shows how often each nucleotide serves as the first position of the codon reading frame. Within framework regions, no one reading frame dominates, whereas within CDRs, the first position (A) of the AGC motif is almost universally used as the first position of the codon.

Figure 35:
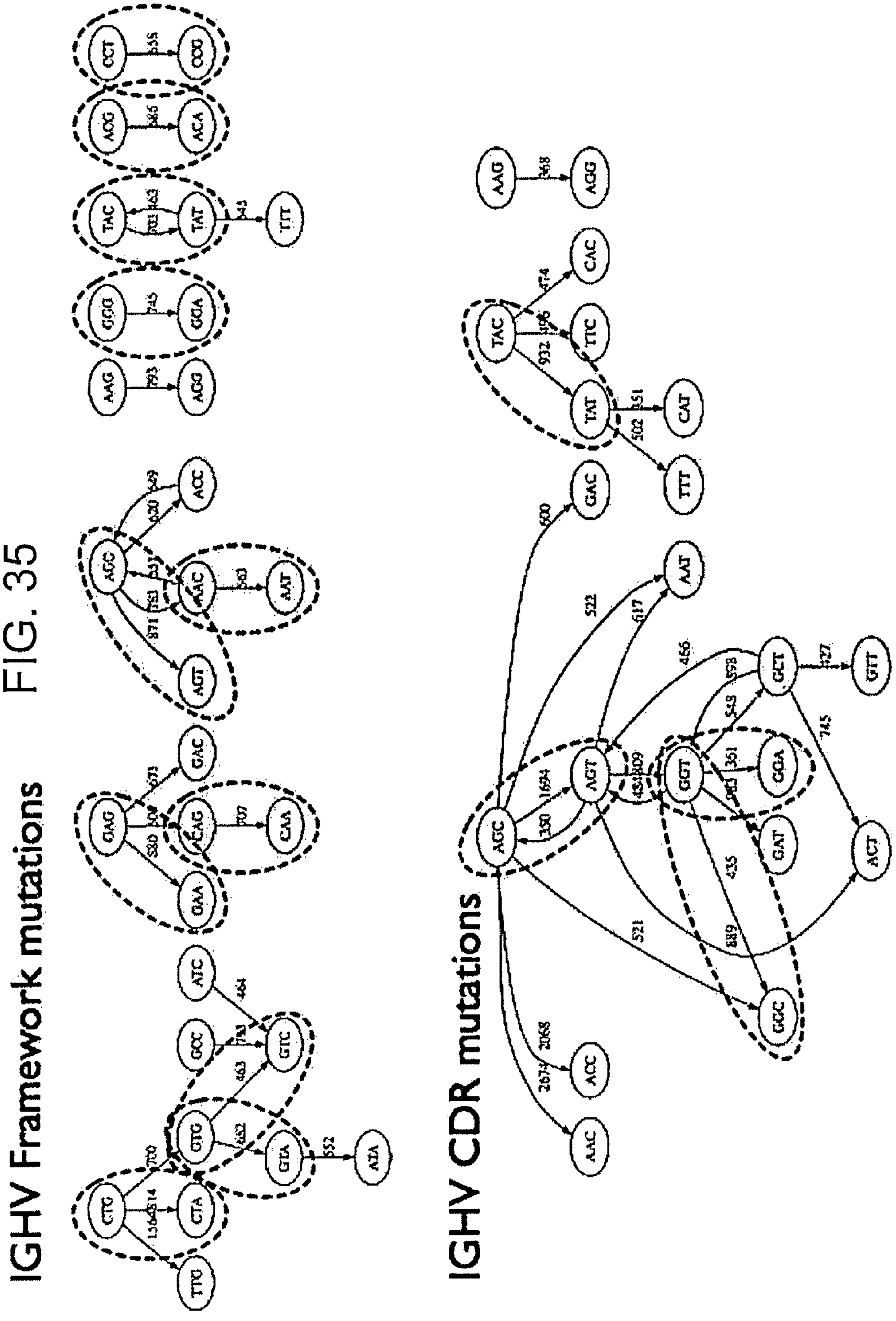
Figure 36A:
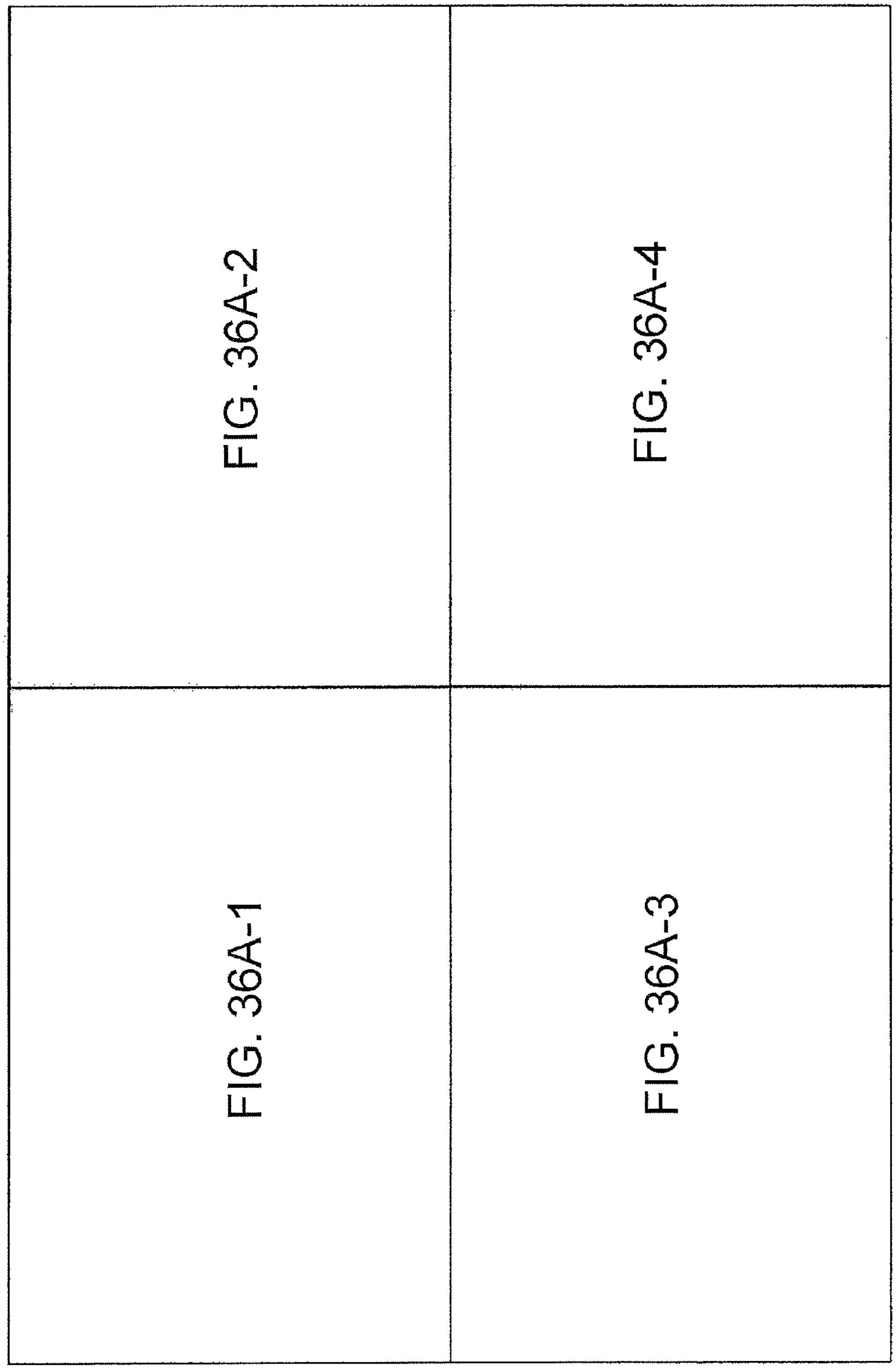
Figure 36B:
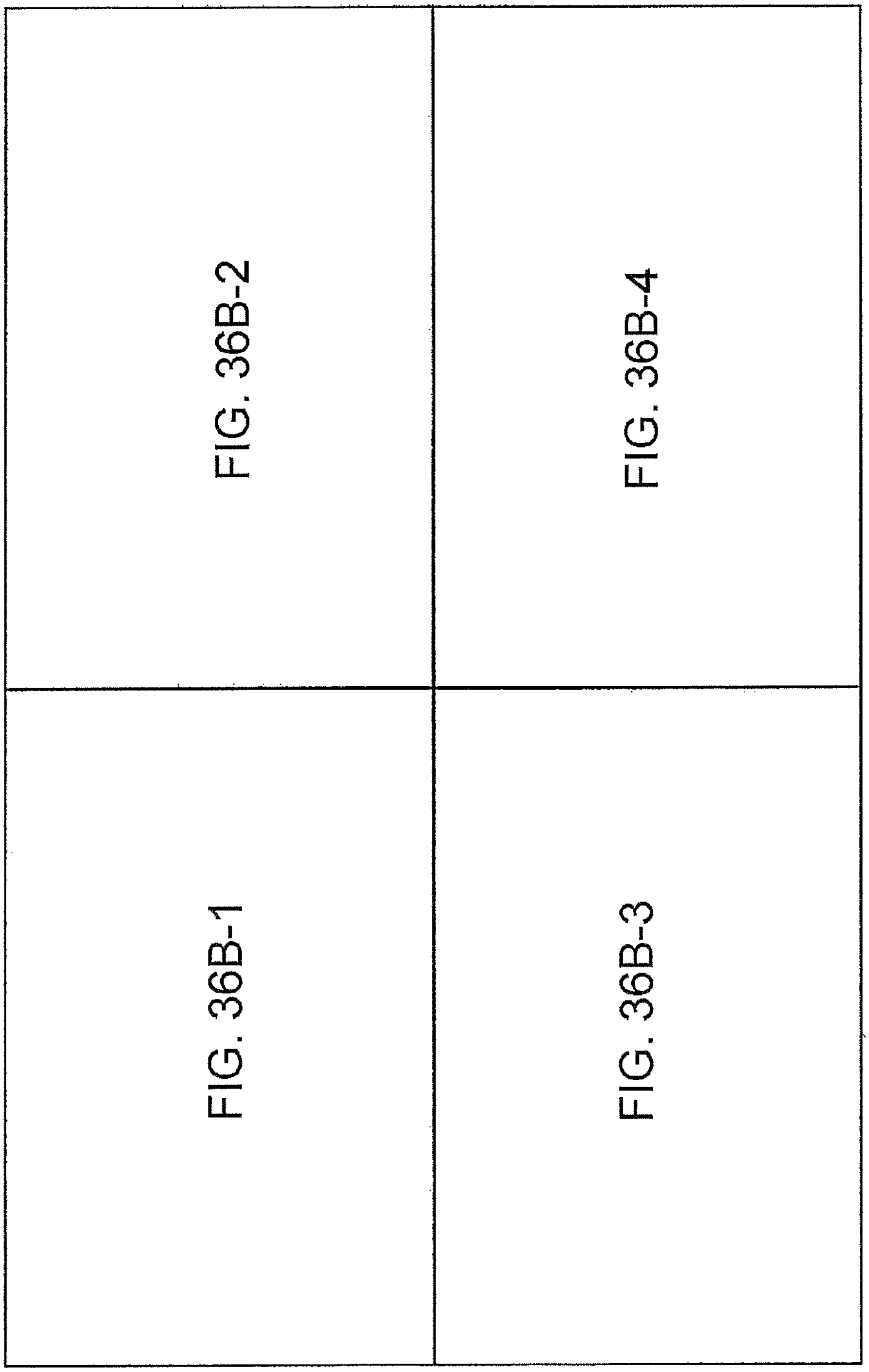
Figure 36C:
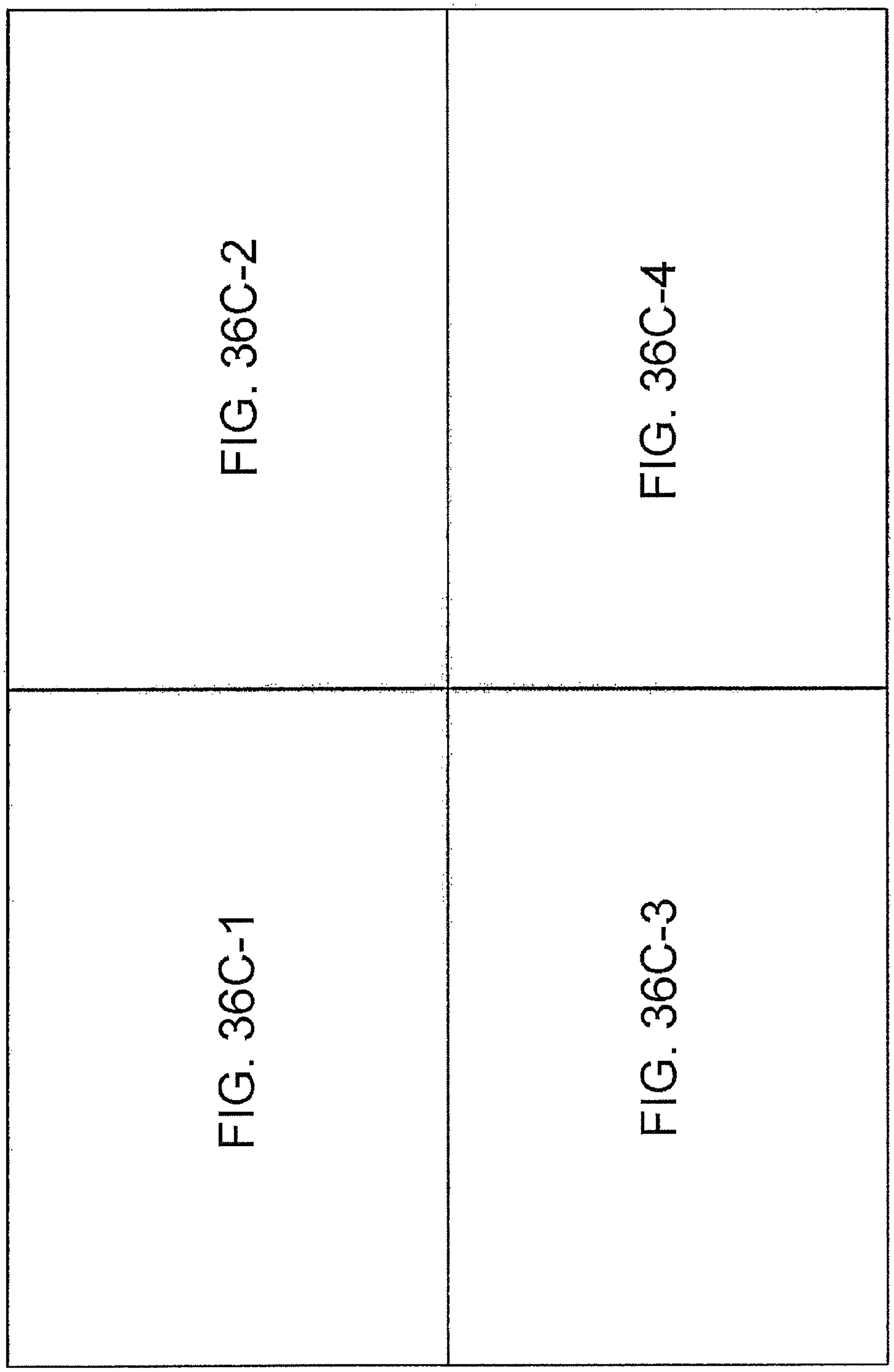
Figure 36D:
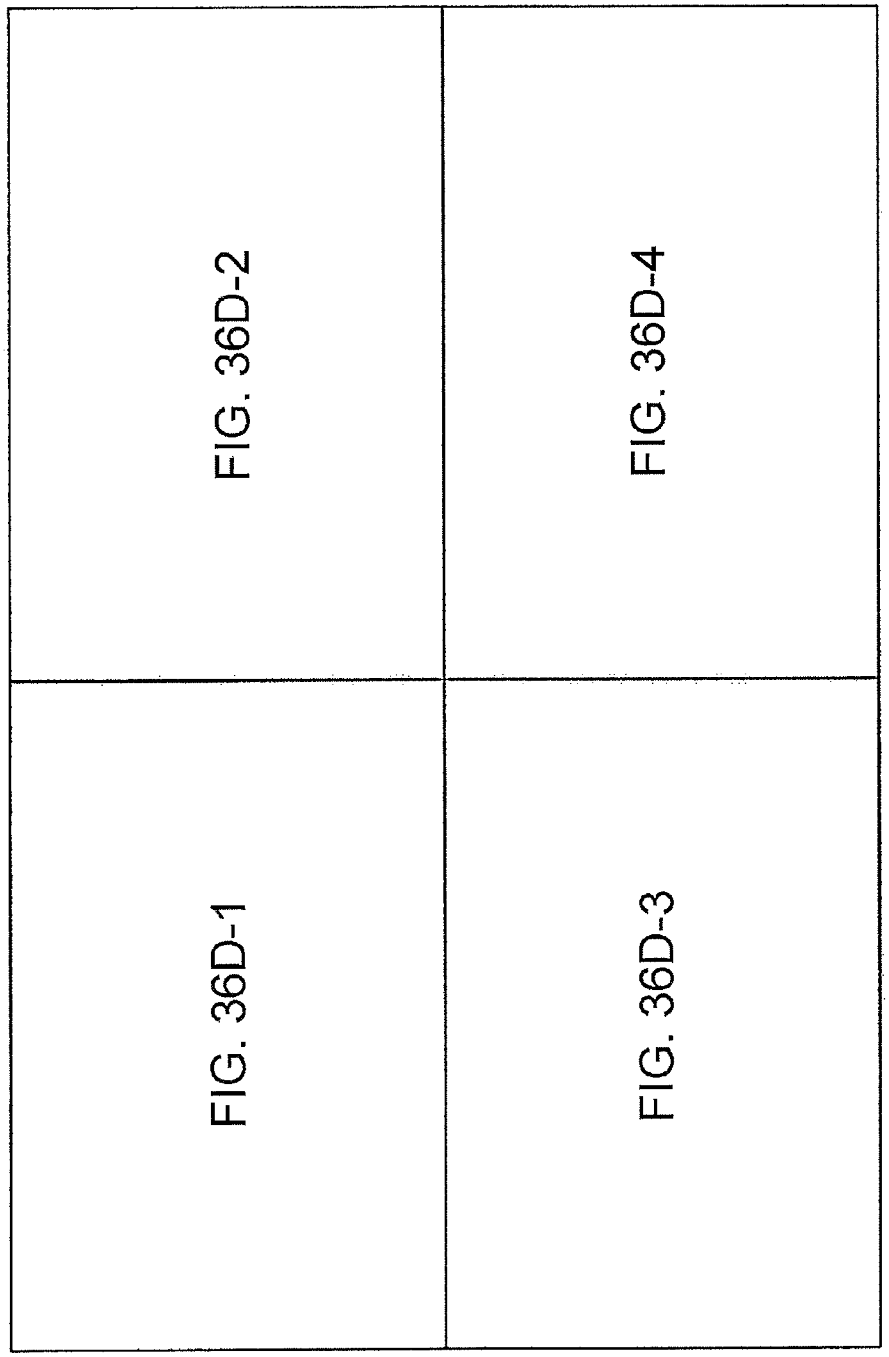

FIG. 35 shows the 20 most hot spot codon hypermutation transition events within the FR and CDR regions of heavy chain antibodies, where the numbers labeling the arrows indicate how often a codon transition event was observed. The codons AGC and AGT (serine), and to a lesser extent TAC and TAT (tyrosine), account for ~50% of the originating mutations observed in affinity matured antibodies. Use of these hot spot codons within the correct reading frame, combined with affinity maturation leads to many fewer observed silent mutations within CDRs compared to framework regions (highlighted by dotted circles in the figure).

FIGS. 36A-36D are tables which show numerical values of transition frequencies for a representative SHM system.

Figure 37:
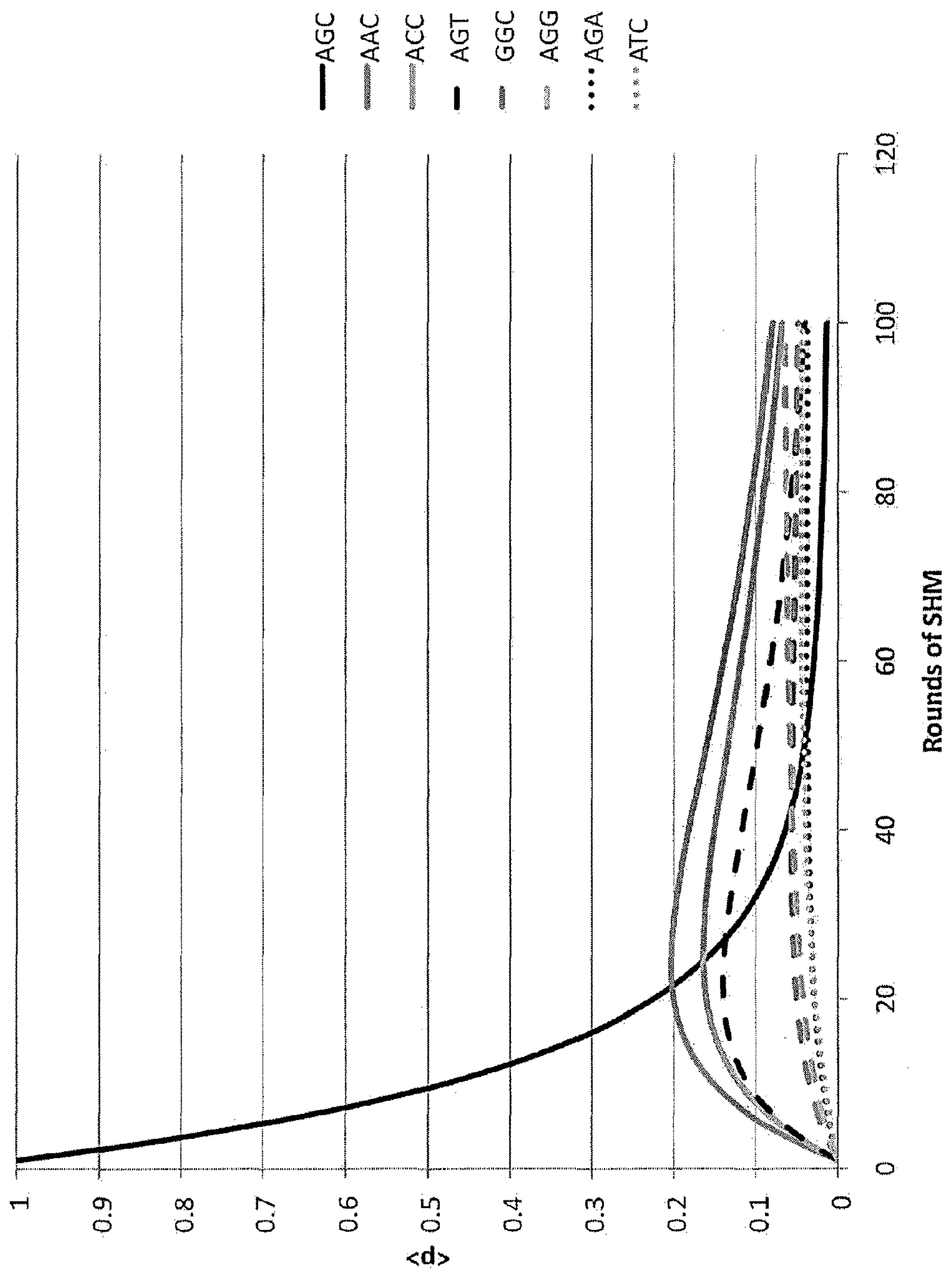

FIG. 37 shows the evolution of the codon AGC (serine), a preferred SHM codon, and the resulting codon frequencies over 50 rounds of SHM-mediated mutagenesis, as calculated in the Markov chain model.

Figure 38:
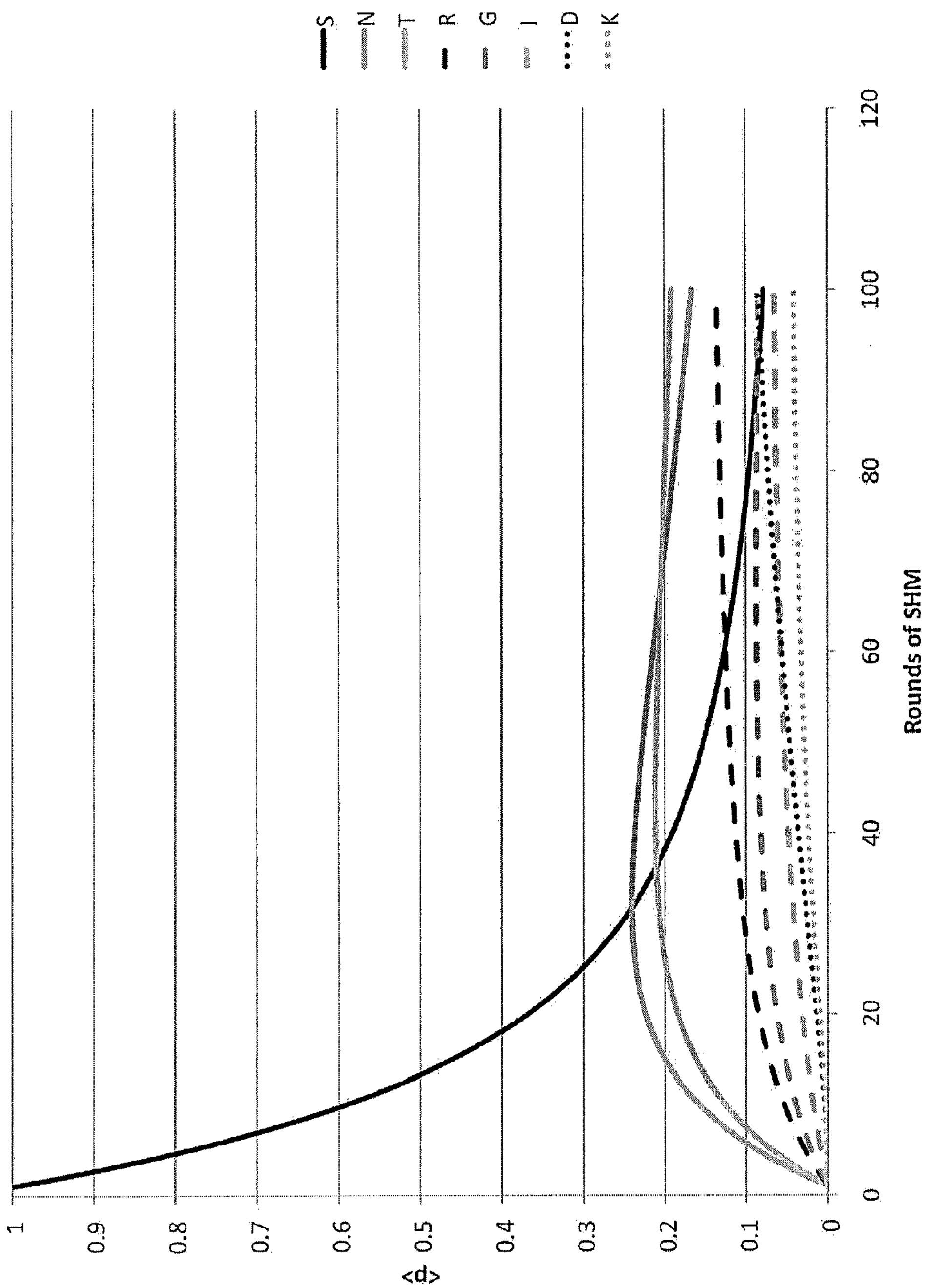

FIG. 38 shows the evolution of the codon AGC (serine), a preferred SHM codon, and the resulting amino acid frequencies encoded by the codons produced in situ, over 50 rounds of SHM-mediated mutagenesis, as calculated in the Markov chain model.

Figure 39:
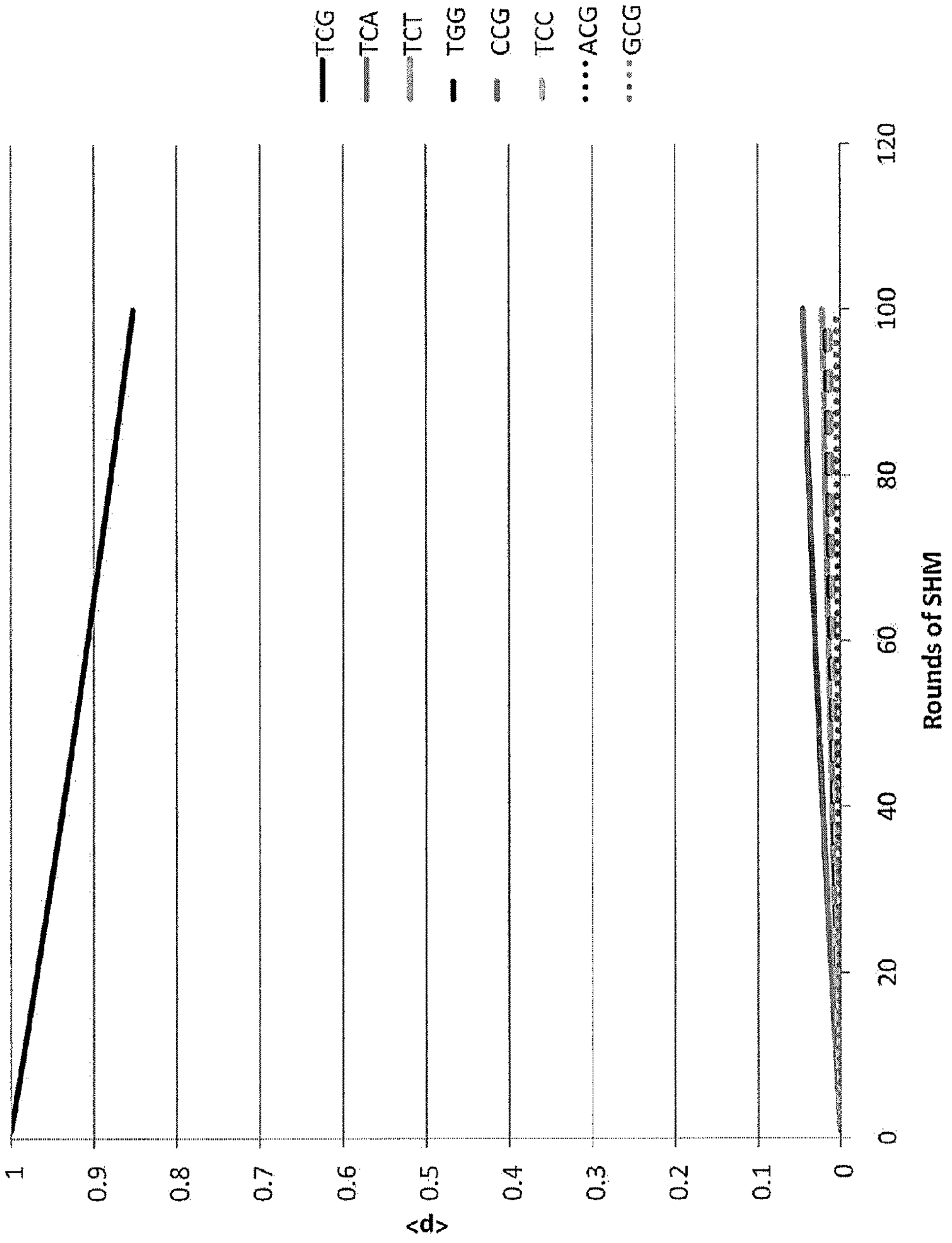

FIG. 39 shows the evolution of the codon TCG (serine), a non-preferred SHM codon, and the resulting codon frequencies over 50 rounds of SHM-mediated mutagenesis, as calculated in the Markov chain model.

Figure 40:
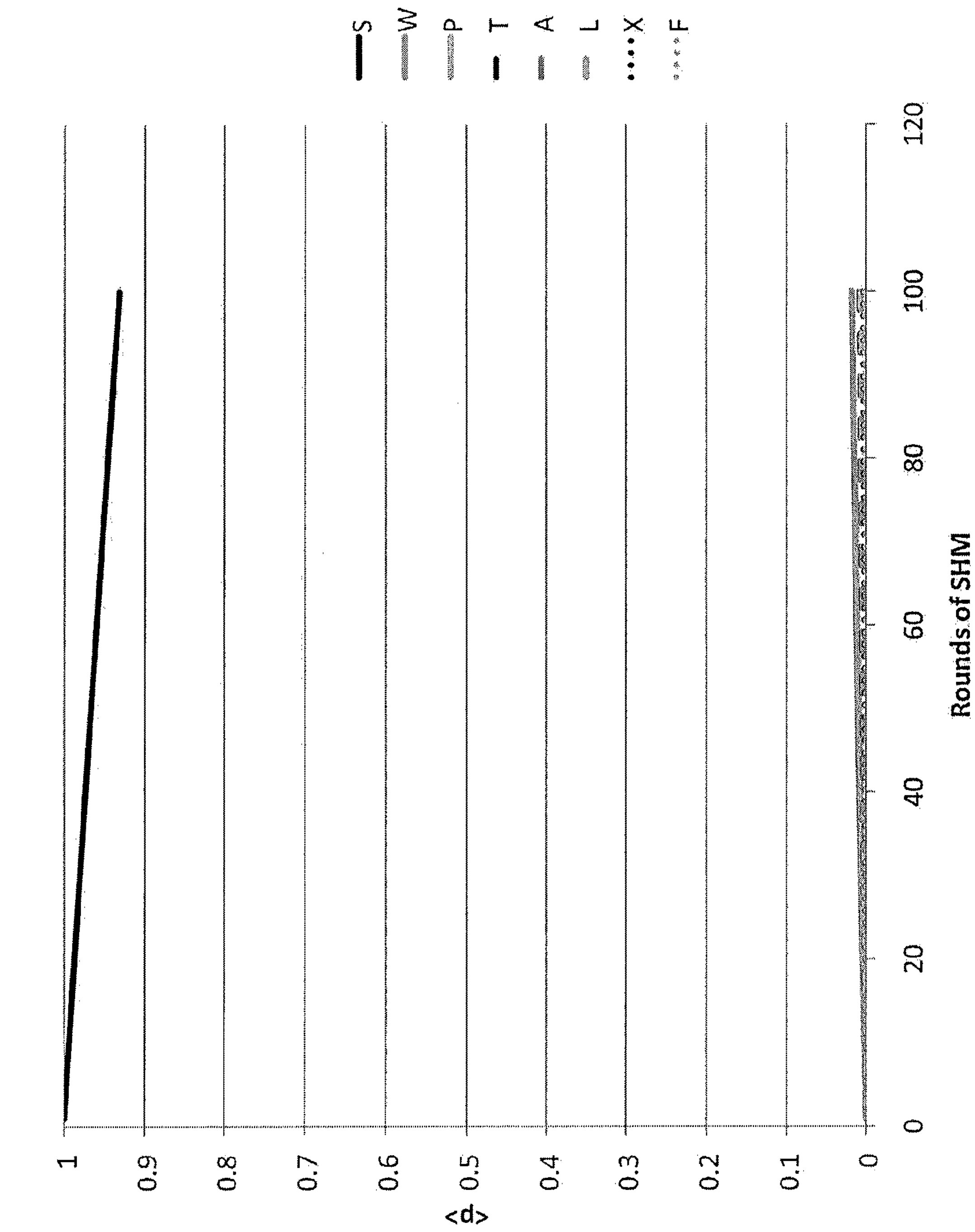

FIG. 40 shows the evolution of the codon TCG (serine), a non-preferred SHM codon, and the resulting amino acid frequencies encoded by the codons produced in situ, over 50 rounds of SHM-mediated mutagenesis, as calculated in the Markov chain model.

Figure 41:
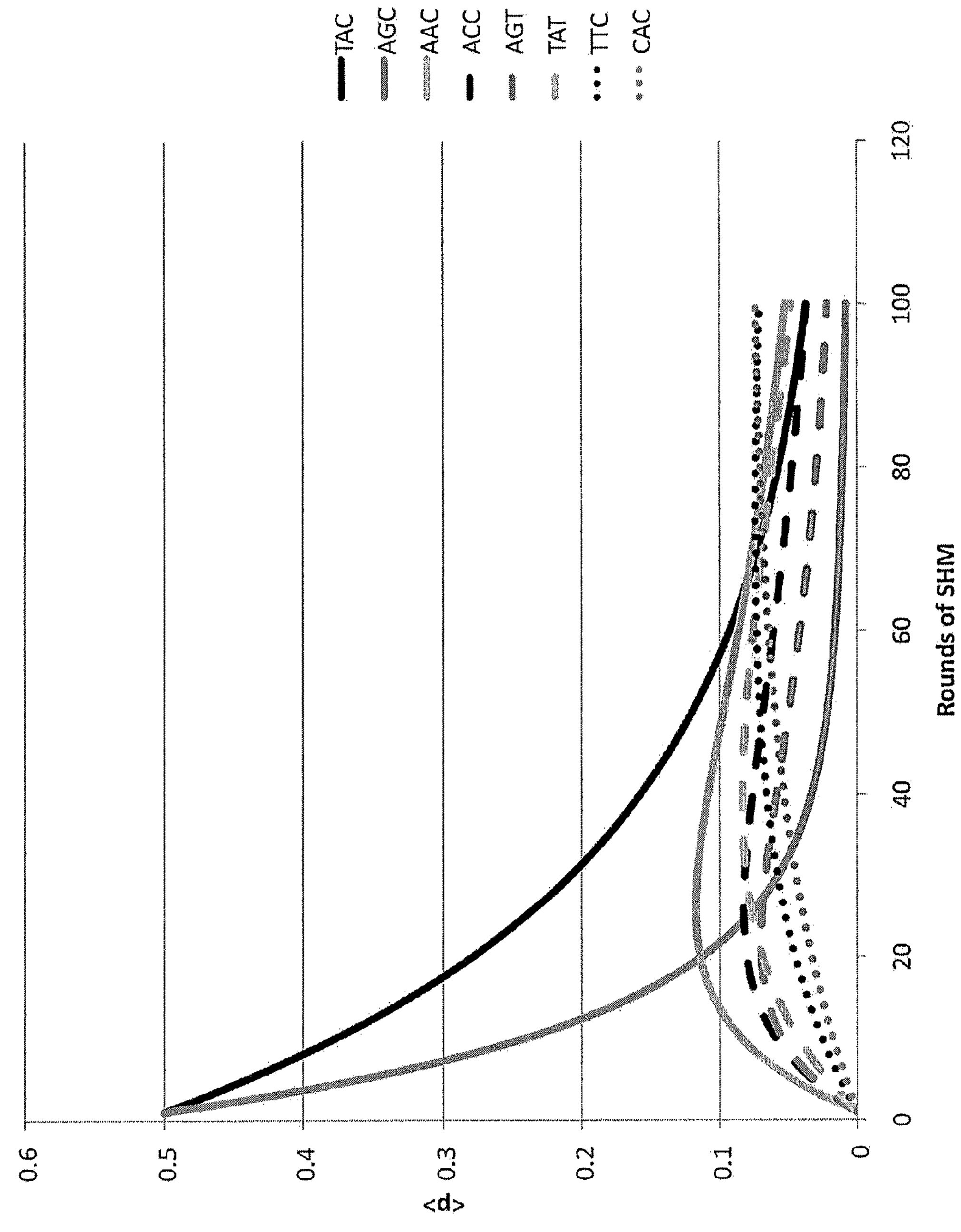

FIG. 41 shows the evolution of the codons AGC/TAC, the "WRC motif" (comprising preferred SHM codons encoding serine and tyrosine) and the resulting codon frequencies over 50 rounds of SHM-mediated mutagenesis, as calculated in the Markov chain model.

Figure 42:
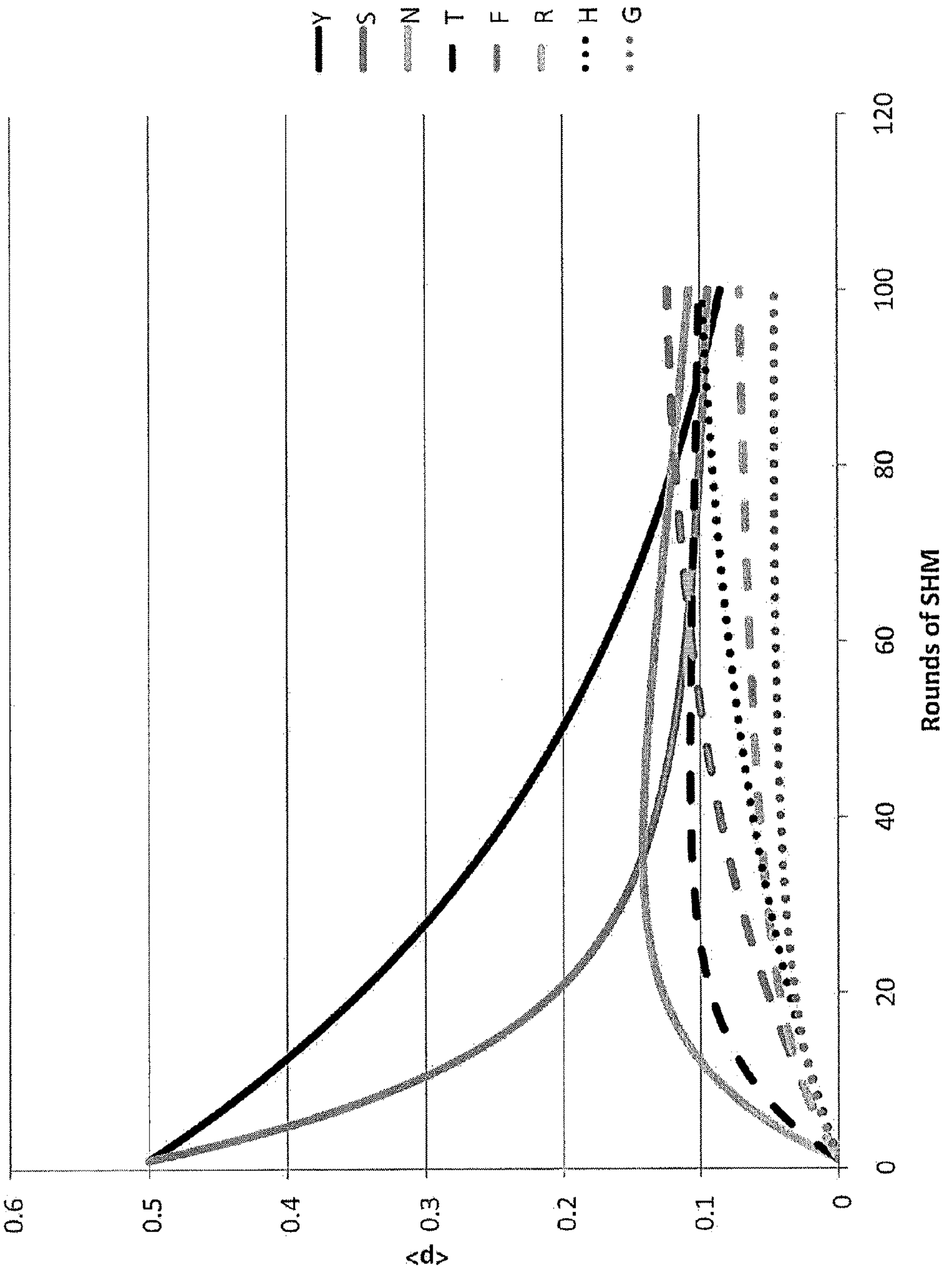

FIG. 42 shows the evolution of the codons AGC/TAC, the "WRC motif" (comprising preferred SHM codons encoding serine and tyrosine) and the resulting amino acid frequencies encoded by the codons produced in situ, over 50 rounds of SHM-mediated mutagenesis, as calculated in the Markov chain model.

Figure 43:
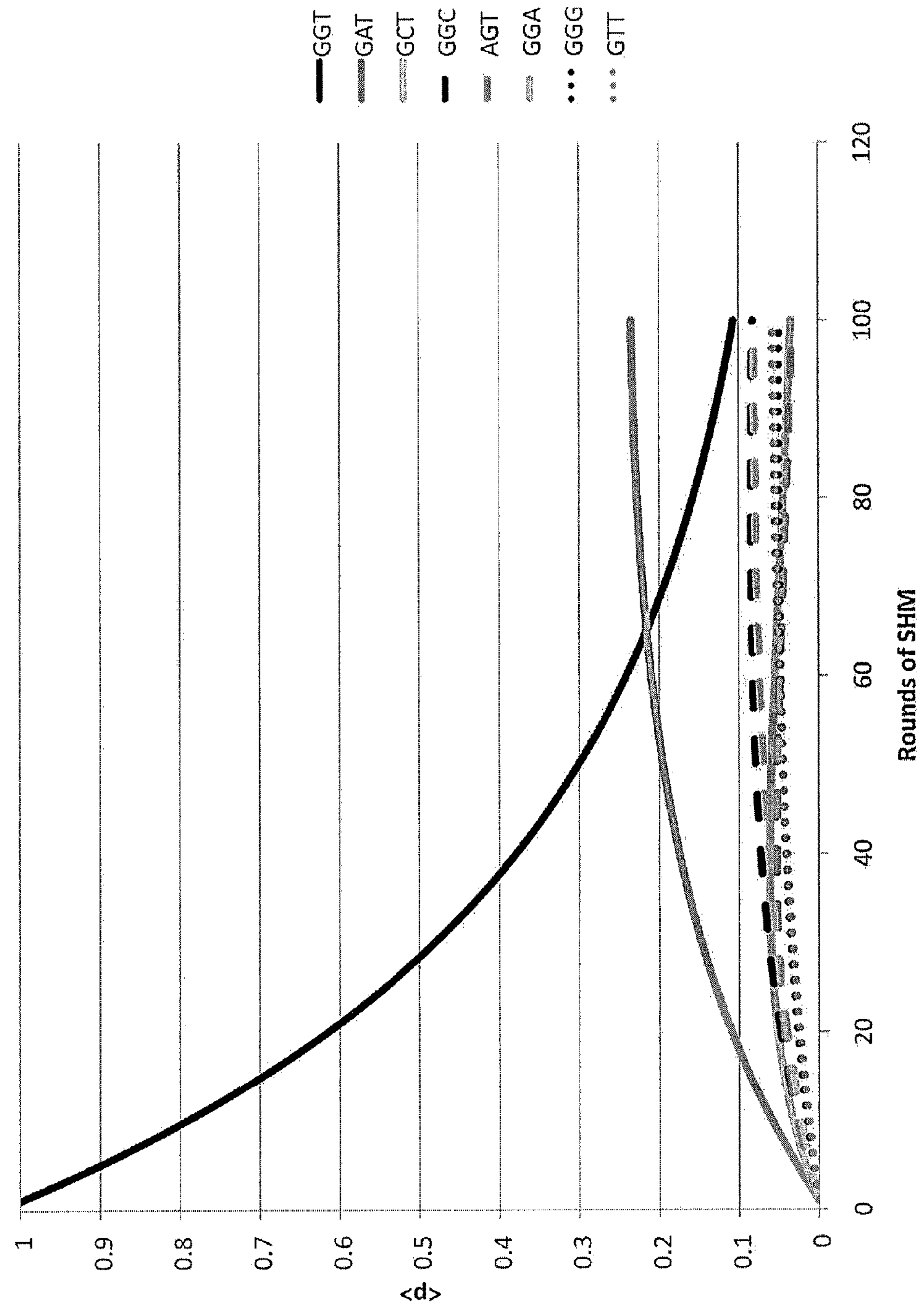

FIG. 43 shows the evolution of the GGT codon (glycine), a preferred SHM codon, and the resulting codon frequencies over 50 rounds of SHM-mediated mutagenesis, as calculated in the Markov chain model. The figure shows the immediate evolution of codons arising from single mutation events, such as GAT (aspartate), GCT (alanine), and AGT (serine). Secondary mutation events acting on these new codons give rise to a tertiary set of codons. For instance, both AGT and GGT under SHM produce the codon AAT, leading to acquisition of asparagine at this position.

Figure 44:
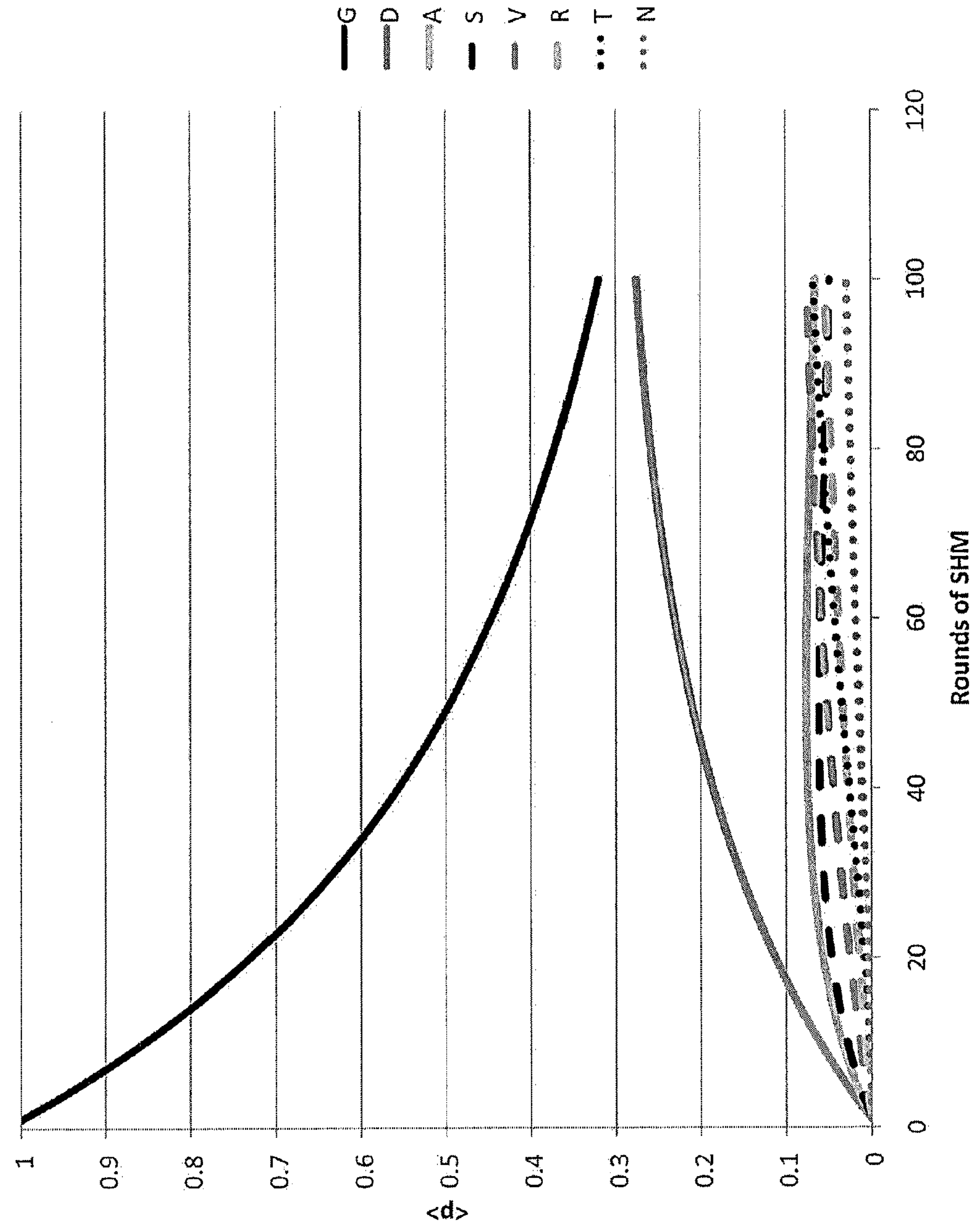

FIG. 44 shows the evolution of a GGT codon (glycine), and the immediate evolution of amino acids arising from single mutation events, such as GAT (aspartate), GCT (alanine), and AGT (serine) over 50 rounds of SHM-mediated mutagenesis, as calculated in the Markov chain model.

Figure 45:
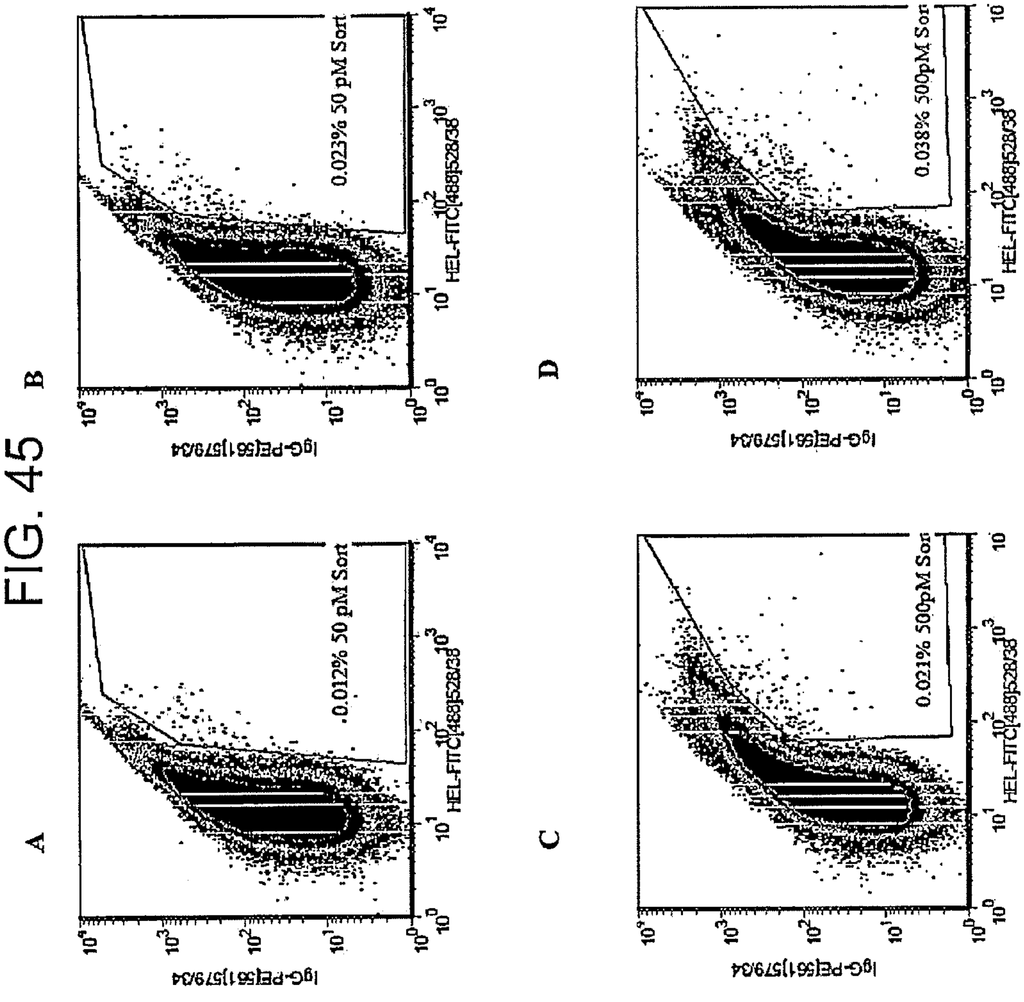

FIG. 45 HEK-293 cells transfected with a low affinity anti-HEL antibody (comprising the light chain mutation N31G) and an constitutive AID expression vector either after stable transfection and selection (panels A and C) or transiently with the addition of re-transfected AID expression vector (panels B and D) were incubated with either 50 pM HEL-FITC (A and B) or 500 pM HEL-FITC (C and D) and living HEL-FITC-binding cells were sorted and expanded in culture for another round of selection and sequence analysis.

Figure 46:
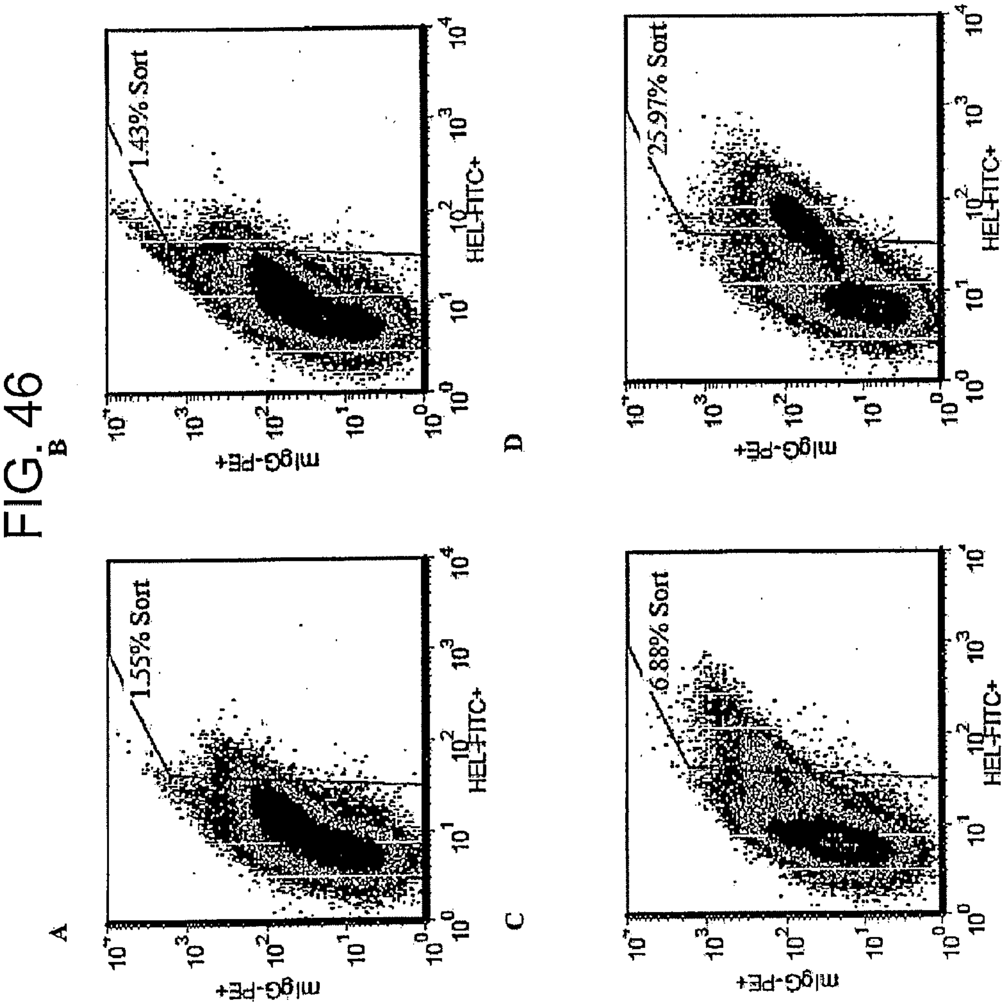

FIG. 46 Previously sorted HEK-293 cells expressing anti-HEL antibodies and constitutive canine AID either after stable transfection and selection (A and C) or transiently with the addition of re-transfected AID expression vector (panels B and D) were incubated with either 50 pM HEL-FITC (A and B) or 500 pM HEL-FITC (C and D) and living HEL-FITC-binding cells were sorted and expanded in culture for another round of selection and sequence analysis.

Figure 47:
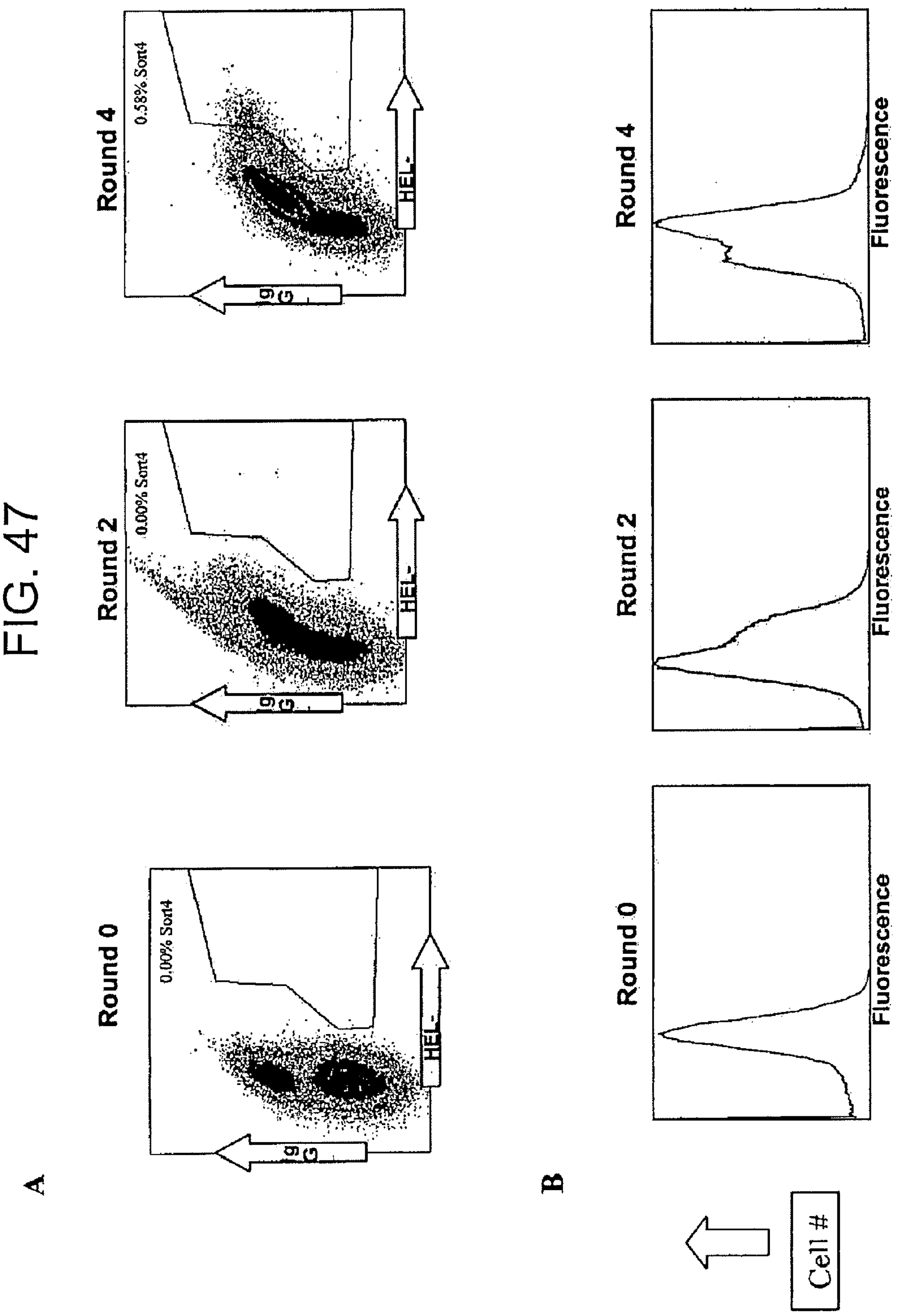

FIG. 47 HEK-293 cells transfected with a low affinity anti-HEL antibody and evolved over 4 rounds of selection and evolution were analyzed by incubation with 50 pM HEL-FITC, as described in Example 13. Panel A shows that over 4 rounds of evolution, a clear increase in positive cells is evident in both the FACS scatter plot (panel A), as well as total number of positive cells gated (panel B).

FIG. 48 Panel A shows a selection of amino sequences around the HyHEL10 light chain CDR1 (SEQ ID NOS: 56, 57 and 58), illustrating the evolved sequence around the site of the Asn 31 mutation introduced in the starting constructs. Panel B shows the corresponding nucleic acid sequences (SEQ ID NOS: 59, 60 and 61). Panel C shows a representation of the measured affinity of the evolved mutants.

Figure 49:
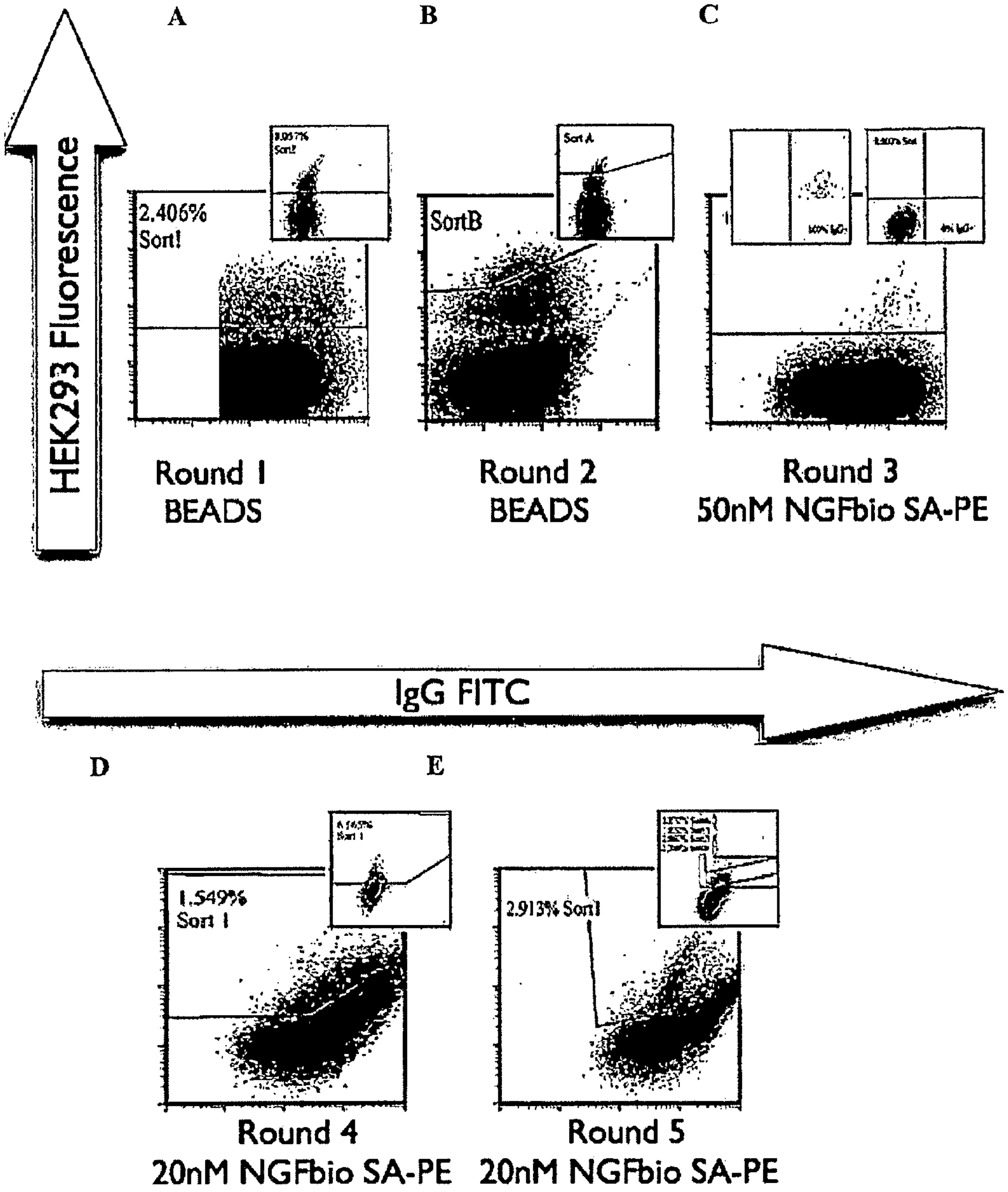

FIG. 49. Shows FACS scattergrams for the isolation of antibodies to NGF selected via the use of intact protein over 5 rounds of selection, as described in Example 15. Panels A and B show FACS results using NGF coupled to beads, and panels C, D and E show FACS scattergrams obtained using 50 nM (panel C) or 20 nM (panels D or E) NGF. Inserts to the graphs show control incubations performed with control cells. In these graphs, the X-axis indicates the extent of IgG expression of the cells and the Y-axis specifies the magnitude of bead binding by cells as described in the Examples.

Figure 50:
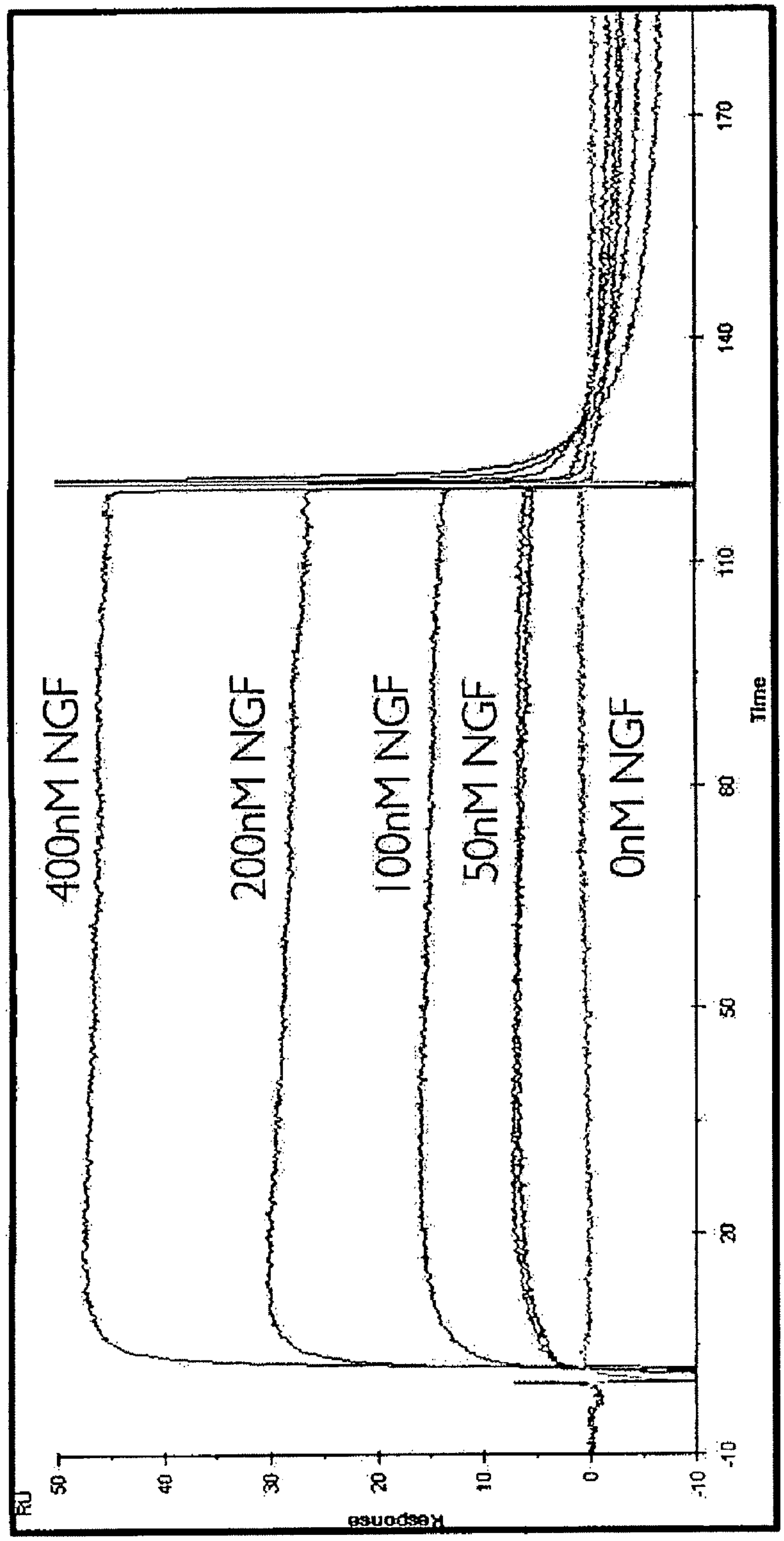

FIG. 50. Shows the results of Biacore analysis of a representative antibody isolated from screening of the surface displayed antibody library with NGF as described in Example 15. A multivariate fit of these data produce a predicted dissociation constant of (Kd) of 670 nM.

FIG. 51 Provides the polynucleotide sequence (A; SEQ ID NO: 458) of a unmodified form of the Teal Fluorescent Protein (TFP). Also shown is the analysis of hot spots (B) and cold spots (C) as illustrated by bold capital letters. 40 CpG methylation sites were present (data not shown).

FIG. 52 Provides the polynucleotide sequence (A; SEQ ID NO: 459) of a synthetic SHM susceptible (hot) form of the Teal Fluorescent Protein (TFP). Also shown is the analysis of hot spots (B) and cold spots (C) as illustrated by bold capital letters. 14 CpG methylation sites were present (data not shown).

Figure 53:
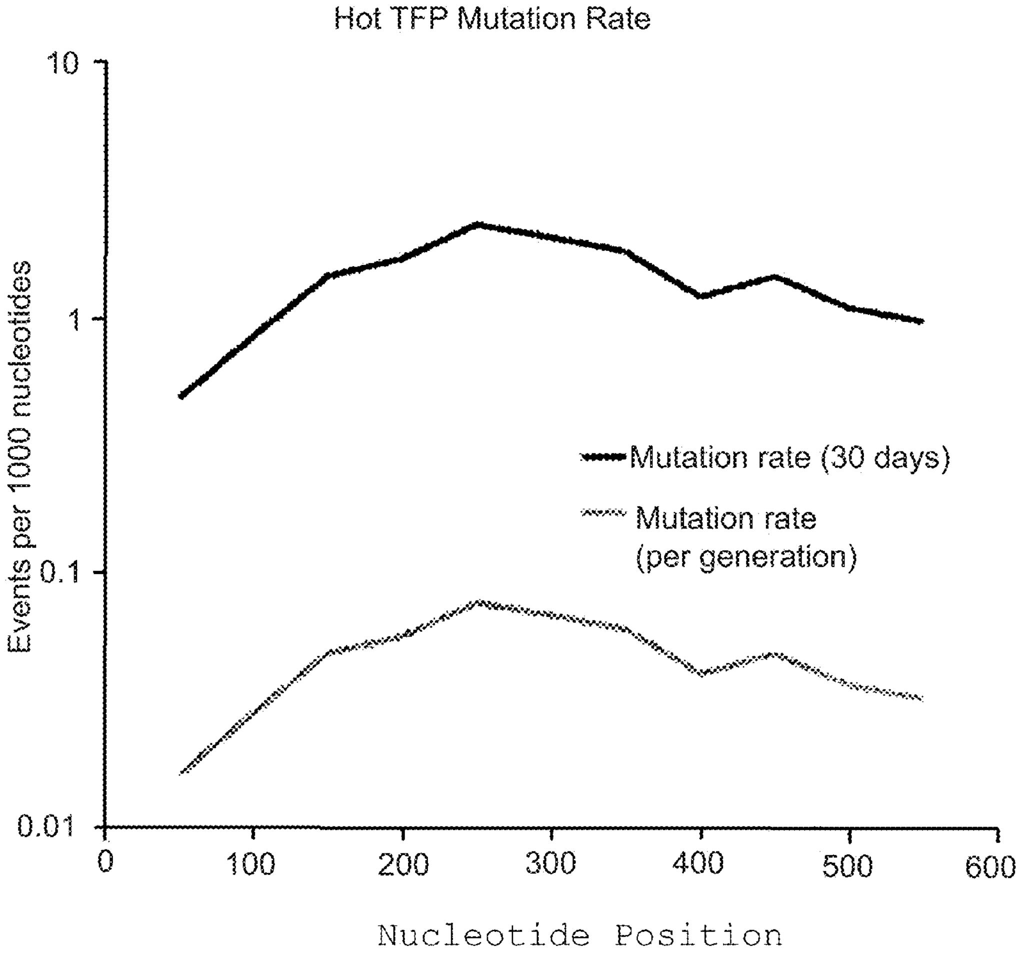

FIG. 53 Provides the polynucleotide sequence (A; SEQ ID NO: 460) of a synthetic SHM resistant (cold) form of the Teal Fluorescent Protein (TFP). Also shown is the analysis of hot spots (B) and cold spots (C) as illustrated by bold capital letters. 21 CpG methylation sites were present (data not shown).

FIG. 53D shows the mutations for a representative segment of the hot and cold TFP constructs. The central row shows the amino acid sequence of TFP (residues 59 thru 87) in single letter format (SEQ ID NO: 461), and the "hot" and "cold" starting nucleic acid sequences encoding the two constructs are shown above (hot; SEQ ID NO: 462) and below (cold) the amino acid sequence (SEQ ID NO: 463). Mutations observed in the hot sequence are aligned and stacked top of the gene sequences, while mutations in the cold TFP sequence are shown below. The results illustrate how "silent" changes to the coding sequences generate dramatic changes in observed AID-mediated SHM rates, demonstrating that engineered sequences can be effectively optimized to create fast or slow rates of SHM.

FIG. 53E shows that the spectrum of mutations generated by AID in the present in vitro tissue culture system mirror those observed in other studies and those seen during in vivo affinity maturation. FIG. 53E shows the mutations generated in the present study (Box (i) upper left, n=118), and compares them with mutations observed by Zan et al. (box (ii) upper right, n=702), Wilson et al. (lower left, n=25000; box (iii)), and a larger analysis of IGHV chains that have undergone affinity maturation (lower right, n=101,926; box (iv)). The Y-axis in each chart indicates the starting nucleotide, the X-axis indicates the end nucleotide, and the number in each square indicates the percentage (%) of time that nucleotide transition is observed. In the present study, the frequency of mutation transitions and transversions was similar to those seen in other data sets. Mutations of C to T and G to A are the direct result of AID activity on cytidines and account for 48% of all mutation events. In addition, mutations at bases A and T account for ~30% of mutation events (i.e., slightly less than frequencies observed in other datasets).

FIG. 53F shows that mutation events are distributed throughout the SHM optimized nucleotide sequence of the hot TFP gene, with a maximum instantaneous rate of about 0.08 events per 1000 nucleotides per generation centered around 300 nucleotides from the beginning of the open reading frame. Stable transfection and selection of a gene with AID (for 30 days) produces a maximum rate of mutation of 1 event per 480 nucleotides. As a result, genes may contain zero, one, two or more mutations per gene.

FIG. 53G Illustrates the distribution of SHM-mediated events observed in hot TFP sequenced genes compared to the significantly reduced pattern of mutations seen in cold TFP (FIG. 53H).

DETAILED DESCRIPTION OF THE INVENTION

I. Somatic Hypermutation Systems

In vitro somatic hypermutation (SHM) systems as described in related priority application U.S. Provisional Application No. 60/902,414, entitled "SOMATIC HYPERMUTATION SYSTEMS," filed on Feb. 20, 2007, involve the use of in vitro somatic hypermutation in conjunction with directed evolution and bioinformatic analysis to create integrated systems that include, but are not limited to, optimized, controlled systems for library design, screening, selection and integrated systems for the data mining These systems include:

I. An expression system designed to create SHM susceptible and or SHM resistant DNA sequences, within a cell or cell-free, environment. The system enables the stable maintenance of a mutagenesis system that provides for high level targeted SHM in a gene template of interest, while significantly preventing non-specific mutagenesis of structural proteins, transcriptional control regions and selectable markers.

II. Polynucleotide libraries that are focused in size and specificity. These libraries can be synthetic libraries, semi-synthetic libraries, and/or seed libraries. In certain aspects, the polynucleotide libraries can be enriched for SHM to seed in situ diversity creation. In one such embodiment, a polynucleotide library can be enriched for SHM wherein the library comprises a plurality of polynucleotides having a nucleic acid sequence encoding a functional portion of a protein of interest that is modified to act as a substrate for SHM.

III. A process based on computational analysis of protein structure, intra-species and inter-species sequence variation, and the functional analysis of protein activity for selecting optimal epitopes that provide for the selection of antibodies with superior selectivity, cross species reactivity, and blocking activity.

The overall result of the integration of these approaches is an integrated system for creating targeted diversity in situ, and for the automated analysis and selection of proteins with improved traits.

In certain embodiments, the present invention is based in part of an improved understanding of the context of multiple rounds of SHM within the reading frame of a polynucleotide sequence, and the underlying logic relationships inherent within codon usage patterns.

In particular, the above systems for in vitro SHM provide new design possibilities for the creation of "seed" libraries that can efficiently serve as the substrate for SHM for the evolution and selection of improved proteins.

i. Definitions

As used herein and in the appended claims, the terms "a," "an" and "the" can mean, for example, one or more, or at least one, of a unit unless the context clearly dictates otherwise. Thus, for example, reference to "an antibody" includes a plurality of such antibodies and reference to "a variable regions" includes reference to one or more variable regions and equivalents thereof known to those skilled in the art, and so forth. In the event that there is a plurality of definitions for a term herein, those in this section prevail unless stated otherwise.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

The terms "comprise" or "comprising" are used in their open, non-limiting sense, that is to say permitting the presence of one or more features or components in addition to the recited feature or features.

The term "consisting essentially of" refers to a product, particularly a peptide sequence, of a defined number of residues which is not covalently attached to a larger product. In the case of the peptide of the invention referred to above, those of skill in the art will appreciate that minor modifications to the N- or C-terminal of the peptide may however be contemplated, such as the chemical modification of the terminal to add a protecting group or the like, e.g. the amidation of the C-terminus.

The term "isolated" refers to the state in which specific binding members or other specific proteins of the invention, or nucleic acids encoding such binding members or proteins will be, in accordance with the present invention. Binding members or other proteins, and nucleic acids encoding them will be free or substantially free of material with which they are naturally associated such as other polypeptides or nucleic acids with which they are found in their natural environment, or the environment in which they are prepared (e.g. cell culture) when such preparation is by recombinant DNA technology practiced in vitro or in vivo. It is to be understood, however, that binding members or other proteins, and nucleic acids encoding them may be formulated with diluents or adjuvants and still for practical purposes be isolated—for example binding members will normally be mixed with gelatin or other carriers if used to coat microtitre plates for use in immunoassays, or will be mixed with pharmaceutically acceptable carriers or diluents when used in diagnosis or therapy. Specific binding members or other specific proteins can be glycosylated, either naturally or by systems of heterologous eukaryotic cells, or they can be (for example if produced by expression in a prokaryotic cell) unglycosylated.

The term "selection" refers to the separation of one or more members, such as polynucleotides, proteins or cells from a library of such members. Selection can involve both detection and selection, for example where cells are selected by use of a fluorescence activated cell sorter (FACS) that detects a reporter gene and then sorts the cells accordingly.

As used herein, "pg" means picogram, "ng" means nanogram, "ug" or "μg" mean microgram, "mg" means milligram, "ul" or "μl" mean microliter, "ml" means milliliter, "l" means liter, "kb" means kilobases, "uM" or "μM" means micromolar, "nM" means nanomolar, "pM" means picomolar, "fM" means femtomolar.

The phrase "pharmaceutically acceptable" refers to molecular entities and compositions that are physiologically tolerable and do not typically produce an allergic or similar untoward reaction, such as gastric upset, dizziness and the like, when administered to a human.

Antibody Terminology

The term "antibody" describes an immunoglobulin whether natural or partly or wholly synthetically produced. The term also covers any polypeptide or protein having a binding domain which is, or is homologous to, an antigen-binding domain. CDR grafted antibodies are also contemplated by this term.

"Native antibodies" and "native immunoglobulins" are usually heterotetrameric glycoproteins of about 150,000 daltons, composed of two identical light (L) chains and two identical heavy (H) chains. Each light chain is typically linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ("$V_H$") followed by a number of constant domains ("$C_H$"). Each light chain has a variable domain at one end ("$V_L$") and a constant domain ("$C_L$") at its other end; the constant domain of the light chain is aligned with the first constant domain of the heavy chain, and the light-chain variable domain is aligned with the variable domain of the heavy chain. Particular amino acid residues are believed to form an interface between the light- and heavy-chain variable domains.

The term "variable domain" refers to protein domains that differ extensively in sequence among family members (i.e. among different isoforms, or in different species). With respect to antibodies, the term "variable domain" refers to the variable domains of antibodies that are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the "framework region" or "FR." The variable domains of native heavy and light chains each comprise four FRs (FR1, FR2, FR3 and FR4, respectively), largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991), pages 647-669). The constant domains are not involved directly in binding an antibody to an antigen, but exhibit various effector functions, such as participation of the antibody in antibody-dependent cellular toxicity.

The term "hypervariable region" when used herein refers to the amino acid residues of an antibody which are responsible for antigen-binding. The hypervariable region comprises amino acid residues from three "complementarity determining regions" or "CDRs," which directly bind, in a complementary manner, to an antigen and are known as CDR1, CDR2, and CDR3 respectively.

In the light chain variable domain, the CDRs typically correspond to residues 24-34 (CDRL1), 50-56 (CDRL2) and 89-97 (CDRL3), and in the heavy chain variable domain the CDRs typically correspond to residues 31-35 (CDRH1), 50-65 (CDRH2) and 95-102 (CDRH3); Kabat et al., Sequences of Proteins of Immunological Interest, 5th Ed. Public Health Service, National Institutes of Health, Bethesda, Md. (1991)) and/or those residues from a "hypervariable loop" (i.e. residues 26-32 (L1), 50-52 (L2) and 91-96 (L3) in the light chain variable domain and 26-32 (H1), 53-55 (H2) and 96-101 (H3) in the heavy chain variable domain; Chothia and Lesk J. Mol. Biol. 196:901 917 (1987)).

As used herein, "variable framework region" or "VFR" refers to framework residues that form a part of the antigen binding pocket or groove and/or that may contact antigen. In some embodiments, the framework residues form a loop that is a part of the antigen binding pocket or groove. The amino acids residues in the loop may or may not contact the antigen. In an embodiment, the loop amino acids of a VFR are determined by inspection of the three-dimensional structure of an antibody, antibody heavy chain, or antibody light chain. The three-dimensional structure may be analyzed for solvent accessible amino acid positions as such positions are likely to form a loop and/or provide antigen contact in an antibody variable domain. Some of the solvent accessible positions can tolerate amino acid sequence diversity and others (e.g. structural positions) will be less diversified. The three dimensional structure of the antibody variable domain may be derived from a crystal structure or protein modeling. In some embodiments, the VFR comprises, consist essentially of, or consists of amino acid positions corresponding to amino acid positions 71 to 78 of the heavy chain variable domain, the positions defined according to Kabat et al., 1991. In some embodiments, VFR forms a portion of Framework Region 3 located between CDRH2 and CDRH3. Preferably, VFR forms a loop that is well positioned to make contact with a target antigen or form a part of the antigen binding pocket.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2. The heavy-chain constant domains (Fc) that correspond to the different classes of immunoglobulins are called α, δ, ϵ, γ, and μ, respectively. The subunit structures and three-dimensional configurations of different classes of immunoglobulins are well known.

The "light chains" of antibodies (immunoglobulins) from any vertebrate species can be assigned to one of two clearly distinct types, called kappa or ("κ") and lambda or ("λ"), based on the amino acid sequences of their constant domains.

The terms "antigen-binding portion of an antibody," "antigen-binding fragment," "antigen-binding domain," "antibody fragment" or a "functional fragment of an antibody" are used interchangeably in the present invention to mean one or more fragments of an antibody that retain the ability to specifically bind to an antigen, (see generally, Holliger et al., Nature Biotech. 23 (9) 1126-1129 (2005)). Non-limiting examples of antibody fragments included within, but not limited to, the term "antigen-binding portion" of an antibody include (i) a Fab fragment, a monovalent fragment consisting of the $V_L$, $V_H$, $C_L$ and $C_{H1}$ domains; (ii) a $F(ab')_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) Nature 341:544 546), which consists of a $V_H$ domain; and (vi) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) Science 242:423 426; and Huston et al. (1988) Proc. Natl. Acad. Sci. USA 85:5879 5883; and Osbourn et al. (1998) Nat. Biotechnol. 16:778). Such single chain antibodies are also intended to be encompassed within the term "antigen-binding portion" of an antibody. Any $V_H$ and $V_L$ sequences of specific scFv can be linked to human immunoglobulin constant region cDNA or genomic sequences, in order to generate expression vectors encoding complete IgG molecules or other isotypes. $V_H$ and $V_L$ can also be used in the generation of Fab, Fv or other fragments of immunoglobulins using either protein chemistry or recombinant DNA technology. Other forms of single chain antibodies, such as diabodies are also encompassed.

"$F(ab')_2$" and "Fab'" moieties can be produced by treating immunoglobulin (monoclonal antibody) with a protease such as pepsin and papain, and includes an antibody fragment generated by digesting immunoglobulin near the disulfide bonds existing between the hinge regions in each of the two H chains. For example, papain cleaves IgG upstream of the disulfide bonds existing between the hinge regions in each of the two H chains to generate two homologous antibody fragments in which an L chain composed of $V_L$ (L chain variable region) and $C_L$ (L chain constant region), and an H chain fragment composed of $V_H$ (H chain variable region) and $C_{H\gamma1}$ (γ1 region in the constant region of H chain) are connected at their C terminal regions through a disulfide bond. Each of these two homologous antibody fragments is called Fab'. Pepsin also cleaves IgG downstream of the disulfide bonds existing between the hinge regions in each of the two H chains to generate an antibody fragment slightly larger than the fragment in which the two above-mentioned Fab' are connected at the hinge region. This antibody fragment is called $F(ab')_2$.

The Fab fragment also contains the constant domain of the light chain and the first constant domain ($C_{H1}$) of the heavy chain. Fab' fragments differ from Fab fragments by the addition of a few residues at the carboxyl terminus of the heavy chain $C_{H1}$ domain including one or more cysteine(s) from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

"Fv" is the minimum antibody fragment which contains a complete antigen-recognition and antigen-binding site. This region consists of a dimer of one heavy chain and one light chain variable domain in tight, non-covalent association. It is in this configuration that the three hypervariable regions of each variable domain interact to define an antigen-binding site on the surface of the $V_H$-$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

"Single-chain Fv" or "sFv" antibody fragments comprise the $V_H$ and $V_L$ domains of an antibody, wherein these domains are present in a single polypeptide chain. Generally, the Fv polypeptide further comprises a polypeptide linker between the $V_H$ and $V_L$ domains which enables the sFv to form the desired structure for antigen binding. For a review of sFv see Pluckthun in The Pharmacology of Monoclonal Antibodies, vol. 113, Rosenburg and Moore eds. Springer-Verlag, New York, pp. 269 315 (1994).

The term "Avimer™" refers to a new class of therapeutic proteins that are from human origin, which are unrelated to antibodies and antibody fragments, and are composed of several modular and reusable binding domains, referred to as A-domains (also referred to as class A module, complement type repeat, or LDL-receptor class A domain). They were developed from human extracellular receptor domains by in vitro exon shuffling and phage display, (Silverman et al., 2005, Nat. Biotechnol. 23:1493-94; Silverman et al., 2006, Nat. Biotechnol. 24:220). The resulting proteins may comprise multiple independent binding domains that may exhibit improved affinity (in some cases sub-nanomolar) and specificity compared with single-epitope binding proteins. See, for example, U.S. Patent Application Publ. Nos. 2005/0221384, 2005/0164301, 2005/0053973 and 2005/0089932, 2005/0048512, and 2004/0175756, each of which is hereby incorporated by reference herein in its entirety.

Each of the known 217 human A-domains comprises ~35 amino acids (~4 kDa) and domains are separated by linkers that average five amino acids in length. Native A-domains fold quickly and efficiently to a uniform, stable structure mediated primarily by calcium binding and disulfide formation. A conserved scaffold motif of only 12 amino acids is required for this common structure. The end result is a single protein chain containing multiple domains, each of which represents a separate function. Each domain of the proteins binds independently and that the energetic contributions of each domain are additive. These proteins were called "Avimers™" from avidity multimers.

As used herein, "natural" or "naturally occurring" antibodies or antibody variable domains, refers to antibodies or antibody variable domains having a sequence of an antibody or antibody variable domain identified from a nonsynthetic source, for example, from a differentiated antigen-specific B cell obtained ex vivo, or its corresponding hybridoma cell line, or from the serum of an animal. These antibodies can include antibodies generated in any type of immune response, either natural or otherwise induced. Natural antibodies include the amino acid sequences, and the nucleotide sequences that constitute or encode these antibodies, for example, as identified in the Kabat database.

The terms "synthetic polynucleotide," "synthetic gene" or "synthetic polypeptide," as used herein, mean that the corresponding polynucleotide sequence or portion thereof, or amino acid sequence or portion thereof, is derived, from a sequence that has been designed, or synthesized de-novo, or modified, compared to the equivalent naturally occurring sequence. Synthetic polynucleotides or synthetic genes can be prepared by methods known in the art, including but not limited to, the chemical synthesis of nucleic acid or amino acid sequences or amplified via PCR (or similar enzymatic amplification systems). Synthetic genes are typically different from unmodified genes or naturally occurring genes, either at the amino acid, or polynucleotide level (or both) and are, typically, located within the context of synthetic expression control sequences. For example, synthetic gene sequences may include amino acid, or polynucleotide, sequences that have been changed, for example, by the replacement, deletion, or addition, of one or more, amino acids, or nucleotides, thereby providing an antibody amino acid sequence, or a polynucleotide coding sequence that is different from the source sequence. Synthetic gene or polynucleotide sequences may not necessarily encode proteins with different amino acids, compared to the natural gene, for example, they can also encompass synthetic polynucleotide sequences that incorporate different codons but which encode the same amino acid; i.e. the nucleotide changes represent silent mutations at the amino acid level. In one embodiment, synthetic genes exhibit altered susceptibility to SHM compared to the naturally occurring or unmodified gene. Synthetic genes can be iteratively modified using the methods described herein and, in each successive iteration, a corresponding polynucleotide sequence or amino acid sequence, is derived, in whole or part, from a sequence that has been designed, or synthesized de novo, or modified, compared to an equivalent unmodified sequence.

The terms "semi-synthetic polynucletide" or "semi-synthetic gene," as used herein, refer to polynucleotide sequences that consist in part of a nucleic acid sequence that has been obtained via polymerase chain reaction (PCR) or other similar enzymatic amplification system which utilizes a natural donor (i.e., peripheral blood monocytes) as the starting material for the amplification reaction. The remaining "synthetic" polynucleotides, i.e., those portions of semi-synthetic polynucleotide not obtained via PCR or other similar enzymatic amplification system can be synthesized de novo using methods known in the art including, but not limited to, the chemical synthesis of nucleic acid sequences.

The term "synthetic variable regions" refers to synthetic polynucleotide sequences that are substantially comprised of optimal SHM hot spots and hot codons that, when combined with the activity of AID and/or one or more error-prone polymerases, can generate a broad spectrum of potential amino acid diversity at each position. Synthetic variable regions may be separated by synthetic frame work sequences that encompass codons that are not specifically targeted for SHM, or that are resistant to SHM but that provide an optimal context for mutagenesis.

The term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA 90:6444 6448 (1993).

Antibodies of the present invention also include heavy chain dimers, such as antibodies from camelids and sharks. Camelid and shark antibodies comprise a homodimeric pair of two chains of V-like and C-like domains (neither has a light chain). Since the $V_H$ region of a heavy chain dimer IgG in a camelid does not have to make hydrophobic interactions with a light chain, the region in the heavy chain that normally contacts a light chain is changed to hydrophilic amino acid residues in a camelid. $V_H$ domains of heavy-chain dimer IgGs are called $V_{HH}$ domains. Shark Ig-NARs comprise a homodimer of one variable domain (termed a V-NAR domain) and five C-like constant domains (C-NAR domains).

In camelids, the diversity of antibody repertoire is determined by the complementary determining regions (CDR) 1, 2, and 3 in the $V_H$ or $V_{HH}$ regions. The CDR3 in the camel $V_{HH}$ region is characterized by its relatively long length averaging 16 amino acids (Muyldermans et al., 1994, Protein Engineering 7(9): 1129). This is in contrast to CDR3 regions of antibodies of many other species. For example, the CDR3 of mouse $V_H$ has an average of 9 amino acids.

Libraries of camelid-derived antibody variable regions, which maintain the in vivo diversity of the variable regions of a camelid, can be made by, for example, the methods disclosed in U.S. Patent Application Ser. No. 20050037421, published Feb. 17, 2005.

"Humanized" forms of non-human (e.g., murine) antibodies are chimeric antibodies which contain minimal sequence derived from non-human immunoglobulin. For the most part, humanized antibodies are human immunoglobulins (recipient antibody) in which hypervariable region residues of the recipient are replaced by hypervariable region residues from a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable regions correspond to those of a non-human immunoglobulin and all, or substantially all, of the FRs are those of a human immunoglobulin sequence. The humanized antibody optionally also will comprise at least a portion of an immunoglobulin constant region (Fc), typically that of a human immunoglobulin. For further details, see Jones et al., Nature 321:522 525 (1986); Reichmann et al., Nature 332:323 329 (1988); and Presta, Curr. Op. Struct. Biol. 2:593 596 (1992).

A "humanized antibody" of the present invention includes synthetic and semi-synthetic antibodies prepared by in vitro somatic hypermutation driven affinity maturation of library-derived polynucleotides. Specifically included are monoclonal antibodies in which part, or all of the complementarity determining regions of the heavy and light chain are derived from a non-human monoclonal antibody, substantially all the remaining portions of the variable regions are derived from human variable region templates as described herein (both heavy and light chain), and the constant regions are derived from human constant region templates likewise described herein. In one aspect, such non-human CDR sequences comprise synthetic polynucleotide sequences that have been optimized for somatic hypermutation, and comprise preferred SHM codons, e.g., preferred SHM hot spot codons. In one embodiment, the CDR3 regions of the heavy and light chain are derived from the non-human antibody.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature 256:495 (1975), or may be made by recombinant DNA methods (see, e.g., U.S. Pat. No. 4,816,567). In certain embodiments, the "monoclonal antibodies" may also be isolated from phage antibody libraries using the techniques described in Clackson et al., Nature 352:624 628 (1991) and Marks et al., J. Mol. Biol. 222:581 597 (1991), for example.

In other embodiments, monoclonal antibodies can be isolated and purified from the culture supernatant or ascites mentioned above by saturated ammonium sulfate precipitation, euglobulin precipitation method, caproic acid method, caprylic acid method, ion exchange chromatography (DEAE or DE52), affinity chromatography using anti-immunoglobulin column or protein A column.

A polyclonal antibody (antiserum) or monoclonal antibody of the present invention can be produced by known methods. Namely, mammals, preferably, mice, rats, hamsters, guinea pigs, rabbits, cats, dogs, pigs, goats, horses, or cows, or more preferably, mice, rats, hamsters, guinea pigs, or rabbits are immunized, for example, with an antigen mentioned above with Freund's adjuvant, if necessary. The polyclonal antibody can be obtained from the serum obtained from the animal so immunized The monoclonal antibodies are produced as follows. Hybridomas are produced by fusing the antibody-producing cells obtained from the animal so immunized and myeloma cells incapable of producing autoantibodies. Then the hybridomas are cloned, and clones producing the monoclonal antibodies showing the specific affinity to the antigen used for immunizing the mammal are screened.

An "isolated specific binding member" is one which has been identified and separated and/or recovered from a component of its natural environment. Contaminant components of its natural environment are materials which would interfere with diagnostic or therapeutic uses for the specific binding member, and may include enzymes, hormones, and other proteinaceous or nonproteinaceous solutes. In preferred embodiments, the specific binding member will be purified (1) to greater than 95% by weight as determined by the Lowry or comparable assay method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated specific binding members include those in situ within recombinant cells since at least one component of the specific binding member's natural environment will not be present. Ordinarily, however, isolated specific binding members will be prepared by at least one purification step.

As used herein, an "intrabody or fragment thereof" refers to antibodies that are expressed and function intracellularly. Intrabodies typically lack disulfide bonds and are capable of modulating the expression or activity of target genes through their specific binding activity. Intrabodies include single domain fragments such as isolated $V_H$ and $V_L$ domains and scFvs. An intrabody can include sub-cellular trafficking signals attached to the N or C terminus of the intrabodies to allow them to be expressed at high concentrations in the sub-cellular compartments where a target protein is located. Upon interaction with the target gene, an intrabody modulates target protein function, and/or achieves phenotypic/functional knockout by mechanisms such as accelerating target protein degradation and sequestering the target protein in a non-physiological sub-cellular compartment. Other mechanisms of intrabody-mediated gene inactivation can depend on the epitope to which the intrabody is directed, such as binding to the catalytic site on a target protein or to epitopes that are involved in protein-protein, protein-DNA or protein-RNA interactions. In one embodiment, an intrabody is a scFv.

The "cell producing an antibody reactive to a protein or a fragment thereof" of the present invention means any cell producing the above-described antibodies or antigen-binding fragments of the present invention.

The term "germline gene segments" refers to the genes from the germline (the haploid gametes and those diploid cells from which they are formed). The germline DNA contain multiple gene segments that encode a single immunoglubin heavy or light chain. These gene segments are carried in the germ cells but cannot be transcribed and translated into heavy and light chains until they are arranged into functional genes. During B-cell differentiation in the bone marrow, these gene segments are randomly shuffled by a dynamic genetic system capable of generating more than 108 specificities. Most of these gene segments are published and collected by the germline database.

As used herein, "library" refers to a plurality of polynucleotides, proteins, or cells comprising a collection of two, or two or more, non-identical but related members. A "synthetic library" refers to a plurality of synthetic polynucleotides, or a population of cells that comprise said pluarality of synthetic polynucleotides. A "semi-synthetic library" refers to a plurality of semi-synthetic polynucleotides, or a population of cells that comprise said plurality of semi-synthetic polynucleotides. A "seed library" refers to a plurality of one or more synthetic or semi-synthetic polynucleotides, or cells that comprise said polynucleotides, that contain one or more sequences or portions thereof, that have been modified to act as a substrate for SHM, e.g., AID-mediated somatic hypermutatin, and that are capable, when acted upon by somatic hypermutation, to create a library of polynucleotides, proteins or cells in situ.

"Antigen" refers to substances that are capable, under appropriate conditions, of inducing a specific immune response and of reacting with the products of that response, that is, with specific antibodies or specifically sensitized T-lymphocytes, or both. Antigens may be soluble substances, such as toxins and foreign proteins, or particulates, such as bacteria and tissue cells; however, only the portion of the protein or polysaccharide molecule known as the antigenic determinant (epitopes) combines with the antibody or a specific receptor on a lymphocyte. More broadly, the term "antigen" may be used to refer to any substance to which an antibody binds, or for which antibodies are desired, regardless of whether the substance is immunogenic. For such antigens, antibodies may be identified by recombinant methods, independently of any immune response.

The term "affinity" refers to the equilibrium constant for the reversible binding of two agents and is expressed as Kd. Affinity of a binding protein to a ligand such as affinity of an antibody for an epitope can be, for example, from about 100 nanomolar (nM) to about 0.1 nM, from about 100 nM to about 1 picomolar (pM), or from about 100 nM to about 1 femtomolar (fM). The term "avidity" refers to the resistance of a complex of two or more agents to dissociation after dilution.

"Epitope" refers to that portion of an antigen or other macromolecule capable of forming a binding interaction with the variable region binding pocket of an antibody. An epitope can be a linear peptide sequence (i.e., "continuous") or can be composed of noncontiguous amino acid sequences (i.e., "conformational" or "discontinuous"). An antibody or antigen-binding fragment can recognize one or more amino acid sequences; therefore an epitope can define more than one distinct amino acid sequence. Epitopes recognized by an antibody or antigen-binding fragment can be determined by peptide mapping and sequence analysis techniques well known to one of skill in the art. Typically, such binding interaction is manifested as an intermolecular contact with one or more amino acid residues of a CDR. Often, the antigen binding involves a CDR3 or a CDR3 pair.

A "cryptic epitope" or a "cryptic binding site" is an epitope or binding site of a protein sequence that is not exposed or substantially protected from recognition within at least one native conformation of the polypeptide, but is capable of being recognized by an antibody or antigen-binding fragment in a second conformation of the polypeptide, or in the denatured, or proteolyzed polypeptide. Amino acid sequences that are not exposed, or are only partially exposed, in only one specific native conformation of the polypeptide structure are potential cryptic epitopes. If an epitope is not exposed, or only partially exposed, then it is likely that it is buried within the interior of the polypeptide, or masked by an interaction with a macromolecular structure. Candidate cryptic epitopes can be identified, for example, by examining the three-dimensional structure of a native polypeptide.

The term "specific" may be used to refer to the situation in which one member of a specific binding pair will not show any significant binding to molecules other than its specific binding partner(s). The term is also applicable where e.g. an antigen binding domain is specific for a particular epitope which is carried by a number of antigens, in which case the specific binding member carrying the antigen binding domain will be able to bind to the various antigens carrying the epitope.

The term "binding" refers to a direct association between two molecules, due to, for example, covalent, electrostatic, hydrophobic, and ionic and/or hydrogen-bond interactions under physiological conditions, and includes interactions such as salt bridges and water bridges.

The term "specific binding member" describes a member of a pair of molecules which have binding specificity for one another. The members of a specific binding pair may be naturally derived or wholly or partially synthetically produced. One member of the pair of molecules has an area on its surface, or a cavity, which specifically binds to and is therefore complementary to a particular spatial and polar organization of the other member of the pair of molecules. Thus, the members of the pair have the property of binding specifically to each other. Examples of types of specific binding pairs include antigen-antibody, Avimer™-substrate, biotin-avidin, hormone-hormone receptor, receptor-ligand, protein-protein, and enzyme-substrate.

The term "adjuvant" refers to a compound or mixture that enhances the immune response, particularly to an antigen. An adjuvant can serve as a tissue depot that slowly releases the antigen and also as a lymphoid system activator that non-specifically enhances the immune response (Hood et al., Immunology, Second Ed., 1984, Benjamin/Cummings: Menlo Park, Calif., p. 384). Often, a primary challenge with an antigen alone, in the absence of an adjuvant, will fail to elicit a humoral or cellular immune response. Previously known and utilized adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, dinitrophenol, and potentially useful human adjuvant such as BCG (bacille Calmette-Guerin) and *Corynebacterium parvum*. Mineral salt adjuvants include but are not limited to: aluminum hydroxide, aluminum phosphate, calcium phosphate, zinc hydroxide and calcium hydroxide. Preferably, the adjuvant composition further comprises a lipid of fat emulsion comprising about 10% (by weight) vegetable oil and about 1-2% (by weight) phospholipids. Preferably, the adjuvant composition further optionally comprises an emulsion form having oily particles dispersed in a continuous aqueous phase, having an emulsion forming polyol in an amount of from about 0.2% (by weight) to about 49% (by weight), optionally a metabolizable oil in an emulsion-forming amount of up to 15% (by weight), and optionally a glycol ether-based surfactant in an emulsion-stabilizing amount of up to about 5% (by weight).

As used herein, the term "immunomodulator" refers to an agent which is able to modulate an immune response. An example of such modulation is an enhancement of antibody production.

An "immunological response" to a composition or vaccine comprised of an antigen is the development in the host of a cellular- and/or antibody-mediated immune response to the composition or vaccine of interest. Usually, such a response consists of the subject producing antibodies, B cells, helper T cells, suppressor T cells, and/or cytotoxic T cells directed specifically to an antigen or antigens included in the composition or vaccine of interest.

Molecular Biological Terminology

The term "nucleotide" as used herein refers to a monomeric unit of a polynucleotide that consists of a heterocyclic base, a sugar, and one or more phosphate groups. The naturally occurring bases (guanine, (G), adenine, (A), cytosine, (C), thymine, (T), and uracil (U)) are typically derivatives of purine or pyrimidine, though it should be understood that naturally and non-naturally occurring base analogs are also included. The naturally occurring sugar is the pentose (five-carbon sugar) deoxyribose (which forms DNA) or ribose (which forms RNA), though it should be understood that naturally and non-naturally occurring sugar analogs are also included. Nucleic acids are typically linked via phosphate bonds to form nucleic acids, or polynucleotides though many other linkages are known in the art (such as, though not limited to phosphorothioates, boranophosphates and the like).

The terms "nucleic acid" and "polynucleotide" as used herein refer to a polymeric form of nucleotides of any length, either ribonucleotides (RNA) or deoxyribonucleotides (DNA). These terms refer to the primary structure of the molecule, and thus include double- and single-stranded DNA, and double- and single-stranded RNA. The terms include, as equivalents, analogs of either RNA or DNA made from nucleotide analogs and modified polynucleotides such as, though not limited to methylated and/or capped polynucleotides.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the non transcribed strand of DNA (i.e., the strand having a sequence homologous to the mRNA).

A DNA "coding sequence" or "coding region" is a double-stranded DNA sequence which is transcribed and translated into a polypeptide in vivo when placed under the control of appropriate expression control sequences. The boundaries of the coding sequence (the "open reading frame" or "ORF") are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and synthetic DNA sequences. A polyadenylation signal and transcription termination sequence will usually be located 3' to the coding sequence. The term "noncoding sequence" or "noncoding region" refers to regions of a polynucleotide sequence that not translated into amino acids (e.g. 5' and 3' untranslated regions).

The term "reading frame" refers to one of the six possible reading frames, three in each direction, of the double stranded DNA molecule. The reading frame that is used determines which codons are used to encode amino acids within the coding sequence of a DNA molecule.

As used herein, an "antisense" nucleic acid molecule comprises a nucleotide sequence which is complementary to a "sense" nucleic acid encoding a protein, e.g., complementary to the coding strand of a double-stranded cDNA molecule, complementary to an mRNA sequence or complementary to the coding strand of a gene. Accordingly, an antisense nucleic acid molecule can hydrogen bond to a sense nucleic acid molecule.

The term "base pair" or ("bp"): a partnership of adenine (A) with thymine (T), or of cytosine (C) with guanine (G) in a double stranded DNA molecule. In RNA, uracil (U) is substituted for thymine.

As used herein a "codon" refers to the three nucleotides which, when transcribed and translated, encode a single amino acid residue; or in the case of UUA, UGA or UAG encode a termination signal. Codons encoding amino acids are well known in the art and are provided for convenience herein in Table 1.

TABLE 1

Codon Usage Table

| Codon | Amino acid | AA | Abbrev. | Codon | Amino acid | AA | Abbrev. |
|---|---|---|---|---|---|---|---|
| UUU | Phenylalanine | Phe | F | UCU | Serine | Ser | S |
| UUC | Phenylalanine | Phe | F | UCC | Serine | Ser | S |
| UUA | Leucine | Leu | L | UCA | Serine | Ser | S |
| UUG | Leucine | Leu | L | UCG | Serine | Ser | S |
| CUU | Leucine | Leu | L | CCU | Proline | Pro | P |
| CUC | Leucine | Leu | L | CCC | Proline | Pro | P |
| CUA | Leucine | Leu | L | CCA | Proline | Pro | P |
| CUG | Leucine | Leu | L | CCG | Proline | Pro | P |
| AUU | Isoleucine | Ile | I | ACU | Threonine | Thr | T |
| AUC | Isoleucine | Ile | I | ACC | Threonine | Thr | T |
| AUA | Isoleucine | Ile | I | ACA | Threonine | Thr | T |
| AUG | Methionine | Met | M | ACH | Threonine | Thr | T |
| GUU | Valine | Val | V | GCU | Alanine | Ala | A |
| GUC | Valine | Val | V | GCC | Alanine | Ala | A |
| GUA | Valine | Val | V | GCA | Alanine | Ala | A |
| GUG | Valine | Val | V | GCG | Alanine | Ala | A |
| UAU | Tyrosine | Tyr | Y | UGU | Cysteine | Cys | C |
| UAC | Tyrosine | Tyr | Y | UGC | Cysteine | Cys | C |
| UUA | | Stop | | UGA | | Stop | |
| UAG | | Stop | | UGG | Tryptophan | Trp | W |
| CAU | Histidine | His | H | CGU | Arginine | Arg | R |
| CAC | Histidine | His | H | CGC | Arginine | Arg | R |
| CAA | Glutamine | Gln | Q | CGA | Arginine | Arg | R |
| CAG | Glutamine | Gln | Q | CGG | Arginine | Arg | R |
| AAU | Asparagine | Asn | N | AGU | Serine | Ser | S |
| AAC | Asparagine | Asn | N | AGC | Serine | Ser | S |
| AAA | Lysine | Lys | K | AGA | Arginine | Arg | R |
| AAG | Lysine | Lys | K | AGG | Arginine | Arg | R |
| GAU | Aspartate | Asp | D | GGU | Glycine | Gly | G |
| GAC | Aspartate | Asp | D | GGC | Glycine | Gly | G |
| GAA | Glutamate | Glu | E | GGA | Glycine | Gly | G |
| GAG | Glutamate | Glu | E | GGG | Glycine | Gly | G |

AA: amino acid; Abbr: abbreviation. It should be understood that the codons specified above are for RNA sequences. The corresponding codons for DNA have a T substituted for U. Optimal codon usage is indicated by codon usage frequencies for expressed genes, for example, as shown in the codon usage chart from the program "Human—High.cod" from the Wisconsin Sequence Analysis Package, Version 8.1, Genetics Computer Group, Madison, Wis. Codon usage is also described in, for example, R. Nussinov, "Eukaryotic Dinucleotide Preference Rules and Their Implications for Degenerate Codon Usage," J. Mol. Biol. 149: 125-131 (1981). The codons which are most frequently used in highly expressed human genes are presumptively the optimal codons for expression in human host cells and, thus, form the bases for constructing a synthetic coding sequence.

As used herein, a "wobble position" refers to the third position of a codon. Mutations in a DNA molecule within the wobble position of a codon typically result in silent or conservative mutations at the amino acid level. For example, there are four codons that encode Glycine, i.e., GGU, GGC, GGA and GGG, thus mutation of any wobble position nucleotide, to any other nucleotide, does not result in a change at the amino acid level of the encoded protein, i. e. is a silent substitution.

Accordingly a "silent substitution" or "silent mutation" is one in which a nucleotide within a codon is modified, but does not result in a change in the amino acid residue encoded by the codon. Examples include mutations in the third position of a codon, as well as in the first position of certain codons, such as the codon "CGG," which when mutated to AGG, still encodes the amino acid Arginine (Arg, or R).

The phrase "conservative amino acid substitution" or "conservative mutation" refers to the replacement of one amino acid by another amino acid with a common property. A functional way to define common properties between individual amino acids is to analyze the normalized frequencies of amino acid changes between corresponding proteins of homologous organisms (Schulz, G. E. and R. H. Schirmer, Principles of Protein Structure, Springer-Verlag). According to such analyses, groups of amino acids may be defined where amino acids within a group exchange preferentially with each other, and therefore resemble each other most in their impact on the overall protein structure (Schulz, G. E. and R. H. Schirmer, Principles of Protein Structure, Springer-Verlag).

Examples of amino acid groups defined in this manner include: a "charged/polar group," consisting of Glu, Asp, Asn, Gln, Lys, Arg and His; an "aromatic, or cyclic group," consisting of Pro, Phe, Tyr and Trp; and an "aliphatic group" consisting of Gly, Ala, Val, Leu, Ile, Met, Ser, Thr and Cys.

Within each group, subgroups may also be identified, for example, the group of charged/polar amino acids may be sub-divided into the sub-groups consisting of the "positively-charged sub-group," consisting of Lys, Arg and His; the negatively-charged sub-group," consisting of Glu and Asp, and the "polar sub-group" consisting of Asn and Gln.

The aromatic, or cyclic group may be sub-divided into the sub-groups consisting of the "nitrogen ring sub-group," consisting of Pro, His and Trp; and the "phenyl sub-group" consisting of Phe and Tyr.

The aliphatic group may be sub-divided into the sub-groups consisting of the "large aliphatic non-polar sub-group," consisting of Val, Leu and Ile; the "aliphatic slightly-polar sub-group," consisting of Met, Ser, Thr and Cys; and the "small-residue sub-group," consisting of, Gly, and Ala.

Examples of conservative mutations include amino acid substitutions of amino acids within the sub-groups above, for example, Lys for Arg and vice versa such that a positive charge may be maintained; Glu for Asp and vice versa such that a negative charge may be maintained; Ser for Thr such that a free —OH can be maintained; and Gln for Asn such that a free —NH2 can be maintained.

"Semi-conservative mutations" include amino acid substitutions of amino acids with the same groups listed above, that do not share the same sub-group. For example, the mutation of Asp for Asn, or Asn for Lys all involve amino acids within the same group, but different sub-groups.

"Non-conservative mutations" involve amino acid substitutions between different groups, for example Lys for Leu, or Phe for Ser, etc.

The term "amino acid residue" refers to the radical derived from the corresponding alpha-amino acid by eliminating the OH portion of the carboxyl group and the H-portion of the alpha amino group. For the most part, the amino acids used in the application are those naturally occurring amino acids found in proteins, or the naturally occurring anabolic or catabolic products of such amino acids which contain amino and carboxyl groups. Alternatively, un-natural amino acids can be incorporated into proteins to facilitate the chemical conjugation to other proteins, toxins, small organic compounds or anti-cancer agents (Datta et al., J Am Chem Soc. (2002) 124 (20):5652-3). In general, the abbreviations used herein for designating the amino acids and the protective groups are based on recommendations of the IUPAC-IUB Commission on Biochemical Nomenclature (see Biochemistry (1972) 11: 1726-1732). The term "amino acid residue" also includes analogs, derivatives and congeners of any specific amino acid referred to herein, as well as C-terminal or N-terminal protected amino acid derivatives (e.g., modified with an N-terminal or C-terminal protecting group). For example, the present invention contemplates the use of amino acid analogs wherein a side chain is lengthened or shorted while still providing a carboxyl, amino or other reactive precursor functional group for cyclization, as well as amino acid analogs having variant side chains with appropriate functional groups).

The term "amino acid side chain" is that part of an amino acid exclusive of the —CH—(NH$_2$)COOH portion, as defined by K. D. Kopple, "Peptides and Amino Acids," W. A. Benjamin Inc., New York and Amsterdam, 1996, pages 2 and 33; examples of such side chains of the common amino acids are —CH$_2$CH$_2$SCH$_3$ (the side chain of methionine), —CH$_2$(CH$_3$)—CH$_2$CH$_3$ (the side chain of isoleucine), —CH$_2$CH(CH$_3$)$_2$ (the side chain of leucine) or H— (the side chain of glycine).

The amino acid residues described herein are preferred to be in the "L" isomeric form. However, residues in the "D" isomeric form can be substituted for any L-amino acid residue, as long as the desired functional property of antibody (immunoglobulin)-binding is retained by the polypeptide. NH$_2$ refers to the free amino group present at the amino terminus of a polypeptide. COOH refers to the free carboxy group present at the carboxy terminus of a polypeptide.

An "amino acid motif" is a sequence of amino acids, optionally a generic set of conserved amino acids, associated with a particular functional activity.

As used herein, the terms "protein," "peptide" and "polypeptide" are used interchangeably to refer to polymers of amino acid residues of any length connected to one another by peptide bonds between the alpha-amino group and carboxy group of contiguous amino acid residues. Polypeptides, proteins and peptides may exist as linear polymers, branched polymers or in circular form. These terms also include forms that are post-translationally modified in vivo, or chemically modified during synthesis.

It should be noted that all amino-acid residue sequences are represented herein by formulae whose left and right orientation is in the conventional direction of amino-terminus to carboxy terminus. Furthermore, it should be noted that a dash at the beginning or end of an amino acid residue sequence indicates a peptide bond to a further sequence of one or more amino-acid residues.

The terms "gene," "recombinant gene" and "gene construct" as used herein, refer to a DNA molecule, or portion of a DNA molecule, that encodes a protein. The DNA molecule can contain an open reading frame encoding the protein (as exon sequences) and can further include intron sequences. The term "intron" as used herein, refers to a DNA sequence present in a given gene which is not translated into protein and is generally found between exons. Usually, it is desirable for the gene to be operably linked to, (or it may comprise), one or more promoters, enhancers, repressors and/or other regulatory sequences to modulate the activity or expression of the gene, as is well known in the art.

As used herein, a "complementary DNA" or "cDNA" includes recombinant polynucleotides synthesized by reverse transcription of mRNA and from which intervening sequences (introns) have been removed.

The term "operably linked" as used herein, describes the relationship between two polynucleotide regions such that they are functionally related or coupled to each other. For example, a promoter (or other expression control sequence) is operably linked to a coding sequence if it controls (and is capable of effecting) the transcription of the coding sequence. Although an operably linked promoter is generally located upstream of the coding sequence, it is not necessarily contiguous with it.

"Expression control sequences" are DNA regulatory sequences, such as promoters, enhancers, polyadenylation signals, terminators, internal ribosome entry sites (IRES) and the like, that provide for the expression of a coding sequence in a host cell. Exemplary expression control sequences are described in Goeddel; Gene Expression Technology: Methods in Enzymology 185, Academic Press, San Diego, Calif. (1990).

A "promoter" is a DNA regulatory region capable of binding RNA polymerase in a cell and initiating transcription of a downstream (3' direction) coding sequence. As used herein, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease 51), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

A large number of promoters, including constitutive, inducible and repressible promoters, from a variety of different sources are well known in the art. Representative sources include for example, viral, mammalian, insect, plant, yeast, and bacterial cell types), and suitable promoters from these sources are readily available, or can be made synthetically, based on sequences publicly available on line or, for example, from depositories such as the ATCC as well as other commercial or individual sources. Promoters can be unidirectional (i.e., initiate transcription in one direction) or bi-directional (i.e., initiate transcription in either a 3' or 5' direction). Non-limiting examples of promoters include, for example, the T7 bacterial expression system, pBAD (araA) bacterial expression system, the cytomegalovirus (CMV) promoter, the SV40 promoter, the RSV promoter. Inducible promoters include the Tet system, (U.S. Pat. Nos. 5,464,758 and 5,814,618), the Ecdysone inducible system (No et al., Proc. Natl. Acad. Sci. (1996) 93 (8) 3346-3351; the T-RE$_x$™ system (Invitrogen Carlsbad, Calif.), LacSwitch® (Stratagene, (San Diego, Calif.) and the Cre-ER$^T$ tamoxifen inducible recombinase system (Indra et al. Nuc. Acid. Res. (1999) 27 (22)4324-4327; Nuc. Acid. Res. (2000) 28 (23) e99; U.S. Pat. No. 7,112,715). See generally, Kramer & Fussenegger Methods Mol. Biol. (2005) 308 123-144) or any promoter known in the art suitable for expression in the desired cells.

As used herein, a "minimal promoter" refers to a partial promoter sequence which defines the transcription start site but which by itself is not capable, if at all, of initiating transcription efficiently. The activity of such minimal promoters depends on the binding of activators such as a tetracycline-controlled transactivator to operably linked binding sites.

The terms "IRES" or "internal ribosome entry site" refer to a polynucleotide element that acts to enhance the translation of a coding sequence encoded with a. polycistronic messenger RNA. IRES elements, mediate the initiation of translation by directly recruiting and binding ribosomes to a messenger RNA (mRNA) molecule, bypassing the 7-methyl guanosine-cap involved in typical ribosome scanning. The presence of an IRES sequence can increase the level of cap-independent translation of a desired protein. Early publications descriptively refer to IRES sequences as "translation enhancers." For example, cardioviral RNA "translation enhancers" are described in U.S. Pat. No. 4,937,190 to Palmenberg et al. and U.S. Pat. No. 5,770,428 to Boris-Lawrie.

The terms "nuclear localization signal" and "NLS" refer to a domain, or domains capable of mediating the nuclear import of a protein or polynucleotide, or retention thereof, within the nucleus of a cell. A "strong nuclear import signal" represents a domain or domains capable of mediating greater than 90% subcellular localization in the nucleus when operatively linked to a protein of interest. Representative examples of NLSs include but are not limited to, monopartite nuclear localization signals, bipartite nuclear localization signals and N and C-terminal motifs. N terminal basic domains usually conform to the consensus sequence K-K/R-X-K/R which was first discovered in the SV40 large T antigen and which represents a monopartite NLS. One non-limiting example of an N-terminal basic domain NLS is PKKKRKV (SEQ ID NO: 439). Also known are bipartite nuclear localization signals which contain two clusters of basic amino acids separated by a spacer of about 10 amino acids, as exemplified by the NLS from nucleoplasmin: KR[PAATKKAGQA]KKKK (SEQ ID NO: 450). N and C-terminal motifs include, for example, the acidic M9 domain of hnRNP A1, the sequence KIPIK (SEQ ID NO: 464) in yeast transcription repressor Matα2 and the complex signals of U snRNPs. Most of these NLSs appear to be recognized directly by specific receptors of the importin β family.

The term "enhancer" as used herein, refers to a DNA sequence that increases transcription of, for example, a gene or coding sequence to which it is operably linked. Enhancers can be located many kilobases away from the coding sequence and can mediate the binding of regulatory factors, patterns of DNA methylation or changes in DNA structure. A large number of enhancers, from a variety of different sources are well known in the art and available as or within cloned polynucleotides (from, e.g., depositories such as the ATCC as well as other commercial or individual sources). A number of polynucleotides comprising promoters (such as the commonly-used CMV promoter) also comprise enhancer sequences. Operably linked enhancers can be located upstream, within, or downstream of coding sequences. The term "Ig enhancers" refers to enhancer elements derived from enhancer regions mapped within the Ig locus (such enhancers include for example, the heavy chain (mu) 5' enhancers, light chain (kappa) 5' enhancers, kappa and mu intronic enhancers, and 3' enhancers, (see generally Paul W E (ed) Fundamental Immunology, 3$^{rd}$ Edition, Raven Press, New York (1993) pages 353-363; U.S. Pat. No. 5,885,827).

"Terminator sequences" are those that result in termination of transcription. Termination sequences are known in the art and include, but are not limited to, poly A (e.g., Bgh Poly A and SV40 Poly A) terminators. A transcriptional termination signal will typically include a region of 3' untranslated region (or "3' ut"), an optional intron (also referred to as intervening sequence or "IVS") and one or more poly adenylation signals ("p(A)" or "pA." Terminator sequences may also be referred to as "IVS−pA," "IVS+p(A)," "3' ut+p(A)" or "3' ut/p(A)." Natural or synthetic terminators can be used as a terminator region.

The terms "polyadenylation," "polyadenylation sequence" and "polyadenylation signal", "Poly A," "p(A)" or "pA" refer to a nucleic acid sequence present in a RNA transcript that allows for the transcript, when in the presence of the polyadenyl transferase enzyme, to be polyadenylated. Many polyadenylation signals are known in the art. Non-limiting examples include the human variant growth hormone polyadenylation signal, the SV40 late polyadenylation signal and the bovine growth hormone polyadenylation signal.

The term "splice site" as used herein refers to polynucleotides that are capable of being recognized by the spicing machinery of a eukaryotic cell as suitable for being cut and/or ligated to a corresponding splice site. Splice sites allow for the excision of introns present in a pre-mRNA transcript. Typically the 5' portion of the splice site is referred to as the splice donor and the 3' corresponding splice site is referred to as the acceptor splice site. The term splice site includes, for example, naturally occurring splice sites, engineered splice sites, for example, synthetic splice sites, canonical or consensus splice sites, and/or non-canonical splice sites, for example, cryptic splice sites.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

"Post-translational modification" can encompass any one of or a combination of modifications including covalent modification, which a protein undergoes after translation is complete and after being released from the ribosome or on the nascent polypeptide co-translationally. Posttranslational modification includes but is not limited to phosphorylation, myristylation, ubiquitination, glycosylation, coenzyme attachment, methylation, S-nitrosylation and acetylation. Posttranslational modification can modulate or influence the activity of a protein, its intracellular or extracellular destination, its stability or half-life, and/or its recognition by ligands, receptors or other proteins. Post-translational modification can occur in cell organelles, in the nucleus or cytoplasm or extracellularly.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15-25 or more nucleotides, although it may contain fewer nucleotides. The polynucleotide primers can be prepared using any suitable method, such as, for example, the phosphotriester on phosphodiester methods see Narang et al., Meth. Enzymol., 68:90, (1979); U.S. Pat. No. 4,356,270; and Brown et al., Meth. Enzymol., 68:109, (1979).

The primers herein are selected to be "substantially" complementary to different strands of a particular target polynucleotide sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

As used herein, the terms "restriction endonucleases" and "restriction enzymes" refer to bacterial enzymes, each of which cut double-stranded DNA at or near a specific nucleotide sequence.

The term "multiple cloning site" as used herein, refers to a segment of a vector polynucleotide which can recognize one or more different restriction enzymes.

A "replicon" is any genetic element (e.g., plasmid, episome, chromosome, yeast artificial chromosome (YAC), or virus) that functions as an autonomous unit of DNA replication in vivo; i.e., capable of replication under its own control, and containing autonomous replicating sequences.

A "vector" or "cloning vector" is a replicon, such as plasmid, phage or cosmid, into which another polynucleotide segment may be introduced so as to bring about the replication of the inserted segment. Vectors typically exist as circular, double stranded DNA, and range in size form a few kilobases (kb) to hundreds of kb. Preferred cloning vectors have been modified from naturally occurring plasmids to facilitate the cloning and recombinant manipulation of polynucleotide sequences. Many such vectors are well known in the art; see for example, by Sambrook (In. "Molecular Cloning: A Laboratory Manual," second edition, edited by Sambrook, Fritsch, & Maniatis, Cold Spring Harbor Laboratory, (1989)), Maniatis, In: Cell Biology: A Comprehensive Treatise, Vol. 3, Gene Sequence Expression, Academic Press, NY, pp. 563-608(1980).

The term "expression vector" as used herein, refers to an agent used for expressing certain polynucleotides within a host cell or in-vitro expression system. The term includes plasmids, episomes, cosmids retroviruses or phages; the expression vector can be used to express a DNA sequence encoding a desired protein and in one aspect includes a transcriptional unit comprising an assembly of expression control sequences. The choice of promoter and other regulatory elements generally varies according to the intended host cell, or in-vitro expression system.

An "episomal expression vector" is able to replicate in the host cell, and persists as an extrachromosomal segment of DNA within the host cell in the presence of appropriate selective pressure. (See for example, Conese et al., Gene Therapy 11 1735-1742 (2004)). Representative commercially available episomal expression vectors include, but are not limited to, episomal plasmids that utilize Epstein Barr Nuclear Antigen 1 (EBNA1) and the Epstein Barr Virus (EBV) origin of replication (oriP). The vectors pREP4, pCEP4, pREP7 from Invitrogen, pcDNA3.1 from Invitrogen, and pBK-CMV from Stratagene represent non-limiting examples of an episomal vector that uses T-antigen and the SV40 origin of replication in lieu of EBNA1 and oriP.

An "integrating expression vector" may randomly integrate into the host cell's DNA, or may include a recombination site to enable the specific recombination between the expression vector and the host cells chromosome. Such integrating expression vectors may utilize the endogenous expression control sequences of the host cell's chromosomes to effect expression of the desired protein. Examples of vectors that integrate in a site specific manner include, for example, components of the flp-in system from Invitrogen (e.g., pcDNA™5/FRT), or the cre-lox system, such as can be found in the pExchange-6 Core Vectors from Stratagene. Examples of vectors that integrate into host cell chromosomes in a random fashion include, for example, pcDNA3.1 (when introduced in the absence of T-antigen) from Invitrogen, pCI or pFN10A (ACT) Flexi® from Promega.

Representative commercially available viral expression vectors include, but are not limited to, the adenovirus-based Per.C6 system available from Crucell, Inc., the lentiviral-based pLP1 from Invitrogen, and the Retroviral Vectors pFB-ERV plus pCFB-EGSH from Stratagene.

Alternatively, the expression vector may be used to introduce and integrate a strong promoter or enhancer sequences into a locus in the cell so as to modulate the expression of an endogenous gene of interest (Capecchi M R. Nat Rev Genet. (2005); 6 (6):507-12; Schindehutte et al., Stem Cells (2005); 23 (1):10-5). This approach can also be used to insert an inducible promoter, such as the Tet-On promoter (U.S. Pat. Nos. 5,464,758 and 5,814,618), in to the genomic DNA of the cell so as to provide inducible expression of an endogenous gene of interest. The activating construct can also include targeting sequence(s) to enable homologous or non-homologous recombination of the activating sequence into a desired locus specific for the gene of interest (see for example, Garcia-Otin & Guillou, Front Biosci. (2006) 11:1108-36). Alternatively, an inducible recombinase system, such as the Cre-ER system, can be used to activate a transgene in the presence of 4-hydroxytamoxifen. (Indra et al. Nuc. Acid. Res. (1999) 27 (22) 4324-4327; Nuc. Acid. Res. (2000) 28 (23) e99; U.S. Pat. No. 7,112,715).

Expression vectors may also include anti-sense, ribozymes or siRNA polynucleotides to reduce the expression of target sequences. (See generally, Sioud M, & Iversen, Curr. Drug Targets (2005) 6 (6):647-53; Sandy et al., Biotechniques (2005) 39 (2):215-24).

As used herein, a "recombination system" refers to one which allows for recombination between a vector of the present application and a chromosome for incorporation of a gene of interest. Recombination systems are known in the art and include, for example, Cre/Lox systems and FLP-IN systems.

As used herein an "in-vitro expression system" refers to cell free systems that enable the transcription, or coupled transcription and translation of DNA templates. Such systems include for example the classical rabbit reticulocyte system, as well as novel cell free synthesis systems, (J. Biotechnol. (2004) 110 (3) 257-63; Biotechnol Annu. Rev. (2004) 10 1-30).

As used herein, a "Cre/Lox" system refers to one such as described by Abremski et al., Cell, 32: 1301-1311 (1983) for a site-specific recombination system of bacteriophage P1. Methods of using Cre-Lox systems are known in the art; see, for example, U.S. Pat. No. 4,959,317, which is hereby incorporated in its entirety by reference. The system consists of a recombination site designated loxP and a recombinase designated Cre. In methods for producing site-specific recombination of DNA in eukaryotic cells, DNA sequences having first and second lox sites are typically introduced into eukaryotic cells and contacted with Cre, thereby producing recombination at the lox sites.

As used here, "FLP-IN" recombination refers to systems in which a polynucleotide activation/inactivation and site-specific integration system has been developed for mammalian cells. The system is based on the recombination of transfected sequences by FLP, a recombinase derived from Saccharomyces. In several cell lines, FLP has been shown to rapidly and precisely recombine copies of its specific target sequence. FLP-IN systems have been described in, for example, U.S. Pat. Nos. 5,654,182 and 5,677,177).

The term "transfection," "transformation," or "transduction" as used herein, refers to the introduction of one or more exogenous polynucleotides into a host cell by using one or physical or chemical methods. Many transfection techniques are known to those of ordinary skill in the art including but not limited to calcium phosphate DNA co-precipitation (see Methods in Molecular Biology, Vol. 7, Gene Transfer and Expression Protocols, Ed. E. J. Murray, Humana Press (1991)); DEAE-dextran; electroporation; cationic liposome-mediated transfection; tungsten particle-facilitated microparticle bombardment (Johnston, S. A., Nature 346: 776-777 (1990)); and strontium phosphate DNA co-precipitation (Brash D. E. et al. Molec. Cell. Biol. 7: 2031-2034 (1987). Phage or retroviral vectors can be introduced into host cells, after growth of infectious particles in packaging cells that are commercially available.

The terms "cells," "cell cultures," "cell line," "recombinant host cells," "recipient cells" and "host cells" are often used interchangeably and will be clear from the context in which they are used. These terms include the primary subject cells and any progeny thereof, without regard to the number of transfers. It should be understood that not all progeny are exactly identical to the parental cell (due to deliberate or inadvertent mutations or differences in environment). However, such altered progeny are included in these terms, so long as the progeny retain the same functionality as that of the originally transformed cell. For example, though not limited to, such a characteristic might be the ability to produce a particular recombinant protein. A "mutator positive cell line" is a cell line containing cellular factors that are sufficient to work in combination with other vector elements to effect hypermutation. The cell line can be any of those known in the art or described herein. A "clone" is a population of cells derived from a single cell or common ancestor by mitosis.

A "reporter gene" refers to a polynucleotide that confers the ability to be specifically detected, (or detected and selected) typically when expressed with a cell of interest. Numerous reporter gene systems are known in the art and include, for example alkaline phosphatase (Berger, J., et al., Gene 66 1-10 (1988); Kain, S R., Methods Mol. Biol. 63 49-60 (1997)), beta-galactosidase (U.S. Pat. No. 5,070,012), chloramphenicol acetyltransferase (Gorman et al., Mol. Cell. Biol. 2 1044-51 (1982)), beta glucuronidase, peroxidase, beta lactamase (U.S. Pat. Nos. 5,741,657, 5,955,604), catalytic antibodies, luciferases (U.S. Pat. Nos. 5,221,623; 5,683,888; 5,674,713; 5,650,289; 5,843,746) and naturally fluorescent proteins (Tsien, R Y, Annu. Rev. Biochem. 67 509-544 (1998)). The term "reporter gene," also includes any peptide which can be specifically detected based on the use of one or more, antibodies, epitopes, binding partners, substrates, modifying enzymes, receptors, or ligands that are capable of, or desired to (or desired not to), interact with the peptide of interest to create a detectable signal. Reporter genes also include genes that can modulate cellular phenotype.

The term "selectable marker gene" as used herein, refers to polynucleotides that allow cells carrying the polynucleotide to be specifically selected for or against, in the presence of a corresponding selective agent. Selectable markers can be positive, negative or bifunctional. Positive selectable markers allow selection for cells carrying the marker, whereas negative selectable markers allow cells carrying the marker to be selectively eliminated. The selectable marker polynucleotide can either be directly linked to the polynucleotides to be expressed, or introduced into the same cell by co-transfection. A variety of such marker polynucleotides have been described, including bifunctional (i.e., positive/negative) markers (see, e.g., WO 92/08796, published May 29, 1992, and WO 94/28143, published Dec. 8, 1994), hereby incorporated in their entirety by reference herein. Specific examples of selectable markers of drug-resistance genes include, but are not limited to, ampicillin, tetracycline, blasticidin, puromycin, hygromycin, ouabain or kanamycin. Specific examples of selectable markers are those, for example, that encode proteins that confer resistance to cytostatic or cytocidal drugs, such as the DHFR protein, which confers resistance to methotrexate (Wigler et al., Proc. Natl. Acad. Sci. USA, 77:3567 (1980); O'Hare et al., Proc. Natl. Acad. Sci. USA, 78:1527 (1981)); the GPF protein, which confers resistance to mycophenolic acid (Mulligan & Berg, Proc. Natl. Acad. Sci. USA, 78:2072 (1981)), the neomycin resistance marker, which confers resistance to the aminoglycoside G-418 (Colberre-Garapin et al., J. Mol. Biol., 150:1 (1981)); the Hygromycin protein, which confers resistance to hygromycin (Santerre et al., Gene, 30:147 (1984)); murine Na+, K+-ATPase alpha subunit, which confers resistance to ouabain (Kent et al., Science, 237:901-903 (1987); and the Zeocin™ resistance marker (available commercially from Invitrogen). In addition, the herpes simplex virus thymidine kinase (Wigler et al., Cell, 11:223 (1977)), hypoxanthine-guanine phosphoribosyltransferase (Szybalska & Szybalski, Proc. Natl. Acad. Sci. USA, 48:2026 (1962)), and adenine phosphoribosyltransferase (Lowy et al., Cell, 22:817 (1980)) can be employed in tk-, hgprt- or aprt-cells, respectively. Glutamine synthetase permits the growth of cells in glutamine(GS)-free media (see, e.g., U.S. Pat. Nos. 5,122,464; 5,770,359; and 5,827,739). Other selectable markers encode, for example, puromycin N-acetyl transferase or adenosine deaminase.

"Homology" or "identity" or "similarity" refers to sequence similarity between two peptides or between two nucleic acid molecules. Homology and identity can each be determined by comparing a position in each sequence which may be aligned for purposes of comparison. When an equivalent position in the compared sequences is occupied by the same base or amino acid, then the molecules are identical at that position; when the equivalent site occupied by the same or a similar amino acid residue (e.g., similar in steric and/or electronic nature), then the molecules can be referred to as homologous (similar) at that position. Expression as a percentage of homology/similarity or identity refers to a function of the number of identical or similar amino acids at positions shared by the compared sequences. A sequence which is "unrelated" or "non-homologous" shares less than 40% identity, less than 35% identity, less than 30% identity, or less than 25% identity with a sequence of the present invention. In comparing two sequences, the absence of residues (amino acids or nucleic acids) or presence of extra residues also decreases the identity and homology/similarity.

The term "homology" describes a mathematically based comparison of sequence similarities which is used to identify genes or proteins with similar functions or motifs. The nucleic acid and protein sequences of the present invention may be used as a "query sequence" to perform a search against public databases to, for example, identify other family members, related sequences or homologs. Such searches can be performed using the NBLAST and XBLAST programs (version 2.0) of Altschul, et al. (1990) J. Mol. Biol. 215:403-10. BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997) Nucleic Acids Res. 25(17): 3389-3402. When utilizing BLAST and Gapped BLAST programs, the default parameters of the respective programs (e.g., XBLAST and BLAST) can be used (See www.ncbi.nlm.nih.gov).

As used herein, "identity" means the percentage of identical nucleotide or amino acid residues at corresponding positions in two or more sequences when the sequences are aligned to maximize sequence matching, i.e., taking into account gaps and insertions. Identity can be readily calculated by known methods, including but not limited to those described in (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48: 1073 (1988). Methods to determine identity are designed to give the largest match between the sequences tested. Moreover, methods to determine identity are codified in publicly available computer programs. Computer program methods to determine identity between two sequences include, but are not limited to, the GCG program package (Devereux, J., et al., Nucleic Acids Research 12(1): 387 (1984)), BLASTP, BLASTN, and FASTA (Altschul, S. F. et al., J. Molec. Biol. 215: 403-410 (1990) and Altschul et al. Nuc. Acids Res. 25: 3389-3402 (1997)). The BLAST X program is publicly available from NCBI and other sources (BLAST Manual, Altschul, S., et al., NCBI NLM NIH Bethesda, Md. 20894; Altschul, S., et al., J. Mol. Biol. 215: 403-410 (1990). The well known Smith Waterman algorithm may also be used to determine identity.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

SHM Related Terminology

The term "activation-induced cytidine deaminase" or ("AID") refers to members of the AID/APOBEC family of RNA/DNA editing cytidine deaminases capable of mediating the deamination of cytosine to uracil within a DNA sequence. (See generally Conticello et al., Mol. Biol. Evol. 22 No 2 367-377 (2005), Evolution of the AID/APOBEC Family of Polynucleotide (Deoxy)cytidine Deaminases); U.S. Pat. No. 6,815,194). Suitable AID enzymes include all vertebrate forms of the enzyme, including, for example, primate, rodent, avian and bony fish. Representative examples of AID enzymes include without limitation, human (accession No. NP_065712), rat, chicken, canine and mouse (accession No. NP_033775) forms. In one embodiment, AID enzymes include the mutation L198A.

The term "AID homolog" refers to the enzymes of the Apobec family and include, for example, Apobec-1, Apobec3C or Apobec3G (described, for example, by Jarmuz et al., (2002) Genomics, 79: 285-296) (2002)). AID and AID homologs further include, without limitation, modified polypeptides, or portions thereof, which retain the activity of a native AID/APOBEC polypeptides (e.g. mutants or muteins) that retain the ability to deaminate a polynucleotide sequence. The term "AID activity" includes activity mediated by AID and AID homologs.

The term "substrate for SHM" refers to a synthetic or semi-synthetic polynucleotide sequence which is acted upon by AID and/or error prone DNA polymerases to effect a change in the nucleic acid sequence of the synthetic or semi-synthetic polynucleotide sequence.

The term "transition mutations" refers to base changes in a DNA sequence in which a pyrimidine (cytidine (C) or thymidine (T) is replaced by another pyrimidine, or a purine (adenosine (A) or guanosine (G) is replaced by another purine.

The term "transversion mutations" refers to base changes in a DNA sequence in which a pyrimidine (cytidine (C) or thymidine (T) is replaced by a purine (adenosine (A) or guanosine (G), or a purine is replaced by a pyrimidine.

The term "base excision repair" refers to a DNA repair pathway that removes single bases from DNA such as uridine nucleotides arising by deamination of cytidine. Repair is initiated by uracil glycosylase that recognizes and removes uracil from single- or double-stranded DNA to leave an abasic site.

The term "mismatch repair" refers to the repair pathway that recognizes and corrects mismatched bases, such as those that typically arise from errors of chromosomal DNA replication.

As used herein, the term "SHM hot spot" or "hot spot" refers to a polynucleotide sequence, or motif, of 3-6 nucleotides that exhibits an increased tendency to undergo somatic hypermutation, as determined via a statistical analysis of SHM mutations in antibody genes (see Tables 2 and 3 which provide a relative ranking of various motifs for SHM, and Table 6 which lists canonical hot spots and cold spots). The statistical analysis can be extrapolated to analysis of SHM mutations in non-antibody genes as described elsewhere herein. For the purposes of graphical representations of hot spots in Figures, the first nucleotide of a canonical hot spot is represented by the letter "H."

Likewise, as used herein, a "SHM coldspot" or "cold spot" refers to a polynucleotide or motif, of 3-6 nucleotides that exhibits a decreased tendency to undergo somatic hypermutation, as determined via a statistical analysis of SHM mutations in antibody genes (see Tables 2 and 3 which provide a relative ranking of various motifs for SHM, and Table 6 which lists canonical hot spots and cold spots). The statistical analysis can be extrapolated to analysis of SHM mutations in non-antibody genes as described elsewhere herein. For the purposes of graphical representations of cold spots in Figures, the first nucleotide of a canonical cold spot is represented by the letter "C."

The term "somatic hypermutation motif" or "SHM motif" refers to a polynucleotide sequence that includes, or can be altered to include, one or more hot spots or cold spots, and which encodes a defined set of amino acids. SHM motifs can be of any size, but are conveniently based around polynucleotides of about 2 to about 20 nucleotides in size, or from about 3 to about 9 nucleotides in size. SHM motifs can include any combination of hot spots and cold spots, or may lack both hot spots and cold spots.

The term "preferred SHM motif" refers to an SHM motif that includes one or more preferred (canonical) SHM codons (See Table 6 and Table 9 infra).

The terms "preferred hot spot SHM codon," "preferred hot spot SHM motif," "preferred SHM hot spot codon" and "preferred SHM hot spot motif," all refer to a codon including, but not limited to codons AAC, TAC, TAT, AGT, or AGC. Such sequences may be potentially embedded within the context of a larger SHM motif, recruits SHM mediated mutagenesis and generates targeted amino acid diversity at that codon.

As used herein, a polynucleotide sequence has been "optimized for SHM" if the polynucleotide, or a portion thereof has been altered to increase or decrease the frequency and/or location of hot spots and/or cold spots within the polynucleotide. A polynucleotide that has been made "susceptible to SHM" if the polynucleotide, or a portion thereof, has been altered to increase the frequency and/or location of hot spots within the polynucleotide or to decrease the frequency (density) and/or location of cold spots within the polynucleotide. Conversely, a polynucleotide sequence has been made "resistant to SHM" if the polynucleotide sequence, or a portion thereof, has been altered to decrease the frequency (density) and/or location of hot spots within the open reading frame of the polynucleotide sequence. In general, a sequence can be prepared that has a greater or lesser propensity to undergo SHM mediated mutagenesis by altering the codon usage, and/or the amino acids encoded by polynucleotide sequence.

Optimization of a polynucleotide sequence refers to modifying about 1%, about 2%, about 3%, about 4%, about 5%, about 10%, about 20%, about 25%, about 50%, about 75%, about 90%, about 95%, about 96%, about 97%, about 98%, about 99%, 100% or any range therein of the nucleotides in the polynucleotide sequence. Optimization of a polynucleotide sequence also refers to modifying about 1, about 2, about 3, about 4, about 5, about 10, about 20, about 25, about 50, about 75, about 90, about 95, about 96, about 97, about 98, about 99, about 100, about 200, about 300, about 400, about 500, about 750, about 1000, about 1500, about 2000, about 2500, about 3000 or more, or any range therein of the nucleotides in the polynucleotide sequence such that some or all of the nucleotides are optimized for SHM-mediated mutagenesis. Reduction in the frequency (density) of hot spots and/or cold spots refers to reducing about 1%, about 2%, about 3%, about 4%, about 5%, about 10%, about 20%, about 25%, about 50%, about 75%, about 90%, about 95%, about 96%, about 97%, about 98%, about 99%, 100% or any range therein of the hot spots or cold spots in a polynucleotide sequence. Increasing the frequency (density) of hot spots and/or cold spots refers to increasing about 1%, about 2%, about 3%, about 4%, about 5%, about 10%, about 20%, about 25%, about 50%, about 75%, about 90%, about 95%, about 96%, about 97%, about 98%, about 99%, 100% or any range therein of the hot spots or cold spots in a polynucleotide sequence.

The position or reading frame of a hot spot or cold spot is also a factor governing whether SHM mediated mutagenesis that can result in a mutation that is silent with regards to the resulting amino acid sequence, or causes conservative, semi-conservative or non conservative changes at the amino acid level. As discussed below, these design parameters can be manipulated to further enhance the relative susceptibility or resistance of a nucleotide sequence to SHM. Thus both the degree of SHM recruitment and the reading frame of the motif are considered in the design of SHM susceptible and SHM resistant polynucleotide sequences.

As used herein, "somatic hypermutation" or "SHM" refers to the mutation of a polynucleotide sequence initiated by, or associated with the action of activation-induced cytidine deaminase, uracil glycosylase and/or error prone polymerases on that polynucleotide sequence. The term is intended to include mutagenesis that occurs as a consequence of the error prone repair of the initial lesion, including mutagenesis mediated by the mismatch repair machinery and related enzymes.

As used herein, the term "UDG" refers to uracil DNA glycosylase, one of several DNA glycosylases that recognize different damaged DNA bases and remove them before replication of the genome. Typically, DNA glycosylases remove DNA bases that are cytotoxic or cause DNA polymerase to introduce errors, and are part of the base excision repair pathway for DNA. Uracil DNA glycosylase recognizes uracil in DNA, a product of cytidine deamination, leading to its removal and potential replacement with a new base.

The term "pol eta" (also called PolH, RAD30A, XPV, XP-V) refers to a low-fidelity DNA polymerase that plays a role in relication through lesions, for instance, replication through UV-induced thymidine dimers. The gene for pol eta is defective in Xeroderma pigmentosum variant type protein, XPV. On non-damaged DNA, pol eta misincorporates incorrect nucleotides at a rate of approximately 3 per 100 bp, and is especially error-prone when replicating through templates containing WA dinucleotides (W=A or T) (Gearhart and Wood, 2001). Pol eta has been shown to play an important role as an A/T mutator during SHM in immunoglobulin variable genes (Zeng et al., 2001). Representative examples of pol eta include without limitation, human (GenBank Accession No. BAA81666), rat (GenBank Accession No. XP_001066743), chicken (GenBank Accession No. NP 001001304), canine (GenBank Accession No. XP_532150) and mouse (GenBank Accession No. NP_109640) forms.

The term "pol theta" (also called PolQ) refers to a low-fidelity DNA polymerase that may play a role in crosslink repair (Gearhart and Wood, Nature Rev Immunol 1: 187-192 (2001)) and contains an intrinsic ATPase-helicase domain (Kawamura et al., Int. J. Cancer 109(1):9-16 (2004)). The polymerase is able to efficiently replicate through an abasic site by functioning both as a mispair inserter and as a mispair extender (Zan et al., EMBO Journal 24, 3757-3769 (2005)). Representative examples of pol theta include without limitation, human (GenBank Accession No. NP_955452), rat (GenBank Accession No. XP_221423), chicken (GenBank Accession No. XP_416549), canine (GenBank Accession No. XP_545125), and mouse (GenBank Accession No. NP_084253) forms. Pol ete and Pol theta are sometimes referred to collectively as "error prone polymerases."

Phage Display Terminology

"Phage display" is a technique by which variant polypeptides are displayed as fusion proteins to at least a portion of a coat protein on the surface of phage, e.g., filamentous phage, particles. A utility of phage display lies in the fact that large libraries of randomized protein variants can be rapidly and efficiently sorted for those sequences that bind to a target molecule with high affinity. Display of peptide and protein libraries on phage has been used for screening millions of polypeptides for ones with specific binding properties. Polyvalent phage display methods have been used for displaying small random peptides and small proteins through fusions to either gene III or gene VIII of filamentous phage. Wells and Lowman, Curr. Opin. Struct. Biol., 3:355-362 (1992), and references cited therein. In monovalent phage display, a protein or peptide library is fused to a gene III or a portion thereof, and expressed at low levels in the presence of wild type gene III protein so that phage particles display one copy or none of the fusion proteins. Avidity effects are reduced relative to polyvalent phage so that sorting is on the basis of intrinsic ligand affinity, and phagemid vectors are used, which simplify DNA manipulations. Lowman and Wells, Methods: A companion to Methods in Enzymology, 3:205-0216 (1991).

A "phagemid" is a plasmid vector having a bacterial origin of replication, e.g., Co1E1, and a copy of an intergenic region of a bacteriophage. Phagemids may be used on any known bacteriophage, including filamentous bacteriophage and lambdoid bacteriophage. Generally, the plasmid will also contain a selectable marker for antibiotic resistance. Segments of DNA cloned into these vectors can be propagated as plasmids. When cells harboring these vectors are provided with all genes necessary for the production of phage particles, the mode of replication of the plasmid changes to rolling circle replication to generate copies of one strand of the plasmid DNA and package phage particles. The phagemid may form infectious or non-infectious phage particles. This term includes phagemids, which contain a phage coat protein gene or fragment thereof linked to a heterologous polypeptide gene as a gene fusion such that the heterologous polypeptide is displayed on the surface of the phage particle.

The term "phage vector" means a double stranded replicative form of a bacteriophage containing a heterologous gene and capable of replication. The phage vector has a phage origin of replication allowing phage replication and phage particle formation. The phage is preferably a filamentous bacteriophage, such as an M13, fl, fd, Pf3 phage or a derivative thereof, or a lambdoid phage, such as lambda, 21, phi80, phi81, 82, 424, 434, etc., or a derivative thereof.

The term "coat protein" means a protein, at least a portion of which is present on the surface of the virus particle. From a functional perspective, a coat protein is any protein, which associates with a virus particle during the viral assembly process in a host cell, and remains associated with the assembled virus until it infects another host cell. The coat protein may be the major coat protein or may be a minor coat protein. A "major" coat protein is generally a coat protein which is present in the viral coat at preferably at least about 5, more preferably at least about 7, even more preferably at least about 10 copies of the protein or more. A major coat protein may be present in tens, hundreds or even thousands of copies per virion. An example of a major coat protein is the p8 protein of filamentous phage.

A "fusion protein" and a "fusion polypeptide" refer to a polypeptide having two portions covalently linked together, where each of the portions is a polypeptide having a different property. The property may be a biological property, such as activity in vitro or in vivo. The property may also be a simple chemical or physical property, such as binding to a target molecule, catalysis of a reaction, etc. The two portions may be linked directly by a single peptide bond or through a peptide linker containing one or more amino acid residues. Generally, the two portions and the linker will be in reading frame with each other.

II. Introduction to Somatic Hypermutation (SHM)

Natural mechanisms for generating antibody diversification have evolved utilizing the process of somatic hypermutation (SHM), which triggers diversification of the variable region of immunoglobulin genes, generating the secondary antibody repertoire thereby allowing affinity maturation of a humoral response. Thus, by directing hypermutation to defined hypervariable regions of an immunoglobulin (Ig) protein scaffold and applying selective pressure to identify improved antibodies, the immune system has developed a diversification strategy capable of rapidly evolving high affinity antibodies within about three weeks in response to antigen exposure.

AID is expressed within activated B cells and is an essential protein factor for SHM, as well as class switch recombination and gene conversion (Muramatsu et al., 2000; Revy et al., 2000). AID belongs to a family of enzymes, the APOBEC family, which share certain features with the metabolic cytidine deaminases but differs from them in that AID deaminates nucleotides within single stranded polynucleotides, and cannot utilize free nucleotide as a substrate. Other enzymes of the AID/APOBEC family can also act to deaminate cytidine on single stranded RNA or DNA (Conticello et al., (2005)).

The human AID protein comprises 198 amino acids and has a predicted molecular weight of 24 kDa. The human AID gene is located at locus 12p13, close to APOBEC-1. The AID protein has a cytidine/deoxycytidine deaminase motif, is dependent on zinc, and can be inhibited by tetrahydrouridine (THU) which is a specific inhibitor of cytidine deaminases.

Even prior to the discovery of AID, it was noted that SHM occurs more frequently in cytidines that are within the context of WRCY (AT/GA/C/AT) motifs. There is now accumulating evidence that this motif for SHM likely represents a composite of this hot spot motif for AID deamination and for initiating error prone repair by the DNA polymerases pol eta and pol theta (Rogozin et al. (2004); Zan et al. (2005)).

High levels of DNA transcription have been shown necessary but alone are not sufficient for AID mediated mutagenesis. In vivo, SHM begins about 80 to about 100 nucleotides from the transcription start site, but decreases in frequency as a function of distance from the promoter. AID has been shown in vitro to interact directly with the transcriptional elongation complex, but not the transcriptional initiation complex, and this interaction may be dependent upon the dissociation of the initiation factors, that occurs as the transcriptional initiation complex converts to the fully processive, elongation-competent transcription elongation complex (Besmer et al., 2006).

Since AID is only able to deaminate cytidines on single stranded DNA, it is likely that the requirement for transcription reflects the generation of single stranded regions by transcription bubbles. Studies with purified AID in vitro however suggest that AID binding is sequence independent, potentially allowing a scanning mode for hot spot capture that is driven by active transcription of the gene. In vitro studies suggest that AID has an apparent Kd for single stranded DNA in the range of 0.3 to 2 nM, and that the complex has a half life of 4-8 minutes. The turnover number of purified AID on single stranded DNA is approximately one deamination every 4 minutes, (Larijani et al., (2006)).

AID acts on DNA to deaminate cytidine residues to uracil residues on either strand of the transcribed DNA molecule. If the initial (C→U) lesion is not further modified prior to, or during DNA replication then an adenosine (A) can be inserted opposite the U nucleotide, ultimately resulting in C→T or G→A transition mutations. The significance of this change at the amino acid level depends upon the location of the nucleotide within the codon within the reading frame. If this mutation occurs in the first or second position of the codon, the result is likely to be a non conservative amino acid substitution. By contrast, if the change occurs at the third position of the codon reading frame, within the wobble position, the practical effect of the mutation at the amino level will be slight because the effect of the nucleotide change will be silent or result in a conservative amino acid substitution.

Alternatively, the C→U lesion, and potentially the neighboring bases can be acted upon by DNA repair machinery, which in SHM, leads to repair in an error prone fashion. Studies in knock out mice have established that base excision repair via uracil DNA glycosylase (UDG), plays a role in mediating the mutation of A and T residues close to hot spot motifs; (Shen et al (2006)). Additionally there is increasing evidence that the creation of abasic sites by UDG recruits error prone polymerases, such as pol eta and pol theta, and that these polymerases introduce additional mutations at all base positions in the surrounding sequence (Watanabe et al. (2004); Neuberger et al (2005)). It is believed that pol eta is central to the creation of A mutations during SHM and is particularly error prone for coding strand adenosines proceeded by A or T (W/A) that are preferentially mutated to G.

It has been observed that in antibody genes, codon usage and precise concomitant hot spot/cold spot targeting of AID activity and pol eta errors in the CDRs and FRs, respectively, has evolved under selective pressure to maximize mutations in the variable regions and minimize mutations in the framework regions (Zheng et al., JEM 201(9): 1467-1478 (2005)) for example, observed that the precise alignment of C and G nucleotides within the codons preferentially used within an antibody gene causes most C to T and G to A mutations to be silent or conservative. Juxaposed on the precise placement of Cs and Gs, Zheng et al., also observed the preferential placement of As and Ts in hot spots of pol eta in the variable regions and the exclusion from these sites in the framework regions.

The regulation of SHM in vivo and the determinants that direct and limit SHM to the Ig locus has been the subject of intense debate and experimental research. The rate of SHM observed in vivo has been shown to be at least partially dependent upon, for example, the following factors: 1) the AID expression levels and AID activity levels within a particular cell type; (Martin et al. (2002), Rucci et al., (2006)), 2) the degree of AID post translational modification and degree of nuclear localization; (McBride et al. (2006), Pasqualucci et al. (2006), Muto et al. (2006)), 3) the presence of immune locus specific enhancer regions, E-box motifs, or associated cis acting binding factors; (Komori et al. (2006), Schoetz, et al. (2006)), 4) the proximity of the targeted sequence to the transcriptional initiation site/promoter region; (Rada et al., (2001)), 5) the rate of transcription of the target sequence; (Storb et al., (2001)), 6) the degree of target gene methylation; (Larijani et al (2005)), 7) the genomic context of the target gene, if integrated into the cell's genomic DNA; 8) the presence or absence of auxiliary factors, such as Pol Eta, MSH2; (Shen et al. (2006)), 9) the existence of hotspot or coldspot sequences within the target sequence; (Zheng et al. (2005)), 10) the existence of inhibitory factors; (Santa-Marta, et al. (2006)), 11) rate of DNA repair within the cell type of interest, (Poltoratsky (2006)), 12) the formation local DNA or RNA hairpins structures; (Steele et al. (2006)), and 13) the phosphorylation state of histone H2B (Odegard et al. (2005)).

III. Polynucleotides for Somatic Hypermutation

The degree to which a polynucleotide sequence or motif is a SHM "hot spot" or "cold spot" is derived from a statistical analysis of SHM mutations identified in antibody sequences, as described in priority US application No. 60/902,414, and is shown in Tables 2 and 3 below. These Tables show the 3-mer, 4-mer, and 6-mer motifs ranked by z-score for their ability to attract SHM-mediated mutation.

TABLE 2

| 3-mer | 3-mer z-score | 4-mer | 4-mer z-score | 4-mer | 4-mer z-score | 4-mer | 4-mer z-score | 4-mer | 4-mer z-z-score |
|---|---|---|---|---|---|---|---|---|---|
| ATA | 271.09 | AATA | 249.23 | TACC | 92.73 | ACGA | 19.69 | CTGG | -55.05 |
| AGC | 185.10 | AGCA | 225.50 | GAAA | 89.97 | TTTT | 17.21 | CGGA | -56.07 |
| TAT | 178.79 | ATAT | 224.06 | CTGC | 88.23 | TTCT | 16.95 | ACGG | -58.65 |
| CAG | 176.52 | AACA | 215.78 | CCAA | 87.55 | GATC | 16.55 | GCCT | -61.62 |
| ACA | 161.58 | ATAA | 213.14 | TATC | 86.83 | TGTA | 15.70 | CGCC | -62.50 |
| CCA | 156.43 | ATCA | 193.93 | CCCA | 86.81 | CCCC | 14.29 | CTTG | -63.02 |
| ATT | 128.07 | TACA | 190.78 | GCTA | 84.30 | TTCC | 8.07 | AGTG | -64.08 |
| AAT | 123.91 | CACA | 183.94 | CTTA | 83.60 | CGCA | 7.95 | GGAC | -66.33 |
| CAC | 113.31 | ACAA | 182.20 | GCAA | 83.41 | CCTG | 6.44 | CCCG | -68.14 |
| CAT | 106.72 | ATTA | 174.57 | ATCC | 82.88 | AAGT | 6.21 | GTGA | -69.31 |
| GCT | 99.04 | CAGA | 172.86 | GAAT | 82.09 | GTTA | 5.83 | TTGT | -70.87 |
| TCA | 92.35 | AACT | 171.38 | ATTC | 80.57 | GTAA | 5.54 | GCGA | -71.78 |
| TAC | 90.32 | AGAT | 167.36 | AGCC | 79.90 | GACT | 5.46 | GTTT | -73.35 |
| ACT | 84.63 | ACAG | 165.72 | CTCA | 78.97 | TCCT | 4.16 | GGGA | -75.77 |

TABLE 2-continued

| 3-mer | 3-mer z-score | 4-mer | 4-mer z-score | 4-mer | 4-mer z-score | 4-mer | 4-mer z-score | 4-mer | 4-mer z-z-score |
|---|---|---|---|---|---|---|---|---|---|
| ATC | 82.30 | CAAC | 163.72 | CCAG | 78.46 | GACC | 2.64 | CGTA | -76.30 |
| AGA | 78.69 | TATA | 159.43 | AGTA | 78.05 | GGAT | -0.62 | TCGA | -76.40 |
| CTA | 71.32 | ATAC | 157.31 | TAGC | 76.80 | TCTG | -1.62 | CGAG | -78.05 |
| GCA | 70.80 | ACTA | 152.17 | ATTT | 74.50 | GCTG | -2.06 | AGGG | -81.46 |
| GAT | 68.06 | CAGC | 148.78 | ACTG | 74.10 | GATG | -2.19 | GAGT | -82.94 |
| CTG | 67.83 | ACCA | 146.54 | TCAC | 71.95 | ACCG | -2.66 | CCGG | -85.06 |
| ACC | 65.99 | AAGC | 145.36 | CTGA | 68.58 | TTTC | -4.30 | GAGG | -85.74 |
| GAA | 59.03 | AGAA | 144.62 | CCTA | 67.05 | TAGT | -4.65 | GTTG | -86.35 |
| TGA | 56.50 | AAAA | 136.44 | TCTA | 66.67 | CGCT | -5.54 | TCCG | -88.86 |
| ATG | 52.18 | ACAT | 135.69 | AATG | 66.07 | AGCG | -5.58 | GTTC | -89.62 |
| CAA | 48.79 | AGCT | 134.58 | GCAT | 65.56 | CCCT | -7.38 | CGGC | -90.00 |
| AAA | 39.39 | CAAT | 133.12 | ACCC | 62.47 | CCTC | -7.50 | GCGC | -91.60 |
| AAC | 37.15 | GATA | 131.74 | TCAT | 61.22 | TGGA | -8.79 | CTCG | -92.05 |
| TTA | 35.04 | ACAC | 130.35 | TGCT | 61.11 | CTGT | -10.50 | TGGC | -92.93 |
| TAA | 31.78 | ATCT | 128.86 | CTAG | 59.03 | GTAT | -10.53 | TCGC | -96.14 |
| AAG | 24.73 | CACC | 125.86 | ACTT | 58.98 | TATG | -13.14 | TGTG | -96.30 |
| CTT | 17.61 | CATA | 125.75 | AGAG | 58.81 | AAGG | -13.25 | TTGG | -100.73 |
| TTC | 16.92 | ATAG | 121.65 | TTAC | 57.51 | CCGC | -13.98 | GGTT | -102.17 |
| GTA | 15.61 | TAAT | 121.29 | TTTA | 56.94 | ATGG | -13.99 | GCCG | -104.21 |
| TAG | 13.84 | CAAA | 121.00 | TCAG | 56.45 | CGAA | -14.21 | CCGT | -105.94 |
| GGA | 11.44 | TATT | 120.42 | ATGC | 54.70 | TCTT | -15.45 | GTCT | -108.78 |
| TTT | 6.80 | CTAA | 119.93 | AGAC | 53.01 | TGAC | -16.19 | GGCC | -110.06 |
| AGT | 2.60 | CATC | 118.61 | TGAT | 51.51 | CCTT | -16.61 | GACG | -112.93 |
| CTC | -1.47 | TTCA | 117.73 | GCAC | 51.04 | CACG | -19.16 | TGGT | -115.42 |
| TCC | -5.22 | AAAC | 116.35 | AGGA | 50.16 | GGCA | -21.99 | GTGC | -117.74 |
| CCT | -5.42 | TTAT | 114.64 | TAAG | 49.76 | TCCC | -23.02 | TTCG | -118.98 |
| CCC | -7.09 | AAAT | 114.43 | CAGT | 49.09 | AACG | -26.20 | ACGT | -121.92 |
| GAG | -8.26 | CCAT | 113.51 | ACTC | 46.69 | CGAT | -27.41 | GCGG | -124.24 |
| TGC | -14.70 | ACCT | 111.92 | AGTT | 45.47 | AGGT | -29.09 | TGCG | -126.58 |
| TCT | -18.88 | TAAC | 111.26 | CAAG | 43.20 | TCTC | -29.53 | TGGG | -127.63 |
| GAC | -23.11 | CTAT | 110.83 | CTCC | 43.07 | TTGC | -29.86 | GTCC | -128.75 |
| AGG | -27.85 | TAAA | 110.30 | GTAC | 42.84 | CCGA | -32.32 | GGGC | -132.40 |
| GCC | -38.10 | CCAC | 110.05 | GAAC | 42.62 | TGAG | -34.69 | GGGG | -133.41 |
| TGG | -40.97 | AATT | 109.92 | GAGC | 41.24 | ATGT | -34.90 | TCGT | -135.34 |
| TTG | -43.86 | TGCA | 107.12 | GCCA | 40.88 | TAGG | -37.28 | GGTG | -135.80 |
| ACG | -61.29 | CATT | 106.83 | GCTT | 39.88 | GGCT | -38.30 | CGTT | -136.77 |
| GTT | -62.25 | TCAA | 104.12 | CAGG | 37.16 | GCCC | -40.66 | TGTC | -137.57 |
| CGA | -62.60 | AAAG | 103.76 | GATT | 35.99 | GGAG | -44.01 | GTGT | -142.24 |

TABLE 2-continued

| 3-mer | 3-mer z-score | 4-mer | 4-mer z-score | 4-mer | 4-mer z-score | 4-mer | 4-mer z-score | 4-mer | 4-mer z-z-score |
|---|---|---|---|---|---|---|---|---|---|
| TGT | −64.56 | TACT | 101.53 | GACA | 35.71 | TGTT | −44.49 | CGGT | −144.04 |
| GGC | −70.30 | AAGA | 100.90 | CTTC | 34.67 | CGAC | −45.06 | GTGG | −149.24 |
| CGC | −82.93 | CACT | 100.32 | CTCT | 33.87 | GGTA | −46.07 | CGTC | −155.95 |
| CCG | −85.43 | AACC | 99.86 | GAAG | 31.97 | AGGC | −46.08 | GGTC | −158.84 |
| GGG | −97.46 | GCAG | 99.17 | TTGA | 31.29 | TACG | −46.78 | TCGG | −159.56 |
| GTG | −110.90 | ATGA | 98.38 | CTTT | 28.94 | AGTC | −46.82 | CGGG | −159.99 |
| GGT | −112.41 | CTAC | 95.93 | TTAG | 27.86 | ACGC | −47.10 | GGGT | −162.17 |
| CGG | −116.32 | TCCA | 95.63 | GGAA | 26.38 | ATCG | −48.15 | GGCG | −171.27 |
| GCG | −118.80 | AATC | 95.61 | ATTG | 25.55 | GTCA | −52.15 | CGCG | −172.40 |
| TCG | −125.83 | TGAA | 93.81 | CATG | 24.39 | TTTG | −52.48 | CGTG | −180.34 |
| GTC | −126.67 | TTAA | 93.67 | GCTC | 22.00 | GTAG | −53.73 | GCGT | −194.57 |
| CGT | −130.10 | TAGA | 93.03 | GAGA | 21.55 | TGCC | −54.56 | GTCG | −207.74 |

TABLE 3

| 6-mer | 6-mer z-score | 6-mer | 6-mer z-score | 6-mer | 6-mer z-score | 6-mer | 6-mer z-score |
|---|---|---|---|---|---|---|---|
| ACAGCT | 266.45 | GCTGTT | 33.73 | AGAGGA | 3.16 | GCTGTC | −19.65 |
| ATTAAT | 248.7 | AAGAAT | 33.68 | GGGATT | 3.16 | ACCGCG | −19.66 |
| ATAATA | 227 | GATTCT | 33.67 | ACGGAT | 3.13 | GTGAGA | −19.68 |
| CAGCTA | 223.27 | ACCGCC | 33.57 | TGCTAG | 3.1 | GGCCAC | −19.7 |
| AATATA | 220.6 | ACAGGG | 33.56 | TATGCG | 3.06 | CCTAGT | −19.71 |
| AATACA | 215.65 | CAAGAC | 33.52 | GACCTG | 3 | TCTTCG | −19.73 |
| AGCTAC | 211.24 | CCACTG | 33.47 | TTGGAT | 2.99 | GTGATC | −19.73 |
| AGATAT | 211.07 | AAGTAA | 33.38 | TACTTG | 2.98 | ATGTAG | −19.77 |
| AGCTAA | 210.24 | TGTACT | 33.36 | GACAAG | 2.95 | GTGACT | −19.79 |
| ATATAT | 209.3 | CTGAAG | 33.36 | TATGAG | 2.93 | GACGGC | −19.8 |
| AATACT | 203.19 | AGACCT | 33.33 | GACTCT | 2.87 | AGGGGC | −19.83 |
| ATATAC | 192.44 | ACTAGA | 33.32 | GTTGTA | 2.85 | ATTCCG | −19.84 |
| ATAACT | 190.78 | AAATCT | 33.23 | GTCACC | 2.84 | GTTTCC | −19.85 |
| ATATTA | 189.76 | GCTATG | 33.22 | CATGTC | 2.82 | GGCAAG | −19.96 |
| ATAGCA | 186.89 | TTGATT | 33.18 | TGGTAC | 2.78 | CGGCAT | −19.96 |
| ATACCA | 186.58 | TGCTGC | 33.18 | CTCCTT | 2.78 | TCCCGC | −19.96 |
| ATACAA | 181.41 | AGAAGA | 33.16 | ATCTGT | 2.78 | AGTGTT | −19.97 |
| GCAGCT | 180.69 | AATGGA | 33.11 | AGGACT | 2.76 | GCCGAC | −19.99 |
| ATTACA | 180.46 | TTCCCA | 33.1 | GGTAAC | 2.76 | CCGATT | −20.01 |
| CAGCTC | 180.29 | AATGGT | 33.08 | TCCCAT | 2.75 | ATTCGG | −20.03 |
| ATAGCT | 180.08 | GTTACA | 33.07 | CAATTT | 2.73 | TACCGT | −20.03 |
| AATAAT | 179.41 | TCAGGA | 33.04 | GCTGGT | 2.69 | TCAGGG | −20.08 |

TABLE 3-continued

| 6-mer | 6-mer z-score | 6-mer | 6-mer z-score | 6-mer | 6-mer z-score | 6-mer | 6-mer z-score |
|---|---|---|---|---|---|---|---|
| AGCTAT | 178.14 | TACACG | 32.96 | ACGATT | 2.63 | GTTTGA | −20.11 |
| CAGCTT | 176.31 | TTACTT | 32.93 | CGAACT | 2.6 | GCTCCG | −20.13 |
| ATATCT | 174.41 | TAAAGA | 32.93 | GACACG | 2.58 | CCTGGT | −20.17 |
| AGCTGC | 169 | CACTTT | 32.87 | ATGTGA | 2.58 | CCTCTT | −20.18 |
| CAGCTG | 167.78 | AACTGG | 32.82 | CCTAAA | 2.57 | ACGTGA | −20.22 |
| AGCTGA | 167.41 | CTCACC | 32.81 | TGGCAT | 2.49 | GTCTAA | −20.25 |
| AATAAA | 167.35 | ACATGC | 32.79 | CTGGTA | 2.48 | TAAGGG | −20.27 |
| ACTACA | 167.11 | AGCCTG | 32.79 | ACTTTC | 2.47 | TCCCCG | −20.29 |
| AACAGC | 167.08 | TCCCAG | 32.78 | GAGTAG | 2.46 | CACGTC | −20.32 |
| ATTATT | 166.89 | ACATGG | 32.77 | TTTCCT | 2.4 | GGCAGG | −20.33 |
| AAGCTA | 166.44 | CACTTA | 32.69 | CCACAC | 2.39 | CGTAAC | −20.35 |
| ACTACT | 164.71 | CCCCCA | 32.63 | TGTTCA | 2.38 | GAGGCC | −20.36 |
| AATACC | 164.29 | ATGATG | 32.59 | AACTTA | 2.38 | TAGTCT | −20.36 |
| TATTAT | 164.1 | GCAGAG | 32.58 | TGTTGA | 2.35 | AGGGAG | −20.39 |
| ACAGCA | 161.72 | ACATAA | 32.53 | GAAAGG | 2.33 | ACTCGT | −20.39 |
| AGCAGA | 160.66 | AAAGTA | 32.47 | ACGGCA | 2.33 | CGCTTA | −20.4 |
| AGCAAT | 159.61 | AAAAGA | 32.46 | GAGCCG | 2.32 | GCGGAA | −20.46 |
| TAATAC | 159.28 | GAACAT | 32.46 | TCTTAG | 2.32 | GGCTAA | −20.5 |
| AATCCA | 156.67 | CAATTC | 32.4 | CAATGT | 2.29 | CCTTCG | −20.52 |
| AATAGA | 156.3 | CCACTT | 32.39 | GTCCAT | 2.28 | TAAGTT | −20.52 |
| TATACA | 155.5 | GGCTTT | 32.37 | ACCGCA | 2.24 | TTGGCT | −20.53 |
| AGCTCC | 153.55 | TTCAAC | 32.34 | CTCCTG | 2.22 | CCGGAG | −20.53 |

TABLE 3-continued

| 6-mer | 6-mer z-score | 6-mer | 6-mer z-score | 6-mer | 6-mer z-score | 6-mer | 6-mer z-score |
|---|---|---|---|---|---|---|---|
| CATATA | 152.22 | GCTTAT | 32.32 | CTAGAG | 2.19 | ACGCCG | -20.58 |
| ATACAT | 151.77 | CAGGAT | 32.32 | TCATTC | 2.19 | GTCTCT | -20.59 |
| TATATT | 150.71 | AGCCCT | 32.3 | AAGGCA | 2.18 | CCGAAC | -20.66 |
| TAATAT | 150.37 | CAATGC | 32.26 | CCCTTT | 2.15 | AGGGTT | -20.69 |
| ATTACT | 150.2 | TGTATC | 32.2 | AGGTTC | 2.11 | GGTCAC | -20.72 |
| TCAGCT | 149.79 | TGATCT | 32.2 | CTTAAC | 2.1 | AGTGGT | -20.73 |
| AACTAC | 149.11 | CTGTTA | 32.12 | TTGACC | 2.07 | TGTCAC | -20.75 |
| AAAGCT | 148.88 | ACAATT | 32.12 | GCTTTC | 2.06 | CCCCCG | -20.77 |
| CAGCAT | 147.47 | TATCTT | 32.05 | AGACAA | 2.06 | TTCGAT | -20.79 |
| ATACAC | 147.42 | ATTCAA | 32.04 | TTTCTG | 2.02 | CGTAGT | -20.82 |
| ATAGAT | 147.33 | TTCAAA | 32.03 | GGTGAT | 2.01 | GCGGCA | -20.82 |
| ATCAGC | 147.06 | CAGACC | 31.98 | CCTCAT | 1.99 | TCCGAG | -20.86 |
| AGATAC | 146.34 | ACATGA | 31.9 | GAGAGC | 1.95 | TCAAGT | -20.87 |
| AGCACA | 146.01 | CTAAGC | 31.75 | GCCTTC | 1.91 | CCGTCT | --0.88 |
| CAGATA | 145.75 | CTAAGA | 31.7 | TGATGC | 1.88 | GGAGGT | -20.93 |
| TAGCTA | 145.22 | ATAAAG | 31.69 | AGAGGC | 1.87 | CTGACG | -20.94 |
| TTAGCT | 144.8 | AACTAG | 31.56 | GATGAC | 1.87 | TGCCTC | -20.94 |
| AAGCTG | 143.55 | GTACCT | 31.55 | GTTTCT | 1.83 | AGTCAG | -20.95 |
| CACAGC | 141.38 | AGATAG | 31.51 | TAACGA | 1.8 | TTCTCT | -20.97 |
| ACAACT | 140.89 | CAAAAT | 31.5 | CTTACC | 1.79 | CGGTTC | -20.97 |
| CATACA | 139.87 | GTGAAT | 31.48 | ACTGAC | 1.72 | TGTCTA | -21 |
| AGCAGC | 139.64 | AGCCAA | 31.4 | ACGCAA | 1.7 | TCTCCG | -21.04 |
| ACTATT | 139.36 | GAGATG | 31.33 | CGAATC | 1.69 | CACTCG | -21.05 |
| CCAGCT | 137.43 | GGAGAA | 31.29 | GGACAG | 1.64 | TGACGA | -21.15 |
| GATACA | 136.87 | AATTGC | 31.29 | GCCGAT | 1.64 | GTCTCA | -21.17 |
| AGCTTC | 136.64 | ATGGCT | 31.23 | TGGGAA | 1.62 | GTCAAG | -21.27 |
| AGCTCA | 136.52 | GCAAAT | 31.22 | AGACGC | 1.6 | CTTGGC | -21.28 |
| ACCAGC | 136.02 | TAGAAC | 31.2 | TTACCC | 1.58 | ACGTCC | -21.28 |
| AAATAC | 135.35 | ATGGAA | 31.19 | CAACCG | 1.55 | CGGTGA | -21.32 |
| AGCTTA | 135.22 | GATGGA | 31.15 | CCCTCC | 1.51 | TTGGGA | -21.4 |
| AGAGCT | 134.71 | CTGCTC | 31.09 | TTCAGG | 1.48 | TCGTAA | -21.4 |
| TAACTA | 134.57 | CCAGAC | 31.09 | TCACGA | 1.48 | CGGAAC | -21.42 |
| TACTAC | 134.52 | ACTCAT | 31.09 | TGCTTT | 1.44 | GGTATG | -21.43 |
| AACTAT | 133.79 | CGAACA | 31.02 | AGGGGA | 1.42 | ACCGGT | -21.5 |
| ATAAAC | 132.79 | AGCCAG | 31.01 | ACGGAC | 1.41 | CCGGAA | -21.51 |
| TAGATA | 132.74 | GGATAC | 31.01 | CTCCCC | 1.38 | TCGTTA | -21.53 |
| AACACA | 131.7 | GCAGAA | 30.98 | ACCTTG | 1.35 | AATGTC | -21.55 |
| CTAATA | 131.46 | GTAAAT | 30.95 | AGAGTA | 1.3 | CATGTG | -21.55 |

TABLE 3-continued

| 6-mer | 6-mer z-score | 6-mer | 6-mer z-score | 6-mer | 6-mer z-score | 6-mer | 6-mer z-score |
|---|---|---|---|---|---|---|---|
| AATAGC | 130.99 | TTTATA | 30.85 | GCCAAA | 1.29 | GCGAGA | -21.58 |
| GAGCTA | 130.78 | TGCTTC | 30.8 | AAAGTG | 1.28 | TTTAGG | -21.6 |
| ATACTA | 130.56 | CTCAAC | 30.7 | CCCCTG | 1.21 | GAGGTA | -21.69 |
| ATATCA | 130.47 | AAAGAC | 30.65 | TTGAAC | 1.21 | CCGGCC | -21.71 |
| CTACTA | 130.24 | GCTCAA | 30.56 | GATGAG | 1.21 | TGTGGA | -21.72 |
| ATACAG | 129.95 | ACAGTC | 30.55 | GCGCTG | 1.2 | CTCTCT | -21.73 |
| CCAGCA | 129.73 | CACAAG | 30.53 | TCAATG | 1.17 | GTGGCT | -21.74 |
| CAGCAG | 129.37 | TGGATA | 30.52 | CTTGGA | 1.16 | GCCGCC | -21.76 |
| AATGCA | 128.88 | GCATAG | 30.51 | AGGGAA | 1.14 | GACCGA | -21.76 |
| ACTAAT | 128.87 | ACCTGG | 30.5 | GTTGAA | 1.14 | GGTCAT | -21.8 |
| AGCTTT | 128.11 | CTCCCA | 30.43 | AGAGTT | 1.08 | TCCCTG | -21.84 |
| ATCCAC | 128.11 | TGATTC | 30.33 | AGACGG | 1.08 | GCGCTA | -21.87 |
| GAAGCT | 126.98 | GCTGTA | 30.33 | TTGGAA | 1.05 | TCCGTA | -21.87 |
| CAGCAA | 126.51 | GCATAC | 30.26 | TCTCCC | 1.02 | TTGTTG | -21.9 |
| ACCACC | 126.44 | TCAAGC | 30.25 | CTCTAA | 1.01 | GTCCTA | -21.93 |
| GCTACA | 126.36 | CAGAAT | 30.22 | TCTGAG | 1 | GCCACG | -21.95 |
| AGCTGT | 126.35 | TCATAC | 30.18 | TCGATT | 0.95 | TGCGTA | -21.97 |
| ATAACA | 126.34 | CATCCT | 30.14 | ACGAAT | 0.83 | TCCGAA | -21.99 |
| AGTTAT | 125.56 | TGAAAC | 30.04 | TGGAGG | 0.82 | GCCGGA | -22.01 |
| TTACTA | 125.4 | AAACTC | 30 | CATGGT | 0.82 | GAGCGG | -22.07 |
| AATTAC | 124.76 | GCATTT | 29.91 | GAAGAG | 0.81 | TTCTCG | -22.07 |
| AATTCA | 123.97 | AAGGAC | 29.86 | TTCCTG | 0.78 | GACGAA | -22.08 |
| CAGCAC | 123.54 | ACAAAA | 29.84 | CGCTTT | 0.75 | CTGCCG | -22.11 |
| ACAGCC | 123.25 | GAGTAT | 29.79 | CGGAGA | 0.75 | CTGGTT | -22.11 |
| TTAATA | 122.8 | AAATGA | 29.74 | GATAAG | 0.72 | AGGCCG | -22.12 |
| AGTATT | 122.69 | AGCGGA | 29.72 | GGCATT | 0.71 | GAGTCT | -22.25 |
| CAACTA | 122.15 | GAATTA | 29.71 | GGCAGT | 0.67 | ATGGCG | -22.26 |
| CAATAA | 121.87 | AGTGAA | 29.7 | ATTCGA | 0.67 | GGGCAC | -22.28 |
| AGCAAC | 121.8 | AACAAG | 29.69 | CATTTG | 0.59 | AGTCGC | -22.31 |
| ATCTAC | 121.63 | TCAAGA | 29.63 | TCTTAA | 0.58 | GCGGAG | -22.37 |
| TACACC | 121.61 | AACCTT | 29.53 | ATTGAG | 0.55 | TCTCGA | -22.4 |
| AGCACC | 121.59 | GAATAA | 29.53 | TTTTCC | 0.54 | GACCGC | -22.5 |
| ATAGCC | 120.05 | CTCACA | 29.49 | CAAAAC | 0.47 | CTCGAC | -22.51 |
| TAGCTG | 119.3 | TCACAA | 29.46 | AGTGAC | 0.47 | ACGGGC | -22.53 |
| AAAACA | 119.25 | CCCATC | 29.46 | GCCTCC | 0.45 | GCGCAA | -22.56 |
| ATTATA | 119.17 | TGTGCA | 29.41 | GACGCT | 0.39 | CTCCCG | -22.58 |
| AGTACT | 118.38 | ATTGGA | 29.27 | CATCCG | 0.39 | GTATGT | -22.6 |
| CACCAT | 117.87 | ATTGAA | 29.23 | CTATGG | 0.38 | GGGCAA | -22.61 |

TABLE 3-continued

| 6-mer | 6-mer z-score | 6-mer | 6-mer z-score | 6-mer | 6-mer z-score | 6-mer | 6-mer z-score |
|---|---|---|---|---|---|---|---|
| ATCTAT | 116.19 | ATAATG | 29.22 | TCATGG | 0.37 | ATCTCG | −22.63 |
| ACCATT | 115.23 | CCTTTA | 29.21 | GGGACA | 0.36 | AGTGCC | −22.66 |
| TACTAT | 115.17 | GGAACT | 29.21 | CCTGCC | 0.36 | GTCTTC | −22.66 |
| TCAGCA | 115.13 | TTCAGA | 29.18 | CAGGGA | 0.34 | CGGGAA | −22.68 |
| AGCATA | 114.84 | GCAACA | 29.12 | TTCGCA | 0.32 | CGATGT | −22.69 |
| TATTAA | 114.69 | ATAATC | 29.11 | AAGGTG | 0.25 | GACTTA | −22.7 |
| CAAGCT | 113.83 | CTCATA | 29.07 | GATGTT | 0.2 | CGCGCA | −22.71 |
| AGATGA | 113.27 | GAATAC | 29 | TTTTAG | 0.18 | GACGAC | −22.71 |
| GATATA | 112.88 | CTGATC | 29 | TGGTGA | 0.16 | GGGGCT | −22.72 |
| TAGCTT | 112.54 | ACCAAG | 28.96 | CTGTGA | 0.14 | TCCCGA | −22.78 |
| TATTAC | 111.72 | CACAGG | 28.94 | GGCAGA | 0.11 | TCAACG | −22.81 |
| AGCTCT | 111.46 | ATTTCC | 28.86 | GTGTAT | 0.1 | CGTCAA | −22.81 |
| TCACCA | 111.34 | GCATAA | 28.83 | CCCTAA | 0.09 | GATGGG | −22.81 |
| ATAGTA | 110.66 | TCCCAC | 28.82 | TCTCCT | 0.06 | TGCCTT | −22.82 |
| ATACCT | 110.48 | GAGCAA | 28.81 | ACTCGA | 0.05 | TACGGT | −22.84 |
| AGCATC | 109.68 | TCCAGA | 28.65 | TACCTC | 0 | TTTGCG | −22.87 |
| TATCTA | 109.46 | TTCCAT | 28.63 | AATCGC | −0.05 | CGCCCC | −22.92 |
| TACAAC | 108.83 | GGCACA | 28.6 | ACTTAA | −0.05 | GAGGTC | −22.93 |
| GCAGCA | 108.59 | TTTCTT | 28.55 | CTCAAA | −0.06 | ATTGGG | −22.97 |
| AGTAAT | 108.57 | TAAACC | 28.53 | GCCCCC | −0.1 | CGGACT | −22.99 |
| TGCACA | 108.53 | AAATTA | 28.46 | GGTTAA | −0.11 | AACGTA | −23.02 |
| TTTATT | 108.51 | CTTGCA | 28.46 | GCGAAA | −0.15 | ACGTTC | −23.04 |
| ATGATA | 108.34 | ACCTCT | 28.41 | CTAGTT | −0.16 | GACTCG | −23.1 |
| CAAATA | 108.12 | TCAGTA | 28.39 | TCCCCC | −0.21 | CTGTTG | −23.16 |
| ACAATA | 107.6 | GAAGTT | 28.37 | AACTTG | −0.22 | GCTGGG | −23.19 |
| AATAGT | 107.19 | TACATT | 28.33 | CTCCGC | −0.27 | CGTTTT | −23.21 |
| AACAAC | 107.08 | GACCCA | 28.32 | AAACGA | −0.29 | TACGAG | −23.26 |
| CACCAG | 107.01 | GACCAT | 28.29 | TGCCCC | −0.34 | GCCAGT | −23.28 |
| TAGCTC | 106.68 | CCACAT | 28.23 | CGCTGC | −0.35 | TTCGTA | −23.29 |
| TACAGC | 106.65 | CATTTT | 28.22 | AAAAGG | −0.35 | CCTCCG | −23.29 |
| AACTGA | 106.63 | ATCGCT | 28.15 | TGCATG | −0.38 | TTCTGG | −23.3 |
| GCATAT | 106.63 | AAGGAA | 28.11 | CAGACG | −0.39 | GGGGAC | −23.32 |
| GAGCTG | 106.39 | TATAGT | 27.92 | TGACAC | −0.39 | GATCGC | −23.32 |
| ATTCAC | 106.22 | TAACTT | 27.89 | CGATGA | −0.4 | CCCGAC | −23.33 |
| AAATAA | 105.92 | CTTAGC | 27.87 | TTAAGG | −0.41 | CGGGAT | −23.34 |
| TAGCAA | 105.71 | CTTAAG | 27.83 | TTGGAG | −0.41 | GTGTTA | −23.34 |
| CCAGAT | 105.22 | CCTGCT | 27.78 | GCCCAA | −0.41 | GTAGAC | −23.35 |
| ACCATC | 105.14 | GATACG | 27.7 | AGGTTA | −0.42 | GCAGGG | −23.38 |

TABLE 3-continued

| 6-mer | 6-mer z-score | 6-mer | 6-mer z-score | 6-mer | 6-mer z-score | 6-mer | 6-mer z-score |
|---|---|---|---|---|---|---|---|
| AATAAC | 105.1 | TAGACA | 27.69 | ATTTAG | −0.45 | AGAGGG | −23.41 |
| TACCAT | 104.92 | GGTTCA | 27.68 | AGATTA | −0.46 | ACGGTT | −23.42 |
| AGAACA | 104.85 | ATGCTT | 27.68 | AGGTTT | −0.49 | CGCCTA | −23.43 |
| ATCATA | 104.56 | TTCATT | 27.66 | GCCTAT | −0.53 | GGGCTA | −23.43 |
| ATCACC | 104.5 | TAATCC | 27.62 | TCATGC | −0.55 | GTACGA | −23.43 |
| AGAAAT | 104.29 | ATATGT | 27.59 | CTCATG | −0.58 | TTTGAG | −23.44 |
| ATATAA | 104.19 | CCACGA | 27.56 | CAGTCC | −0.59 | TACGTA | −23.44 |
| CATATC | 103.97 | AAAATC | 27.56 | GTATGA | −0.64 | GTGACC | −23.47 |
| ATTCCA | 103.78 | GAAGTA | 27.52 | CCTCTA | −0.65 | CTCGCT | −23.49 |
| GGAGCT | 102.99 | TGCTCC | 27.5 | CATTCT | −0.65 | ATTGTC | −23.58 |
| TACAGA | 102.58 | CCCATA | 27.47 | CCGACA | −0.73 | TTAAGT | −23.58 |
| TACTAA | 102.18 | TTAACC | 27.43 | AGTTAG | −0.81 | TTACGC | −23.64 |
| ATCACT | 102.01 | TAGAGC | 27.38 | GCCAAG | −0.86 | GTTAAG | −23.65 |
| ATATGA | 101.89 | AGGCTA | 27.34 | ATTCTG | −0.86 | CCGGCA | −23.74 |
| AAACAG | 101.82 | GCAAAA | 27.32 | GAGTTG | −0.88 | AACGGT | −23.77 |
| ACACAG | 101.77 | GCTCAT | 27.31 | AAAGAG | −0.91 | CGAGTT | −23.8 |
| ACACCA | 101.38 | AGGACC | 27.3 | TGTGCT | −0.96 | GGCCGA | −23.81 |
| ACAACC | 101.23 | AGACTA | 27.27 | TCTAAG | −0.96 | GCGGTA | −23.82 |
| TAAGCT | 100.84 | CCATTC | 27.24 | AAACTT | −1.01 | GCAACG | −23.84 |
| CAATAG | 100.69 | ACGACT | 27.24 | GCGGCT | −1.04 | GCGATC | −23.9 |
| CTATTA | 100.61 | AGGAAA | 27.08 | TTAGAC | −1.04 | CTCCGA | −23.94 |
| TTACCA | 100.56 | TTCCAG | 27 | TTAAAC | −1.08 | CGGCCT | −23.97 |
| AGTACA | 100.42 | TCACCC | 26.94 | AAGGTT | −1.14 | TCCGAT | −23.99 |
| AACCAC | 100.39 | AAATTC | 26.9 | AGTTGG | −1.15 | AGACGT | −24.01 |
| CCACCA | 100.19 | AACTGT | 26.84 | AGAGGT | −1.2 | TTTCGA | −24.02 |
| AAACAC | 99.94 | TTCTAT | 26.75 | CCCTAG | −1.2 | TTTTGT | −24.03 |
| ATAAAT | 99.38 | TAATGG | 26.71 | CCGCTC | −1.21 | ATTCGT | −24.04 |
| GCTATA | 99.35 | ACAACG | 26.66 | GCATGG | −1.24 | TCACGT | −24.05 |
| GTAGCT | 99.14 | AGGTGA | 26.64 | GCTAGA | −1.26 | CCTGGG | −24.05 |
| CAGCCA | 99.11 | AGGAAC | 26.59 | ACGATC | −1.27 | TGTAAG | −24.09 |
| TTCAGC | 99 | TGGTAT | 26.57 | CGTGCA | −1.27 | AATGCG | −24.13 |
| AGACAC | 98.97 | AAACAT | 26.53 | TTTAGC | −1.32 | CGTTCT | −24.15 |
| AGCACT | 98.85 | AGTTGC | 26.52 | CTCATT | −1.33 | CCGAGG | −24.17 |
| CCAATA | 98.8 | CAGTGA | 26.47 | CGCAGT | −1.35 | TCTAGG | −24.2 |
| AAACCA | 98.68 | GATTCC | 26.47 | AATTGT | −1.36 | TGGGTA | −24.22 |
| CAGCCT | 98.34 | AGCGAC | 26.44 | TGACAG | −1.37 | GTGTTT | −24.23 |
| AAGCAC | 98.34 | ATCAAG | 26.44 | ATGCCT | −1.38 | TGATGT | −24.25 |
| ACTGCA | 98.25 | ACCCCT | 26.4 | AAGTTC | −1.41 | TAGGTT | −24.27 |

TABLE 3-continued

| 6-mer | 6-mer z-score | 6-mer | 6-mer z-score | 6-mer | 6-mer z-score | 6-mer | 6-mer z-score |
|---|---|---|---|---|---|---|---|
| AGAAGC | 98.23 | CCCCAG | 26.4 | CTTGAC | -1.45 | ACTTAG | -24.29 |
| CCATCA | 98.1 | CGTATT | 26.39 | TTTTGA | -1.48 | AACGTC | -24.31 |
| CAACCA | 97.53 | TACTTT | 26.39 | ATAACG | -1.48 | AGGTTG | -24.34 |
| CAACTG | 97.51 | AGACAG | 26.37 | GCATTC | -1.49 | GTAGCG | -24.4 |
| ATTAGC | 97.37 | TTATGA | 26.36 | ATCGGC | -1.51 | GTTAAC | -24.41 |
| AATATT | 96.98 | CAAGAG | 26.32 | GTAATG | -1.54 | TATGGG | -24.43 |
| ACCACA | 96.82 | TGCAGT | 26.31 | TAAACT | -1.55 | TAGCGC | -24.44 |
| ATATGC | 96.53 | AGGAGA | 26.3 | GAATGG | -1.56 | CGTCAC | -24.48 |
| GTATTA | 96.49 | CCATGC | 26.27 | AATTTG | -1.6 | TTCCGA | -24.5 |
| CATAGC | 96.33 | GAAAGC | 26.23 | CCTCCC | -1.61 | GACTAG | -24.54 |
| GTATAT | 96.2 | ACGATA | 26.23 | CGGATT | -1.62 | TGGGGA | -24.57 |
| ACCAAC | 96.14 | CAAGGC | 26.22 | TTGAGA | -1.64 | GCGCTT | -24.58 |
| CAGATC | 96.05 | CTTTAT | 26.22 | GTGAAG | -1.66 | TTCTGT | -24.59 |
| AACATA | 96.05 | CATTCC | 26.22 | GCCCCT | -1.7 | GGAGTC | -24.6 |
| AGATCC | 95.89 | GAAAAT | 26.2 | CGTTTA | -1.73 | CGCCTG | -24.62 |
| CTACCA | 95.82 | CATTGC | 26.13 | GAGGAA | -1.76 | CGATTG | -24.63 |
| GATCCA | 95.8 | TATACG | 26.08 | CGTTCA | -1.77 | GGTGAC | -24.68 |
| ATTGCT | 95.61 | GTAGAA | 26.03 | TTCGAA | -1.81 | TCGTAG | -24.68 |
| ACCATA | 95.61 | GGACCA | 26.02 | ATCGAC | -1.83 | TGTCAA | -24.69 |
| CATCTA | 95.61 | GCTCTT | 25.97 | TTTTTC | -1.87 | GGGTTC | -24.7 |
| CCAGCC | 95.4 | TGTTAC | 25.87 | TGCGCA | -1.89 | TTCGAC | -24.76 |
| ACCTAC | 95.39 | TCCCCA | 25.78 | ACCGAA | -1.9 | TGTGTA | -24.79 |
| TCAACT | 95.32 | TCCATT | 25.78 | CTGCGC | -1.93 | GAGTGA | -24.81 |
| ATGCAC | 95.22 | AGAAAA | 25.72 | AAGTCA | -1.93 | GACGAG | -24.82 |
| GAAATA | 95.07 | CCCAAG | 25.69 | TTACGA | -2 | CTAGGG | -24.83 |
| TATAGC | 94.95 | GTGCAT | 25.62 | TGGACT | -2.05 | GTTGAG | -24.87 |
| TACCAC | 94.81 | TTTTAT | 25.58 | TACGCT | -2.06 | TGACGC | -24.87 |
| AGCTAG | 94.59 | ACCTTT | 25.53 | GAGGCA | -2.1 | CGCAAC | -24.94 |
| CCATAT | 94.32 | CTACGA | 25.52 | TTGATG | -2.12 | CGCCTC | -24.96 |
| TATATA | 94.2 | CCTTAA | 25.52 | ACCGAT | -2.13 | GAGCGA | -24.96 |
| CATATT | 94.16 | GGCATA | 25.52 | TACTCT | -2.17 | CAAGTG | -25.01 |
| TAATAA | 94.05 | GAAAAC | 25.47 | CGCCAG | -2.18 | TGGTGC | -25.01 |
| AGAACT | 93.81 | AGTTTT | 25.42 | GAGTTA | -2.18 | ACGGCG | -25.02 |
| TATCAC | 93.66 | GAATTC | 25.36 | CACGTT | -2.2 | CGAGGC | -25.03 |
| CACCAC | 93.38 | GATCAC | 25.35 | CTGCGA | -2.22 | TACGCG | -25.05 |
| AAAGCC | 93.36 | CACACC | 25.27 | GTGCTT | -2.23 | CATGGG | -25.06 |
| CTACAG | 93.16 | AAGCCG | 25.26 | AATGAG | -2.24 | CTGTCC | -25.07 |
| GCAGAT | 93.16 | ACTGAG | 25.25 | AGTGTA | -2.25 | GTAAGC | -25.1 |

TABLE 3-continued

| 6-mer | 6-mer z-score | 6-mer | 6-mer z-score | 6-mer | 6-mer z-score | 6-mer | 6-mer z-score |
|---|---|---|---|---|---|---|---|
| AGATCA | 93.03 | ATCTAA | 25.24 | CTTATG | -2.26 | CGTGTA | -25.17 |
| ACTTCA | 92.78 | AGACTG | 25.18 | TCTCTG | -2.27 | ATGCCG | -25.2 |
| ACACAC | 91.91 | AAGTTA | 25.15 | CCTAAT | -2.29 | ACGTAC | -25.24 |
| ACCACT | 91.48 | TCACTG | 25.11 | GGAATG | -2.29 | TTCCGC | -25.28 |
| AAGCTT | 91.27 | ATCGCA | 25.08 | CCATTG | -2.34 | GTCTTT | -25.31 |
| ACCAAT | 90.89 | CGATAT | 25.02 | CGATAA | -2.35 | TCCGGA | -25.33 |
| CTAGCT | 90.83 | GTCATA | 24.99 | ACTTGA | -2.35 | TTGTGA | -25.35 |
| ATTTAT | 90.72 | AACCCT | 24.98 | TTGGTA | -2.35 | AGTTCG | -25.37 |
| CAGTTA | 90.71 | TTAATG | 24.97 | TAGAGA | -2.36 | AGCGGT | -25.47 |
| CATAGA | 90.61 | ACTTTT | 24.96 | GACATT | -2.38 | GCCCGA | -25.51 |
| ATACTG | 90.19 | ACGCAG | 24.82 | GGGAAC | -2.38 | CTGGGC | -25.54 |
| ATTACC | 90 | ATTTAA | 24.79 | TGACAA | -2.38 | TAGTGC | -25.55 |
| TATCAT | 89.91 | TGATTT | 24.76 | GTGCAG | -2.42 | TTGCCC | -25.57 |
| ACTATA | 89.16 | CTGATG | 24.75 | CGGCTC | -2.43 | TCTTGT | -25.63 |
| TACACA | 89.01 | ATCTTA | 24.75 | ATTGTT | -2.45 | TGCGCC | -25.65 |
| GCTGAA | 88.67 | TATGTA | 24.71 | ATGAGT | -2.46 | CGAGAG | -25.69 |
| CCATTA | 88.62 | GAAGAC | 24.69 | GGATGA | -2.48 | TATGTC | -25.72 |
| TGCTAT | 88.19 | TTACCT | 24.69 | GTTCTA | -2.49 | TGTCCT | -25.75 |
| TACATA | 88.12 | TAGATT | 24.68 | GTTAAA | -2.5 | AATCGG | -25.77 |
| CACCAA | 88.08 | ATAAGT | 24.67 | ATGTTC | -2.57 | TTTCCG | -25.78 |
| ATAGTT | 87.88 | CGGATA | 24.54 | CCTAGC | -2.61 | TATGTG | -25.8 |
| CACCTA | 87.77 | CTTTTA | 24.43 | CCCTAC | -2.61 | TGGGCA | -25.88 |
| GCACCA | 87.64 | ACCACG | 24.41 | AGAATG | -2.65 | GCTTGC | -26.03 |
| CTATCA | 87.58 | ACAGGA | 24.4 | CGAAGC | -2.7 | TCGACC | -26.05 |
| GCTATT | 87.58 | TATGGA | 24.4 | CGGTAA | -2.71 | TTAGCG | -26.06 |
| TATTAG | 87.34 | TTACTC | 24.37 | CTAATC | -2.72 | CCGTTC | -26.08 |
| CCACCT | 87.28 | GCAAAG | 24.34 | ACCTAA | -2.76 | CTAACG | -26.09 |
| AGAACC | 87.26 | GAGGCT | 24.32 | GCGCCA | -2.8 | GGCGAT | -26.11 |
| ACTACC | 87.25 | ATCATG | 24.24 | GTCCCA | -2.83 | GTTAGC | -26.11 |
| TATAAT | 87.06 | TGTTAT | 24.2 | CGAGCA | -2.88 | GTGGCA | -26.14 |
| ATTTCA | 86.86 | GCAAGA | 24.19 | TCAGGT | -2.9 | CCGGGA | -26.15 |
| TAGCAG | 86.76 | CTGGAA | 24.11 | AGAGTC | -2.92 | GCCTGG | -26.17 |
| AAGCTC | 86.67 | CTATTT | 24.06 | GAGGAC | -2.92 | CTTAGG | -26.18 |
| AACCAA | 86.61 | TCCATG | 24.06 | ACGAAA | -2.95 | AACGCG | -26.19 |
| AATATC | 86.37 | AGTGCT | 24.05 | AGGCAG | -2.97 | CGCGAA | -26.21 |
| TAGTAA | 86.29 | AGCGCC | 24.04 | GGACCT | -2.98 | ATCGTC | -26.24 |
| GCTGAT | 86.25 | CTGTAA | 24.03 | TCACTC | -3.01 | CTTGGG | -26.27 |
| TATATC | 86.21 | GAGCCT | 24.03 | GACTGG | -3.03 | GCACGC | -26.29 |

TABLE 3-continued

| 6-mer | 6-mer z-score | 6-mer | 6-mer z-score | 6-mer | 6-mer z-score | 6-mer | 6-mer z-score |
|---|---|---|---|---|---|---|---|
| TAATTA | 86.14 | ACCCAT | 24.03 | CTTGAG | -3.03 | GAGAGT | -26.3 |
| AACCAT | 86.06 | TGGAGC | 23.99 | CGAGCC | -3.07 | GCATGC | -26.3 |
| ATAGAC | 86.03 | ATGGAC | 23.95 | GGCTGT | -3.1 | ATCGTT | -26.33 |
| CCATCT | 85.84 | CAGCGG | 23.91 | GCCGCT | -3.11 | GAGGTG | -26.36 |
| TTATTA | 85.75 | TAAGAA | 23.9 | GGACAA | -3.11 | TTAACG | -26.36 |
| TCAGCC | 85.73 | GCATTA | 23.88 | TACCCT | -3.12 | CTGCGG | -26.38 |
| ACATAC | 85.65 | AGTCAT | 23.86 | GTCAGC | -3.12 | ACGGGA | -26.47 |
| ACATAG | 85.6 | GGAACC | 23.86 | CTGTTC | -3.18 | GGCCTG | -26.49 |
| CACAAT | 85.55 | CCCTCA | 23.86 | CCGAAT | -3.21 | CCTGCG | -26.49 |
| GTAATA | 85.54 | AACCTA | 23.83 | AGAGCG | -3.21 | AGGGTA | -26.49 |
| GAAGCA | 85.45 | CTTACA | 23.77 | ATGGTG | -3.29 | GAACGT | -26.5 |
| TCATAT | 85.24 | GGTAAT | 23.77 | TCCTTT | -3.3 | TTTGGT | -26.53 |
| CAGCCC | 85.03 | GGAGCC | 23.69 | CATGAC | -3.31 | ACGGAG | -26.54 |
| ACCTAT | 84.68 | CCCACC | 23.65 | TAGACC | -3.31 | GGAGCG | -26.73 |
| AGCCAC | 84.68 | GGAGAT | 23.63 | GGACTC | -3.32 | CCGCCG | -26.75 |
| CAGTAA | 84.62 | GTAGTT | 23.62 | CCCTGC | -3.32 | CCTACG | -26.76 |
| CCAACA | 84.17 | CTGAGC | 23.61 | GGAAGG | -3.35 | GTAACG | -26.81 |
| AAAAGC | 84.12 | TTTCAC | 23.61 | GGTTCT | -3.38 | CCCGTA | -26.81 |
| AACTGC | 83.95 | CTGAGA | 23.59 | GCAATC | -3.41 | GCTTCG | -26.82 |
| CCAACT | 83.78 | CATAGG | 23.58 | AGTCTT | -3.46 | TAGTCG | -26.83 |
| ATCATT | 83.47 | TTTCAT | 23.55 | TACGGA | -3.49 | CGTCCA | -26.91 |
| AGAGCA | 83.38 | AAGTAT | 23.48 | CGCACT | -3.51 | TGAGTC | -27.01 |
| GATACT | 83.35 | AATTCC | 23.45 | GCCTGC | -3.57 | CTCTGG | -27.01 |
| CCACAG | 83.35 | TACATG | 23.39 | GGACCC | -3.57 | ATTGCG | -27.01 |
| ATAATT | 83.26 | GGAAAT | 23.35 | GCCTTT | -3.58 | CGATGG | -27.05 |
| TAAACA | 83.21 | TGACCT | 23.35 | TTTAGT | -3.6 | GCTAGG | -27.14 |
| ACATAT | 82.99 | CGCACA | 23.34 | GGTGCT | -3.6 | GGGAGT | -27.16 |
| GCTACT | 82.86 | TACGAC | 23.32 | CGACTC | -3.65 | ATGTCT | -27.2 |
| CAGTAT | 82.76 | ATTTTC | 23.32 | GGATAG | -3.69 | CTGGGT | -27.21 |
| ATCACA | 82.36 | CCTGAA | 23.3 | GGATGC | -3.7 | GGACGA | -27.23 |
| TCAACA | 82.34 | ACAGTG | 23.28 | ACTCTT | -3.73 | CGTTTC | -27.24 |
| AGCCCA | 82.25 | AATCGA | 23.28 | ATTGCC | -3.84 | ATGACG | -27.27 |
| AATTAT | 82.21 | ATCTCT | 23.2 | TGAACG | -3.84 | TTCGCT | -27.27 |
| ATCATC | 82.17 | GACATG | 23.19 | CTTTTT | -3.89 | AGGGTG | -27.33 |
| TGCTAC | 81.84 | AAGTAG | 23.18 | GAATGC | -3.91 | CTTCGG | -27.4 |
| GCTTCA | 81.55 | ATACCG | 23.16 | TATAGG | -3.92 | CGAAGT | -27.41 |
| CCACTA | 81.49 | GGCAGC | 23.07 | GTATAG | -3.93 | TTGCCT | -27.41 |
| GCTGCA | 81.44 | TCTACA | 23.02 | GAGCGC | -3.96 | GGATCG | -27.41 |

TABLE 3-continued

| 6-mer | 6-mer z-score | 6-mer | 6-mer z-score | 6-mer | 6-mer z-score | 6-mer | 6-mer z-score |
|---|---|---|---|---|---|---|---|
| TAGTTA | 80.97 | CTAAAA | 23 | ATTGTG | -3.97 | AGGCGC | -27.45 |
| AATCAA | 80.92 | ACACGC | 23 | TCAGAG | -3.97 | GGGTTA | -27.47 |
| CAATTA | 80.84 | ACCCTG | 22.98 | GGGATC | -3.98 | ACGCGC | -27.48 |
| CTGCTA | 80.71 | TGAAAG | 22.87 | CCGCCA | -4 | TTGTCA | -27.57 |
| ATATAG | 80.66 | CACATG | 22.71 | TGTCCA | -4.01 | TAGTGT | -27.58 |
| TGCACC | 80.52 | CCTGTA | 22.67 | TGTTCT | -4.03 | GAGGTT | -27.6 |
| AAGACA | 80.5 | TGGTAA | 22.66 | AGGCCA | -4.04 | TGTCTC | -27.6 |
| TAATAG | 80.31 | CAGAGT | 22.64 | CCTTAC | -4.05 | GTGATG | -27.65 |
| TGCAGC | 80.23 | CCGCTA | 22.64 | TTTTCT | -4.07 | GGTCCT | -27.65 |
| CCTCCA | 80.17 | GGAATC | 22.63 | CATCGA | -4.09 | CGGACC | -27.65 |
| GATGCA | 80.15 | TTCAAT | 22.52 | AGCGAA | -4.12 | TCGCTT | -27.66 |
| AACTCC | 80.09 | CTGCTT | 22.49 | AAAGGG | -4.12 | TCGGAA | -27.69 |
| TCCAGC | 80.02 | CCTATT | 22.49 | GGGAGA | -4.13 | ACGTCA | -27.74 |
| ACACTG | 79.79 | GGTGCA | 22.48 | CTGAGT | -4.13 | TTCCCG | -27.84 |
| TATAAC | 79.77 | CAGGAG | 22.48 | GAAGTC | -4.15 | GCACGT | -27.87 |
| TTATAA | 79.58 | CCCCAC | 22.46 | CGTAGC | -4.16 | GTCGCA | -27.88 |
| CAACAA | 79.5 | AGGCTC | 22.43 | CGGCAC | -4.18 | CGTTAA | -27.93 |
| GCTAAT | 79.35 | CTAACT | 22.4 | TGCGAA | -4.19 | ACCTCG | -27.95 |
| TGATAC | 79 | CCAAGC | 22.4 | TCTTTT | -4.21 | TGGGAG | -27.96 |
| AGATCT | 78.63 | GCAGAC | 22.36 | ACGGAA | -4.22 | CTGTGT | -27.97 |
| ATAACC | 78.57 | CCAGGT | 22.36 | CCGACT | -4.25 | TAGCGT | -28.06 |
| AGAAAC | 78.2 | ACTGTT | 22.3 | ACCTGT | -4.26 | AGGACG | -28.08 |
| ATTGCA | 78.18 | ACCCTC | 22.25 | ATCGTA | -4.29 | GGCCTC | -28.1 |
| AACACC | 78.06 | CTATGC | 22.23 | TATGGT | -4.29 | AGTACG | -28.14 |
| TGCATT | 78 | TCTAAT | 22.15 | TAATCG | -4.31 | TAAGCG | -28.21 |
| CAACTC | 77.9 | TGGAAA | 22.14 | CGATTC | -4.32 | CTGCGT | -28.23 |
| GTACTA | 77.86 | CAGTTT | 22.08 | GGGAGC | -4.38 | TGTGTT | -28.25 |
| ACTCCA | 77.83 | TAATTC | 22.08 | CTCTAC | -4.38 | GGGTAA | -28.26 |
| CAGATG | 77.71 | TCACTT | 22.06 | CGTACA | -4.41 | TTTTCG | -28.33 |
| TGCAGA | 77.69 | TTTTTA | 22.01 | CAAGTT | -4.42 | GCGTTT | -28.33 |
| AAGAAA | 77.67 | CCTTCC | 21.92 | TAAGGC | -4.46 | TCTCGG | -28.34 |
| TCCACC | 77.66 | ATCGAT | 21.89 | AAGCGA | -4.46 | GCGGAC | -28.36 |
| TAACCA | 77.39 | AAAATG | 21.87 | GGTACC | -4.48 | CGACTT | -28.38 |
| TAACAG | 77.34 | GCACAA | 21.78 | GACAGT | -4.49 | CGACGA | -28.4 |
| TTATAT | 77.04 | TGCACT | 21.71 | CCGCAA | -4.53 | GTTAGT | -28.44 |
| TCTATT | 76.92 | AAGACC | 21.69 | GCTAAC | -4.61 | CCTCGC | -28.53 |
| ACACTA | 76.75 | AATTGA | 21.68 | TCCCTA | -4.62 | TTGCGA | -28.62 |
| CACTAA | 76.68 | GCATCC | 21.65 | CAGGTG | -4.63 | GTCGCT | -28.65 |

TABLE 3-continued

| 6-mer | 6-mer z-score | 6-mer | 6-mer z-score | 6-mer | 6-mer z-score | 6-mer | 6-mer z-score |
|---|---|---|---|---|---|---|---|
| GTAGCA | 76.59 | CACTGT | 21.65 | CAATGG | -4.64 | GTTCTG | -28.7 |
| AGCCAT | 76.52 | GAAAAA | 21.64 | TAGTCA | -4.67 | CGCGGA | -28.75 |
| TCATCT | 76.5 | GCTCAG | 21.6 | TAGACG | -4.67 | GACGTA | -28.8 |
| CACTAT | 76.28 | AACACG | 21.59 | CGTGAA | -4.7 | ATGTGT | -28.81 |
| CAATAT | 76.05 | GTTGCA | 21.57 | AGACGA | -4.7 | CCGCGT | -28.84 |
| CACAGA | 76.03 | GCCCCA | 21.54 | AAGCGT | -4.74 | TTAGGC | -28.88 |
| AGTTAC | 75.97 | GACTAT | 21.53 | TGGGAT | -4.81 | CTTTGG | -28.94 |
| ATACTC | 75.91 | GACCAG | 21.52 | CCGAAG | -4.83 | TACCGG | -29 |
| TATATG | 75.77 | GTTCAT | 21.39 | CGAAAA | -4.87 | GTAAGT | -29.01 |
| CACTAC | 75.68 | GAGAAT | 21.24 | AGCCCG | -4.93 | ACGAGG | -29.02 |
| ATTTCT | 75.56 | TAAAAG | 21.2 | GGCTGG | -4.96 | ACGTAG | -29.02 |
| TACCAA | 75.44 | GAATTT | 21.15 | GTCACT | -4.99 | TGGCTC | -29.02 |
| GCAATA | 75.24 | CACCGT | 21.13 | CAACGA | -4.99 | GCTTGG | -29.05 |
| ATCTCA | 74.72 | GATTAT | 21.11 | TGACCC | -5 | ACGTTA | -29.06 |
| ACAGAT | 74.63 | TTTCAA | 21.05 | GCCGCA | -5.04 | AGGAGG | -29.07 |
| TCACCT | 74.58 | ATCCTC | 21.03 | GTTCAA | -5.06 | TGACGG | -29.11 |
| CATCAG | 74.49 | CTGGAT | 21 | TCGCTG | -5.07 | CCACGT | -29.16 |
| TCAGAT | 74.33 | CCTATA | 20.97 | GTGAAC | -5.11 | CGTATG | -29.17 |
| AGTAAC | 74.08 | ATAGGA | 20.97 | CCTTAG | -5.16 | CGGGCA | -29.21 |
| CTACAC | 73.7 | TAGGTA | 20.96 | ATAGGG | -5.17 | AACGGG | -29.25 |
| AATGAT | 73.53 | GGATTT | 20.93 | CAGTGC | -5.18 | CTCCGG | -29.27 |
| ATTAGT | 73.5 | ACTCAC | 20.88 | AGGCGA | -5.2 | GGGCCA | -29.28 |
| TAGTAC | 73.49 | CGACTA | 20.85 | CGAACC | -5.2 | CGTACC | -29.28 |
| TAACTG | 73.35 | GGATCA | 20.8 | ACTCCG | -5.21 | CCGTAC | -29.41 |
| AAAATA | 73.29 | CTACCC | 20.78 | CTCCTC | -5.24 | CGTACT | -29.46 |
| AAAACT | 73.19 | ACTTAC | 20.74 | GGTCCA | -5.25 | CTGTCT | -29.48 |
| ATTTAC | 72.97 | GATAAC | 20.71 | AAATTG | -5.27 | TGCCTG | -29.64 |
| ATCTGA | 72.97 | GATCCC | 20.66 | CAAGTC | -5.27 | CTGTGG | -29.64 |
| ATCCAT | 72.95 | TACGCA | 20.62 | TACCCG | -5.28 | TGGTTG | -29.7 |
| ATACCC | 72.75 | GCCACC | 20.56 | CTTTCC | -5.29 | GGTTGA | -29.72 |
| AACTTC | 72.62 | AGACTC | 20.56 | GCACTC | -5.29 | GAGGGC | -29.76 |
| AATACG | 72.39 | GACTCA | 20.5 | TTGGCA | -5.3 | TTCGGC | -29.83 |
| AAATCA | 72.22 | CCTTAT | 20.39 | ACTTGC | -5.32 | GGTTGC | -29.89 |
| TTCACA | 72.18 | TAGGAT | 20.38 | AGTCCC | -5.32 | TCTGGT | -29.9 |
| CAGATT | 72.08 | AACATT | 20.37 | TGGCAC | -5.33 | CCTCGG | -29.96 |
| CAGAAA | 71.97 | ATGCTC | 20.32 | GTGGAA | -5.33 | GTTGAC | -30 |
| ACACAT | 71.91 | ACTCTA | 20.3 | GGCCAT | -5.36 | TTGACG | -30.03 |
| AAGATA | 71.91 | CTGCCA | 20.29 | GCGGAT | -5.39 | AACGTT | -30.07 |

TABLE 3-continued

| 6-mer | 6-mer z-score | 6-mer | 6-mer z-score | 6-mer | 6-mer z-score | 6-mer | 6-mer z-score |
|---|---|---|---|---|---|---|---|
| CTGCAG | 71.63 | TGGCTA | 20.29 | GCGCAT | -5.4 | CCGACC | -30.12 |
| GCAACT | 71.57 | AGTCCA | 20.26 | GGGGAA | -5.4 | GGGTTT | -30.13 |
| GATATT | 71.57 | CAGTCA | 20.24 | TCTAGA | -5.4 | GTCTAC | -30.13 |
| AGATTC | 71.53 | TTCCAA | 20.24 | ACTTGG | -5.44 | ACGACG | -30.19 |
| ACCAGA | 71.47 | GACATA | 20.22 | TGCGAT | -5.45 | CGGGCT | -30.2 |
| CTATAT | 71.38 | TCTATC | 20.15 | GCGATA | -5.45 | GTAGAG | -30.23 |
| TGATAT | 71.06 | TCCTGA | 20.13 | TGCCCA | -5.45 | GGAACG | -30.3 |
| AAGAGC | 70.89 | ATGGCA | 20.05 | TGGCTT | -5.48 | GTCTTA | -30.3 |
| ATACGC | 70.65 | GTAGCC | 20.05 | AGAGAG | -5.48 | GCTGGC | -30.31 |
| CTGATA | 70.47 | CCTGGA | 20 | TTGCTT | -5.51 | CGTGCT | -30.39 |
| GATAAA | 70.39 | CTTAGA | 20 | AATGTG | -5.57 | CTACGT | -30.41 |
| ACATCC | 70.36 | AACGCT | 19.94 | TTACGG | -5.57 | CTTTCG | -30.42 |
| AAACTA | 70.26 | CGCTAC | 19.9 | AAGGTC | -5.59 | TGTCCC | -30.46 |
| ATCAAT | 70.13 | CTGTAG | 19.87 | TGAGAC | -5.62 | CGGTAG | -30.52 |
| GAAACA | 70.11 | CACTCA | 19.87 | GACTGT | -5.69 | TCTGCG | -30.54 |
| CATCAT | 70.01 | CTTCTA | 19.83 | TTAGTG | -5.71 | TCGATG | -30.54 |
| AGCTTG | 70.01 | TCCTTC | 19.8 | CATTGG | -5.71 | TCGGAC | -30.58 |
| TGAGCT | 69.96 | CAAGTA | 19.73 | CAGGTC | -5.73 | TCCGGC | -30.61 |
| CTATAA | 69.96 | ATCAGG | 19.71 | TCCCTT | -5.8 | TTCGAG | -30.64 |
| ATTCAT | 69.85 | TATTGG | 19.66 | CGAATT | -5.82 | CCCTCG | -30.66 |
| TACTGC | 69.83 | AGTTCC | 19.66 | AATGTT | -5.82 | CCGCGA | -30.67 |
| CAGAGA | 69.69 | ACACTC | 19.6 | GGCAAT | -5.83 | ACGTGC | -30.67 |
| CATTTA | 69.68 | AATTTA | 19.59 | TAGGAC | -5.91 | GGCCTA | -30.68 |
| AGCTGG | 69.06 | ACATTG | 19.58 | TACGGC | -5.94 | CCGGAC | -30.7 |
| GAATCA | 68.99 | GAAATC | 19.45 | TCTTCT | -5.95 | GCGTAA | -30.77 |
| TTATTT | 68.98 | TGAAGT | 19.45 | GGGCTC | -5.97 | GTCCTC | -30.77 |
| ATCTGC | 68.96 | GTACAT | 19.44 | TCGCAT | -5.98 | TTCGGA | -30.82 |
| TAGCAC | 68.84 | CTTTAA | 19.44 | CTAGGC | -5.98 | CCCCGC | -30.82 |
| ATGCTA | 68.58 | CATTGA | 19.38 | CCTTTT | -5.99 | AGCGCG | -30.84 |
| TATACT | 68.54 | GGCTTC | 19.38 | CCAGTG | -6 | CTCGCC | -30.85 |
| TCATCA | 68.5 | CACGAA | 19.33 | CACGAG | -6.01 | GGCTAG | -30.87 |
| AGATGC | 68.48 | TATCCT | 19.28 | TCCTAA | -6.03 | CTTACG | -30.96 |
| ATAGCG | 68.46 | ATGGAG | 19.27 | TAGGCA | -6.08 | GATGTC | -30.96 |
| CATACT | 68.15 | AATAGG | 19.25 | TCTAAC | -6.1 | GGACGC | -30.98 |
| TAGCAT | 68.15 | GTATAA | 19.24 | CACCCG | -6.13 | ACGTCT | -30.99 |
| TACAAA | 68.02 | AATAAG | 19.23 | CTACGG | -6.14 | TGTCAG | -31 |
| TACCTA | 67.99 | GGATTC | 19.19 | AGGTGC | -6.16 | ACGCGA | -31.01 |
| CATCTT | 67.88 | TCTATG | 19.13 | CCCATG | -6.17 | GTTCGA | -31.06 |

TABLE 3-continued

| 6-mer | 6-mer z-score | 6-mer | 6-mer z-score | 6-mer | 6-mer z-score | 6-mer | 6-mer z-score |
|---|---|---|---|---|---|---|---|
| ATCAAC | 67.83 | ACCCTT | 19.09 | ACGCCC | -6.17 | TTGAGG | -31.08 |
| ACCTTC | 67.82 | ACTTTA | 19.01 | CGATCC | -6.18 | TCGTAC | -31.09 |
| TTAGCA | 67.82 | CCAATC | 19 | GAAACG | -6.2 | TTAGGG | -31.1 |
| AGTAGC | 67.72 | TCTGTA | 18.99 | ATGTGC | -6.21 | TGCCGC | -31.12 |
| TTGCTA | 67.61 | GCTCTA | 18.93 | GCAAGC | -6.24 | TAGGCC | -31.12 |
| TAAGCA | 67.57 | GATCTT | 18.92 | AAATCG | -6.25 | CCCGGG | -31.15 |
| AATATG | 67.49 | GGATTA | 18.85 | CCTCTC | -6.29 | CGACCT | -31.16 |
| TCACTA | 67.42 | CGTATA | 18.83 | ACCGGC | -6.31 | CGAGTC | -31.3 |
| CATTAA | 67.2 | ACGAAC | 18.75 | TTTAGA | -6.33 | TCTGAC | -31.36 |
| AGCAAA | 67.17 | ATTCTT | 18.75 | CGACTG | -6.33 | GTCCCT | -31.46 |
| GGCTAT | 67.15 | AGGTCA | 18.72 | AGGCAA | -6.33 | TCTGGG | -31.48 |
| ATGCAA | 67.06 | TAGAAA | 18.72 | GGACAC | -6.35 | CGCGTA | -31.55 |
| ACACCC | 67.05 | CGTAAT | 18.7 | TAGCCC | -6.37 | TGAGGG | -31.55 |
| GCAGTA | 67.04 | GTACAG | 18.63 | TCTGGA | -6.37 | CGGGGA | -31.59 |
| AGTAAA | 67 | ATGTAA | 18.6 | TAAAGT | -6.37 | CGACGC | -31.63 |
| TTCACC | 66.71 | TTCATG | 18.6 | TGAGTT | -6.37 | TGAGGT | -31.63 |
| GATACC | 66.69 | AGTTTC | 18.56 | AAACCG | -6.45 | TTTGGC | -31.64 |
| CTACAA | 66.54 | TAGTTG | 18.52 | ACCCGG | -6.51 | CGTCAG | -31.68 |
| CTGAAA | 66.27 | TGGACA | 18.5 | CCTGAC | -6.51 | GATGTG | -31.69 |
| ATGTAT | 66.24 | ATTTGC | 18.49 | AAATTT | -6.52 | TGGCGA | -31.75 |
| CACCTT | 66.08 | CACCGC | 18.45 | AACTCG | -6.52 | GTGAGC | -31.75 |
| ACCCAG | 65.77 | CTCTAT | 18.44 | AAGGGC | -6.52 | GTCGTA | -31.76 |
| ATATCC | 65.64 | CAATCT | 18.42 | TTTTGC | -6.54 | TCTGGC | -31.78 |
| CAAAGC | 65.58 | GAGAAG | 18.39 | GGAAGT | -6.61 | GTGTCT | -31.81 |
| ACAGTA | 65.5 | ACATTC | 18.38 | GGTTAC | -6.66 | GCGTCA | -31.86 |
| CATACC | 65.47 | ATTTGA | 18.37 | TCGTAT | -6.68 | GCGCCT | -31.88 |
| TGAATT | 65.43 | TTGCAA | 18.35 | GTTCTC | -6.7 | CCTGTG | -31.89 |
| TATTCA | 65.2 | AAGATT | 18.34 | GGAAAG | -6.72 | AGTCGT | -31.89 |
| GATATC | 65.15 | AAAGGA | 18.34 | TCCTTG | -6.72 | TCGGTA | -31.95 |
| ACAAAT | 65.04 | ATTGTA | 18.33 | GCGAAT | -6.75 | CCGGTT | -31.95 |
| CCATTT | 64.91 | TTAAAA | 18.28 | AGTCTC | -6.77 | CGCGCT | -31.96 |
| AAAAAC | 64.81 | ATATCG | 18.27 | GGCACT | -6.8 | CTTGGT | -31.98 |
| GCTCCA | 64.64 | ATAGTG | 18.25 | GCTCTG | -6.8 | TTACGT | -32.02 |
| AAGCCA | 64.61 | GAGACT | 18.19 | CTACCT | -6.8 | GTGTAC | -32.06 |
| CCTTCA | 64.45 | GCTTAA | 18.18 | TTGACA | -6.81 | CGCTTG | -32.07 |
| GAGCTT | 64.45 | TGATTA | 18.16 | AGCGTA | -6.81 | CCGACG | -32.12 |
| ATAGAA | 64.31 | GGATCC | 18.16 | AGCGTT | -6.83 | CCGTGT | -32.13 |
| TGAAGC | 64.22 | AGCACG | 18.12 | TCGCAG | -6.85 | GTATCG | -32.13 |

TABLE 3-continued

| 6-mer | 6-mer z-score | 6-mer | 6-mer z-score | 6-mer | 6-mer z-score | 6-mer | 6-mer z-score |
|---|---|---|---|---|---|---|---|
| GAACCA | 64.2 | AACCGC | 18.1 | CGAAAT | -6.88 | TTAGTC | -32.13 |
| ACAGAC | 64.16 | TTGCTG | 18.05 | GCCCTT | -6.9 | TCGGCC | -32.14 |
| ACAGAG | 64.14 | CCAAGG | 17.94 | CATCGT | -6.91 | CATGCG | -32.19 |
| TGTATA | 64 | AGGCTT | 17.91 | AATTAG | -7 | GTCAGA | -32.21 |
| TGAACC | 63.94 | CGCAAA | 17.91 | GACGAT | -7 | ACGTTG | -32.23 |
| TTATCA | 63.94 | CCGATA | 17.87 | AACCGG | -7.03 | CGCATG | -32.23 |
| AACAGA | 63.94 | TCAAAT | 17.85 | TTGCCA | -7.04 | TCCTGT | -32.37 |
| GATTCA | 63.93 | CCGAGA | 17.85 | CTAGCC | -7.1 | GCGAGC | -32.37 |
| ATGAAT | 63.83 | GCCATT | 17.84 | CACGGT | -7.11 | ACGTGT | -32.41 |
| GCTGCT | 63.71 | GCCATA | 17.82 | CTCTTC | -7.13 | ATGCGG | -32.41 |
| CACACA | 63.58 | GCACTA | 17.75 | AACGCC | -7.15 | TGGTCC | -32.44 |
| GCAGCC | 63.54 | ACTCTG | 17.67 | GTTATG | -7.15 | ATGGGT | -32.58 |
| TAGCCA | 63.4 | AGTAAG | 17.64 | ACTGTG | -7.15 | CGTCTC | -32.61 |
| GAGCTC | 63.35 | CGCTCA | 17.58 | TAATGT | -7.16 | TGTGCC | -32.64 |
| AACTCA | 63.19 | TATCCC | 17.54 | CCAACG | -7.21 | CTTGTC | -32.65 |
| GTATCA | 63.01 | AACTCT | 17.47 | GCCTTG | -7.21 | GGCGGA | -32.72 |
| CATAAT | 62.96 | TCCACG | 17.46 | CCTTGT | -7.23 | GTCTGA | -32.74 |
| TCCACA | 62.68 | GGAGAC | 17.43 | TTCTGC | -7.23 | CTGGTC | -32.79 |
| CAGAAG | 62.65 | CTTGAA | 17.42 | TAAGAC | -7.23 | GGGGGA | -32.83 |
| CCCAGC | 62.57 | TCTCAT | 17.31 | GCTGTG | -7.24 | AGGGTC | -32.86 |
| CGCTAT | 62.55 | TAGCGA | 17.31 | CCCCTC | -7.25 | TAGTCC | -32.91 |
| CCTACT | 62.52 | CTAAAG | 17.28 | GACTAA | -7.25 | CGGGTA | -32.94 |
| CAATAC | 62.45 | CACTCC | 17.24 | CGCTCC | -7.27 | GCGTTA | -32.98 |
| CAACTT | 62.28 | CCGTAT | 17.21 | GCGACT | -7.27 | GACCGT | -33 |
| AGAATC | 62.21 | GAGAAA | 17.2 | TTCCCT | -7.28 | GATCGT | -33.15 |
| GAGCAC | 62.17 | AACTTT | 17.19 | CGCCCA | -7.29 | ATCGGT | -33.22 |
| TCTGCA | 62.09 | CACTCT | 17.18 | TGCGCT | -7.33 | CACGGG | -33.24 |
| CAATCC | 61.99 | GACTCC | 17.16 | CCCCCC | -7.34 | GACGTT | -33.25 |
| AGAATT | 61.72 | GCACCC | 17.12 | TTAGAG | -7.34 | CACGCG | -33.27 |
| CATTAC | 61.65 | TTATCT | 17.12 | CCTGTT | -7.36 | GGTAAG | -33.36 |
| ACTGCT | 61.63 | TAGCCT | 17.07 | TCTTCC | -7.38 | GTCGAT | -3.37 |
| AACACT | 61.62 | CCTACC | 16.97 | CCATCG | -7.38 | GATGCG | -33.38 |
| GTAACA | 61.62 | TAAGAT | 16.95 | TCTAAA | -7.39 | GGACCG | -33.38 |
| TATCAG | 61.58 | GCAATG | 16.95 | CTAATT | -7.42 | GCCCCG | -33.46 |
| ATGAAC | 61.56 | GGTAAA | 16.95 | AAGCGC | -7.42 | GCGGGA | -33.56 |
| CAACAT | 61.55 | AAAATT | 16.92 | CTCTGT | -7.48 | GGTCCC | -33.6 |
| TCAATA | 61.47 | AACGGC | 16.9 | AGGCCT | -7.48 | GTATGG | -33.62 |
| TGCATC | 61.37 | CTATCT | 16.81 | TAGGAA | -7.51 | CCCGTT | -33.63 |

TABLE 3-continued

| 6-mer | 6-mer z-score | 6-mer | 6-mer z-score | 6-mer | 6-mer z-score | 6-mer | 6-mer z-score |
|---|---|---|---|---|---|---|---|
| GCACAG | 61.24 | TATCTC | 16.81 | GTTCTT | -7.54 | CGCGAT | -33.69 |
| AGAGCC | 61.12 | GCTCCC | 16.8 | GTATTC | -7.63 | CCGTGC | -33.75 |
| AGTATA | 61.1 | CTGACA | 16.79 | ACGAGA | -7.68 | GACGGT | -33.89 |
| GTAGAT | 60.86 | CATGGC | 16.78 | ATGTTT | -7.68 | CGACCG | -33.91 |
| TACACT | 60.8 | GACCTC | 16.77 | GGGTAT | -7.76 | CCTGTC | -33.96 |
| TATCCA | 60.75 | CCTTGA | 16.76 | ACTAGG | -7.77 | GTAGTG | -34.01 |
| AGCATT | 60.65 | CTCATC | 16.72 | CGGAAA | -7.79 | GGGTCA | -34.05 |
| ATTAAA | 60.65 | CACGGA | 16.69 | ATGGCC | -7.82 | TAGGGC | -34.19 |
| ACAAGC | 60.61 | CTATGT | 16.65 | GTTATC | -7.85 | GTTACG | -34.32 |
| ACTGAT | 60.54 | TAGAAG | 16.62 | TCGACT | -7.87 | AGGTAG | -34.33 |
| CAACAG | 60.42 | CATAAG | 16.58 | CTTCTT | -7.9 | GGCCGC | -34.45 |
| ATGCTG | 60.37 | GGAAGC | 16.58 | AACGAT | -7.91 | GCGGCC | -34.5 |
| TATCAA | 60.3 | CGCAGA | 16.48 | GATCGA | -7.94 | GCCTCG | -34.53 |
| AGTTGA | 60.16 | AACGCA | 16.48 | CTCTAG | -8 | CGAACG | -34.71 |
| TTTACT | 60.02 | CGAAGA | 16.41 | CTAACC | -8.08 | GTCGAA | -34.72 |
| CTTCAC | 59.96 | TAACCT | 16.4 | CTAGGA | -8.08 | CGTCCC | -34.81 |
| GAAGAT | 59.8 | CTGATT | 16.33 | GATTGT | -8.1 | CTAAGT | -4.82 |
| CATCTG | 59.68 | CAGGCA | 16.28 | CCCGCA | -8.1 | CCGGTA | -34.83 |
| ATCCCA | 59.65 | GAAAAG | 16.25 | CGAGTA | -8.11 | GTCTGC | -34.87 |
| CAACAC | 59.49 | CCCAAC | 16.24 | TGGGCT | -8.15 | TCGTGA | -34.87 |
| AACATC | 59.39 | TAGTGA | 16.23 | GGCTTA | -8.19 | CGGAGT | -4.91 |
| AAGCAG | 59.37 | TTGCAG | 16.2 | TCGGCT | -8.24 | GGGTAC | -34.91 |
| CATCAC | 59.3 | TGAAGG | 16.18 | GATGGC | -8.25 | GTGGAC | -34.93 |
| ACTAGC | 59.24 | TTTGAA | 16.15 | ACGCAT | -8.3 | ACGGTC | -34.94 |
| ACAACA | 59.21 | TACCTT | 16.14 | CCGCTT | -8.3 | CTCGTA | -34.95 |
| CATAAC | 59.02 | GCACAC | 16.12 | TGGCTG | -8.32 | TCGAGT | -35 |
| TATTTC | 58.98 | ATGACC | 15.97 | ACTCTC | -8.35 | TCTGTG | -35 |
| CCATAA | 58.89 | TTAAGC | 15.91 | GCCCAC | -8.37 | GGTTGT | -35.09 |
| CACCCT | 58.6 | GTTGCT | 15.9 | CGCTGG | -8.37 | AGGGGT | -35.15 |
| ACACCG | 58.31 | CATGTA | 15.9 | TTGCTC | -8.38 | TACGTT | -35.18 |
| TACTAG | 58.31 | ACGACC | 15.86 | TGGTAG | -8.38 | TCGTCA | -35.34 |
| TGAATA | 58.12 | CAGGTT | 15.84 | CTCTGA | -8.49 | AAGTGT | -35.39 |
| ACAATC | 58.11 | AAAAGT | 15.82 | TACTCG | -8.59 | TGTAGG | -35.44 |
| AGGAGC | 58.09 | AGACCA | 15.79 | TGAGAG | -8.6 | GCGGTT | -35.48 |
| TGAGCA | 57.87 | GCTTGA | 15.71 | GCACCG | -8.61 | TACGTC | -35.52 |
| TATGAT | 57.78 | GATGTA | 15.67 | ATGGGA | -8.69 | TGTTGC | -35.56 |
| TATACC | 57.77 | TGACAT | 15.66 | TGACTG | -8.7 | TTGGTG | -35.57 |
| GATATG | 57.64 | TTCTCC | 15.65 | CGATTT | -8.72 | AGCGTG | -35.58 |

TABLE 3-continued

| 6-mer | 6-mer z-score | 6-mer | 6-mer z-score | 6-mer | 6-mer z-score | 6-mer | 6-mer z-score |
|---|---|---|---|---|---|---|---|
| TCTGCT | 57.47 | TTAGAA | 15.63 | CGGAGC | -8.74 | CTGGCG | -35.58 |
| AGTAGT | 57.38 | TTAGAT | 15.61 | CGGATC | -8.78 | TGTACG | -35.8 |
| ACCAAA | 57.17 | ATTTTA | 15.6 | AGTCAA | -8.79 | CGTCAT | -35.87 |
| TGTAAT | 57.16 | TTAAAT | 15.52 | TTCCTA | -8.79 | TCCTCG | -6.02 |
| CAGCGA | 57.12 | GGTACA | 15.49 | CCTAGG | -8.79 | GGGCCT | -36.04 |
| AAGCAT | 57.06 | CATCGC | 15.48 | GTTGGA | -8.82 | CTAGTC | -36.07 |
| GATGCT | 57.03 | GCCATC | 15.39 | AGTCTG | -8.83 | TGTTGG | -36.07 |
| CATTTC | 56.98 | AATTTT | 15.39 | CAAGGT | -8.85 | GTGGAG | -36.09 |
| AAGATG | 56.93 | TCAATC | 15.38 | AATTCG | -8.91 | GGCCGT | -36.15 |
| ATCCAG | 56.88 | ACCCAA | 15.38 | ATTCGC | -8.93 | GTTTGC | -36.17 |
| CATATG | 56.87 | CTGTTT | 15.36 | GAAAGT | -8.99 | CCCCGT | -36.18 |
| TGGATT | 56.83 | CCAGAG | 15.35 | CTAGAC | -9 | GTGGTT | -36.22 |
| TGCAAC | 56.76 | AGAAGG | 15.33 | AACGAA | -9.02 | CGCCCT | -36.23 |
| CACCTC | 56.75 | TCATTT | 15.32 | CGACAA | -9.03 | TCGCCC | -36.23 |
| CAGACT | 56.73 | CCAGTC | 15.26 | GCCTAG | -9.04 | GATCGG | -36.23 |
| ATGCAG | 56.72 | AGTAGG | 15.25 | AAGTGC | -9.06 | TGACCG | -36.25 |
| GTAACT | 56.7 | TGCAAG | 15.23 | GGTGTA | -9.06 | GGGTGA | -36.29 |
| AGTAGA | 56.45 | AGGATC | 15.22 | GATAGG | -9.08 | TTCCGT | -36.3 |
| TATGCA | 56.42 | GACAAC | 15.19 | TTTGCC | -9.1 | ATCGGG | -36.36 |
| GGAATA | 56.3 | TCCTCC | 15.19 | TTTAAG | -9.1 | TCCCGG | -36.42 |
| AGTATC | 56.23 | TCAATT | 15.18 | CCCCCT | -9.1 | TGGCCA | -36.53 |
| CATTAG | 56.19 | TCAAAA | 15.15 | CGATAG | -9.13 | GTGTAG | -36.53 |
| CAGTAC | 56.18 | CCTGAT | 15.13 | ATCCCG | -9.15 | ATGCGT | -36.65 |
| TACATC | 56.14 | ATCCGC | 15.08 | GTCACA | -9.21 | GCCCGC | -36.69 |
| AAAGCA | 56.13 | GACCTT | 15.07 | GTCCAG | -9.24 | TGGCGC | -36.74 |
| TCTCCA | 56.01 | TTATTC | 15.07 | CAAACG | -9.25 | GTGGGA | -36.74 |
| ACAGAA | 55.96 | GCTAAG | 15.01 | AGGCCC | -9.29 | TGTTCG | -36.88 |
| GGAGCA | 55.88 | CTCAAG | 14.96 | AGGGAC | -9.3 | TGGCCT | -36.92 |
| CAGCCG | 55.8 | CAGGCC | 14.89 | CTGACC | -9.3 | GGTCTA | -36.94 |
| CTGCAC | 55.6 | ATGTAC | 14.83 | GCTGCG | -9.34 | TGCGGC | -36.96 |
| AGCAGT | 55.46 | CTTCTG | 14.71 | TTTCTC | -9.36 | CGTGAC | -37 |
| CACATA | 55.45 | AGACAT | 14.69 | CGACAG | -9.37 | TAACGT | -37.18 |
| TATCTG | 55.37 | TAAGTA | 14.61 | TGAGGA | -9.41 | TCGTTT | -37.19 |
| TACTCA | 55.36 | TTGAAG | 14.6 | CCAGGG | -9.43 | CGCTAG | -37.2 |
| CTTATA | 55.34 | ATGTTA | 14.54 | AGTCTA | -9.43 | CGGCCG | -37.2 |
| GACACA | 55.17 | TGGAAC | 14.52 | GCCGAA | -9.48 | CTTGCG | -37.21 |
| TGTATT | 55.14 | GGCTCC | 14.47 | TCCCTC | -9.49 | AGGCGG | -37.21 |
| GAATCT | 55.12 | ATAAGG | 14.45 | AAGTCT | -9.51 | CGTTGA | -37.28 |

TABLE 3-continued

| 6-mer | 6-mer z-score | 6-mer | 6-mer z-score | 6-mer | 6-mer z-score | 6-mer | 6-mer z-score |
|---|---|---|---|---|---|---|---|
| AACAGT | 55.1 | CTTATT | 14.45 | AGGGCC | -9.52 | TGTTTG | -37.33 |
| ATCAGA | 55.06 | ATCCTG | 14.42 | GCAGTC | -9.54 | GTAAGG | -37.38 |
| GCATCT | 54.8 | TGTTTA | 14.41 | ATGTTG | -9.55 | CGGACG | -37.41 |
| AACTAA | 54.79 | TGAGAA | 14.39 | GTAAAC | -9.56 | CGCCGT | -37.43 |
| CAGCGC | 54.76 | CACGCC | 14.39 | GAGTTT | -9.58 | CGGAGG | -37.44 |
| ACACAA | 54.74 | CCATGT | 14.39 | ATGCGC | -9.6 | CGTTCC | -37.45 |
| TAACAA | 54.73 | ACGCTG | 14.36 | CTCCCT | -9.65 | TGCGAG | -37.46 |
| TGCATA | 54.73 | TCCAGT | 14.34 | TTTTGG | -9.67 | GTTGGT | -37.56 |
| TTACAG | 54.68 | CTACAT | 14.31 | GTCAAT | -9.69 | TTTGTC | -37.57 |
| GAAGCC | 54.6 | AGTGCA | 14.28 | TAGGAG | -9.7 | GAGGGT | -37.59 |
| AAGAAC | 54.37 | AATCTT | 14.25 | CTTCGA | -9.71 | TAAGTC | -37.59 |
| TTACTG | 54.36 | GGCTCA | 14.24 | AGTTTA | -9.73 | GGCTCG | -37.63 |
| GTTTAT | 54.25 | CCCTAT | 14.21 | GTAAAG | -9.78 | GACGCG | -37.63 |
| ACCAGT | 54.25 | CCAGGC | 14.21 | CGCCAC | -9.81 | GGGTCT | -37.66 |
| AATCCT | 54.22 | CTGGAG | 14.2 | GACAGG | -9.82 | TCGCTC | -37.67 |
| ACAAAG | 54.18 | ACCCGC | 14.16 | AGGAAG | -9.83 | TCTCGC | -37.72 |
| TCACAG | 54.18 | GGTATA | 14.14 | ACGTAT | -9.85 | TTTGTG | -37.74 |
| ACTATG | 54.15 | GACTTC | 14.11 | GAACGC | -9.88 | ATCGCG | -37.75 |
| GATGAT | 54.08 | AAGAGA | 14.08 | AAGAGT | -9.91 | GGGGTT | -37.76 |
| TGCAAT | 54.03 | GCTTCC | 14 | CACTTG | -9.92 | GTCACG | -37.82 |
| GTAATT | 53.95 | AGCGCT | 14 | GCGATT | -9.92 | GGTCTT | -37.95 |
| TTAGTA | 53.95 | AGACTT | 13.99 | CGCCAA | -9.93 | CCCGTC | -37.96 |
| CATGAA | 53.93 | AAACGC | 13.99 | GCTTAC | -9.94 | CTAGCG | -37.99 |
| CATCTC | 53.89 | TCACCG | 13.98 | TGACTT | -9.94 | CGCACG | -38.02 |
| AGCCTC | 53.8 | CACGCA | 13.93 | CATGTT | -9.95 | TTAGGT | -38.03 |
| CACATT | 53.79 | CCCAGG | 13.91 | TGATTG | -9.97 | CGGGAG | -38.06 |
| AATTAA | 53.78 | CTCTGC | 13.88 | TCACGG | -9.98 | GTTTAG | -38.11 |
| GCACAT | 53.76 | CGAGAA | 13.83 | TCGAAT | -9.98 | GCCCGT | -38.11 |
| ATTGAT | 53.75 | TATAGA | 13.82 | CTCTTG | -10.02 | GTCCGA | -38.11 |
| AAAACC | 53.75 | AAAGCG | 13.82 | GTGATT | -10.03 | AGTGAG | -38.2 |
| TACCAG | 53.61 | GAGTAA | 13.8 | GAACGA | -10.03 | CTTGTG | -38.23 |
| ACTAGT | 53.57 | GATTGA | 13.77 | TGTTCC | -10.05 | TCGAGG | -38.24 |
| AAAGAT | 53.54 | TTGAAA | 13.74 | TGTTTC | -10.07 | TTGGCC | -38.25 |
| CTCCAA | 53.42 | TAATTT | 13.71 | TCTTAT | -10.08 | AGTCCG | -38.38 |
| CACACT | 53.37 | AGTTGT | 13.57 | GAGACG | -10.09 | CGGTTT | -38.45 |
| CCACAA | 53.24 | GGAGTA | 13.54 | CGGTTA | -10.12 | TGCGTT | -38.48 |
| TACAAT | 53.13 | TAAACG | 13.52 | GCATGT | -10.13 | CGTGAT | -38.53 |
| CTATTG | 53.01 | CCGCTG | 13.48 | GGATGT | -10.15 | GCGTTC | -38.53 |

TABLE 3-continued

| 6-mer | 6-mer z-score | 6-mer | 6-mer z-score | 6-mer | 6-mer z-score | 6-mer | 6-mer z-score |
|---|---|---|---|---|---|---|---|
| TAGTAG | 52.94 | GGCTGC | 13.46 | CCTTGG | -10.18 | TTGGGG | -38.54 |
| GATCAT | 52.84 | GGTACT | 13.42 | GAATCG | -10.2 | GGTTTG | -38.55 |
| AATCAT | 52.81 | GTGCAA | 13.36 | GGGCTG | -10.21 | CGGTAC | -38.57 |
| ATTCAG | 52.71 | TCTGAA | 13.23 | TAGAGT | -10.25 | TGGCCC | -38.57 |
| AGTACC | 52.64 | TCCAGG | 13.15 | TAGCGG | -10.25 | GCTCGC | -38.62 |
| AAAAAT | 52.58 | CTTTAC | 13.11 | GCAGTG | -10.25 | ACGCGT | -38.63 |
| CAGAAC | 52.37 | GGAAAA | 13.07 | GTCCAC | -10.28 | TGTGAC | -38.71 |
| ACAGTT | 52.35 | ATCCTT | 13.06 | GAGTAC | -10.33 | GACCGG | -38.72 |
| TGAAAT | 52.33 | GAAGGT | 13.04 | CCACCG | -10.36 | GCGCCC | -38.73 |
| GAGATC | 52.3 | GATTAA | 13 | CGACAT | -10.37 | ACCGGG | -38.81 |
| CATTCA | 52.24 | CAATTG | 12.98 | GGGGAT | -10.38 | GGTGCC | -38.81 |
| CGAGCT | 52.22 | CATGCC | 12.96 | CGCTAA | -10.4 | TTGTCC | -38.88 |
| GATAGC | 52.17 | TCTTTA | 12.95 | CCGTTT | -10.41 | TTGCCG | -38.89 |
| TCATTA | 52.11 | GATTTT | 12.9 | TCTAGC | -10.42 | ACGGGT | -38.92 |
| CTCCAG | 52.03 | TTTGAT | 12.87 | GGGATG | -10.45 | ATGTGG | -39 |
| CAGAGC | 51.98 | CCACTC | 12.84 | CTGTGC | -10.48 | GGTCTC | -39.04 |
| TGCTGA | 51.92 | TGTACA | 12.83 | CTAAGG | -10.8 | CGTAAG | -39.11 |
| CCAAGA | 51.92 | TATGCC | 12.83 | TTGATC | -10.5 | TTCGTT | -39.12 |
| ATAAGC | 51.86 | GCTGCC | 12.82 | ATTGGC | -10.52 | TACGGG | -39.13 |
| TTACAC | 51.85 | ATGGTT | 12.82 | AGCCGT | -10.56 | GTCATG | -39.17 |
| AGATGG | 51.72 | GTTCCA | 12.79 | ACTGGG | -10.56 | GGACGT | -39.21 |
| TCTACT | 51.69 | ATCCCT | 12.79 | CTGGCT | -10.58 | CGGGAC | -39.25 |
| TTACAA | 51.68 | ACTAAG | 12.76 | ACGCCT | -10.59 | TGGGTT | -39.32 |
| TGCAAA | 51.62 | ATTCTC | 12.75 | ATACGT | -10.63 | GAGTGC | -39.35 |
| TAGTAT | 51.42 | AACCTC | 12.75 | GGTAGC | -10.65 | CTCTCG | -39.4 |
| TTTATC | 51.26 | CCTATG | 12.71 | TGTCAT | -10.65 | CGCGAC | -39.42 |
| CCCAGA | 51.25 | GAATGA | 12.69 | GATGCC | -10.66 | TAGGGG | -39.5 |
| GACTAC | 51.19 | ACAAGT | 12.63 | GGTTTA | -10.7 | GGCACG | -39.52 |
| ATTCTA | 51.19 | TACTGT | 12.62 | GTGCTC | -10.84 | CCGCGC | -39.55 |
| CAAAAA | 51.15 | AGGTAA | 12.62 | TAAGGA | -10.86 | TGGACG | -39.58 |
| ATACTT | 51.15 | AACGAC | 12.6 | CTTAAT | -10.91 | GGCGAC | -39.6 |
| ATACGA | 51.08 | TCCGCT | 12.59 | GATCCG | -10.94 | CTGGGG | -39.69 |
| ATCTTC | 51.06 | TCAAAC | 12.55 | CGAGAT | -11 | CGGGTT | -39.73 |
| ACATCA | 51.04 | GCACTT | 12.49 | GGCGAA | -11.02 | GTGCCT | -39.76 |
| AACCCA | 51 | AATGCC | 12.48 | CCGCAT | -11.03 | TTGGGC | -39.77 |
| CATAAA | 50.95 | ACGCTT | 12.45 | GGCGCT | -11.04 | GCCGTC | -39.8 |
| TGAAGA | 50.88 | CAACGC | 12.44 | GCACGA | -11.04 | GGCCAG | -39.84 |
| TAGATG | 50.83 | TAACTC | 12.43 | TGCCGA | -11.07 | CCGTCC | -39.9 |

TABLE 3-continued

| 6-mer | 6-mer z-score | 6-mer | 6-mer z-score | 6-mer | 6-mer z-score | 6-mer | 6-mer z-score |
|---|---|---|---|---|---|---|---|
| CTGCAT | 50.78 | TCTTAC | 12.42 | GGCATC | -11.1 | GCGCGA | -39.9 |
| CAAGCA | 50.65 | CTTCCC | 12.42 | TCGGCA | -11.1 | CGCGGC | -39.95 |
| AAATCC | 50.5 | ACACTT | 12.38 | GATTAG | -11.14 | TCGGGA | -39.98 |
| GAACTA | 50.47 | TTTTAA | 12.23 | TCCTTA | -11.15 | GTCTTG | -40.04 |
| CTATGA | 50.36 | GAACCG | 12.23 | CTAAAC | -11.17 | AGTGGG | -40.12 |
| ACTTAT | 50.3 | GGGAAT | 12.21 | CGGAAG | -11.23 | CCGGGG | -40.16 |
| CCAAAT | 50.25 | TTCTCA | 12.16 | CTTTGT | -11.26 | TTTGGG | -40.17 |
| CCTGCA | 50.24 | TGCTCT | 12.15 | TTAGGA | -11.27 | CTTCGT | -40.23 |
| TACTCC | 50.15 | GTACAC | 12.13 | CCGGAT | -11.36 | CGGTCA | -40.24 |
| GAGCAG | 50.07 | TTTTTT | 12.1 | ATTAAG | -11.38 | CACGTG | -40.28 |
| TACCCA | 50.02 | GTTTCA | 12.07 | GTGCTG | -11.41 | GGTGAG | -40.43 |
| ACCTCC | 49.97 | CCCAAT | 12.04 | CTCTCC | -11.45 | GTCGAC | -40.48 |
| GTTATA | 49.88 | TTCAAG | 12.03 | TATTCG | -11.47 | TGCTCG | -40.49 |
| CATCAA | 49.87 | TTGAAT | 12 | GCCCTG | -11.51 | TGGGGC | -40.62 |
| TGATAA | 49.86 | AGTATG | 11.99 | TCGCCA | -11.54 | GGAGGG | -40.68 |
| AATCAC | 49.84 | TAGTTT | 11.98 | TGTAGA | -11.62 | TGTGAG | -40.75 |
| ATTAGA | 49.71 | CGACCA | 11.98 | CTAGTG | -11.62 | GGGGCC | -40.89 |
| CATCCC | 49.63 | GCATGA | 11.98 | CCGCCC | -11.66 | GGTGGT | -40.9 |
| GTATTT | 49.61 | CAGGAC | 11.97 | CAAGCG | -11.66 | AGGCGT | -40.91 |
| ACCTGA | 49.59 | GCCTCA | 11.96 | GGTGGA | -11.74 | TCCGTC | -40.92 |
| ACTGAA | 49.51 | GTCTAT | 11.95 | ATTAGG | -11.75 | TCCGCG | -40.92 |
| CATCCA | 49.5 | CTATCC | 11.89 | GCCTAC | -11.77 | GTACCG | -41.02 |
| TAACAC | 49.46 | TGCCAT | 11.88 | CTCACT | -11.78 | AGGTGT | -41.07 |
| AGAGAT | 49.39 | CGATCA | 11.82 | AAGCGG | -11.79 | GCTCGT | -41.08 |
| AGCATG | 49.33 | AAGGAT | 11.76 | AACCGT | -11.81 | TTTCGT | -41.14 |
| CAACCC | 49.27 | GTGGAT | 11.71 | AGATCG | -11.85 | TGCCCG | -41.17 |
| ACTTCT | 49.23 | CCATGG | 11.69 | TGACTC | -11.92 | CGATCG | -41.22 |
| ATGATC | 49.2 | TCAACC | 11.69 | TTCTTG | -11.94 | CGTCTT | -41.34 |
| GATAGA | 49.19 | TCCCAA | 11.68 | ATCGCC | -11.99 | TTCCGG | -41.5 |
| GAACAG | 48.99 | GCTGAC | 11.66 | ATCGAA | -11.99 | GTTTTG | -41.52 |
| CCAAAA | 48.88 | TCAAAG | 11.63 | GGTTTT | -12.02 | GCGAGT | -41.58 |
| GAAACT | 48.8 | GACACT | 11.61 | TGGCAA | -12.04 | GGGGAG | -41.63 |
| GACAGC | 48.76 | TCCAAG | 11.61 | CGCCTT | -12.06 | CTAGGT | -41.64 |
| CAATGA | 48.7 | CGGCTA | 11.53 | TTGTAG | -12.07 | CCGTGG | -41.64 |
| ACAAGA | 48.64 | GCCATG | 11.51 | ACTTGT | -12.08 | GAGGCG | -41.68 |
| CTCAGA | 48.55 | GCCCAT | 11.46 | TGGTTT | -12.08 | CCGCGG | -41.7 |
| AGATAA | 48.54 | GAGCCA | 11.41 | ACTCGG | -12.09 | TTGTGC | -41.74 |
| CTAGCA | 48.43 | GAAAGA | 11.4 | TATGGC | -12.1 | TTTCGG | -41.75 |

TABLE 3-continued

| 6-mer | 6-mer z-score | 6-mer | 6-mer z-score | 6-mer | 6-mer z-score | 6-mer | 6-mer z-score |
|---|---|---|---|---|---|---|---|
| ATCAAA | 48.36 | GCGTAT | 11.39 | TTGGTT | -12.12 | GCGTAC | -41.83 |
| TCTTCA | 48.34 | AAACGG | 11.38 | GCGATG | -12.19 | GTACGC | -41.88 |
| GATGAA | 48.34 | CCCAGT | 11.36 | CAGGGT | -12.2 | GAGTCG | -41.9 |
| ATCCAA | 48.27 | ACACGT | 11.35 | AGTTTG | -12.24 | TCCGTG | -42.01 |
| AACCAG | 48.27 | TTCCCC | 11.35 | TAATCT | -12.24 | CGGCGA | -42.01 |
| CACATC | 48.25 | GGCACC | 11.33 | AAACGT | -12.25 | CTCCGT | -42.07 |
| TCCAAC | 48.16 | AGCCGG | 11.32 | CGCAAT | -12.28 | TTGCGC | -42.08 |
| TAAAGC | 48.1 | TTAAAG | 11.31 | CCCTCT | -12.28 | GTGCCC | -42.11 |
| AGACCC | 48.09 | CTATAG | 11.27 | GGGCAT | -12.33 | GCGTGA | -42.12 |
| CAGGAA | 48.07 | ATCTTG | 11.27 | AGTGGC | -12.33 | GTAGGC | -42.16 |
| TTAACA | 48.04 | TACTGG | 11.23 | GCCAGG | -12.34 | CTCGTT | -42.19 |
| TTATTG | 48 | CTCAAT | 11.2 | TAAGGT | -12.35 | GTGCGA | -42.23 |
| CATGGA | 47.99 | GCTAAA | 11.18 | GGCCTT | -12.37 | AGTGCG | -42.39 |
| CTTCCA | 47.96 | GGTTAT | 11.16 | GGGAAG | -12.37 | CGCCCG | -42.43 |
| CAGTTG | 47.94 | TGCCAC | 11.14 | TGCCTA | -12.4 | GGCGTA | -42.43 |
| ATATGG | 47.86 | GAGACC | 11.07 | CCGTCA | -12.43 | GAGCGT | -42.48 |
| GTATCT | 47.79 | GTTACC | 11.04 | GTATTG | -12.44 | TCGTTC | -42.53 |
| CTTCAA | 47.73 | AGGAGT | 11.04 | GTGACA | -12.48 | AAGTCG | -42.67 |
| GAGAAC | 47.72 | CCGCAG | 11.03 | CGGCAG | -12.51 | GTCAGG | -42.73 |
| TTCACT | 47.71 | CAAATT | 11.02 | TGTGAT | -12.53 | CGTTAG | -42.84 |
| AAAGAA | 47.71 | CTTCTC | 10.99 | GACGCA | -12.56 | TCGGTT | -42.92 |
| ACACCT | 47.51 | TATGTT | 10.99 | CAAGGG | -12.58 | TCGCGA | -42.92 |
| AGTTCA | 47.47 | AATTTC | 10.99 | GAGTCA | -12.63 | GGGAGG | -42.93 |
| ACCTGC | 47.45 | ACCGCT | 10.99 | GCCGAG | -12.66 | GGGACG | -42.94 |
| TATGCT | 47.44 | CCCGCT | 10.9 | CTTTCT | -12.68 | GTCAGT | -43.2 |
| TTGTAT | 47.43 | CGATTA | 10.87 | GACTTT | -12.69 | TGCCGT | -43.2 |
| ACAGGC | 47.42 | ACATCG | 10.86 | GGTCAA | -12.72 | GGGGTA | -43.2 |
| TCCATA | 47.27 | CCGGCT | 10.85 | TCGCAC | -12.75 | GCGTCT | -43.23 |
| TATTCC | 47.17 | TAGATC | 10.82 | TCTTGC | -12.82 | GCCGCG | -43.26 |
| GGCTGA | 47.15 | AAGTTG | 10.82 | CCTTTG | -12.82 | AGTCGG | -43.28 |
| TGCTAA | 47.05 | CTTGAT | 10.79 | TTCGCC | -12.88 | TCCGTT | -43.36 |
| ACCCCA | 46.96 | TACCGC | 10.78 | TGGTCA | -12.91 | CTCGGG | -43.37 |
| GTAGTA | 46.89 | AAAGGC | 10.74 | GCGCTC | -12.95 | GGGCCC | -43.5 |
| ATCCTA | 46.79 | GATCTA | 10.72 | GAAGTG | -12.95 | TAGGCG | -43.53 |
| CGCATA | 46.68 | TCCCCT | 10.64 | GCCTCT | -12.96 | GGTCAG | -43.58 |
| AATTCT | 46.54 | GATAGT | 10.62 | AGGTGG | -12.96 | GGGTAG | -43.61 |
| GGATCT | 46.23 | GGATAA | 10.61 | CAGTGG | -13 | TACGTG | -43.67 |
| TTATAG | 46.2 | TGAGTA | 10.57 | GTACCC | -13.02 | GTCCTG | -43.69 |

TABLE 3-continued

| 6-mer | 6-mer z-score | 6-mer | 6-mer z-score | 6-mer | 6-mer z-score | 6-mer | 6-mer z-score |
|---|---|---|---|---|---|---|---|
| ACTAAA | 46.2 | GGAGTT | 10.54 | TTCCTC | -13.04 | CGCCGC | -43.8 |
| CAGACA | 46.2 | ACGCAC | 10.52 | TCGACA | -13.05 | CTGGCC | -43.85 |
| GTACCA | 46.16 | CCCATT | 10.51 | TGGCAG | -13.07 | TAGGGT | -43.88 |
| CAAAGA | 46.13 | TGTAAC | 10.49 | CCGAAA | -13.09 | GCCGGG | -43.92 |
| ACTCCT | 46.11 | GATTTC | 10.48 | CTGCCT | -13.11 | GGTTAG | -43.96 |
| CACAGT | 46.1 | TAACCC | 10.46 | ATGGGC | -13.12 | CCGGGT | -44.07 |
| AAACCT | 46.05 | AATGTA | 10.46 | ACCGAG | -13.13 | CTCGTC | -44.16 |
| CGCTGA | 46.02 | ACGGCC | 10.46 | CGTAGA | -13.16 | GTCTAG | -44.19 |
| AATGAA | 45.98 | TGCAGG | 10.44 | GGGCTT | -13.18 | GGTGTT | -44.21 |
| GTTACT | 45.95 | CTGTAC | 10.44 | CCGAGC | -13.19 | CCGGGC | -44.24 |
| TACAAG | 45.86 | AACATG | 10.43 | GACTTG | -13.23 | AGTGTG | -44.25 |
| AGGAAT | 45.81 | ACTGGT | 10.38 | CTGACT | -13.26 | CGAGGG | -44.3 |
| ACTCAA | 45.79 | AAGGCC | 10.36 | GAGGGA | -13.28 | GTTGGC | -44.3 |
| ATGACA | 45.7 | TAAAGG | 10.29 | AGTCGA | -13.32 | CGGCGC | -44.3 |
| ACCATG | 45.69 | TATTGT | 10.25 | CCCGAG | -13.32 | AGTGTC | -44.31 |
| CATAGT | 45.61 | GGAGGA | 10.19 | CTTCCT | -13.32 | CGTTGT | -44.33 |
| ATATTG | 45.6 | AAGTGA | 10.18 | TCACGC | -13.37 | GTTCGC | -44.35 |
| AGGTAT | 45.57 | ATTTGG | 10.18 | TAGGTG | -13.39 | GTTGCC | -44.36 |
| CTCAGC | 45.54 | TGTTTT | 10.17 | CCTCTG | -13.41 | GGCGGT | -44.48 |
| ATATTC | 45.46 | CAAAGT | 10.16 | GCGACA | -13.46 | TTCGCG | -44.51 |
| CTACTC | 45.36 | AGTCAC | 10.14 | GCTAGC | -13.46 | TTGCGG | -44.57 |
| TACAGG | 45.33 | CTGAGG | 10.12 | TCATCG | -13.48 | GTGTTC | -44.64 |
| CCTCAG | 45.33 | CTAGAT | 10.11 | CCCGCC | -13.49 | ATGTCG | -44.73 |
| CACTGC | 45.24 | AATTGG | 10.08 | GTCCAA | -13.5 | GGCGGC | -44.81 |
| GCACCT | 45.13 | GGAAGA | 10.08 | TGGAGT | -13.55 | TCGGAG | -44.82 |
| ACTATC | 45.05 | CTCTTA | 10.04 | ACGAGT | -13.6 | GACGGG | -44.82 |
| CTGCTG | 44.96 | CTCTCA | 9.99 | CCCGGC | -13.6 | CGTCCT | -44.86 |
| AGCCTT | 44.9 | GAACTT | 9.97 | ACGGTA | -13.65 | TCGACG | -44.94 |
| GGTATT | 44.89 | AGAGAA | 9.94 | TCCTGG | -13.65 | GGACGG | -44.99 |
| TAAATA | 44.79 | GAGGAT | 9.93 | CGATCT | -13.73 | TGGTGG | -44.99 |
| TTCCAC | 44.78 | GGGAAA | 9.93 | CAATCG | -13.76 | TCCCGT | -45.06 |
| CAAAAG | 44.78 | CCCTGA | 9.92 | CTACGC | -13.79 | TGTCGA | -45.08 |
| TTTCAG | 44.77 | CCAATG | 9.9 | ATCACG | -13.84 | GCTCGG | -45.1 |
| TAATGA | 44.74 | TCATGA | 9.89 | CGCTCT | -13.89 | GGGCCG | -45.15 |
| TTACAT | 44.73 | CCTTCT | 9.88 | CCCGAT | -13.92 | GTTTGT | -45.27 |
| AACCCC | 44.73 | TCATTG | 9.81 | CGGTAT | -13.94 | GAGGGG | -45.32 |
| ATGGTA | 44.66 | TACCCC | 9.78 | AAGTCC | -13.95 | TTCGTG | -45.45 |
| CACTGA | 44.64 | TTCTGA | 9.75 | GGCATG | -14 | GCGAGG | -45.47 |

TABLE 3-continued

| 6-mer | 6-mer z-score | 6-mer | 6-mer z-score | 6-mer | 6-mer z-score | 6-mer | 6-mer z-score |
|---|---|---|---|---|---|---|---|
| CAAATC | 44.64 | AGAACG | 9.72 | ATGAGG | -14.05 | CCTCGT | -45.53 |
| CATGCT | 44.62 | ACGCTA | 9.69 | AGGTCT | -14.05 | GCCCGG | -45.6 |
| GCTTCT | 44.61 | CTCCTA | 9.69 | CTTAGT | -14.06 | GTCTGT | -45.62 |
| TCCATC | 44.59 | TCCGCA | 9.59 | ACTCGC | -14.08 | TTGTCT | -45.66 |
| TCAGTT | 44.56 | TTCACG | 9.57 | ACGAAG | -14.09 | CGGTGT | -45.71 |
| ACTGCC | 44.54 | CGAATA | 9.54 | GGGACT | -14.1 | CGTTTG | -45.74 |
| CTTCAT | 44.49 | ATTTTG | 9.43 | AAGACG | -14.11 | GGTAGG | -45.84 |
| TGCTCA | 44.45 | GCCACA | 9.39 | TCCTGC | -14.11 | GTCCGC | -45.88 |
| TGGAAT | 44.41 | CCTAGA | 9.37 | GCTCTC | -14.12 | GCCGGC | -45.88 |
| CTTCAG | 44.4 | TTATCC | 9.33 | TCTACG | -14.14 | CGCGTT | -45.93 |
| ACATCT | 44.4 | AGGCAC | 9.29 | TTGAGT | -14.15 | ACGGGG | -45.94 |
| CACCTG | 44.39 | GGCAAA | 9.28 | TCGAAC | -14.16 | CCGTTG | -45.97 |
| ATGCAT | 44.36 | AACCCG | 9.28 | CCCTTG | -14.27 | TCTGTC | -46.05 |
| CCAACC | 44.33 | GTTAAT | 9.27 | GTTCCT | -14.28 | GGGCGA | -46.06 |
| CATTAT | 44.25 | AATGGC | 9.23 | GTCTCC | -14.29 | GACGTG | -46.08 |
| CTAGTA | 44.22 | GTATAC | 9.16 | ACCGTC | -14.35 | TTGGTC | -46.16 |
| TACAGT | 44.18 | CAGTCT | 9.12 | TCTTTG | -14.39 | GCCGGT | -46.32 |
| TACTGA | 44.12 | CTCAGT | 9.12 | GGTTCC | -14.39 | TTGCGT | -46.32 |
| CTACTG | 44.1 | TTTATG | 9.09 | GTTCCC | -14.42 | GGGTTG | -46.34 |
| TAGAAT | 44.07 | TGAGCC | 9.05 | CGCTGT | -14.51 | GGCGAG | -46.43 |
| ACAGCG | 44.06 | GGTGAA | 9.04 | CAACGT | -14.53 | CGTGTT | -46.44 |
| ATGGAT | 44.04 | TAAAAT | 9.04 | CAGGCG | -14.56 | GGGTCC | -46.51 |
| TTCATA | 43.92 | CACACG | 9.02 | TACGCC | -14.59 | TGGGCC | -46.53 |
| ATAAAA | 43.84 | GTACTT | 9.02 | CGAAAC | -14.6 | GCGTTG | -46.58 |
| ACTCAG | 43.83 | TTACCG | 9 | TCTTTC | -14.65 | CGACGG | -46.68 |
| CTGCAA | 43.65 | GCCAGA | 8.99 | TGCCCT | -14.67 | AGGGGG | -46.69 |
| CAGGCT | 43.52 | TCGCTA | 8.97 | GCCCTA | -14.68 | GTGTCA | -46.75 |
| TGATAG | 43.5 | GGCTCT | 8.95 | GTTTTC | -14.68 | GCGTAG | -46.76 |
| AGAGAC | 43.5 | GACAGA | 8.93 | GTATGC | -14.7 | TAGGTC | -46.77 |
| CCATGA | 43.49 | GGAATT | 8.9 | GAAGGG | -14.72 | CGCGAG | -46.79 |
| CTACTT | 43.4 | TATTCT | 8.89 | CGAAAG | -14.79 | TGAGTG | -47.04 |
| ACATTA | 43.36 | CCGCAC | 8.89 | GATTCG | -14.79 | GACGTC | -47.04 |
| GAATAG | 43.29 | TGCCAA | 8.87 | CGATGC | -14.9 | GTCGGA | -47.14 |
| GCAGTT | 43.25 | GCCAAC | 8.84 | TGAGCG | -14.92 | GGTTGG | -47.18 |
| CACAAA | 43.25 | GATCCT | 8.82 | ACGCGG | -14.93 | TCGCGC | -47.26 |
| TGAACT | 43.25 | ACGCCA | 8.74 | CTCGAG | -14.94 | GCGCCG | -47.28 |
| TGAGAT | 43.21 | AAAAAG | 8.73 | TGCGGA | -14.95 | TGTCTG | -47.32 |
| CACTAG | 43.13 | CCAAAC | 8.69 | ATGTCC | -15.01 | GCCGTG | -47.35 |

TABLE 3-continued

| 6-mer | 6-mer z-score | 6-mer | 6-mer z-score | 6-mer | 6-mer z-score | 6-mer | 6-mer z-score |
|---|---|---|---|---|---|---|---|
| CCCCAT | 43.06 | TAACCG | 8.68 | CGGCCA | -15.02 | CGTTGC | -47.38 |
| CTAACA | 42.92 | TTGAGC | 8.68 | ACCTAG | -15.05 | TCGTCT | -47.39 |
| CCAGTA | 42.86 | GCATTG | 8.65 | GTCAAA | -15.06 | GGCGCC | -47.47 |
| CTCCAT | 42.76 | CACTGG | 8.65 | GTGCCA | -15.08 | GGGGGC | -47.53 |
| CAAGAT | 42.74 | GTAAGA | 8.62 | CCCCGA | -15.11 | TTGTGG | -47.6 |
| GAACCC | 42.71 | GACAAA | 8.62 | CTGGCA | -15.12 | CGGTCC | -47.61 |
| CCAGAA | 42.65 | CCCTTC | 8.61 | AAGGCG | -15.13 | CGCGCC | -47.71 |
| TTCATC | 42.62 | TTAATC | 8.61 | GATTGC | -15.14 | TTCGGT | -47.79 |
| AACCTG | 42.6 | GTACAA | 8.54 | TTTGAC | -15.14 | TGACGT | -47.8 |
| AGCCCC | 42.52 | ATAAGA | 8.53 | GTAGGT | -15.16 | TGTCCG | -47.88 |
| CCTACA | 42.47 | AATCCG | 8.5 | GTTGTT | -15.17 | TGTTGT | -47.91 |
| GGATAT | 42.47 | TTCTTC | 8.39 | CCTAAC | -15.17 | CCCGGT | -48.15 |
| TCCACT | 42.41 | CATGAG | 8.38 | GGACTT | -15.18 | GCGTCC | -48.17 |
| ATTACG | 42.39 | GAAATT | 8.32 | CGTAAA | -15.2 | TCCGGG | -48.25 |
| AAGATC | 42.32 | CATACG | 8.31 | TCATGT | -15.21 | CCCGCG | -48.5 |
| AGCCTA | 42.29 | TCTGAT | 8.28 | GGGACC | -15.22 | TCGTCC | -48.56 |
| ACACGG | 42.21 | GACCAA | 8.27 | GGGCAG | -15.23 | GTTCGT | -48.56 |
| CTGAAT | 42.18 | TAAGAG | 8.24 | CTGGTG | -15.25 | GTTCCG | -48.59 |
| CTATTC | 42.04 | GGATTG | 8.2 | GGATGG | -15.27 | TTGGCG | -48.69 |
| ACAATG | 42.01 | CAAATG | 8.17 | CCGTTA | -15.31 | TGGCCG | -48.69 |
| TCATAA | 42 | CCACGG | 8.17 | GACGCC | -15.32 | GCGACG | -48.74 |
| TGAATC | 41.89 | GAGAGA | 8.12 | CGCATC | -15.33 | GGAGTG | -48.78 |
| ATCAGT | 41.74 | GCTTAG | 8.08 | ACGCTC | -15.33 | GTTAGG | -49.18 |
| GATTTA | 41.74 | CAGCGT | 8.07 | AAAGTC | -15.35 | GGCCGG | -49.22 |
| AATCTG | 41.72 | GTGCTA | 8.07 | GGGGCA | -15.38 | CGGTTG | -49.22 |
| GCTGGA | 41.71 | TTAACT | 8.05 | CTCGCA | -15.38 | TCTCGT | -49.23 |
| AGCGAT | 41.68 | TGATCC | 8.04 | GCACGG | -15.39 | CGAGCG | -49.24 |
| TATTTT | 41.67 | AATGAC | 8.04 | AGCGAG | -15.4 | CGAGGT | -49.43 |
| GAATCC | 41.64 | GTAACC | 8.01 | ACTGGC | -15.44 | CGTCTG | -49.43 |
| TTTACC | 41.63 | CTCAGG | 8 | CTGTCA | -15.51 | CTCGGT | -49.55 |
| AGCAGG | 41.62 | CGATAC | 7.98 | AGCGTC | -15.52 | TTCGTC | -49.6 |
| AAATAT | 41.58 | CTTTTC | 7.89 | GAGGAG | -15.53 | GGCGTT | -49.72 |
| ATTATC | 41.55 | TTCAGT | 7.81 | GTGTAA | -15.58 | TCGGCG | -49.79 |
| GAGATA | 41.47 | CCCCTT | 7.75 | TTGTAC | -15.6 | CGTCGA | -49.86 |
| CCAGGA | 41.41 | TGCACG | 7.71 | TCAGTG | -15.65 | GTGACG | -49.87 |
| TCATAG | 41.39 | TTCTTA | 7.71 | GGCGCA | -15.71 | CGACGT | -49.9 |
| GCTTTT | 41.33 | TAATGC | 7.7 | GCGAAC | -15.71 | GGTACG | -49.96 |
| ATGACT | 41.26 | CCTGAG | 7.69 | TCTCTA | -15.73 | CGGTGC | -50.01 |

TABLE 3-continued

| 6-mer | 6-mer z-score | 6-mer | 6-mer z-score | 6-mer | 6-mer z-score | 6-mer | 6-mer z-score |
|---|---|---|---|---|---|---|---|
| GAACTG | 41.19 | TATCCG | 7.64 | CCCGAA | -15.75 | GTACGG | -50.02 |
| CTGAAC | 41.19 | GACATC | 7.64 | TGAGGC | -15.76 | CGTGAG | -50.26 |
| GGCTAC | 41.14 | GACCCC | 7.61 | CCCCGG | -15.78 | CGGCGG | -50.36 |
| AGCTCG | 41.12 | CTTTGA | 7.6 | CCTCGA | -15.83 | TTGTGT | -50.37 |
| ACCCAC | 41.04 | TTAAGA | 7.56 | TATCGG | -15.85 | GAGTGG | -50.58 |
| CAATCA | 41.01 | CACGAC | 7.55 | ATCCGT | -15.86 | TTCGGG | -50.66 |
| AGCGCA | 40.99 | TAAATT | 7.54 | AGCGGG | -15.87 | TGTGTC | -50.68 |
| ACTCCC | 40.96 | ATTGAC | 7.51 | CCCACG | -15.87 | TGGGTC | -50.7 |
| CTCCAC | 40.95 | AGAAAG | 7.5 | ACTGTC | -15.88 | GGTCGA | -50.8 |
| AATCTA | 40.93 | TTTGCT | 7.5 | GTTTAA | -15.92 | GTTTGG | -50.88 |
| GCATCA | 40.9 | CCAAAG | 7.46 | TAGTGG | -15.97 | CCCGTG | -51.09 |
| ATTTTT | 40.87 | CACGGC | 7.4 | AATGGG | -15.99 | GTTTCG | -51.17 |
| TGAAAA | 40.84 | GTTTTT | 7.39 | ATCGAG | -15.99 | CGAGTG | -51.21 |
| TCACAT | 40.84 | TGTGAA | 7.37 | GTCCTT | -16.01 | GAGTGT | -51.21 |
| ATTCCT | 40.83 | GTAATC | 7.37 | AACGTG | -16.03 | TGGTGT | -51.9 |
| TTGATA | 40.69 | CGTATC | 7.36 | CGCAAG | -16.03 | TCGGGC | -51.42 |
| CACAAC | 40.69 | TACGAT | 7.3 | GGCCCT | -16.05 | TGCGCG | -51.46 |
| TATTGA | 40.61 | GGACAT | 7.28 | CACGTA | -16.06 | TCGCCG | -51.51 |
| AGGCTG | 40.57 | CCCTTA | 7.23 | TAGGGA | -16.09 | CCGGTC | -51.68 |
| AATGCT | 40.53 | GATTTG | 7.22 | CGGCAA | -16.12 | CGCGTC | -51.71 |
| TATTTG | 40.53 | ATTTGT | 7.2 | CCTAAG | -16.15 | GTCGTT | -51.72 |
| CAGGTA | 40.51 | ACATGT | 7.19 | TCGAGA | -16.16 | TGGTCT | -51.83 |
| CATGCA | 40.5 | CACGCT | 7.18 | GCCTGA | -16.16 | CGCGGT | -51.85 |
| AAACTG | 40.46 | TGCTGG | 7.14 | GACCCG | -16.19 | GGTCTG | -51.86 |
| AACAAA | 40.38 | CACCGA | 7.05 | GTTAGA | -16.27 | CTCGCG | -51.88 |
| CTTTCA | 40.38 | ATCCGA | 7.01 | TGCTTG | -16.27 | CTCGTG | -51.94 |
| CAAACT | 40.38 | TAGTTC | 6.93 | TCGAGC | -16.29 | CGGGCC | -52.44 |
| TATTTA | 40.37 | CTGGAC | 6.9 | ACGGTG | -16.32 | GTACGT | -52.73 |
| GGAACA | 40.37 | CCTCAC | 6.9 | TCGATC | -16.34 | AGGGCG | -52.77 |
| GCCACT | 40.35 | TGAATG | 6.89 | CAGGGG | -16.36 | GTGCCG | -52.81 |
| CGCAGC | 40.24 | GCCCAG | 6.83 | GAATGT | -16.41 | GTGAGT | -52.89 |
| TAAATC | 40.2 | CGGCTG | 6.82 | TTGACT | -16.46 | TGTGGT | -52.99 |
| AGGTAC | 40.19 | CTTGTA | 6.77 | TCAGTC | -16.47 | CGGTCT | -53.11 |
| ACTGTA | 40.17 | AATCTC | 6.73 | GCTCGA | -16.48 | TCGTGG | -53.14 |
| GAAGGA | 40.16 | AAGAAG | 6.68 | AATCGT | -16.48 | CGGGGC | -53.26 |
| CAGTTC | 40.09 | GAATTG | 6.67 | GCCCTC | -16.49 | TCGTTG | -53.27 |
| TTTTAC | 40.04 | AAGGAG | 6.63 | GACGGA | -16.49 | ACGTGG | -53.35 |
| TGAACA | 40 | TAGGCT | 6.62 | AAGAGG | -16.52 | GGTTCG | -53.38 |

TABLE 3-continued

| 6-mer | 6-mer z-score | 6-mer | 6-mer z-score | 6-mer | 6-mer z-score | 6-mer | 6-mer z-score |
|---|---|---|---|---|---|---|---|
| GCTATC | 39.99 | TTTGTA | 6.58 | CGTTAC | -16.52 | ACGTCG | -53.48 |
| GCTTTA | 39.98 | TTCTAA | 6.55 | ATCCGG | -16.55 | GGCCCG | -53.53 |
| ATTAAC | 39.98 | TCTCAG | 6.51 | TTATGT | -16.55 | CGTGCC | -53.55 |
| GAATAT | 39.96 | ACCCTA | 6.51 | CTTCGC | -16.56 | TGGGGG | -53.57 |
| CCATCC | 39.94 | TTATGC | 6.47 | GAGTCC | -16.57 | CGGCGT | -53.63 |
| TACCTG | 39.93 | CTGGGA | 6.46 | GAGAGG | -16.6 | CGTAGG | -53.63 |
| CAAACC | 39.91 | TTTGGA | 6.43 | TGTCTT | -16.61 | GTCTGG | -53.69 |
| CACTTC | 39.84 | CTTTGC | 6.39 | AGAGTG | -16.64 | GTGAGG | -53.7 |
| TTATAC | 39.76 | GGAAAC | 6.38 | ACCCCG | -16.65 | CGTACG | -53.71 |
| TTGCAT | 39.73 | AACCGA | 6.33 | TAACGG | -16.65 | GTTGTC | -53.73 |
| CTGTAT | 39.67 | ACGATG | 6.33 | CTCGGC | -16.66 | TTGGGT | -53.74 |
| GAAACC | 39.64 | GCTACG | 6.32 | TAGAGG | -16.67 | CGTCCG | -53.8 |
| AGTGAT | 39.53 | CTTTAG | 6.28 | CTTCCG | -16.75 | TGCCGG | -53.82 |
| CAAGCC | 39.3 | GCAGGC | 6.25 | AACGGA | -16.76 | TCGTGC | -53.92 |
| AGGATT | 39.29 | CTGCCC | 6.22 | AAGTTT | -16.76 | CGGGTC | -54 |
| CAGTAG | 39.29 | TTCTTT | 6.2 | GCCTGT | -16.77 | GTCGAG | -54.01 |
| AGAATA | 39.23 | GCACTG | 6.19 | AGTCCT | -16.79 | CGTTGG | -54.19 |
| ATGCCA | 39.23 | ATAGTC | 6.11 | GAACGG | -16.8 | CCGGCG | -54.27 |
| GTGATA | 39.2 | GCTCAC | 6.11 | GGCAAC | -16.84 | TCCGGT | -54.32 |
| AATCCC | 39.2 | ATTGGT | 6.09 | CTCGGA | -16.85 | GCGGGT | -54.37 |
| AACAAT | 39.16 | GTACTG | 6.09 | TCGATA | -16.85 | TCGTGT | -54.38 |
| GAAGAA | 39.02 | GGTATC | 6.07 | ATGGGG | -16.85 | CGCCGG | -54.53 |
| TAACAT | 39 | CCCAAA | 6.05 | GGAGGC | -16.88 | CGCTCG | -54.55 |
| CAAACA | 38.97 | CATTGT | 5.96 | CCGCCT | -16.93 | GTCCGT | -54.62 |
| AGGATA | 38.8 | GTGCAC | 5.86 | CCTCCT | -16.95 | GGTGGC | -54.7 |
| AAATGG | 38.8 | GTTTTA | 5.81 | AAGGGG | -16.95 | TGCGTC | -54.83 |
| TTTAAT | 38.75 | GCAAAC | 5.79 | ACCGTG | -17 | GGGTGC | -54.96 |
| TTTACA | 38.66 | CGCACC | 5.79 | GCCTAA | -17.04 | GTCGCC | -55.39 |
| GACACC | 38.6 | CTACCG | 5.78 | TGGGAC | -17.08 | TGTGCG | -55.49 |
| CTTACT | 38.54 | GGGATA | 5.77 | TGGATG | -17.08 | CGTGTC | -55.5 |
| TAAAAC | 38.52 | ACAGGT | 5.76 | TATCGC | -17.09 | GGCGTC | -55.61 |
| TCAGCG | 38.41 | GCTGAG | 5.75 | GGACTA | -17.1 | GCGCGC | -55.66 |
| TTTGCA | 38.37 | AAATGT | 5.7 | CGAAGG | -17.11 | CTGTCG | -55.74 |
| ACAAAC | 38.35 | TGTAGT | 5.67 | TCTAGT | -17.14 | GTCCCG | -56.36 |
| GATCTC | 38.32 | TGATGG | 5.64 | GTCAAC | -17.15 | GCGGGC | -56.49 |
| TGGATC | 38.23 | ATGCCC | 5.63 | TTCTAG | -17.16 | GTAGGG | -56.76 |
| AAAAAA | 38.16 | TTTCCC | 5.63 | CGAGAC | -17.19 | TGTCGC | -56.8 |
| CACGAT | 38.16 | GCCAAT | 5.59 | AAGGGT | -17.2 | TCGCGG | -56.94 |
| TTTTCA | 38.15 | AAGGTA | 5.58 | GCGAAG | -17.21 | TGGCGT | -57.03 |
| AAACAA | 38.11 | GTATCC | 5.56 | GCAAGT | -17.22 | GTGCGC | -57.04 |
| AATCAG | 38.1 | TGGACC | 5.48 | CGGCCC | -17.26 | TTGTCG | -57.09 |
| ATGAGA | 38.04 | AGGCAT | 5.46 | ATTTCG | -17.3 | GTGTTG | -57.15 |
| CCAATT | 38.03 | GATGGT | 5.44 | GTGGTA | -17.33 | TGGGGT | -57.19 |
| CTATAC | 37.99 | TTCCTT | 5.44 | TGGTTC | -17.37 | GGTCGC | -57.25 |
| AGGACA | 37.98 | TGGAAG | 5.39 | GCATCG | -17.37 | CGTGGC | -57.9 |
| GAACAA | 37.98 | CCTATC | 5.33 | GTACTC | -17.39 | GGGCGC | -58.19 |
| TCCAAA | 37.84 | CGGACA | 5.31 | ACGTAA | -17.4 | TGCGGT | -58.27 |
| TTTCCA | 37.82 | AGGGCT | 5.22 | CTTGTT | -17.4 | TGGCGG | -58.3 |
| ACTGGA | 37.81 | TTTAAC | 5.22 | GGACTG | -17.41 | GGGGGT | -58.38 |
| AAGCAA | 37.77 | TTGTAA | 5.21 | GCCGTA | -17.43 | TCGGGT | -58.51 |
| ATGAAG | 37.77 | ATAGGC | 5.18 | CCTGGC | -17.44 | CCGGTG | -58.6 |
| ACAAGG | 37.76 | TGTTAA | 5.15 | AACGAG | -17.52 | CGTTCG | -58.67 |
| AAGCCC | 37.72 | TGACTA | 5.12 | CGCAGG | -17.55 | TCGGTC | -58.82 |
| GCTCCT | 37.68 | CCCCTA | 5.11 | TCTTGG | -17.58 | GTCGGC | -58.88 |
| ACACGA | 37.64 | AGATGT | 5.1 | AGACCG | -17.62 | GTGGTC | -58.88 |
| AGCCGA | 37.6 | GACAAT | 5.09 | TGCGAC | -17.65 | GTGTGA | -59.14 |
| CCAGCG | 37.57 | GATCAA | 5.07 | CAGTCG | -17.66 | CGTGGT | -59.24 |
| ATCCCC | 37.48 | GCCAGC | 5.05 | GCCGTT | -17.66 | GTGGCC | -59.29 |
| TGTAGC | 37.33 | TCATCC | 5.04 | TAACGC | -17.67 | GCGGTC | -59.3 |
| AGCCGC | 37.29 | AGTTAA | 4.96 | CGACAC | -17.69 | GCGCGT | -59.36 |
| TCAGAA | 37.28 | TCTCAC | 4.95 | CCCGGA | -17.72 | AGGTCG | -59.5 |
| TAAAAA | 37.16 | ACGGCT | 4.94 | GTCATT | -17.72 | GTCTCG | -59.51 |
| GATAAT | 37.15 | TCTATA | 4.87 | ATCGGA | -17.74 | GGTGTC | -59.7 |
| TCCTAC | 37.13 | GTAGGA | 4.85 | CCGAGT | -17.76 | TGGTCG | -59.72 |
| TACTTC | 37.09 | TTTCTA | 4.85 | GGTTTC | -17.8 | GCGGTG | -60.02 |
| GAAATG | 36.99 | CAGAGG | 4.84 | CGCATT | -17.82 | TGCGTG | -60.04 |
| ATATTT | 36.91 | TTTTTG | 4.77 | CCTTGC | -17.83 | GTGTGT | -60.05 |
| GAACTC | 36.81 | TCCTAT | 4.76 | TCTGCC | -17.83 | GGGGTC | -60.15 |
| CTAATG | 36.79 | GAAGGC | 4.74 | GCAAGG | -17.84 | CGCGCG | -60.19 |
| AACAGG | 36.76 | TCAGAC | 4.73 | CCCTGG | -17.85 | TGGGCG | -60.25 |
| AAGGCT | 36.76 | GCAGCG | 4.71 | GTTTAC | -17.87 | GCGTGT | -60.27 |
| TCCAAT | 36.72 | AGTGGA | 4.7 | AGGTCC | -17.91 | GTTGGG | -60.36 |
| TATGAC | 36.67 | CCACGC | 4.69 | GCTTGT | -17.93 | TGCGGG | -60.39 |
| ACCTCA | 36.63 | TTGTTA | 4.62 | CCGATC | -17.95 | TGTGGC | -60.71 |
| TGATGA | 36.62 | CTTAAA | 4.62 | TCGAAA | -17.95 | GCGCGG | -60.73 |
| AAGCCT | 36.59 | ACTGCG | 4.61 | CTTGCC | -17.99 | CGTCGC | -60.8 |

TABLE 3-continued

| 6-mer | 6-mer z-score | 6-mer | 6-mer z-score | 6-mer | 6-mer z-score | 6-mer | 6-mer z-score |
|---|---|---|---|---|---|---|---|
| GAGACA | 36.59 | GTTCAC | 4.59 | TCCGAC | -18 | CCGTCG | -60.85 |
| ATGATT | 36.47 | TCAAGG | 4.58 | TATCGA | -18 | GTGGTG | -60.86 |
| CCACCC | 36.46 | AGGATG | 4.56 | GATTGG | -18.08 | GTTCGG | -61.52 |
| GCAATT | 36.27 | CCCTGT | 4.46 | CGTTAT | -18.09 | GGGCGG | -61.53 |
| CCCACA | 36.26 | CAAAGG | 4.45 | TATCGT | -18.16 | TCGCGT | -61.64 |
| TACTTA | 36.25 | TTTAAA | 4.39 | TTTCGC | -18.18 | GTGTCC | -61.73 |
| TGACCA | 36.23 | TTATGG | 4.38 | AAGTGG | -18.22 | GGGTGT | -61.79 |
| CCATAG | 36.13 | CTAGAA | 4.37 | GGCCCC | -18.22 | GGGGGG | -62.06 |
| ATTCCC | 36.08 | CCGTAA | 4.36 | GGCCCA | -18.24 | TGTGTG | -62.08 |
| CCCACT | 36.08 | TAGCCG | 4.36 | ACCGGA | -18.25 | GCGTGC | -62.32 |
| AAACCC | 35.99 | ACTTTG | 4.36 | TCAGGC | -18.26 | CGGGGG | -62.44 |
| GAACCT | 35.97 | GACTGA | 4.33 | CGTCTA | -18.28 | CGGGCG | -62.52 |
| GTTATT | 35.96 | TCACAC | 4.31 | GTCATC | -18.3 | GGCGTG | -62.89 |
| CCATAC | 35.9 | GGTAGA | 4.27 | GACCTA | -18.31 | TCGGTG | -63.03 |
| TTCTAC | 35.9 | GACTGC | 4.25 | TTGTTC | -18.38 | GGCGGG | -63.07 |
| ATGAGC | 35.85 | AGATTG | 4.24 | TCCTAG | -18.4 | GTTGTG | -63.22 |
| GATCAG | 35.85 | CGGCTT | 4.23 | ACCCGT | -18.48 | GGTCGT | -63.3 |
| TATGAA | 35.79 | ATGTCA | 4.23 | ATCGTG | -18.49 | TCGGGG | -63.6 |
| CAAGAA | 35.7 | TCTTGA | 4.2 | TTGGAC | -18.49 | GTTGCG | -64.3 |
| TATAAG | 35.62 | CTTTTG | 4.2 | CGGAAT | -18.51 | GGGCGT | -64.62 |
| ATCTCC | 35.59 | TGTAAA | 4.2 | CAACGG | -18.61 | TCGTCG | -64.83 |
| ACTACG | 35.54 | GCTTTG | 4.19 | ACCGTT | -18.62 | GGTCCG | -64.88 |
| GAACAC | 35.49 | CCAAGT | 4.16 | CCGTAG | -18.63 | GCGGCG | -64.99 |
| TATTGC | 35.48 | TGTACC | 4.15 | TGCCAG | -18.65 | GTGCGG | -65.11 |
| TAAATG | 35.47 | AAAGTT | 4.14 | TGTTAG | -18.77 | GGTGCG | -65.21 |
| ATGAAA | 35.43 | ACCGTA | 4.1 | CGACCC | -18.77 | GCGTGG | -65.85 |
| GATCTG | 35.38 | TACGAA | 4.04 | TTGTTT | -18.77 | GGGGCG | -66.57 |
| TATAAA | 35.37 | CTTATC | 3.94 | TCGCAA | -18.77 | CGCGTG | -66.73 |
| ATACGG | 35.34 | CCTCAA | 3.94 | ATGGTC | -18.81 | GTGTGC | -66.98 |
| ATTATG | 35.3 | ACCCGA | 3.93 | CGTGGA | -18.81 | GTCCGG | -67.1 |
| CAAGGA | 35.22 | GTTGAT | 3.93 | TCCTCT | -18.83 | GTGCGT | -67.14 |
| AAATAG | 35.19 | TGCTGT | 3.92 | TCGCCT | -18.84 | TGTCGT | -67.26 |
| AAGACT | 35.13 | GTTCAG | 3.91 | TCGGAT | -18.89 | TGTGGG | -67.31 |
| ACCCCC | 35.07 | TGGTTA | 3.91 | GCGACC | -18.9 | CGGTCG | -67.35 |
| AGATTT | 35.05 | AAAACG | 3.88 | ACGTTT | -18.91 | CGGGGT | -67.36 |
| GAGCAT | 35.02 | GCGCAG | 3.86 | TTAGCC | -18.92 | CGCGGG | -67.6 |
| CCCCAA | 35.02 | CCTTTC | 3.85 | CTCTTT | -18.92 | TGTCGG | -67.61 |
| AAATGC | 35 | TCTCAA | 3.85 | ACTTCG | -18.95 | CGTCGG | -68.18 |

TABLE 3-continued

| 6-mer | 6-mer z-score | 6-mer | 6-mer z-score | 6-mer | 6-mer z-score | 6-mer | 6-mer z-score |
|---|---|---|---|---|---|---|---|
| TGATCA | 34.95 | ATCTAG | 3.83 | CTATCG | -18.96 | GGCGCG | -68.24 |
| GAGCCC | 34.9 | GAGATT | 3.8 | GCGCAC | -18.96 | GGGGTG | -68.68 |
| ATCTGG | 34.82 | ACGACA | 3.75 | TCGAAG | -18.97 | CGTCGT | -68.69 |
| AGAAGT | 34.81 | TAGACT | 3.73 | TTATCG | -19.01 | GTCGGT | -68.84 |
| ACTAAC | 34.76 | TGTATG | 3.7 | TAAGTG | -19.03 | TGGGTG | -69.08 |
| TGGAGA | 34.73 | GCTAGT | 3.7 | TGATCG | -19.03 | GTCGTC | -69.14 |
| TAATCA | 34.7 | TAAGCC | 3.7 | CTCGAT | -19.04 | GCGTCG | -69.26 |
| CAACCT | 34.69 | AAAGGT | 3.68 | CTCGAA | -19.13 | CGGGTG | -69.69 |
| GACCAC | 34.64 | CTAAAT | 3.65 | CTCACG | -19.18 | GGGTGG | -69.98 |
| GTAAAA | 34.56 | CAGTGT | 3.61 | GGCTTG | -19.19 | GTGGGC | -70.27 |
| TCTACC | 34.54 | GAGTTC | 3.56 | CGCCGA | -19.19 | CGTGTG | -71.38 |
| GATTAC | 34.54 | AGGGCA | 3.54 | CTTGCT | -19.24 | CGGTGG | -71.52 |
| CCAGTT | 34.52 | CGCTTC | 3.53 | GTAGTC | -19.28 | CGTGCG | -71.83 |
| ACCAGG | 34.5 | TACCGA | 3.51 | CACCGG | -19.31 | GCGGGG | -72.46 |
| GCAACC | 34.48 | TCCTCA | 3.51 | TTTGTT | -19.31 | GTGGGT | -73.21 |
| ACATTT | 34.47 | AGCAAG | 3.5 | TCTGTT | -19.32 | GTCGCG | -73.55 |
| ACTTCC | 34.46 | GAAGCG | 3.49 | TTTACG | -19.34 | GTCGTG | -73.94 |
| AAGTAC | 34.43 | GCCTTA | 3.43 | GTCCCC | -19.35 | GTGGCG | -73.94 |
| ACCTTA | 34.43 | TTAGTT | 3.4 | CGAGGA | -19.35 | GTGGGG | -74.96 |
| TAATTG | 34.26 | ACCGAC | 3.39 | CGGATG | -19.35 | GGTGGG | -75.37 |
| CACCCA | 34.26 | GCAGGA | 3.39 | CCGATG | -19.37 | CGTGGG | -75.74 |
| ATCTTT | 34.13 | ATGCGA | 3.38 | CATCGG | -19.38 | GGGTCG | -76.6 |
| TTAATT | 34.07 | ACGAGC | 3.35 | GGTAGT | -19.38 | GTCGGG | -80.38 |
| TTGCAC | 34.06 | GCAGGT | 3.33 | CCGTGA | -19.41 | GGTCGG | -81.93 |
| CACCCC | 34.06 | AGGGAT | 3.33 | TCCGCC | -19.41 | GGTGTG | -82.57 |
| CATGAT | 34.02 | CAGGGC | 3.29 | TCTCTT | -19.42 | GTGTCG | -84.85 |
| ATAGGT | 33.92 | AAGGGA | 3.26 | GGAGAG | -19.43 | GTGTGG | -90.52 |
| GCTACC | 33.92 | AGCGGC | 3.25 | CATTCG | -19.47 | | |
| ATAGAG | 33.86 | GACCCT | 3.25 | CGAATG | -19.54 | | |
| AGTTCT | 33.81 | CGCCAT | 3.18 | TCTCTC | -19.56 | | |
| TGCTTA | 33.8 | GTGAAA | 3.17 | GGCCAA | -19.57 | | |

As one of skill in the art will appreciate, the rank ordering of the SHM motifs described above provides for a method whereby synthetic gene constructs can be created that are more susceptible to SHM relative to a starting sequence by the replacement of any specific SHM motif with one that has a greater probability of SHM mediated mutagenesis. Conversely synthetic gene constructs can be created that are more resistant to SHM relative to a starting sequence by the replacement of any specific SHM motif with one that has a lower probability of SHM mediated mutagenesis.

In certain embodiments, polynucleotide motifs having rank-ordered z-scores in the top 5% of all equivalent length polynucleotide motifs can be considered SHM "hot spots," and can be inserted into a gene to make a polynucleotide sequence more SHM susceptible. In certain other embodiments, polynucleotide motifs having rank-ordered z-scores in the top 10% of all equivalent length polynucleotide motifs can be considered SHM "hot spots," and can be inserted into a gene to make a polynucleotide sequence more SHM susceptible. In still other embodiments, polynucleotide motifs having rank-ordered z-scores in the top 15% of all equivalent length polynucleotide motifs can be considered SHM "hot spots," and can be inserted into a gene to make a polynucleotide sequence more SHM susceptible. In yet other embodiments, polynucleotide motifs having rank-ordered z-scores in the top 20% of all equivalent length polynucleotide motifs can be considered SHM "hot spots," and can be inserted into a gene to make a polynucleotide sequence more SHM susceptible. In yet still other embodiments, polynucleotide motifs having rank-ordered z-scores in the top 25% of all equivalent length polynucleotide motifs can be considered SHM "hot spots," and can be inserted into a gene to make a polynucleotide sequence more SHM susceptible.

Likewise, polynucleotide motifs having rank-ordered z-scores in the bottom 5% of all equivalent length polynucleotide motifs can be considered SHM "cold spots," and can be inserted into a gene to make a polynucleotide sequence more SHM resistant. In other embodiments, polynucleotide motifs having rank-ordered z-scores in the bottom 10% of all equivalent length polynucleotide motifs can be considered SHM "cold spots," and can be inserted into a gene to make a polynucleotide sequence more SHM resistant. In still other embodiments, polynucleotide motifs having rank-ordered z-scores in the bottom 15% of all equivalent length polynucleotide motifs can be considered SHM "cold spots," and can be inserted into a gene to make a polynucleotide sequence more SHM resistant. In yet other embodiments, polynucleotide motifs having rank-ordered z-scores in the bottom 20% of all equivalent length polynucleotide motifs can be considered SHM "cold spots," and can be inserted into a gene to make a polynucleotide sequence more SHM resistant. In yet still other embodiments, polynucleotide motifs having rank-ordered z-scores in the bottom 25% of all equivalent length polynucleotide motifs can be considered SHM "cold spots," and can be inserted into a gene to make a polynucleotide sequence more SHM resistant.

The position or reading frame of a hot spot or cold spot is also an important factor governing whether SHM mediated mutagenesis that can result in a mutation that is silent with regards to the resulting amino acid sequence, or causes conservative, semi-conservative or non conservative changes at the amino acid level. As discussed below, these design parameters can be manipulated to further enhance the relative susceptibility or resistance of a nucleotide sequence to SHM.

Thus both the degree of SHM recruitment and the reading frame of the motif are considered in the design of SHM susceptiable and SHM resistant polynucleotide sequences.

An optimized polynucleotide sequence has been made "susceptible for SHM" or "hot" if the polynucleotide sequence, or a portion thereof, has been altered, or designed, to increase the frequency and/or location of hot spots within the open reading frame and/or has been altered, or designed, to decrease the frequency and/or location of cold spots within the open reading frame of the polynucleotide sequence compared to the wild type polynucleotide sequence.

Conversely, an optimized polynucleotide sequence has been made "resistant to SHM" or "cold" if the polynucleotide sequence, or a portion thereof, has been altered to decrease the frequency and/or location of hot spots within the open reading frame of the polynucleotide sequence, and/or has been altered, or designed, to increase the frequency and/or location of cold spots within the open reading frame of the polynucleotide sequence compared to the wild type polynucleotide sequence.

Provided herein is a strategy to design nucleotide templates to either maximize or minimize the tendency of a polynucleotide to undergo SHM, while at the same time maximizing protein expression, RNA stability, and the presence of conveniently located restriction enzyme sites.

Also provided herein are synthetic versions of a polynucleotide that are altered to either enhance, or decrease the impact of SHM on the rate of mutagenesis of that polynucleotide compared to its wild type's susceptibility to undergo SHM (i.e., SHM susceptible or SHM resistent).

Also provided herein are synthetic versions of a polynucleotide in which specific regions of a polynucleotide have been optimized to be either SHM resistant or SHM susceptible. In one embodiment, functional portion and/or regions of a polynucleotide can be hot (e.g., ligand binding, enzymatic activity, etc.) while other regions (e.g., those needed for structural folding, conformation, etc.) of a polynucleotide can be made cold.

The SHM susceptible sequences facilitate the rapid evolution and selection of improved mutant versions of proteins and the system combines the power of rational design with accelerated random mutagenesis and directed evolution.

Also included in the invention are SHM resistant polynucleotide sequences that allow for conserved regions to be resistant to SHM-mediated mutagenesis, while simultaneously targeting desired sequences for increased susceptibility to SHM-mediated mutagenesis. Thus it is possible to optimize particular functional portions and/or regions of a polynucleotide that appear to be directly involved in a functional attribute of a protein encoded by the polynucleotide.

In one non-limiting example, nucleotides to be optimized can encode amino acids that can lie within, or within about 5 Å of a specific functional or structural attribute of interest. Specific examples of functional portions and/or regions include, but are not limited to, amino acids within CDRs of antibodies, binding pockets of receptors, catalytic clefts of enzymes, protein-protein interaction domains, of co-factors, allosteric binding sites, etc.

Polynucleotides for which these methods are applicable include any polynucleotide sequence that can be transcribed and a functional assay devised for screening. Preferred polynucleotide sequences include those encoding proteins, polypeptides and peptides such as, for example, specific binding members, antibodies or fragment thereof, an antibody heavy chain or portion thereof, an antibody light chain or portion thereof, an intrabodies, selectable marker genes, enzymes, receptors, peptide growth factors and hormones, co-factors, and toxins.

Other non-limiting examples of molecules for use herein include polynucleotides that have enzymatic or binding activity without the need for translation into a protein or peptide sequence, such polynucleotides including for example, enzymatic nucleic acids, antisense nucleic acids, triplex forming oligonucleotides, 2,5-A chimeras, RsiNA, dsRNA, allozymes, abd aptamers.

Biologically active molecules of the invention also include molecules capable of modulating the pharmacokinetics and/or pharmacodynamics of other biologically active molecules, for example, lipids and polymers such as polyamines, polyamides, polyethylene glycol and other polyethers. For example, polypeptides are those such as, for example, VEGF, VEGF receptor, Diptheria toxin subunit A, *B. pertussis* toxin, CC chemokines (e.g., CCL1-CCL28), CXC chemokines (e.g., CXCL1-CXCL16), C chemokines (e.g., XCL1 and XCL2) and $CX_3C$ chemokines (e.g., $CX_3CL1$), IFN-gamma, IFN-alpha, IFN-beta, TNF-alpha, TNF-beta, IL-1, IL-2, IL-3, IL-4, IL-5, IL-6, IL-7, IL-10, IL-12, IL-13, IL-15, TGF-beta, TGF-alpha, GM-CSF, G-CSF, M-CSF, TPO, EPO, human growth factor, fibroblast growth factor, nuclear co-factors, Jak and Stat family members, G-protein signaling molecules such as chemokine receptors, JNK, Fos-Jun, NF-κB, I-κB, CD40, CD4, CD8, B7, CD28 and CTLA-4.

IV. Strategies for Designing Polynucleotide Sequences that are SHM Resistant or SHM Susceptible The design and use of SHM optimized sequences is described in priority U.S. application No. 60/902,414.

One strategy for altering the ability of a polynucleotide to undergo SHM is through altering the codon usage to modulate SHM hot spot and/or cold spot density, this approach enables hot spot density to be increased or decreased without impact on the primary amino acid sequence of the protein of interest.

In addition to optimizing hot spot and/or cold spot density, it is also desirable to consider the following characteristics such that the optimized polynucleotides are efficiently translated, and stable in a host system. As discussed below, these design parameters can be conveniently optimized using an iterative computer algorithm.

The density of CpG dinucleotides motifs: Excessive CG motifs can result in gene methylation leading to gene silencing, and can be normalized to the density found in highly transcribed gene in the host system in question (see for example, Kameda et al., Biochem. Biophys. Res. Commun. (2006) 349(4): 1269-1277).

The ability of single stranded sequences to form stem-loop structures: the formation of stem-loop structures can result inefficient transcription and or translation, particularly when located near the 5' region of the coding frame (see, e.g., Zuker M., Mfold web server for nucleic acid folding and hybridization prediction. Nucl. Acid Res. (2003); 31(13): 3406-3415). Stem loop structure formation can be minimized by avoiding repetitive or palindromic stretches of greater than 6 nucleotides, for example, near the 5' end. Alternatively, longer stems are acceptable if the loop contains greater than about 25 nucleotides (nt).

Codon Usage: Appropriate codon usage, i.e., the use of codons that encode for more common and frequently used tRNAs, rather than very rare tRNAs, is important to enable efficient translation in the expression system being used (see generally Nakamura et al., Nuc. Acid. Res. (2000) 28 (1): 292, "Codon usage tabulated from international DNA sequence databases: status for the year 2000;" which includes codon frequency tables of each of the complete protein sequences in the GenBank DNA sequence database as of 2000). Generally codon usage is more important near the 5' end of the gene where transcription of the polynucleotide begins and rare codons should be avoided in this region where ever possible. Preferred is the elimination of about 80% or more of the codons that are used less than 10% of the time within the coding frame of the expressed genes in the organism of interest.

GC content: Generally this should be matched, to the GC content of highly expressed genes in the host organism, for example in mammalian systems GC content should be less than about 60%.

Restriction sites: Restriction sites should be placed judiciously where desired. Similarly, important restriction sites (i.e. those that are intended to be used to clone the entire gene, or other genes) within a polynucleotide should be removed where not desired by altering wobble positions.

Stretches of the same nucleotide: Minimize or eliminate stretches of the same nucleotide to less six (6) contiguous nucleotides.

In addition, expression can be further optimized by including a Kozak consensus sequence [i.e., (a/g)cc(a/g)ccATGg] at the start codon. Kozak consensus sequences useful for this purpose are known in the art (Mantyh et al. PNAS 92: 2662-2666 (1995); Mantyh et al. Prot. Exp. & Purif. 6,124 (1995)).

Non-preferred codon usage: Avoid or minimize the usage of certain codons ("non preferred SHM codons") that can be mutated in one step to create a stop codon. "Non preferred codons" include, UGG (Trp), UGC (Cys), UCA (Ser), UCG (Ser), CAA, (Q) GAA (Glu) and CAG (Gln).

Beyond sequence specific constraints within the coding sequence of the polynucleotide of interest, additional design criteria for engineering a polynucleotide sequence with altered susceptibility to SHM includes the following factors:

The choice of promoter; a strong promoter will generally induce a higher rate of transcription resulting a higher overall rate of mutagenesis compared to a weaker promoter. Further, an inducible promoter, such as the tet-promoter enables expression, and hence SHM, to be inducibly controlled, to switch on, or off, transcription and mutagenesis of the polynucleotide of interest. Gossen and Bujard, Tight control of gene expression in mammalian cells by tetracycline-responsive promoters. Proc Natl Acad Sci USA. 1992 Jun. 15; 89(12):5547-51; Gossen et al., Transcriptional activation by tetracyclines in mammalian cells. Science. 1995 Jun. 23; 268(5218):1766-9.

The location of the coding sequence relative to the transcriptional start point; generally for high level mutagenesis, the polynucleotide of interest should be located between about 50 nucleotides, and 2 kb of the transcriptional start site.

One convenient approach to optimizing a polynucleotide sequence to SHM, involves analyzing the corresponding amino acid sequence of interest via a computer algorithm that compares and scores (according to the parameters above) possible alternative polynucleotides sequences that can be used, via alternative codon usage to encode for the amino acid sequence of interest. By iteratively replacing codons, or groups of codons (tiles, or SHM motifs) with progressively preferred sequences it is possible to computationally evolve a polynucleotide sequence with desired properties. Specifically, for example, a sequence that is SHM susceptiable, or that is resistant to SHM, and yet also exhibits reasonable translational efficiency, stability, minimizes restriction sites and avoids rare codons in the particular organism of interest.

Using this approach, a library of files can be generated that is based on the starting amino acid or polynucleotide sequence. In one non limiting example of the analysis and optimization strategy, the library can be created based on the analysis of groups of 9 nucleotides, corresponding to 3 codons (a "tile"). Each tile can be scored for the attributes described above, to create an initial library data set of tiles, containing hundreds of thousands of 9-mer permutations, and their respective scores.

A representative sample of a section of the library file is shown in Table 4 which shows the potential diversity in nucleotide sequences arising from alternative codon usage for just the three amino acids, Serine (S), Arginine (R) and Leucine (L). A person of skill in the art readily appreciates that a complete set of files can be readily assembled for all possible amino acid combinations using known codon usage patterns.

TABLE 4

Representative polynucleotide diversity encoding a three amino acid sequence (Ser Arg Leu)

| 3-mer AA | Potential nucleotides | SEQ ID NO | Hot-spots | Cold-spots | CpG | MaxNt(πp(AA)) | Log |
|---|---|---|---|---|---|---|---|
| SRL | AGTCGACTT | 68 | 0 | 2 | 1 | 1 | -5 |
| SRL | AGTCGACTG | 69 | 0 | 2 | 1 | 1 | -3 |
| SRL | AGTCGATTA | 70 | 0 | 1 | 1 | 2 | -5 |
| SRL | AGTCGACTA | 71 | 0 | 2 | 1 | 1 | -5 |
| SRL | AGTCGACTC | 72 | 0 | 3 | 1 | 1 | -4 |
| SRL | AGTCGATTG | 73 | 0 | 1 | 1 | 2 | -5 |
| SRL | AGTAGGCTT | 74 | 2 | 0 | 0 | 2 | -4 |
| SRL | AGTAGGCTG | 75 | 2 | 0 | 0 | 2 | -2 |
| SRL | AGTAGGTTA | 76 | 2 | 0 | 0 | 2 | -4 |
| SRL | AGTAGGCTA | 77 | 2 | 0 | 0 | 2 | -4 |
| SRL | AGTAGGCTC | 78 | 2 | 1 | 0 | 2 | -3 |
| SRL | AGTAGGTTG | 79 | 2 | 0 | 0 | 2 | -4 |
| SRL | AGTCGTCTT | 80 | 0 | 2 | 1 | 1 | -5 |
| SRL | AGTCGTCTG | 81 | 0 | 2 | 1 | 1 | -3 |
| SRL | AGTCGTTTA | 82 | 0 | 1 | 1 | 3 | -5 |
| SRL | AGTCGTCTA | 83 | 0 | 2 | 1 | 1 | -5 |
| SRL | AGTCGTCTC | 84 | 0 | 3 | 1 | 1 | -4 |
| SRL | AGTCGTTTG | 85 | 0 | 1 | 1 | 3 | -5 |
| SRL | AGTAGACTT | 86 | 1 | 1 | 0 | 1 | -4 |
| SRL | AGTAGACTG | 87 | 1 | 1 | 0 | 1 | -2 |
| SRL | AGTAGATTA | 88 | 1 | 0 | 0 | 2 | -4 |
| SRL | AGTAGACTA | 89 | 1 | 1 | 0 | 1 | -4 |
| SRL | AGTAGACTC | 90 | 1 | 2 | 0 | 1 | -3 |
| SRL | AGTAGATTG | 91 | 1 | 0 | 0 | 2 | -4 |
| SRL | AGTCGGCTT | 92 | 1 | 1 | 1 | 2 | -4 |
| SRL | AGTCGGCTG | 93 | 1 | 1 | 1 | 2 | -2 |
| SRL | AGTCGGTTA | 94 | 1 | 1 | 1 | 2 | -4 |
| SRL | AGTCGGCTA | 95 | 1 | 1 | 1 | 2 | -4 |
| SRL | AGTCGGCTC | 96 | 1 | 2 | 1 | 2 | -3 |
| SRL | AGTCGGTTG | 97 | 1 | 1 | 1 | 2 | -4 |
| SRL | AGTCGCCTT | 98 | 0 | 2 | 1 | 2 | -4 |
| SRL | AGTCGCCTG | 99 | 0 | 2 | 1 | 2 | -2 |
| SRL | AGTCGCTTA | 100 | 0 | 1 | 1 | 2 | -4 |
| SRL | AGTCGCCTA | 101 | 0 | 2 | 1 | 2 | -4 |
| SRL | AGTCGCCTC | 102 | 0 | 3 | 1 | 2 | -3 |
| SRL | AGTCGCTTG | 103 | 0 | 1 | 1 | 2 | -4 |
| SRL | TCACGACTT | 104 | 0 | 1 | 1 | 1 | -5 |

TABLE 4-continued

Representative polynucleotide diversity encoding a three amino acid sequence (Ser Arg Leu)

| 3-mer AA | Potential nucleotides | SEQ ID NO | Hot-spots | Cold-spots | CpG | MaxNt(πp(AA)) | Log |
|---|---|---|---|---|---|---|---|
| SRL | TCACGACTG | 105 | 0 | 1 | 1 | 1 | -3 |
| SRL | TCACGATTA | 106 | 0 | 0 | 1 | 2 | -5 |
| SRL | TCACGACTA | 107 | 0 | 1 | 1 | 1 | -5 |
| SRL | TCACGACTC | 108 | 0 | 2 | 1 | 1 | -4 |
| SRL | TCACGATTG | 109 | 0 | 0 | 1 | 2 | -5 |
| SRL | TCAAGGCTT | 110 | 1 | 0 | 0 | 2 | -4 |
| SRL | TCAAGGCTG | 111 | 1 | 0 | 0 | 2 | -2 |
| SRL | TCAAGGTTA | 112 | 1 | 0 | 0 | 2 | -4 |
| SRL | TCAAGGCTA | 113 | 1 | 0 | 0 | 2 | -4 |
| SRL | TCAAGGCTC | 114 | 1 | 1 | 0 | 2 | -3 |
| SRL | TCAAGGTTG | 115 | 1 | 0 | 0 | 2 | -4 |
| SRL | TCACGTCTT | 116 | 0 | 1 | 1 | 1 | -5 |
| SRL | TCACGTCTG | 117 | 0 | 1 | 1 | 1 | -3 |
| SRL | TCACGTTTA | 118 | 0 | 0 | 1 | 3 | -5 |
| SRL | TCACGTCTA | 119 | 0 | 1 | 1 | 1 | -5 |
| SRL | TCACGTCTC | 120 | 0 | 2 | 1 | 1 | -4 |
| SRL | TCACGTTTG | 121 | 0 | 0 | 1 | 3 | -5 |
| SRL | TCAAGACTT | 122 | 0 | 1 | 0 | 2 | -4 |
| SRL | TCAAGACTG | 123 | 0 | 1 | 0 | 2 | -2 |
| SRL | TCAAGATTA | 124 | 0 | 0 | 0 | 2 | -4 |
| SRL | TCAAGACTA | 125 | 0 | 1 | 0 | 2 | -4 |
| SRL | TCAAGACTC | 126 | 0 | 2 | 0 | 2 | -3 |
| SRL | TCAAGATTG | 127 | 0 | 0 | 0 | 2 | -4 |
| SRL | TCACGGCTT | 128 | 1 | 0 | 1 | 2 | -4 |
| SRL | TCACGGCTG | 129 | 1 | 0 | 1 | 2 | -2 |
| SRL | TCACGGTTA | 130 | 1 | 0 | 1 | 2 | -4 |
| SRL | TCACGGCTA | 131 | 1 | 0 | 1 | 2 | -4 |
| SRL | TCACGGCTC | 132 | 1 | 1 | 1 | 2 | -3 |
| SRL | TCACGGTTG | 133 | 1 | 0 | 1 | 2 | -4 |
| SRL | TCACGCCTT | 134 | 0 | 1 | 1 | 2 | -4 |
| SRL | TCACGCCTG | 135 | 0 | 1 | 1 | 2 | -2 |
| SRL | TCACGCTTA | 136 | 0 | 0 | 1 | 2 | -4 |
| SRL | TCACGCCTA | 137 | 0 | 1 | 1 | 2 | -4 |
| SRL | TCACGCCTC | 138 | 0 | 2 | 1 | 2 | -3 |
| SRL | TCACGCTTG | 139 | 0 | 0 | 1 | 2 | -4 |
| SRL | AGCCGACTT | 140 | 1 | 2 | 1 | 2 | -5 |

TABLE 4-continued

Representative polynucleotide diversity encoding a three amino acid sequence (Ser Arg Leu)

| 3-mer AA | Potential nucleotides | SEQ ID NO | Hot-spots | Cold-spots | CpG | MaxNt | Log (πp (AA)) |
|---|---|---|---|---|---|---|---|
| SRL | AGCCGACTG | 141 | 1 | 2 | 1 | 2 | −3 |
| SRL | AGCCGATTA | 142 | 1 | 1 | 1 | 2 | −5 |
| SRL | AGCCGACTA | 143 | 1 | 2 | 1 | 2 | −5 |
| SRL | AGCCGACTC | 144 | 1 | 3 | 1 | 2 | −4 |
| SRL | AGCCGATTG | 145 | 1 | 1 | 1 | 2 | −5 |
| SRL | AGCAGGCTT | 146 | 2 | 0 | 0 | 2 | −4 |
| SRL | AGCAGGCTG | 147 | 2 | 0 | 0 | 2 | −2 |
| SRL | AGCAGGTTA | 148 | 2 | 0 | 0 | 2 | −4 |
| SRL | AGCAGGCTA | 149 | 2 | 0 | 0 | 2 | −4 |
| SRL | AGCAGGCTC | 150 | 2 | 1 | 0 | 2 | −3 |
| SRL | AGCAGGTTG | 151 | 2 | 0 | 0 | 2 | −4 |
| SRL | AGCCGTCTT | 152 | 1 | 2 | 1 | 2 | −5 |
| SRL | AGCCGTCTG | 153 | 1 | 2 | 1 | 2 | −3 |
| SRL | AGCCGTTTA | 154 | 1 | 1 | 1 | 3 | −5 |
| SRL | AGCCGTCTA | 155 | 1 | 2 | 1 | 2 | −5 |
| SRL | AGCCGTCTC | 156 | 1 | 3 | 1 | 2 | −4 |
| SRL | AGCCGTTTG | 157 | 1 | 1 | 1 | 3 | −5 |
| SRL | AGCAGACTT | 158 | 1 | 1 | 0 | 1 | −4 |
| SRL | AGCAGACTG | 159 | 1 | 1 | 0 | 1 | −2 |
| SRL | AGCAGATTA | 160 | 1 | 0 | 0 | 2 | −4 |
| SRL | AGCAGACTA | 161 | 1 | 1 | 0 | 1 | −4 |
| SRL | AGCAGACTC | 162 | 1 | 2 | 0 | 1 | −3 |
| SRL | AGCAGATTG | 163 | 1 | 0 | 0 | 2 | −4 |
| SRL | AGCCGGCTT | 164 | 2 | 1 | 1 | 2 | −4 |
| SRL | AGCCGGCTG | 165 | 2 | 1 | 1 | 2 | −2 |
| SRL | AGCCGGTTA | 166 | 2 | 1 | 1 | 2 | −4 |
| SRL | AGCCGGCTA | 167 | 2 | 1 | 1 | 2 | −4 |
| SRL | AGCCGGCTC | 168 | 2 | 2 | 1 | 2 | −3 |
| SRL | AGCCGGTTG | 169 | 2 | 1 | 1 | 2 | −4 |
| SRL | AGCCGCCTT | 170 | 1 | 2 | 1 | 2 | −4 |
| SRL | AGCCGCCTG | 171 | 1 | 2 | 1 | 2 | −2 |
| SRL | AGCCGCTTA | 172 | 1 | 1 | 1 | 2 | −4 |
| SRL | AGCCGCCTA | 173 | 1 | 2 | 1 | 2 | −4 |
| SRL | AGCCGCCTC | 174 | 1 | 3 | 1 | 2 | −3 |
| SRL | AGCCGCTTG | 175 | 1 | 1 | 1 | 2 | −4 |
| SRL | TCGCGACTT | 176 | 0 | 1 | 2 | 1 | −6 |
| SRL | TCGCGACTG | 177 | 0 | 1 | 2 | 1 | −4 |

TABLE 4-continued

Representative polynucleotide diversity encoding a three amino acid sequence (Ser Arg Leu)

| 3-mer AA | Potential nucleotides | SEQ ID NO | Hot-spots | Cold-spots | CpG | MaxNt | Log (πp (AA)) |
|---|---|---|---|---|---|---|---|
| SRL | TCGCGATTA | 178 | 0 | 0 | 2 | 2 | −6 |
| SRL | TCGCGACTA | 179 | 0 | 1 | 2 | 1 | −6 |
| SRL | TCGCGACTC | 180 | 0 | 2 | 2 | 1 | −5 |
| SRL | TCGCGATTG | 181 | 0 | 0 | 2 | 2 | −6 |
| SRL | TCGAGGCTT | 182 | 1 | 1 | 1 | 2 | −5 |
| SRL | TCGAGGCTG | 183 | 1 | 1 | 1 | 2 | −3 |
| SRL | TCGAGGTTA | 184 | 1 | 1 | 1 | 2 | −5 |
| SRL | TCGAGGCTA | 185 | 1 | 1 | 1 | 2 | −5 |
| SRL | TCGAGGCTC | 186 | 1 | 2 | 1 | 2 | −4 |
| SRL | TCGAGGTTG | 187 | 1 | 1 | 1 | 2 | −5 |
| SRL | TCGCGTCTT | 188 | 0 | 1 | 2 | 1 | −6 |
| SRL | TCGCGTCTG | 189 | 0 | 1 | 2 | 1 | −4 |
| SRL | TCGCGTTTA | 190 | 0 | 0 | 2 | 3 | −6 |
| SRL | TCGCGTCTA | 191 | 0 | 1 | 2 | 1 | −6 |
| SRL | TCGCGTCTC | 192 | 0 | 2 | 2 | 1 | −5 |
| SRL | TCGCGTTTG | 193 | 0 | 0 | 2 | 3 | −6 |
| SRL | TCGAGACTT | 194 | 0 | 2 | 1 | 1 | −5 |
| SRL | TCGAGACTG | 195 | 0 | 2 | 1 | 1 | −3 |
| SRL | TCGAGATTA | 196 | 0 | 1 | 1 | 2 | −5 |
| SRL | TCGAGACTA | 197 | 0 | 2 | 1 | 1 | −5 |
| SRL | TCGAGACTC | 198 | 0 | 3 | 1 | 1 | −4 |
| SRL | TCGAGATTG | 199 | 0 | 1 | 1 | 2 | −5 |
| SRL | TCGCGGCTT | 200 | 1 | 0 | 2 | 2 | −5 |
| SRL | TCGCGGCTG | 201 | 1 | 0 | 2 | 2 | −3 |
| SRL | TCGCGGTTA | 202 | 1 | 0 | 2 | 2 | −5 |
| SRL | TCGCGGCTA | 203 | 1 | 0 | 2 | 2 | −5 |
| SRL | TCGCGGCTC | 204 | 1 | 1 | 2 | 2 | −4 |
| SRL | TCGCGGTTG | 205 | 1 | 0 | 2 | 2 | −5 |
| SRL | TCGCGCCTT | 206 | 0 | 1 | 2 | 2 | −5 |
| SRL | TCGCGCCTG | 207 | 0 | 1 | 2 | 2 | −3 |
| SRL | TCGCGCTTA | 208 | 0 | 0 | 2 | 2 | −5 |
| SRL | TCGCGCCTA | 209 | 0 | 1 | 2 | 2 | −5 |
| SRL | TCGCGCCTC | 210 | 0 | 2 | 2 | 2 | −4 |
| SRL | TCGCGCTTG | 211 | 0 | 0 | 2 | 2 | −5 |
| SRL | TCCCGACTT | 212 | 0 | 2 | 1 | 3 | −5 |
| SRL | TCCCGACTG | 213 | 0 | 2 | 1 | 3 | −3 |

TABLE 4-continued

Representative polynucleotide diversity encoding a three amino acid sequence (Ser Arg Leu)

| 3-mer AA | Potential nucleotides | SEQ ID NO | Hot-spots | Cold-spots | CpG | MaxNt | Log (πp(AA)) |
|---|---|---|---|---|---|---|---|
| SRL | TCCCGATTA | 214 | 0 | 1 | 1 | 3 | −5 |
| SRL | TCCCGACTA | 215 | 0 | 2 | 1 | 3 | −5 |
| SRL | TCCCGACTC | 216 | 0 | 3 | 1 | 3 | −4 |
| SRL | TCCCGATTG | 217 | 0 | 1 | 1 | 3 | −5 |
| SRL | TCCAGGCTT | 218 | 1 | 0 | 0 | 2 | −4 |
| SRL | TCCAGGCTG | 219 | 1 | 0 | 0 | 2 | −2 |
| SRL | TCCAGGTTA | 220 | 1 | 0 | 0 | 2 | −4 |
| SRL | TCCAGGCTA | 221 | 1 | 0 | 0 | 2 | −4 |
| SRL | TCCAGGCTC | 222 | 1 | 1 | 0 | 2 | −3 |
| SRL | TCCAGGTTG | 223 | 1 | 0 | 0 | 2 | −4 |
| SRL | TCCCGTCTT | 224 | 0 | 2 | 1 | 3 | −5 |
| SRL | TCCCGTCTG | 225 | 0 | 2 | 1 | 3 | −3 |
| SRL | TCCCGTTTA | 226 | 0 | 1 | 1 | 3 | −5 |
| SRL | TCCCGTCTA | 227 | 0 | 2 | 1 | 3 | −5 |
| SRL | TCCCGTCTC | 228 | 0 | 3 | 1 | 3 | −4 |
| SRL | TCCCGTTTG | 229 | 0 | 1 | 1 | 3 | −5 |
| SRL | TCCAGACTT | 230 | 0 | 1 | 0 | 2 | −4 |
| SRL | TCCAGACTG | 231 | 0 | 1 | 0 | 2 | −2 |
| SRL | TCCAGATTA | 232 | 0 | 0 | 0 | 2 | −4 |
| SRL | TCCAGACTA | 233 | 0 | 1 | 0 | 2 | −4 |
| SRL | TCCAGACTC | 234 | 0 | 2 | 0 | 2 | −3 |
| SRL | TCCAGATTG | 235 | 0 | 0 | 0 | 2 | −4 |
| SRL | TCCCGGCTT | 236 | 1 | 1 | 1 | 3 | −4 |
| SRL | TCCCGGCTG | 237 | 1 | 1 | 1 | 3 | −2 |
| SRL | TCCCGGTTA | 238 | 1 | 1 | 1 | 3 | −4 |
| SRL | TCCCGGCTA | 239 | 1 | 1 | 1 | 3 | −4 |
| SRL | TCCCGGCTC | 240 | 1 | 2 | 1 | 3 | −3 |
| SRL | TCCCGGTTG | 241 | 1 | 1 | 1 | 3 | −4 |
| SRL | TCCCGCCTT | 242 | 0 | 2 | 1 | 3 | −4 |
| SRL | TCCCGCCTG | 243 | 0 | 2 | 1 | 3 | −2 |
| SRL | TCCCGCTTA | 244 | 0 | 1 | 1 | 3 | −4 |
| SRL | TCCCGCCTA | 245 | 0 | 2 | 1 | 3 | −4 |
| SRL | TCCCGCCTC | 246 | 0 | 3 | 1 | 3 | −3 |
| SRL | TCCCGCTTG | 247 | 0 | 1 | 1 | 3 | −4 |
| SRL | TCTCGACTT | 248 | 0 | 2 | 1 | 1 | −5 |
| SRL | TCTCGACTG | 249 | 0 | 2 | 1 | 1 | −3 |
| SRL | TCTCGATTA | 250 | 0 | 1 | 1 | 2 | −5 |

TABLE 4-continued

Representative polynucleotide diversity encoding a three amino acid sequence (Ser Arg Leu)

| 3-mer AA | Potential nucleotides | SEQ ID NO | Hot-spots | Cold-spots | CpG | MaxNt | Log (πp(AA)) |
|---|---|---|---|---|---|---|---|
| SRL | TCTCGACTA | 251 | 0 | 2 | 1 | 1 | −5 |
| SRL | TCTCGACTC | 252 | 0 | 3 | 1 | 1 | −4 |
| SRL | TCTCGATTG | 253 | 0 | 1 | 1 | 2 | −5 |
| SRL | TCTAGGCTT | 254 | 1 | 0 | 0 | 2 | −4 |
| SRL | TCTAGGCTG | 255 | 1 | 0 | 0 | 2 | −2 |
| SRL | TCTAGGTTA | 256 | 1 | 0 | 0 | 2 | −4 |
| SRL | TCTAGGCTA | 257 | 1 | 0 | 0 | 2 | −4 |
| SRL | TCTAGGCTC | 258 | 1 | 1 | 0 | 2 | −3 |
| SRL | TCTAGGTTG | 259 | 1 | 0 | 0 | 2 | −4 |
| SRL | TCTCGTCTT | 260 | 0 | 2 | 1 | 1 | −5 |
| SRL | TCTCGTCTG | 261 | 0 | 2 | 1 | 1 | −3 |
| SRL | TCTCGTTTA | 262 | 0 | 1 | 1 | 3 | −5 |
| SRL | TCTCGTCTA | 263 | 0 | 2 | 1 | 1 | −5 |
| SRL | TCTCGTCTC | 264 | 0 | 3 | 1 | 1 | −4 |
| SRL | TCTCGTTTG | 265 | 0 | 1 | 1 | 3 | −5 |
| SRL | TCTAGACTT | 266 | 0 | 1 | 0 | 1 | −4 |
| SRL | TCTAGACTG | 267 | 0 | 1 | 0 | 1 | −2 |
| SRL | TCTAGATTA | 268 | 0 | 0 | 0 | 2 | −4 |
| SRL | TCTAGACTA | 269 | 0 | 1 | 0 | 1 | −4 |
| SRL | TCTAGACTC | 270 | 0 | 2 | 0 | 1 | −3 |
| SRL | TCTAGATTG | 271 | 0 | 0 | 0 | 2 | −4 |
| SRL | TCTCGGCTT | 272 | 1 | 1 | 1 | 2 | −4 |
| SRL | TCTCGGCTG | 273 | 1 | 1 | 1 | 2 | −2 |
| SRL | TCTCGGTTA | 274 | 1 | 1 | 1 | 2 | −4 |
| SRL | TCTCGGCTA | 275 | 1 | 1 | 1 | 2 | −4 |
| SRL | TCTCGGCTC | 276 | 1 | 2 | 1 | 2 | −3 |
| SRL | TCTCGGTTG | 277 | 1 | 1 | 1 | 2 | −4 |
| SRL | TCTCGCCTT | 278 | 0 | 2 | 1 | 2 | −4 |
| SRL | TCTCGCCTG | 279 | 0 | 2 | 1 | 2 | −2 |
| SRL | TCTCGCTTA | 280 | 0 | 1 | 1 | 2 | −4 |
| SRL | TCTCGCCTA | 281 | 0 | 2 | 1 | 2 | −4 |
| SRL | TCTCGCCTC | 282 | 0 | 3 | 1 | 2 | −3 |
| SRL | TCTCGCTTG | 283 | 0 | 1 | 1 | 2 | −4 |

Each polynucleotide sequence is ranked based on the following attributes; number of SHM hot and cold motifs, number of CpG motifs, MaxNt (maximum number of nucleotides in a single stretch) and codon usage frequency of the host cell to be used. The term "Log(πp(AA)" contained in the final column of Table 4 was calculated as the log of the product of the individual probabilities of observing each of the amino acids in the trimer, given by the formula:

$$Log(\pi p(AA)=ln(p(codon_{i-1}|amino\ acid_{i-1})*p(codon_i|amino\ acid_i)*p(codon_{i+1}|amino\ acid_{i+1}).$$

Individual probabilities for each amino acid were based on published codon usage patterns in the organism of interest, in this case, for mammalian cells. (See generally Nakamura et al., Nucleic Acid Res. (2000) 28 (1): 292 Codon usage tabulated from international DNA sequence databases: status for the year 2000).

As can be readily seen from the Table above, codon usage diversity alone enables polynucleotide sequences to be created that vary widely in their susceptibility to somatic hypermutation, as measured by the number of hot or cold spots present within the sequence.

This analysis readily identifies potential combinations of codons that are optimized for SHM and minimize CpGs and use optimal codons for efficient translation. For example, the sequences listed below represent top ranking hot sequences because they comprise the maximum number of hot spots and no cold spots.

TABLE 5

Top Hot Spot Sequences

| 3-mer AA | Potential nucleo-tides | SEQ ID NO | Hot Spots | Cold Spots | CpG | MaxNt | Log (np (AA)) |
|---|---|---|---|---|---|---|---|
| SRL | AGTAGGCTT | 284. | 2 | 0 | 0 | 2 | -4 |
| SRL | AGTAGGCTG | 285. | 2 | 0 | 0 | 2 | -2 |
| SRL | AGTAGGTTA | 286. | 2 | 0 | 0 | 2 | -4 |
| SRL | AGTAGGCTA | 287. | 2 | 0 | 0 | 2 | -4 |
| SRL | AGCAGGCTT | 288. | 2 | 0 | 0 | 2 | -4 |
| SRL | AGCAGGCTG | 289. | 2 | 0 | 0 | 2 | -2 |
| SRL | AGCAGGTTA | 290. | 2 | 0 | 0 | 2 | -4 |
| SRL | AGCAGGCTA | 291. | 2 | 0 | 0 | 2 | -4 |
| SRL | AGCAGGTTG | 292. | 2 | 0 | 0 | 2 | -4 |
| SRL | AGTAGGTTG | 293. | 2 | 0 | 0 | 2 | -4 |

Of these, the sequences AGTAGGCTG (SEQ ID NO: 285) and AGCAGGCTG (SEQ ID NO: 289) are preferred because they encompass codons with a higher frequency of use in mammalian cells.

Having defined and scored all possible 9-mer nucleotide tiles, it is possible to scan through a starting amino acid or nucleotide template, identifying positions in the gene/protein that can be improved by substitution from the tile library. This process can be conveniently completed using a computer algorithm, such as the perl program SHMredesign.pl; the code of which is shown below:

```
#! /usr/bin/perl
############
#
#       by PM Bowers
#       Apr 15th 2006
#       Anaptys Biosciences Inc.
#
#       A program to redesign protein and nucleic acid sequences to be hot or cold
to SHM
#
############
#################################################################################
#################
#
#       Read in the genetic code, amino acids, and mammalian codon usage frequencies
#
#       $cod_aa{ }          ->      mapping of codon to amino acid
#       $cod_anti{ }        ->      mapping of codon to its opposite strand sequence
#       $codnum{ }          ->      frequency per 1000 of observing the codon in mammals
#       $tot_cod{ }         ->      frequency per 1000 of observing that codon in mammals, given
the identity of the amino acid
#       $aa cod { } { }     ->      maps an amino acid to its codons with the frequency found in
mammalian genes
#################################################################################
###############
open(GENE, ." /geneticcode.txt");
while (<GENE>) {
        if (/^ (\S+) \s+ (\S+) \s+ (\S+) \s+ (\S+) \t (\d+) \t (\d+) /) {
          $one=$1; $four=$4; $five=$5; $six=$6; $thr=$3;
          $cod_aa{$one}=$thr;
          $cod_anti{$one}=$four;
          $codnum{$one}=$five;
          $tot_cod{$one}=int(1000*$five/$six);
          if (!defined($i{$cod_aa{$one}})) { $i{$cod aa{$one}}=1 }
          for ($j=$i{$cod_aa{$one}}; $j<=$i{$cod_aa{$one}}+$tot_cod{$one}; $j++) {
                  $aa_cod{$thr}{$j}=$one;
```

-continued

```
                }
                $i{$cod_aa{$one}}=$j;
   }
}
close (GENE);
################################################################################
###############
#
#       Read in motifs that are hot or cold to SHM, for assessing output only
#
#       $hot{ }             ->   hash containing a list of 4-mer hot spots
#       $cold{ }            ->   hash containing a list of 3-mer cold spots
#
################################################################################
###############
open(SHM, . " /hotncold.txt");
while (<SHM>) {
   if (/^ (\S+) \s+ (\S+)/) {
        $one=$1; $two=$2;
        if ($one eq 'COLD') {
                $cold{$two}++;
        }
        if ($one eq 'HOT') {
                $hot{$two}++;
        }
   }
}
close (SHM);
################################################################################
###############
#
#       Read in a library of all 9-mer nucleotide motifs that have been
#       scored for several properties, including # hot SHM motifs, # cold spots, #
CpG motifs,
#       the length of the longest uninterupted stretch of the same nucleotide, and a
codon usage score
#
#       $hotsc{ } { }                 ->      hash mapping the tiles 3-mer aa and 9-mer na to the number
of SHM hot spots it contains
#       $coldsc{ } { }                ->      hash mapping the tiles 3-mer aa and 9-mer na to the number
of SHM cold spots it contains
#       $cgsc{ } { }                  ->      hash mapping the tiles 3-mer aa and 9-mer na to the number
of CpG motifs it contains
#       $longsc{ } { }                ->      hash mapping the tiles 3-mer aa and 9-mer na to the length
of its longest stretch of the same na
#       $codindexsc{ } { }            ->      hash mapping the tiles 3-mer aa and 9-mer na to its
aggregate codon usage score
#
################################################################################
###############
open(LIB, "gunzip -c ./3mer_library.txt.gz |");
while  (<LIB>) {
   if    (/^ (\S+) \t (\S+) \t (\d+) \t (\d+) \t (\d+) \t (\d+) \t (\S+)/) {
                  $hotsc{$1}{$2}=$3;
                  $coldsc{$1}{$2}=$4;
                  $cgsc{$1}{$2}=$5;
                  $longsc{$1}{$2}=$6;
                  $codindexsc{$1}{$2}=$7;
   }
}
close (LIB) ;
################################################################################
############
#
#       Program begins by reading in a fasta-like file containing a amino acid or
nucleic acid sequence
#       and a second line that contains design instructions for each position in the
construct
#       '+'             make this position hot to SHM
#       '-'             make this position cold to SHM
#       '.'             this position is neutral to SHM
#
#       Usage:    ./SHMdesign.pl inputfile.fasta A/N
#       where either A or N is given to indicate an amino acid or nucleic acid
sequence
#
#       $seq    ->    captures the sequence vector
#       $change    ->    captures the design change vector
#
################################################################################
```

-continued

```
############
open (FILE, "$ARGV[0]");
while (<FILE>) {
        if (/ \ < (\S+) /) {
          $change=$1;
        }
        if (/ \ > (\S+) /) {
          $seq=uc ($1) ;
        }
}
close (FILE) ;
##################################################################################
############
#
#    if an amino acid sequence is indicated, a starting nucleic acid sequence is
generated that
#    is consistent with codon usage, and loaded into the arrays listed below.
Else, if a nucleic
#    acid sequence was given as a starting reference the sequence is taken
directly from the
#    input file and loaded into arrays
#
#    $aa_vector [ ]     ->  array containing amino acid identities of the sequence
#    $ch_vector [ ]     ->  array containing amino acid identifies of the design changes
#    $nuc_vector [ ]    ->  array containing codons for each position
#    $length            ->  variable holding the length of the construct in amino
acids/codons
#
##################################################################################
############
if ($ARGV [1] eq 'A') {
    @aa_array=split (//, $seq) ;
        foreach $aa (@aa_array) {
        chomp $aa;
        $count++; $aa vector+$count+=$aa;
    }
    @ch_array=split (//, $change) ;
    foreach $ch (@ch_array) {
        chomp $ch;
        $count2++; $ch_vector [$count2] =$ch;
    }
    if ($count != $count2) {print "COUNT Mismatch\n"}
    for ($length=1; $length<=$count; $length++) {
        $r=int (rand(1000) +1) ;
        $nuc_vector [$length] =$aa_cod {$aa_vector[$length]}{$r};
    }
} elsif ($ARGV [1] eq 'N') {
    $count=0;
    @nuc_array=split (//, $seq);
        foreach $nuc (@nuc_array) {
        chomp $nuc;
        $length = int ($count/3) +1; $nuc_vector [$length] .= $nuc; $count++;
    }
    $count2=0 ;
    @ch_array=split (//, $change);
        foreach $ch (@ch_array) {
        chomp $ch;
        $length = int ($count2/3) +1; $ch_vector [$length] = $ch; $count2++;
    }
    if ($count != $count2) {print "COUNT Mismatch\n"}
    $templength = int($count/3);
    for ($length=1; $length<=$templength; $length++) {
        $aa_vector [$length] =$cod_aa{$nuc_vector [$length]};
    }
} else {print "\n\n input format:\n ./SHMdesign.pl inputfile.fasta A/N \n\n";
exit; }
##############################################################################
#
#         The program begins the process of construct optimization with 20 rounds
#         of 100 attempted tile substitutions at random positions throughout the
construct.
#         At the beginning of each round
for ($j=1; $j<=20; $j++) {
############ Print starting state for the round ##########################
          print "ITERATION\t$j\n";undef $nuclear; $length2=0;
### Amino acid sequence of construct
          for ($i=1; $i<=$length; $i++) {
            print "$cod_aa{$nuc_vector [$i]}    ";
          } print "\n";
### Nucleic acid sequence of the construct
```

```
            for ($i=1; $i<=$length; $i++) {
              print "$nuc_vector [$i]";
              @temp=split (//, $nuc_vector [$i]); foreach $n (@temp) { $length2++;
              $nuclear [$length2] =$n }
            } print "\n";
### SHM Design vector for the construct
            for ($i=1; $i<=$length; $i++) {
            print "$ch_vector [$i]    ";
            } print "\n";
            for ($i=1; $i<=$length2; $i++) {
### SHM hot spots for the construct
            $temp="$nuclear [$i]."“$nuclear [$i+1]."“$nuclear [$i+2]."“$nuclear [$i+3]";
              if (defined ($hot{$temp})) {print "+"} else {print " "}
            } print "\n";
### SHM cold spots for the construct
            for ($i=1; $i<=$length2; $i++) {
              $temp="$nuclear [$i]."“$nuclear [$i+1]."“$nuclear [$i+2]";
              if (defined ($cold{$temp})) { print "–" } else {print " "}
            } print "\n";
### CpG motifs within the construct
            for ($i=1; $i<=$length2; $i++) {
              $temp="$nuclear [$i]."“$nuclear [$i+1]";
              if ($temp eq 'CG') { print "C" } else {print " "}
            } print "\n";
############ End printing section #####################################
### Substitute 100 3mer amino acid positions ##########################
#
#       At a randomly chosen position in the construct, a 9-mer nucleic acid in-frame
section is chosen
#       all other nucleotide sequences consistent with the amino acid sequence are
evaluated,
#       depending on whether this position is designated a hot, cold or neutral, and
the sequence that results in the best
#       design improvement is chosen and subsitiued. After a 100 interations, the
programs evaluates its current state
#       and prints to the screen
#
#       $position -> randomly chosen position within the construct
#       $nucleicacid -> current 9-mer nucleic acid at the position chosen for
evaluation
#       $aminoacid -> current 3-mer amino acid at the position chosen for evaluation
#       $better -> flag for best sequence substitution at the position, if one is
selected
#       $cur_coldsc, $cur_hotsc, $cur_cgsc, $cur_codindexsc -> place holders for the
scores
#       of the currently selected 9-mer/3-mer at the position being evaluated
#
###################################################################################
for ($k=1; $k<=100; $k++) {
              $position=int (rand($1ength-4))+2;
              $pos1=$position-1; $pos2=$position; $pos3=$position+1;
              $nucleicacid="$nuo_vector [$pos1] $nuc_vector [$pos2] $nuc_vector[$pos3]";
$aminoacid="$cod_aa{$nuo_vector [$pos1]}$cod_aa{$nuo_vector [$pos2]}$cod_aa{$nuc_ve
otor [$pos3]}";
              $cur_hotsc=$hotsc{$aminoacid}{$nucleicacid};
              $cur_coldsc=$coldsc{$aminoacid}{$nucleicacid};
              $cur_cgsc=$cgsc{$aminoacid}{$nucleicacid};
              $cur_longsc=$longsc{$aminoacid}{$nucleicacid};
              $cur_codindexsc=$codindexsc{$aminoacid}{$nucleicacid};
#             print "$k\t$position\t$length\t$aminoacid\t$nucleicacid\t
#                     $cur_hotsc\t$cur_coldsc\t$cur_cgsc\t$cur_longsc\t
#                     $cur_codindexsc\n";
              undef $better;
              if ($ch_vector[$pos2] eq '–') {
                foreach $spot3 (keys %{$hotsc{$aminoacid}}) {
                  if (($cur_coldsc < $coldsc{$aminoacid}{$spot3}) &&
                     ($cur_hotsc >= $hotsc{$aminoacid}{$spot3}) &&
                     ($cur_cgsc >= $cgsc{$aminoacid}{$spot3}) &&
                     ($cur_codindexsc <= $codindexsc{$aminoacid}{$spot}) &&
                     ($longsc{$aminoacid}{$spot} <=4)) {
                          $better=$spot3;
```

-continued

```
                                        $cur_coldsc = $coldsc{$aminoacid}{$spot3};
                                        $cur_hotsc = $hotsc{$aminoacid}{$spot3};
                                        $cur_cgsc = $cgsc{$aminoacid}{$spot3};
                                        $cur_codindexsc = $codindexsc{$aminoacid}{$spot};
                                }
                        }
                }
                if ($ch_vector [$pos2] eq '+') {
                        foreach $spot3 (keys %{$hotsc{$aminoacid}}) {
                                if (($cur_coldsc >= $coldsc{$aminoacid}{$spot3}) &&
                                        ($cur_hotsc < $hotsc{$aminoacid}{$spot3}) &&
                                        ($cur_cgsc >= $cgsc{$aminoacid}{$spot3}) &&
                                        ($cur_codindexsc <= $codindexsc{$aminoacid}{$spot}) &&
                                        ($longsc{$aminoacid}{$spot} <=3)) {
                                                $better=$spot3;
                                                $cur_coldsc = $coldsc{$aminoacid}{$spot3};
                                                $cur_hotsc = $hotsc{$aminoacid}{$spot3};
                                                $cur_cgsc = $cgsc{$aminoacid}{$spot3};
                                                $cur_codindexsc = $codindexsc{$aminoacid}{$spot};
                                }
                        }
                }
                if ($ch_vector [$pos2] eq '.') {
                        foreach $spot3 (keys %{$hotsc{$aminoacid}}) {
                                if (($cur_cgsc >= $cgsc{$aminoacid}{$spot3}) &&
                                        ($cur_codindexsc <= $codindexsc{$aminoacid}{$spot}) &&
                                        ($longsc{$aminoacid}{$spot} <=3)) {
                                                $better=$spot3;
                                                $cur_coldsc = $coldsc{$aminoacid}{$spot3};
                                                $cur_hotsc = $hotsc{$aminoacid}{$spot3};
                                                $cur_cgsc = $cgsc{$aminoacid}{$spot3};
                                                $cur_codindexsc = $codindexsc{$aminoacid}{$spot};
                                }
                        }
                }
##########################################################################################
############################
#
#       if the variable $better is defined after exhaustively searching for an
improved nucleic acid sequence
#       at the position, substitute that sequence into the evolving $nuc_vector
sequence, then proceed with the next trial
#
#       else, go to the next of the 100 random trails and try again
#
##########################################################################################
########################
        if (defined ($better)) {
                @array=split (//, $better) ; $tempcount=0; $tempvector [1]=' ';
$tempvector [2]=' '; $tempvector [3]=' ';
                        foreach $nuc (@array) {
                                chomp $nuc;
                                $new_position = int($tempcount/3) +1;
                                $tempvector [$new_position] .= $nuc; $tempcount++;
        }
#######     print
"$nuc_vector [$pos1] . $nuc_vector [$pos2] . $nuc_vector [$pos3] \t$tempvector [1] . $tempve
ctor [2] . $tempvector [3] \n";
                        $nuc_vector [$pos1] =$tempvector [1];
                        $nuc_vector [$pos2] =$tempvector [2];
                        $nuc_vector [$pos3] =$tempvector [3];
        }
    }
}
exit;
```

In addition to the file of potential 3 amino acid tiles shown above, the program also calls upon a file of hot spots and cold spots as outlined below, and a listing of the genetic code to translate amino acid sequences to polynucleotide sequences:

TABLE 6

Canonical Hot and Cold Motifs

| Coldspots | Hotspots | |
|---|---|---|
| CCC | TACC | GGTA |
| CTC | TACA | TGTA |
| GCC | TACT | AGTA |
| GTC | TGCC | GGCA |
| GGG | TGCA | TGCA |
| GAG | TGCT | AGCA |
| GGC | AACC | GGTT |
| GAC | AACA | TGTT |
| | AACT | AGTT |
| | AGCC | GGCT |
| | AGCA | TGCT |
| | AGCT | AGCT |

When a starting amino acid template is given (for instance when the underlying DNA sequence may not be known), the algorithm begins by first generating a DNA nucleotide sequence that is consistent with both the given amino acid sequence and known codon usage in that organism. The starting nucleotide template contains an additional line that instructs the perl program SHMredesign.pl as to whether HOT or COLD sites should be incorporated at a given position, making it possible to silence or minimize SHM in portions of evolving proteins, while simultaneously directing SHM to areas for targeting, for instance, the CDRs of an antibody molecule. A given 9-mer in the polynucleotide can be compared with all other possible nonameric oligonucleotides that would encode the same three amino acids at that position.

If a sequence, or portion thereof, is being optimized for SHM (being made "hot"), an exhaustive search of all nucleotide sequences consistent with the amino acid sequence is made, and the nucleotide sequence of the evolving construct is replaced by a new nucleotide sequence if the following conditions are met: (1) the new 9-mer (SHM motif) contains more hot spots that the existing sequence, (2) the new 9-mer contains a number of cold spots equal to or less than the evolving sequence, (3) the new 9-mer contains a number of CpG sequence motifs equal to or less than the evolving sequence, (4) the evolving sequence has a codon usage score that equals or improves known aggregate codon usage at the position, and (5) the sequence does not contain a stretch of any one nucleotide greater than 4 residues.

If a sequence, or portion thereof, is being made resistant to SHM (being made "cold"), an exhaustive search of all nucleotide sequences consistent with the amino acid sequence is made, and the nucleotide sequence of the evolving construct is replaced by a new nucleotide sequence if the following conditions are met: (1) the new 9-mer (SHM motif) contains more cold spots that the existing sequence, (2) the new 9-mer contains a number of hot spots equal to or less than the evolving sequence, (3) the new 9-mer contains a number of CpG sequence motifs equal to or less than the evolving sequence, (4) the evolving sequence has a codon usage score that equals or improves known aggregate codon usage at the position, and (5) the new 9-mer nucleotide sequence does not contain a stretch of any one nucleotide greater than 4 residues.

If a sequence is being optimized for other factors other than SHM (being made "neutral"), an exhaustive search of all nucleotide sequences consistent with the amino acid sequence is made, and the nucleotide sequence of the evolving construct is replaced by the new nucleotide sequence if the following conditions are met: (1) the new 9-mer contains a number of CpG sequence motifs equal to or less than the evolving sequence, (2) the evolving sequence has a codon usage score that equals or improves known aggregate codon usage at the position, and (3) the new 9-mer nucleotide sequence does not contain a stretch of any one nucleotide greater than 4 residues.

As further described in the priority related application No. 60/902,414, one is able to start from any given polynucleotide sequence and use this approach to generate polynucleotide sequences that rapidly converge to a small number of possible sequences that are optimized for the properties described herein.

Following computational analysis, a final optimized polynucleotide can be synthesized using standard methodology and sequenced to confirm correct synthesis. Once the sequence of the polynucleotide has been confirmed, the polynucleotide can be inserted into a vector. The vector can be introduced into a host cell as described herein and tested for expression, activity, or increased or decreased susceptibility to SHM.

One of skill in the art will recognize that there are many potential approaches, and computational methods which could be used to find the best codon usage to maximize hot spot or cold spot density, and that the invention is not intended to be limited to any one specific method of determining the optimum sequence.

As described further below, the creation of synthetic polynucleotide sequences with SHM resistant and or SHM susceptible sequences enables the development of novel diversity generating polynucleotide libraries, e.g., seed libraries.

V. Construction of Synthetic Targeted Libraries for SHM Mediated Diversification ("Seed Libraries")

Static libraries are typically limited in their size and scope. Phage display libraries, for example can display as many as $10^{12}$ members, and ribosomal libraries have been constructed that potentially contain ~$10^{16}$ members. Libraries presented on the surface of bacterial and mammalian cells are not usually this complex, typically with fewer than $10^9$ members. In addition, robust library construction and selection usually requires that libraries contain several fold redundancy, which further limits this theoretically complexity, and makes screening the entire library slow, expensive, and in some cases in-practical.

Despite these levels of complexity, such static libraries can explore only a small fraction of possible sequence space, i.e., the potential number of possible permutations within a polynucleotide region of interest. For example, a heavy chain IgG sequence may contain more than 30 amino acids within the CDR1, CDR2, and CDR3 complementarity regions, giving this single chain more than $20^{30}$ possible permutations, dwarfing even the largest of potential static libraries. Because of this limitation, researchers have explored methodologies for evolving protein sequences and libraries. SHM, as addressed in the present application, uses activation induced cytidine deaminase (AID) and error-prone polymerases as the mechanism for evolving antibody sequences undergoing affinity maturation. Such a system can facilitate on-going mutagenesis and selection at each position of interest within a polynucleotide library of a given gene and can provide for the selective exploration of functional sequence space. Such a search strategy enables a much more productive region of sequence space to be explored, thereby making the methods described herein very attractive for the rapid development of new functionalities and therapeutics.

Additionally, and as discussed below, SHM introduces specific nucleotide transitions at each position of a "hot spot" motif with a frequency that can quantified. This spectrum of nucleotide transitions results in different possible silent or non-silent amino acid transitions, depending on which of the three possible reading frames is used. By defining the most likely codon transitions mediated by SHM and the sequential flow of mutation events, "preferred hot spot SHM codons" can be chosen in such a way as to generate a specific panel of amino acid transitions that can be exploited to enhance the functionality of the library at each amino acid position (see, for example, FIGS. 1, 2, 4 and 6).

Thus, the creation of synthetic polynucleotide seed libraries with preconceived areas of SHM resistant and SHM susceptible regions enables the selective directed evolution and selection of proteins, that maximally exploits the diversity generating and targeting properties of SHM.

In the case of antibodies, this typically means targeted diversification of complementarity determining regions (CDRs) to improve binding to an epitope of interest or to alter the CDRs such that new or altered epitopes can be bound. Simplified CDR libraries containing four and even 2 amino acid alphabets (serine and tyrosine) have also been described and were found to be capable of binding antigens with high affinity and selectivity. See, e.g., Fellouse F A, Li B, Compaan D M, Peden A A, Hymowitz S G, Sidhu S S Molecular recognition by a binary code. J Mol Biol. (2005) 348:1153-62; and Fellouse F A, Wiesmann C, Sidhu S S Synthetic antibodies from a four-amino-acid code: a dominant role for tyrosine in antigen recognition. Proc Natl Acad Sci USA. (2004) 101:12467-72.

In one aspect, a synthetic gene is one that does naturally undergo SHM when expressed in a B cell (i.e., an antibody gene). In another aspect, a synthetic gene is one that does not naturally undergo SHM when expressed in a B cell (i.e., a non-antibody gene). In the case of non-antibody polypeptides, such as enzymes and other protein classes, this refers to the targeted diversification of regions of the enzyme or protein of interest which regulates the functional or biological activity of said enzyme or protein, such as, but not limited to, binding specificity, enzymatic function, fluorescence, or other properties. Libraries are usually combined with one or more selection strategies as disclosed below, which allow the improved, or functional members of the library to be separated from the non-functional members of the library.

In one aspect, the present invention includes a synthetic seed library that is capable of rapid evolution through AID mediated mutagenesis. This synthetic seed library can have the following properties: i) The library is easy to synthesize and is based around a limited number of discrete functional sequences; ii) The library contains synthetic polynucleotide sequences that comprises one or more synthetic variable regions that act as substrates for SHM and include a high density of preferred SHM codons, e.g., preferred SHM hot spot codons (see Table 9 infra); iii) The library contains synthetic polynucleotide sequences that comprises one or more synthetic framework regions that are resistant to SHM mediated mutagenesis and include a low density of SHM hot spots; iv) The library does not contain, or contains a minimum number of, certain codons, ("non preferred codons") that can be mutated to stop codons in one step through SHM, including, UGG (Trp), UGC (Cys), UCA (Ser), UCG(Ser), CAA (Gln), GAA (Glu) and CAG (Gln); v) From the starting set of codons, SHM-mediated mutagenesis produces a large potential diversity at each position selected for mutagenesis, while minimizing changes through essential regions of the protein and the creation of stop codons.

A. Library Design

A library around a specific protein of interest can be designed in light of any conventional techniques and/or information regarding structure activity relationships, homology between different species, and x-ray or NMR structural information of the protein, or protein family in question. Specific design criteria are provided below, and in related application No. 60/902,414, entitled "Somatic Hypermutation Systems."

In certain embodiments of the present invention, initial library design can involve the following steps:

1. The amino acid sequence of the protein of interest is identified, and the corresponding polynucleotide sequence determined or reverse transcribed conceptually.

2. Any relevant structural information on the protein of interest, and related proteins, or on homologous proteins of interest is obtained.

3. A sequence comparison is preformed on the protein of interest compared to all other proteins from closely related species, and known isoforms. In certain embodiments, a sequence alignment would be created to identify conserved and variable amino acid sequences.

This information can be used to establish whether a specific amino acid or protein region is likely to be important in a functional or structural, attribute of the protein of interest, and whether it is conserved or variant across functional isoforms of the protein across protein families.

Based on this information, it is possible to establish particular regions of interest that appear to be directly involved in a functional attribute of the protein of interest. For example, these amino acids will lie within, or within about 5 A of a specific functional or structural attribute of interest. Specific examples include, but are not limited to, amino acids within CDRs of antibodies, binding pockets of receptors, catalytic clefts of enzymes, protein-protein interaction domains, of co-factors, allosteric binding sites etc.

Based on the structural and sequence analysis as set forth herein, one or more polynucleotides may be designed to create improved templates for SHM mediated mutagenesis. In certain embodiments, the present invention can incorporate one or more of the following concepts:

i) Highly conserved amino acids, or amino acids known, or believed to directly contribute key binding energy are initially conserved, and the codon usage within their immediate vicinity changed to either create a cold spot motif, or altered to promote mostly conservative amino acid changes during SHM.

ii) Amino acid domains that appear to be involved in maintaining the core structural framework of the protein are initially conserved, and their codon usage changed to promote mostly conservative amino acid changes during SHM. Amino acid residues in particularly important frame work regions can be altered to use a higher percentage of cold spots, and utilize codons that are resistant, or result in silent mutations during SHM.

iii) Amino acids in regions of interest can be varied to incorporate synthetic variable regions enabling high efficiency SHM, as described below.

iv) Amino acids that are not identified as playing clearly identified roles can be codon optimized to enable effective SHM, i.e. the frequency of SHM hot spots can be maximized and the frequency of SHM cold spots can be minimized.

B. The Design of Synthetic Variable Regions to Act as Substrates for SHM

The rank ordering of susceptibility to mutagenicity of all SHM hot spots for AID and/or error prone polymerases is described above and in Section III of priority U.S. Application No. 60/902,414. We further identified a reading frame context that is critical for generation of silent vs. non-silent mutations. Herein we describe a synthetic seed library approach that includes the use of a high-density of preferred SHM hot spot codons that can act as a substrate for SHM which can lead to the generation of diverse amino acids at each library position which is desired to be mutated. Such high density SHM motifs are particularly important at the boundary of synthetic variable regions to ensure efficient mutagenesis.

i. WAC Based Motifs

Polynucleotide sequences comprising only the sequence WAC (WAC, where W=A or T is encoded in equal proportions, and where the reading frame of reference places C at the wobble or $3^{rd}$ position of each codon) provides for a high density of hot spots. This pattern produces only 4 potential 6-mer nucleotide patterns containing only two codons encoding the 2 amino acids, Asparagine and tyrosine.

TABLE 7

| Codons | SEQ ID NO | Amino acids |
|---|---|---|
| AACTAC | 298 | Asn Tyr |
| AACAAC | 299 | Asn Asn |
| TACTAC | 300 | Tyr Tyr |
| TACAAC | 301 | Tyr Asn |

Figure 3:
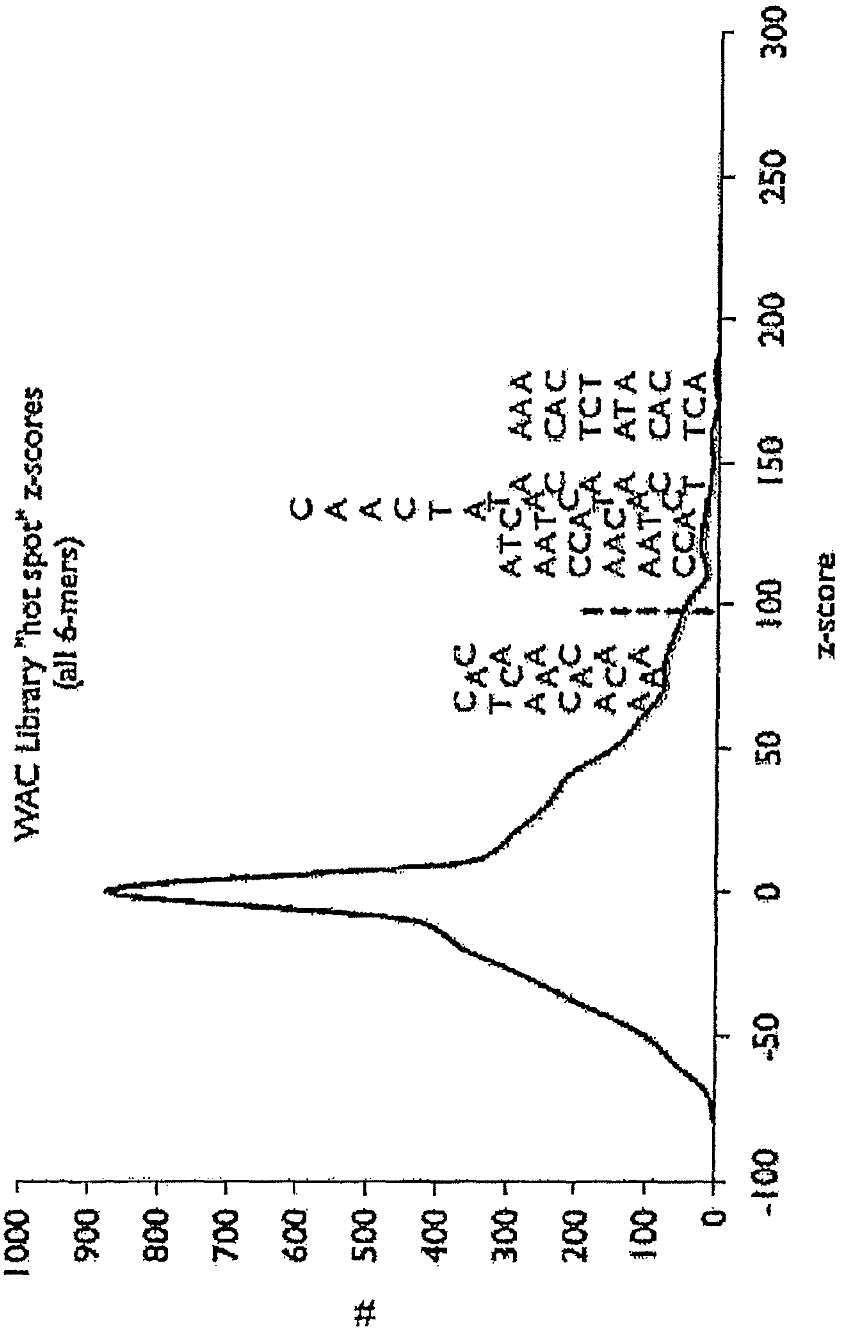
FIG. 3—A histogram of all possible 6-mer nucleotide z-scores describing their ability to attract (positive z-score) or repel (negative z-score) SHM-mediated mutations. Also shown (at the corresponding z-score) on the distribution are nucleotide sequences found in the WAC library. The dotted line indicates the boundary for the top 5% of all SHM recruiting hotspot motifs. As seen in the figure, nucleotide sequences contained in the WAC library provide a high density of hot spots. The assembly of degenerate codons (WACW) results in a subset of possible 4-mer hot spots described by Rogozin et al. (WRCH), where R=A or G, H=A or C or T, and W=T or A.

All of the motifs encoded by the WAC library, given in any of the three possible reading frames, produce a concatenation of hot spots. FIG. 3, which compares these motifs with all other possible 4096 6-mer nucleotide combinations for their ability to recruit SHM-mediated machinery. Longer assemblies result in the same high density of SHM “hot spots” with no “cold spots.” It is also worth noting that this assembly of degenerate codons (WACW) results in a subset of possible 4-mer hot spots described by Rogozin et al. (WRCH), where R=A or G, H=A or C or T, and W=T or A.

Figure 4:
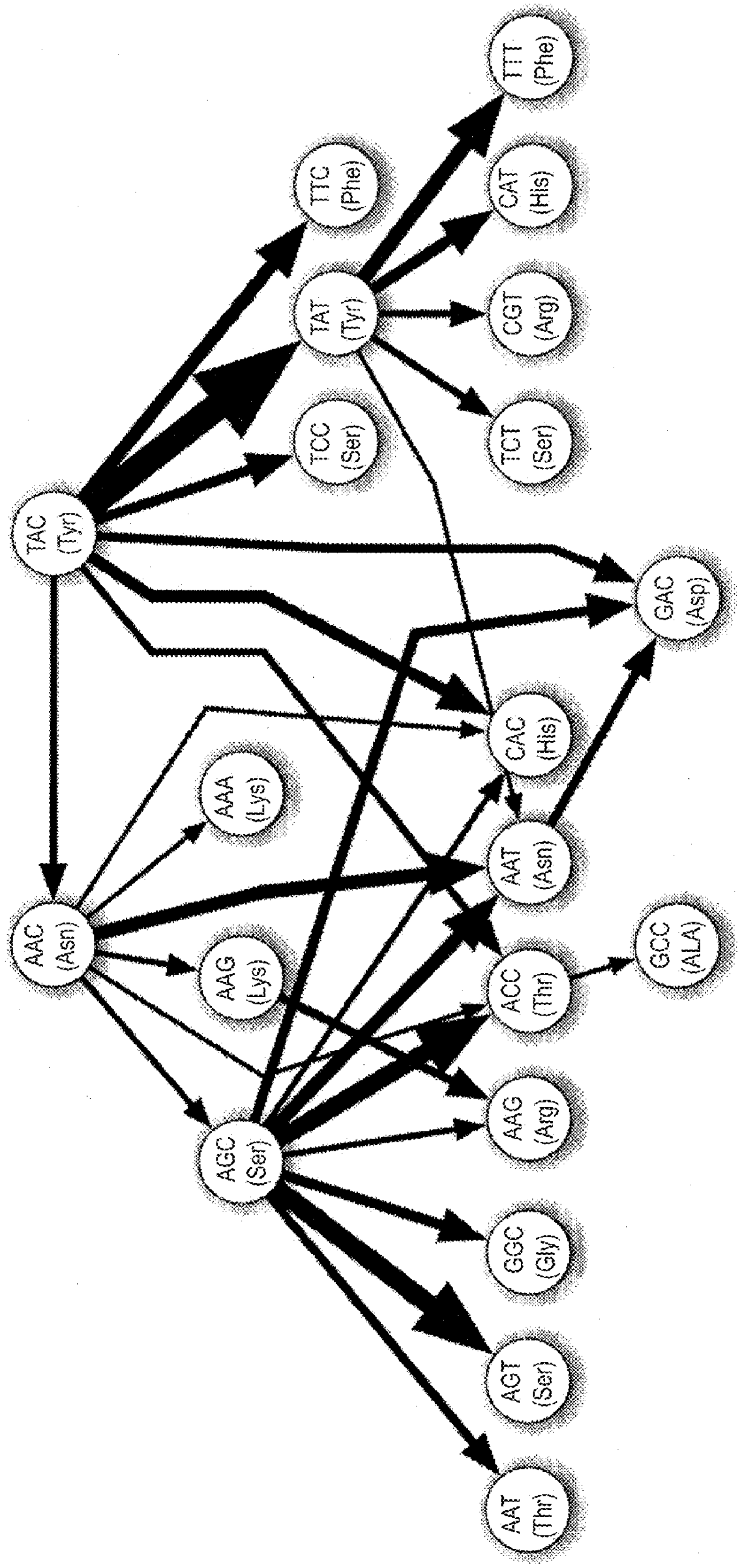
FIG. 4—Preferred SHM hot spot codons AAC and TAC, which can be the basis for a synthetic library, e.g. a seed library, can result in a set of primary and secondary mutation events that create considerable amino acid diversity, as judged by equivalent SHM mutation events observed in Ig heavy chains antibodies. From these two codons, basic amino acids (histidine, lysine, arginine), an acidic amino acid (Aspartate), hydrophilic amino acids (serine, threonine, asparagine, tyrosine), hydrophobic amino acids (Alanine, and phenylalanine), and glycine are generated as a result of SHM events.

As seen in FIG. 4, the preferred SHM hot spot codons AAC and TAC, which can be the basis for a synthetic library as described herein, can result in a set of primary and secondary mutation events that create considerable amino acid diversity, as judged by equivalent SHM mutation events observed in Ig heavy chains antibodies. From these two codons, basic amino acids (histidine, lysine, arginine), an acidic amino acid (aspartate), hydrophilic amino acids (serine, threonine, asparagine, tyrosine), hydrophobic amino acids (alanine, and phenylalanine), and glycine are generated as a result of SHM events.

ii. WRC Based Motifs

A second potential synthetic high density SHM motif, termed here the WRC motif (WRC, where W=A or T, R=G or A, C=Cytidine, and where the reading frame of reference places C at the wobble or $3^{rd}$ position of each codon) would be one that contains two possible codons: AGC and TAC. Again four possible 6-mer nucleotides are possible:

TABLE 8

| Codons | SEQ ID NO | Amino acids |
|---|---|---|
| AGCTAC | 294 | Ser Tyr |
| AGCAGC | 295 | Ser Ser |
| TACAGC | 296 | Tyr Ser |
| TACTAC | 297 | Tyr Tyr |

Figure 5:
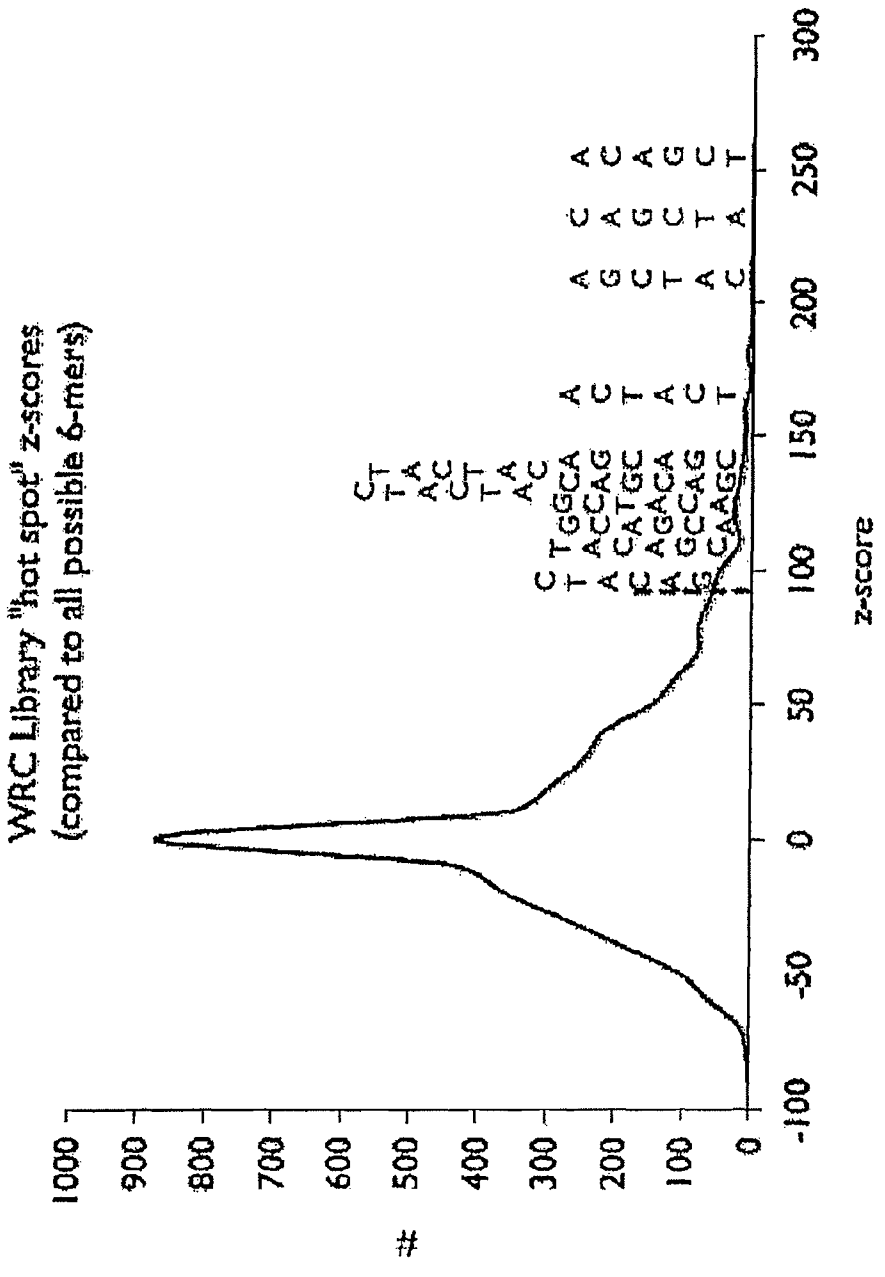
FIG. 5—A histogram of all possible 6-mer nucleotide z-scores describing their ability to attract (positive z-score) or repel (negative z-score) SHM-mediated mutations. Also shown (at the corresponding z-score) on the distribution are nucleotide sequences found in the WRC library. The dotted line indicates the boundary for the top 5% of all SHM recruiting hotspot motifs. As seen in the figure, nucleotide sequences contained in the WRC library provide a high density of hot spots. The assembly of degenerate codons (WRCW) results in a subset of possible 4-mer hot spots described by Rogozin et al. (WRCH), where R=A or G, H=A or C or T, and W=T or A.

The distribution of all 4096 6-mer nucleotide z-scores describing the hotness or coldness of the motif to SHM-mediated mutation is illustrated in FIG. 5. The z-scores for all permuations of 6-mers in the WRC synthetic library are superimposed on this distrubtion, with the dashed line denoting the top 5% of all possible motifs.

Figure 6:
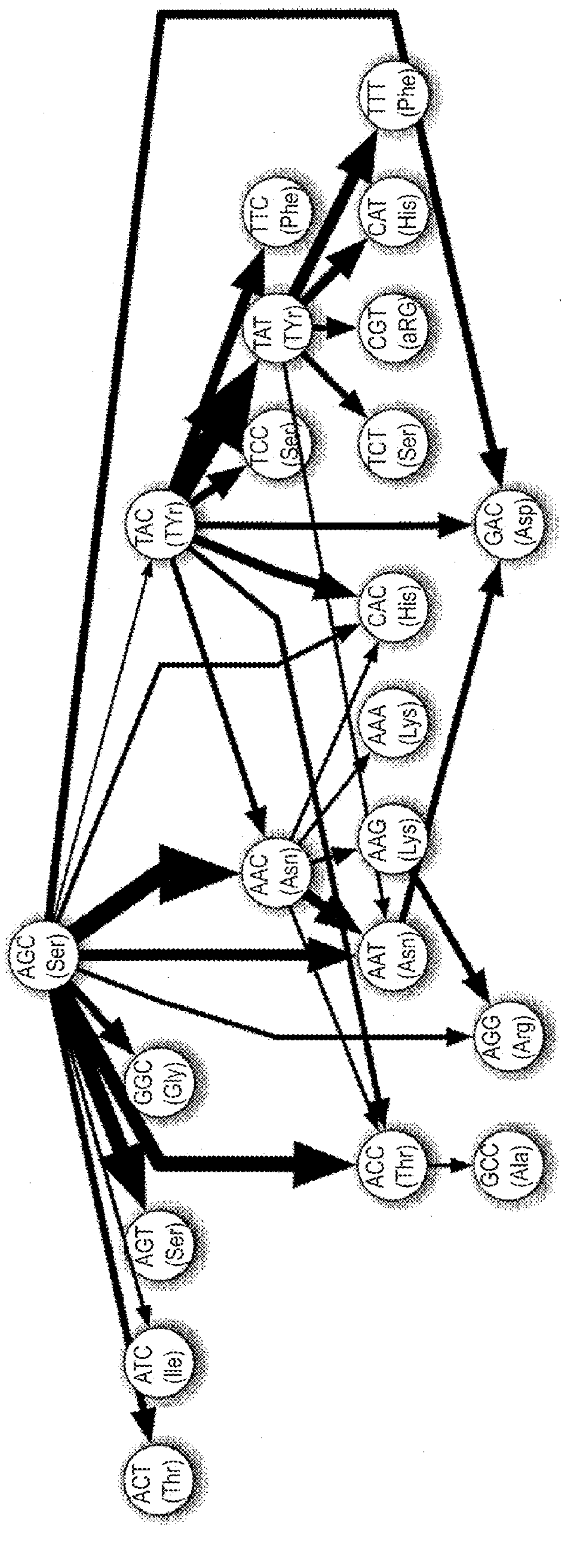
FIG. 6—The series of mutation events that lead to the creation of amino acid diversity, starting from "preferred SHM hot spot codons" AGC and TAC, as observed in affinity matured IGV heavy chain sequences. 4200 primary and secondary SHM mutation events identified and analyzed from the NCBI database, starting from codons encoding asparagine and tyrosine, lead to a set of functionally diverse amino acids.

The series of mutation events that lead to the creation of amino acid diversity, starting from “preferred SHM hot spot codons” AGC and TAC, as observed in affinity matured IGV heavy chain sequences is illustrated in FIG. 6. 4200 primary and secondary mutation events, starting from codons encoding asparagine and tyrosine, lead to a set of functionally diverse amino acids.

Again, this motif results in an unusually high density of optimal SHM hot spots and hot codons, as visualized in FIG. 5, when compared with all other 6-mer nucleotide motifs. Like the WAC synthetic motif, the WRC synthetic motif presents preferred SHM hot spot codons that, when combined with the SHM activity of AID and one or more error-prone polymerases, generates a broad spectrum of potential amino acid diversity at each position (FIG. 6).

Thus, in one aspect, such synthetic preferred SHM motifs (e.g, WAC-based motifs and WRC-base motifs) can be targeted to specific regions of interest within a polynucleotide sequence that encode specific domains, or sub domains of interest, e.g. a nucleic acid sequence which encodes a functional portion of a protein, to act as a substrate for SHM and for which a high degree of diversity is desired.

In another aspect, preferred SHM motifs (e.g., WAC or WRC motifs) can be inserted systematically throughout the open reading frame of the protein of interest. For example, for a 100 amino acid residue protein, 300 discrete polynucleotides can be generated in which a preferred SHM motif (e.g., WAC or WRC motif) is separately introduced once into every possible position within the protein. Each of these 100 polynucleotides can then be screened, either separately, or after being pooled into a library, to identify optimal amino acid substitutions at each position. The improved mutations at each position can then be re-combined to create a next generation construct comprising all of best individual amino acids identified at each position.

iii. Region Mutagenesis

To provide for effective mutagenesis within larger domains, codons usage can be modified, as discussed previously to increase the density of hot spots without altering the amino acid sequence, throughout the region of interest, e.g, a nucleic acid sequence which encodes a functional portion of a protein. This approach has the advantage of needing no preconceived idea of where SHM should be targeted, or what specific amino acids are essential for activity.

In another aspect, for regions in which efficient SHM is required, a synthetic variable region can be created by both changing codon usage and by making conservative amino acid substitutions so as to insert codons that have an improved hot spot density, to further enhance the density of SHM hot spots within a targeted region. Suitable amino acid substitutions can be selected from those listed below in Table 9, while observing the same overall criteria for stable gene creation, and domain structure.

TABLE 9

| Codons | Amino Acid | Group/Sub group | Use in place of: |
|---|---|---|---|
| | | Preferred SHM Codons | |
| AGC/AGU | Ser | Aliphatic/Slightly non polar | Thr/Cys |
| GGU | Gly | Aliphatic/Small residue | Ala |
| GCU/GCA | Ala | Aliphatic/Small residue | Gly |
| CUA/UUG/CUU | Leu | Aliphatic/Large | Val/Met |
| | | Charged | |
| AAA/AAG | Lys | Charged/Positive | Arg |
| CAU | His | Charged/Positive | Arg/Phe |
| GAU | Asp | Charged/Negative | Glu |
| GAG | Glu | Charged/Negative | Asp |
| | | Charged/Polar | |
| CAG | Gln | Charged/Polar | Asn |
| AAU/AAC | Asn | Charged/Polar | Gln |
| | | Aromatic/Phenyl | |
| UAU/UAC | Tyr | Aromatic/Phenyl | Trp |
| UUU/UUA/UUC | Phe | Aromatic/Phenyl | Trp/Phe |

In some embodiments, the amino acids Trp, Pro and Gly are conserved where their location suggests a functional or structural role. Other than these amino acids, if an amino acid to be optimized is not listed, an amino acid from the same sub-group or group as listed above is selected.

In certain embodiments, such synthetic variable regions can be interspersed with framework regions containing primarily SHM resistant sequences, which can be designed as described previously (see generally U.S. application No. 60/902,414, entitled "Somatic Hypermutation Systems").

Depending on the amount of information available, a number of distinct library design strategies may be employed, ranging from a very aggressive targeted approach based on the use of preferred SHM motifs (e.g., WAC or WRC motifs), to a more conservative strategy of using fairly selective amino acid replacements, to a cautious strategy in which only codon usage is changed. An advantage of the present invention is that each approach results in the generation of only one distinct nucleotide sequence; thus all of these strategies can be subjected to SHM mediated diversity in parallel without significant additional burden.

C. Sub-Libraries of Improved Variants

Additionally the use of a dynamic evolving system for creating and selecting improved variants of proteins of interest, including antibodies or binding proteins, as disclosed herein, enables the sequential directed evolution of improved proteins. This can be accomplished, for example, through the creation of secondary seed libraries, that comprise SHM optimized sequences at, or around, positions previously identified in the starting, or germline, sequence to be mutated by AID, and to have direct impact on a specific desired trait, for example, in the case of antibodies, improved affinity or cross reactivity.

Importantly, such a system enables the on-going ability to analyze the sequences of the variable domains of different clones to be isolated, and to determine the mutations introduced into the protein via somatic hypermutation in each case to determine their distribution within the clones analyzed; for example, in the case of an antibody, the location of the mutations within the coding region of the heavy and light chains, and their structural context. Mutations so identified can thus be analyzed based on their position within the structure of the protein. In certain embodiments, key mutations that occur between different evolving clones can be optimized for SHM, and may then be recombined between, or within families to rapidly generate hybrid antibodies that exhibit favorable increases in affinity or selectivity that represent the sum of all, or a sub set of all mutations observed, thereby both maximizing the analysis of useful diversity in the population, and enabling further evolution of the protein via SHM. Such a conceptual recombination approach enables the rapid evolution of the selected antibodies and binding proteins, and avoids the systematic accumulation of neutral or disadvantageous mutations within the population, and thus provides for significant improvements in both efficiency and effectiveness in the overall process.

Furthermore, an understanding of the factors that target the somatic hypermutation machinery to specific sites within the protein of interest, in conjunction with specific insight into how these sequences are utilized to generate amino acid diversity, enables the development of specific algorithms that provide for the predictive creation of diversity in a heterologous system undergoing SHM. Such an approach is based on both an understanding of the amino acids that are likely to be created, or not created, as a result of SHM acting on a codon, as well as the temporal sequence of amino acid created that results from SHM acting on a specific, or degenerate codon, or a preferred SHM codon, or a non preferred SHM codon, or any particular SHM motif. This analysis enables the development of DNA constructs that promote or repel mutations in a SHM system, and exhibit efficient and predictable mutagenesis to create diversity in situ.

By combining this understanding with knowledge of the most favorable positions for mutations actually identified from a highly selected evolving system, it is possible to create a system that enables the rapid and effective mutagenesis of proteins.

As shown in Examples 12 and 13, this approach enables the analysis and design of improved seed libraries that has several advantages, including the ability to efficiently design low complexity seed libraries that can be evolved through SHM to create large theoretical complexity which is enriched in functionally improved forms.

Thus in one aspect, the present invention includes a composition of matter comprising a seed library of polynucleotides encoding a plurality of one or more polypeptide species, wherein said polynucleotides comprise at least one or more codons which have been identified as being mutated via AID mediated mutagenesis to influence a desired property of said one or more polypeptides, and all, or a subset of all, of said one or more codons have been altered from the wild type form and optimized for somatic hypermutation.

In one non-limiting embodiment of this method, all, or a subset of all, of said one or more codons have been altered from their AID mutated form and optimized for further somatic hypermutation.

The present invention also provides a method of making a protein of interest with a desired property, the method comprising the steps of: a. synthesizing a seed library of polynucleotides encoding a plurality of one or more polypeptide species of interest that have at least one region of interest of a protein of interest, wherein the seed library of polynucleotides comprise at least one synthetic nucleic acid sequence that encodes at least one region of interest and has been modified to act as a substrate for AID mediated somatic hypermutation; b. joining in operable combination a seed library of polynucleotides encoding a plurality of one or more polypeptide species of interest of a protein of interest into an expression vector; c. transforming a host cell with the expression vector, so that the protein of interest is produced by expression of the seed library of polynucleotides encoding a plurality of one or more polypeptide species of interest of a protein of interest; and wherein the host cell expresses AID, or can be induced to express AID via the addition of an inducing agent; d. optionally inducing AID activity, or allowing AID mediated mutagenesis to occur on the seed library; e. identifying a cell or cells within the population of cells which expresses a mutated protein having a desired property, and f. establishing one or more clonal populations of cells from the cell or cells identified in step (e).

In other embodiments, provided herein is a method of making a protein of interest with a desired or identified property, said method comprising the steps of: (a) synthesizing a seed library of polynucleotides encoding one or more proteins, wherein said seed library of polynucleotides comprises at least one synthetic polynucleotide that has been optimized for SHM; (b) joining in operable combination said seed library of polynucleotides into an expression vector; (c) transforming a host cell with said expression vector, so that said one or more proteins is produced by expression of said seed library of polynucleotides; and wherein said host cell expresses AID activity or can be induced to express AID activity via the addition of an inducing agent; (d) if needed, inducing AID activity; (e) identifying a cell or cells within the population of cells which express(es) one or more mutated proteins having said desired or identified property, and (f) establishing one or more clonal populations of cells from the cell or cells identified in step (e).

In other embodiments, provided herein is a method of making an antibody or antigen-binding fragment thereof with a desired property, the method comprising the steps of: a. synthesizing a seed library of polynucleotides encoding a plurality of one or more antibody heavy chain proteins or fragments that have at least one CDR, wherein the polynucleotides comprise at least one synthetic nucleic acid sequence that encodes the at least one CDR and has been modified to act as a substrate for AID mediated somatic hypermutation; b. synthesizing a seed library of polynucleotides encoding a plurality of one or more antibody light chain proteins or fragments that have at least one CDR, wherein the seed library of polynucleotides comprise at least one synthetic nucleic acid sequence that encodes the at least one CDR and has been modified to act as a substrate for AID mediated somatic hypermutation; c. joining in operable combination the seed library of polynucleotides encoding the plurality of antibody heavy chain proteins or fragments thereof and the seed library of polynucleotides encoding the plurality of antibody light chain proteins or fragments thereof into expression vectors; d. transforming a host cell with the expression vectors, so that an antibody or an antigen-binding fragment thereof is produced by coexpression of a heavy chain sequence from the seed library of polynucleotides encoding a plurality of antibody heavy chain proteins or fragments thereof and a light chain sequence from the seed library of polynucleotides encoding a plurality of antibody light chain proteins or fragments thereof, either on the same or different expression vectors; and wherein the host cell expresses AID, or can be induced to express AID via the addition of an inducing agent; e. optionally inducing AID activity, or allowing AID mediated mutagenesis to occur on the seed libraries of polynucleotides; f. identifying a cell or cells within the population of cells which expresses a mutated antibody or an antigen-binding fragment thereof having the desired property, and g. establishing one or more clonal populations of cells from the cell or cells identified in step (f).

In other embodiments, provided herein is a method of making an antibody or antigen-binding fragment thereof with a desired or identified property, said method comprising the steps of: (a) synthesizing a first seed library of first polynucleotides encoding a plurality of one or more antibody heavy chain proteins or fragments thereof that have at least one heavy chain CDR, wherein said first seed library of polynucleotides comprises at least one first synthetic polynucleotide that has been optimized for SHM; (b) synthesizing a second seed library of second polynucleotides encoding said plurality of one or more antibody light chain proteins or fragments thereof that have at least one light chain CDR, wherein said second seed library of polynucleotides comprises at least one second synthetic polynucleotide that has been optimized for SHM; (c) joining in operable combination said first and second seed libraries of polynucleotides into expression vectors; (d) transforming a host cell with said expression vectors, so that an antibody or an antigen-binding fragment thereof is produced by coexpression of a heavy chain sequence from said first seed library of polynucleotides and a light chain sequence from said second seed library of polynucleotides (either on the same or different expression vectors); and wherein said host cell expresses AID activity or can be induced to express AID activity via the addition of an inducing agent; (e) if needed, inducing AID activity; (f) identifying a cell or cells within the population of cells which expresses one or more mutated antibodies or antigen-binding fragments thereof having the desired or identified property, and (g) establishing one or more clonal populations of cells from the cell or cells identified in step (f).

In still other embodiments, provided herein is a method of co-evolving a plurality of proteins, the method comprising the steps of: a. synthesizing a first seed library of polynucleotides encoding a plurality of one or more polypeptide species of interest that have at least one region of interest of a first protein of interest, wherein the seed library of polynucleotides comprise at least one synthetic nucleic acid sequence that encodes the at least one region of interest and has been modified to act as a substrate for AID mediated somatic hypermutation; b. synthesizing a second seed library of polynucleotides encoding a plurality of one or more polypeptide species of interest that have at least one region of interest of a second protein of interest, wherein the seed library of polynucleotides comprise at least one synthetic nucleic acid sequence that encodes the at least one region of interest and has been modified to act as a substrate for AID mediated somatic hypermutation; c. joining in operable combination the seed library of polynucleotides encoding the plurality of polypeptide species of interest of the first protein of interest and the seed library of polynucleotides encoding the plurality of polypeptide species of interest of the second protein of interest into expression vectors; d. transforming a host cell with the expression vectors, so that the first and second proteins of interest are produced by coexpression of the first and second seed libraries of polynucleotides, either on the same or different expression vectors; and wherein the host cell expresses AID, or can be induced to express AID via the addition of an inducing agent; e. optionally inducing AID activity, or allowing AID mediated mutagenesis to occur on the seed libraries of polynucleotides; f. identifying a cell or cells within the population of cells which expresses a mutated first or second protein of interest having the desired property, and g. establishing one or more clonal populations of cells from the cell or cells identified in step (f).

In one aspect, provided herein is a method of co-evolving a plurality of proteins, said method comprising the steps of: (a) synthesizing a first seed library of polynucleotides encoding one or more proteins, wherein said first seed library of polynucleotides comprise at least one first synthetic polynucleotide that has been optimized for SHM; (b) synthesizing a second seed library of polynucleotides encoding one or more proteins, wherein said second seed library of polynucleotides comprise at least one second synthetic polynucleotide that has been optimized for SHM; (c) joining in operable combination said first and second seed libraries of polynucleotides into expression vectors; (d) transforming a host cell with said expression vectors, so that said one or more first and second proteins are produced by coexpression of said first and second seed libraries of polynucleotides, either on the same or different expression vectors; and wherein said host cell expresses AID activity or can be induced to express AID activity via the addition of an inducing agent; (e) if needed, inducing AID activity; (f) identifying a cell or cells within the population of cells which expresses one or more mutated proteins having the desired or identified property, and (g) establishing one or more clonal populations of cells from the cell or cells identified in step (f).

In certain aspects, the methods described herein comprise at least one synthetic nucleic acid sequence that has been modified to act as a substrate for AID mediated somatic hypermutation by the insertion of somatic hypermutation motifs. In certain embodiments, the at least one synthetic nucleic acid sequence has been modified to act as a substrate for AID mediated somatic hypermutation by the insertion of one or more preferred SHM codons. In other embodiments, the at least one synthetic nucleic acid sequence has been modified to act as a substrate for AID mediated somatic hypermutation by the insertion of one or more WAC motif, WRC motif, or a combination thereof.

In one embodiment of any of these methods, the identified codon may be replaced with a preferred (canonical) SHM codon or preferred (canonical) hot spot SHM codon which introduces a conservative amino acid substitution, compared to either the wild-type or AID modified codon. In another embodiment of any of these methods, the identified codon may be replaced with a preferred SHM codon or preferred hot spot SHM codon which introduces a semi-conservative mutation at the amino acid level, compared to either the wild-type or AID modified codon. In another embodiment of any of these methods, the identified codon may be replaced with a preferred SHM codon or preferred hot spot SHM codon which introduces a non-conservative mutation at the amino acid level compared to either the wild-type or AID modified codon. In one embodiment, insertion of one or more preferred SHM codons is by insertion of one or more amino acids substitutions in said region of interest, said amino acid substitutions being silent, conservative, semi-conservative, non-conservative or a combination thereof. Modifications to polynucleotides made using the methods described herein can render at least one polynucleotide sequence susceptible or resistant to SHM.

In another aspect, the present invention includes a composition of matter comprising a seed library of polynucleotides encoding a plurality of one or more polypeptide species, wherein said polynucleotides comprise at least one or more codons which have been identified as being mutated via AID mediated mutagenesis to influence a desired property of said one or more polypeptides, and all, or a subset of all, of said one or more codons have been altered from the wild type form and made resistant to somatic hypermutation.

In certain aspects of the present invention, provided herein are compositions of matter comprising a seed library of polynucleotides encoding one or more proteins, wherein said seed library of polynucleotides comprises at least one synthetic polynucleotide that has been optimized for SHM by insertion of one or more preferred SHM codons. In other aspects, at least one synthetic polynucleotide has been optimized for SHM by reducing the density of non-preferred codons. Synthetic polynucleotides can be made resistant to SHM or made susceptible to SHM using the methods described herein.

In one non-limiting of this method, all, or a subset of all, of said one or more codons have been altered from their AID mutated form and made resistant to somatic hypermutation.

In another aspect, the present invention includes a composition of matter comprising a seed library of polynucleotides encoding a plurality of one or more polypeptide species, wherein said polynucleotides comprise at least one or more codons which have been identified as being mutated via AID mediated mutagenesis to influence a desired property of said one or more polypeptides, and a first subset of said one or more codons have been altered from the wild type form and optimized for somatic hypermutation, and a second subset of said one or more codons have been altered from their AID mutated form and made resistant to somatic hypermutation.

In another aspect, the present invention includes a composition of matter comprising a seed library of polynucleotides encoding a plurality of one or more polypeptide species, wherein said polynucleotides comprise at least one or more codons which have been identified as being mutated via AID mediated mutagenesis to influence a desired property of said one or more polypeptides, and a first subset of said one or more codons have been altered from the AID mutated form and optimized for somatic hypermutation, and a second subset of said one or more codons have been altered from their wild type form and made resistant to somatic hypermutation.

In one aspect of these methods, or any of the methods disclosed herein, the identified codon may be altered without changing the amino acid which it encodes, through the replacement of the identified codon by a codon with a higher, or lower probability of SHM. In one aspect, the identified codon may be replaced with a preferred SHM codon, or preferred hot spot SHM codon. In another aspect, if the identified codon is a non preferred codon, it may be replaced with a codon of higher, lower, or similar probability of SHM, provided however that the replacement codon is not also non-preferred.

Alternatively, in another aspect of these methods, the identified codon may be altered to change both its susceptibility to SHM and the amino acid which it encodes. In one aspect the identified codon may be replaced with a preferred SHM codon or preferred hot spot SHM codon.

In one embodiment of any of these methods, the identified codon may be replaced with a preferred SHM codon or preferred hot spot SHM codon which introduces a conservative amino acid substitution, compared to either the wild-type or AID modified codon. In another embodiment of any of these methods, the identified codon may be replaced with a preferred SHM codon or preferred hot spot SHM codon which introduces a semi-conservative mutation at the amino acid level, compared to either the wild-type or AID modified codon. In another embodiment of any of these methods, the identified codon may be replaced with a preferred SHM codon or preferred hot spot SHM codon which introduces a non-conservative mutation at the amino acid level, compared to either the wild-type or AID modified codon.

VI. Proteins of Interest

In general, the term "proteins of interest" relates to proteins, or portions thereof, for which it is desired that the polynucleotide encoding the protein is modified for SMH by AID in order to rapidly create, select and identify improved variants of that protein. Such modified polynucleotides can be made more susceptible to SHM, thereby inducing amino acid changes when the polynucleotide is subjected to AID as a result of codon usage, and/or the addition of SHM motifs to act as substrates for AID-mediated SHM and screened for improved function.

Any protein for which the amino acid, or corresponding nucleotide sequence is known, or available (e.g., can be cloned into a vector of the present invention) and a phenotype or function can be improved is a candidate for use in the vectors and SHM systems provided herein. Proteins of interest include, for example, surface proteins, intracellular proteins, membrane proteins and secreted proteins from any naturally occurring or synthetic source. Exemplary, but non-limiting types of proteins for use in the synthetic, semi-synthetic and/or seed libraries provided herein include an antibody heavy chain or portion thereof, an antibody light chain or portion thereof, an enzyme, a receptor, a structural protein, a co-factor, a polypeptide, a peptide, an intrabody, a selectable marker, a toxin, growth factor, peptide hormone, and any other protein which can be optimized, is intended to be included.

Biologically active proteins (molecules) also include molecules capable of modulating the pharmacokinetics and/or pharmacodynamics of other biologically active proteins (molecules), for example, lipids and polymers such as polyamines, polyamides, polyethylene glycol and other polyethers. For example, polypeptides are those such as, for example, VEGF, VEGF receptor, Diptheria toxin subunit A, *B. pertussis* toxin, CC chemokines (e.g., CCL1-CCL28), CXC chemokines (e.g., CXCL1-CXCL16), C chemokines (e.g., XCL1 and XCL2) and $CX_3C$ chemokines (e.g., $CX_3CL1$), IFN-gamma, IFN-alpha, IFN-beta, TNF-alpha, TNF-beta, IL-1, IL-2, IL-3, IL-4, IL-5, IL-6, IL-7, IL-10, IL-12, IL-13, IL-15, TGF-beta, TGF-alpha, GM-CSF, G-CSF, M-CSF, TPO, EPO, human growth factor, fibroblast growth factor, nuclear co-factors, Jak and Stat family members, G-protein signaling molecules such as chemokine receptors, JNK, Fos-Jun, NF-κB, I-κB, CD40, CD4, CD8, B7, CD28 and CTLA-4.

Additionally, there are a variety of other component nucleotide sequences, such as coding sequences and genetic elements that can make up the core system that one would, in some embodiments, prefer not to hypermutate to maintain overall system integrity. These component nucleotide sequences include without limitation, i) selectable markers such as neomycin, blasticidin, ampicillin, etc; ii) reporter genes (e.g. fluorescent proteins, epitope tags, reporter enzymes); iii) genetic regulatory signals, e.g. promoters, inducible systems, enhancer sequences, IRES sequences, transcription or translational terminators, kozak sequences, splice sites, origin of replication, repressors; iv) enzymes or accessory factors used for high level enhanced SHM, or it's regulation, or measurement, such as AID, pol eta, transcription factors, and MSH2; v) signal transduction components (kinases, receptors, transcription factors) and vi) domains or sub domains of proteins such as nuclear localization signals, transmembrane domains, catalytic domains, protein-protein interaction domains, and other protein family conserved motifs, domains and sub-domains.

In general, one of ordinary skill in the art, based on the teaching herein, would be readily able to select a protein of interest as a suitable candidate for modification to optimize a polypeptide's susceptibility to SHM, and devise a suitable assay to monitor the desired trait of the protein of interest.

Depending on the nature of the protein of interest, and amount of information available on the protein of interest, a practioner can follow any combination of the following strategies prior to mutagenesis to create the starting polynucleotide.

1. No codon optimization: Although it may typically be desirable to enhance the number of hot spots within the polynucleotide sequence encoding a protein of interest, it should be noted that any wild type protein will be expected to undergo a certain amount of SHM, and can be used in the present invention without codon optimization, or any specific knowledge of the actual sequence. Additionally certain proteins, for example antibodies, naturally comprise polynucleotide sequences which have evolved suitable codon usage, and do not require codon modification.

2. Global hot spot optimization: In some aspects, the number of hotspots in a polynucleotide encoding a protein can be increased, as described herein. This approach can be applied to the entire coding region of the gene, thereby rendering the entire protein more a more efficient substrate for SHM. As discussed herein, this approach may be preferred if relatively little is known about structure activity relationships within the protein, or between related protein isotypes.

3. Selective hot spot modification: Alternatively, as discussed herein, a polynucleotide sequence encoding the protein of interest can be selectively, and or systematically modified through the targeted replacement of regions of interest, e.g. a nucleic acid sequence which encodes a functional portion of a protein, with synthetic variable regions, that provide for a high density of hot spots or preferred SHM motifs which can act as substrates for SHM and seed maximal diversity through SHM at specific loci.

One of ordinary skill in the art would understand, based on the teachings provided herein, that any or all of the above approaches may be undertaken using the present invention. In certain embodiments of the present invention, however, global hot spot modification and selective hot spot modification, can be used together to generate synthetic, semi-synthetic, and/or seed libraries likely to lead to faster and more efficient generation of diversity in the polynucleotide sequence encoding a protein, both within specific regions of interest and throughout the entire protein.

Following design of the required optimized polynucleotide encoding the protein of interest, it can be synthesized using standard methodology and sequenced to confirm correct synthesis. Once the sequence of the polynucleotide has been confirmed, the polynucleotide can be inserted into a vector of the present invention, and the vector then introduced into a host cell as described herein to effect mutagenesis.

Once introduced into a suitable host cell, cells can be induced to express AID, and/or other factors to initiate SHM, thereby inducing on-going sequence diversification of the protein of interest. After an appropriate period of time (e.g., 2-5 cell divisions), the resulting host cells, including variants of the protein of interest, can be screened and improved mutants identified and separated for the cell population. This process can be iteratively repeated to selectively improve the properties of the protein of interest.

A cell-surface displayed protein can be created through the creation of a chimeric molecule of a protein of interest coupled in frame to a suitable transmembrane domain. In the case of mammalian cell expression, for example, a MHC type 1 transmembrane domain such as that from H2kk (including peri-transmembrane domain, transmembrane domain, and cytoplasmic domain; NCBI Gene Accession number AK153419) can be used. Likewise the surface expression of proteins in prokaryotic cells (such as *E. coli* and *Staphylococcus*) insect cells, and yeast is well established in the art. For reviews, see for example Winter, G. et al., Annu. Rev. Immunol. (1994) 12:433-55; Plückthun, A., (1991) Bio/Technology 9: 545-551; Gunneriusson et al., (1996) J. Bacteriol 78 1341-1346; Ghiasi et al., (1991) Virology 185 187-194; Boder and Wittrup, (1997) Nat. Biotechnol. 15 553-557; and Mazor et al., (2007) Nat. Biotech. 25(5) 563-565.

Surface displayed antibodies or proteins can be created through the secretion and then binding (or association) of the secreted protein on the cell surface. Conjugation of the antibody or protein to the cell membrane can occur either during protein synthesis or after the protein has been secreted from the cell. Conjugation can occur via covalent linkage, by binding interactions (e.g., mediated by specific binding members) or a combination of covalent and non-covalent linkage.

In yet another aspect, proteins can be coupled to a cell through the creation of an antibody or binding protein fusion protein comprising a first specific binding member that specifically binds to a target of interest fused to a second binding member specific for display on a cell surface (e.g., in the case of exploiting the binding of protein A and a Fc domain: protein A is expressed on and attached to a cell surface and binds to, and localizes, a secreted antibody (or a protein of interest expressed as an Fc fusion protein)).

Transfection of appropriate expression vectors containing the corresponding polynucleotide sequences into suitable mutator positive cells can be performed using any art recognized or known transfection protocol. An exemplary surface expressed library of proteins is described in Examples 4 and 5.

Cells expressing a plurality of antibodies or binding proteins from the transfections above can, optionally, be characterized to select cells expressing specific ranges of surface expression of the protein on the cell surface using conventional assays including, but not limited to, FACS.

Staining of light and heavy chain expression can be accomplished, for example, by using commercially available fluorescein Isothiocyanate (FITC) or R-Phycoerythrin (R-PE) conjugated rat anti-mouse Ig, kappa light chain, and FITC or R-PE conjugated rat anti-mouse Ig Glmonoclonal antibodies (BD Pharmingen). Staining can be performed using the manufacture's suggested protocols, usually via incubation of the test cells in the presence of labeled antibody for 30 minutes on ice. Expression levels of cellular antigen expression can be quantified using Spherotech rainbow calibration particles (Spherotech, IL).

Transfected cell populations exhibiting specific ranges of expression can be selected. For example, cells with a surface copy number of greater than about 10,000, about 50,000, about 100,000, or about 500,000 proteins per cell can be selected, and can then be used for efficient affinity profiling.

Populations of stably transfected cells can be created via, for example, growth for 2 to 3 weeks in the presence of appropriate selectable agents; the resulting cell library can be frozen and stored as a cell bank. Alternatively, cells can be transiently transfected and used within a few days of transfection.

It may be desirable in some instances to convert a surface displayed protein into a secreted protein for further characterization. Conversion can be accomplished through the use of a specific linker that can be cleaved by incubation with a selective protease such as factor X, thrombin or any other selective proteolytic agent. It is also possible to include polynucleotide sequences that enable the genetic manipulation of the encoded protein in the vector (i.e., that allow excision of a surface attachment signal from the protein reading frame). For example, the insertion of one or more unique restriction sites, or cre/lox elements, or other recombination elements that enable the selective removal of an attachment signal and subsequent intracellular accumulation (or secretion) of the protein of interest at will. Further examples include the insertion of flanking loxP sites around an attachment signal (such as a transmembrane domain) allowing for efficient cell surface expression of a protein of interest. However, upon expression of the cre recombinase in the cell, recombination occurs between the LoxP sites resulting in the loss of the attachment signal, and thus leading to the secretion of the protein of interest.

Once a polypeptide has been optimized to a determined degree, the cell or population of cells expressing an optimized polypeptide of interest can be isolated or enriched and the phenotype (function) of the optimized polypeptide can be assayed using art-recognized assays.

Cells can then be re-grown, SHM re-induced, and re-screened over a number of cycles to effect iterative improvements in the desired function. At any point, the polynucleotide sequence encoding the protein of interest can be rescued and/or sequenced to monitor on-going mutagenesis.

For example, episomal plasmid DNA can be extracted (or amplified by co-expression with SV40 T Antigen (J. Virol. (1988) 62 (10) 3738-3746)) and then extracted and amplified by PCR using DNA primers that are specific for the polynucleotide or interest or flanking regions, using standard methodology. Alternatively, total RNA can be isolated from various cell populations that have been isolated by flow cytometry or magnetic beads; episomal DNA and/or total RNA and can be amplified by RT-PCR using primers that are specific for the polynucleotide or interest or flanking regions using standard methodology. Clones can be sequenced using automated DNA sequences from companies such as Applied Biosystems (ABI-377 or ABI 3730 DNA sequencers). Sequences can be analyzed for frequency of nucleotide insertions and deletions compared to the starting sequence.

A. Antibodies and Fragments Thereof

With respect to antibodies, the present invention provides the ability to bypass the need for immunization in vivo to select antibodies that bind to key surface epitopes that are aligned with producing the most robust biological effects on target protein function. Additionally, mammalian antibodies intrinsically process optimal codon usage patterns for targeted SHM, greatly simplifying template design strategies. For certain antigens, in vivo immunization leads to epitope selection that does not impact target function, thereby hindering the selection of potent and efficacious antibody candidates. In still other embodiments, the present invention can provide for the rapid evolution of site-directed antibodies that have potent activity by nature of the role of that epitope in determining target protein function. This provides the ability to scan target proteins for optimal epitope position and produce best in class antibodies drugs for use in the clinic.

As described herein, all naturally occurring germline, affinity matured, synthetic, or semi-synthetic antibodies, as well as fragments thereof, may be used in the present invention. In general, such antibodies can be altered through SHM to improve one or more of the following functional traits: affinity, avidity, selectivity, thermostability, proteolytic stability, solubility, folding, immunotoxicity and expression. Depending upon the antibody format, antibody libraries can comprise separate heavy chain and light chain libraries which can be co-expressed in a host cell. In certain embodiments, full length antibodies can be secreted, and/or surface displayed at the plasma membrane of the host cell. In still other embodiments, heavy and light chain libraries can be inserted in to the same expression vector, or different expression vectors to enable simultaneous co-evolution of both antibody chains.

In certain embodiments, full length cDNA libraries of naturally occurring antibodies, either human or non-human, can be used and subjected to on-going selection and SHM-mediated mutagenesis using the present systems. In other embodiments, all or a portion of a naturally occurring antibody, for example an isolated CDR, may be amplified and the resulting library inserted to an existing naturally occurring, or synthetic antibody template to create a focused library. In one embodiment, a library of naturally occurring CDR3 regions may be created and inserted in a synthetic antibody or fragment thereof, thereby creating a semi-synthetic antibody library.

In one embodiment, increasing the hotspot density in specific sub regions of antibodies or fragments thereof (e.g., $F(ab')_2$, Fab', Fab, Fv, scFv, dsFv, dAb or a single chain binding polypeptide) can result in targeted mutagenesis of that region leading to the evolution and selection of a protein with improved characteristics such as one or more of increased binding affinity, increased binding avidity and/or decreased non-specific binding. In another embodiment, the use synthetic antibodies with increased hotspots in the constant region (e.g., Fc) can result in increased binding affinity for an Fc receptor (FcR), thereby modulating signal cascades. Heavy chains and light chains, or portions thereof, can be simultaneously modified using the procedures described herein.

Intrabodies used in the methods provided herein can be modified to improve or enhance folding of the heavy and/or light chain in the reducing environment of the cytoplasm. Alternatively, or in addition, a sFv intrabody can be modified to stabilize frameworks that can fold properly in the absence of intradomain disulfide bonds. Intrabodies can also be modified to increase, for example, one or more of the following characteristics: binding affinity, binding avidity, epitope accessibility, competition with endogenous proteins for the target epitope, half-life, target sequestration, post-translational modification of the target protein, etc. Because intrabodies act within the cell, their activity is more analogous to assay methodologies required for enzyme activity assays, which are discussed below in section B.

1. Polynucleotide Identification and Design

A convenient starting point for the creation and evolution of targeted antibody libraries is the use of semi-synthetic libraries that comprise CDRs that are derived from naturally occurring CDR sequences which are readily available from any suitable donor cells, and which can be ligated to predefined synthetic human antibody scaffolds. Additionally, because naturally occurring CDRs have evolved with a high hot spot density, they make a logical starting place for the development of seed libraries. Furthermore, the naturally occurring CDR3 sequence includes significant additional length diversity that is introduced via the action of terminal transferase activity and which can be exploited for the development of focused libraries using, for example, CDR1, CDR2 or CDR3 domains of different lengths.

Such libraries comprise (a) a plurality of representative human variable domain template polynucleotide fragments selected from each of the λ, κ, and H chain antibody isoforms, (b) a plurality of human CDR3 domains of the λ, κ, and H variable domains, and (c) one of a plurality of human constant region template fragments selected for each of the λ, κ, and H isoforms, wherein a fragment from each of the pluralities (a)-(c) is ligated to a create full-length light and heavy chain sub libraries, which may be subsequently combined to create a master library.

In other embodiments, the antibody libraries comprise multiple representative human variable domains templates which best represent germline sequences which are the commonly used antecedents of mature recombined antibodies seen in vivo.

In other embodiments, antibody libraries comprise CDR regions of the λ, κ, and H variable domains which are PCR amplified. In other embodiments the CDR regions are synthetic, and in one aspect derived from non human CDR regions.

The semi-synthetic antibody libraries described herein can further comprise human constant region templates for each of the λ, κ, and H isoforms.

Variable Domain Polynucleotide Fragments

As discussed in Example 4, a limited number of human germline polynucleotide sequences contribute to the majority λ, κ, and H antibody genes actually used to generate mature antibodies. The use of these optimized scaffolds enables the selection of optimal variable domains and constant regions that are most relevant to any specific target class, and most similar to human therapeutic antibodies.

Each polynucleotide sequences template variable domain is designed to include suitable unique restriction sites for sub-cloning, and ligation of CDRs and constant domains. Polynucleotides can be synthesized using standard methodology using commercially available vendors (e.g. DNA 2.0, Menlo Park, Calif.) and are sequenced to confirm correct synthesis. Once the sequence of the polynucleotide has been confirmed, the polynucleotide can be inserted into a suitable cloning vector for assembly of the entire antibody chain. In one embodiment, the template variable domains lack the CDR3 region.

Amplification of CDRs

In order to prepare a composition of polynucleotides comprising a substantial portion of the immunological gene repertoire, a starting source material having the genes coding for the $V_H$ and $V_L$ polypeptides is required. Preferably the source will be a heterogeneous population of antibody producing cells, i.e. B lymphocytes (B cells). In certain embodiments, rearranged B cells such as those found in the circulation (e.g. peripheral blood monocytes), spleen, tonsils or bone marrow of a vertebrate can be the starting source material. (Rearranged B cells are those in which immunoglobulin gene translocation, i.e., rearrangement, has occurred as evidenced by the presence in the cell of mRNA with the immunoglobulin gene V, D and J region transcripts adjacently located thereon.)

In certain embodiments, it is desirable to bias the repertoire for a preselected activity, such as by using as a source of nucleic acid cells (source cells) from vertebrates in any one of various stages of age, health and immune response. In one embodiment, a healthy animal can be repeatedly immunized prior to collecting rearranged B cells to obtain a repertoire enriched for genetic material producing a ligand binding target polypeptide of high affinity. In other embodiments, a healthy animal whose immune system has not been recently challenged is used to collect rearranged B cells thereby producing a repertoire that is not biased towards the production of genetic material with a high affinity to a target polypeptide.

It should be noted that the greater the genetic heterogeneity of the population of cells from which the polynucleotides are obtained, the greater the diversity of the immunological repertoire that will be made available for initial screening according to the method of the present invention. Thus, cells from different individuals, particularly those having an immunologically significant age difference, and cells from individuals of different strains, gender, races or species can be advantageously combined to increase the heterogeneity of the initial repertoire.

In certain embodiments of the present invention, the source cells are obtained from a vertebrate, preferably a mammal, which has been immunized or partially immunized with an antigenic ligand (antigen) against which activity is sought, i.e., a preselected antigen. The immunization can be carried out conventionally. Antibody titer in the animal can be monitored to determine the stage of immunization desired, which stage corresponds to the amount of enrichment or biasing of the repertoire desired. Partially immunized animals typically receive only one immunization and cells are collected therefrom shortly after a response is detected. Fully immunized animals display a peak titer, which is achieved with one or more repeated injections of the antigen into the host mammal, normally at 2 to 3 week intervals. Usually three to five days after the last challenge, the spleen is removed and the genetic repertoire of the spleenocytes, about 90% of which are rearranged B cells, is isolated using standard procedures. See, Current Protocols in Molecular Biology, Ausubel et al., eds., John Wiley & Sons, NY.

The polynucleotides coding for $V_H$ and $V_L$ polypeptides can be derived from cells producing IgA, IgD, IgE, IgG or IgM, most preferably from IgM and IgG, producing cells.

Methods for preparing fragments of genomic DNA from which immunoglobulin variable region genes can be cloned as a diverse population are well known in the art. See for example Hellmann et al., Methods In Enzymol., 152:180-183, (1987); Frischauf, Methods In Enzymol., 152:183-190 (1987); Frischauf, Methods In Enzymol., 152:190-199 (1987); and DiLella et al., Methods In Enzymol., 152:199-212 (1987). (The teachings of the references cited herein are hereby incorporated by reference.)

The desired gene repertoire can be isolated from either genomic material containing the gene expressing the variable region or the messenger RNA (mRNA) which represents a transcript of the variable region. The difficulty in using the genomic DNA from other than non-rearranged B lymphocytes is in juxtaposing the sequences coding for the variable region, where the sequences are separated by introns. The DNA fragment(s) containing the proper exons must be isolated, the introns excised, and the exons then spliced in the proper order and in the proper orientation. For the most part, this can be difficult, so that the alternative technique employing rearranged B cells are the method of choice because the C D and J immunoglobulin gene regions have translocated to become adjacent, so that the sequence is continuous (free of introns) for the entire variable regions.

Where mRNA is utilized, the cells will be lysed under RNase inhibiting conditions. In one embodiment, the first step is to isolate the total cellular mRNA by hybridization to an oligo-dT cellulose column. The presence of mRNAs coding for the heavy and/or light chain polypeptides can then be assayed by hybridization with DNA single strands of the appropriate genes. Upon isolation of the mRNA representing the transcripts of the genetic material encoding the variable regions genes of the starting source material, reverse transcription may be performed in a single step or in an optional combined reverse transcription/PCR procedure to generate a population of cDNA polynucleotides representative of CDR3 diversity within the starting source material.

In certain embodiments, the present invention includes methods for the generation of semi-synthetic antibody libraries that comprise (a) a plurality of variable domain polynucleotide fragments selected from each of the λ, κ, and H chain antibody isoforms, (b) a plurality of CDR3 domains of the λ, κ, and H variable domains, and (c) one of a plurality of constant region template fragments selected for each of the λ, κ, and H isoforms, wherein a fragment from each of the pluralities (a)-(c) is ligated to a create full-length light and heavy chain library. In one embodiment, the semi-synthetic antibody library is specific for the λ isoform. In another embodiment, the semi-synthetic antibody library is specific for the κ isoform. In still another embodiment, the semi-synthetic antibody library is specific for the H isoform.

In other embodiments, the semi-synthetic antibody libraries comprise multiple representative variable domains templates from each of the λ, κ, and H isoforms selected for PCR amplification and/or chemical synthesis. These templates are chosen so that each of the λ, κ, and H isoforms is represented by several variable domains which best represent germline sequence space and which are the commonly used antecedents of mature recombined antibodies seen in the sequence and structural databases.

In certain embodiments, the representative variable domains can be the λ isoform. In certain other embodiments, the representative variable domains can be the λ isoform. In still other embodiments, the representative variable domains can be the H isoform.

In one embodiment of the present invention, the variable domain templates are generated by PCR amplification. In another embodiment, the variable domain templates are generated by chemical synthesis.

In still other embodiments, semi-synthetic antibody libraries comprise CDR3 regions of the λ, κ, and H variable domains which are PCR amplified using primers specific for the 3rd framework region and the constant region. In one embodiment, the primers are specific for CDR3 regions of the λ isoform. In another embodiment, the primers are specific for CDR3 regions of the κ isoform. In still another embodiment, the primers are specific for CDR3 regions of the H isoform.

The semi-synthetic antibody libraries described herein can further comprise constant region templates for each of the λ, κ, and H isoforms selected for PCR amplification and/or chemical synthesis. In certain embodiments, the constant region can be the λ isoform. In certain other embodiments, the constant region can be the κ isoform. In still other embodiments, the constant region can be the H isoform. In one embodiment of the present invention, the constant region templates are generated by PCR amplification. In another embodiment, the constant region templates are generated by chemical synthesis.

In other embodiments of the present invention, antibodies can be made using synthetic, rather than naturally occurring CDR sequences. This approach enables more rational design strategies to be employed, for example to enable the development of focused libraries to specific classes of antigens.

In certain embodiments, to produce the polynucleotides encoding the CDR3 regions of the $V_H$ chain and $V_L$ chain by primer extension, the nucleotide sequence of a primer is selected to hybridize with a plurality of immunoglobulin heavy chain genes at a site substantially adjacent to the CDR3 coding region. To hybridize to a plurality of different CDR3 nucleic acid strands, the primer must be a substantial complement of a nucleotide sequence conserved among the different strands. In a preferred embodiment, primers are constructed that include or introduce restriction sites that can then be used to anneal the library with the 3' end of the template variable regions and the selected constant domains.

If the polynucleotides encoding the CDR3 regions of the $V_H$ chain and $V_L$ chain are to be produced by polymerase chain reaction (PCR) amplification, two primers must be used for each coding strand of nucleic acid to be amplified. The first primer becomes part of the sense (plus or coding) strand and hybridizes to a nucleotide sequence conserved among the polynucleotides which are upstream or span a portion the CDR3 regions of the $V_H$ chain and $V_L$ chain within the repertoire. To produce the polynucleotides encoding the CDR3 regions of the $V_H$ chain, first primers are therefore chosen to hybridize to (i.e. be complementary to) conserved regions within the FR3 region of immunoglobulin H isoform genes and the like. Likewise, to produce the polynucleotides encoding the CDR3 regions of the $V_L\lambda$ and $V_L\kappa$ chains, first primers are chosen to hybridize with (i.e. be complementary to) a conserved region within the FR3 region or which span the 5' portion of the $V_L\lambda$ and $V_L\kappa$ isoform CDR3 region.

Second primers become part of the noncoding (minus or complementary) strand and hybridize to a nucleotide sequence conserved among plus strands. To produce the polynucleotides encoding the CDR3 regions of the $V_H$ chain, second primers are therefore chosen to hybridize with a conserved nucleotide sequence at the 5' end of the $C_H$-coding immunoglobulin gene. Likewise, to produce the polynucleotides encoding the CDR3 regions of the $V_L\lambda$ and $V_L\kappa$ chains, second primers are therefore chosen to hybridize with a conserved nucleotide sequence at the 5' end of the $C_L$-coding immunoglobulin genes.

Preparation of the CDR3 Region Libraries

The strategy used for cloning, i.e., substantially reproducing, the polynucleotides encoding the CDR3 regions of the Ig $V_H$ and $V_L$ within the isolated repertoire will depend, as is well known in the art, on the type, complexity, and purity of the polynucleotides making up the repertoire.

In certain embodiments, the method comprises the cloning of the polynucleotides encoding the CDR3 regions of the $V_H$ chain and $V_L$ chain from a genetic repertoire comprised of polynucleotide coding strands, such as mRNA and/or the relevant coding region of genomic DNA.

In one embodiment, the genetic repertoire is in the form of double stranded genomic DNA, which is usually first denatured, typically by melting, into single strands. The genomic DNA is subjected to a first primary extension reaction by treating (contacting) the DNA with a first polynucleotide synthesis primer having a pre-selected nucleotide sequence. The first primer is capable of initiating the first primer extension reaction by hybridizing to a nucleotide sequence, preferably at least about 10 nucleotides in length and more preferably at least about 20 nucleotides in length, conserved within the repertoire. The first primer is sometimes referred to herein as the “sense primer” because it hybridizes to the non-coding or anti-sense strand of a nucleic acid and, after one round of priming and extension, becomes an integrated part of the sense (or coding) strand. In addition, the second primer is sometimes referred to herein as the “anti-sense primer” because it hybridizes to a coding or sense strand of a nucleic acid and, after one round of priming and extension, becomes an integrated part of the anti-sense (or non-coding) strand.

The first primer extension is performed by mixing the first primer, preferably a predetermined amount thereof, with the polynucleotides of the repertoire, preferably a predetermined amount thereof, to form a first primer extension reaction admixture. The admixture is maintained under polynucleotide synthesizing conditions for a time period, which is typically predetermined, sufficient for the formation of a first primer extension reaction product, thereby producing a plurality of different CDR3 regions polynucleotide complements. The complements are then subjected to a second primer extension reaction by treating them with a second polynucleotide synthesis primer having a pre-selected nucleotide sequence. The second primer is capable of initiating the second reaction by hybridizing to a nucleotide sequence, preferably at least about 10 nucleotides in length and more preferably at least about 20 nucleotides in length, conserved among a plurality of different $V_H$-coding gene complements such as those, for example, produced by the first primer extension reaction. This is accomplished by mixing the second primer, preferably a predetermined amount thereof, with the complement nucleic acids, preferably a predetermined amount thereof, to form a second primer extension reaction admixture. The admixture is maintained under polynucleotide synthesizing conditions for a time period, which is typically predetermined, sufficient for the formation of a first primer extension reaction product, thereby producing a gene library containing a plurality of different polynucleotides encoding the CDR3 regions.

A plurality of first primers and/or a plurality of second primers can be used in each amplification, or an individual pair of first and second primers can be used. In any case, the products of amplifications using the same or different combinations of first and second primers can be combined to increase the diversity of the gene library.

In an alternate embodiment, the method comprises the cloning of the polynucleotides encoding the CDR3 regions of the $V_H$ chain and $V_L$ chain from a genetic repertoire comprised of mRNA by subjecting the mRNA to a reverse transcriptase reaction to yield cDNA. Methods for producing such cDNA are well known in the art. The cDNA is subjected to a primer extension reaction similar to the above-described second primer extension reaction, i.e., a primer extension reaction using a polynucleotide synthesis primer capable of hybridizing to a nucleotide sequence conserved among a plurality of different $V_H$-coding gene complements.

The primer extension reaction is performed using any suitable method. Generally it occurs in a buffered aqueous solution, preferably at a pH of 7-9, most preferably about 8. Preferably, a molar excess (for genomic nucleic acid, usually about $10^6$:1 primer:template) of the primer is admixed to the buffer containing the template strand. A large molar excess is preferred to improve the efficiency of the process.

The deoxyribonucleotide triphosphates dATP, dCTP, dGTP, and dTTP are also admixed to the primer extension (polynucleotide synthesis) reaction admixture in adequate amounts and the resulting solution is heated to about 90° C.-100° C. for about 1 to 10 minutes, preferably from 0.5 to 4 minutes. After this heating period the solution cool to the calculated annealing temperature or sometimes 2° to 6° C. below the calculated annealing temperature of the oligonucleotide, which is preferable for primer hybridization. To the cooled mixture is added an appropriate agent for inducing or catalyzing the primer extension reaction, and the reaction is allowed to occur under conditions known in the art. The synthesis reaction may occur at from room temperature up to a temperature above which the inducing agent no longer functions efficiently. Thus, for example, if thermostable DNA polymerase is used as inducing agent, the temperature is generally no greater than about 40° C.

The inducing agent can be any compound or system which will function to accomplish the synthesis of primer extension products, including enzymes. Suitable enzymes for this purpose include, for example, *E. coli*, DNA polymerase I, Klenow fragment of *E. coli* DNA polymerase I, T4 DNA polymerase, other available DNA polymerases, reverse transcriptase, and other enzymes, including heat-stable enzymes, which will facilitate combination of the nucleotides in the proper manner to form the primer extension products which are complementary to each nucleic acid strand. Generally, the synthesis will be initiated at the 3' end of each primer and proceed in the 5' direction along the template strand, until synthesis terminates, producing molecules of different lengths. There may be inducing agents, however, which initiate synthesis at the 5' end and proceed in the above direction, using the same process as described above.

The newly synthesized strand and its complementary nucleic acid strand form a double-stranded molecule which can be used in the succeeding steps of the amplification process.

After producing the DNA homologs representative of the plurality of polynucleotides encoding the CDR3 regions of the $V_H$ chains and $V_L$ chains within the immunological repertoire of the starting source material, the homologs are typically amplified to produce a quantity sufficient for ligation into the appropriate $V_H$ and $V_L$ synthetic constructs. Methods of amplification are known in the art and include subjecting the DNA homologs to a polymerase chain reaction (PCR) prior to ligating them into the appropriate $V_H$ and $V_L$ synthetic constructs. In one such embodiment, the first and/or second primer extension reactions used to produce the gene library are the first and second primer extension reactions in a polymerase chain reaction.

PCR is normally carried out by cycling, i.e., simultaneously performing in one admixture, the above described first and second primer extension reactions, each cycle comprising polynucleotide synthesis followed by denaturation of the double stranded polynucleotides formed. Methods and systems for amplifying a DNA homolog are described in U.S. Pat. No. 4,683,195 and No. 4,683,202, both to Mullis et al.

In preferred embodiments only one pair of first and second primers is used per amplification reaction. The amplification reaction products obtained from a plurality of different amplifications, each using a plurality of different primer pairs, are then combined.

The DNA homologs representative of the plurality of polynucleotides encoding the CDR3 regions produced by PCR amplification are typically in double-stranded form and have contiguous or adjacent to each of their termini a nucleotide sequence defining an endonuclease restriction site. Digestion of the DNA homologs representative of the plurality of polynucleotides encoding the CDR3 regions having restriction sites at or near their termini with one or more appropriate endonucleases results in the production of DNA homologs having cohesive termini of predetermined specificity.

Preparation of Synthetic CDRs

As discussed previously, synthetic CDR sequences can be modified to include preferred SHM motifs to act as a substrate for efficient, targeted mutation. In one aspect such SHM motifs may be based on random, semi-random or designed combinations of "WAC" motifs, or "WRC" motifs. Examples of such motifs include any combination of preferred SHM codons encoding Ser, Tyr and Asn.

In one embodiment such synthetic CDRs comprise at least one sequence selected from i) to vi)

| | | |
|---|---|---|
| i) | $-X_1X_2X_3X_4X_5-$ | (SEQ ID NO: 62) |
| ii) | $-X_1X_2X_3X_4X_5X_6-$ | (SEQ ID NO: 63) |
| iii) | $-X_1X_2X_3X_4X_5X_6X_7-$ | (SEQ ID NO: 64) |

-continued

| | | |
|---|---|---|
| iv) | $-X_1X_2X_3X_4X_5X_6X_7X_8-$ | (SEQ ID NO: 65) |
| v) | $-X_1X_2X_3X_4X_5X_6X_7X_8X_9-$ | (SEQ ID NO: 66) |
| vi) | $-X_1X_2X_3X_4X_5X_6X_7X_8X_9X_{10}-$ | (SEQ ID NO: 67) |

where $X_1$, $X_2$, $X_3$, $X_4$, $X_5$, $X_6$, $X_7$, $X_8$, $X_9$ and $X_{10}$ are each independently selected from the amino acids Ser, Tyr and Asn.

In one aspect, any one of such motifs may also be separated by one or more polynucleotide sequences that encode amino acid residues of particular interest. In aspect such amino acids are independently selected from the group consisting of Gly, Pro, Trp, His, and Met.

In another aspect, such synthetic CDRs may be comprised of random, semi random or designed, repeating, or non repeating, sequences of Ser, Asn and Tyr up to about 50 amino acids.

In another aspect such synthetic CDRS may be comprised from preferred SHM codons. In one embodiment, such codons (i.e. corresponding to $X_1$, $X_2$, $X_3$ etc above) are independently selected from the group consisting of AGC, UAU, UAC, UUU, UUA, UUC, GCU, GCA, AAA, AAG, GAG, CAG, AAU, AAC, CUA, UUG, CUU, AUU, AUA and AUC.

Synthetic CDRs can range in size from about 5 amino acids to about 40 amino acids in length. Longer CDRs specifically CDRs of about 25 to about 60 amino acids are also contemplated. In certain embodiments of the present invention, such synthetic CDRs can comprise at least 50% preferred SHM codons, or more preferably, at least 70% preferred SHM codons, or most preferred at least 80% preferred SHM codons.

In one aspect of the present invention, a seed library of diverse synthetic CDRs can be constructed in which some, or every position in the CDR is randomly assigned a preferred SHM codon. Typically the diversity of each such synthetic CDR libraries will range from about $3^5$ (3 codons each randomly assigned to all 5 positions) to $3^{10}$ (3 codons each randomly assigned to all 10 positions) to $13^5$ (top 13 codons each randomly assigned to all 5 positions) to $13^{10}$ (top 13 codons each randomly assigned to all 10 positions).

In another embodiment, one or more of the synthetic CDR1, CDR2 and CDR3 regions of the heavy and light chain are derived from a non-human antibody. In another embodiment, only the CDR3 regions of the heavy and light chain are derived from the non-human antibody. In one aspect, such non-human CDR sequences comprise synthetic polynucleotide sequences that have been optimized for somatic hypermutation, and comprise preferred SHM codons and/or preferred SHM hot spot codons. Such synthetic CDR sequences, when incorporated into the human libraries of the present invention, provide a method of rapidly humanizing non human antibodies via SHM mediated mutagenesis and screening, as described below.

For use herein, each synthetic, variable region can also be designed to include suitable unique restriction sites for subcloning, and ligation of CDRs and constant domains.

Polynucleotides can be synthesized using standard methodology using commercially available vendors (e.g. DNA 2.0, Menlo Park, Calif.) and are sequenced to confirm correct synthesis. Once the sequence of the polynucleotide has been confirmed, the polynucleotide can be inserted into a suitable cloning vector, as described above, for assembly of the entire antibody heavy or light chain sub libraries as appropriate. In one embodiment, the synthetic CDRs are inserted to a synthetic variable domain template lacking consensus CDR regions, and then ligated into synthetic constant domains, as described herein with regard to semi-synthetic full length antibody libraries.

Once each of the sub-libraries has been assembled into one or more expression vectors suitable for SHM they may be introduced into a host cell as described herein to effect mutagenesis.

As described below, specific screens to detect and select surface exposed or secreted antibodies with improved traits, typically involve several rounds of mutation and selection based on the simultaneous selection of multiple parameters, for example, affinity, avidity, selectivity and thermostability in order to evolve the overall best antibody.

Information from specific types of libraries, for example, libraries comprising antibodies having a binding specificity to different types of antigen or libraries comprising CDRs of different lengths, can be used to aid in the design process for subsequent focused libraries.

2. Template Constant Domains

Any mammalian heavy-chain constant domains (Fc) that correspond to the different antibody classes (i.e. IgA, IgD, IgE, IgG, or IgM) or subclasses (isotypes), e.g., IgG1, IgG2, IgG3, IgG4, IgA, and IgA2 can be used as a scaffold, depending on the desired functionality of the antibody. Preferred constant domains include human constant domains of the IgG class, and in particular IgG1, IgG2, and IgG4 subclasses. Suitable light chain constant domains include kappa and lambda. Preferred light chain constant domains are human.

Each polynucleotide template constant domain is designed to include suitable unique restriction sites for sub-cloning, and ligation of CDRs and variable domains. Polynucleotides can be synthesized using standard methodology using commercially available vendors (e.g. DNA 2.0, Menlo Park, Calif.) and are sequenced to confirm correct synthesis. Once the sequence of the polynucleotide has been confirmed, the polynucleotide can be inserted into a suitable cloning vector for assembly of the entire antibody chain.

3. Library Assembly

In certain embodiments, antibody library assembly involves completing the assembly of one or more sub-libraries by ligation of the various elements together.

Specifically, the heavy chain library involves the ligation of the Ig $V_H$ CDR3 Region Libraries into a cloning vector comprising one or more of a plurality of chemically synthesized polynucleotides encoding a portion of the template heavy chain variable domain (i.e. lacking its endogenous CDR3 domain), and a chemically synthesized polynucleotide encoding the template heavy chain constant domain to yield a semi-synthetic antibody library representative of the diversity of a rearranged full length heavy chain.

κ Light chain library assembly involves the ligation of the Ig $V_L$κ CDR3 Region Libraries into a cloning vector comprising one or more of a plurality of chemically synthesized polynucleotides encoding a portion of the template κ variable domain (i.e. lacking its endogenous CDR3 domain) and a chemically synthesized polynucleotide encoding the κ light chain constant domain to yield a semi-synthetic antibody library representative of the diversity of a rearranged full length κ light chain.

λ Light chain library assembly involves the ligation of the Ig $V_L$λ CDR3 Region Libraries into a cloning vector comprising one or more of a plurality of chemically synthesized polynucleotides encoding a portion of the template λ variable domain (i.e. lacking its endogenous CDR3 domain) and a chemically synthesized polynucleotide encoding the λ light chain constant domain to yield a semi-synthetic antibody library representative of the diversity of a rearranged full length λ light chain.

Once each of the sub-libraries has been assembled into one or more expression vectors, sub-libraries can be introduced into an appropriate host cell as described herein. In certain embodiments, each of the sub-libraries is assembled into one or more expression vectors suitable for SHM, after which the one or more expression vectors suitable for SHM comprising each of the sub-libraries can be introduced into a host cell as described herein to effect mutagenesis.

4. Screening Methodology

Specific screens to detect and select surface exposed or secreted antibodies with improved traits, are well known in the art, and are described in detail below in Section X. In general, such screens will involve several rounds of selection based on the simultaneous selection of multiple parameters, for example, affinity, avidity, selectivity and thermostability in order to evolve the overall best antibody.

Once an antibody or fragment thereof has been optimized using SHM, the phenotype/function of the optimized antibody or fragment thereof can be further analyzed using art-recognized assays. Assays for antibodies or fragments thereof include, but are not limited to, enzyme-linked immunosorbant assays (ELISA), enzyme-linked immunosorbant spot (ELISPOT assay), gel detection and fluorescent detection of mutated IgH chains, Scatchard analysis, BIACOR analysis, western blots, polyacrylamide gel (PAGE) analysis, radioimmunoassays, etc. which can determine binding affinity, binding avidity, etc. Such assays are more fully described in Section X below.

Once optimized antibodies have been identified, episomal DNA can be extracted (or amplified by co-expression with SV40 T Antigen (J. Virol. (1988) 62 (10) 3738-3746)) and then extracted and subjected to PCR using variable heavy chain ($V_H$) leader region and/or variable light chain ($V_L$) leader region specific sense primers and isotype specific anti-sense primers. Alternatively, total RNA from selected sorted cell populations can be isolated subjected to RT-PCR using variable heavy chain ($V_H$) leader region and/or variable light chain ($V_L$) leader region specific sense primers and isotype specific anti-sense primers. Clones can be sequenced using standard methodologies and the resulting sequences can be analyzed for frequency of nucleotide insertions and deletions, receptor revision and V gene selection. The resulting data can be used to populate a database linking specific amino acid substitutions with changes in one or more of the desired properties. Such databases can then be used to recombine favorable mutations or to design next generation polynucleotide library with targeted diversity in newly identified regions of interest, e.g. nucleic acid sequences which encode a functional portion of a protein.

B. Non-Antibody Proteins of Interest

With respect to non-antibody proteins, the present invention provides the ability to bypass the need for in vivo introduction of a library of randomly modified proteins to rapidly select modified proteins that produce the most robust biological effect or exhibit improved desired properties/activities. Thus, the present invention allows for the rapid evolution of improved proteins by scanning target proteins for optimal functional and/or structural regions and evolving such regions using the methods described herein. This provides the ability to scan target proteins for optimal functional region(s) and produce best in class protein drugs for use in the clinic.

1. Enzymes

Enzymes and pro-enzymes present another category of polypeptides which can be readily improved, and for which SHM is useful. Of particular interest is the application of the present invention to the co-evolution of multiple enzymatic pathways, involving the simultaneous mutation of two or more enzymes. In one aspect, the expression of two synthetic libraries of polynucleotides encoding proteins of interest in which both synthetic polynucleotides libraries are located in proximity to a promoter, and expressed and co-evolved in the same cell simultaneously. In one embodiment, the promoter is a bi-directional promoter such as a bi-directional CMV promoter. In another embodiment, the two synthetic libraries of polynucleotides encoding proteins of interest are placed in front of two uni-directional promoters. The two promoters can be the same promoter or different promoters. The two synthetic libraries of polynucleotides encoding proteins of interest can be in the same vector or on different vectors. Enzymes and enzyme systems of particular note include, for example, enzymes associated with microbiological fermentation, metabolic pathway engineering, protein manufacture, bio-remediation, and plant growth and development.

Many high throughput screening approaches to measure, select and evolve enzymes with improved traits, are well known in the art, and are outlined in Section X. In general, such screens involve several rounds of selection based on the simultaneous selection of multiple parameters, for example, pH stability, Km, Kcat, thermostability, solubility, proteolytic stability, substrate specificity, co-factor dependency, and tendency for hetero or homo dimerization.

a. Polynucleotide Identification and Design

As described previously, the starting point for mutagenesis is typically either a cDNA clone of the gene of interest, or its amino acid or polynucleotide sequence. A useful starting point for library development is to run a sequence comparison search with this starting sequence using one of several publicly available databases, for example the PDB database, (www.ncbi.nih.gov/genbank). Such databases include virtually all known sequence information and include appropriate analysis tools.

Such searches typically generate information on areas of identity and divergence between related isoforms of the gene of interest and between the same gene in different organisms.

In addition, the creation of cladograms that show the degree of relatedness of different polynucleotide sequences for example by using the phylip 3.65 ProtMLK program (see Numerical methods for inferring evolutionary trees. *Quarterly Review of Biology* 57:379-404) which can provide important insights on the evolution of related sequences to help develop a template polynucleotide, for example by identifying all enzymes within a specific class or family of interest.

Such genes can be simultaneously evolved by co-expressing AID and or other auxiliary enzymes into a host cell comprising such enzymes. In a preferred case, such enzymes have been codon optimized for SHM.

This approach exploits the ability to identify mutations that not only confer an advantage to specific subsystem in question, but also positively impact the overall system which is linked to cell growth and viability.

b. Screening Methodology

Many high throughput screening approaches are well known in the art and can be readily applied to identify and select improved enzymes (see generally, Olsen et al., Methods. Mol. Biol. (2003) 230 329-349; Turner, Trends Biotechnol. (2003) 21(11) 474-478; Zhao et al., Curr. Opin. Biotechnol. (2002) 13(2) 104-110; Mastrobattista et al., Chem Biol. (2005) 12 (12) 1291-300), In general the screening modality used will depend on the nature of the enzyme and whether the enzyme of interest is intracellular, or extracellular, and further whether it is membrane associated or freely secreted.

In general, initial screens that provide useful quantitative information over a wide dynamic window, and which have a high screening capacity are preferred. Representative screening approaches include, for example, assays based on the altered ability, or speed of growth of improved cells, and/or based on the sorting of cells using a flow cytometer, that can detect the presence of intracellular fluorogenic reaction products or altered reporter gene expression (Specific protocols for FACS based optimization of enzyme activity are reviewed in the following references; Farinas et al., Comb. Chem. High Throughput Screen (2006) 9(4) 321-8; Becker et al., Curr. Opin. Biotechnol. (2004) 15(4) 323-9; Daugherty et al., J. Immunol Methods (2000) 243 (1-2) 211-227.

Once an enzyme or set of enzymes has been optimized using SHM, a complete biochemical analysis of the optimized enzyme(s) can be further analyzed using art-recognized assays. Additionally as previously discussed, once optimized enzymes have been identified, episomal DNA can be extracted or amplified by co-expression with SV40 T Antigen (J. Virol. (1988) 62 (10) 3738-3746), then extracted and subjected to PCR using specific primers. Alternatively, total RNA can be obtained from selected cell populations and subjected to RT-PCR using specific primers. Clones can be sequenced using standard methodologies and the resulting sequences can be analyzed for the frequency of nucleotide mutations. The resulting data can be used to populate a database linking specific amino acid substitutions with changes in one or more of the desired properties. Such databases may then be used to recombine favorable mutations, or to design next generation polynucleotide library with targeted diversity in newly identified regions of interest, e.g. nucleic acid sequences which encode a functional portions of a protein.

2. Receptors

Receptors bind ligands and encompass a broad genus of naturally occurring and synthetic polypeptides encoding specific binding members, including, but not limited to, cell-bound receptors such as antibodies (B cell receptors), T cell receptors, Fc receptors, G-coupled protein receptors, cytokine receptors, carbohydrate receptors, and Avimer based receptors.

In general such receptors will be altered through SHM to improve one or more of the following traits; affinity, avidity, selectivity, thermostability, proteolytic stability, solubility, dimerization, folding, immunotoxicity, coupling to signal transduction cascades and expression.

a. Polynucleotide Identification and Design

As described previously, the starting point for mutagenesis is typically either a cDNA clone of the gene of interest, or it's amino acid or polynucleotide sequence. To maximize the effectiveness of SHM it is preferred (but not essential) that the starting polynucleotide sequence is modified to maximize the density of hot spots and to reduce the density of cold spots. Such methods are disclosed in sections IV and V of the present specification.

In general, such receptors possess clearly defined regions that can be either targeted for mutagenesis through the use of SHM optimized sequences, or conserved during mutagenesis through the use of SHM resistant sequences. Regions typically targeted for mutagenesis include sites of post-translational modification, surface exposed loop domains, positions of variation between species, protein-protein interaction domains, and binding domains. Regions typically conserved during mutagenesis include transmembrane domains, invariant amino acid positions, signal sequences, and intracellular trafficking domains. Alternatively a scanning approach can be used to systematically insert hot spot motifs throughout the reading frame of the receptor of interest, as described previously.

b. Screening Methodology

Many high throughput screening approaches are well known in the art and can be readily applied to identify and select improved receptors. In general high throughput screening approaches are preferred. Representative screening approaches include, for example, binding assays, growth assays, reporter gene assays and FACS based assays.

Once an enzyme or set of enzymes has been optimized using SHM, a complete pharmacological analysis of the optimized receptor can be further analyzed using art-recognized assays. Additionally as previously discussed, once an optimized receptor has been identified, episomal DNA can be extracted or amplified by co-expression with SV40 T Antigen (J. Virol. (1988) 62 (10) 3738-3746), then extracted and subjected to PCR using specific primers. Alternatively, total RNA can be obtained from selected cell populations and subjected to RT-PCR using specific primers. Clones can be sequenced using standard methodologies and the resulting sequences can be analyzed for the frequency of nucleotide mutations. The resulting data can be used to populate a database linking specific amino acid substitutions with changes in one or more of the desired properties. Such databases may then be used to recombine favorable mutations or to design next generation polynucleotide library with targeted diversity in newly identified regions of interest, e.g., nucleic acid sequences which encodes functional portions of a protein.

VII. Methods for Antibody Humanization

As previously stated, monoclonal antibodies represent a distinct class of biotherapeutics with a great deal of promise. However, the development of monoclonal antibodies for use in human clinical therapies is often delayed or prevented due to problems associated with the immunogenicity of monoclonal antibodies which are derived from non-human sources (i.e., murine monoclonal antibodies). Although it is possible to graft the CDRs of the non human antibody into a human scaffold this typically results in a significant drop in binding affinity, and as a result, requires extensive site directed mutagenesis in order to create a high affinity humanized antibody with binding characteristics that are comparable to the starting non human antibody. In light of this problem, provided herein are methods of rapidly humanizing non-human monoclonal antibodies to reduce their immunogenic activity thereby enabling their use as human therapeutics.

In certain aspects, the present invention provides a method for humanizing a non human antibody, comprising the steps of: a) synthesizing a seed library of polynucleotides encoding one or more human antibody heavy chain protein scaffolds comprising at least one synthetic nucleic acid sequence which encodes all or part of at least one CDR domain derived from the non human antibody heavy chain protein; b) synthesizing a seed library of polynucleotides encoding a plurality of one or more human antibody light chain protein scaffolds comprising at least one synthetic nucleic acid sequence which encodes all or part of at least one CDR domain derived from the non human antibody light chain protein; c) cloning the antibody heavy chain protein scaffolds and antibody light chain protein scaffolds into expression vectors; d) transforming a host cell with the expression vectors, so that an antibody is produced by coexpression of a heavy chain from the antibody heavy chain protein scaffolds and a light chain from the light chain protein scaffolds, e) optionally inducing AID activity in the host cell, or allowing AID mediated mutagenesis to occur on the seed libraries; f) identifying a cell or cells within the population of cells which expresses a humanized antibody having binding characteristic of said non human antibody, and g) establishing one or more clonal populations of cells from the cell or cells identified in step (f).

Library construction for antibody humanization uses the same overall methodology as discussed above for creation of synthetic and semi-synthetic antibody libraries in Sections V and VI.

A. Template Variable Domains Identification

The identification of polynucleotide sequences for use as variable domain templates suitable for humanizing a non-human monoclonal antibody is typically based on the homology of the non human antibody to known human germline variable domain sequences. Specifically it is preferred that human variable domains are initially selected that exhibit the greatest degrees of homology to the non human antibody heavy and light variable domains.

In one aspect, the top 10 most related heavy chain variable domain templates, and the top 10 most related light chain variable domain templates are used to create an initial seed library.

In another aspect, the top 5 most related heavy chain variable domain templates, and the top 5 most related light chain variable domain templates are used to create an initial seed library.

In one aspect, the top 2 most related heavy chain variable domain templates, and the top 2 most related light chain variable domain templates are used to create an initial seed library.

Each polynucleotide sequence template variable domain is designed to include suitable unique restriction sites for sub-cloning, and ligation of CDRs and constant domains. Polynucleotides can be synthesized using standard methodology using commercially available vendors (e.g. DNA 2.0, Menlo Park, Calif.) and are sequenced to confirm correct synthesis. Once the sequence of the polynucleotide has been confirmed, the polynucleotide can be inserted into a suitable cloning vector for assembly of the entire antibody chain. In one embodiment, the template variable domains lack the CDR regions.

B. Template Constant Domains

Any polynucleotide sequence encoding a human heavy-chain constant domains (Fc) that correspond to the different antibody classes (i.e. IgA, IgD, IgE, IgG, or IgM) or subclasses (isotypes), e.g., IgG1, IgG2, IgG3, IgG4, IgA, and IgA2 can be used as a scaffold, depending on the desired functionality of the antibody. Preferred constant domains include human constant domains of the IgG class, and in particular IgG1, IgG2, and IgG4 subclasses. Suitable human light chain constant domains include kappa and lambda.

Each polynucleotide template constant domain is designed to include suitable unique restriction sites for sub-cloning, and ligation of CDRs and variable domains. Polynucleotides can be synthesized using standard methodology using commercially available vendors (e.g. DNA 2.0, Menlo Park, Calif.) and are sequenced to confirm correct synthesis. Once the sequence of the polynucleotide has been confirmed, the polynucleotide can be inserted into a suitable cloning vector for assembly of the entire antibody chain.

C. Non-Human Monoclonal Antibody CDR Regions

The CDR regions of any non-human monoclonal antibody is suitable for use in the methods for humanization described herein. In a preferred embodiment, the synthetically produced CDR regions comprise unique restriction sites for ligation of the CDR regions into the human variable domains and human constant domains described herein.

In certain embodiments, the polynucleotide sequence encoding all, or a portion of a CDR3 region of a characterized non-human monoclonal antibody can be synthetically produced based upon the known amino acid sequence of the CDR3 region of the monoclonal antibody. In a preferred aspect, the CDR3 polynucleotide sequence has been optimized for somatic hypermutation. In one aspect the SHM optimized sequence is optimized for SHM by the insertion of somatic hypermutation motifs. In another aspect, the SHM optimized sequence is optimized for SHM by the insertion of one or more preferred SHM codons. In another aspect, the SHM optimized sequence is optimized for SHM by the insertion of one or more WAC motif, WRC motif, or one or more combinations thereof.

In other embodiments, the polynucleotides encoding the CDR3 regions of the VH chain and VL chain of the non-human monoclonal antibody can be produced by polymerase chain reaction (PCR) amplification. As is known to one of skill in the art, two primers must be used for each coding strand of nucleic acid to be amplified. The first primer becomes part of the sense (plus or coding) strand and hybridizes to a nucleotide sequence conserved among the polynucleotides which are upstream or span a portion the CDR3 regions of the VH chain and VL chain within the repertoire. To produce the polynucleotides encoding the CDR3 regions of the VH chain, first primers are therefore chosen to hybridize to (i.e. be complementary to) conserved regions within the FR3 region of immunoglobulin H isofom genes and the like. Likewise, to produce the polynucleotides encoding the CDR3 regions of the VLλ and VLκ chains, first primers are chosen to hybridize with (i.e. be complementary to) a conserved region within the FR3 region or which span the 5' portion of the VLλ and VLκ isoform CDR3 region.

Second primers become part of the noncoding (minus or complementary) strand and hybridize to a nucleotide sequence conserved among plus strands. To produce the polynucleotides encoding the CDR3 regions of the VH chain, second primers are therefore chosen to hybridize with a conserved nucleotide sequence at the 5' end of the CH-coding immunoglobulin gene. Likewise, to produce the polynucleotides encoding the CDR3 regions of the VLλ and VLκ chains, second primers are therefore chosen to hybridize with a conserved nucleotide sequence at the 5' end of the CL-coding immunoglobulin genes.

Irrespective of the methods used to generate the polynucleotide sequence encoding the CDR3 region of the monoclonal antibody of interest, once the polynucleotide sequence encoding the CDR3 region is isolated it can then be ligated with the polynucleotide sequences encoding the human variable domains and human constant domains described herein to yield a polynucleotide sequence encoding a full length humanized monoclonal antibody.

D. Assembly of the Humanized Monoclonal Antibody Library

In one aspect, the methods described herein for humanizing a heavy chain antibody involve the ligation of all of the non human Ig VH CDR domains (or in one aspect, only the CDR3 domain) into a plurality of cloning vectors comprising a polynucleotide described herein which encodes a plurality of human template heavy chain variable domains (i.e. lacking all endogenous CDR domains, or in one aspect just CDR3), and a polynucleotide encoding the human template heavy chain constant domain to yield a humanized full length heavy chain sub library of the monoclonal antibody of interest.

The methods for humanizing a κ Light chain involve the ligation of the Ig VLκ CDRs (or in one aspect, just CDR3) into a plurality of cloning vectors comprising a chemically synthesized polynucleotide described herein which encodes a plurality of human template κ variable domains (i.e. lacking its endogenous CDR domains, or in one aspect just CDR3) and a chemically synthesized polynucleotide encoding the κ light chain constant domain to yield a humanized full length κ light chain sub library of the monoclonal antibody of interest.

The methods for humanizing a λ Light chain involve the ligation of the Ig VLλ CDRs (or in one aspect, just CDR3) into a plurality of cloning vectors comprising a chemically synthesized polynucleotide described herein which encodes a plurality of human template λ variable domains (i.e. lacking its endogenous CDR domains, or in one aspect just CDR3) and a chemically synthesized polynucleotide encoding the λ light chain constant domain to yield a humanized full length λ light chain sub library of the monoclonal antibody of interest.

Once the full length humanized heavy and light (either κ or λ) chain sub-libraries of the monoclonal antibody of interest have been assembled into one or more expression vectors, they can be introduced into an appropriate host cell as described herein in Section VIII. In certain embodiments, the full length humanized heavy and light (either κ or λ) chain genes of the monoclonal antibody of interest are assembled into one or more expression vectors suitable for SHM, after which the one or more expression vectors suitable for SHM comprising each of the full length humanized heavy and light (either κ or λ) chain genes of the monoclonal antibody can be introduced into a host cell as described herein to effect SHM mediated mutagenesis.

E. Screening Methodology

Specific screens to detect and select surface exposed or secreted humanized antibodies with improved traits, are well known in the art, and are described in detail below in Section X. In general, such screens will involve several rounds of selection based on the simultaneous selection of multiple parameters, for example, affinity, avidity, selectivity and thermostability in order to evolve the overall best humanized antibody.

VIII. Systems for the Expression of Polynucleotide Libraries

In vitro expression and hypermutation systems for use herein include cell free systems that enable the transcription, or coupled transcription and translation of DNA templates and, in certain embodiments, enable the on-going mutagenesis via SHM. In one embodiment, such in vitro translation systems can be used in combination with ribosome display to enable the ongoing mutagenesis and selection of proteins.

In vitro translation systems include for example the classical rabbit reticulocyte system, as well as novel cell free synthesis systems, (J. Biotechnol. (2004) 110 (3) 257-63; Biotechnol Annu. Rev. (2004) 10 1-30). Systems for ribosome display are described for example in Villemagne et al., J. Imm. Meth. 2006 313 (1-2) 140-148).

In certain embodiments, the synthetic libraries, semi-synthetic libraries and/or seed libraries described herein can utilize phage display technology by exploiting the capability of bacteriophage to express and display biologically functional protein molecule on its surface. Generally, a phage library can be created by inserting the synthetic or semi-synthetic libraries described above into gene 3 of M13 or T7 phage. Each inserted constructed of the synthetic or semi-synthetic library is expressed at the N-terminal of the gene 3 product, a minor coat protein of the phage. As a result, peptide libraries that contain diverse peptides can be constructed. The phage library can then be affinity screened against immobilized target molecule of interest, such as an antigen, and specifically bound phages are recovered and amplified by infection into *Escherichia coli* host cells. Typically, the target molecule of interest such as a receptor (e.g., polypeptide, carbohydrate, glycoprotein, nucleic acid) is immobilized by covalent linkage to a chromatography resin to enrich for reactive phage by affinity chromatography) and/or labeled for screen plaques or colony lifts. This procedure is called biopanning. Finally, amplified phages can be sequenced for deduction of the specific peptide sequences.

A variety of solid phases have been used successfully for biopanning with phage display libraries, including plastic ELISA plates or uncoated cell culture dishes, magnetic particles, glass beads, and beaded agarose. The most convenient and commonly used solid phase is plastic and the most commonly used method for coating is non-covalent adsorption. However, because the adsorption of proteins onto plastic surfaces is thought to involve hydrophobic interactions, some ligands, particularly highly hydrophilic proteins or low molecular weight compounds, may bind inefficiently to plastic unless a covalent attachment method is used. The methods used for the preparation of ELISA plates are directly applicable to biopanning, and detailed ligand immobilization protocols can be found in enzyme immunoassay laboratory manuals. To enhance binding, proteins that adsorb poorly to plastic can be partially denatured with a chaotropic agent such as guanidine, urea, or thiocyanate, or with acid or heat. In addition, target lipids or lipoproteins can be adsorbed to plastic in the presence of deoxycholate. The solid phase used for immobilization of the target ligand usually depends on the volume of phage lysate screened. For most applications, a plastic 96-well ELISA plate (e.g., Corning, No. 25801) allows up to $10^{10}$ phage to be screened in a single well. However, when larger volumes (>0.2 ml) must be screened, uncoated 6 to 24-well plastic cell culture plates can be used. When screening very large lysate volumes (>2 ml), plastic Petri dishes can be used. Larger volumes may be required in the initial rounds of biopanning to ensure that a sufficiently representative sample has been exposed to the target ligand.

Each panning step starts with a mixture of phage, and seeks to select from that mixture phage whose displayed protein binds the target receptor. These phage are specifically "captured" by immobilizing the receptor (in our case, whole cells) on a solid surface; unbound phage are washed away, and the captured phage are eluted (still in infective form), yielding a selected subset of the original phage mixture that is called an "eluate." Usually the eluate from the first round of selection is amplified by infecting the phage into fresh cells, and the amplified eluate then used as input to another round of selection. Altogether, two or three rounds of selection usually suffice to select for a highly enriched population of good binders-assuming, of course, the initial library contains such binders.

In other embodiments, an in vitro expression system comprises a library of synthetic or semi-synthetic polynucleotides that include an expression cassette for the expression of the plurality of synthetic or semi-synthetic polynucleotides encoding a gene of interest. In certain embodiments, the synthetic or semi-synthetic gene comprising a sequence has been optimized for SHM. For ribosome display, the polynucleotide should lack a stop codon so that it remained attached to the ribosome after translation.

To effect transcription and or translation of the gene of interest, the system can include purified or semi-purified components for in vitro transcription and translation, for example via the use of recombinant factors with purified 70S ribosomes. In an expression system utilizing ongoing SHM, the system would further include recombinant, or purified AID and or other factors for SHM/DNA repair.

Cell based expression and hypermutation systems include any suitable prokaryotic or eukaryotic expression system. In certain embodiments, the cell-based expression systems are those that can be used to express AID, can be easily and reliably grown, have reasonably fast growth rates, have well characterized expression systems and can be transformed or transfected easily and efficiently.

A. Prokaryotic Expression Systems

Within these general guidelines, useful microbial hosts include bacteria from the genera *Bacillus, Escherichia* (such as *E. coli*), *Pseudomonas, Streptomyces, Salmonella, Erwinia, Bacillus subtilis, Bacillus brevis*, the various strains of *Escherichia coli* (e.g., HB101, (ATCC NO. 33694) DH5α, DH10, and MC1061 (ATCC NO. 53338)).

B. Eukaryotic Expression Systems i. Yeast

Many strains of yeast cells known to those skilled in the art are also available as host cells for the expression of polypeptides including those from the genera *Hansenula, Kluyveromyces, Pichia*, Rhino-sporidium, *Saccharomyces*, and *Schizosaccharomyces*, and other fungi. Preferred yeast cells include, for example, *Saccharomyces cerivisae* and *Pichia pastoris*.

ii. Insect Cells

Additionally, where desired, insect cell systems can be utilized in the methods of the present invention. Such systems are described, for example, by Kitts et al., Biotechniques, 14:810-817 (1993); Lucklow, Curr. Opin. Biotechnol., 4:564-572 (1993); and Lucklow et al. (J. Virol., 67:4566-4579 (1993). Preferred insect cells include Sf-9 and HI5 (Invitrogen, Carlsbad, Calif.).

iii. Mammalian Expression Systems

A number of suitable mammalian host cells are also known in the art and many are available from the American Type Culture Collection (ATCC), 10801 University Boulevard, Manassas, Va. 20110-2209. Examples include, but are not limited to, mammalian cells, such as Chinese hamster ovary cells (CHO) (ATCC No. CCL61) CHO DHFR-cells (Urlaub et al., Proc. Natl. Acad. Sci. USA, 97:4216-4220 (1980)), human embryonic kidney (HEK) 293 or 293T cells (ATCC No. CRL1573), PER.C6™ cells, or 3T3 cells (ATCC No. CCL92). The selection of suitable mammalian host cells and methods for transformation, culture, amplification, screening and product production and purification are known in the art. Other suitable mammalian cell lines are the monkey COS-1 (ATCC No. CRL1650) and COS-7 cell lines (ATCC No. CRL1651), and the CV-1 cell line (ATCC No. CCL70). Further exemplary mammalian host cells include primate cell lines and rodent cell lines, including transformed cell lines. Normal diploid cells, cell strains derived from in vitro culture of primary tissue, as well as primary explants, are also suitable. Candidate cells can be genotypically deficient in the selection gene, or may contain a dominantly acting selection gene. Other suitable mammalian cell lines include, but are not limited to, mouse neuroblastoma N2A cells, HeLa, mouse L-929 cells, 3T3 lines derived from Swiss, Balb-c or NIH mice, BHK or HaK hamster cell lines, which are available from the ATCC. Each of these cell lines is known by and available for protein expression.

Also of interest are lymphoid, or lymphoid derived cell lines, such as a cell line of pre-B lymphocyte origin. Specific examples include without limitation RAMOS (CRL-1596), Daudi (CCL-213), EB-3 (CCL-85), DT40 (CRL-2111), 18-81, (Jack et al., PNAS (1988) 85 1581-1585), Raji cells, (CCL-86) and derivatives thereof.

Suitable vectors for the expression of the synthetic libraries, semi-synthetic libraries, or seed libraries described herein can be based on any known episomal vector integrating vector, including those described herein, known in the art, or discovered or designed in the future. For use in an SHM system, suitable vectors for the expression of the synthetic or semi-synthetic libraries described herein can be based on any of the vectors described priority U.S. Provisional Patent Application No. 60/902,414, which can be co-transfected into a host cell endogenously expressing AID. In other embodiments useful in an SHM system, suitable vectors for the expression of the synthetic libraries, semi-synthetic libraries, or seed libraries described herein can be based on any of the vectors described priority U.S. Provisional Patent Application No. 60/902,414, which can be co-transfected into a host cell with a separate vector containing the nucleic acid sequence of AID.

Expression vectors can also include suitable secretion signals or transmembrane domains to exert the secretion or surface attachment of the protein libraries of interest. In some cases, a surface displayed protein can be converted into a secreted protein so that the secreted proteins can be further characterized. Conversion can be accomplished, for example, through the inclusion and use of a specific cleavable linker that can be cleaved by incubation of a selective protease such as factor X, thrombin or any other selective proteolytic agent. It is also possible to include polynucleotide sequences that enable the genetic manipulation of the encoded protein in the vector (i.e., that allow excision of a surface attachment signal from the protein reading frame). For example, the insertion of one or more unique restriction sites, cre/lox elements, or other recombination elements that enable the selective removal of an attachment signal. Further examples include the insertion of flanking loxP sites around the attachment signal (e.g., a transmembrane domain) in the expression vector.

A plasmid encoding the cre recombinase protein (open reading frame synthesized by DNA2.0 and inserted into an expression vector) can be transiently transfected or virally transduced into a cell population of interest. Action by the expressed cre recombinase protein leads to the in situ removal of the transmembrane domain portion of the coding region resulting in translation and production of a secreted form of a protein in the transfected cell population, which can then be used for further studies.

Representative commercially available viral expression vectors include, but are not limited to, the adenovirus-based Per.C6 system available from Crucell, Inc., the lentiviral-based pLP1 from Invitrogen, and the Retroviral Vectors pFB-ERV plus pCFB-EGSH from Stratagene.

An episomal expression vector suitable for the expression of the synthetic libraries, semi-synthetic libraries or seed libraries described herein is able to replicate in the host cell, and persists as an extrachromosomal episome within the host cell in the presence of appropriate selective pressure. (See for example, Conese et al., Gene Therapy 11 1735-1742 (2004)). Representative commercially available episomal expression vectors include, but are not limited to, episomal plasmids that utilize Epstein Barr Nuclear Antigen 1 (EBNA1) and the Epstein Barr Virus (EBV) origin of replication (oriP), specific examples include the vectors pREP4, pCEP4, pREP7 from Invitrogen. The amplification of such OriP based vectors can be achieved via the further incorporation of an SV40 origin of replication in the vector, and the transient expression of the SV40 T antigen.

The vectors pcDNA3.1 (Invitrogen) and pBK-CMV (Stratagene) represent non-limiting examples of an episomal vector that uses T-antigen and the SV40 origin of replication in lieu of EBNA1 and oriP.

An integrating expression vector suitable for the expression of the synthetic, semi-synthetic libraries, or seed libraries described herein can randomly integrate into the host cell's DNA, or can include a recombination site to enable the specific recombination between the expression vector and the host cells chromosome. Such integrating expression vectors can utilize the endogenous expression control sequences of the host cell's chromosomes to effect expression of the desired protein. Examples of vectors that integrate in a site specific manner include, for example, components of the flp-in system from Invitrogen (e.g., pcDNA™5/FRT), or the cre-lox system, such as can be found in the pExchange-6 Core Vectors from Stratagene. Examples of vectors that integrate into host cell chromosomes in a random fashion include, for example, pcDNA3.1 (when introduced in the absence of T-antigen) from Invitrogen, pCI or pFN10A (ACT) Flexi® from Promega.

Alternatively, the expression vector can be used to introduce and integrate a strong promoter or enhancer sequences into a locus in the cell so as to modulate the expression of an endogenous gene of interest (Capecchi M R. Nat Rev Genet. (2005); 6 (6):507-12; Schindehutte et al., Stem Cells (2005); 23 (1):10-5). This approach can also be used to insert an inducible promoter, such as the Tet-On promoter (U.S. Pat. Nos. 5,464,758 and 5,814,618), in to the genomic DNA of the cell so as to provide inducible expression of an endogenous gene of interest. The activating construct can also include targeting sequence(s) to enable homologous or non-homologous recombination of the activating sequence into a desired locus specific for the gene of interest (see for example, Garcia-Otin & Guillou, Front Biosci. (2006) 11:1108-36). Alternatively an inducible recombinase system, such as the Cre-ER system can be used to activate a transgene in the presence of 4-hydroxytamoxifen. (Indra et al. Nuc. Acid. Res. (1999) 27 (22) 4324-4327; Nuc. Acid. Res. (2000) 28 (23) e99; U.S. Pat. No. 7,112,715).

Elements to be included in an expression vector for use in the present invention are well known in the art, and any existing vector can be readily modified for use in the present invention, for example, through the insertion or replacement of one or more polynucleotide sequences with synthetic polynucleotide sequences as described above.

IX. Somatic Hypermutation Systems

In one aspect, the polynucleotide libraries (e.g., synthetic libraries, semi-synthetic libraries, and/or seed libraries) of the present invention are introduced into a somatic hypermutation system as described in priority U.S. Provisional Patent Application No. 60/902,414.

This invention provides for a system that enables mutations be directed to specific genes or regions of interest (made "hot" or SHM susceptible), and be directed away from structural or marker genes that are functionally required within the cell or episome, to maintain overall system functionality and/or stability (made "cold" or SHM resistant). Such systems allow for stable maintenance of a mutagenesis system that provides for high level targeted SHM in a polynucleotide library of interest, while sufficiently preventing non-specific mutagenesis of structural proteins, transcriptional control regions and selectable markers.

In part, such a system is based around the creation of a more stable version of cytidine deaminase that can provide for high level sustained SHM. Additionally, the system includes a variety of other component nucleotide sequences, such as coding sequences and genetic elements that can make up the core system that are optimized for somatic hypermutation and maintain overall system integrity. These component nucleotide sequences include without limitation, i) selectable markers such as neomycin, blasticidin, ampicillin, etc; ii) reporter genes (e.g., fluorescent proteins, epitope tags, reporter enzymes); iii) genetic regulatory signals, e.g., promoters, inducible systems, enhancer sequences, IRES sequences, transcription or translational terminators, kozak sequences, splice sites, origin of replication, repressors; iv) enzymes or accessory factors used for high level enhanced SHM, or it's regulation, or measurement, such as AID, pol eta, transcription factors, and MSH2; v) signal transduction components (kinases, receptors, transcription factors) and vi) domains or sub domains of proteins such as nuclear localization signals, transmembrane domains, catalytic domains, protein-protein interaction domains, and other protein family conserved motifs, domains and sub-domains.

In one aspect, the vectors described herein comprising the synthetic or semi-synthetic libraries of the present invention can be transfected into a host cell that contains endogenous AID. In another aspect, the vectors described herein comprising the synthetic or semi-synthetic libraries of the present invention can be co-transfected into a host cell that contains endogenous AID with a separate vector containing the nucleic acid sequence of AID such that AID is over-expressed in the cell. In yet another aspect, the vectors described herein comprising the synthetic or semi-synthetic libraries of the present invention can be modified to include the sequence of cold AID for transfection into a host cell that does, or does not, contain endogenous AID.

In one embodiment, the cold AID is a mutant form of the enzyme which exhibits increased mutator activity. Mutant forms of AID can contain a strong nuclear import signal (NLS) a mutation that alters the activity of the nuclear export signal or both.

In one aspect, the mutated AID contains a modified nuclear export sequence made by one or more mutations independently selected at positions 180 to 198 of AID (SEQ ID NO: 11), which one or more mutations enhance mutator activity of the modified AID.

In one embodiment, the modified AID protein has a modified nuclear export sequence containing at least one mutation selected from among L181A, L183A, L189A, L196A and L198A. In another embodiment, the modified AID protein has a modified nuclear export sequence containing at least two, at least three or at least four mutations selected from among L181A, L183A, L189A, L196A and L198A.

In another aspect, the modified AID protein has a modified nuclear export sequence containing at least one mutation selected from among D187E, D188E, D191E, T1951 and L198A. In another aspect, the modified AID protein has a modified nuclear export sequence containing at least two, at least three or at least four mutations selected from D187E, D188E, D191E, T1951 and L198A.

Mutated AID polypeptides can also contain a nuclear localization signal which can be N-terminal or C-terminal. In one non-limiting example, a mutated AID can contain a strong nuclear localization signal such as, but not limited to PKKKRKV (SEQ ID NO: 439). In another non-limiting example, the NLS can be a sequence conforming to the motif K-K/R-X-K/R.

Mutated AID polypeptides described herein can contain both a strong NLS and a modified nuclear export sequence. In one embodiment, the modified nuclear export sequence can include one or more of the following mutations: L181A, L183A, L189A, L196A and L198A. In another embodiment, the modified nuclear export sequence can include one or more of the following mutations: D187E, D188E, D191E, T1951 and L198A.

In any of these mutant forms of AID, the gene may SHM resistant, SHM susceptible, or can include the appropriate optimal codon usage for expression of the AID in the host cell of choice without regard for SHM susceptibility. When used in expression system to target SHM to a protein of interest, the mutant form of AID can be SHM resistant.

In a preferred embodiment, a SHM system comprising the synthetic libraries, semi-synthetic libraries, or seed libraries described herein comprises one or more of the: i) a polynucleotide that has been altered to positively influence the rate of SHM experienced by that polynucleotide, and ii) a polynucleotide that has been altered, to negatively influence the rate of SHM.

Typically such systems will be used with an expression vector with expression control sequences to enable the expression of one or more polynucleotides of interest in a mutator cell line. Suitable expression vectors can be based on any known viral, or non-viral vector or an artificial chromosome. An expression system can include any combination of different replicons which can be used in sum to create a coordinated system for SHM.

In another aspect, a SHM system comprising the synthetic or semi-synthetic libraries described herein can further comprise one or more expression vectors with one or more of the following additional elements selected from among: i) an inducible system to regulate the expression of AID, or an AID homolog, ii) one or more Ig enhancers, iii) one or more E-boxes, iv) one or more auxiliary factors for SHM, v) one or more factors for stable episomal expression, such as EBNA1, EBP2 and/or ori-P, vi) one or more selectable marker genes, vii) one or more factors to enable the selective amplification of the vectors (i.e. SV40 ori and means for expressing SV40 T-Antigen) and viii) any combination thereof.

If an inducible system is used, such as the Tet-controlled system, doxycycline can be added to the medium to induce expression of the polynucleotide of interest, or AID for a period of time (e.g., 1 hour (hr), 2 hrs, 4 hrs, 6 hrs, 8 hrs, 10 hrs, 15 hrs, 20 hrs, 24 hrs or any other time) prior to analysis by an appropriate assay. The cells can be allowed to grow for a certain time to provide for on-going diversification, for example, for 1-3 cell generations, or in certain cases 3-6 generations, or in some cases 6 to 10 generations, or longer.

Cells can be iteratively grown, assayed and selected as described herein to selectively enrich those cells that express a polynucleotide of interest exhibiting a desired property. Suitable assay and enrichment strategies (e.g., fluorescent activated cell sorting (FACS); affinity separation, enzyme activity, toxicity, receptor binding, growth stimulation, etc.) are described below.

Once a population of cells has been obtained that is of interest, the polynucleotides of interest can be rescued and the corresponding mutations sequenced and identified. For example, total mRNA, or extrachromosal plasmid DNA can be amplified by co-expression of SV40 T antigen (J. Virol. (1988) 62 (10) 3738-3746) and/or can be extracted from cells and used as a template for polymerase chain reaction (PCR) or reverse transcriptase (RT)-PCR to clone the modified polynucleotide using appropriate primers. Mutant polynucleotides can be sub-cloned into a vector and expressed in *E. coli*. A tag (e.g., His-6 tag) can be added to the carboxy terminus to facilitate protein purification using chromatography.

X. Screening and Enrichment Systems

Polypeptides generated by the expression of the synthetic libraries, semi-synthetic libraries, or seed libraries of polynucleotides described herein can be screened for improved phenotype using a variety of standard physiological, pharmacological and biochemical procedures. Such assays include for example, biochemical assays such as binding assays, fluorescence polarization assays, solubility assays, folding assays, thermostability assays, proteolytic stability assays, and enzyme activity assays (see generally Glickman et al., J.

Biomolecular Screening, 7 No. 1 3-10 (2002); Salazar et al., Methods. Mol. Biol. 230 85-97 (2003)), as well as a range of cell based assays including signal transduction, motility, whole cell binding, flow cytometry and fluorescent activated cell sorting (FACS) based assays. Cells expressing polypeptide of interest encoded by a synthetic or semi-synthetic library as described herein can be enriched any art-recognized assay including, but not limited to, methods of coupling peptides to microparticles.

Many FACS and high throughput screening systems are commercially available (see, e.g., Zymark Corp., Hopkinton, Mass.; Air Technical Industries, Mentor, Ohio; Beckman Instruments Inc., Fullerton, Calif.; Precision Systems, Inc., Natick, Mass.) that enable these assays to be run in a high throughput mode. These systems typically automate entire procedures, including all sample and reagent pipetting, liquid dispensing timed incubations, and final readings of the microplate in detector(s) appropriate for the assay. These configurable systems provide high throughput and rapid start up as well as a high degree of flexibility and customization. The manufacturers of such systems provide detailed protocols for various high throughput systems. Thus, for example, Zymark Corp. provides technical bulletins describing screening systems for detecting the modulation of gene transcription, ligand binding, and the like.

A. Cell-Based Methods to Measure Activities.

1. Signal Transduction Based Assays

Proteins such as, for example, growth factors, enzymes, receptors and antibodies can influence signal transduction within a cell or cell population, and thereby influence transcriptional activity that can be detected using a reporter gene assay. Such modulators can behave functionally as full or partial agonists, full or partial antagonists, or full or partial inverse agonists.

Thus in one assay format, signal transduction assays can be based on the use of cells comprising a reporter gene whose expression is directly or indirectly regulated by the protein of interest, which can be measured by a variety of standard procedures.

Reporter plasmids can be constructed using standard molecular biological techniques by placing cDNA encoding for the reporter gene downstream from a suitable minimal promoter (that is, any sequence that supports transcription initiation in eukaryotic cells) that sits 5' to the coding sequence of the reporter gene. A minimal promoter can be derived from a viral source such as, for example: SV40 early or late promoters, cytomegalovirus (CMV) immediate early promoters, or Rous Sarcoma Virus (RSV) early promoters; or from eukaryotic cell promoters, for example, beta actin promoter (Ng, Nuc. Acid Res. 17:601-615, 1989; Quitsche et al., J. Biol. Chem. 264:9539-9545, 1989), GADPH promoter (Alexander, M. C. et al., Proc. Nat. Acad. Sci. USA 85:5092-5096, 1988, Ercolani, L. et al., J. Biol. Chem. 263:15335-15341, 1988), TK-1 (thymidine kinase) promoter, HSP (heat shock protein) promoters, or any eukaryotic promoter containing a TATA box.

A reporter plasmid also typically includes an element 5' to the minimal promoter that contains a consensus recognition sequence, usually repeated 2 to 7 times in a concatenate, to the appropriate branch of the signal transduction pathway for which monitoring is desired. Examples include, but are not limited to: cyclic AMP response elements (CRE, which responds to changes in intracellular cAMP concentrations, available from Stratagene in phagemid vector pCRE-Luc, Cat. No. 219076), serum response elements (SRE, Stratagene phagemid vector pSRE-Luc. Cat. No. 219080), nuclear factor B response elements (NF-kB, Stratagene phagemid vector pNFKB-Luc Cat. No. 219078), activator protein 1 response elements (AP-1, Stratagene phagemid vector pAP-1-Luc, Cat. No. 219074), serum response factor response elements (Stratagene phagemid vector pSRF-Luc, Cat. No. 219082), or p53 binding sites.

Numerous reporter gene systems are known in the art and include, for example, alkaline phosphatase Berger, J., et al. (1988) Gene 66 1-10; Kain, S. R. (1997) Methods. Mol. Biol. 63 49-60), .beta.-galactosidase (See, U.S. Pat. No. 5,070,012, issued Dec. 3, 1991 to Nolan et al., and Bronstein, I., et al., (1989) J. Chemilum. Biolum. 4 99-111), chloramphenicol acetyltransferase (See Gorman et al., Mol Cell Biol. (1982) 2 1044-51), .beta.-glucuronidase, peroxidase, beta-lactamase (U.S. Pat. Nos. 5,741,657 and 5,955,604), catalytic antibodies, luciferases (U.S. Pat. Nos. 5,221,623; 5,683,888; 5,674,713; 5,650,289; 5,843,746) and naturally fluorescent proteins (Tsien, R. Y. (1998) Annu. Rev. Biochem. 67 509-44).

Alternatively, intermediate signal transduction events that are proximal to gene regulation can also be observed, such as, by measuring fluorescent signals from reporter molecules that respond to intracellular changes including, but not limited to, fluctuations in calcium concentration due to release from intracellular stores, alterations in membrane potential or pH, increases in inositol triphosphate ($IP_3$) or cAMP concentrations, or release of arachidonic acid.

As used herein, agonists refer to modulators that stimulate signal transduction and can be measured using various combinations of the construct elements listed above. As used herein, partial agonists refer to modulators able to stimulate signal transduction to a level greater than background, but less than 100% as compared to a full agonist. A superagonist is able to stimulate signal transduction to greater than 100% as compared to a full agonist reference standard.

As used herein, antagonists refer to modulators that have no influence on signal transduction on their own, but are able to inhibit agonist- (or partial agonist-) induced signaling. As used herein, partial antagonists refer to modulators that have no influence on signal transduction on their own, but are able to inhibit agonist- (or partial agonist-) induced signaling to an extent that is measurable, but less than 100%.

As used herein, inverse agonists refer to modulators that are able to inhibit agonist- (or partial agonist-) induced signaling, and are also able to inhibit signal transduction when added alone.

2. Motility Assays

Agonistic activity on several categories of cell surface molecules (e.g., GPCR's such as chemokine receptors, histamine H4, cannabinoid receptors, etc.) can lead to cell movements. Thus, partial or full agonist or antagonist activities of test molecules can be monitored via effects on cell motility, such as in chemotaxis assays (Ghosh et al., (2006) J Med Chem. May 4; 49(9):2669-2672), chemokinesis (Gillian et al., (2004) ASSAY and Drug Development Technologies. 2(5): 465-472) or haptotaxis (Hintermann et al., (2005) J. Biol. Chem. 280(9): 8004-8015).

3. Whole Cell Binding Assays

Binding assays that utilize receptors, membrane associated antibodies, and cell surface proteins can be performed using whole cells (as opposed to membrane preparations) in order to monitor activity or binding selectivity of proteins of interest. Such assays can also be used to directly select desired cell populations via the use of FACS. (Fitzgerald et al., (1998) J Pharmacol Exp Ther. 1998 November; 287(2):448-456; Baker, (2005) Br J Pharmacol. February; 144(3):317-22)

A large number of fluorescently tagged compounds are available to perform whole cell binding assays. In addition, specific peptides can be readily labeled in order to profile the binding affinity and selectivity of membrane associated antibodies. In general peptides can be conjugated to a wide variety of fluorescent dyes, quenchers and haptens such as fluorescein, R-phycoerythrin, and biotin. Conjugation can occur either during peptide synthesis or after the peptide has been synthesized and purified.

Biotin is a small (244 kilodaltons) vitamin that binds with high affinity to avidin and streptavidin proteins and can be conjugated to most peptides without altering their biological activities. Biotin-labeled peptides are easily purified from unlabeled peptides using immobilized streptavidin and avidin affinity gels, and streptavidin or avidin-conjugated probes can be used to detect biotinylated peptides in, for example, ELISA, dot blot or Western blot applications.

N-hydroxysuccinimide esters of biotin are the most commonly used type of biotinylation agent. N-hydroxysuccinimide-activated biotins react efficiently with primary amino groups in physiological buffers to form stable amide bonds. Peptides have primary amines at the N-terminus and can also have several primary amines in the side chain of lysine residues that are available as targets for labeling with N-hydroxysuccinimide-activated biotin reagents. Several different N-hydroxysuccinimide esters of biotin are available, with varying properties and spacer arm length (Pierce, Rockford, Ill.). The sulfo-N-hydroxysuccinimide ester reagents are water soluble, enabling reactions to be performed in the absence of organic solvents.

Alternatively, peptides can be conjugated with R-Phycoerythrin, a red fluorescent protein. R-Phycoerythrin is a phycobiliprotein isolated from marine algae. There are several properties that make R-Phycoerythrin ideal for labeling peptides, including an absorbance spectra that includes a wide range of potential excitation wavelengths, solubility in aqueous buffers and low nonspecific binding. R-Phycoerythrin also has a high fluorescence quantum yield (0.82 at 578 nanometers) that is temperature and pH independent over a broad range. Conjugating peptides with R-Phycoerythrin can be accomplished using art-recognized techniques described in, for example, Glazer, A N and Stryer L. (1984). Phycofluor probes. Trends Biochem. Sci. 9:423-7; Kronick, M N and Grossman, P D (1983) Immunoassay techniques with fluorescent phycobiliprotein conjugates. Clin. Chem. 29:1582-6; Lanier, L L and Loken, M R (1984) Human lymphocyte subpopulations identified by using three-color immunofluorescence and flow cytometry analysis: Correlation of Leu-2, Leu-3, Leu-7, and Leu-11 cell surface antigen expression. J Immunol, 132:151-156; Parks, D R et al. (1984) Three-color immunofluorescence analysis of mouse B-lymphocyte subpopulations. Cytometry 5:159-68; Hardy, R R et al. (1983) demonstration of B-cell maturation in X-linked immunodeficient mice by simultaneous three-color immunofluorescence. Nature 306:270-2; Hardy R R et al. (1984) J. Exp. Med. 159:1169-88; and Kronick, M N (1986) The use of phycobiliproteins as fluorescent labels in immunoassay. J Immuno Meth. 92:1-13.

A number of cross-linkers can be used to produce phycobiliprotein conjugates including, but not limited to, N-Succinimidyl 3-[2-pyridyldithio]-propionamido, (Succinimidyl 6-(3-[2-pyridyldithio]-propionamido)hexanoate, or (Sulfosuccinimidyl 6-(3-[pyridyldithio]-propianamido)hexanoate. Such cross-linkers react with surface-exposed primary amines of the phycobiliprotein and create pyridyldisulfide group(s) that can be reacted with peptides that contain either free sulfhydryl groups or primary amines.

Another option is to label peptides with fluorescein isothiocyanate (molecular weight 389). The isothiocyanate group on the fluorescein will cross-link with amino, sulfhydryl, imidazoyl, tyrosyl or carbonyl groups on peptides, but generally only derivatives of primary and secondary amines yield stable products. Fluorescein isothiocyanate has an excitation and emission wavelengths at 494 and 520 nanometers respectively and a molar extinction coefficient of 72,0000 $M^{-1}$ $cm^{-1}$ in an aqueous buffer at pH 8 (Der-Balian G, Kameda, N and Rowley, G. (1988) Fluorescein labeling of Fab while preserving single thiol. Anal. Biochem. 173:59-63).

4. Whole Cell Activity Assays

Many proteins, including enzymes, intrabodies and receptors can be directly assayed within a living cell, or when surface displayed on the surface. Typically for successful FACS based screening a fluorescent or fluorogenic membrane permeant substrate is required, many such reagents are commercially available, for example from Molecular Probes (Invitrogen, CA). An increase in enzyme activity typically results in increased production of a fluorescent product that is trapped within the cell resulting in cells with more fluorescence which can be separated from less fluorescent cells, for example by FACS. Additionally many high throughput microplate screens exist for screening of protein libraries that exploit virtually any existing assay of enzymatic activity, see generally, Geddie, et al., Meth. Enzymol. 388 134-145 (2004).

5. Cell Growth Assays

The expression, or activity of a variety of proteins such as, for example, growth factors, enzymes, receptors and antibodies can influence the rate of growth of a host cell which be exploited either as an assay, or as a means of separating improved proteins.

Thus in one assay format, cells can be diluted to a limiting dilution and cells which grow more rapidly detected and selected. In one aspect such growth based assays can involve the ability to grow in the presence of a new substrate for which an improved enzymatic pathway of metabolism is required, for example a new carbon source. In another embodiment, growth assays can involve selection in the presence of a toxin, where a de-activation mechanism for the toxin is required. In another case, growth can be desired in response to the presence of a specific ligand, where high affinity binding of the ligand is required.

B. Selection and Enrichment Strategies

1. Flow Cytometry and FACS

Flow cytometry and the related flow sorting (also known as fluorescence activated cell sorting, or FACS) are methods by which individual cells can be quantitatively assayed for the presence of a specific component or component variant based upon staining with a fluorescent reporter. Flow cytometry provides quantitative, real time analysis of living cells, and can achieve efficient cell sorting rates of 50,000 cells/second, and is capable of selecting individual cells or defined populations. Many commercial FACS systems are available, for example BD Biosciences (CA), Cytopeia (Seattle, Wash.) Dako Cytomation (Australia).

A FACS can be equipped with a variety of lasers, which can produce a wide range of available wavelengths for multiple parameter analysis, and for use with different fluorophores. Classically the water cooled ion lasers using argon, krypton, or a mix of both can produce several specific lines; 408 nm, 568 nm, and 647 nm for example are major emission lines for Krypton; 488 nm, 457 nm, and others are argon lines. These lasers require high voltage multiphase power and cooling water, but can produce high power outputs. Additionally tunable and non tunable diode lasers exist, for example a 408 nm line can be stably created via a light emitting diode (LED) and this can be easily added to a sorter. Additionally dye lasers can be used to further extend the range of available wavelengths available for FACS analysis.

During FACS analysis, cells are stained with the specific reporter and then hydrodynamically focused into a single cell steam for interrogation with a laser which excites the fluorescent moiety. Fluorescent emission is detected through a wavelength restricted optical pathway and converted to numeric data correlated to an individual cell. In the case of flow sorting, predefined subsets of emission criteria can be met and the cells of interest diverted into a collection receptacle for further use by electrostatic repulsion or mechanical action (Herzenberg L A, Sweet R G, Herzenberg L A: Fluorescence activated cell sorting, Sci Amer 234(3):108, March 1976).

FACS based approaches are compatible with signal transduction based assays, activity based assays, and binding assays, and with a wide variety of proteins of interest, including for example, antibodies, receptors, enzymes and any surface displayed protein. FACS can be efficiently applied to most mammalian, yeast and bacterial cells, as well as fluorescently tagged beads.

In one embodiment, FACS can be used to screen a library of cells expressing surface displayed proteins (e.g., surface displayed antibodies) that are undergoing, or have undergone, SHM mediated diversity. In this approach, a cell surface displayed library is used and the displayed proteins are first incubated with fluorescently tagged antigen in solution. The FACS instrument is able to separate the high affinity protein members of the library, which have greater fluorescence intensity, from the lower affinity members. The use of optimized binding protocols in conjunction with FACS based selection has been shown to be capable of evolving antibodies with up to femtomolar affinities, See, e.g., Boder et al. PNAS, (2000) 97: 10701-10705; Boder et al., (2000) Meth. Enzymol. (2000) 328: 430-444; VanAntwerp et al., Biotechnol. Prog. (2000) 16: 31-37).

In order to effectively select and rapidly evolve, the antibodies and binding proteins which have high affinity to an antigen of interest, protocols can be established that can facilitate the isolation of antibodies with a broad range of affinities to the antigens of interest, and yet eliminate proteins that bind to labeling or coupling reagents. These protocols involve both a progression in the stringency of the cell population selected, and a decrease in the concentration and density of the target antigen presented to the cells.

With respect to the stringency or fraction of the total cell population collected during each round of selection, initial screens will generally use relatively low discrimination factors in order to capture as many proteins as possible that possess small incremental improvements in binding characteristics. For example, a typical initial sort may capture the top 10%, top 5% or top 2% of all cells that bind a target. Large improvements in affinity may be the result of combinations of mutations, each of which contribute small additive effects to overall affinity. (Hawkins et al., (1993) J. Mol. Biol. 234: 958-964). Therefore, recovery of all library clones with even marginally improved affinities (2-3 fold) is desirable during the early stages of library screening, and sorting gates can be optimized to recover as many clones as possible with minimum sacrifice in enrichment.

These selected cells can subsequently be allowed to recover and grown using standard culture conditions for a number of days until the population has reached a reasonable number to allow for a subsequent round of FACS sorting, analysis, mutagenesis, cell banking, or to determine sequence information. As discussed below, subsequent rounds of selection to identify higher affinity binders can be achieved by progressively decreasing the density and concentration of labeled binding peptide used in the preincubation steps prior to FACS analysis.

Following a successful first round of sorting, the collected cells can be re-grown to amplify the population and then resorted. At this, and subsequent stages of sorting, greater enrichments are possible since more copies of each desirable clone are present within the examined cell population. For example only about the top 1%, top 0.5%, top 0.2%, or top 0.1% of the cells in the population may be selected in order to identify significantly improved clones. With respect to establishing optimal binding and selection strategies, first generation hits, including germline antibodies, typically have low affinities and relatively rapid off rates. For example, Sagawa et al. (Mol. Immunology, 39: 801-808 (2003)) observed that the apparent affinity for germline Abs is typically in the range of $2\times10^4$ to $5\times10^6$ $M^{-1}$, but that this affinity increases to around $10^9$ $M^{-1}$ during affinity maturation (i.e., an effect that is mediated primarily by decreasing the off rate ($K_{off}$)).

The binding characteristics of weak binding antibodies may slow the screening of early generation, non-optimized libraries because specific, but low affinity binding antibodies typically have rapid off rates and tend therefore tend to be lost during wash steps. Loss of these specific binders may result in the isolation of antibodies that bind non-specifically to components used in the selection process (Cumbers et al., Nat. Biotechnol. 2002 November; 20(11): 1129-113).

To maximize the selection of proteins with relatively low affinities (i.e., having a Kd greater than about 500 nM), binding interactions are stabilized to prevent the dissociation of binding peptides during the screening process, and include appropriate blocking reagents to eliminate binding to coupling reagents and support matrices. To achieve this goal, initial screens should use fluorescently tagged beads loaded with a high density of antigens to exploit avidity effects, based on the use of multiple binding interactions to increase the binding strength of low affinity interactions, while also including pre-incubations with coupling and labeling reagents such as streptavidin, avidin, and naked beads etc., to eliminate non-specific binding (see generally, Aggarwal et al., (2006) Bioconjugate Chem. 17 335-340; Wrighton et al., (1996) Science 273 458-64; Terskikh et al. (1997) PNAS 94 1663-8; Cwirla et al., (1997) Science 276 1696-9; and Wang et al. (2004) J. Immunological methods 294 23-35).

By careful control of bead loading density, washing and pre-incubation conditions it has been demonstrated that even such low affinity binding interactions can be reproducibly monitored, (Werthen et al., (1993) BBA 326-332). Importantly these improvements to binding efficiency have been demonstrated to occur without any significant increase in non-specific reactivity (Giordano et al., (2001) Nat. Med. 7 1249-53). As discussed above, selections generally will also be based on using a relatively low stringency cut off during FACS to ensure that all of these weak binding library members are selected.

To further eliminate non-specific members of the library (i.e., those that bind to the beads, or coupling reagents, rather than the binding peptides), the resultant cell populations are screened directly with either polymeric binding peptide or intact polymeric antigen using distinct coupling reagents (e.g., via the use of biotinylated antigen coupled to streptavidin-fluorophore conjugate to form an antigen-streptavidin fluorescent complex). Coupling or labeling of the binding peptide to biotin or fluorophores can be achieved using standard, art-recognized protocols, as described herein and in the Examples.

Streptavidin binds biotin with femtomolar affinity and forms tetramers in physiological conditions, thereby generating a tetravalent complex when preincubated with singly biotinylated antigen (which is subsequently termed a streptavidin microaggregate as described below). Streptavidin preloading can increase the effective antigen concentration up to 500-fold, and is useful for isolating weak antigen binders that bind specifically to the antigen. Employment of streptavidin microaggregates is useful for isolating antibodies ranging in affinity from very weak to moderate (Kd greater than about 200 nM) affinities. Furthermore, biotinylated epitopes can be pre-reacted with streptavidin-fluorophore at room temperature for 10 to 15 minutes in order to create microaggregates prior to contacting cell populations. The microaggregates are subsequently allowed to contact cells simultaneously for 15 to 30 minutes prior to addition of secondary reagents, such as anti-human IgG-fluorophore conjugates. In one experimental approach, cells are centrifuged at 1500×g for 5 minutes and resuspended in a small volume (typically 500 μL to 1 mL) of DAPI (PBS, 1% BSA, 2 μg/mL DAPI). In a second approach termed "homogeneous assay conditions," cells are resuspended directly in DAPI into which antigen-streptavidin microaggregate and goat-anti-human IgG-fluorophore are added. This second approach is particularly desirable for more weakly interacting antibodies (Kd greater than about 200 nM), where minimizing dissociation time may be more relevant.

At higher affinities (with Kd>10 nM, but less than about 100 nM), libraries are more easily screened directly for improved affinity by incubating the library with monomeric binding peptide or full length target protein under equilibrium binding conditions at a concentration of binding peptide that is ideally less than the Kd of the starting (wild type) interaction (apparent Kds can be readily determined by a series of analytical FACS experiments conducted with a range of antigen concentrations, ahead of a sort). Under these conditions, cells that possess antibodies and binding proteins with higher affinities will possess significantly more fluorescently labeled binding peptide than weaker binders, allowing the most fluorescent cells in the population to be easily selected for further optimization. Typically, FACS sorting gates can be established that select about the top 0.5% to about 0.1% of cells. In one non-limiting method, about the top 0.2% of cells are selected.

As recognized by Boder and Wittrup (Biotechnol. Prog. (1998) 14 55-62), the screening of very high affinity protein-ligand interactions (Kd<10 nM) can be accomplished by screening for decreased off-rate rather than directly for affinity. In this approach, cells are labeled to saturation with fluorescent binding peptide, followed by addition of an excess of non-fluorescent ligand. Cell associated fluorescence decays exponentially with time approaching a background level and the dissociation reaction is stopped after a fixed duration, usually by extensive dilution with cold buffer. The duration of the competition reaction determines the difference in observed fluorescence for different library clones and, thus, determines the range of kinetic improvements likely to be selected from the library. For a competitive dissociation reaction, the presence of excess non-fluorescent ligand can yield an effective forward reaction rate of zero. Mean fluorescence intensity at a given time after the initiation of the competition reaction is a function of the off-rate ($K_{off}$). (VanAntwerp & Wittrup (2000) Biotechnol. Prog. 16 31-37; Boder et al. (2000) PNAS 97 10701-10705; and Foote and Eisen (2000) PNAS 97 10679-10681). Cells in the population that express antibodies with improved affinities and more stable binding can be systematically identified by progressively increasing the length of time for the competition reaction, and then selecting the most fluorescent cells remaining in the population for further optimization.

Under these conditions, cells that possess surface displayed antibodies and binding proteins with higher affinities will exhibit significantly more bead or streptavidin-biotinylated antigen microaggregate binding compared to cells that express proteins with little or no binding. The most fluorescently labeled cells (displaying proteins with the highest affinity) can then be separated from the rest of the cells in the population using standard FACS sorting protocols, as described, for example, in Example 9.

Once a selected cell population has been created that expresses a protein that exhibits reproducible binding to a binding peptide, it can be characterized with two or more intact proteins to confirm that the antibodies or binding proteins exhibit the desired pattern of cross-reactivity and/or specificity (e.g., to both mouse and human variants of the protein of interest), or to two different members of a related gene family, but not to an unrelated, or more distantly related, protein.

In one embodiment, this can be accomplished using multiparameter FACS using two or more proteins species labeled with two differently colored detectable tags (e.g., FITC and phycoerythrin) which can be simultaneously analyzed in a flow cytometer. Using this approach, it is possible to identify cells that display binding to only one protein, or are capable of binding to both proteins. The population of cells that exhibits the required dual specific binding can be selected by the FACS operator based upon the number of cells sorted and the percentage of cells identified that exhibit polyspecificity. As described previously, these selected cells can subsequently be allowed to recover and grown using standard culture conditions for a number of days until the population has reached a reasonable number to enable either a subsequent round of FACS sorting, analysis, cell banking, or to determine sequence information.

Selected binders from the library can be further characterized as described herein, and the sequence of the antibody or binding protein determined after PCR of cellular DNA, RT-PCR of RNA isolated from the selected cell population, or episome rescue.

Candidate antibodies and binding proteins can be iteratively subjected to rounds of hypermutation and selection in order to evolve populations of cells expressing antibodies or binding proteins with enhanced binding properties as described herein. Cells that preferentially and/or selectively bind to the binding peptide with a higher affinity are selected and allowed to expand. If needed, another round of mutagenesis is repeated and, again, cells that exhibit improved, selective, and high affinity binding, are retained for further propagation and growth. The new improved variants obtained can be further characterized as described herein, and the sequence of the heavy and light chains determined after RT-PCR or episome rescue.

Mutations that are identified in the first one, two or three rounds of hypermutation/selection can be recombined combinatorially into a set of new templates within the original parental backbone context, and all, or a subset of the resulting templates, can be subsequently transfected into cells which are then selected by FACS sorting. The best combination(s) of mutations are thus isolated and identified, and either used in a subsequent round of hypermutation/selection, or if the newly identified template(s) demonstrate sufficiently potent affinity, are used instead in experiments for further functional characterization.

In another embodiment, FACS can be used to screen a library of cells expressing intracellular proteins that are undergoing, or have undergone, SHM mediated diversity creation. In this approach, a membrane permeable fluorogenic, or florescent reagent is used and first pre-incubated with the library of cells to allow uptake and conversion of the reagent. The FACS instrument is able to separate the high activity protein members of the library, which are able to convert a greater percentage of the reagent and are more fluorescent than cells comprising lower activity members. (See, e.g., Farinas, Comb. Chem. High Throughput Screen. (2006) 9: (4) 321-328).

Fluorescent moieties to be detected include, but are not limited to, compounds such as fluorescein (commonly called FITC), phycobiliproteins such as phycoerythrin (PE) and allophycocyanin (APC) (Kronick, M. N. J. Imm. Meth. 92:1-13 (1986)), fluorescent semiconductor nanocrystals such as Quantum dot (QDot) bioconjugates for ultrasensitive nonisotopic detection (Chan W C, Nie S. Science 281: 2016-8 (1998)), and coumarin derivatives such as Fluorescent Acylating Agents derived from 7-Hydroxycoumarin.

Fluorescence can also reported from fluorescent proteins such as Teal Fluorescent Protein (TFP), from chemical stains of cellular components such as DAPI bound to DNA, from fluorescent moieties covalently conjugated to antibodies that recognize cellular products, from fluorescent moieties covalently conjugated to ligands of cellular receptors, and from fluorescent moieties covalently conjugated to substrates of cellular enzymes.

Cells stained with membrane impermeant reporters, such as antibodies, can be sorted for subsequent processing to recover components such as genes, episomes, or proteins of interest. Cells stained for surface expression components or stained with cell membrane permeant reporters can also be sorted intact for propagation.

2. Affinity Separation

Affinity separation based on the use microparticles enables the separation of surface displayed proteins based on affinity to a specific compound or sequence of interest. This approach is rapid, can easily be scaled up, and can be used iteratively with living cells.

Paramagnetic polystyrene microparticles are commercially available (Spherotech, Inc., Libertyville, Ill.; Invitrogen, Carlsbad, Calif.) that couple compounds or peptides to microparticle surfaces that have been modified with functional groups or coated with various antibodies or ligands such as, for example, avidin, streptavidin or biotin.

In one aspect paramagnetic beads can be used in which the paramagnetic property of microparticles allows them to be separated from solution using a magnet. The microparticles can be easily re-suspended when removed from the magnet thereby enabling the selective separation of cells that find to the attached probe.

In one embodiment, peptides can be coupled to paramagnetic polystyrene microparticles coated with a polyurethane layer in a tube. The hydroxyl groups on the microparticle surface are activated by reaction with p-toluensulphonyl chloride (Nilsson K and Mosbach K. “p-Toluenesulfonyl chloride as an activating agent of agarose for the preparation of immobilized affinity ligands and proteins.” Eur. J. Biochem. 1980:112: 397-402). The resulting sulphonyl ester can subsequently react covalently with peptide amino or sulfhydryl groups. The peptides are quickly absorbed onto the surface of the activated microparticles followed by the formation of covalent amine bonds with further incubation. The microparticles ($2^{09}$ microparticles/milliliter) are washed two times by placing the tube containing 1 milliliter (ml) of microparticles on a magnet, allowing the microparticles to migrate to the magnet side of the tube, removing the supernatant, and re-suspending the microparticles in 1 ml of 100 millimolar (mM) borate buffer, pH 9.5. After washing, the microparticles are re-suspended in 100 mM borate buffer, pH 9.5 at a concentration of $1^{09}$ microparticles/ml. Eleven nanomoles of peptide are added to the microparticles and the microparticle/peptide mixture is vortexed for 1 minute to mix. The microparticles are incubated with peptides at room temperature for at least 48 hours with slow tilt rotation. To ensure an optimal orientation of the peptide on the microparticles, bovine serum albumin (BSA) is added to the microparticle/peptide mixture to a final concentration of 0.1% (weight/volume) after incubation has proceeded for 10 minutes. After incubation, the tube containing the microparticle/peptide mixture is placed on the magnet until the microparticles migrate to the magnet side of the tube. The supernatant is removed and the microparticles are washed four times with 1 ml phosphate buffered saline solution (PBS), pH 7.2 containing 1% (weight/volume) BSA. Finally, the microparticles are re-suspended in 1 ml PBS solution, pH 7.2 containing 1% (weight/volume) BSA.

Alternatively, paramagnetic polystyrene microparticles containing surface carboxylic acid can be activated with a carbodiimide followed by coupling to a peptide, resulting in a stable amide bond between a primary amino group of the peptide and the carboxylic acid groups on the surface of the microparticles (Nakajima N and Ikade Y, Mechanism of amide formation by carbodiimide for bioconjugation in aqueous media, Bioconjugate Chem. 1995, 6(1), 123-130; Gilles M A, Hudson A Q and Borders C L Jr, Stability of water-soluble carbodiimides in aqueous solution, Anal Biochem. 1990 Feb. 1; 184(2):244-248; Sehgal D and Vijay I K, a method for the high efficiency of water-soluble carbodiimide-mediated amidation, Anal Biochem. 1994 April; 218(1):87-91; Szajani B et al, Effects of carbodiimide structure on the immobilization of enzymes, Appl Biochem Biotechnol. 1991 August; 30(2):225-231). The microparticles ($2^9$ microparticles/milliliter) are washed twice with 1 ml of 25 mM 2-[N-morpholino]ethane sulfonic acid, pH 5 for 10 minutes with slow tilt rotation at room temperature. The washed microparticles are re-suspended in 700 microliters (μL) 25 mM 2-[N-morpholino]ethane sulfonic acid, pH 5 followed by the addition of 21 nanomoles of peptide re-suspended in 25 mM 2-[N-morpholino]ethane sulfonic acid, pH 5 to the microparticle solution. The microparticle/peptide mixture is mixed by vortexing and incubated with slow tilt rotation for 30 minutes at room temperature. After this first incubation, 300 μL of ice-cold 100 milligram (mg)/mL 1-ethyl-3-(3-dimethylaminopropyl) carbodiimide hydrochloride re-susp in 25 mM 2-[N-morpholino]ethane sulfonic acid, pH 5 is added to the peptide/microparticle mixture and incubated overnight at 4° Celsius with slow tilt rotation. The peptide-coupled microparticles are washed four times with 1 ml 50 mM Tris pH 7.4/0.1% BSA for 15 minutes at room temperature with slow tilt rotation. After washing, the peptide-coupled microparticles are re-suspended at a concentration of $1^9$ microparticles/ml in PBS solution, pH 7.2 containing 1% (weight/volume) BSA.

Another option is to couple biotinylated peptides to paramagnetic polystyrene microparticles whose surfaces have been covalently linked with a monolayer of streptavidin. Briefly, one ml of the streptavidin microparticles are transferred to a microcentrifuge tube and washed four times by placing the tube on a magnet and allowing the microparticles to collect on the magnet side of the tube. The solution is then removed and the microparticles are gently re-suspended in 1 ml of PBS solution, pH 7.2 containing 1% (weight/volume)

BSA. After the final wash, the microparticles are re-suspended in 1 ml of PBS solution, pH 7.2 containing 1% (weight/volume) BSA; and 33 picomoles of biotinylated peptide are added to the microparticle solution. The microparticle/peptide solution is incubated for 30 minutes at room temperature with slow tilt rotation. After coupling, the unbound biotinylated peptide is removed from the microparticles by washing four times with PBS solution, pH 7.2 containing 1% (weight/volume) BSA. After the final wash, the microparticle/peptide mixture is re-suspended to a final bead concentration of $1^9$ microparticles/ml. (Argarana C E, Kuntz I D, Birken S, Axel R, Cantor C R. Molecular cloning and nucleotide sequence of the streptavidin gene. Nucleic Acids Res. 1986; 14(4):1871-82; Pahler A, Hendrickson W A, Gawinowicz Kolks M A, Aragana C E, Cantor C R. Characterization and crystallization of core streptavidin. J Biol Chem 1987:262(29):13933-7)

The identification, selection and use of specific peptide sequences for use in the present inventions is disclosed in commonly owned priority application No. 60/995,970, filed Sep. 28, 2007.

XI. Pharmaceutical Formulations

Pharmaceutical formulations comprising a protein of interest, e.g., an antibody, identified by the methods of the present invention can be prepared for storage by mixing the protein having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN®, PLURONICS® or polyethylene glycol (PEG).

The formulation described herein can also contain more than one active compound as necessary for the particular indication being treated. Such molecules are suitably present in combination in amounts that are effective for the purpose intended.

In one embodiment, the pharmaceutical formulations can comprise an antibody identified by the methods described herein. In certain embodiments, the pharmaceutical formulation can be in a microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

In still other embodiments, sustained-release preparations can be prepared. Suitable examples of sustained-release preparations include semi-permeable matrices of solid hydrophobic polymers containing the protein, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and .gamma. ethyl-L-glutamate, non-degradable ethylene-vinyl acetate, degradable lactic acid-glycolic acid copolymers such as the Lupron Depot® (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated proteins remain in the body for a long time, they can denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization can be achieved by modifying sulfhydryl residues, lyophilizing from acidic solutions, controlling moisture content, using appropriate additives, and developing specific polymer matrix compositions.

XII. Non-Therapeutic Uses

The proteins of interest, e.g., antibodies, identified by the methods of the present invention can be used non-therapeutic agents, for example, as affinity purification agents. In such an embodiment, a protein of interest is immobilized on a solid phase such a Sephadex resin or filter paper, using methods well known in the art. The immobilized protein is contacted with a sample containing the target of interest (or fragment thereof) to be purified, and thereafter the support is washed with a suitable solvent that will remove substantially all the material in the sample except the target protein, which is bound to the immobilized antibody. Finally, the support is washed with another suitable solvent, such as glycine buffer, pH 5.0, which will release the target protein.

Proteins identified by the methods of the present invention can also be useful in diagnostic assays for the targeted protein, e.g., detecting its expression in specific cells, tissues, or serum. Such diagnostic methods can be useful in cancer diagnosis.

For diagnostic applications, the proteins will typically be labeled with a detectable moiety. In certain embodiments, the detectable moiety can be selected from the following categories: (a) Radioisotopes, such as $^{35}S$, $^{14}C$, $^{125}I$, $^{3}H$, and $^{131}I$. The antibody can be labeled with the radioisotope using the techniques described in Current Protocols in Immunology, Volumes 1 and 2, Coligen et al., Ed. Wiley-Interscience, New York, N.Y., Pubs. (1991) for example and radioactivity can be measured using scintillation counting; (b) Fluorescent labels such as rare earth chelates (europium chelates) or fluorescein and its derivatives, rhodamine and its derivatives, dansyl, Lissamine, phycoerythrin and Texas Red are available; (c) enzyme-substrate labels.

Various enzyme substrate labels are known in the art and U.S. Pat. No. 4,275,149 provides a review of some of these. The enzyme generally catalyzes a chemical alteration of the chromogenic substrate which can be measured using various techniques. For example, the enzyme can catalyze a color change in a substrate, which can be measured spectrophotometrically. Alternatively, the enzyme can alter the fluorescence or chemiluminescence of the substrate. Techniques for quantifying a change in fluorescence are described above. The chemiluminescent substrate becomes electronically excited by a chemical reaction and can then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al., Methods for the Preparation of Enzyme-Antibody Conjugates for use in Enzyme Immunoassay, in Methods in Enzymol. (ed J. Langone & H. Van Vunakis), Academic press, New York, 73:147 166 (1981).

In certain embodiments, enzyme-substrate combinations can include, for example: (i) Horseradish peroxidase (HRPO) with hydrogen peroxidase as a substrate, wherein the hydrogen peroxidase oxidizes a dye precursor (e.g., orthophenylene diamine (OPD)); (ii) alkaline phosphatase (AP) with para-Nitrophenyl phosphate as chromogenic substrate; and (iii) β-D-galactosidase (β-D-Gal) with a chromogenic substrate (e.g., p-nitrophenyl-β-D-galactosidase) or fluorogenic substrate 4-methylumbelliferyl-β-D-galactosidase.

Numerous other enzyme-substrate combinations are available to those skilled in the art. For a general review of these, see U.S. Pat. Nos. 4,275,149 and 4,318,980.

The proteins identified by the methods of the present invention can be employed in any known assay method, such as competitive binding assays, direct and indirect sandwich assays, and immunoprecipitation assays. Zola, Monoclonal Antibodies: A Manual of Techniques, pp. 147 158 (CRC Press, Inc. 1987).

The antibodies can also be used for in vivo diagnostic assays. Generally, the antibody is labeled with a radio nuclide (such as $^{111}In$, $^{14}C$, $^{131}I$, $^{125}I$, $^{3}H$, $^{32}P$ or $^{35}S$) so that the tumor can be localized using immunoscintiogropahy.

XIII. Therapeutic Uses

For therapeutic applications, the proteins, including but not limited to antibodies, identified by the methods of the present invention can be administered to a mammal, preferably a human, in a pharmaceutically acceptable dosage form such as those discussed above, including those that can be administered to a human intravenously as a bolus or by continuous infusion over a period of time, by intramuscular, intraperitoneal, intra-cerebrospinal, subcutaneous, intra-articular, intrasynovial, intrathecal, oral, topical, or inhalation routes. Proteins including but not limited to antibodies identified by the methods of the present invention also can be suitably administered by intra tumoral, peritumoral, intralesional, or perilesional routes, to exert local as well as systemic therapeutic effects. The intraperitoneal route is expected to be particularly useful, for example, in the treatment of ovarian tumors.

For the prevention or treatment of disease, the appropriate dosage of a therapeutic protein will depend on the type of disease to be treated, as defined above, the severity and course of the disease, whether the protein is administered for preventive or therapeutic purposes, previous therapy, the patient's clinical history and response to the protein, and the discretion of the attending physician. The antibody is suitably administered to the patient at one time or over a series of treatments.

XIV. Databases

The invention includes methods of producing computer-readable databases comprising the sequence and identified mutations of certain proteins, including, but not limited to, sequences of binding domains, or active sites, as well as their binding characteristics, activity, stability characteristics and three-dimensional molecular structure. Specifically included in the present invention is the use of such a database to aid in the design and optimization of a protein of interest, based on a database of mutations created from the protein of interest, or related proteins or portions thereof.

In other embodiments, the databases of the present invention can comprise mutations of a protein or proteins that have been identified by screening to bind to a specific target, or other representations of such proteins such as, for example, a graphic representation or a name.

By "database" is meant a collection of retrievable data. The invention encompasses machine readable media embedded with or containing information regarding the amino acid and nucleic structure of a protein or proteins, such as, for example, its sequence, structure, and the activity or binding activity, as described herein. Such information can pertain to subunits, domains, and/or portions thereof such as, for example, portions comprising active sites, accessory binding sites, and/or binding pockets in either liganded (bound) or unliganded (unbound) forms.

Alternatively, the information can be that of identifiers which represent specific structures found in a protein. As used herein, "machine readable medium" refers to any medium that can be read and accessed directly by a computer or scanner. Such media can take many forms, including but not limited to, non-volatile, volatile and transmission media. Non-volatile media, i.e., media that can retain information in the absence of power, includes a ROM. Volatile media, i.e., media that cannot retain information in the absence of power, includes a main memory.

Transmission media includes coaxial cables, copper wire and fiber optics, including the wires that comprise the bus. Transmission media can also take the form of carrier waves; i.e., electromagnetic waves that can be modulated, as in frequency, amplitude or phase, to transmit information signals. Additionally, transmission media can take the form of acoustic or light waves, such as those generated during radio wave and infrared data communications.

Such media also include, but are not limited to: magnetic storage media, such as floppy discs, flexible discs, hard disc storage medium and magnetic tape; optical storage media such as optical discs or CD-ROM; electrical storage media such as RAM or ROM, PROM (i.e., programmable read only memory), EPROM (i.e., erasable programmable read only memory), including FLASH-EPROM, any other memory chip or cartridge, carrier waves, or any other medium from which a processor can retrieve information, and hybrids of these categories such as magnetic/optical storage media. Such media further include paper on which is recorded a representation of the amino acid or polynucleotide sequence, that can be read by a scanning device and converted into a format readily accessed by a computer or by any of the software programs described herein by, for example, optical character recognition (OCR) software. Such media also include physical media with patterns of holes, such as, for example, punch cards and paper tape.

Specifically included in the present invention is the transmission of data from the data base via transmission media to third party site to aid in the design and optimization of a protein of interest.

A variety of data storage structures are available for creating a computer readable medium having recorded thereon the amino acid or polynucleotide sequences of the invention or portions thereof and/or activity data. The choice of the data storage structure can be based on the means chosen to access the stored information. All format representations of the amino acid or polynucleotide sequences described herein, or portions thereof, are contemplated by the present invention. By providing computer readable medium having stored thereon the sequences of the invention, one can routinely access the SHM mediated changes in amino acid or polynucleotide sequence and related information for use in modeling and design programs, to create improved proteins.

A computer can be used to display the sequence of the protein or peptide structures, or portions thereof, such as, for example, portions comprising active sites, accessory binding sites, and/or binding pockets, in either liganded or unliganded form, of the present invention. The term "computer" includes, but is not limited to, mainframe computers, personal computers, portable laptop computers, and personal data assistants ("PDAs") which can store data and independently run one or more applications, i.e., programs. The computer can include, for example, a machine readable storage medium of the present invention, a working memory for storing instructions for processing the machine-readable data encoded in the machine readable storage medium, a central processing unit operably coupled to the working memory and to the machine readable storage medium for processing the machine readable information, and a display operably coupled to the central processing unit for displaying the structure coordinates or the three-dimensional representation.

The computers of the present invention can also include, for example, a central processing unit, a working memory which can be, for example, random-access memory (RAM) or "core memory," mass storage memory (for example, one or more disk drives or CD-ROM drives), one or more cathode-ray tube ("CRT") display terminals or one or more LCD displays, one or more keyboards, one or more input lines, and one or more output lines, all of which are interconnected by a conventional bi-directional system bus. Machine-readable data of the present invention can be inputted and/or outputted through a modem or modems connected by a telephone line or a dedicated data line (either of which can include, for example, wireless modes of communication). The input hardware can also (or instead) comprise CD-ROM drives or disk drives. Other examples of input devices are a keyboard, a mouse, a trackball, a finger pad, or cursor direction keys. Output hardware can also be implemented by conventional devices. For example, output hardware can include a CRT, or any other display terminal, a printer, or a disk drive. The CPU coordinates the use of the various input and output devices, coordinates data accesses from mass storage and accesses to and from working memory, and determines the order of data processing steps. The computer can use various software programs to process the data of the present invention. Examples of many of these types of software are discussed throughout the present application.

EXAMPLES

While a number of embodiments of the present invention have been shown and described herein, such embodiments are provided by way of example only. It should be understood that various alternatives to the embodiments of the invention described herein may be employed in practicing the invention. It is intended that the following claims define the scope of the invention and that methods and structures within the scope of these claims and their equivalents be covered thereby.

Example 1

Creation of Synthetic Polynucleotides Encoding Blasticidin

By decreasing the likelihood of somatic hypermutation in a vector element, such as a selectable marker, an enzyme involved in SHM, or a reporter gene, the vector and system for exerting and tracking SHM becomes more stable, thereby enabling somatic hypermutation to be more effectively targeted to a polynucleotide or library of polynucleotides of interest.

A. Polynucleotide Design

In general, sequences are engineered for SHM using the teaching described herein, and as elaborated in sections III and IV of U.S. application No. 60/902,414, entitled "Systems for Somatic Hypermutation." In the following examples, sequence optimization is based on the hot spot and cold spot definitions listed herein in Table 6), and using the computer program SHMredesign:

Using this program, every position within the sequence is annotated with either a '+', '−', or '.' symbol to designate whether it is desired to obtain a hotter, a colder, or a neutral change in SHM susceptibility at that specific position, where '+' designates a hot spot, '−' cold spot, and '.' a neutral position. For example, the following input sequence for blasticidin is used to identify SHM resistant versions at every position of the blasticidin gene.

(SEQ ID NO: 302)

```
>ATGGCCAAGCCTTTGTCTCAAGAAGAATCCACCCTCATTGAAAGAGCAACGGCTACAATCAACAGCATCCCCATCTCTGA

AGACTACAGCGTCGCCAGCGCAGCTCTCTCTAGCGACGGCCGCATCTTCACTGGTGTCAATGTATATCATTTTACTGGGGG

ACCTTGCGCAGAACTCGTGGTGCTGGGCACTGCTGCTGCTGCGGCAGCTGGCAACCTGACTTGTATCGTCGCGATCGGAAA

TGAGAACAGGGGCATCTTGAGCCCCTGCGGACGGTGCCGACAGGTTCTTCTCGATCTGCATCCTGGGATCAAAGCCATAGT

GAAGGACAGTGATGGACAGCCGACGGCAGTTGGGATTCGTGAATTGCTGCCCTCTGGTTATGTGTGGGAGGGCTAA

<-------------------------------------------------------------------------------

--------------------------------------------------------------------------------

--------------------------------------------------------------------------------

--------------------------------------------------------------------------------

---------------------------------------------------------------------------
```

By comparison, the following input file is used to identify hotter versions of the blasticidin gene that are more susceptible to SHM at every position of the gene.

```
                                    (SEQ ID NO: 303)
>ATGGCCAAGCCTTTGTCTCAAGAAGAATCCACCCTCATTGAAAGAGC
AACGGCTACAATCAACAGCATCCCCATCTCTGAAGACTACAGCGTCGC
CAGCGCAGCTCTCTCTAGCGACGGCCGCATCTTCACTGGTGTCAATGT
ATATCATTTTACTGGGGGACCTTGCGCAGAACTCGTGGTGCTGGGCAC
TGCTGCTGCTGCGGCAGCTGGCAACCTGACTTGTATCGTCGCGATCGG
AAATGAGAACAGGGGCATCTTGAGCCCCTGCGGACGGTGCCGACAGGT
TCTTCTCGATCTGCATCCTGGGATCAAAGCCATAGTGAAGGACAGTGA
TGGACAGCCGACGGCAGTTGGGATTCGTGAATTGCTGCCCTCTGGTTA
TGTGTGGGAGGGCTAA

<+++++++++++++++++++++++++++++++++++++++++++++++
++++++++++++++++++++++++++++++++++++++++++++++++
++++++++++++++++++++++++++++++++++++++++++++++++
++++++++++++++++++++++++++++++++++++++++++++++++
++++++++++++++++++++++++++++++++++++++++++++++++
++++++++++++++++++++++++++++++++++++++++++++++++
++++++++++++++++++++++++++++++++++++++++++++++++
++++++++++++++++++++++++++++++++++++++++++++++++
++++++++++++++++
```

As described previously, during this process, all nucleotide sequences over a 9 base region consistent with the wild type protein's amino acid sequence are enumerated and scored for the number of hot spots, cold spots, CpG motifs, codon usage, and stretches of the same nucleotide. The program then determines whether it is possible to replace any random sequence with a hotter, a colder, or a neutral polynucleotide tile encoding the same three amino acids.

Figure 7:
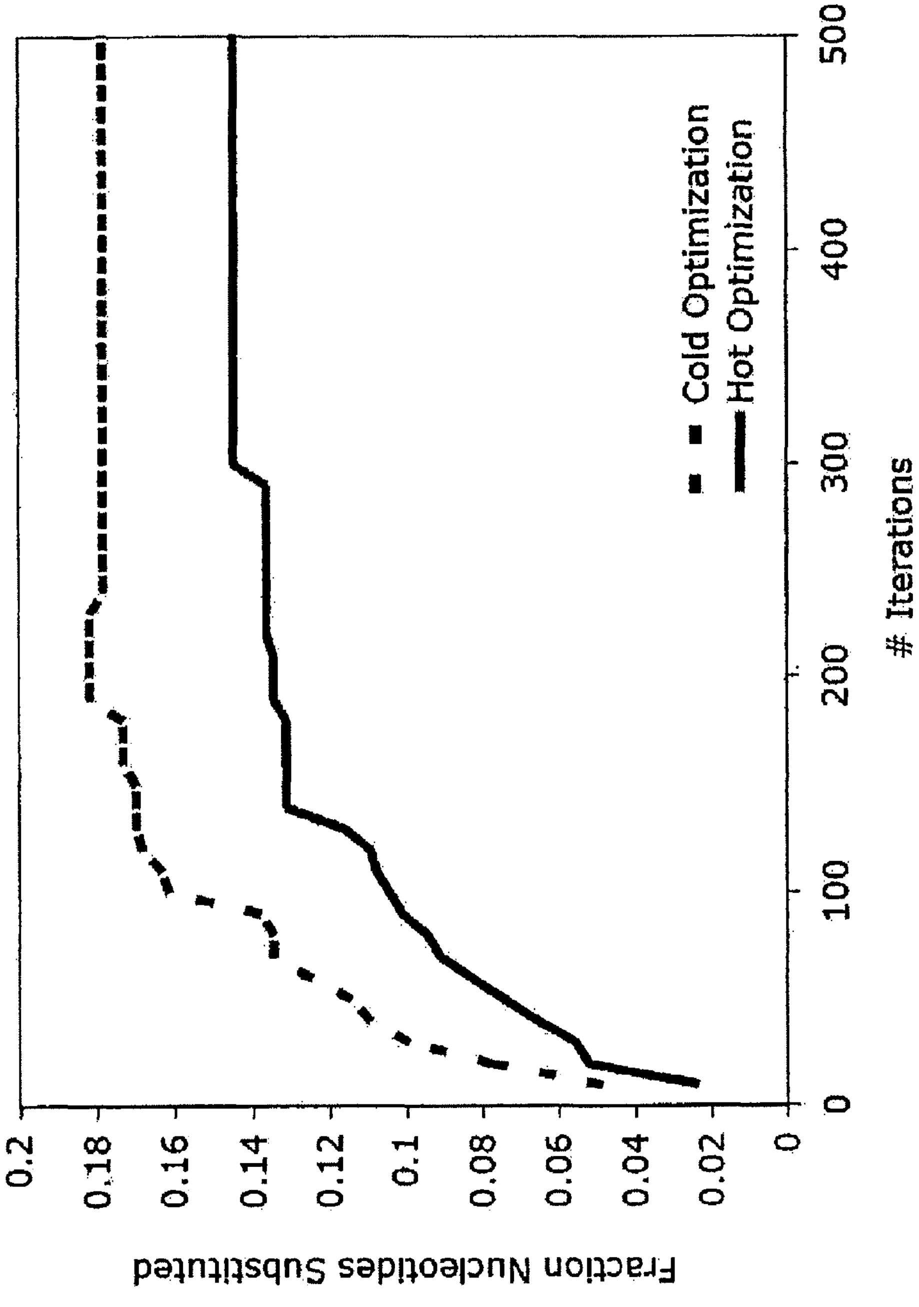
FIG. 7—Illustrates the convergence of sequence optimization with progressive iterations of replacement using the program SHMredesign. The figure shows both optimization toward an idealized hot and cold sequence, in this case starting with native canine AID nucleotide sequence.

As shown in FIG. 7, this approach, as applied to canine AID quickly, (within a few hundred tile substitutions), converges to identify a cold optimized canine AID new sequence, which differs from the original sequence through the substitution 15-20% of the nucleotide sequence. The majority of changes occur early in the iterative cycle and are usually complete after about 500 iterations. As one might expect, larger genes require a larger number of iterations to reach a fully optimized sequence. Routinely, the use of 2000 to 3000 iterations is more than sufficient for the majority of genes.

Analysis of a number of unmodified genes at random demonstrates that most mammalian genes use codons that create on average about 9 to 15 cold spots per 100 nucleotides, and with a median density of about 13.8 cold spots/100 nucleotides, and have a hot spot density of between about 7 to 13 hot spots per 100 nucleotides, with a median density of about 8.3 hot spots per 100 nucleotides.

The initial starting sequence, as well as the frequency of hot spots, cold spots and CpGs for the unmodified, blasticidin gene are shown in FIG. 8.

1. Cold Blasticidin

An optimized sequence for a SHM resistant (cold) version of blasticidin created using this approach is shown in FIG. 9, together with the resulting changes in frequency of hot spots and cold spots. Optimization of the blasticidin sequence to make the sequence more resistant to somatic hypermutation resulted in an increase of 188% in number of cold spots (an increase of 73), and reduced the number of hot spots by 57% (a decrease of 15). Overall, the frequency of cold spots increased to an average density of about 28 cold spots per 100 nucleotides from an initial density of about 15 cold spots per 100 nucleotides, and the overall frequency of hot spots decreased from about 9 hot spots per 100 nucleotides, in the unmodified gene to about 5 hot spots per 100 nucleotides in the SHM resistant form.

2. Hot Blasticidin

An optimized sequence for a SHM susceptible version of blasticidin created using this approach is shown in FIG. 10, together with the resulting changes in frequency of hot spots and cold spots. Optimization of the blasticidin sequence to make the sequence more susceptible to somatic hypermutation resulted in an increase of about 197% in number of hot spots (an increase of 34), and reduced the number of cold spots by about 56% (a decrease of 26). Overall, the frequency of hot spots increased to an average density of about 17 hot spots per 100 nucleotides from an initial density of about 9 hot spots per 100 nucleotides, and the overall frequency of cold spots decreased from about 15 cold spots per 100 nucleotides in the unmodified gene to about 9 cold spots per 100 nucleotides in the SHM susceptible form.

B. Cloning and Analysis

After final review to ensure that the synthetic polynucleotide sequence is free of extraneous restriction sites, the complete polynucleotide sequence is synthesized (DNA 2.0, Menlo Park, Calif.), cloned into one of DNA2.0's cloning vectors (see Table 10 below), and sequenced to confirm correct synthesis.

TABLE 10

| Construct | DNA2.0 source plasmid | restriction sites (5', 3') | vector that insert was cloned into |
|---|---|---|---|
| cold TFP | pJ15 | Sac1, BsrG1 | AB136 |
| hot TFP | pJ15 | Sac1, BsrG1 | AB102 |
| GFP* stop (Y82stop) | pJ31 | Sac1, BsrG1 | AB105 |
| cold hygromycin | pJ2 | NgoMIV, Xba1 | AB179, AB163 |
| native puromycin | pJ51 | NgoMIV, Xba1 | AB150, AB161 |
| cold blasticidin | pJ13 | NgoMIV, Xba1 | AB102, AB153 |
| cold AID | pJ45 | Sac1, BsrG1 | AB135, AB174 |
| Heavy chains scaffolds | | | |
| H1 | pJ31 | SgrAI, EagI | ANA320 |
| H2-H9 | pJ51 | | |
| Kappa Light chains K1 | pJ31 | SbfI, BsmBI | XX13 |
| K2-K4 | pJ51 | | |
| Lambda Light chains | | | |
| L1 | pJ31 | SbfI, BbsI | XX13 |
| L2-L5 | pJ51 | | |

Other elements, for example E-box motifs or Ig enhancer elements, are created by either oligo synthesis or PCR amplification as described in U.S. Patent application No. 60/902,414, entitled "Somatic Hypermutation Systems," filed on Feb. 20, 2007, and specifically incorporated herein in its entirety.

To test the functionality of the new synthetic inserts, coding regions are excised from DNA2.0 source vectors using restriction enzymes as listed in Table 10 above, and inserted into expression vectors (Table 10) using standard recombinant molecular biological techniques. Insertion of selection markers (i.e., cold blasticidin, cold hygromycin, and native puromycin) into the AB series of vectors places them down stream of the EMCV IRES sequence (AB150, AB102, AB179; see FIG. 17A) or downstream of the pSV promoter (AB161, AB153, AB163; see FIG. 17B).

To test functional activity of the optimized synthetic genes, Hek 293 cells are plated at $4\times10^5$/well, in 6-well microtiter dish. After 24 hours, transfections are performed using Fugene6 reagent from Roche Applied Sciences (Indianapolis, Ind.) at a reagent-to-DNA ratio of 3 μL:1 μg DNA per well. This ratio is also maintained for transfections with multiple plasmids. Transfections are carried out in accordance with manufacturer's protocol.

To determine the relative stability/susceptibility of each construct to somatic hypermutation, stable cell lines of each transfected cell population are created, and tested to determine the relative speed by which they accumulate SHM mediated mutations. Because the majority of these mutations result in a loss of function, relative mutagenesis load are conveniently measured as a loss of fluorescence via FACS (see below and Example 2).

FACS Analysis. Prior to FACS analysis, cells are harvested by trypsinization, washed twice in PBS containing 1% w/v BSA, and re-suspended in 200 μl PBS/1% BSA containing 2 ng/ml DAPI. Cells are analyzed in the Cytopeia Influx with 200 mW 488 nm and 50 mW 403 nm laser excitation. Up to one million cells per sample are acquired. DAPI fluorescence is measured through a 460/50 bandpass filter. GFP fluorescence is measured through a 528/38 bandpass filter. Percent GFP expression is reported as percentage of DAPI excluding live cells with no detectable GFP fluorescence above cellular background.

Reversion assays to test for function of the canine AID gene. GFP* (GFP with a stop codon introduced by site directed mutagenesis at position 82 [Y82stop]) is co-transfected with AB174 (cold canine AID), and cells are analyzed by flow cytometry 3 days post transfection, placed under antibiotic selection and analyzed further by flow cytometry every other day for 13-15 days.

Antibiotic selections. Antibiotic concentrations used in the selection of Hek 293 cells are determined empirically by performing a kill curve (i.e., determining the minimal concentration of antibiotic that kills all un-transfected—and thus antibiotic sensitive—cells). At 3 days post transfection, cells are plated at $4\times10^5$/well and selected at the following concentrations: 1.5 μg/ml puromycin (Clontech, Mountain View, Calif.); 16 μg/mL blasticidin (Invitrogen, Carlsbad, Calif.); and 360 μg/mL hygromycin (Invitrogen, Carlsbad, Calif.).

Resistance marker genes are tested to determine functionality by transfection of the appropriate expression plasmid (i.e. AB102 for blasticidin, AB179 for hygromycin) in Hek 293 cells based on their ability to promote drug resistance cell growth in the presence of 16 μg/mL blasticidin (Invitrogen, Carlsbad, Calif.); and 360 μg/mL hygromycin (Invitrogen, Carlsbad, Calif.) for two weeks.

Transfection of the AB102 containing cold blasticidin resulted in the creation of drug resistant colonies of transfected hek 293 cells at comparable rates as the wild type gene.

Example 2

Creation of Synthetic Polynucleotides Encoding Enzymes Involved in SHM

Cytidine Deaminase (AID)

Analysis of sequence variations in cytidine deaminase (AID) between mammalian species (rat, chimpanzee, mouse, human, dog, cow, rabbit, chicken, frog, zebra fish, fugu and tetraodon (puffer fish)) as compared to humans demonstrates that organisms as distantly related as human and frog display a surprisingly high (70%) sequence identity, and >80% sequence similarity. In addition, it has been shown that AID from other organisms can be substituted for human AID in somatic hypermutation (SHM), and that all mammalian species of AID are functionally equivalent.

Shown in FIG. 11 is a comparison of human AID with other terrestrial AIDs in order to identify a potential beginning construct for SHM in vivo. The figure provides a sequence alignment of AID from human (H_sap/1-198), mouse (M_musc/1-198), canine (C_fam/1-198), rat (R_norv/1-199), and chimpanzee (P_trog/1-199). FIG. 15 illustrates the sequence identity between human, canine and mouse AID proteins As shown by FIG. 11, canine AID has overall 94% amino acid identity to human and mouse AID and, thus, is selected as the starting point for codon optimization. To optimize codon usage, the canine amino acid sequences are reverse translated and then iteratively optimized.

AID is known to contain a nuclear export signal, which is contained within the C-terminal 10 amino acids (McBride et al., Somatic hypermutation is limited by CRM1-dependent nuclear export of activation-induced deaminase, J Exp Med. 2004 May 3; 199(9):1235-44; Ito et al., Activation-induced cytidine deaminase shuttles between nucleus and cytoplasm like apolipoprotein B mRNA editing catalytic polypeptide 1, PNAS 2004 Feb. 17; 101(7):1975-80.) For purposes of the experiments described below, the canine AID contains a leucine to alanine mutation at position 198, while the human AID construct retains the unmutated, intact nuclear export signal.

A. Polynucleotide Design

As described in Example 1, SHM sequence optimization is completed using the computer program SHMredesign, based on the hot spot and cold spot definitions listed in Table 6; the resulting hot and cold versions of canine AID are shown in FIG. 13 and FIG. 14 respectively. The starting sequence for canine AID is shown in FIG. 12, together with the initial analysis of hot spot and cold spot frequency.

1. Hot AID

Optimization of the AID sequence to make the sequence more susceptible to somatic hypermutation resulted in an increase of about 200% in number of hot spots (an increase of 43), and reduced the number of cold spots by about 30% (a decrease of 23). Overall the frequency of hot spots increased to an average density of about 14 hot spots per 100 nucleotides from an initial density of about 7 hot spots per 100 nucleotides, and the overall frequency of cold spots decreased from about 13 cold spots per 100 nucleotides in the native gene to about 9 cold spots per 100 nucleotides in the SHM susceptible form (see FIG. 13).

2. Cold AID

Optimization of the canine AID sequence to make the sequence more resistant to somatic hypermutation resulted in an increase of 186% in number of cold spots (an increase of 68), and reduced the number of hot spots by about 35% (a decrease of 14). Overall the frequency of cold spots increased to an average density of about 25 cold spots per 100 nucleotides from an initial density of about 13 cold spots per 100 nucleotides, and the overall frequency of hot spots decreased from about 7 hot spots per 100 nucleotides, in the native gene to about 5 hot spots per 100 nucleotides in the SHM resistant form (see FIG. 14).

B. Cloning and Analysis

After final review to ensure that the synthetic polynucleotide sequence is free of extraneous restriction sites, the complete polynucleotide sequence was synthesized (DNA 2.0, Menlo Park, Calif.), cloned into one of DNA2.0's cloning vectors (see Table 10 in Example 1), sequenced to confirm correct synthesis and tested for activity as described below and in Example 1.

To determine canine AID activity, the cold or wild type versions of AID are co transfected with expression vectors expressing the GFP* construct that contains a stop codon within it's coding region (as described in Example 1). Either in the presence or absence of Ig enhancer elements within the target vector sequence. Mutation of the stop codon by AID results in the creation of a functional fluorescent protein that is a direct indicator of AID activity.

In this experiment, cells are harvested by trypsinization, washed twice in PBS containing 1% w/v BSA, and resuspended in 200 μl PBS/1% BSA containing 2 ng/ml DAPI. Cells were analyzed in the Cytopeia Influx with 200 mW 488 nm and 50 mW 403 nm laser excitation. Up to one million cells per sample were acquired and revertants were determined as percentage of DAPI excluding live cells with detectable GFP fluorescence above cellular background.

FIG. 16A shows the predicted effect of AID activity on protein function, in this type of assay. Of note is the observation that mutagenesis can produce mutations that both initially restore or improve function and later reduce or eliminate function. The balance in these two rates generates early and rare mutation events that restore function, followed by secondary and tertiary mutation events that destroy function in these proteins. The net effect of these competing rates on the observation of gain-of-function events in a population can be seen in FIG. 16A. Given three different assumptions regarding number of inactivating mutations needed to silence GFP, one would expect to observe three very different profiles of reversion events as a function of time, dependent on the rate of enzymatic activity of the AID.

Thus, although initial reversion rates can provide an accurate assessment of AID activity, long term studies of activity require an analysis of the rate of extinction of activity, rather than reversion of fluorescence.

To test this possibility, a cell line that is stably expressing a fluorescent protein is transfected with 2 concentrations of expression vector containing cold canine AID. Cells are stably maintained in culture and sample assayed for total fluorescence after the indicated periods of time.

Prior to FACS analysis, cells are harvested by trypsinization, washed twice in PBS containing 1% w/v BSA, and resuspended in 200 μl PBS/1% BSA containing 2 ng/ml DAPI. Cells are analyzed in the Cytopeia Influx with 200 mW 488 nm and 50 mW 403 nm laser excitation. DAPI fluorescence is measured through a 460/50 bandpass filter. GFP fluorescence is measured through a 528/38 bandpass filter. Percent GFP expression is reported as percentage of DAPI excluding live cells with no detectable GFP fluorescence above cellular background.

The results, shown in FIG. 16B, show a steady and sustained progressive, dose dependent decrease in GFP expression (shown as increasing GFP extinction) with time when co-expressed with increasing amounts of cold AID. The data are consistent with the hypothesis that cold AID is able to introduce multiple mutations into a target gene, and is both functional and stable when expressed in a "cold form" for many days.

To directly compare the ability of cold canine AID to exert mutagenesis, initial reversion assays are set up comparing cold canine AID with wild type human AID. Hek 293 cells are transfected with the expression vectors (as described above in Example 1) containing either the GFP* as described above, or GFP* with the Kappa E3 and intronic enhances inserted 5' to the CMV promoter, together with either human or cold canine AID. Selection for stable expression began 3 days post transfection. Prior to FACS analysis, cells are harvested by trypsinization, washed twice in PBS containing 1% w/v BSA, and resuspended in 200 μl PBS/1% BSA containing 2 ng/ml DAPI. Cells are analyzed in the Cytopeia Influx with 200 mW 488 nm and 50 mW 403 nm laser excitation. Up to one million cells per sample are acquired. DAPI fluorescence was measured through a 460/50 bandpass filter. GFP fluorescence is measured through a 528/38 bandpass filter. Percent GFP expression is reported as percentage of DAPI excluding live cells with no detectable GFP fluorescence above cellular background.

The results show (FIG. 16C) that canine AID exhibited significantly enhanced reversion activity compared to human AID. Also in this experiment is shown the effect of the kappa 3'E and intronic enhancers on the rate of reversion experienced by the target gene when these were included in the expression vector. As shown inclusion of the enhancer elements further enhanced reversion frequency.

Example 3

Vectors for Somatic Hypermutation

Vectors are constructed from sub-fragments that are each synthesized by DNA2.0 (Menlo Park, Calif.). Vectors are able to simultaneously express multiple open reading frames and are capable of stable, episomal replication in mammalian cells that are naturally permissive or rendered to be permissive (i.e., via co-expression of human EBP2 (Habel et al., 2004; Kapoor et al., 2001) for replication of Epstein Barr Virus (EBV) origin of replication (oriP) containing vectors.

Plasmids are rendered highly modular through the strategic placement of one or more restriction endonuclease recognition sequences (restriction sites) between discreet fragments throughout the vector.

A. Vectors Formats.

In the first format (FIG. 17A); vectors contain an internal ribosome entry site (IRES) from the encephalomyocarditis virus (EMCV). Elements contained within the vectors are operably linked together as shown in FIG. 17A and, in some cases, include the following functional elements (numbers refer to corresponding sequence information found further below in this section): 1) CMV promoter; 2) Multicloning sites; 3) Gene of interest; 4) IRES; 5) Eukaryotic selectable marker such as blasticidin S deaminase (bsd), hygromycin phosphotransferase (hyg) or puromycin-N-acetyl-transferase; 6) Terminator sequences, (3' untranslated region, small intron and polyA signals from SV40 ("IVS pA")); 7) Epstein Barr Virus (EBV) origin of replication (oriP) (preceded by optional intergenic spacer region); 8) Prokaryotic origin of replication ColE1; 9) Prokaryotic selectable marker such as beta lactamase (bla) gene or kanamycin (kan); 10) gene fragment for copy number determination (such as beta actin or glucose-6-phosphate dehydrogenase (G6PDH), and Ig enhancers.

In a second format, (FIG. 17B), the expression vectors are made without an IRES, but contain instead an independent expression cassette for expressing a selectable marker gene. This expression cassette can include, 11) the SV40 immediate early promoter (pSV) and eukaryotic selectable marker, and IVS pA as described above. Elements contained within the vectors are operably linked together as shown in FIG. 17 and typically include the following functional elements: CMV promoter, multicloning sites, gene of interest, IVS pA, Epstein Barr Virus (EBV) origin of replication (oriP), pSV, selectable marker, IVS pA, prokaryotic origin of replication ColE1, prokaryotic selectable marker such as beta lactamase (bla) gene, or kanamycin (kan), gene fragment for copy number determination, Ig enhancers, and multicloning sites.

In a third format, (FIG. 18A) vectors contain a bidirectional promoter that drives expression of 2 different genes oriented in opposite directions. This vector also contains IRES sequences to generate 1 or 2 bi- or tri-cistronic messages. Elements contained within the vectors are operably linked together as shown in FIG. 18 using the same functional elements as described previously.

In a fourth format, (FIG. 18B) vectors contain a bidirectional promoter, one or more IRES sequences that express bi- or tri-cistronic messages, and an independent, cis-linked cassette from which a eukaryotic selectable marker is expressed.

Any of the vectors can be interchanged with each other to form hybrids. In addition, any of the strong constitutive eukaryotic promoters contained on the episomal vector can be substituted with an inducible promoter (i.e. the reverse tetracycline transactivator promoter system [prtTA]) to achieve conditional expression of a desired gene. In this case, one of the other genes of interest should encode the transactivating protein, which can be expressed in cis on the same episome (as shown in FIG. 19), or supplied in trans on a second, transfected episomal vector.

The orientations for the prokaryotic selectable marker and colEI origin of replication provided in sections 8 and 9 below (SEQ ID NOS: 313, 314 and 315), and in FIGS. 17-19 are not absolute and can be reversed with respect to the remainder of the vector. Similarly, the orientation of the independent expression cassette (pSV—selectable marker (or other gene of interest)—IVS pA) can also be reversed with respect to the remainder of the vector (i.e. transcribing toward the oriP instead of the current portrayal of transcription away from the oriP). Additionally, enhancer elements, such as Ig enhancers may be placed either 5' or 3' to the gene of interest, or may excluded.

B. Representative Sequences of Functional Elements

1. A strong transcriptional promoter that works in eukaryotic cells. In FIGS. 17-19, the CMV promoter is used and the sequence is provided as SEQ ID NO: 304 (the TATA box sequence is shown underlined). The CMV promoter is altered to remove SacI and BsrGI sites.

(SEQ ID NO: 304)

AGCTTGGCCCATTGCATACGTTGTATCCATATCATAATATCTACATTTA

TATTGGCTCATGTCCAACATTACCGCCATGTTGACATTGATTATTGACT

AGTTATTAATAGTAATCAATTACGGGGTCATTAGTTCATAGCCCATATA

TGGAGTTCCGCGTTACATAACTTACGGTAAATGGCCCGCCTGGCTGACC

GCCCAACGACCCCCGCCCATTGACGTCAATAATGACGTATGTTCCCATA

GTAACGCCAATAGGGACTTTCCATTGACGTCAATGGGTGGAGTATTTAC

GGTAAACTGCCCACTTGGCAGTACATCAAGTGTATCATATGCCAAGTAC

GCCCCCTATTGACGTCAATGACGGTAAATGGCCCGCCTGGCATTATGCC

CAGTACATGACCTTATGGGACTTTCCTACTTGGCAGTACATCTACGTAT

TAGTCATCGCTATTACCATGGTGATGCGGTTTTGGCAGTACATCAATGG

GCGTGGATAGCGGTTTGACTCACGGGGATTTCCAAGTCTCCACCCCATT

GACGTCAATGGGAGTTTGTTTTGGCACCAAAATCAACGGGACTTTCCAA

AATGTCGTAACAACTCCGCCCCATTGACGCAAATGGGCGGTAGGCGTGT

ACGGTGGGAGGTCTATATAAGCAGAGCTGGTTTAGTGAACCGTCAGATC

GCCTA.

2. A region encoding multiple restriction sites termed a multicloning site (mcs) region:

(SEQ ID NO: 305)

TTCCCTGCAGGATTGTTTAAACACCAGATCTGCTTGAATCCGCGGATAA

GAGGACTAGTATTCGTCTCACTAGGGAGAGCTCCTA.

3. A gene of interest such as, for example, specific binding member, antibody or fragment thereof, antibody heavy or light chain, enzyme, receptor, peptide growth hormone or transcription factor.

4. An internal ribosome entry site (IRES), in FIGS. 17-19 from the encephalomyocarditis virus (EMCV)-permits the concomitant bicistronic expression of two open reading frames (ORF's): one 5' to itself, and a second 3' to itself. A region containing 2 restriction sites (BsrGI and AscI) is shown 5' to the IRES (lower case letters). The 3' end of the IRES includes an NgoMIV site.

(SEQ ID NO: 306)

tgtacaatccgcgtgagacgatcggcgcgccCGCCCCTCTCCCTCCCCC

CCCCCTAACGTTACTGGCCGAAGCCGCTTGGAATAAGGCCGGTGTGCGT

TTGTCTATATGTTATTTTCCACCATATTGCCGTCTTTTGGCAATGTGAG

GGCCCGGAAACCTGGCCCTGTCTTCTTGACGAGCATTCCTAGGGGTCTT

TCCCCTCTCGCCAAAGGAATGCAAGGTCTGTTGAATGTCGTGAAGGAAG

CAGTTCCTCTGGAAGCTTCTTGAAGACAAACAACGTCTGTAGCGACCCT

TTGCAGGCAGCGGAACCCCCCACCTGGCGACAGGTGCCTCTGCGGCCAA

AAGCCACGTGTATAAGATACACCTGCAAAGGCGGCACAACCCCAGTGCC

ACGTTGTGAGTTGGATAGTTGTGGAAAGAGTCAAATGGCTCTCCTCAAG

CGTATTCAACAAGGGGCTGAAGGATGCCCAGAAGGTACCCCATTGTATG

GGATCTGATCTGGGGCCTCGGTGCACATGCTTTACATGTGTTTAGTCGA

GGTTAAAAAAACGTCTAGGCCCCCCGAACCACGGGGACGTGGTTTTCCT

TTGAAAAACACGATGATAATATGGCCGGC.

5. The open reading frame (ORF) for a mammalian selectable marker gene, such as, for example, blasticidin S deaminase (bsd) (SEQ ID NO: 308), hygromycin phosphotransferase (hyg) (SEQ ID NO: 309), or puromycin-N-acetyl-transferase (SEQ ID NO: 310). Start and stop codons are underlined. 3' to each ORF is an XbaI site (TCTAGA; SEQ ID NO: 307) used in the cloning step.

Blasticidin S Deaminase (bsd; Cold Spot Optimized)

(SEQ ID NO: 308)

ATGGCCAAGCCTTTGTCTCAAGAAGAATCCACCCTCATTGAAAGGGCCA

CTGCTACAATCAACAGCATCCCCATCTCTGAAGACTACTCTGTCGCCAG

CGCAGCTCTCTCCTCTGACGGGAGAATCTTCACTGGTGTCAATGTATAT

CATTTTACTGGGGGACCTTGCGCAGAGCTTGTGGTCCTGGGGACTGCTG

CTGCTGCTGCAGCCGGAAACCTGACTTGTATCGTCGCCATAGGGAATGA

GAACAGAGGCATCTTGAGCCCCTGTGGGAGATGCAGACAAGTCCTCCTG

-continued

GACCTCCATCCTGGGATCAAAGCCATAGTGAAGGACAGTGATGGACAGC

CCACAGCCGTTGGGATCAGGGAGTTGCTGCCATCTGGTTATGTGTGGGA

GGGCTAATCTAGA.

Hygromycin Phosphotransferase (hyg; Cold Spot Optimized)

(SEQ ID NO: 309)

ATGAAAAAGCCTGAACTGACTGCCACCTCTGTTGAGAAGTTTTTAATAG

AGAAGTTTGACTCTGTGTCAGACCTCATGCAGCTTTCTGAGGGAGAGGA

GTCTAGAGCCTTTAGCTTTGATGTGGGGGGAGAGGCTATGTCCTGAGA

GTCAATAGCTGTGCAGATGGTTTCTACAAAGATAGGTATGTCTATAGAC

ATTTTGCATCCGCCGCCCTCCCCATTCCAGAGGTCCTTGACATTGGGGA

ATTCTCAGAGAGCCTGACCTATTGCATTTCCCGGAGAGCCCAGGGTGTG

ACTCTTCAAGACCTGCCTGAGACAGAACTCCCTGCAGTGCTCCAGCCCG

TCGCCGAGGCCATGGATGCAATCGCCGCCGCAGACCTCAGCCAGACCTC

GGGGTTTGGGCCCTTTGGCCCCCAGGGGATAGGCCAATACACTACATGG

AGAGATTTCATATGCGCTATTGCTGACCCCCATGTGTATCACTGGCAAA

CTGTGATGGACGACACAGTCTCAGCCTCTGTCGCACAAGCCCTGGACGA

GCTGATGCTTTGGGCCGAGGACTGCCCAGAGGTCAGACATCTCGTCCAT

GCCGACTTTGGGTCAAACAATGTCCTGACGGACAATGGGAGAATCACTG

CTGTCATTGACTGGAGCGAGGCCATGTTTGGGGACTCCCAATACGAGGT

CGCCAACATCTTCTTCTGGAGACCCTGGTTGGCTTGTATGGAGCAGCAG

ACCCGTTACTTTGAGAGGAGGCATCCAGAGCTCGCTGGGAGCCCTAGAT

TGAGGGCCTATATGCTCAGGATAGGGCTTGACCAACTCTATCAGAGCTT

GGTTGACGGCAATTTTGATGACGCAGCTTGGGCTCAGGGGAGATGCGAC

GCCATAGTGAGGAGTGGGGCCGGGACTGTCGGGAGAACTCAGATCGCCA

GGAGGTCAGCTGCCGTCTGGACTGACGGCTGTGTAGAAGTCTTAGCCGA

CTCTGGGAACAGGAGACCCAGCACTCGTCCAGAGGCCAAGGAATGATCT

AGA.

Puromycin-N-acetyl-transferase (Pur; Wild Type Sequence).

Contains a Kozak consensus sequence immediately 5' to the start codon (underlined). Stop codon is also underlined.

(SEQ ID NO: 310)

CACCATGACCGAGTACAAGCCCACGGTGCGCCTCGCCACCCGCGACGAC

GTCCCCCGGGCCGTTCGCACCCTCGCCGCCGCGTTCGCCGACTACCCCG

CCACGCGCCACACCGTGGACCCGGACAGGCACATCGAGCGGGTCACCGA

GCTGCAAGAACTCTTCCTCACGCGCGTCGGGCTCGACATCGGCAAGGTG

TGGGTCGCGGACGACGGCGCCGCTGTGGCGGTCTGGACCACGCCGGAGA

GCGTCGAAGCGGGGGCGGTGTTCGCCGAGATCGGCCCGCGCATGGCCGA

GTTGAGCGGTTCCCGGCTGGCCGCGCAGCAACAGATGGAAGGCCTCCTG

GCGCCGCACCGGCCCAAGGAGCCCGCGTGGTTCCTGGCTACCGTCGGAG

TCTCGCCCGACCACCAGGGCAAGGGTCTGGGCAGCGCCGTCGTGCTCCC

-continued

CGGAGTGGAGGCTGCCGAGCGTGCCGGGGTGCCCGCCTTCCTCGAGACC

TCCGCGCCCCGCAACCTCCCCTTCTACGAGCGGCTCGGCTTCACCGTCA

CCGCCGACGTCGAGGTGCCCGAAGGACCGCGCACCTGGTGCATGACCCG

CAAGCCCGGTGCCTGATCTAGA.

6. Terminator sequences, WS-pA (shown with 3' BamHI).

(SEQ ID NO: 311)

GGATCTTTGTGAAGGAACCTTACTTCTGTGGTGTGACATAATTGGACAA

ACTACCTACAGAGATTTAAAGCTCTAAGGTAAATATAAAATTTTTAAGT

GTATAATGTGTTAAACTACTGATTCTAATTGTTGTGGTATTTTAGATTC

CAACCTATGGAACTTATGAATGGGAGCAGTGGTGGAATGCCTTTAATGA

GGAAAACCTGTTTTGCTCAGAAGAAATGCCATCTAGTGATGATGAGGCT

ACTGCTGACTCTCAACATTCTACTCCTCCAAAAAAGAAGAGAAAGGTAG

AAGACCCCAAGGACTTTCCTTCAGAATTGGTAAGTTTTTTGAGTCATGC

TGTGTTTAGTAATAGAACTCTTGCTTGCTTTGCTATTTACACCACAAAG

GAAAAAGCTGCACTGCTATACAAGAAAATTATGGAAAAATATTTGATGT

ATAGTGCCTTGACTAGAGATCATAATCAGCCATACCACATTTGTAGAGG

TTTTACTTGCTTTAAAAAACCTCCCACACCTCCCCCTGAACCTGAAACA

TAAAATGAATGCAATTGTTGTTGTTAACTTGTTTATTGCAGCTTATAAT

GGTTACAAATAAAGCAATAGCATCACAAATTTCACAAATAAAGCATTTT

TATCACTGCATTCTAGTTGTGGTTTGTCCAAACTCATCAATGTATCTTA

TCATGTCTGGATCC.

7. Sequence of EBV oriP. This element permits episomal replication in EBV oriP permissive cells that express Epstein Barr Nuclear Antigen 1 (EBNA1). The oriP sequence is preceded by an optional intergenic spacer region (small letters):

(SEQ ID NO: 312)

actgtcttctttatcatgcaactcgtaggacaggtgccctggccgggtc cGCAGGAAAAGGACAAGCAGCGAAAATTCACGCCCCCTTGGGAGGTGGC

GGCATATGCAAAGGATAGCACTCCCACTCTACTACTGGGTATCATATGC

TGACTGTATATGCATGAGGATAGCATATGCTACCCGGATACAGATTAGG

ATAGCATATACTACCCAGATATAGATTAGGATAGCATATGCTACCCAGA

TATAGATTAGGATAGCCTATGCTACCCAGATATAAATTAGGATAGCATA

TACTACCCAGATATAGATTAGGATAGCATATGCTACCCAGATATAGATT

AGGATAGCCTATGCTACCCAGATATAGATTAGGATAGCATATGCTACCC

AGATATAGATTAGGATAGCATATGCTATCCAGATATTTGGGTAGTATAT

GCTACCCAGATATAAATTAGGATAGCATATACTACCCTAATCTCTATTA

GGATAGCATATGCTACCCGGATACAGATTAGGATAGCATATACTACCCA

GATATAGATTAGGATAGCATATGCTACCCAGATATAGATTAGGATAGCC

TATGCTACCCAGATATAAATTAGGATAGCATATACTACCCAGATATAGA

TTAGGATAGCATATGCTACCCAGATATAGATTAGGATAGCCTATGCTAC

CCAGATATAGATTAGGATAGCATATGCTATCCAGATATTTGGGTAGTAT

-continued

```
ATGCTACCCATGGCAACATTAGCCCACCGTGCTCTCAGCGACCTCGTGA

ATATGAGGACCAACAACCCTGTGCTTGGCGCTCAGGCGCAAGTGTGTGT

AATTTGTCCTCCAGATCGCAGCAATCGCGCCCCTATCTTGGCCCGCCCA

CCTACTTATGCAGGTATTCCCCGGGGTGCCATTAGTGGTTTTGTGGGCA

AGTGGTTTGACCGCAGTGGTTAGCGGGGTTACAATCAGCCAAGTTATTA

CACCCTTATTTTACAGTCCAAAACCGCAGGGCGGCGTGTGGGGGCTGAC

GCGTGCCATCACTCCACAATTTCAAGAGAAAGAGTGGCCACTTGTCTTT

GTTTATGGGCCCCATTGGCGTGGAGCCCCGTTTAATTTTCGGGGGTGTT

AGAGACAACCAGTGGAGTCCGCTGCTGTCGGCGTCCACTCTCTTTCCCC

TTGTTACAAATAGAGTGTAACAACATGGTTCACCTGTCTTGGTCCCTGC

CTGGGACACATCTTAATAACCCCAGTATCATATTGCACTAGGATTATGT

GTTGCCCATAGCCATAAATTCGTGTGAGATGGACATCCAGTCTTTACGG

CTTGTCCCCACCCCATGGATTTCTATTGTTAAAGATATTCAGAATGTTT

CATTCCTACACTAGGATTTATTGCCCAAGGGGTTTGTGAGGGTTATATT

GGTGTCATAGCACAATGCCACCACTGAACCCATCGTCCAAATTTTATTC

TGGATGCGTCACCTGAAACCTTGTTTTCGAGCACCTCACATACACCTTA

CTGTTCACAACTCAGCAGTTATTCTATTAGCTAAACGAAGGAGAATGAA

GAAGCAGGCGAAGATTCAGGAGAGTTCACTGCCCGCTCCTTGATCTTCA

GCCACTGCCCTTGTGACTAAAATGGTTCACTACCCTCGTGGAATCCTGA

CCCCATGTAAATAAAACCGTGACAGCTCATGGGGTGGAGATATCGCTG

TTCCTTAGGACCCTTTTACTAACCCTAATTCGATAGCATATGCTTCCCG

TTGGGTAACATATGCTATTGAATTAGGGTTAGTCTGGATAGTATATACT

ACTACCCGGGAAGCATATGCTACCCGTTTAGGGTTAACAAGGGGGCCTT

ATAAACACTATTGCTAATGCCCTCTTGAGGGTCCGCTTATCGGTAGCTA

CACAGGCCCCTCTGATTGACGTTGGTGTAGCCTCCCGTAGTCTTCCTGG

GCCCCTGGGAGGTACATGTCCCCCAGCATTGGTGTAAGAGCTTCAGCCA

AGAGTTACACATAAAGG.
```

8. Sequence of *Escherichia coli* origin of replication colE1, derived from vector pJ15 and pJ31 from DNA2.0 (Menlo Park, Calif.): colE1

```
                                           (SEQ ID NO: 313)
AAAAGGGGCCCGAGCTTAAGACTGGCCGTCGTTTTACAACACAGAAAGA

GTTTGTAGAAACGCAAAAAGGCCATCCGTCAGGGGCCTTCTGCTTAGTT

TGATGCCTGGCAGTTCCCTACTCTCGCCTTCCGCTTCCTCGCTCACTGA

CTCGCTGCGCTCGGTCGTTCGGCTGCGGCGAGCGGTATCAGCTCACTCA

AAGGCGGTAATACGGTTATCCACAGAATCAGGGGATAACGCAGGAAAGA

ACATGTGAGCAAAAGGCCAGCAAAAGGCCAGGAACCGTAAAAAGGCCGC

GTTGCTGGCGTTTTTCCATAGGCTCCGCCCCCCTGACGAGCATCACAAA

AATCGACGCTCAAGTCAGAGGTGGCGAAACCCGACAGGACTATAAAGAT

ACCAGGCGTTTCCCCCTGGAAGCTCCCTCGTGCGCTCTCCTGTTCCGAC

CCTGCCGCTTACCGGATACCTGTCCGCCTTTCTCCCTTCGGGAAGCGTG
```

-continued

```
GCGCTTTCTCATAGCTCACGCTGTAGGTATCTCAGTTCGGTGTAGGTCG

TTCGCTCCAAGCTGGGCTGTGTGCACGAACCCCCCGTTCAGCCCGACCG

CTGCGCCTTATCCGGTAACTATCGTCTTGAGTCCAACCCGGTAAGACAC

GACTTATCGCCACTGGCAGCAGCCACTGGTAACAGGATTAGCAGAGCGA

GGTATGTAGGCGGTGCTACAGAGTTCTTGAAGTGGTGGCTAACTACGG

CTACACTAGAAGAACAGTATTTGGTATCTGCGCTCTGCTGAAGCCAGTT

ACCTTCGGAAAAAGAGTTGGTAGCTCTTGATCCGGCAAACAAACCACCG

CTGGTAGCGGTGGTTTTTTTGTTTGCAAGCAGCAGATTACGCGCAGAAA

AAAAGGATCTCAAGAAGATCCTTTGATCTTTTCTACGGGGTCTGACGCT

CAGTGGAACGACGCGCGCGTAACTCACGTTAAGGGATTTTGGTCATGAG

CTTGCGCCGTCCCGTCAAGTCAGCGTAATGCTCTG.
```

9A. Sequence of beta lactamase (bla) gene for resistance. The open reading frame (ORF) is shown in reverse orientation.

```
                                           (SEQ ID NO: 314)
CTTACCAATGCTTAATCAGTGAGGCACCTATCTCAGCGATCTGTCTATT

TCGTTCATCCATAGTTGCCTGACTCCCCGTCGTGTAGATAACTACGATA

CGGGAGGGCTTACCATCTGGCCCCAGCGCTGCGATGATACCGCGAGAAC

CACGCTCACCGGCTCCGGATTTATCAGCAATAAACCAGCCAGCCGGAAG

GGCCGAGCGCAGAAGTGGTCCTGCAACTTTATCCGCCTCCATCCAGTCT

ATTAATTGTTGCCGGGAAGCTAGAGTAAGTAGTTCGCCAGTTAATAGTT

TGCGCAACGTTGTTGCCATCGCTACAGGCATCGTGGTGTCACGCTCGTC

GTTTGGTATGGCTTCATTCAGCTCCGGTTCCCAACGATCAAGGCGAGTT

ACATGATCCCCCATGTTGTGCAAAAAAGCGGTTAGCTCCTTCGGTCCTC

CGATCGTTGTCAGAAGTAAGTTGGCCGCAGTGTTATCACTCATGGTTAT

GGCAGCACTGCATAATTCTCTTACTGTCATGCCATCCGTAAGATGCTTT

TCTGTGACTGGTGAGTACTCAACCAAGTCATTCTGAGAATAGTGTATGC

GGCGACCGAGTTGCTCTTGCCCGGCGTCAATACGGGATAATACCGCGCC

ACATAGCAGAACTTTAAAAGTGCTCATCATTGGAAAACGTTCTTCGGGG

CGAAAACTCTCAAGGATCTTACCGCTGTTGAGATCCAGTTCGATGTAAC

CCACTCGTGCACCCAACTGATCTTCAGCATCTTTTACTTTCACCAGCGT

TTCTGGGTGAGCAAAAACAGGAAGGCAAAATGCCGCAAAAAAGGGAATA

AGGGCGACACGGAAATGTTGAATACTCATATTCTTCCTTTTTCAATATT

ATTGAAGCATTTATCAGGGTTATTGTCTCATGAGCGGATACATATTTGA

ATGTATTTAGAAAAATAAACAAATAGGGGTCAGTGTTACAACCAATTAA

CCAATTCTGAACATTATCGCGAGCCCATTTATACCTGAATATGGCTCAT

AACACCCCTTGCAGTGCGACTAACGGCATGAAGCTCGTCGGGGCGTACG.
```

9B. Sequence of kanamycin (kan), derived from vector pJ31 from DNA2.0 (Menlo Park, Calif.). The open reading frame (ORF) is shown in reverse orientation.

(SEQ ID NO: 315)
CTTAGAAAAACTCATCGAGCATCAAATGAAACTGCAATTTATTCATATCAGGATTATCAATACCATATTTTT

GAAAAAGCCGTTTCTGTAATGAAGGAGAAAACTCACCGAGGCAGTTCCATAGGATGGCAAGATCCTGGTA

TCGGTCTGCGATTCCGACTCGTCCAACATCAATACAACCTATTAATTTCCCCTCGTCAAAAATAAGGTTATC

AAGTGAGAAATCACCATGAGTGACGACTGAATCCGGTGAGAATGGCAAAAGTTTATGCATTTCTTTCCAGA

CTTGTTCAACAGGCCAGCCATTACGCTCGTCATCAAAATCACTCGCATCAACCAAACCGTTATTCATTCGTG

ATTGCGCCTGAGCGAGGCGAAATACGCGATCGCTGTTAAAAGGACAATTACAAACAGGAATCGAGTGCAA

CCGGCGCAGGAACACTGCCAGCGCATCAACAATATTTTCACCTGAATCAGGATATTCTTCTAATACCTGGA

ACGCTGTTTTTCCGGGGATCGCAGTGGTGAGTAACCATGCATCATCAGGAGTACGGATAAAATGCTTGATG

GTCGGAAGTGGCATAAATTCCGTCAGCCAGTTTAGTCTGACCATCTCATCTGTAACATCATTGGCAACGCT

ACCTTTGCCATGTTTCAGAAACAACTCTGGCGCATCGGGCTTCCCATACAAGCGATAGATTGTCGCACCTG

ATTGCCCGACATTATCGCGAGCCCATTTATACCCATATAAATCAGCATCCATGTTGGAATTTAATCGCGGCC

TCGACGTTTCCCGTTGAATATGGCTCATATTCTTCCTTTTTCAATATTATTGAAGCATTTATCAGGGTTATTG

TCTCATGAGCGGATACATATTTGAATGTATTTAGAAAAATAAACAAATAGGGGTCAGTGTTACAACCAATT

AACCAATTCTGAACATTATCGCGAGCCCATTTATACCTGAATATGGCTCATAACACCCCTTGCAGTGCGACT

AACGGCATGAAGCTCGTCGGGGAAATAATGATTTTATTTTGACTGATAGTGACCTGTTCGTTGCAACAAAT

TGATAAGCAATGCTTTCTTATAATGCCAACTTTGTACAAGAAAGCTGGGTTTTTTTTTTAGCCTGCTTTTTTG

TACAAAGTTGGCATTATAAAAAAGCATTGCTCATCAATTTGTTGCAACGAACAGGTCACTATCAGTCAAAA

TAAAATCATTATTT.

10. A moiety used for determination of episomal copy number per cell. Ideally, the moiety should contain a sequence that exists uniquely in the genome. Shown below are 2 fragments, beta actin and G6PDH that can be used in vectors known in the art or described herein. Each fragment is bounded by a BsiWI and a Cla I site.

Beta Actin Moiety (SEQ ID NO: 316)
CGTACGTACTCCTGCTTGCTGATCCACATCTGCTGGAAGGTGGACAGCGAGGCCAGGATGGAGCCGCCGAT

CCACACGGAGTACTTGCGCTCAGGAGGAGCAATGAAGCTTATCTGAGGAGGGAAGGGGACAGGCAGTGAG

GACCCTGGATGTGACAGCTCCAAGCTTCCACACACCACAGGACCCCACAGCCGACCTGCCCAGGTCAGCTC

AGGCAGGAAAGACACCCACCTTGATCTTCATTGTGCTGGGTGCCAGGGCAGTGATCTCCTTCTGCATCCTG

TCATCGAT.

Human Glucose-6-Phosphate Dehydrogenase (hG6PDH) Moiety (SEQ ID NO: 317)
CGTACGAGGTGAGGCTGCAGTTCCATGATGTGTCCGGCGACATCTTCCACCAGCAGTGCAAGCGCAACGAG

CTGGTGATCCGCGTGCAGCCCAACGAGGCCGTGTACCAGAGAAGGAGCAGTGTGGAGGGTGGGCGGCCTG

GGCCCGGGGGACTCCACATGGTGGCAGGCAGTGGCATCAGCAAGACACTCTCTCCCTCACAGAACGTGAA

GCTCCCTGACGCCTACGAGCGCCTCATCCTGGACGTCTTCTGCGGGAGCCAGATGCACTTCGTGCGCAGGA

ATCGAT.

11. pSV, immediate early promoter from SV40. The sequence is preceded by a BstBI site and followed by an NgoMIV site.

(SEQ ID NO: 318)
```
TTCGAAGCTGTGGAATGTGTGTCAGTTAGGGTGTGGAAAGTCCCCAGGCTCCCCAGCAGGCAGAAGTATGC

AAAGCATGCATCTCAATTAGTCAGCAACCAGGTGTGGAAAGTCCCCAGGCTCCCCAGCAGGCAGAAGTAT

GCAAAGCATGCATCTCAATTAGTCAGCAACCATAGTCCCGCCCCTAACTCCGCCCATCCCGCCCCTAACTC

CGCCCAGTTCCGCCCATTCTCCGCCCCATGGCTGACTAATTTTTTTTATTTATGCAGAGGCCGAGGCCGCCT

CGGCCTCTGAGCTATTCCAGAAGTAGTGAGGAGGCTTTTTTGGAGGCCTAGGCTTTTGCAAAAAGCTCTGA

CCCCTCACAAGGAGCCGGC.
```

Ig Enhancers.

Representative Ig enhancer sequences include the heavy or light chain enhancers. The Kappa 3' enhancer region (Ek3') (See Meyer, K. B. and Neuberger, M. S., EMBO J. 8 (7), 1959-1964 (1989)), and Kappa intronic enhancer Eki LOCUS L80040 7466 bp ROD Sep. 2, 2003 are shown below by way of example. At least 1 major active element within the enhancer regions is the E box sequence: CAGGTG$(N)_{13}$CAGGTG (SEQ ID NO: 319) [core sequence: CANNTG; SEQ ID NO: 320] Storb et al., Immunity 19:235-242, 2003). The Ek3' and Eki enhancer elements are obtained from Dr. Neuberger (MRC, UK). The Ek3' sequence is amplified by PCR from Neuberger plasmid identification #1352, using the following primers, which contain an XhoI and EcoRI site, respectively, that are used for cloning:

(SEQ ID NO: 321)
```
GACTACCTCGAGccagcttaggctacacagag
```
and

```
GTAGTCGAATTCCCACATGTCTTACATGGTATATG.
```

The Eki enhancer sequence is amplified from Dr. Neuberger's vector (identification #Me123) using oligonucleotides GACTACGAATTCtcctgaggacacagtgatag (SEQ ID NO: 322) and GTAGTCGCGGCCGCCTAGTTCCTAGCTACTTCTTTA (SEQ ID NO: 323), which encode an EcoRI and NotI restriction site, respectively. Resulting fragments are digested with the appropriate restriction enzyme, and cloned sequentially into mcs2 (described in below): Ek3' is cloned into the XhoI and EcoRI sites of mcs2, and the resulting plasmid is then digested with EcoRI plus NotI into which the Eki fragment is subsequently ligated to generate vector AB156.

As described above, E boxes are known to be present in the kappa enhancer region. Consequently, a synthetic cassette consisting of 3 tandemly arrayed E boxes is synthesized using the complementary oligonucleotides AATTCaggtgctggggtagggagcaggtgctacactgcagaccaggtgctGC (SEQ ID NO: 324) and ggccgcagcacctggtctgcagtgtagcacctgctccctaccccagcacctg (SEQ ID NO: 325), which when annealed contain EcoRI and NotI overhangs. The annealed oligo product is thus cloned into the EcoRI and NotI sites of mcs2 to generate vector AB157.

A representative Ig-kappa locus 3' enhancer element is listed below. (Accession number X15878)

(SEQ ID NO: 326)
```
CCAGCTTAGGCTACACAGAGAAACTATCTAAAAAATAATTACTAACTACTTAATAGGAGATTGGATGTTAA

GATCTGGTCACTAAGAGGCAGAATTGAGATTCGAAGCCAGTATTTTCTACCTGGTATGTTTTAAATTGCAGT

AAGGATCTAAGTGTAGATATATAATAATAAGATTCTATTGATCTCTGCAACAACAGAGAGTGTTAGATTTG

TTTGGAAAAAAATATTATCAGCCAACATCTTCTACCATTTCAGTATAGCACAGAGTACCCACCCATATCTCC

CCACCCATCCCCCATACCAGACTGGTTATTGATTTTCATGGTGACTGGCCTGAGAAGATTAAAAAAAGTAA

TGCTACCTTATTGGGAGTGTCCCATGGACCAAGATAGCAACTGTCATAGCTACCGTCACACTGCTTTGATCA

AGAAGACCCTTTGAGGAACTGAAAACAGAACCTTAGGCACATCTGTTGCTTTCGCTCCCATCCTCCTCCAA

CAGCCTGGGTGGTGCACTCCACACCCTTTCAAGTTTCCAAAGCCTCATACACCTGCTCCCTACCCCAGCACC

TGGCCAAGGCTGTATCCAGCACTGGGATGAAAATGATACCCCACCTCCATCTTGTTTGATATTACTCTATCT

CAAGCCCCAGGTTAGTCCCCAGTCCCAATGCTTTTGCACAGTCAAAACTCAACTTGGAATAATCAGTATCC

TTGAAGAGTTCTGATATGGTCACTGGGCCCATATACCATGTAAGACATGTGG.
```

A representative Kappa intronic enhancer region, Eki is presented below:

```
                                                         (SEQ ID NO: 327)
TCCTGAGGACACAGTGATAGGAACAGAGCCACTAATCTGAAGAGAACAGAGATGTGACAGACTACACTAA

TGTGAGAAAAACAAGGAAAGGGTGACTTATTGGAGATTTCAGAAATAAAATGCATTTATTATTATATTCCC

TTATTTTAATTTTCTATTAGGGAATTAGAAAGGGCATAAACTGCTTTATCCAGTGTTATATTAAAAGCTTAA

TGTATATAATCTTTTAGAGGTAAAATCTACAGCCAGCAAAAGTCATGGTAAATATTCTTTGACTGAACTCTC

ACTAAACTCCTCTAAATTATATGTCATATTAACTGGTTAAATTAATATAAATTTGTGACATGACCTTAACTG

GTTAGGTAGGATATTTTTCTTCATGCAAAAATATGACTAATAATAATTTAGCACAAAAATATTTCCCAATAC

TTTAATTCTGTGATAGAAAAATGTTTAACTCAGCTACTATAATCCCATAATTTTGAAAACTATTTATTAGCT

TTTGTGTTTGACCCTTCCCTAGCCAAAGGCAACTATTTAAGGACCCTTTAAAACTCTTGAAACTACTTTAGA

GTCATTAAGTTATTTAACCACTTTTAATTACTTTAAAATGATGTCAATTCCCTTTTAACTATTAATTTATTTT

AAGGGGGGAAAGGCTGCTCATAATTCTATTGTTTTTCTTGGTAAAGAACTCTCAGTTTTCGTTTTTACTACC

TCTGTCACCCAAGAGTTGGCATCTCAACAGAGGGGACTTTCCGAGAGGCCATCTGGCAGTTGCTTAAGATC

AGAAGTGAAGTCTGCCAGTTCCTCCCAGGCAGGTGGCCCAGATTACAGTTGACCTGTTCTGGTGTGGCTAA

AAATTGTCCCATGTGGTTACAAACCATTAGACCAGGGTCTGATGAATTGCTCAGAATATTTCTGGACACCC

AAATACAGACCCTGGCTTAAGGCCCTGTCCATACAGTAGGTTTAGCTTGGCTACACCAAAGGAAGCCATAC

AGAGGCTAATACCAGAGTATTCTTGGAAGAGACAGGAGAAAATGAAAGCCAGTTTCTGCTCTTACCTTATG

TGCTTGTGTTCAGACTCCCAAACATCAGGAGTGTCAGATAAACTGGTCTGAATCTCTGTCTGAAGCATGGA

ACTGAAAAGAATGTAGTTTCAGGGAAGAAAGGCAATAGAAGGAAGCCTGAGAATATCTTCAAAGGGTCAG

ACTCAATTTACTTTCTAAAGAAGTAGCTAGGAACTAG.
```

Vector construction is described in priority U.S. application No. 60/902,414.

Example 4

Identification of Representative Human Scaffold Antibody Variable Domains

To identify the germline variable antibody domains that are used most often in the generation of mature antibodies during the process of recombination, SHM, and selection, 850 antibody heavy and light chain sequences available from the PDB database to the 39λ light chains, 44 κ light chains, and 55 heavy chains germline variable domain sequences are compared.

In addition, a similar comparison is made to 21,000 Genbank Human (www.ncbi.nih.gov/genbank) IgG heavy and light chain sequences. Using the PDB database as a source for comparison has several advantages: it contains antibodies bound almost entirely to peptides and proteins, many to proteins of therapeutic interest, most of the bound antibodies bind with high-affinity to their targets, and antibody sequences are derived from many sources and libraries. Mapping variable domains to Genbank sequences provides a statistically significant analysis of the commonly used germline sequence.

Variable domain template identification is conducted by creating cladograms for each of the three variable domain isoform classes using the phylip 3.65 ProtMLK program ("Numerical methods for inferring evolutionary trees." *Quarterly Review of Biology* 57:379-404). This program implements the maximum likelihood method for protein amino acid sequences under the constraint that the trees estimated must be consistent with a molecular clock, the assumption that the tips of the tree are all equidistant, in branch length, from its root. It uses the Dayhoff probability model of change between amino acids with the following assumptions: a) each position in the sequence evolves independently; b) different lineages evolve independently; c) each position undergoes substitution at an expected rate which is chosen from a series of specified rates (each with a probability of occurrence); d) all relevant positions are included in the sequence, not just those that have changed or those that are "phylogenetically informative"; and e) the probabilities of change between amino acids are given by the model of Jones, Taylor, and Thornton (1992), the PMB model of Veerassamy, Smith and Tillier (2003), or the PAM model of Dayhoff (Dayhoff and Eck, 1968; Dayhoff et. al., 1979).

In addition, each of the germline variable domains are evaluated to determine how frequently each germline variable domain was the likely antecedent for a mature antibody observed in a sequence or structural database. Presumably, each of these variable domains contributes differentially to the binding distinct antigen classes (proteins, haptens, polysaccharides, etc). Understanding which variable sequences contribute commonly to binding proteins targets and incorporating these variable template regions provides for the creation of a functionally enriched antibody library.

Figure 20A:
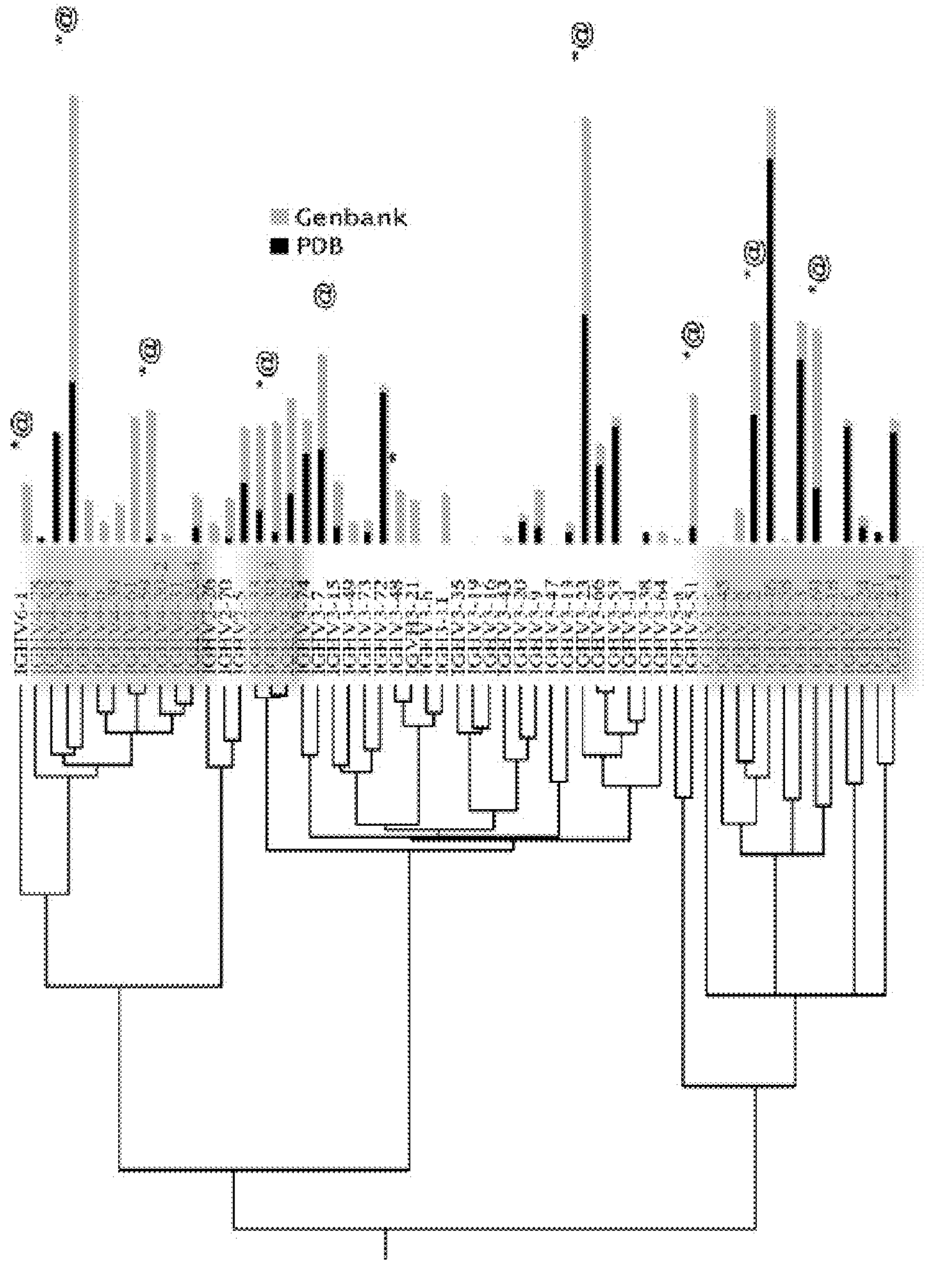
FIG. 20—Shows the frequency with which various immunoglobulin heavy variable (IgVH) genes are found in the Genbank and PDB databases (20A).
FIGS. 20B and 20C provide the same data for the kappa and lambda light chain variable regions, respectively.

This comparison demonstrated that the variable regions for the λ light chains, κ light chains, and heavy chain isoforms segregate into a small number of highly related sub-clades. It is observed (FIGS. 20(A), (B) and (C),) that certain members of these sub-clades contribute many times to antibodies found in the PDB and Genbank databases, whereas other germline variable regions are seldom observed to contribute. For instance, variable domains IGLV4-IGLV11 are not observed to contribute to antibody sequences from the PDB and rarely in Genbank, whereas usage of IGLV1-IGLV3 variable domains account for almost all mature antibody sequences containing a IGL light chain.

Figure 20B:
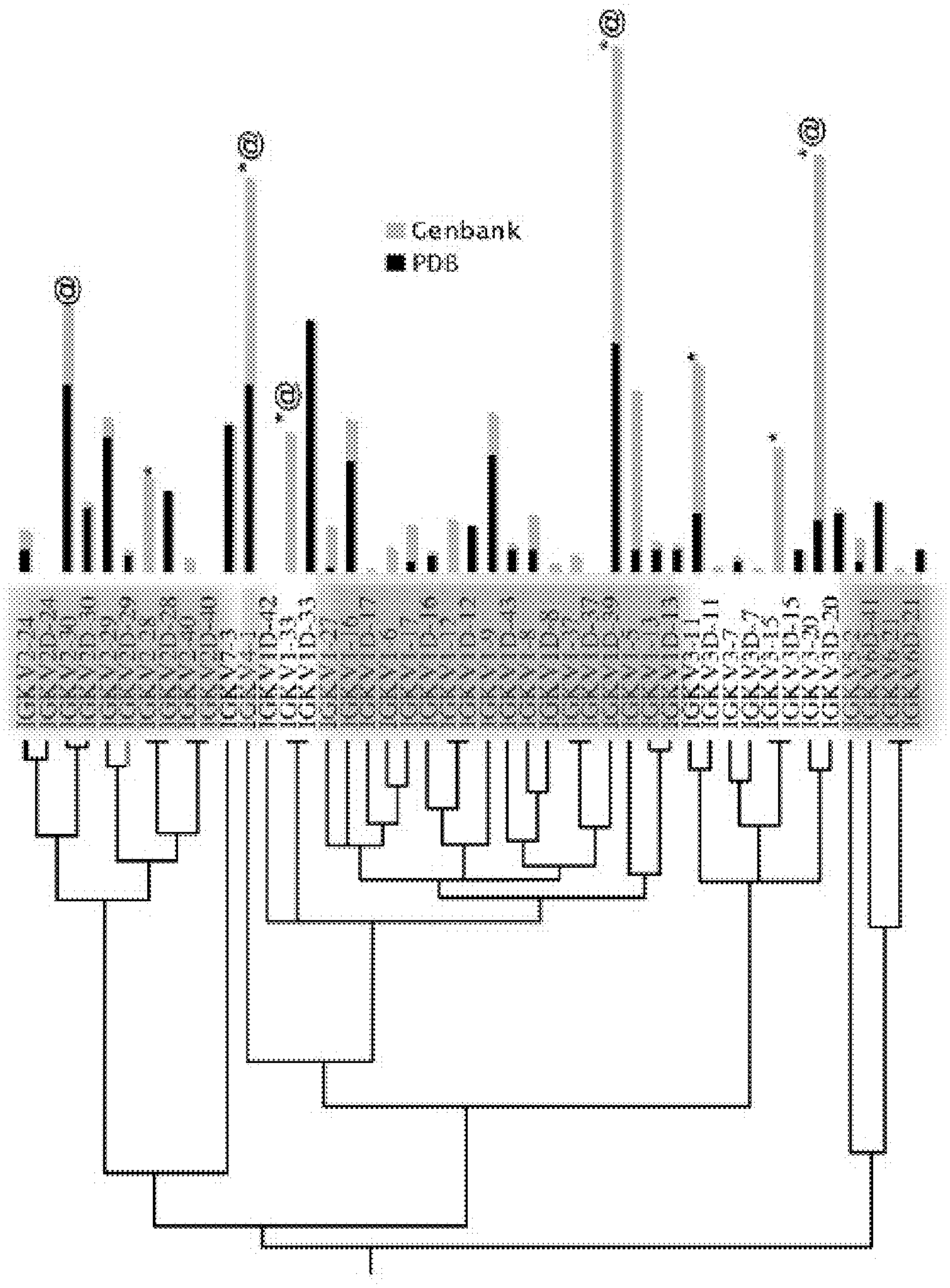
Figure 20C:
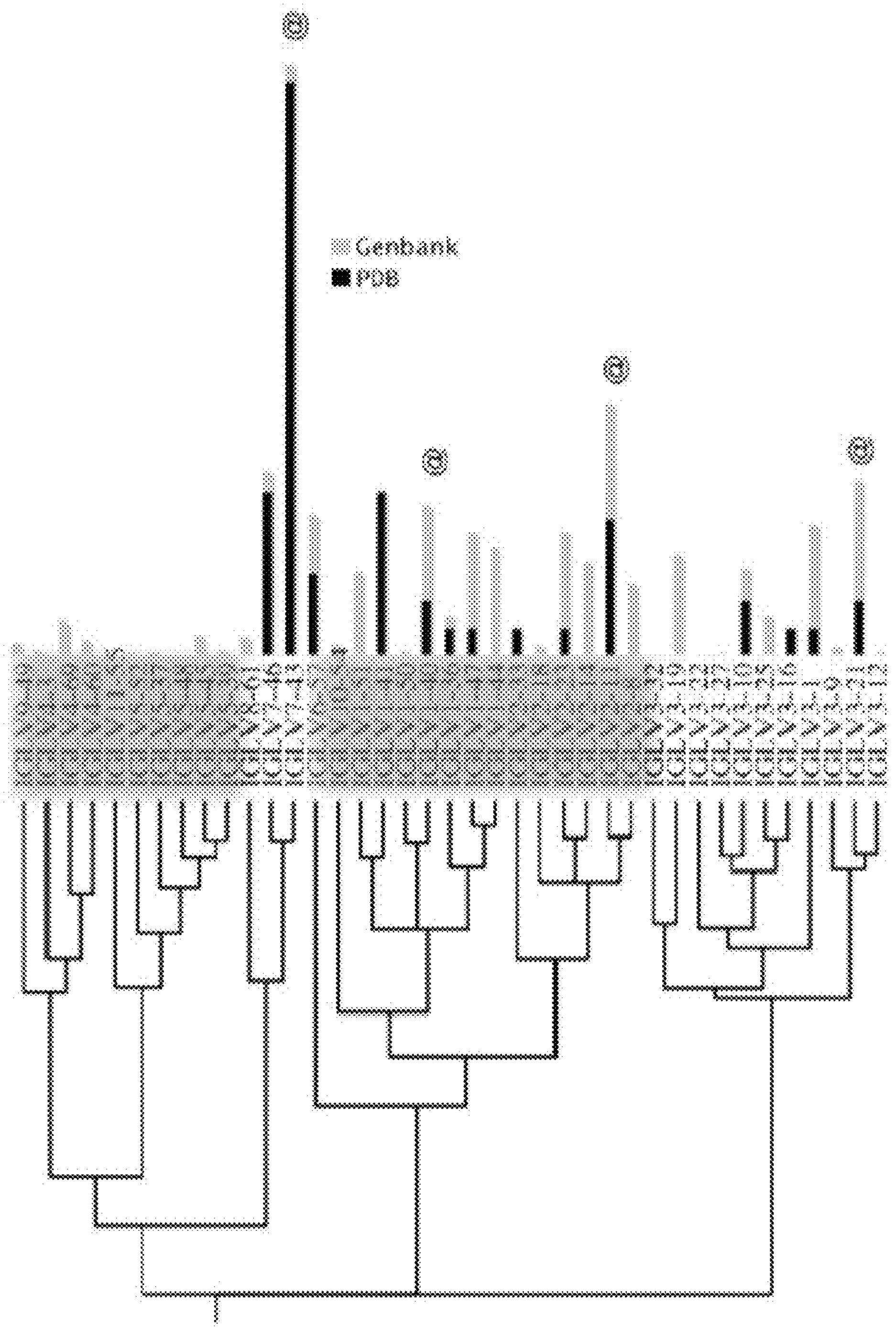

Eighteen germline variable sequences are identified that represent most λ, κ, and H sub-clades and that are used often in the generation of mature antibodies during the process of recombination, SHM, selection. In FIG. 20, the heavy chain, κ light chain, and λ light chain isoform variable domain cladograms and frequency distributions for germline usage are shown, with an @ highlighting those members chosen for use as a variable region template for the semi-synthetic antibody libraries described herein. Table 11 lists the selected template variable regions that are identified for synthesis as described below. While we have selected a set of highly used and represented variable template regions for constructing the library, the minor differences between members of different variable regions and the ability of antibodies to employ different variable regions to recognize the same epitope, suggest that one might also use other germline variable regions, subsets of those regions chosen in Table 11, or some combination of both as templates for the antibody library described herein.

For example, Heavy Chains IGHV4-55, IGHV4-61, IGHV2-5, IGHV3-30, IGHV3-74, IGHV3-72, IGHV3-66, IGHV3-53, IGHV1-46 and IGHV7.4-1; Kappa Light Chains IGKV2.24, IGKV2D-30, IGKV2.29, IGKV2.28. IGKV7-3, IGKV1D-33, IGKV1-9 and IGKV6D-41; and Lambda Light Chains IGLV4-69, IGLV6-57, IGLV1-41, IGKV1-47, IGLV2-23, IGLV3-1 and IGLV3-10.

TABLE 11

Template Variable Regions Identified for the Semi-Synthetic Antibody Libraries

| Heavy Chains Isoform IGHV | Kappa Light Chains Isoform IGKV<br>Most preferred | Lambda Light Chains Isoform IGLV |
|---|---|---|
| IGHV6-1 | IGKV4-1 | IGLV2-11 |
| IGHV3-30 | IGKV3-20 | IGLV1-40 |
| IGHV4-34 | IGKV2D-30 | IGLV3-21 |
| IGHV3-7 | IGKV1D-39 | IGLV7-43 |
| IGHV4-59 | IGKV1-33 | |
| IGHV3-23 | | |
| IGHV5-51 | | |
| IGHV1-69 | | |
| IGHV1-2 | | |

Example 5

Synthesis and Cloning of Human Scaffold Antibody Variable Domains

The amino acid sequences and NCBI Entrez Gene IDs of the 9 variable region scaffolds chosen for use in the construction of the initial heavy chain library repertoire, the 5 variable region scaffolds chosen for use in the construction of kappa light chain library repertoire, and the 4 variable region scaffolds chosen for use in the construction of the lambda light chain library repertoire are shown in Table 12, below. The gene identifier Entrez Gene ID can be found at www.ncbi.nlm.nih.gov/entrez/query.fcgi?CMD=search&DB=gene.

TABLE 12

Variable Region Scaffolds

| Variable Region Name | NCBI Entrez Gene ID | Amino acid sequence |
|---|---|---|
| IGHV6-1 (H1) | 28385 | MSVSFLIFLPVLGLPWGVLSQVQLQQSGPGLVKPSQTLSLTCAISGDS VSSNSAAWNWIRQSPSRGLEWLGRTYYRSKWYNDYAVSVKSRITIN PDTSKNQFSLQLNSVTPEDTAVYYCAR (SEQ ID NO: 328) |
| IGHV4-34 (H2) | 28395 | MKHLWFFLLLVAAPRWVLSQVQLQQWGAGLLKPSETLSLTCAVYG GSFSGYYWSWIRQPPGKGLEWIGEINHSGSTNYNPSLKSRVTISVDTS KNQFSLKLSSVTAADTAV (SEQ ID NO: 329) |
| IGHV4-59 (H3) | 28392 | MKHLWFFLLLVAAPRWVLSQVQLQESGPGLVKPSETLSLTCTVSGG SISSYYWSWIRQPPGKGLEWIGYIYYSGSTNYNPSLKSRVTISVDTSK NQFSLKLSSVTAADTAV (SEQ ID NO: 330) |
| IGHV3-30-3 (H4) | 57290 | MEFGLSWVFLVALLRGVQCQVQLVESGGGVVQPGRSLRLSCAASGF TFSSYAMHWVRQAPGKGLEWVAVISYDGSNKYYADSVKGRFTISRD NSKNTLYLQMNSLRAEDTAV (SEQ ID NO: 331) |
| IGHV3-7 (H5) | 28452 | MELGLSWVFLVAILEGVQCEVQLVESGGGLVQPGGSLRLSCAASGF TFSSYWMSWVRQAPGKGLEWVANIKQDGSEKYYVDSVKGRFTISR DNAKNSLYLQMNSLRAEDTAV (SEQ ID NO: 332) |
| IGHV3-23 (H6) | 28442 | MEFGLSWLFLVAKIKGVQCEVQLLESGGGLVQPGGSLRLSCAASGFT FSSYAMSWVRQAPGKGLEWVSAISGSGGSTYYADSVKGRFTISRDN SKNTLYLQMNSLRAEDTAV (SEQ ID NO: 333) |
| IGHV5-51 (H7) | 28388 | MGSTAILALLLAVLQGVCSEVQLVQSGAEVKKPGESLKISCKGSGYS FTSYWIGWVRQMPGKGLEWMGIIYPGDSDTRYSPSFQGQVTISADKS ISTAYLQWSSLKASDTAV (SEQ ID NO: 334) |
| IGHV1-2 (H8) | 28474 | MDWTWRILFLVAAATGAHSQVQLVQSGAEVKKPGASVKVSCKASG YTFTGYYMHWVRQAPGQGLEWMGRINPNSGGTNYAQKFQGRVTST RDTSISTAYMELSRLRSDDTAV (SEQ ID NO: 335) |

TABLE 12-continued

| Variable Region Scaffolds | | |
|---|---|---|
| Variable Region Name | NCBI Entrez Gene ID | Amino acid sequence |
| IGHV1-69 (H9) | 28461 | MDWTWRFLFVVAAATGVQSQVQLVQSGAEVKKPGSSVKVSCKASG GTFSSYAISWVRQAPGQGLEWMGGIIPIFGTANYAQKFQGRVTITAD ESTSTAYMELSSLRSEDTAV (SEQ ID NO: 336) |
| IGKV2-30 (K1) | 28919 | MRLPAQLLGLLMLWVPGSSGDVVMTQSPLSLPVTLGQPASISCRSSQ SLVYSDGNTYLNWFQQRPGQSPRRLIYKVSNWDSGVPDRFSGSGSG TDFTLKISRVEAEDVAVY (SEQ ID NO: 337) |
| IGKV4-1 (K2) | 28908 | MVLQTQVFISLLLWISGAYGDIVMTQSPDSLAVSLGERATINCKSSQS VLYSSNNKNYLAWYQQKPGQPPKLLIYWASTRESGVPDRFSGSGSG TDFTLTISSLQAEDVAVY (SEQ ID NO: 338) |
| IGKV1-33 (K3) | 28933 | MDMRVPAQLLGLLQLWLSGARCDIQMTQSPSSLSASVGDRVTITCQ ASQDISNYLNWYQQKPGKAPKLLIYDASNLETGVPSRFSGSGSGTDF TFTISSLQPEDIAVY (SEQ ID NO: 339) |
| IGKV1D-39 (K4) | 28893 | MDMRVPAQLLGLLLLWLRGARCDIQMTQSPSSLSASVGDRVTITCR ASQSISSYLNWYQQKPGKAPKLLIYAASSLQSGVPSRFSGSGSGTDFT LTISSLQPEDFAVY (SEQ ID NO: 340) |
| IGKV3-20 (K5) | 28912 | METPAQLLFLLLLWLPDTTGEIVLTQSPGTLSLSPGERATLSCRASQS VSSSYLAWYQQKPGQAPRLLIYGASSRATGIPDRFSGSGSGTDFTLTI SRLEPEDFAVY (SEQ ID NO: 341) |
| IGLV7-43 (L1) | 28776 | MAWTPLFLFLLTCCPGSNSQTVVTQEPSLTVSPGGTVTLTCASSTGA VTSGYYPNWFQQKPGQAPRALIYSTSNKHSWTPARFSGSLLGGKAA LTLSGVQPEDEA (SEQ ID NO: 342) |
| IGLV1-40 (L2) | 28825 | MAWSPLLLTLLAHCTGSWAQSVLTQPPSVSGAPGQRVTISCTGSSSNI GAGYDVHWYQQLPGTAPKLLIYGNSNRPSGVPDRFSGSKSGTSASL AITGLQAEDEA (SEQ ID NO: 343) |
| IGLV2-11 (L3) | 28816 | MAWSPLLLTLLAHCTGSWAQSALTQPRSVSGSPGQSVTISCTGTSSD VGGYNYVSWYQQHPGKAPKLMIYDVSKRPSGVPDRFSGSKSGNTAS LTISGLQAEDEA (SEQ ID NO: 344) |
| IGLV3-21 (L4) | 28796 | MAWTVLLLGLLSHCTGSVTSYVLTQPPSVSVAPGKTARITCGGNNIG SKSVHWYQQKPGQAPVLVIYYDSDRPSGIPERFSGSNSGNTATLTISR VEAEDEA (SEQ ID NO: 345) |

TABLE 13

| Constant Region Scaffolds | | |
|---|---|---|
| Constant Region Name | Genbank accession no. | Amino acid sequence |
| The human IgG1 heavy chain constant region | AAH53984. | LAPSSKSTSGGTAALGCLVKDYFPEPVTVSWNSGALTSGVHTFP AVLQSSGLYSLSSVVTVPSSSLGTQTYICNVNHKPSNTKVDKKVE PKSCDKTHTCPPCPAPELLGGPSVFLFPPKPKDTLMISRTPEVTCV VVDVSHEDPEVKFNWYVDGVEVHNAKTKPREEQYNSTYRVVS VLTVLHQDWLNGKEYKCKVSNKALPAPIEKTISKAKGQPREPQV YTLPPSRDELTKNQVSLTCLVKGFYPSDIAVEWESNGQPENNYK TTPPVLDSDGSFFLYSKLTVDKSRWQQGNVFSCSVMHEALHNH YTQKSLSLSPGK* (SEQ ID NO: 346) |
| The human Ig kappa constant region (IGKC) | AAH93097, or AAI10395 | QLKSGTASVVCLLNNFYPREAKVQWKVDNALQSGNSQESVTEQ DSKDSTYSLSSTLTLSKADYEKHKVYACEVTHQGLSSPVTKSFN RGEC* (SEQ ID NO: 347) |
| The human Ig lambda constant region (IGLC) | CAA40957, S25755, S25740 or CAA40942 | TLFPPSSEELQANKATLVCLISDFYPGAVTVAWKADSSPVKAGV ETTTPSKQSNNKYAASSYLSLTPEQWKSHKSYSCQVTHEGSTVE KTVAPTECS* (SEQ ID NO: 348) |

TABLE 13-continued

| Constant Region Scaffolds | | |
|---|---|---|
| Constant Region Name | Genbank accession no. | Amino acid sequence |
| The H2kk peritransmembrane, transmembrane and cytoplasmic domains | AK153419 | LEPPPSTVSNMATVAVLVVLGAAIVTGAVVAFVMKMRRRNTGG KGGDYALAPGSQTSDLSLPDCKVMVHDPHSLA* (SEQ ID NO: 349) |

A sequence encoding the H2kk peritransmembrane, transmembrane and cytoplasmic domains was appended to the human IgG1 heavy chain constant region (not including the stop codon) to generate a chimeric immunoglobulin gene. The resulting chimeric protein encodes an IgG1 immunoglobulin molecule that is retained on the cell surface.

The H2kk transmembrane domain sequence can be modified via the insertion of flanking LoxP sites (as indicated below) to create a construct which converts a surface-expressed antibody into a secreted antibody upon the regulated expression of cre recombinase. In the nucleic acid sequence below (SEQ ID NO: 451), the C-terminal portion of constant domain of the IgG heavy chain is shown, indicating the locations of the 2 loxP sites (underlined) flanking the H2kk transmembrane domain (capital letters). Relevant restriction sites are boxed.

GCTAGCaccctcctccaagagcacctctgggggcacagcggccctgggctgcctggtcaaggactacttccccgaacctgtgacggtgtcgtggaactcaggcgccctg accagcggcgtgcacaccttcccggctgtcctacagtcctcaggactctactccctcagcagcgtggtgacagtgccctccagcagcttgggcacccagacctacatctgcaac gtgaatcacaagcccagcaacaccaaggtggacaagaaagttgagcccaaatcttgtgacaaaactcacacatgcccaccgtgcccagcacctgaactcctggggggaccgt cagtcttcctcttccccccaaaacccaaggacaccctcatgatctcccggacccctgaggtcacatgcgtggtggtggacgtgagccacgaggaccctgaggtcaagttcaact ggtacgtggacggcgtggaggtgcataatgccaagacaaagccgcgggaggagcagtacaacagcacgtaccgggtggtcagcgtcctcaccgtcctgcaccaggactgg ctgaatggcaaggagtacaagtgcaaggtctccaacaaagccctcccagcccccatcgagaaaaccatctccaaagccaaagggcagccccgagaaccacaggtgtacacc ctgcccccatcccgggatgagctgaccaagaaccaggtcagcctgacctgcctggtcaaaggcttctatcccagcgacatcgccgtggagtgggagagcaatgggcagccg gagaacaactacaagaccacgcctcccgtgctggactccgacggctccttcttcctctacagcaagctcaccgtggacaagagcaggtggcagcaggggaacgtcttctcatg ctccgtgatgcatgaggctctgcacaaccactacacgcagaagagcctctccctgtctccgggtaaactcGAGATAACTTCGTATAGCATACATTATA CGAAGTTATctCCTCCTCCATCCACTGTCTCCAACATGGCGACCGTTGCTGTTCTGGTTGTCCTTGGAGCTGC

AATAGTCACTGGAGCTGTGGTGGCTTTTGTGATGAAGATGAGAAGGAGAAACACAGGTGGAAAAGGAGGG

GACTATGCTCTGGCTCCAGGCTCCCAGACCTCTGATCTGTCTCTCCCAGATTGTAAAGTGATGGTTCATGAC

CCTCATTCTCTAGCGTGACTCGAGTGAataacttcgtataATGTATGCtatacgaagttatGGCCGGCCAGAATTCGGCGCG

CC (SEQ ID NO: 451)

Corresponding amino acid sequence for the modified loxP modified transmembrane domain is shown below. LoxP sites are shown underlined; sequence after the stop codon (*) is not shown.

(SEQ ID NO: 452)

. . . LAPSSKSTSGGTAALGCLVKDYFPEPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTLMISRTPEVTCVVVDVSHEDPEVKFN

WYVDGVEVHNAKTKPREEQYNSTYRVVSVLTVLHQDWLNGKEYKCKVSNKALPAPIEKTISKAKGQPREPQV

YTLPPSRDELTKNQVSLTCLVKGFYPSDIAVEWESNGQPENNYKTTPPVLDSDGSFFLYSKLTVDKSRWQQGNV

FSCSVMHEALHNHYTQKSLSLSPGKLEITSYSIHYTKLSPPPSTVSNMATVAVLVVLGA*

Expression of cre recombinase in the cell leads to the recombination and loss of the transmembrane domain resulting in the in situ creation of a secreted form of the protein in the transfected cell population which can then used for further studies.

Cre recombinase (Accession numbers: P06956, AAY72404, and YP_006472)

(SEQ ID NO: 453)

```
MSNLLTVHQNLPALPVDATSDEVRKNLMDMFRDRQAFSEHTWKMLLSV

CRSWAAWCKLNNRKWFPAEPEDVRDYLLYLQARGLAVKTIQQHLGQLN

MLHRRSGLPRPSDSNAVSLVMRRIRKENVDAGERAKQALAFERTDFDQ

VRSLMENSDRCQDIRNLAFLGIAYNTLLRIAEIARIRVKDISRTDGGR

MLIHIGRTKTLVSTAGVEKALSLGVTKLVERWISVSGVADDPNNYLFC

RVRKNGVAAPSATSQLSTRALEGIFEATHRLIYGAKDDSGQRYLAWSG

HSARVGAARDMARAGVSIPEIMQAGGWTNVNIVMNYIRNLDSETGAMV

RLLEDGD
```

Accession number. NC_005856 (from YP_006472).

(SEQ ID NO: 454)

```
atgtccaatttactgaccgtacaccaaaatttgcctgcattaccggt

cgatgcaacgagtgatgaggttcgcaagaacctgatggacatgttca

gggatcgccaggcgttttctgagcatacctggaaaatgcttctgtcc

gtttgccggtcgtgggcggcatggtgcaagttgaataaccggaaatg

gtttcccgcagaacctgaagatgttcgcgattatcttctatatcttc

aggcgcgcggtctggcagtaaaaactatccagcaacatttgggccag

ctaaacatgcttcatcgtcggtccgggctgccacgaccaagtgacag

caatgctgtttcactggttatgcggcggatccgaaaagaaaacgttg

atgccggtgaacgtgcaaaacaggctctagcgttcgaacgcactgat

ttcgaccaggttcgttcactcatggaaaatagcgatcgctgccagga

tatacgtaatctggcatttctggggattgcttataacaccctgttac

gtatagccgaaattgccaggatcagggttaaagatatctcacgtact

gacggtgggagaatgttaatccatattggcagaacgaaaacgctggt

tagcaccgcaggtgtagagaaggcacttagcctgggggtaactaaac
```

-continued

```
tggtcgagcgatggatttccgtctctggtgtagctgatgatccgaat

aactacctgttttgccgggtcagaaaaaatggtgttgccgcgccatc

tgccaccagccagctatcaactcgcgccctggaagggattttgaag

caactcatcgattgatttacggcgctaaggatgactctggtcagaga

tacctggcctggtctggacacagtgcccgtgtcggagccgcgcgaga

tatggcccgcgctggagtttcaataccggagatcatgcaagctggtg

gctggaccaatgtaaatattgtcatgaactatatccgtaacctggat

agtgaaacaggggcaatggtgcgcctgctggaagatggcgattag.
```

The corresponding nucleic acid sequences corresponding to these genes, set forth below, are made by DNA 2.0 (Menlo Park, Calif.), and correct synthesis is confirmed by sequence analysis.

The nucleic acid clones are provided in DNA2.0 vectors (i.e. pJ31 or pJ51), which are devoid of most 6 bp restriction endonuclease recognition sites. For the purposes of the construction of the immunoglobulin library, suitable vectors must not include any of the following restriction sites: AclI (AACGTT; SEQ ID NO: 350), AscI (GGCGCGCC; SEQ ID NO: 351), BbsI (GAAGAC [SEQ ID NO: 352]; GTCTTC [SEQ ID NO: 353]), BsmBI (CGTCTC [SEQ ID NO: 354]; GAGACG [SEQ ID NO: 355]), EagI (CGGCCG; SEQ ID NO: 356), FseI (GGCCGGCC; SEQ ID NO: 357), MfeI (CAATTG; SEQ ID NO: 358), NheI (GCTAGC; SEQ ID NO: 359), SbfI (CCTGCAGG; SEQ ID NO: 360), SgrAI (CRCCGGYG; SEQ ID NO: 361).

The poly nucleotides sequences of the heavy chain variable domain scaffolds used for the construction of one embodiment of the polynucleotide libraries of the invention are provided below. In these sequences, the following landmarks for the heavy chain sequences are:

SgrAI boxed sequence; Kozak, unboxed capital letters; IGHV, small letters; EagI boxed capital letters; initial small stuffer for CDR3 (underlined small letters); NheI boxed capital letters; IgG1 constant region, small letters; XhoI, boxed capital letters; transmembrane domain and cytoplasmic tail, unboxed capital letters; AscI cloning site, boxed capital letters.

Heavy Chain Variable Regions

Sequence H1; SEQ ID NO: 362. IgHV1-2-stuffer region-IgG1 constant—H2kk peritransmembrane, transmembrane and cytoplasmic domains. (1570 bp) (Vh1). Landmark restriction sites are shown in boxed letters. (The stuffer region, shown in underlined small letters, was replaced by bona fide CDR3 region sequences obtained by PCR of human peripheral blood lymphocyte RNA.)

CACCGGTGCCACCATGgactggacctggaggatcctcctcctggtggcagcagccacaggagcccactcccaggttcagctggtgcagtctggggctgaggtg aagaagcctggggcctcagtgaaggtctcctgcaaggcttctggatacaccttcaccggctactatatgcactgggttcgacaggcccctggacaagggcttgagtggatggga cggatcaaccctaacagtggtggcacaaactatgcacagaagtacagggcagagttaccagtaccagggacacgtccatcagcacagcctacatggaactaagcaggctga gatcagacgacaCGGCCGtgtattactgtgcagaGCTAGCaccctcctccaagagcacctctgggggcacagcggcctgggctgcctggtcaaggactacttccc cgaacctgtgacggtgtcgtggaactcaggcgccctgaccagcggcgtgcacaccttcccggctgtcctacagtcctcaggactctactccctcagcagcgtggtgacagtgc cctccagcagcttgggcacccagacctacatctgcaacgtgaatcacaagcccagcaacaccaaggtggacaagaaagttgagcccaaatcttgtgacaaaactcacacatgc ccaccgtgcccagcacctgaactcctggggggaccgtcagtcttcctcttccccccaaaacccaaggacaccctcatgatctcccggaccccctgaggtcacatgcgtggtggtg gacgtgagccacgaggaccctgaggtcaagttcaactggtacgtggacggcgtggaggtgcataatgccaagacaaagccgcgggaggagcagtacaacagcacgtaccg -continued ggtggtcagcgtcctcaccgtcctgcaccaggactggctgaatggcaaggagtacaagtgcaaggtctccaacaaagccctcccagcccccatcgagaaaaccatctccaaa
gccaaagggcagccccgagaaccacaggtgtacaccctgcccccatcccgggatgagctgaccaagaaccaggtcagcctgacctgcctggtcaaaggcttctatcccagc
gacatcgccgtggagtgggagagcaatgggcagccggagaacaactacaagaccacgcctcccgtgctggactccgacggctccttcttcctctacagcaagctcaccgtgg
acaagagcaggtggcaggggaacgtcttctcatgctccgtgatgcatgaggctctgcacaaccactacacgcagaagagcctctccctgtctccgggtaactcGAG
CCTCCTCCATCCACTGTCTCCAACATGGCGACCGTTGCTGTTCTGGTTGTCCTTGGAGCTGCAATAGTCACTGGAGCTGTG
GTGGCTTTTGTGATGAAGATGAGAAGGAGAAACACAGGTGGAAAAGGAGGGGACTATGCTCTGGCTCCAGGCTCCCAGACC
TCTGATCTGTCTCTCCCAGATTGTAAAGTGATGGTTCATGACCCTCATTCTCTAGCGTGAggccggccaaggcgcgcc Sequence H2; SEQ ID NO: 363. IGHV1-69 (347 bp) (Vh2)

CACCGGTGCCACCATGgactggacctggaggttcctctttgtggtggcagcagctacaggtgtccagtcccaggtgcagctggttcagtctggggctgaggtga
agaagcctgggtcctcggtgaaggtctcctgcaaggcttctggaggcaccttcagcagctatgctatcagctgggtgcgacaggcccctggacaagggcttgagtggatggga
gggatcatccctatctttggtacagcaaactacgcacagaagttccagggcagagtcacgattaccgctgacgaatccacgagcacagcctacatggaactaagcagcctgag
atcagaggacaCGGCCG Sequence H3; SEQ ID NO: 364. IGHV3-7 (347 bp) (Vh3)

CACCGGTGCCACCATGgaattgggactaagctgggttttccttgttgctattttagaaggtgtccagtgtgaggtgcagctggtggagtctgggggaggcttggtcc
agcctggggggtccctgagactctcctgtgcagcctctggattcacctttagtagctattggatgagctgggtccgccaggctccagggaaggggctggagtgggtggccaac
ataaagcaagatggaagtgagaaatactatgtggactctgtgaagggccgattcaccatctccagagacaacgccaagaactcactgtatctgcaaatgaacagcctgagagcc
gaggacaCGGCCG Sequence H4; SEQ ID NO: 365. IGHV3-23 (347 bp) (Vh4)

CACCGGTGCCACCATGgagtttgggctgagctggctttttcttgtggctattttaaaaggtgtccagtgtgaggtgcagctgttggagtctgggggaggcttggtaca
gcctggggggtccctgagactctcctgtgcagcctctggattcacctttagcagctatgccatgagctgggtccgccaggctccagggaaggggctggagtgggtctcagctat
tagtggtagtggtggtagcacatactacgcagactccgtgaagggccggttcaccatctccagagacaattccaagaacacgctgtatctgcaaatgaacagcctgagagccga
ggacaCGGCCG Sequence H5; SEQ ID NO: 366. IGHV3-30-3 (347 bp) (Vh5)

CACCGGTGCCACCATGgagtttggactaagctgggttttcctcgttgctcttttaagaggtgtccagtgtcaggtgcagctggtggagtctgggggaggcg
tggtccagcctgggaggtccctgagactctcctgtgcagcgtctggattcaccttcagtagctatgctatgcactgggtccgccaggctccaggcaaggggc
tggagtgggtggcagttatatcatatgatggaagcaataaatactacgcagactccgtgaagggccgattcaccatctccagagacaattccaagaacacgc
tgtatctgcaaatgaacagcctgagagctgaggacaCGGCCG Sequence H6; SEQ ID NO: 367. IGHV4-34 (344 bp) (Vh6)

CACCGGTGCCACCATGaaacacctgtggttcttcctcctcctggtggcagctcccagatgggtcctgtcccaggtgcagctacaacagtggggcgcaggact gttgaagccttcggagaccctgtccctcacctgcgctgtctatggtgggtccttcagtggttactactggagctggatccgccagcccccagggaaggggct ggagtggattggggaaatcaatcatagtggaagcaccaactacaacccgtccctcaagagtcgagtcaccatatcagtagacacgtccaagaaccagttctc cctgaagctgagttctgtgaccgctgcggacaCGGCCG Sequence H7; SEQ ID NO: 368. IGHV4-59 (344 bp) (Vh7)

CACCGGTGCCACCATGaaacatctgtggttcttccttctcctggtggcagctcccagatgggtcctgtcccaggtgcagctgcaggagtcgggcccaggact ggtgaagccttcggagaccctgtccctcacctgcactgtctctggtggctccatcagtagttactactggagctggatccggcagcccccagggaagggact ggagtggattgggtatatctattacagtgggagcaccaactacaacccctccctcaagagtcgagtcaccatatcagtagacacgtccaagaaccagttctc cctgaagctgagttctgtgaccgctgcggacaCGGCCG Sequence H8; SEQ ID NO: 369. IGHV5-51 (347 bp) (Vh8)

CACCGGTGCCACCATGgggtcaaccgccatcctcgccctcctcctggctgttctccaaggagtctgttccgaggtgcagctggttcagtctggagcagagg tgaaaaagcccggggagtctctgaaaatctcctgtaagggttctggatacagctttaccagctactggatcggctgggtgcgccagatgcccgggaaaggcc tggagtggatggggatcatctatcctggtgactctgataccagatacagcccgtccttccaaggccaagttaccatctcagccgacaagtccatcagcaccg cctacctgcagtggagcagcctgaaggcctcggacaCGGCCG Sequence H9; SEQ ID NO: 370. IGHV6-1 (359 bp) (Vh9)

CACCGGTGCCACCATGtctgtctccttcctcatcttcctgcccgtgctgggcctcccatggggtgtcctgtcacaggtacagctgcagcagtcaggtccag gactggtgaagccctcgcagaccctctcactcacctgtgccatctccggggacagtgtctctagcaacagtgctgcttggaactggatcaggcagtccccat cgagaggccttgagtggctgggaaggacatactacaggtccaagtggtataatgattatgcagtatctgtgaaaagtcgaataaccatcaacccagacacat ccaagaaccagttctccctgcagctgaactctgtgactcccgaggacaCGGCCG Kappa Variable Region Light Chains SbfI, boxed letters; Kozak consensus sequence, unboxed capital letters; IGKV4-1 variable sequences, small letters; BsmBI restriction site, boxed capital letters; small initial stuffer for cdr3, underlined small letters; MfeI restriction site, boxed capital letters; k constant region, small letters; AscI site site restriction site, boxed capital letters.

Sequence K1; SEQ ID NO: 371. IGKV4-1 (650 bp) (Vκ1)

cctgcaggCCACCATGgtgttgcagacccaggtcttcatttctctgttgctctggatctctggtgcctacggggacatcgtgatgacccagtctccagactc cctggctgtgtctctgggcgagagggccaccatcaactgcaagtccagccagagtgttttatacagctccaacaataagaactacttagcttggtaccagca gaaaccaggacagcctcctaagctgctcatttactgggcatctacccgggaatccggggtccctgaccgattcagtggcagcgggtctgggacagatttcac tctcaccatcagcagcctacaggctgaagatgtggcagtgtattaGAGACGtgtatttacCAATTGaaatctggaactgcctctgttgtgtgcctgctgaat aacttctatcccagagaggccaaagtacagtggaaggtggataacgccctccaatcgggtaactcccaggagagtgtcacagagcaggacagcaaggacagc acctacagcctcagcagcaccctgacgctgagcaaagcagactacgagaaacacaaagtctacgcctgcgaagtcacccatcagggcctcagctcgcccgtc acaaagagcttcaacaggggagagtgttgaGGCGCGCC Sequence K2; SEQ ID NO: 372. IGKV3-20 (342 bp) (Vκ2)

cctgcaggCCACCATGgaaaccccagcgcagcttctcttcctcctgctactctggctcccagataccaccggagaaattgtgttgacgcagtctccaggcac
cctgtctttgtctccaggggaaagagccaccctctcttgcagggccagtcagagtgttagcagcagctacttagcctggtaccagcagaaacctggccaggc
tcccaggctcctcatctatggtgcatccagcagggccactggcatcccagacaggttcagtggtagtgggtctgggacagacttcactctcaccatcagcag
actggagcctgaagattttgcagtgtattaGAGACG Sequence K3; SEQ ID NO: 373. IGKV2D-30 (354 bp) (Vκ3)

cctgcaggCCACCATGaggctccctgcccagctcctggggctgctaatgctctgggtcccaggatccagtggggatgttgtgatgactcagtctccactctc
cctgcccgtcacccttggacagccggcctccatctcttgcaggtctagtcaaagcctcgtatacagtgatggaaacacctacttgaattggtttcagcagag
gccaggccaatctccaaggcgcctaatttataaggtttctaactgggactctggggtcccagacagattcagcggtagtgggtcaggcactgatttcacact
gaaaatcagcagggtggaggctgaggatgttgcagtgtattaGAGACG Sequence K4; SEQ ID NO: 374. IGKV1D-39 (345 bp) (Vκ4)

cctgcaggCCACCATGgacatgagggtccccgcccagctcctggggctcctgctactctggctccgaggtgccagatgtgacatccagatgacccagtctcc
atcctccctgtctgcatctgtaggagacagagtcaccatcacttgccgggcaagtcagagcattagcagctatttaaattggtatcagcagaaaccagggaa
agcccctaagctcctgatctatgctgcatccagtttgcaaagtggggtcccatcaaggttcagtggtagtggatctgggacagatttcactctcaccatcag
cagtctgcaacctgaagattttgcagtgtattaGAGACG Sequence K5: SEQ ID NO: 375. IGKV1-33 (345 bp) (Vκ5)

cctgcaggCCACCATGgacatgagggtccctgcccagctcctggggctcctgcagctctggctctcaggtgccagatgtgacatccagatgacccagtctcc
atcctccctgtctgcatctgtaggagacagagtcaccatcacttgccaggcgagtcaggacattagcaactatttaaattggtatcagcagaaaccagggaa
agcccctaagctcctgatctacgatgcatccaatttggaaacaggggtcccatcaaggttcagtggaagtggatctgggacagattttactttcaccatcag
cagcctgcagcctgaagatattgcagtgtattaGAGACG Lambda Light Chains.

SbfI, boxed small letters; Kozak consensus sequence, unboxed capital letters; IGLV1-40 variable region, small letters; BbsI restriction site, boxed capital letters (note that this is a class II restriction site which cleaves outside of its recognition site, overhang of GGCT is indicated by underlined and bolded capital letters); small initial stuffer for cdr3, underlined small letters; AclI boxed capital letters; IGLC3 lambda constant region, small letters; AscI site Bold-underline in L1 indicates unwanted BbsI that needs to be mutated Sequence L1; SEQ ID NO: 376. IGLV1-40 (639 bp) (Vλ1)

cctgcaggCCACCATGgcctggtctcctctcctcctcactctcctcgctcactgcacagggtcctgggcccagtctgtgctgacgcagccgccctcagtgtc
tggggccccagggcagagagttaccatctcctgcactgggagcagctccaacatggggcaggttatgatgtacactggtaccagcagcttccaggaacagcc
cccaaactcctcatctatggtaacagcaatcggccctcaggggtccctgaccgattctctggctccaagtctggcacctcagcctccctggccatcactggg
ctccaggctGAAGACGAGGCTgattattaAACGTTgttcccaccctcctctgaggagcttcaagccaacaaggccacactggtgtgtctcataagtgacttc
tacccgggagccgtgacagttgcctggaaggcagatagcagccccgtcaaggcgggggtggagaccaccacaccctccaaacaaagcaacaacaagtacgcg -continued gccagcagctacctgagcctgacgcctgagcagtggaagtcccacaaaagctacagctgccaggtcacgcatgaagggagcaccgtggagaagacagttgcc cctacggaatgttcatgaGGCGCGCC Sequence L2; SEQ ID NO: 377. IGLV2-11 (329 bp) (Vλ2)

cctgcaggCCACCATGgcctggtctcctctcctcctcactctcctcgctcactgcacagggtcctgggcccagtctgccctgactcagcctcgctcagtgtcc gggtctcctggacagtcagtcaccatctcctgcactggaaccagcagtgatgttggtggttataactatgtctcctggtaccaacagcacccaggcaaagcc cccaaactcatgatttatgatgtcagtaagcggccctcaggggtccctgatcgcttctctggctccaagtcggcaacacggcctccctgaccatctctgggc tccaggctGAAGACGAGGCT

Sequence L3; SEQ ID NO: 378. IGLV3-21 (320 bp) (Vλ3)

cctgcaggCCACCATGgcctggaccgttctcctcctcggcctcctctctcactgcacaggctctgtgacctcctatgtgctgactcagccaccctcagtgtc agtggccccaggaaagacggccaggattacctgtgggggaaacaacattggaagtaaaagtgtgcactggtaccagcagaagccaggccaggcccctgtgct ggtcatctattatgatagcgaccggccctcagggatccctgagcgattctctggctccaactctgggaacacggccaccctgaccatcagcagggtcgaagc cGAAGACGAGGCT

Sequence L4; SEQ ID NO: 379. IGLV7-43 (329 bp) (Vλ4)

cctgcaggCCACCATGgcctggactcctctctttctgttcctcctcacttgctgcccagggtccaattctcagactgtggtgactcaggagccctcactgac tgtgtccccaggagggacagtcactctcacctgtgcttccagcactggagcagtcaccagtggttactatccaaactggttccagcagaaacctggacaagc acccagggcactgatttatagtacaagcaacaaacactcctggacccctgcccggttctcaggctccctccttgggggcaaagctgccctgacactgtcagg tgtgcagcctGAAGACGAGGCT

Cloning

The heavy chain, kappa light chain, and lambda light chain libraries are assembled in the vector pJ31 starting with the H1, L1 and K1 variable domains, as shown in FIG. 21. Each prototypic library contains (a) a replaceable variable region (Vh1, Vκ1, or Vλ1); (b) a small stuffer region bounded by restriction sites into which synthetic, or PCR-amplified heavy chain, κ light chain and λ light chain derived CDR3 regions are inserted; (See Examples 6, 7 and 8) and (c) the heavy chain, κ light chain and λ light chain constant regions respectively. (These cloning vectors and the overall cloning strategy are shown schematically in FIG. 21A, FIG. 21B, and FIG. 21C, respectively).

To minimize background ligation of cut vectors, a longer stiffer of 671 bp is cloned into the EagI+NheI sites of plasmid pJ31-Vh1 to generate vector pJ31-Vh1s (FIG. 21A step 2), into the BsmBI+MfeI sites of pJ31-Vκ1 to generate pJ31-Vκ1s (FIG. 21B step 7), and into the BbsI+AclI sites of pJ31-Vλ1 to generate pJ31-Vλ1s (FIG. 21C step 12).

This step facilitates the excision of double-cut vector away from any vector that might be only singly or incompletely double-cut, from a preparative agarose gel to minimize background during the CDR3 cloning step.

The sequences H2 (Vh2) through H9 (Vh9), containing heavy chain variable regions flanked by restriction sites SgrAI and EagI, are cloned in place of H1 (Vh1) in vector pJ31-Vh1s to generate constructs pJ31-Vh2s through -Vh9s (FIG. 21A step 3); Similarly variable kappa light regions K2-K5 (Vκ2-Vκ5) are cloned in place of K1 (Vκ1) to generate constructs pJ31-Vk2s through -Vκ5s (FIG. 21B step 8); and variable lambda light chains L2-L4 (Vλ2-Vλ4) are cloned in place of L1 (Vλ1) to generate constructs pJ31-Vλ2s through -Vλ4s (FIG. 21C step 13).

Thus this process creates a total of 18 intermediate cloning vectors, in which each of the 9 heavy chain scaffolds, 5 kappa light chain scaffolds and 4 lambda light chain scaffolds were inserted into the plasmid pJ31. These intermediate plasmids were then used to introduce PCR amplified CDR3, and can also be used to introduce fully synthetic CDRs as described below.

The theoretical diversity resulting from such a library construct is greatly reduced relative to that expected using all possible variable regions. In present library, a potential 11,016 (9V×204D×6J) (IGHV) heavy chains may be observed after artificial recombination and assembly. Likewise, there is a potential for 25 (5V×5J) kappa chains and 28 (4V×7J) lambda chains that might be observed. This leads, ignoring potential non-templated mutations at the domain junctions, for a total predicted complexity of 583848 members (11016H×(25K+28L)). In contrast, 67320 heavy (55V×204D×6J), 220 kappa chains (44V×5J), and 273 lambda chains (39V×7J) would be representation of the human IgG näive locus, for a total theoretical complexity of $3.318\times10^7$ members. Therefore, we have maintained the total antigen binding capability of our library, while reducing its total complexity by an estimated 56.8 fold ($3.318\times10^7$/583848), providing for robust and redundant presentation of all library members for selection.

Example 6

PCR Amplification of CDRs

Preparation of Oligonucleotide Primers Specific for the CDR3 Region

The choice of a primer's nucleotide sequence depends in general on factors such as the distance on the nucleic acid from the region coding for the desired sequence, its hybridization site on the nucleic acid relative to any second primer to be used, the number of genes in the repertoire it is to hybridize to, and the like.

Primers are designed and selected within the 3' end of the framework 3 region and the 5' end of the appropriate constant domains to enable the CDR3 regions of Ig λ, κ, and H chain isoforms to be PCR amplified. Restriction sites are chosen based on several criteria: The restriction sites must be as close as possible, but not overlap, the CDR3 regions; but should not include any known sites in the germline sequences of the D and J regions that compose the CDR3, such that digestion of the PCR product would reduce the overall diversity of the library and should be compatible with the cloning vectors to which they are to be inserted, specifically for example, the vectors described in Examples 3, 4 and 5 above; and as outlined in FIG. 21.

The diversity-enriched naturally occurring CDR3 regions are generated via PCR mediated amplification as described below:

Total RNA from seven different donors is isolated from the peripheral blood monocytes (PBMC's; AllCells, Inc., Emeryville, Calif.) and pooled.

HPLC purified oligonucleotides are ordered from Allele Biotech, (San Diego, Calif.). Total RNA is reverse transcribed using oligos H8a, H9a, K7a, L8a (as described below in Table 14) to generate amplified cDNA to IgG, IgM, Igκ and Igλ, respectively, using the Superscript 3 protocol as provided by Invitrogen Corporation (Carlsbad, Calif.).

Double-stranded cDNA copies of the highly diverse CDR3 populations are amplified by PCR using combinations of sense and antisense oligonucleotides listed below using standard PCR amplification conditions.

Heavy Chain Oligonucleotides for PCR Amplification

```
H1b.   ggaatcCGGCCGtgtattactgtgcaaga
       (heavy chain sense oligo for IGHV6-1, EagI
       site; SEQ ID NO: 380)

H2b.   ggaatcCGGCCGtgtattactgtgcgaaa
       (heavy chain sense oligo for IGHV3-30-3, EagI
       site; SEQ ID NO: 381)

H3b.   ggaatcCGGCCGtgtattactgtgcgaga
       (heavy chain sense oligo for IGHV4-34 (1
       mismatch), IGHV3-7) (1 mismatch), IGVH4-59,
       IGHV1-69, IGHV1-2, and IGHV5-51 (1 mismatch,,
       EagI site; SEQ ID NO: 382)
```

-continued

```
H4b.   ggaatcCGGCCGtatattactgtgcgaaa
       (heavy chain sense oligo for IGHV3-23, EagI
       site; SEQ ID NO: 383)

H5b.   ggaatcgGCTAGCgggaagacggatgggcccttg
       (heavy chain antisense from IgG constant,
       NheI site; SEQ ID NO: 384)

H6b.   ggaatcgGCTAGCgggaagaccgatgggcccttg
       (heavy chain antisense from IgG constant,
       NheI site; SEQ ID NO: 385)

H7b.   ggaatcgGCTAGCgggaaaagggttggggcgga
       (heavy chain antisense from IgM constant,
       NheI site; SEQ ID NO: 386)

H8a.   gaagtagtccctgaccaggc
       (reverse transcription primer for IgG;
       SEQ ID NO: 387)

H9a.   aagtcctgtgcgaggcagc
       (reverse transcription primer for IgM;
       SEQ ID NO: 388)
```

Restriction sites are shown in capital letters.

Kappa Light Chain Oligonucleotides for PCR Amplification

```
K1b.   ggaatcCGTCTCgTATtactgtcagcaatattatag
       (kappa CDR3 sense for IGKV4-1, BsmBI site;
       SEQ ID NO: 389)

K2b.   ggaatcCGTCTCgTATtactgtcagcagtatggtag
       (kappa CDR3 sense for IGKV3-20, BsmBI site;
       SEQ ID NO: 390)

K3b.   ggaatcCGTCTCgTATtactgcatgcaaggtacaca
       (kappa CDR3 sense for IGKV2D-30, BsmBI site;
       SEQ ID NO: 391)

K4b.   ggaatcCGTCTCgTATtactgtcaacagagttacag
       (kappa CDR3 sense for IGKV1D-39, BsmBI site;
       SEQ ID NO: 392)

K5b.   ggaatcCGTCTCgTATtactgtcaacagtatgataa
       (kappa CDR3, sense for IGKV1-33, BsmBI site;
       SEQ ID NO: 393)

K6b.   ggaatcCAATTGctcatcagatggcgggaag
       (kappa CDR3 antisense for all kappa light
       chains (MfeI site; SEQ ID NO: 394)

K7a.   ggcctctctgggatagaag
       (kappa CDR3 reverse transcription primer for
       IgK; SEQ ID NO: 395).
```

Lambda Light Chain Oligonucleotides for PCR Amplification

```
L1b.   ggaatcGAAGACGAGGCTgattattactgccagtcct
       (lambda CDR3 sense for IGLV1-40 with BbsI
       site; SEQ ID NO: 396)

L2b.   ggaatcGAAGACGAGGCTgattattactgctgctcat
       (lambda CDR3 sense for IGLV2-11 with BbsI
       site; SEQ ID NO: 397)

L3b.   ggaatcGAAGACGAGGCTgactattactgtcaggtgt
       (lambda CDR3 sense for IGLV3-21 with BbsI
       site; SEQ ID NO: 398)

L4b.   ggaatcGAAGACGAGGCTgagtattactgcctgctct
       (lambda CDR3 sense for IGLV7-43 with BbsI
       site; SEQ ID NO: 399)
```

-continued

```
L5b.  ggaatcAACGTTaccgtggggttggccttg
      (lambda CDR3 antisense from constant with
      AclI site; SEQ ID NO: 400)

L6b.  ggaatcAACGTTaccgagggggcagccttg
      (lambda CDR3 antisense from constant with
      AclI site; SEQ ID NO: 401)

L7b.  ggaatcAACGTTaccgatggggcagccttg
      (lambda CDR3 antisense from constant with
      AclI site; SEQ ID NO: 402)

L8a.  gctcccgggtagaagtcac
      (reverse transcription primer for lambda
      CDR3 (primers all lambda light chains);
      SEQ ID NO: 403)
```

PCR conditions are as follows:

Kappa, PCR condition A used for K2b, K3b, with K6b:

95° C.x3' for 1 cycle; then 95° C.x30," 60° C.x30," 72° C.x30," for 3 cycles; then 95° C.x30," 70° C.x30," 72° C.x30" for 30 cycles; then 72° C.x5'.

Kappa, PCR condition B used for K1b, K4b and K5b with K6b:

95° C.x3' for 1 cycle; then 95° C.x30," 55° C.x30," 72° C.x30" for 3 cycles; then 95° C.x30," 68° C.x20," 72° C.x30" for 30 cycles; then 72° C.x5'.

PCR conditions for Lambda:

95° C.x3' for 1 cycle; then 95° C.x30," 58° C.x30," 72° C.x30" for 3 cycles; then 95° C.x30," 66° C.x30," 72° C.x30" for 33 cycles; then 72° C.x5'.

PCR conditions for IgG and IgM:

95° C.x3' for 1 cycle; then 95° C.x30," 60° C.x30," 72° C.x30" for 3 cycles; then 95° C.x30," 68° C.x30," 72° C.x30" for 33 cycles; then 72° C.x5'.

The final total diversity in PCR amplified products from each of these reactions is directly related to the antibody repertoire in the human immune system, which is very great. Indeed, the bands resulting from PCR appear as a smear on agarose gels in the range of 100 to 200 bp. The ranking of thickness of the visualized bands (i.e. how heterogenous the population sizes were) was mu>gamma>kappa=lambda.

The sequence of 34 independent IgM-derived CDR3 clones that resulted from PCR using oligos H2b+H7b was obtained (data not shown). No two sequences were identical, and the insert coding size ranged from 3 to 27 amino acids.

After successful PCR amplification of the CDR3 regions, the resulting PCR products are gel purified and the restriction endonuclease digested products are ligated into the antibody heavy chain, kappa light chain and lambda light chain scaffolds in the pJ31 cloning vectors as described in Example 7 in place of the pre-existing stuffer fragments (FIG. 21A step 4, FIG. 21B step 9, and FIG. 21C step 14, respectively), as described below.

TABLE 14

| reaction # | Reverse transcription primer | oligo 1 | oligo 2 | Ig species amplified |
|---|---|---|---|---|
| 1 | H8A | H5b | H1b | IgG |
| 2 | H8A | H6b | H1b | IgG |
| 3 | H8A | H5b | H2b | IgG |
| 4 | H8A | H6b | H2b | IgG |
| 5 | H8A | H5b | H3b | IgG |
| 6 | H8A | H6b | H3b | IgG |
| 7 | H8A | H5b | H4b | IgG |
| 8 | H8A | H6b | H4b | IgG |
| 9 | H9A | H7b | H1b | IgM |
| 10 | H9A | H7b | H2b | IgM |
| 11 | H9A | H7b | H3b | IgM |
| 12 | H9A | H7b | H4b | IgM |
| 13 | K7a | K6b | K1b | kappa |
| 14 | K7a | K6b | K2b | kappa |
| 15 | K7a | K6b | K3b | kappa |
| 16 | K7a | K6b | K4b | kappa |
| 17 | K7a | K6b | K5b | kappa |
| 18 | L8a | L5b | L1b | lambda |
| 19 | L8a | L6b | L1b | lambda |
| 20 | L8a | L7b | L1b | lambda |
| 21 | L8a | L5b | L2b | lambda |
| 22 | L8a | L6b | L2b | lambda |
| 23 | L8a | L7b | L2b | lambda |
| 24 | L8a | L5b | L3b | lambda |
| 25 | L8a | L6b | L3b | lambda |
| 26 | L8a | L7b | L3b | lambda |
| 27 | L8a | L5b | L4b | lambda |
| 28 | L8a | L6b | L4b | lambda |
| 29 | L8a | L7b | L4b | lambda |

Example 7

Ligation of PCR Amplified CDRs into Antibody Scaffolds

A. Ligation and Sub Cloning of the PCR Amplified CDRS into the Heavy and Light Scaffolds is Accomplished as Described Below:

Transformation into bacteria is accomplished via electroporation using the protocol as follows: Ligated DNA (5-40 ng) is electroporated into 20 μL of EP-Max 10b electrocompetent cells from BioRad (Hercules, Calif.) in a 0.1 cm gap cuvette using BioRad's Gene Pulser XCell Electroporator with settings of 1.8 kV, capacitance of 25 μF, and 200 ohms of resistance. Following electroporation, 600 μL SOC was added to each tube and entire contents were plated on a 15 cm ampicillin-containing agar plate.

The IgG and IgM PCR amplified CDR3s from Example 6 above, and the intermediate 9 heavy chain cloning vectors from Example 5 (i.e. $VH_{1-9}$-stuffer-IgG constant region) are digested with the restriction enzymes EagI+NheI (FIG. 21A step 4) and gel purified.

The kappa light chain PCR amplified CDR3s from Example 6 above, and the and the 5 κ light chain intermediate cloning vectors from Example 5 are cut with the restriction enzymes BsmBI+MfeI (FIG. 21B step 9) and gel purified.

The lambda light chain PCR amplified CDR3s from Example 6 above, and the 4λ light chain intermediate cloning vectors from Example 5 are cut with the restriction enzymes BbsI+AclI (FIG. 21C step 14) and gel purified.

All digested CDR3s are then ligated into their appropriate intermediate cut cloning vectors to generate completed heavy chain, kappa light and lambda light chains semi synthetic polynucleotide sub libraries (i.e. stuffer regions have been replaced with the highly diverse, PCR-amplified CDR3 regions).

Prior to ligation the intermediate cloning vectors from Example 5 can be pooled, for example the 9 heavy chain vectors ($VH_{1-9}$-stuffer-IgG constant region), the 5 κ light chain vectors ($V\kappa_{1-5}$-stuffer-IGKC kappa constant region the 4λ light chain vectors ($V_{\lambda 1-4}$-stuffer-IGLC3 lambda constant region) can be pooled into 3 separate pools (i.e. one pool each of heavy-, κ-, and λ-intermediate cloning vectors) prior to addition and ligation of CDR3's. Alternatively, the vectors can be kept separate, in which case one can set up 18 separate ligations.

The 9 separate (or pool) of complete heavy chain polynucleotide library vectors containing the highly diverse naturally occurring CDR3 collection described above, are digested and then sub-cloned into the SgrAI and FseI sites of the final eukaryotic episomal expression vector, pABLh (FIG. 21A step 5).

The complete kappa and lambda light chain polynucleotide libraries are kept as two independent pools. Each set of inserts, κ and λ, are digested and then sub-cloned into the SbfI and AscI sites of the final eukaryotic episomal expression vectors, pABLK (FIG. 21B step 10) and pABLλ (FIG. 21C step 15).

The integrity and diversity of the library is confirmed by sequencing the CDR3 inserts from a representative and statistically significant number of clones (i.e., 50 to 200 samples from each of the heavy, κ and λ chain sub libraries).

Plasmid stocks of the library expression vectors were prepared using standard procedures and stored frozen, until required.

B. Creation of Cell Surface Expression Libraries

One day prior to transfection, HEK-293 cells are seeded at a density of three million cells per T75 flask in 10 mL of DMEM medium containing 10% fetal bovine serum. A total of 50 flasks are prepared for transfection and subsequently incubated at 37° C., in a tissue culture incubator with 5% carbon dioxide overnight.

The next day, a mixture of 30 mL OptiMEM (Invitrogen Corporation, Carlsbad, Calif.), 1.2 mL of HD-Fugene (Roche Diagnostics Corp., Indianapolis, Ind.), 90 μg of Ig heavy chain DNA (i.e., vector pABLh) and 90 μg of Ig light chain (i.e., vector pABLκ and/or vector pABLλ) DNA are mixed and incubated for 25-30 minutes at room temperature. A volume of approximately 540 μl is added to each T75 flask containing the HEK-293 cells and the cells are incubated at 37° C., 5% carbon dioxide.

Three days post-transfection, the cells are transferred to T225 flasks containing 25 mL DMEM medium containing 10% fetal bovine serum. Blasticidin (15 μg/mL), and puromycin (1.5 μg/mL) are added after cell attachment in order to select for successfully transfected cells. The cells are incubated at 37° C., 5% carbon dioxide during a selection process of two-four weeks. During this time, cells are monitored for growth, the medium is exchanged and the cells are expanded into additional T225 flasks as required.

After selection, the cells are screened to confirm high level surface expression of antibodies as described below and then used to create a cell bank. Cell banks are created from pooling the cells from one hundred T225 flasks.

Cells are harvested by trypsinization treatment and then pelleted by gentle centrifugation. The cell pellets are resuspended in cell freezing medium at a concentration of $5.8\times10^7$ cells/ml. One mL of cells is dispensed into each of ninety cryovials. The vials are incubated overnight at −80° C. and then transferred to liquid nitrogen for long-term storage.

C. Creation of a Dynamic Cell Surface Antibody Library

One day prior to transfection, HEK-293 cells comprising an inducible or constitutive AID expression vector with a hygromycin selectable marker gene (as described in Example 3) are seeded at a density of three million cells per T75 flask in 10 mL of DMEM medium containing 10% fetal bovine serum. A total of 50 flasks are prepared for transfection and subsequently incubated overnight at 37° C. in a tissue culture incubator with 5% carbon dioxide.

The next day, a mixture of 30 mL OptiMem, 1.2 mL of HD-Fugene, 90 μg of Ig heavy chain DNA (i.e., vector pABLh) and 90 μg of Ig light chain (i.e., vector pABLκ and or vector pABLλ) DNA are mixed and incubated for 25-30 minutes at room temperature. A volume of approximately 540 μl is added to each T75 flask containing the HEK-293 cells and the cells are incubated at 37° C., 5% carbon dioxide.

Three days post-transfection, the cells are transferred to T225 flasks containing 25 mL DMEM medium containing 10% fetal bovine serum and 50 micrograms per mL of G418 antibiotic. Hygromycin (350 μg/mL), blasticidin (15 μg/mL), and puromycin (1.5 μg/mL) are added after cell attachment in order to select for successfully transfected cells. The cells are incubated at 37° C., 5% carbon dioxide during a selection process of two-four weeks. During this time cells are monitored for growth, the medium is exchanged and the cells are expanded into additional T225 flasks as required.

Cells stably expressing heavy and light chain (i.e., functional antibodies) from the initial selections above are characterized to establish copy number of expressed antibody on the cell surface by FACS. Briefly fluorescently tagged antibodies to the heavy and light chain are used to stain samples of transfected cells from the library using commercially available fluorescein Isothiocyanate (FITC) or R-Phycoerythrin (R-PE) conjugated goat anti-human-IgG (Sigma). Staining is performed using the manufacture's suggested protocols, usually via incubation of the test cells in the presence of labeled antibody for 30 minutes on ice. Expression levels are quantified using Bang Beads (Bang Laboratories Inc., Fishers, Ind.) with five different microbead populations with defined human IgG-binding capacities. The geometric mean fluorescence intensity of each population is determined by flow cytometry and plotted against their individual IgG-binding capacity to generate a linear regression curve. This curve can then be used to convert the geometric mean fluorescence of each cell line into an average IgG expression level. Heavy and light chains designed using the methods described herein are further elucidated in Example 13.

D. Creation of Cell Banks

Cell banks are created from pooling the cells from one hundred T225 flasks. Briefly, cells are harvested from plates by trypsinization and then pelleted by gentle centrifugation. The cell pellets are resuspended in cell freezing medium at a concentration of $5.8\times10^7$ cells/ml. One mL of cells is dispensed into each of ninety cryovials. The vials are incubated overnight at −80° C. and transferred to liquid nitrogen for long-term storage.

E. Conversion of Surface Displayed Libraries to Secreted Libraries

Polynucleotides encoding the IgG1 constant region, a DNA fragment of a portion of the juxtamembrane, and complete transmembrane and cytoplasmic domain from the murine histocompatibility 2, K region (H2kk, NCBI accession number AK153419) are synthesized by (DNA 2.0 Menlo Park, Calif.). Silent mutations are introduced during synthesis near the 5' end of the IgG constant region to create a convenient NheI site. Two XhoI restriction sites are introduced by site directed mutagenesis; the first is introduced between the two synthetic fragments, and a second XhoI restriction site and an adjacent in-frame stop codon are introduced distal to the cytoplasmic domain sequence, as shown below.

Sequence of IgG1 constant region, with contiguous H2kk transmembrane domain.

gctagcaccctcctccaagagcacctctgggggcacagcggccctgggctgcctggtcaaggactacttccccgaacctgtgacggtgtcgtggaactcaggcgccctgacc
agcggcgtgcacaccttcccggctgtcctacagtcctcaggactctactccctcagcagcgtggtgacagtgccctccagcagcttgggcacccagacctacatctgcaacgtg
aatcacaagcccagcaacaccaaggtggacaagaaagttgagcccaaatcttgtgacaaaactcacacatgcccaccgtgcccagcacctgaactcctggggggaccgtcag
tcttcctcttccccccaaaacccaaggacaccctcatgatctcccggacccctgaggtcacatgcgtggtggtggacgtgagccacgaggaccctgaggtcaagttcaactggt
acagtggacggcgtggaggtgcataatgccaagacaaagccgcgggaggagcagtacaacagcacgtaccgggtggtcagcgtcctcaccgtcctgcaccaggactggctg
aatggcaaggagtacaagtgcaaggtctccaacaaagccctcccagcccccatcgagaaaaccatctccaaagccaaagggcagccccgagaaccacaggtgtacaccctg
cccccatcccgggatgagctgaccaagaaccaggtcagcctgacctgcctggtcaaaggcttctatcccagcgacatcgccgtggagtgggagagcaatgggcagccggag
aacaactacaagaccacgcctcccgtgctggactccgacggctccttcttcctctacagcaagctcaccgtggacaagagcaggtggcagcaggggaacgtcttctcatgctcc
gtgatgcatgaggctctgcacaaccactacacgcagaagagcctctccctgtctccgggtaaactcgagCCTCCTCCATCCACTGTCTCCAACATGG
CGACCGTTGCTGTTCTGGTTGTCCTTGGAGCTGCAATAGTCACTGGAGCTGTGGTGGCTTTTGTGATGAAGA
TGAGAAGGAGAAACACAGGTGGAAAAGGAGGGGACTATGCTCTGGCTCCAGGCTCCCAGACCTCTGATCT
GTCTCTCCCAGATTGTAAAGTGATGGTTCATGACCCTCATTCTCTAGCGTGACTCGAGtgaggccggcca*gaattc*ggc
gcgcc (SEQ ID NO: 455).

Features as shown in 5' to 3' order are: NheI site (boxed small letters), IgG1 constant region coding sequence (small letters), XhoI site (introduced between the constant and juxtamembrane region, in small, boxed letters); murine H2kk sequence that contains a small juxtamembrane region and transmembrane and cytoplasmic domains (capital letters, the native stop codon is underlined), $2^{nd}$ XhoI site sequence (boxed and in capitals), and adjacent in-frame stop codon (small underlined letters); additional cloning sites are shown in small letters, the EcoRI site used in later cloning steps is boxed and italicized.

This fragment is reclaimed with NheI and EcoRI and cloned into the cognate sites of the expression vector ANA327 (vector format 1, with blasticidin resistance) using standard cloning methodology. Digestion of vector with XhoI is followed by self-religation to remove the transmembrane, juxtamembrane and cytoplasmic domains (the capital letters in the sequence above) and generate the vector ANA346 for the production of secreted production of proteins. In this case, the second stop codon (tga shown in underlined in the sequence above) serves as the in-frame translation stop for the secreted form of the IgG1 heavy chain. Cotransfection of the expression vector above, along with appropriate expression vectors for the desired kappa or lambda light chain, in HEK 293 cells permitted subsequent secretion of the protein into the tissue culture media in reasonable yield. The resultant secreted proteins can be produced and purified to determine binding or functional characteristics using standard methodology and as further described herein.

As shown in Examples 4, 5 and 6 above, this library format enables a diverse repertoire of high affinity antibodies to be readily selected and affinity matured. The results from screening this library indicate that relatively low repertoire libraries of less than $<10^6$ members can be successfully used to create high affinity antibodies when combined with on-going hypermutation of the antibodies displaying the preferred binding and/or functional characteristics.

Example 8

Synthetic CDRs

A synthetic polynucleotide sequence of the present invention is shown schematically in FIG. 22. In this example, a synthetic CDR3 domain that contains two circularly permuted WRC motifs containing preferred SHM codons with the preferred hot spots (AGCTAC; SEQ ID NO: 404) is contained within 2 nonameric ideal cold spots (GTCGTCGTC; SEQ ID NO: 405) to create a boundary of SHM resistant sequence. As shown below, the reading frame context of the hot spots (bold) may be manipulated (underlining) so that the hot spot motif can be introduced into each of the available three reading frames.

GTCGTCGTCAGCTACAGCTACGTCGTCGTC . . . first reading frame; SEQ ID NO: 406;

GTCGTCGTCCAGCTACAGCTAGTCGTCGTC . . . second reading frame; SEQ ID NO: 407; and GTCGTCGTCACAGCTACAGCTGTCGTCGTC . . . third reading frame; SEQ ID NO: 408;

As shown in FIG. 22, this synthetic CDR sequence provides an opportunity to demonstrate the ability of synthetic preferred SHM motifs to selectively drive targeted diversity generation at the amino acid level, while minimizing mutations in SHM resistant sequences. The systematic placement of the hot spot in each reading frame demonstrates the impact of the reading frame context on amino acid mutation generation. The construct further provides for the ability to for the elimination of non-mutated vectors through the use of a restriction enzyme which recognizes the native sequence making the analysis of mutated sequences more efficient (because non mutated sequences are eliminated). In addition, the experiment can be conducted in the absence of selective pressure to select for, or against any specific type of mutational event.

A. Synthesis and Cloning

The complete polynucleotide sequence of one of the three synthetic CDR3 antibody constructs is shown below. In this sequence the synthetic SHM optimized sequence is shown in capitals; hot spots are shown as bold capital letters and cold spots are shown as italicized capital letters. Also shown in the sequence below in bold, lowercase letters is the location of the BbsI+AclI restriction digestion sites that are used in Examples 3, 4, 5, 6, and 7 to ligate the PCR amplified, naturally-occurring, CDR3 sequences into the antibody scaffolds created previously:

SEQ ID NO: 409.

atgaaacacctgtggttcttcctcctcctggtggcagctcccagatgg gtcctgtcccaggtgcagctacaacagtggggcgcaggactgttgaag ccttcggagaccctgtccctcacctgcgctgtctatggtgggtccttc agtggttactactggagctggatccgccagcccccagggaaggggctg gagtggattggggaaatcaatcatagtggaagcaccaactacaacccg tccctcaagagtcgagtcaccatatcagtagacacgtccaagaaccag ttctccctgaagctgagctctgtgaccgccgcggacacggccgtgtat tactgtgcgaga*GTCGTCGTCAG*CTACAG*CTACGTCGTCGTC*gctgaa tacttccagcactggggccagggcaccctggtcaccgtctcctcagcc tccaccaagggcccatcggtcttcccgctagcaccctcctccaagagc acctctgggggcacagcggccctgggctgcctggtcaaggactacttc cccgaaccggtgacggtgtcgtggaactcaggcgccctgaccagcggc gtgcacaccttcccggctgtccttcagtcctcaggactctactccctc agcagcgtggtgaccgtgccctccagcagcttgggcacccagacctac atctgcaacgtgaatcacaagcccagcaacaccaaggtggacaagaaa gttgagcccaaatcttgtgacaaaactcacacatgcccaccgtgccca gcacctgaactcctgggggggaccgtcagtcttcctcttccccccaaaa cccaaggacaccctcatgatctcccggacccctgaggtcacatgcgtg gtggtggacgtgagccacgaagaccctgaggtcaagttcaactggtac gtggacggcgtggaggtgcataatgccaagacaaagccgcgggaggag cagtacaacagcacgtaccgggtggtcagcgtcctcaccgtcctgcac caggactggctgaatggcaaggagtacaagtgcaaggtctccaacaaa gccctcccagcccccatcgagaaaaccatctccaaagccaaagggcag ccccgagaaccacaggtgtacaccctgcccccatcccgggatgagctg accaagaaccaggtcagcctgacctgcctggtcaaaggcttctatccc agcgacatcgccgtggagtgggagagcaatgggcagccggagaacaac tacaagaccacgcctcccgtgctggactccgacggctccttcttccta tacagcaagctcaccgtggacaagagcaggtggcagcaggggaacgtc ttctcatgctccgtgatgcatgaggctctgcacaaccactacacgcag The actual synthetic sequences of all of the synthetic CDR3 sequences, used for cloning and construction is shown below:

SEQ ID NO: 410.

acacggccgtgtattactgtgcgagaGTCGTCGTCAGCTACAGCTACGT
CGTCGTCgctgaatacttccagcactggggccagggcaccctggtcacc
gtctcctcagcctccaccaagggcccatcggtcttcccgctagcac;

SEQ ID NO: 411.

acacggccgtgtattactgtgcgagaGTCGTCGTCCAGCTACAGCTAGT
CGTCGTCgctgaatacttccagcactggggccagggcaccctggtcacc
gtctcctcagcctccaccaagggcccatcggtcttcccgctagcac;

SEQ ID NO: 412.

acacggccgtgtattactgtgcgagaGTCGTCGTCACAGCTACAGCTGT
CGTCGTCgctgaatacttccagcactggggccagggcaccctggtcacc
gtctcctcagcctccaccaagggcccatcggtcttcccgctagcac;

The corresponding nucleic acid sequences corresponding to these sequences, set forth above, can be made by DNA2.0 (Menlo Park, Calif.), and correct synthesis confirmed by sequence analysis.

These sequences can be inserted into the heavy chain scaffolds described previously, using the same methodology and cloning steps as described in the heavy chains scaffolds as described in Examples 5, 6 and 7, with the naturally occurring PCR amplified CDR3s.

B. Analysis and Testing

The ideal CDR3 hot spot, in each permutation shown above, contains a single SfcI restriction site that enables the removal of all sequences within a library population that have not undergone SHM at that position. This simplifies and speeds up analysis by eliminating non mutated sequences from being rescued and cloned.

To establish selective mutagenesis and diversity generation in the constructs, the following steps are followed.

1. Transfection of Cells

Hek 293 cells are plated to a density of about $4\times10^5$/well, in 6-well microtiter dish. After 24 hours, transfections are performed using Fugene6 reagent from Roche Applied Sciences (Indianapolis, Ind.) at a reagent-to-DNA ratio of 3 μg:1 μg DNA per well with the expression vectors comprising the synthetic heavy chains and representative light chain which confer blasticidin and hygromycin resistance respectively. Transfections are carried out in accordance with manufacturer's protocol.

Cells stabling expressing synthetic heavy chain constructs are created using standard methodology as described above, and are characterized to establish copy number of expressed antibody on the cell surface by FACS. Briefly fluorescently tagged antibodies to the heavy and light chain are used to stain transfected cells and those exhibiting a copy number of greater than 500,000 intact heavy and light chains are selected.

Staining of light and heavy chain expression can be accomplished, for example, by using commercially available fluorescein isothiocyanate (FITC) or R-Phycoerythrin (R-PE) conjugated rat anti-mouse Ig, kappa light chain, and FITC or R-PE conjugated rat anti-mouse Ig Glmonoclonal antibodies (BD Pharmingen). Staining can be performed using the manufacturer's suggested protocols, usually via incubation of the test cells in the presence of labeled antibody for 30 minutes on ice.

Expression levels can be quantified using Spherotech rainbow calibration particles (Spherotech, IL) that enables the quantitative analysis of cellular antigen expression to be determined.

Cells stably expressing heavy and light chain at a high level can be isolated by FACS sorting using standard flow and sorting protocols, and selected cells can be subsequently grown up for use as substrates for analysis.

Selected cells expressing heavy and light chains as described above can then be transfected with an expression vector containing an inducible, cold AID using standard transfection conditions as described above. Three days post transfection, selective pressure is exerted, and a new stable cell population is propagated that includes the inducible AID expression vector.

This population of cells is grown up, and AID expression is induced via the addition of tetracycline or an analog thereof for about 6 to 24 hours. The cells are allowed to expand for about 2 to 5 days, and the cycle repeated 2 to 5 times to generate diversity within the synthetic CDRs.

After an appropriate time, for example 2 to 3 weeks, vectors can be rescued from the cells and the corresponding heavy chain cDNA sequences analyzed to determine the pattern of mutations achieved with each synthetic CDR. For example, a PCR amplified fragment can be digested with SfcI, and then the fragment is reamplified to permit the cloning of DNA in which the SfcI site has been eliminated, presumably due to the action of AID.

2. Episomal Rescue

As episomal vectors remain unintegrated and easily separable from a host cell's chromosomal material, plasmids can be recovered by the method of Hirt (Hirt, 1967; Kapoor and Frappier, 2005; Yates et al., 1984), transformed into competent bacteria and further manipulated to verify the sequence, identity and/or properties of the encoded polypeptides.

Using an estimate of an average of 3 resident episomes of 8000 base pairs (bp) each per cell, one can expect a yield of approximately 30 picogram (pg) per million cells (see, e.g., Formula 1). Assuming a transformation efficiency into electrocompetent *E. coli* of $10^7$ colonies per μg of relaxed circle DNA, one can expect approximately 300 *E. coli* colonies, each representing a single recovered episome, to result per million mammalian cells.

$$(10^6\ \text{cells} \times 3\ \text{episomes/cell}) \times (660\ \text{g/mol/bp}) \times (8000\ \text{bp/episome}) \times (10^6\ \text{colonies/}\mu\text{g}) \times (10^6\ \mu\text{g/g}) \div (6 \times 10^{23}\ \text{episomes/mol}) = 2.6 \times 10^{-11}\ \text{g(DNA per } 10^6\ \text{cells)}. \quad \text{Formula 1:}$$

Plasmids can also be recovered using a standard alkaline lysis procedure, e.g., as per a protocol from Qiagen, Inc. (for procedure, see e.g., www1.qiagen.com/literature/handbooks/PDF/PlasmidDNAPurification/PLS_QP_Miniprep/1034641_HB_QIAprep__112005.pdf; and Wade-Martins et al., Nuc Acids Res 27:1674-1682 (1999)). In one aspect, transfected mammalian cells are treated the same way as the *E. coli* described in the Qiagen protocol. Episomes present in the final eluate are transformed into competent *E. coli* as described above. Using either the Hirt supernatant or alkaline lysis method requires beginning with a significant cell population for isolating resident episomes. In one non-limiting example, starting with 50,000 clonally derived cells, one might expect to obtain 10 to 20 recovered episomes as manifested in colonies of transformed *E. coli*.

Another standard method to characterize transfected genes, whether episomal or integrated, involves performing a Polymerase Chain Reaction (PCR) reaction directly on the relevant cell population followed by cloning and characterizing individual resulting PCR fragments. This method has the advantage of not requiring a large starting population of cells. PCR amplification of the resident active antibody open reading frame can successfully be performed on as little as a single cell. This has the effect of foreshortening the time from isolation of a cell of interest to the point of sequencing the responsible open reading frame.

Still another option is to perform Reverse Transcriptase-Polymerase Chain Reaction (RT-PCR) on the isolated cells thus identifying and characterizing the resident polypeptide(s) via expressed mRNA.

Alternatively the library can be used as the starting point for the affinity maturation of an antibody to any specific target antigen or epitope of interest, for example as described in Example 9 below.

Example 9

Selection and Affinity Maturation of an Antibody from a Nucleic Acid Library As described previously, antibodies provide a natural template through which somatic hypermutation can be applied to create mutant proteins with enhanced properties. Such improved antibodies can be selected based upon affinity selection, for example via FACS or via binding to magnetic beads.

A. Synthesis and Cloning.

The construction of prototypic heavy and light chain and light chain constructs is described in Examples 4-8.

In order to express antibody on the cell surface, the heavy chain is created as a chimeric molecule with a murine H2kk (MHC type I) peri-transmembrane domain, transmembrane domain, and cytoplasmic domain. The H2kk sequences are determined from accession number AK153419 at the National Center for Biotechnology Information (NCBI) nucleotide database.

The nucleotide sequence of the full length chimeric, cell-surface associated scaffold heavy chain is listed in Example 5. The nucleotide sequences of the scaffold kappa and lambda heavy chains are shown in Example 5.

1. Transfection of Cells

Hek 293 cells are plated at a density of $4 \times 10^5$/well, in 6-well microtiter dish. After 24 hours, transfections are performed using Fugene6 reagent from Roche Applied Sciences (Indianapolis, Ind.) at a reagent-to-DNA ratio of 3 μL:1 μg DNA per well with the desired combinations of heavy chain and light chain expression vectors. Heavy and light chain expression vectors confer blasticidin and hygromycin resistance respectively. Transfections are carried out in accordance with manufacturer's protocol.

2. Selection by Peptides

A simple test case, antibodies can be selected against the well characterized antigen hen egg lysozyme (HEL). An unlabeled and biotinylated monomeric peptide sequence that comprises the majority of the hen egg lysozyme (HEL) binding surface is synthesized. Dimeric peptide sequences can also be synthesized to compare whether presenting the peptide as a dimer would enhance antibody binding by increasing the avidity of the antibody-peptide interaction. A tandem dimer and a branched multiple antigenic peptide (MAP) dimer can also tested. Peptides as well as biotinylated or unlabeled HEL protein can be coupled to paramagnetic polystyrene microparticle surfaces that had been modified with functional groups or coated with streptavidin (Invitrogen, 1600 Faraday Ave., PO Box 6482, Carlsbad, Calif. 92008).

3. Coupling HEL Protein and Peptides to Tosylactivated Microparticles

The HEL protein and peptides are coupled to 2.8 micron Tosylactivated paramagnetic polystyrene microparticles in a 1.5 ml microcentrifuge tube (Nilsson K and Mosbach K. Eur. J. Biochem. 1980:112: 397-402). The microparticles (2e09 microparticles/milliliter) are washed and resuspended in 100 mM borate buffer, pH 9.5 at a concentration of 1e09 microparticles/ml. Eleven nanomoles of peptide or 6 ug/ml HEL are added to the microparticles and the microparticle/peptide mixture was incubated at room temperature for at least 48 hours with slow tilt rotation. After incubation, the supernatant is removed and the microparticles are washed with 1 ml phosphate buffered saline solution (PBS), pH 7.2 containing 1% (weight/volume) BSA. Finally, the microparticles are resuspended in 1 ml PBS solution, pH 7.2 containing 1% (weight/volume) BSA.

4. Coupling Biotinylated HEL Protein and Peptides to Streptavidin-Conjugated Microparticles Another option is to couple biotinylated peptides to paramagnetic polystyrene microparticles whose surfaces have been covalently linked with a monolayer of streptavidin. Briefly, the streptavidin microparticles are washed, resuspended in 1 ml PBS solution, pH 7.2 containing 1% (weight/volume) BSA and 33 picomoles of biotinylated peptide or approximately 10 ug/ml biotinylated HEL are added to the microparticle solution. The microparticle/peptide solution can be incubated for 30 minutes at room temperature with slow tilt rotation. After coupling, the microparticles can be washed and resuspended to a final microparticle concentration of 1e09 microparticles/ml. (Argarana et al. 1986; 14(4): 1871-82; Pahler et al. J Biol Chem 1987:262(29):13933-7).

5. Cell Selection

Transfected HEK 293 cells are screened in order to isolate cells that bind to the peptide-conjugated paramagnetic microparticles. A similar control cell line that does not express antibody is used as a negative control for the selections.

The cells are washed with an equal volume of PBS solution, pH 7.2 and resuspended in PBS solution, pH 7.2 containing 1% (weight/volume) BSA to a final cell concentration of 1e07 cells/ml. The cells are pre-cleared by adding 1e06 naked microparticles to the cells and incubating on a rotator at 4° C. for 30 minutes. The unbound cells are gently transferred to a new tube. Peptide-conjugated or naked microparticles (1e07) are transferred into the tube with the cells and the cell:microparticle mixture can be incubated on a rotator at 4° C. for 30 minutes. The unbound cells are removed and the microparticle: cell mixture can be washed with cold PBS/1% BSA. The microparticles and attached cells are resuspended in 100 ul cell culture medium and can be grown initially in one well of a 96-well plate. The number of microparticle-bound cells can be determined and the cells expanded until the next round of selection. The number of microparticle-bound cells selected on the peptide-conjugated microparticles is compared with cells bound to the naked microparticles and to the cells that do not express antibody.

6. In Vitro Affinity Maturation

Cells stabling expressing heavy and light chain (i.e. are expressing functional antibodies) from the initial selections above are characterized to establish copy number of expressed antibody on the cell surface by FACS. Briefly fluorescently tagged antibodies to the heavy and light chain are used to stain transfected cells and those exhibiting a copy number of greater than 500,000 intact heavy and light chains are selected.

Staining of light and heavy chain expression can be accomplished, for example, by using commercially available fluorescein Isothiocyanate (FITC) or R-Phycoerythrin (R-PE) conjugated rat anti-mouse Ig, kappa light chain, and FITC or R-PE conjugated rat anti-mouse Ig Glmonoclonal antibodies (BD Pharmingen). Staining can be performed using the manufacture's suggested protocols, usually via incubation of the test cells in the presence of labeled antibody for 30 minutes on ice.

Expression levels can be quantified using Spherotech rainbow calibration particles (Spherotech, IL) that enables the quantitative analysis of cellular antigen expression to be determined.

Cells stably expressing heavy and light chain at a high level can be isolated by FACS sorting using standard flow and sorting protocols, and selected cells can be subsequently grown up for use as substrates for affinity maturation.

Selected cells expressing heavy and light chains as described above can then be transfected with an expression vector containing an inducible, cold AID polynucleotide sequence using standard transfection conditions as described above. Three days post transfection, selective pressure is exerted, and a new stable cell population is propagated that includes the inducible AID expression vector.

This population of cells is grown up, and AID expression is induced via the addition of tetracycline or an analog thereof for about 6 to 24 hours. The cells are allowed to expand for about 2 to 5 days, and then selected using the HEL protein or peptide coupled beads as described above.

Cells that preferentially and/or selectively bind to the HEL protein or peptides with a higher affinity are selected and allowed to expand. If required, another round of AID induction and mutagenesis is repeated, as described above, and again cells that exhibit improved, selective, and high affinity binding, are retained for further propagation and growth.

The new improved variants obtained can be further characterized as described herein, and the sequence of the heavy and light chains determined after RT-PCR, or episome rescue, as described in Example 8.

Example 10

Application of SHM Libraries to the Directed Evolution of Enzyme Pathways

The evolution of bacteria with resistance to existing therapeutic regimens has sparked interest in the discovery and development of novel antibiotics. Ideal candidates for further research are those that act via multiple modes of action, making resistance significantly more difficult to attain. One such antibiotic is Nisin.

Nisin is a natural product of *Lactococcus lactic*, a lantibotic with a broad spectrum of activity against Gram-positive bacteria, commonly used in food preservation against such pathogens as *Listeria monocytogenes* and *Clostridium botulinum*. (Bavin et al., Lancet. 1952 Jan. 19; 1(3):127-9)) Nisin is a ribosomally translated and post-translated peptide, which despite decades of use by the food industry, has not seen the induction of common resistance mechanisms. This finding is likely a result of two facts: one, the mode of action of Nisin biocidal activity comes from its binding to Lipid II and secondary induction of pore formation, (Breukink et al., (2006)). Lipid II is a bacterial cell-wall component that is not easily modified by Gram-positive bacteria and whose use forms a rate-limiting step in the generation of the bacterial cell wall. Nisin also acts to inhibit spore formation.

Nisin is currently in preclinical development for the treatment of several bacterial pathogens. It displays a spectrum of activity towards several pathogens, including multi drug-resistant *Streptococcus pneumoniae*, vancomycin-resistant *Enterococcus faecium*, and *Strepococcus pyogenes*, all areas where new therapeutics are desperately needed (Goldstein et al., (1998)). In one study, Nisin was shown to be 8-16 times more potent in the treatment of *S. pneumoniae* (in mice) than vancomycin (Brumfitt et al., 2002).

Despite these promising features, Nisin and other lantibotics suffer from several important limitations. Bacteria, even closely related (isogenic) species, display a significant variation in their sensitivity to Nisin and other lantibiotics. Secondly, Nisin is cleared quickly from mammalian circulatory system. For Nisin to become a truly efficacious therapeutic, it will need to have improved pharmacodynamic properties with a broad spectrum of biocidal activity. Here we discuss application of SHM to engineer a Nisin with improved qualities.

Biosynthesis of bioactive Nisin has been to shown to be dependent on only five *L. lactis* proteins, NisA, NisB, NisC, NisP, and NisT (Kuipers et al., 2004, Rink et al., (2005)). NisA encodes for a precursor peptide which is dehydrated at several serine and threonine positions by NisB, leading to a modified peptide that is cyclized at five positions by NisC. Finally the pro-antibiotic has its leader peptide cleaved by protease NisP, and is excreted to the media by transporter NisT (See FIG. 23) The five thioester rings, each catalyzed by NisC, are termed lanthionines, and define the lantibiotic family of modified peptide antibiotics.

The modular nature of this pathway, easy assay for bioactivity, broad specificity and activity of the dehydratase and cyclase NisB and NisC, make this an ideal target for SHM driven co-evolution to produce novel antibiotic constructs. In one approach such a strategy could be based on making certain genes, or portions of genes more susceptible to SHM, while making other genes, or portions of those genes, resistant to SHM.

The amino acid sequences of the 5 genes involved in Nisin biosynthesis are shown below: In these sequences, bold residues indicate those positions to be made hot to SHM, while underlined residues are those to be made cold to SHM.

SEQ ID NO: 413

NisA, Native Gene > NisA|gi|530218|gb|
AAA26948.1|nisin [*Lactococcuslactis*];
MSTKDFNLDLVSVSKKDSGASPRITSISLCTPGCKTGALMGCNMKTAT
CHCSIHVSK

SEQ ID NO: 414

NisC, Native Gene > NisC|gi|44045|emb|
CAA48383.1|nisC [L*actococcus lactis*];
MRIMMNKKNIKRNVEKIIAQWDERTRKNKENFDFGELTLSTGLPGIIL
MLAELKNKDNSKIYQKKIDNYIEYIVSKLSTYGLLTGSLYSGAAGIAL
SILHLREDDEKYKNLLDSLNRYIEYFVREKIEGFNLENITPPDYDVIE
GLSGILSYLLLINDEQYDDLKILIINFLSNLTKENNGLISLYIKSENQ
MSQSESEMYPLGCLNMGLAHGLAGVGCILAYAHIKGYSNEASLSALQK
IIFIYEKFELERKKQFLWKDGLVADELKKEKVIREASFIRDAWCYGGP
GISLLYLYGGLALDNDYFVDKAEKILESAMQRKLGIDSYMICHGYSGL
IEICSLFKRRLNTKKFDSYMEEFNVNSEQILEEYGDESGTGFLEGISG
CILVLSKFEYSINFTYWRQALLLFDDFLKGGKR

SEQ ID NO: 415

NisB, Native Gene > gi|473018|emb|CAA79468.1|
NisB protein [*Lactococcus lactis*];
MIKSSFKAQPFLVRNTILSPNDKRSFTEYTQVIETVSKNKVFLEQLLL
ANPKLYNVMQKYNAGLLKKKRVKKLFESIYKYYKRSYLRSTPFGLFSE
TSIGVFSKSSQYKLMGKTTKGIRLDTQWLIRLVHKMEVDFSKKLSFTR
NNANYKFGDRVFQVYTINSSELEEVNIKYTNVYQIISEFCENDYQKYE
DICETVTLCYGDEYRELSEQYLGSLIVNHYLISNLQKDLLSDFSWDTF
LTKVEAIDEDKKYIIPLKKVQKFIQEYSEIEIGEGIEKLKEIYQEMSQ
ILENDNYIQIDLISDSEINFDVKQKQQLEHLAEFLGNTTKSVRRTYLD
DYKDKFIEKYGVDQEVQITELFDSTFGIGAPYNYNHPRNDFYESEPST
LYYSEEEREKYLSMYVEAVKNHNVINLDDLESHYQKMDLEKKSELQGL
ELFLNLAKEYEKDIFILGDIVGNNNLGGASGRFSALSPELTSYHRTIV
DSVERENENKEITSCEIVFLPENIRHANVMHTSIMRRKVLPFFTSTSH
NEVQLTNIYIGIDEKEKFYARDISTQEVLKFYITSMYNKTLFSNELRF
LYEISLDDKFGNLPWELIYRDFDYIPRLVFDEIVISPAKWKIWGRDVN
NKMTIRELIQSKEIPKEFYIVNGDNKVYLSQENPLDMEILESAIKKSS
KRKDFIELQEYFEDENIINKGQKGRVADVVVPFIRTRALGNEGRAFIR
EKRVSVERREKLPFNEWLYLKLYISINRQNEFLLSYLPDIQKIVANLG -continued GKLFFLRYTDPKPHIRLRIKCSDLFLAYGSILEILKRSQKNRIMSTFD
ISIYDQEVERYGGFDTLELSEAIFCADSKIIPNLLTLIKDTNNDWKVD
DVSILVNYLYLKCFFQNDNKKILNFLNLVSPKKVKENVNEKIEHYLKL
LKVDNLGDQIFYDKNFKELKHAIKNLFLKMIAQDFELQKVYSIIDSII
HVHNNRLIGIERDKEKLIYYTLQRLFVSEEYMK

SEQ ID NO: 416

NisP, Native Gene > gi|730155|sp|Q07596|
NISP_LACLA Nisin leader peptide-processing
serine protease nisP precursor;
MKKILGFLFIVCSLGLSATVHGETTNSQQLLSNNINTELINHNSNAIL
SSTEGSTTDSINLGAQSPAVKSTTRTELDVTGAAKTLLQTSAVQKEMK
VSLQETQVSSEFSKRDSVTNKEAVPVSKDELLEQSEVVVSTSSIQKNK
ILDNKKKRANFVTSSPLIKEKPSNSKDASGVIDNSASPLSYRKAKEVV
SLRQPLKNQKVEAQPLLISNSSEKKASVYTNSHDFWDYQWDMKYVTNN
GESYALYQPSKKISVGIIDSGIMEEHPDLSNSLGNYFKNLVPKGGFDN
EEPDETGNPSDIVDKMGHGTEVAGQITANGNILGVAPGITVNIYRVFG
ENLSKSEWVARAIRRAADDGNKVINISAGQYLMISGSYDDGTNDYQEY
LNYKSAINYATAKGSIVVAALGNDSLNIQDNQTMINFLKRFRSIKVPG
KVVDAPSVFEDVIAVGGIDGYGNISDFSNIGADAIYAPAGTTANFKKY
GQDKFVSQGYYLKDWLFTTANTGWYQYVYGNSFATPKVSGALALVVDK
YGIKNPNQLKRFLLMNSPEVNGNRVLNIVDLLNGKNKAFSLDTDKGQD
DAINHKSMENLKESRDTMKQEQDKEIQRNTNNNFSIKNDFHNISKEVI
SVDYNINQKMANNRNSRGAVSVRSQEILPVTGDGEDFLPALGIVCISI
LGILKRKTKN

SEQ ID NO: 417

NisT, Native Gene > gi|44044|emb|CAA48382.1|
nisT [*Lactococcus lactis*];
MDEVVKEFTSKQFFYTLLTLPSTLKLIFQLEKRYAIYLIVLNAITAFV
PLASLFIYQDLINSVLGSGRHLINIIIIYFIVQVITTVLGQLESYVSG
KFDMRLSYSINMRLMRTTSSLELSDYEQADMYNIIEKVTQDSTYKPFQ
LFNAIIVELSSFISLLSSLFFIGTWNIGVAILLLIVPVLSLVLFLRVG
QLEFLIQWQRASSERETWYIVYLLTHDFSFKEIKLNNISNYFIHKFGK
LKKGFINQDLAIARKKTYFNIFLDFILNLINILTIFAMILSVRAGKLL
IGNLVSLIQAISKINTYSQTMIQNIYIIYNTSLFMEQLFEFLKRESVV
HKKIEDTEICNQHIGTVKVINLSYVYPNSNAFALKNINLSFEKGELTA
IVGKNGSGKSTLVKIISGLYQPTMGIIQYDKMRSSLMPEEFYQKNISV
LFQDFVKYELTIRENIGLSDLSSQWEDEKIIKVLDNLGLDFLKTNNQY
VLDTQLGNWFQEGHQLSGGQWQKIALARTFFKKASIYILDEPSAALDP
VAEKEIFDYFVALSENNISIFISHSLNAARKANKIVVMKDGQVEDVGS
HDVLLRRCQYYQELYYSEQYEDNDE NisB, NisP and NisT As described above, the creation of SHM resistant "cold" versions of the essential genes NisP and NisT means that these genes will tend to mutate at a lower rate than SHM susceptible genes that are targeted for diversity generation. Both NisP and NisT currently have broad specificity for the Nisin and do not add to the potential diversity of the post-translationally modified peptide. In this initial example, NisB is also made SHM resistant; however it could also be selectively mutated following the same guidelines outlined below for NisA. Corresponding wild type and cold versions of these genes are shown in FIGS. 24, 25, 26, 27 and 28.

NisA Peptide

As shown above, the majority of the leader peptide region of the NisA peptide should be made cold to SHM mediated mutagenesis because this sequence is absolutely necessary for substrate recognition by NisBCPT. The bulk of the remainder of the NisA peptide sequence should be made hot to SHM mediated mutagenesis, or alternatively, as shown above key residues involved in the generation of the lanthionines may be made SHM resistant thereby reducing the rate of their mutagenesis.

Corresponding wild type and cold versions of the NisA polynucleotide sequence are shown in FIG. 29. Codon optimization of NisA results in the creation of 20 cold spots and elimination of all but one hot spot in the leader sequence, and the creation of 17 hot spots, compared to 8 hot spots in the wild type sequence, in the rest of the molecule.

NisC Protein

Regions of NisC involved in substrate recognition and cyclization, such as those outlined above (bold residues, above), can be made hot to SHM mediated mutation, so that they have a greater probability of generating mutants with alternate activities and specificities thereby creating mature Nisin molecules with altered modifications and bioactivity. Structural areas that govern only stability of the protein can be made cold. Corresponding wild type and cold versions of the NisC polynucleotide sequence are shown in FIGS. 30 and 31.

A specific example of the creation of a targeted hot spot in this gene is shown below.

In this example, an additional hot spot has been inserted into the region of interest (LSTG) and a cold spot has been removed. Additionally the flanking sequence has been made significantly more SHM resistant.

```
                                        SEQ ID NO: 418
. . . N . . . F . . . D . . . F . . . G . . . E
. . . L . . . T . . . L . . . S . . . T . . . G
. . . L . . . P . . . G
amino acid sequence;

Native polynucleotide sequence:
HhhhhhhhhhhhhhhhHhhhhhhhhhhhhHhhhhhhhhhhhhHhh    hot
                                                 spots

cccccccCcccccCCcCccccCcCcCcCccccccCCccccccccc    cold
                                                 spots

Optimized polynucleotide sequence:
HhhhhhhhhhhhhhhhHhhhhhhhhhhHhHhhhhhhhhhhhhhh     hot
                                                 spots

ccccccCcccccCCcCccCcccCcccCcccccccCcCcCCccCc     cold
                                                 spots
```

After final review to ensure that the synthetic polynucleotide sequence is free of extraneous restriction sites, the complete synthetic polynucleotide sequences can be synthesized (DNA 2.0, Menlo Park, Calif.), and cloned appropriate cloning vectors and sequenced to confirm correct synthesis.

Synthetic genes may then be introduced into expression vectors and transformed into an appropriate bacterial strain, for example a *Lactococcus lactis* strains as previously described (Mota-Meira et al., 1997) together with AID, (Besmer et al., 2006) or an AID homolog such as an Apobec-1 enzyme.

Screening may be accomplished by allowing the SHM mediated generated diversity to evolve *L. lactis* co-cultured with Gram-positive bacterial targets that are currently poorly targeted by Nisin. Eventually strains of *L. lactis* will evolve that comprise mutated Nisin genes with enhanced activity against the chosen bacterial target.

Mass spectroscopy of the supernatant of evolved cell-cultures can be used to assess the progress of the process (i.e. identified novel lantibiotics with improved activity to a pathogen).

Example 10

References

1. Brumfitt W, Salton M R, Hamilton-Miller J M. Nisin, alone and combined with peptidoglycan-modulating antibiotics: activity against methicillin-resistant *Staphylococcus aureus* and vancomycin-resistant *enterococci.*
2. J Antimicrob Chemother. 2002 November; 50(5):731-4.
3. BAVIN E M, BEACH A S, FALCONER R, FRIEDMANN R. Nisin in experimental tuberculosis Lancet. 1952 Jan. 19; 1(3):127-9.
4. Mota-Meira M, Lacroix C, LaPointe G, Lavoie M C. Purification and structure of mutacin B-Ny266: a new lantibiotic produced by *Streptococcus mutans*. FEBS Lett. 1997 Jun. 30; 410(2-3):275-9.
5. Goldstein B P, Wei J, Greenberg K, Novick R. Activity of nisin against *Streptococcus pneumoniae*, in vitro, and in a mouse infection model. J Antimicrob Chemother. 1998 August; 42(2):277-8.
6. Breukink E, de Kruijff B. Lipid II as a target for antibiotics. Nat Rev Drug Discov. 2006 April; 5(4):321-32.
7. Li B, Yu J P, Brunzelle J S, Moll G N, van der Donk W A, Nair S K. Structure and mechanism of the lantibiotic cyclase involved in nisin biosynthesis. Science. 2006 Mar. 10; 311(5766):1464-7.
8. Besmer E, Market E, Papavasiliou F N. The transcription elongation complex directs activation-induced cytidine deaminase-mediated DNA deamination. Mol Cell Biol. 2006 June; 26(11):4378-85.
9. Kuipers A, de Boef E, Rink R, Fekken S, Kluskens L D, Driessen A J, Leenhouts K, Kuipers O P, Moll G N. NisT, the transporter of the lantibiotic nisin, can transport fully modified, dehydrated, and unmodified prenisin and fusions of the leader peptide with non-lantibiotic peptides. J Biol Chem. 2004 May 21; 279(21):22176-82.
10. Rink R, Kuipers A, de Boef E, Leenhouts K J, Driessen A J, Moll G N, Kuipers O P. Lantibiotic structures as guidelines for the design of peptides that can be modified by lantibiotic enzymes. Biochemistry. 2005 Jun. 21; 44(24): 8873-82.

Example 11

The Design of Synthetic Libraries for Rapid Evolution of Enzymes Via Somatic Hypermutation Zinc-Finger Proteins Exhibiting Altered DNA-Binding Specificity Transcription factors bind to DNA and RNA and are located in the nucleus of eukaryotic cells. Transcription factors are candidates for somatic hypermutation as described herein to optimize the activity of the factors.

There are several families of transcription factors in eukaryotic organisms, of which, $Cys_2His_2$ zinc finger proteins are the most common. Zinc finger domains are stabilized by a single zinc metal coordinated by two histidine and two cysteine residues. Each domain contains approximately 30 amino acid residues; and each domain contains a mixed β-sheet-α-helix secondary structure, with residues in the α-helix mediating DNA or RNA binding contacts (FIG. 32). Proteins are commonly organized in tandem arrays of fingers, with each finger binding an adjacent tri-nucleotide sub-site (FIG. 32) or region within the major DNA or RNA groove, and with specific amino acids making specific DNA or RNA base contacts (see, FIG. 33, for example).

Transcription factors with engineered DNA-binding specificity provide a powerful and broadly applicable technology with scientific and therapeutic functions. For example, zinc finger proteins exhibiting specificity for a gene target could enhance or inhibit transcription, or sequester an mRNA message yet to be translated. Likewise, fusion of a zinc-finger protein with a protein domain containing, for example, an enzymatic, therapeutic, or diagnostic activity could provide another productive avenue for design of diagnostic and therapeutic proteins. Examples of zinc finger proteins include, but are not limited to, those that bind and fluoresce in recognition of a cancer specific DNA lesion or target a therapeutic moiety to a specific genomic region. In one aspect, zinc finger nucleases (ZFNs), have the potential to be a powerful tool for targeting genome alteration in plants, insects, and humans. ZFNs combine an engineered zinc finger protein joined to a non-specific endonuclease domain, capable of introducing double-stranded lesions that stimulate homologous and non-homologous recombination. The ability to modify a specific genomic region or target therapeutics of interest has utility in vitro and ex vivo research and gene therapy applications. The application of this technology relies on the ability to design zinc finger domains targeted to a genomic locus of interest.

The structures of numerous native and designed zinc-finger DNA complexes have been determined by x-ray crystallography and rudimentary rules have been established that describe the recognition of a DNA trinucleotide motif by a single zinc finger (Wolfe S A, Grant R A, Elrod-Erickson M, Pabo C O Beyond the "recognition code": structures of two Cys2His2 zinc finger/TATA box complexes *Structure* (2001) 9(8):717-23.). Rational, in silico design of zinc finger proteins that bind larger DNA motifs continues to be studied and various library approaches have been employed to create and select for larger binding sites with higher specificity, some involving multiple rounds of selection and construct manipulation (Rebar et al. 1994). In order to target binding of a zinc finger protein exhibiting specificity to a single region of the *Homo sapiens* genome, a recognition site of at least about 18 nucleotides is typically required. As each finger can utilize up to 4 or 5 amino acids to bind a tri-nucleotide motif and a static library of up to $(20^4)^5$, or $\sim 1 \times 10^{26}$ members, is needed to find an optimal DNA-binding sequence, well beyond the complexity of phage or ribosomal libraries (Roberts, R W, 1999).

Application of SHM to libraries of zinc finger proteins capable of undergoing targeted mutagenesis and selection provides an ideal solution to this design problem. Because somatic hypermutation can generate novel mutations at desirable and undesirable locations (one or more codons) not initially present in a library, several strategies are available for the generation and selection of novel binding proteins.

Each finger of a protein is composed of regions that are essential for their structural stability. To the extent possible, residues in these positions should be made cold to SHM to avoid mutations that could result in loss of function. An example of this is illustrated in FIG. 33: positions that must be conserved for zinc finger binding function to be retained are the cysteine and histidine residues that bind the zinc metal, and conserved aromatic and hydrophobic amino acids. In this example, the amino acid Valine precedes each cysteine in the finger shown in FIG. 33. Neither the valine or cysteine plays any role in DNA binding and recognition. Eight possible codon combinations can be used to encode these two amino acids. Scoring all possible 4096 bi-codon combinations, the hexanucleotide combination GTGTGC ranks $4060^{th}$ of 4096 possible sequences in its ability to recruit SHM; i.e., a "cold spot" to SHM and can be preferentially selected for preventing SHM mediated mutagenesis.

Each zinc finger contains regions and residues that are involved in binding to DNA via direct amino acid, nucleotide base contacts and these are, typically, the positions that are varied in static libraries to create binding variants. Two possible strategies are available for generating diversity at these positions using SHM, in combination or separately with static library approaches, as discussed below:

In a first approach of zinc finger design, it is feasible to identify a close variant of an existing zinc finger DNA-binding construct such as that seen in FIG. 32. In one aspect, an existing binding zinc finger is to be varied in order to bind a DNA sequence that differs at only one DNA base or at a single binding sub site. In this instance, one could create and select zinc finger binding variants that differ at only one or a few amino acid positions within a single finger, or within a localized region. In one non-limiting embodiment, using an existing zinc finger sequence optimized for recruitment of SHM-mediated mutagenesis, while making the remaining, invariant fingers cold to SHM, represents one design. For example, FIG. 32 shows a closer view of finger 1, where successive residues glutamate (E) and histidine (H) make contacts to the DNA. Four possible hex peptides encode EH, one of which, GAGCAC (SEQ ID NO: 419), is significantly more "hot" (susceptible) to SHM-mediated mutagenesis than the other three possibilities. Silent substitutions to the underlying DNA code that create "hot spots" for SHM are desirable. Similarly, silent "cold spot" substitutions to the DNA-binding residues and regions of zinc fingers 2 and 3 which are expected to remain invariant during the course of selection can also be employed.

Figure 1:
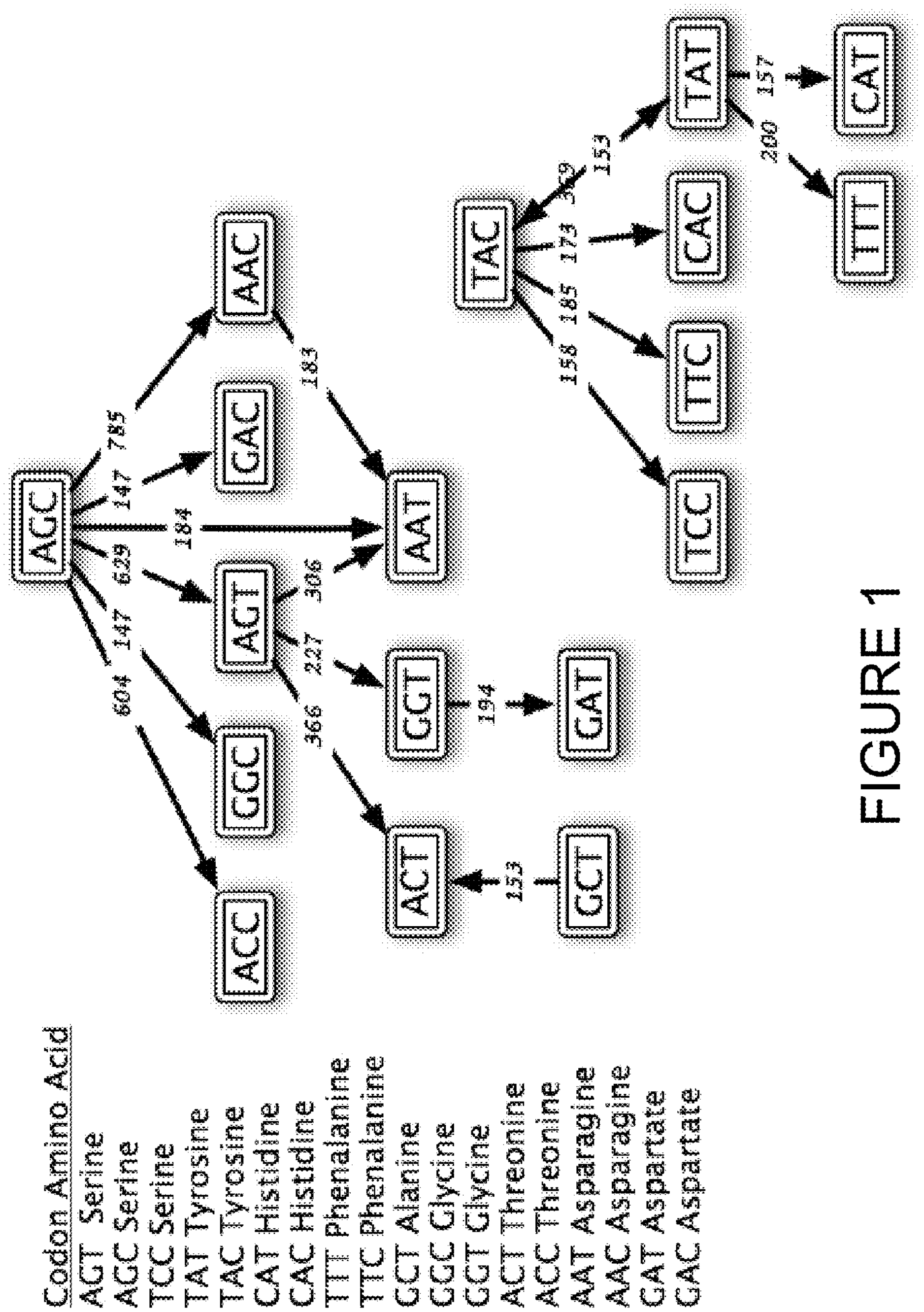
FIG. 1 and FIG. 2 show the 20 most common codon transitions, observed in CDRs and FWs during SHM mediated affinity maturation and demonstrate how simple frame shifts can determine the two radically different patterns of mutagenesis seen in CDRs and FWs. These observations lead directly to a hypothesis that both functional selection during affinity maturation and the reading frame context determines the amino acid diversity generated at SHM hot spot codons.
Figure 2:
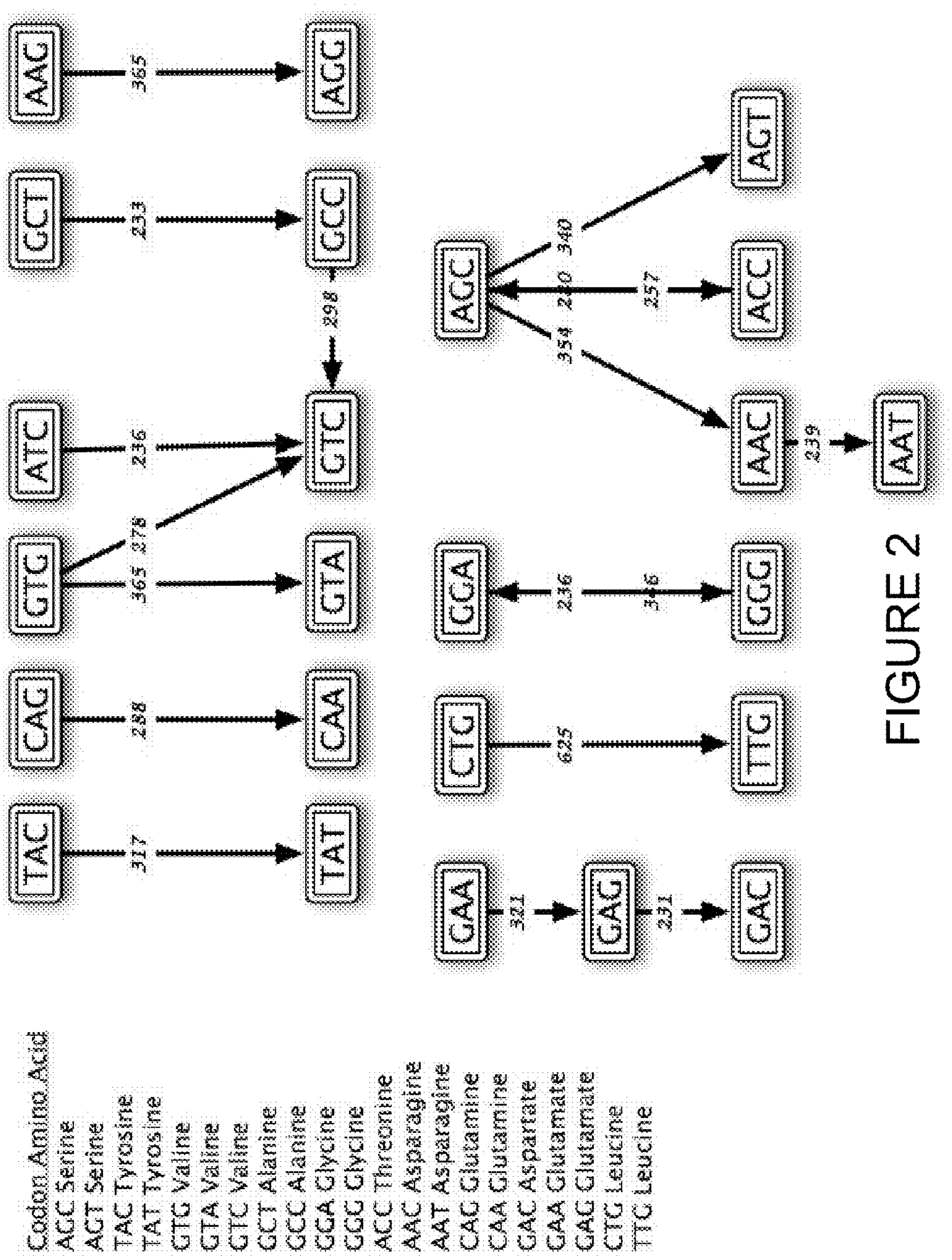

A second approach to library design is the introduction of "preferred hot spot SHM codons" at sites known to mediate DNA-binding contacts and at which diversity should be generated. One finding of the analysis of SHM "hot spots" is that some SHM hot spot motifs presented in the reading frame of reference plays a role in the generation of diversity. As shown in FIG. 1 and FIG. 2 the same SHM-mediated mutagenesis activity spectrum acting on the same hot spot motifs (under selective pressure), produces different outcomes when viewed within complementarity-determining regions (FIG. 1) and framework regions (FIG. 2) of immunoglobulin heavy and light chains. The basis for this finding is that the codon reading frame of reference for the hot spot has an impact on whether an induced mutation is silent (a change in codon that produces no change in amino acid, most common in framework regions) or whether the mutation produces amino acid diversity. As a consequence of this observation, certain codons, such as AGC (serine), TAT, (tyrosine), TAC (tyrosine), and AAC (asparagine), when arranged in randomly assembled libraries (FIG. 3 (WAC) and FIG. 5 (WRC)), generate tightly interleaved hot spots that are natural generators of amino acid diversity, as seen in affinity matured antibodies (FIG. 4 and FIG. 6). A similar approach may then be applied to library design of zinc-finger arrays. The regions known to contribute to DNA binding and specificity, particularly the n-terminal residues of each fingers alpha helix, may be constructed entirely from these simplified codon alphabets. As can be seen in FIG. 4 and FIG. 6, this approach, when paired with SHM-mediated mutagenesis rapid generates a diversity of amino acids (15 of the 20 amino acids) at each position. If we contrast this approach with the more typical construction of static libraries on a three zinc-finger construct, the differences in the resulting library complexity are clear. A simple NNK codon-based library, with 5 NNK library positions per finger and a total of three fingers, would have: $(4*4*2)^\wedge(5*3)=3.77*10^{22}$ potential members. In contrast, a WRC library representation of the same zinc finger library, with 5 randomized positions over three fingers, will have only $2^\wedge(5*3)=32768$ members. The difference, then, is a static library that cannot be even partially represented using any selection techniques, versus SHM-based libraries that can easily and redundantly be presented using a standard selection methods. Finally, these WAC and WRC library methodologies may be paired with strategies, as outlined above, for making functionally conserved and important regions cold to SHM-mediated mutagenesis.

Example 11

References

1. Bae, K. H., Do Kwon, Y., Shin, H. C., Hwang, M. S., Ryu, E. H., Park, K. S., Yang, H. Y., Lee, D. K., Lee, Y., Park, J., Sun Kwon, H., Kim, H W., Yeh, B. I., Lee, H. W., Hyung Sohn, S., Yoon, J., Seol, W. & Kim, J. S. (2003) Human zinc fingers as building blocks in the construction of artificial transcription factors Nat. Biotech. 21, 275-80.

2. Bae, K. H. & Kim, J. S. (2006) One-step selection of artificial transcription factors using an in vivo screening system Mol Cells 21: 376-380.
3. Jamieson, A. C., Miller, J. C. & Pabo, C. O. (2003) Drug Discovery with Engineered Zinc-Finger Proteins Nature Reviews Drug Discovery 2, 361-368.
4. Hurt, J. A., Thibodeau, S. A., Hirsh, A. S., Pabo, C. O. & Joung, J. K. (2003) Highly specific zinc finger proteins obtained by directed domain shuffling and cell-based selection Proc Natl Acad Sci USA 100, 12271-6.
5. Greisman, H. A. & Pabo, C. O. (1997) A general strategy for selecting high-affinity zinc finger proteins for diverse DNA target sites Science 275, 657-61.
6. Joung, J. K., Ramm, E. I. & Pabo, C. O. (2000) A bacterial two-hybrid selection system for studying protein-DNA and protein-protein interactions Proc Natl Acad Sci USA 97, 7382-7.
7. Rebar, E. J. & Pabo, C. O. (1994) Zinc finger phage: affinity selection of fingers with new DNA-binding specificities Science 263, 671-3.
8. Wolfe, S. A., Greisman, H. A., Ramm, E. I. & Pabo, C. O. (1999) Analysis of zinc fingers optimized via phage display: evaluating the utility of a recognition code J Mol Biol 285, 1917-34.
9. Bibikova, M., Beumer, K., Trautman, J. K. & Carroll, D. (2003) Enhancing gene targeting with designed zinc finger nucleases Science 300, 764.
10. Bibikova, M., Golic, M., Golic, K. G. & Carroll, D. (2002) Targeted chromosomal cleavage and mutagenesis in *Drosophila* using zinc-finger nucleases Genetics 161, 1169-75.
11. Porteus, M. H. & Baltimore, D. (2003) Chimeric nucleases stimulate gene targeting in human cells Science 300, 763.
12. Roberts, R. W. (1999) Totally in vitro protein selection using mRNA-protein fusions and ribosome display Curr Opin Chem Biol 3(3):268-73.

Example 12

Design of Optimized Seed Libraries for SHM

Affinity matured antibodies were analyzed in order to characterize nucleotide motifs that recruit somatic hypermutation (SHM) to the site of mutation, and to develop a set of predictive algorithms that determine how any DNA codon, motif, or family of sequences may evolve over time. Application of these findings to in vitro SHM protein evolution, construct and library design are discussed.

Materials and Methods

Identification of SHM Events

Human IGHV, IGKV, and IGLV germline antibody sequences and their allelic forms were assembled from multiple online sources, including the NCBI (www.ncbi.nlm.nih.gov/entrez/), the IMGT antibody database (imgt.cines.fr/), and the VBASE database of human antibody genes (vbase.mrc-cpe.cam.ac.uk/). A total of 232 IGHV, 56 IGKV, and 66 IGLV variable domain germline alleles were identified. Additional structural information, such as those codons falling within framework and complementarity-determining regions (CDRs), Kabat numbering, and the canonical loop turn structures of CDRs were also annotated.

The sequences of human affinity matured antibodies were collected from the antibody database at the National Center for Bioinformatics (NCBI) on Apr. 1, 2007 which can be found at the following world wide web site: ftp.ncbi.nih.gov/blast/db/fasta/igSeqNt.gz.

Our strategy was to first identify the likely originating germline sequence for each affinity matured antibody, followed by an analysis of those residues that undergone modification as a result of SHM-mediated affinity maturation. An un-gapped BLAST alignment between a potential germline antecedent and an affinity matured antibody was accepted if it provided greater than 94% sequence identify over the entire length of the antibody variable region, provided a best match relative to other potential originating germline sequences, and the sequences were not identical. Because this database contains a variety of antibody sequences (IgA, IgE, IgG, IgD, IgM and subtypes thereof.) from both germline and affinity matured antibodies, care was taken to identify accurately the likely changes that arose from SHM-mediated alterations of germline IGHV, IGKV and IGLV sequences. Mutations identified at the 5' and 3' portions (3 residues) of the coding region alignment were not considered further in this analysis.

In this manner, a total of 106909 IGHV, 24378 IGKV and 24965 IGLV mutations were identified in 12956, 4165 and 3811 alignments to germline sequences, respectively.

Identifying DNA Hot Spots/Cold Spots for SHM

DNA sequences that promote or discourage SHM were identified in the following manner: no assumptions were made regarding the size of the SHM hot and cold motif. Likewise, the position of a mutation relative to the site of the motif was allowed to vary. For each mutation, identified as described above, we selected a nucleotide 'window' around the site, usually 9 or 15 nucleotides in length, likely to encompass any motif responsible for recruiting SHM machinery (activation-induced cytidine deaminase (AID) and error-prone polymerases). Within each X-mer nucleotide window, we searched exhaustively for all motifs of length k, where an occurrence includes those sequences that vary at up to c positions within the k-mer motif.

Our measure for the statistical significance of SHM motif occurrences compares the number of times a k-mer motif is observed ($N_s$) in all N X-mer mutation windows with how often it would be expected to occur at random ($Np_s$) (where N is the total number of mutations and $p_s$ is the probability of observing one or more motif occurrences within each X-mer window). A Markov chain was used to estimate $p_s$ for each k-mer motif as described previously (Tompa 1999), using nucleotide transition probabilities taken from human germline IGHV sequences, shown below.

$$ij = \begin{bmatrix} 0.169 & 0.270 & 0.381 & 0.179 \\ 0.289 & 0.287 & 0.101 & 0.321 \\ 0.239 & 0.219 & 0.314 & 0.227 \\ 0.155 & 0.278 & 0.413 & 0.154 \end{bmatrix} \text{ where } i, j \in \{A, C, T, G\}$$

The difference in the number of observed to expected motifs occurrences is given by $N_s - Np_s$, where $\sqrt{Np_s(1-p_s)}$ represents the standard deviation of $Np_s$, and the z-score for each motif is given by $$M_s = (N_s - Np_s)/\sqrt{Np_s(1-p_s)}$$

where $M_s$ is the number of standard deviations by which the observed number of motif occurrences exceeds the expected value. This metric was used to rank order all possible motifs that might recruit or repel SHM.

Results

Analysis of mutations originating from SHM in antibodies undergoing affinity maturation led to several important insights. Preferred nucleotide sequences are used at hot spots to attract the SHM machinery (see for example, Tables 2, 3, 6 and 9), and these hot spots are positioned specifically with regard to the codon reading frame. As shown in FIG. 34, the 3-mer nucleotide motif AGC represents a preferred site for somatic hypermutation events (i.e., one preferred SHM codon). In FIG. 34, the number of mutations observed in the analysis is shown as the line graph in each sub-graph at each position of the codon in the AGC motif found in framework (FR), and complementarity determining regions (CDR) for the heavy and light chains of antibodies. The font size for each nucleotide position of the motif shows how often each nucleotide which serves as the first position of the codon reading frame. Within framework regions, no one reading frame dominates, whereas within CDRs, the first position (A) of the AGC SHM motif is almost universally used as the first position of the codon.

The result is that certain hot spot codons (and therefore amino acids) placed within a specific reading frame context account for the majority of somatic hypermutation events and the resulting diversity created from these events. FIG. 35 shows the 20 most hot spot codon hypermutation transition events within the FR and CDR regions of heavy chain antibodies, where the numbers labeling the arrows indicate how often a codon transition event was observed. The codons AGC and AGT (Serine), and to a lesser extent TAC and TAT (Tyrosine), account for ~50% of the originating mutations observed in affinity matured antibodies. Use of these hot spot codons within the correct reading frame, combined with affinity maturation leads to many fewer observed silent mutations within CDRs (highlighted by dotted circles in FIG. 35). Also, secondary and tertiary SHM events starting from the AGC or TAC codons lead to the potential creation of many of the 20 possible amino acids.

We developed a probabilistic Markov chain model for predicting the temporal diversity generated by SHM which results from SHM acting on a single nucleotide codon, degenerate codon or SHM motif. A Markov chain is a discrete-time stochastic process that can used to calculate all future time states of a system. At each point in time, the system may have changed states from the state the system was in the moment before, or the system may have stayed in the same state. Formally, this can be written as:

$$Pr(X_{n+1}=\chi|X_\eta=\chi_n, \ldots, X_1=\chi_1)=Pr(X_{n+1}=\chi|X_n=\chi_n).$$

Where $X_1$, $X_2$, $X_3$, . . . represent a sequence of random variables with the Markov property, namely that, given the present state, the future and past states are independent. The probability of going from one state i to state j in n time steps is defined as:

$$P^{(n)}_{ij}=Pr(X_n=j|X_0=i)$$

And the single-step transition as $$P_{ij}=Pr(X_i=j|X_0=I)$$

The possible values of $X_i$ form a countable set S called the state space of the chain. Markov chains are often described by a directed graph, where the edges are labeled by the probabilities of going from one state to the other states.

Changes of state are called transitions. In this example, we chose to apply this method to codons undergoing SHM, where the system may exist in any one of 64 possible codon states, and where any codon state may be accessible from a different codon if there is a non-zero probability of a SHM event connecting those two states. Other equivalent methods, including Markov chain Monte Carlo (MCMC), continuous-time Markov chains, and hidden Markov models (HMM), may also be used to solve this time-dependent evolution problem.

The system begins with a probability distribution of starting codon states, whose total probability is equal to 1. For example, a system starting with AAA as the only starting state would be written in matrix form as: [AAA, AAC, AAG, . . . , TTG, TTT]=[1, 0, 0, . . . , 0, 0].

Likewise, a system starting with a degenerate codon composed of half AAA and half TTT would be written in matrix form as: [AAA, AAC, AAG, . . . , TTG, TTT]=[0.5, 0, 0, . . . , 0, 0.5].

A matrix describing the systems transition probabilities between codon states was derived from an analysis of SHM events in heavy and light chain antibody sequences (see Materials and Methods), where each column of the matrix has a normalized probability equal to one. Transition frequencies are presented in FIGS. 36A, 36B, 36C, and 36D.

The marginal distribution Pr (Xn=x) is the distribution over states at time n, and the initial distribution is Pr ($X_0$=x). The evolution of the process through one time step is described by a standard by the equation:

$$Pr(X_n=j)=\Sigma_{r\in S}p_{rj}Pr(X_{n-1}=r)=\Sigma_{r\in S}p_{rj}^{(n)}Pr(X_0=r).$$

where ‘n’ is an integer value and the starting codon distribution has evolved over ‘n’ iterative rounds, cording to the given state transition probabilities.

This system therefore depicts how a SHM system, starting with a specific sequence would evolve over multiple rounds of evolution given any starting codon probability distribution.

FIGS. 37-44 show the accumulation of codon states and their corresponding amino acid frequencies as a function of various rounds of SHM-mediated evolution given different sets of starting codon frequencies.

FIGS. 37 and 38 show the evolution of the codon AGC (serine), a preferred SHM codon, and the resulting amino acid frequencies over 50 rounds of SHM-mediated mutagenesis, as calculated in our Markov chain model. Within a few rounds of mutation, many other amino acids become common. This finding supports FIG. 35, which shows that single codons and their amino acids, in particular AGC/AGT (Serine) and TAC/TAT (Tyrosine), can be utilized by SHM to drive creation of most of the other amino acids in a natural context.

By comparison, equivalent calculations starting from a TCG, non-preferred codon, also coding for serine, are shown in FIGS. 39 and 40, and demonstrate that such non-preferred codons are not just poorer substrates for SHM, but that they generate less diversity as a function of time then do preferred SHM codons.

FIGS. 41 and 42 show the rapid evolution of a mixed AGC/TAC, “WRC motif” comprising preferred SHM codons for Serine and Tyrosine) that prescribes rapid and effective generation of amino acid diversity.

FIGS. 43 and 44 show the evolution of a GGT codon (glycine), with the immediate evolution of codons arising from single mutation events, such as GAT (aspartate), GCT (alanine), and AGT (serine). Secondary mutation events acting on these new codons give rise to a tertiary set of codons. For instance, both AGT and GGT under SHM produce the codon AAT, leading to acquisition of asparagine at this position.

These results confirm that by developing a complete understanding of the probability that a codon will be subject to SHM, in conjunction with specific insight into how these sequences are utilized to generate amino acid diversity, enables the development of specific algorithms that provide for the predictive creation of diversity in a heterologous system undergoing SHM. As shown below, by combining this understanding with knowledge of the most favorable positions for mutations actually identified from a highly selected evolving system, it is possible to develop a rapid and effective system for mutagenesis.

Example 13

HyHEL10 Example of SHM-Mediated Affinity Maturation

An advantage of this SHM-mediated approach to creating diversity is that relatively simple libraries can be used to create an exceptionally large repertoire of sequences during selection and evolution. In order to demonstrate this approach, we affinity matured an existing antibody that has been well described in the literature. HyHEL10 is a mouse antibody first derived from a hybridoma to the antigen hen egg white lysozyme (HEL). The antigen-antibody complex has been fully characterized thermodynamically and by an atom resolution crystal structure.

For example, the constructs listed in Table 15 define a set of antibodies, and sequence variants thereof that have fully defined sequences and affinities, e.g., Pons et al., (1999) Protein Science 8:958-68; and Smith-Gill et al., (1984) J. Immunology 132:963.

TABLE 15

Hen Egg Lysozyme antibody constructs

| Mutations | DNA Sequence | Kd | koff | kon |
|---|---|---|---|---|
| wt LC/wt HC | GGC30-AAC31-AAC32-CTA33 | 3.93E−11 | 8.6E−05 | 2.2E+06 |
| Light chain variants | | | | |
| LC G30(silent)N31A/wt HC | GG**A**30-**GCT**31-AAC32-CTA33 | 1.48E−09 | 8.29E−03 | 5.61E+06 |
| N31G LC/wt HC | GGC30-**GGT**31-AAC32-CTA33 | 2.78E−09 | 1.21E−02 | 4.33E+06 |
| N31S LC/wt HC | GGC30-**AGC**31-AAC32-CTA33 | 7.10E−10 | 9.70E−04 | 1.40E+06 |
| N32S LC/wt HC | GGC30-AAC31-**AGC**32-CTA33 | 1.00E−10 | 1.90E−04 | 1.90E+06 |
| N32G LC/wt HC | GGC30-AAC31-**GGT**32-CTA33 | 6.29E−10 | 2.85E−03 | 4.53E+06 |
| N31SN32S/wt HC | GGC30-**AGC**31-**AGC**32-CTA33 | 2.50E−09 | 6.10E−03 | 2.40E+06 |
| LC L33(silent)/wt HC | GGC30-AAC31-AAC32-TTA33 | 5.96E−11 | 9.33E−05 | 1.56E+06 |
| N31D LC/wt HC | GGC30-**GAT**31-AAC32-CTA33 | 1.1E−10 | | |
| Heavy chain variants | | | | |
| wt LC/Y50A HC | GGG49-**GC**C50-GTA51 | Not detectable | | |
| wt LC/Y33A HC | GAT32-**GC**C33-TGG34 | 2.0E−08 | 4.45E−02 | 2.13E+06 |
| Mixed heavy and light chain variants | | | | |
| LC N31G/Y33A HC | see above | 7.0E−06 | | |
| LC N32G/Y33A HC | see above | 2.00E−08 | | |

Nucleotides in bold represent codons in which defined mutations were made to introduce codons that have been optimized for SHM to enable efficient somatic hypermutation, compared to the "wild type" (HyHEL10) sequence ("wt"), as defined below. LC=Light Chain; HC=heavy Chain.

These positions are previously known to be important for binding, and to have been naturally mutated from the corresponding germline sequence during somatic hypermutation. Specifically, the light chain sequence of HyHEL10 contains the residue Asn31 located within CDR1 that makes a thermodynamically important contact to the HEL antigen residue Lys96. The Gly31 mutant (codon GGT) of HyHEL10 has a dissociation constant of around 2.5 nM, whereas the Asp31 (codon GAT) mutant of HyHEL10 has dissociation constant of around 110 pM, and the wild-type Asn31 (codon of HyHEL10 has a dissociation constant of around 30 pM. We subjected a clonal population of HyHEL10 Gly31 (GGT) mutants, presented on the surface of HEK293 cells, to iterative rounds of FACS based selection against 50 pM FITC-HEL in the presence of SHM as described below.

A. Synthesis and Cloning of ("Wild Type") HyHEL10 Heavy and Light Chain Constructs The prototypic HyHEL10 heavy chain and light chain expression vectors were created by starting with an episomal expression vector, as described in Example 4 (vector format 1; U.S. Application No. 60/902,414, entitled "Somatic Hypermutation Systems"), and using standard molecular genetic manipulations as follows: the original cold puromycin resistance marker in vector AB102 was replaced with cold bsd or with pur using the NgoMIV and XbaI restriction sites, to generate the vectors AB187 and AB197, respectively.

A slightly longer, transcriptionally more robust version of the CMV promoter was exchanged for the original sequence found in AB102 using NheI (the mcs2 restriction site most proximal to the CMV promoter) and SbfI (the most CMV-proximal mcs1 site). The original AB102 CMV promoter included 553 bp of the unmodified CMV sequence upstream from the first T of the TATA box, while the AB187 and AB197 versions included 645 bp upstream from the first T of the TATA box.

The nucleotide sequences for the "wild type" HyHEL10 heavy and light chains (Pons et al., (1999) Protein Science 8:958-68) (sequences below) were synthesized (DNA 2.0, (Menlo Park, Calif.)). For cloning purposes, the heavy chain was bordered by BglII and AscI restriction sites, and the light chain was bounded by SacI and AscI restriction sites.

In order to express HyHEL10 IgG and its mutants thereof on the cell surface, the heavy chain was created as a chimeric molecule with the following features: Kozak consensus sequence; HyHEL10 heavy chain variable region; full-length murine IgG1 constant region; XhoI site; Murine H2kk (MHC type I) peri-transmembrane domain, transmembrane domain and cytoplasmic domain. The H2kk sequences were determined from accession number AK153419 at the National Center for Biotechnology Information (NCBI) nucleotide database.

The nucleotide sequence of the full length chimeric, cell-surface associated HyHEL10 heavy chain is as listed below:

In this sequence, the BglII site is underlined; Kozak sequence is underlined and italicized; stop codon is underlined and bolded; XhoI site is indicated by boxed nucleotides; double underlined sequences are derived from H2kk. The AscI cloning site 3' to the TGA stop codon is indicated by italicized nucleotides.

AGATCTGCTTGAATCCGCGGATAAGAGGACTAGTATTCGTCTCACTAGGGAGAGCTC*ACCACCATG*

AACAAGTTGCTGTGCTGCGCGCTCGTGTTTCTGGACATCTCCATTAAGTGGACCACCCAGGACGTGCAGCT

TCAGGAGTCAGGACCTAGCCTCGTGAAACCTTCTCAGACTCTGTCCCTCACCTGTTCTGTCACTGGCGACTC

CATCACCAGTGATTACTGGAGCTGGATCCGGAAATTCCCAGGGAATAGACTTGAGTACATGGGGTACGTAA

GCTACAGTGGTAGCACTTACTACAATCCATCTCTCAAAAGTCGAATCTCCATCACCCGAGACACATCCAAG

AACCAGTACTACCTGGATTTGAATTCTGTGACTACTGAGGACACAGCCACATATTACTGTGCAAACTGGGA

CGGTGATTACTGGGGCCAAGGGACTCTGGTCACTGTCTCTGCAGCCAAAACGACACCCCCATCTGTCTATC

CACTGGCCCCTGGATCTGCTGCCCAAACTAACTCCATGGTGACCCTGGGATGCCTGGTCAAGGGCTATTTC

CCTGAGCCAGTGACAGTGACCTGGAACTCTGGATCCCTGTCCAGCGGTGTGCACACCTTCCCAGCTGTCCT

GCAGTCTGACCTCTACACTCTGAGCAGCTCAGTGACTGTCCCCTCCAGCCCTCGGCCCAGCGAGACCGTCA

CCTGCAACGTTGCCCACCCGGCCAGCAGCACCAAGGTGGACAAGAAAATTGTGCCCAGGGATTGTGGTTGT

AAGCCTTGCATATGTACAGTCCCAGAAGTATCATCTGTCTTCATCTTCCCCCCAAAGCCCAAGGATGTGCTC

ACCATTACTCTGACTCCTAAGGTCACGTGTGTTGTGGTAGACATCAGCAAGGATGATCCCGAGGTCCAGTT

CAGCTGGTTTGTAGATGATGTGGAGGTGCACACAGCTCAGACGCAACCCCGGGAGGAGCAGTTCAACAGC

ACTTTCCGCTCAGTCAGTGAACTTCCCATCATGCACCAGGACTGGCTCAATGGCAAGGAGTTCAAATGCAG

GGTCAACAGTGCAGCTTTCCCTGCCCCCATCGAGAAAACCATCTCCAAAACCAAAGGCAGACCGAAGGCT

CCACAGGTGTACACCATTCCACCTCCCAAGGAGCAGATGGCCAAGGATAAAGTCAGTCTGACCTGCATGAT

AACAGACTTCTTCCCTGAAGACATTACTGTGGAGTGGCAGTGGAATGGGCAGCCAGCGGAGAACTACAAG

AACACTCAGCCCATCATGAACACGAATGGCTCTTACTTCGTCTACAGCAAGCTCAATGTGCAGAAGAGCAA

CTGGGAGGCAGGAAATACTTTCACCTGCTCTGTGTTACATGAGGGCCTGCACAACCACCATACTGAGAAGA

GCCTCTCCCACTCTCCTGGTAAACTCGAGCCTCCTCCATCCACTGTCTCCAACATGGCGACCGTTGCTGTTC

TGGTTGTCCTTGGAGCTGCAATAGTCACTGGAGCTGTGGTGGCTTTTGTGATGAAGATGAGAAGGAGAAAC

ACAGGTGGAAAAGGAGGGGACTATGCTCTGGCTCCAGGCTCCCAGACCTCTGATCTGTCTCTCCCAGATTG

TAAAGTGATGGTTCATGACCCTCATTCTCTAGCGTGAGGCCGGCCAA*GGCGCGCC*; SEQ ID NO: 420.

The amino acid sequence of the chimeric, cell-surface associated HyHEL10 heavy chain is as listed below. The two amino acids (Leu-Glu) encoded by the synthetic XhoI site are marked by bold-and-underlined; the bold-underline Glu also represents the most amino proximal amino acid of the H2kk domain; double underline indicates the putative transmembrane domain; and the asterisk indicates a stop codon.

(SEQ ID NO: 421)

```
MNKLLCCALVFLDISIKWTTQDVQLQESGPSLVKPSQTLSLTCSVTGDSITSDYWSWIRKFPGNRLEYM

GYVSYSGSTYYNPSLKSRISITRDTSKNQYYLDLNSVTTEDTATYYCANWDGDYWGQGTLVTVSAAKTTPPSV

YPLAPGSAAQTNSMVTLGCLVKGYFPEPVTVTWNSGSLSSGVHTFPAVLQSDLYTLSSSVTVPSSPRPSETVTCN

VAHPASSTKVDKKIVPRDCGCKPCICTVPEVSSVFIFPPKPKDVLTITLTPKVTCVVVDISKDDPEVQFSWFVDDV

EVHTAQTQPREEQFNSTFRSVSELPIMHQDWLNGKEFKCRVNSAAFPAPIEKTISKTKGRPKAPQVYTIPPPKEQ

MAKDKVSLTCMITDFFPEDITVEWQWNGQPAENYKNTQPIMNTNGSYFVYSKLNVQKSNWEAGNTFTCSVLH
```

-continued

EGLHNHHTEKSLSHSPGKLEPPPSTVSNMATVAVLVVLGAAIVTGAVVAFVMKMRRRNTGGKGGDYALAPGS

QTSDLSLPDCKVMVHDPHSLA*

The amino acid and nucleotide sequence of the ("wild type") HyHEL10 kappa light chain is provided below.

Amino acid sequence of the HyHEL10 kappa light chain. Asterisk indicates stop codon.

(SEQ ID NO: 422)

MNKLLCCALVFLDISIKWTTQDIVLTQSPATLSVTPGNSVSLSCRASQSIGNNLHWYQQKSHESPRLLIK

YASQSISGIPSRFSGSGSGTDFTLSINSVETEDFGMYFCQQSNSWPYTFGGGTKLEIKRADAAPTVSIFPPSSEQLTS

GGASVVCFLNNFYPKDINVKWKIDGSERQNGVLNSWTDQDSKDSTYSMSSTLTLTKDEYERHNSYTCEATHKT

STSPIVKSFNRNEC*

The nucleotide sequence of the HyHEL10 kappa light chain. Start and stop codons are underlined. SacI and AscI cloning sites are bolded.

(SEQ ID NO: 423)

GAGCTCACCACAATGAACAAGTTGCTGTGCTGCGCGCTCGTGTTTCTGGACATCTCCATTAAGTGG

ACCACCCAGGATATTGTGCTAACTCAGTCTCCAGCCACCCTGTCTGTGACTCCAGGAAATAGCGTCAGTCTT

TCCTGCAGGGCCAGCCAAAGTATTGGCAACAACCTACACTGGTATCAACAAAAATCACATGAGTCTCCAAG

GCTTCTCATCAAGTATGCTTCCCAGTCCATCTCTGGGATCCCCTCCAGGTTCAGTGGCAGTGGATCAGGGAC

AGATTTCACTCTCAGTATCAACAGTGTGGAGACTGAAGATTTTGGAATGTATTTCTGTCAACAGAGTAACA

GCTGGCCTTACACGTTCGGAGGGGGGACCAAGCTGGAAATAAAACGGGCTGATGCTGCACCAACTGTATC

CATCTTCCCACCATCCAGTGAGCAGTTAACATCTGGAGGTGCCTCAGTCGTGTGCTTCTTGAACAACTTCTA

CCCCAAAGACATCAATGTCAAGTGGAAGATTGATGGCAGTGAACGACAAAATGGCGTCCTGAACAGTTGG

ACTGATCAGGACAGCAAAGACAGCACCTACAGCATGAGCAGCACCCTCACGTTGACCAAGGACGAGTATG

AACGACATAACAGCTATACCTGTGAGGCCACTCACAAGACATCAACTTCACCCATTGTCAAGAGCTTCAAC

AGGAATGAGTGTTGAGGCGCGCC

Mutants of these "wild type" heavy and light chains, as well as the germline sequence, as described above, Table 15, were created using site directed mutagenesis using the QuickChange® Multi Site Directed Mutagenesis kit (Stratagene, CA); sequences were confirmed by sequencing.

B. Transfection of Cells

A stable HEK-293 cell line expressing the [N31G LC/wt HC] anti-HEL immunoglobulin and AID activity was generated by seeding a T75 culture flask with $3\times10^6$ HEK-293 cells in 10 mL DMEM medium containing 10% FBS (Invitrogen Corporation, Carlsbad, Calif.). The following day, 500 µL OptiMEM (Invitrogen Corporation, Carlsbad, Calif.), 20 µL HD-Fugene (Roche Diagnostics Corporation, Indianapolis, Ind.), 1 µg of the optimized AID expression vector, (Example 4) and 1.5 µg each of the heavy and light chain expression vectors were mixed and incubated for approximately 25-30 minutes at room temperature. After incubation this mixture was added drop-wise to the cell culture medium.

Approximately three days post-transfection, the cell growth medium was exchanged with 10 mL DMEM medium containing 10% FBS, 50 µg/mL Geneticin, 10 µL/mL Antibiotic-Antimycotic Solution, 1.5 µg/mL puromycin, 15 µg/mL blasticidin, and 350 µg/mL hygromycin (Invitrogen Corporation, Carlsbad, Calif.) and the cells were incubated for approximately four weeks with periodic reseeding and exchange of the cell culture medium. At the end of the selection period, the cell culture was expanded, archived and a T75 cell culture flask was seeded with $3\times10^6$ HEK-293 cells that were expressing the [N31G LC/wt HC] anti-HEL immunoglobulin and AID activity in 10 mL DMEM medium containing 10% FBS (Invitrogen Corporation, Carlsbad, Calif.). The following day, 500 µL OptiMEM (Invitrogen Corporation, Carlsbad, Calif.), 20 µL HD-Fugene (Roche Diagnostics Corporation, Indianapolis, Ind.), and 3 µg of the AID expression vector DNA described above, were mixed and incubated for approximately 25-30 minutes at room temperature. After incubation, this mixture was added drop-wise to the cell culture medium. After approximately one week of incubation, the original stable HEK-293 cell line expressing the [N31G LC/wt HC] anti-HEL immunoglobulin and AID as well as the culture that has been transiently transfected with additional AID expression vector were prepared for cell sorting.

C. Selection of Higher Affinity Mutants:

The selected HEK-293 cell line expressing the [N31G LC/wt HC] anti-HEL immunoglobulin and AID activity as well as the culture that had been transiently transfected with additional AID expression vector were prepared for cell sorting by collecting the cells, washing with an equal volume of PBS solution, pH 7.2 and resuspending 1e07 cells from each culture in ice-cold PBS solution, pH 7.2 containing 1% (weight/volume) BSA and either 50 pM or 500 pM HEL-FITC at a final cell concentration of 2e05 cells/mL.

Round 1

Hen Egg lysozyme (Sigma Aldrich, MO) was labeled with fluorescein iosthiocyanate (FITC) using the EZ-Label™ FITC protein labeling kit (Pierce, Rockford, Ill.) following the manufacturers directions.

Following incubation for 30 minutes at 4° C., the cells were pelleted by centrifugation and the volume reduced to 200 μL. After transfer to sterile 3 mL tubes, a 1:500 dilution of PE-conjugated goat-anti-mouse immunoglobulin was added to the cells and incubation continued at 4° C. for 30 minutes. The cells were then pelleted by centrifugation and resuspended in 1 mL of sterile ice-cold PBS solution, pH 7.2 containing 1% (weight/volume) BSA plus 2 nanograms/milliliter DAPI. Live IgG-positive cells that were positive for FITC (excitation with a 150 mW 488 nm laser, collection through a 528/38 filter) were isolated by fluorescence activated cell sorting (FACS) using a Cytopiea Influx Cell Sorter at a flow rate of approximately 10,000 events/second (FIG. 45). FACS windows were calibrated to ensure that higher affinity clones could be discriminated using this approach using HyHEL expressing cells.

The results show a small population of cells that in all cases is clearly separated from the main bulk of non-mutated cells. In cells that have been newly transfected with the AID expression (panels B and D of FIG. 45), this population of cells is consistently larger than in the populations of cells that did not receive additional AID expression vector (panels A and C in FIG. 45). These cells were cultured as described below.

Sorted cells were placed in 3 mL DMEM medium containing 10% FBS, 50 μg/mL Geneticin, 10 μL/mL Antibiotic-Antimycotic solution, 1.5 μg/mL puromycin, 15 μg/mL blasticidin, and 350 μg/mL hygromycin (Invitrogen Corporation, Carlsbad, Calif.) in one well of a 6-well plate. The cells were cultured until confluent and then archived and reseeded in one well of a 6-well plate at a cell density of $4\times10^5$ cells/mL. The next day, 100 μL OptiMEM (Invitrogen Corporation, Carlsbad, Calif.), 4 μL Fugene6 (Roche Diagnostics Corporation, Indianapolis, Ind.), and 1 μg of the AID expression vector plasmid DNA were mixed and incubated for approximately 25-30 minutes at room temperature. After incubation this mixture was added drop-wise to the cell culture medium and the cells were cultured and expanded for approximately 7 days. Samples of cells were also taken for sequence analysis.

Round 2

Cells selected using FITC-HEL in the first round, as described above, were then subjected to the same selection conditions (i.e., incubation with either 50 or 500 pM FITC-labeled HEL) in a second round of FACS sorting. Fifty milliliters (1e07 cells) of the cells selected from the first round were incubated in an ice-cold PBS solution, pH 7.2 containing 1% (weight/volume) BSA and either approximately 50 pM or 500 pM HEL-FITC for 30 minutes at 4° C. The cell mixture was pelleted, the volume was reduced to 200 μL and the cells were transferred to sterile 3 ml tubes. A 1:500 dilution of PE-conjugated goat-anti-mouse immunoglobulin was added to the cells and the cells were incubated at 4° C. for 30 minutes. The cells were then pelleted and resuspended 1 mL of an ice-cold PBS solution, pH 7.2 containing 1% (weight/volume) BSA plus 2 nanograms/milliliter DAPI. Live IgG-positive cells that were positive for FITC (excitation with a 150 mW 488 nm laser, collection through a 528/38 filter) were isolated by fluorescence activated cell sorting using a Cytopiea Influx Cell Sorter at a flow rate of approximately 10,000 events/second (FIG. 46).

The results of the second sort show a significantly larger population of cells exhibiting high affinity HEL binding, consistent with the formation of higher affinity mutants by SHM during growth and culture. In cells that have been newly transfected with the AID expression vector, and then incubated with 500 pM HEL (panel D of FIG. 46) this is clearly a much larger population of highly fluorescent cells, 25.9% of the population versus 6.88% compared cells that did not receive additional AID expression vector (panel C in FIG. 46). These results demonstrate that re-transformation with the AID expression vector is effective in promoting a significant improvement in mutagenesis rate.

Continuing this process for 2 additional rounds of mutation with stringent gating on the selected cells (Shown in FIG. 47, panel A) resulted in a profound and significant shift in the binding properties of the selected cells (FIG. 47, panel B).

D. Production of Secreted Immunoglobulins for Functional Analysis

Heavy and light chains of interest may be produced in a secreted form for further functional analysis as described below. In the case of heavy chains obtained from the surface displayed libraries, these are processed as described in Example 3 (i.e., by digestion with XhoI, followed by religation), to remove the transmembrane domain, enabling direct secretion of the antibody into the media.

Approximately one day prior to transfection, $3\times10^6$ HEK-293 cells were seeded in 10 mL DMEM/10% FBS medium in a T75 culture flask and incubated overnight at 37° C. and 5% $CO_2$. On the day of transfection, 500 μL OptiMEM (Invitrogen Corporation, Carlsbad, Calif.), 20 μL HD-Fugene (Roche Diagnostics Corporation, Indianapolis, Ind.), and 1.5 μg each of heavy and light chain expression vectors were mixed and incubated for approximately 25-30 minutes at room temperature. After incubation this mixture was added drop-wise to the cell culture medium.

Approximately three days post-transfection, the cell growth medium was exchanged with 10 mL Freestyle medium (Invitrogen Corporation, Carlsbad, Calif.) and the cells were incubated for an additional 7 days. At the end of the incubation period, the cell culture supernatants were harvested and filtered through a sterile 0.2 μm filter. The secreted immunoglobulins were isolated via standard protein A affinity column chromatography, prior to BIACORE analysis, as described below.

HEL was immobilized onto a research grade CM5 sensor chip using standard amine coupling. Each of three surfaces was first activated for seven minutes using a 1:1 mixture of 0.1 mM N-hydroxysuccinimide (NHS) and 0.4 mM 1-ethyl-3-(3-dimethylaminopropyl)-carbodimide (EDC). Then, the HEL sample is diluted 1- to 50-fold in 10 mM sodium acetate, pH 4.0, and exposed to the activated chip surface for different lengths of time (ten seconds to two minutes) to create three different density surfaces of HEL. Each surface was then blocked with a seven-minute injection of 1 M ethanolamine, pH 8.2. Alternatively biotinylated HEL was diluted 100-fold and injected for different amounts of time to be captured at three different surface densities (60 RU, 45 RU, 12 RU; Response Unit (RU) is termed by Biacore and relates to target molecule per surface area) onto a streptavidin-containing sensor chip. All experiments were performed on a Biacore® 2000 or T100 optical biosensor. Anti-HEL antibodies were supplied at 100 μg/mL and tested in a 3-fold dilution series in Sample Running Buffer over HEL conjugated surfaces. Bound anti-HEL antibody was removed using a five-second pulse with sensor regeneration solution. All data was collected at a temperature-controlled 20° C. The kinetic responses for the antibody injections were analyzed using the non-linear least squares analysis program CLAMP (Myszka, D. G. and Morton, T. A. (1998) Trends Biochem. Sci., 23: 149-150).

E. Sequence Analysis

Sequences of the heavy and light chains isolated in the first sort were determined by PCR amplification of heavy and light chains as described below.

At least 50,000 cells taken from populations of interest were pelleted at 1100×g for 5 min. at 4° C. Pelleted cells were resuspended in 154 distilled $H_2O$ and either used immediately in PCR reactions, or were frozen for later processing.

PCR reactions consisting of 27.6 μL $H_2O$, 5 μL 10×Pfx buffer, 1 μL cells from above, 8 μL of 2.5 μM of each primer (listed below), and 0.4 μL Pfx polymerase (Invitrogen Corp., Carlsbad, Calif.) for a total of 50 μL were run using the following format: 1 cycle of 95° C.×2 min., followed by 35 cycles of 95° C.×30 sec, 55° C. for 30 sec, 68° C. for 45 sec, followed by 1 cycle of 68° C. for 1 min. PCR primers used to amplify the open reading frames are:

Oligo 540: GTGGGAGGTCTATATAAGCAGAGC (SEQ ID NO: 424), which is a forward primer which maps at the 3' end of a CMV promoter region, approximately 140 nucleotides 5' to the ATG start codon for both heavy and light chain open reading frames.

Oligo 554: CAGAGGTGCTCTTGGAGGAGGGT (SEQ ID NO: 425), which is a heavy chain-specific reverse primer which maps in the IgG gamma chain constant region.

Oligo 552: ACACAACAGAGGCAGTTCCAGATT (SEQ ID NO: 426), which is a kappa light chain-specific reverse primer that maps near the amino end of the kappa constant region.

Oligo 577: AGTGTGGCCTTGTTGGCTTGAA (SEQ ID NO: 427), which is a lambda light chain-specific reverse primer that maps to an N-proximal constant region sequence shared by all five functional human lambda genes (IgL1, 2, 3, 6, and 7).

To amplify the heavy chain, oligos 540+554 were used.

To amplify the light chains from a population of cells in which there was likelihood that a mixture of both kappa and lambda light chains would be present, oligos 540, 552 and 577 were used simultaneously. In this case, the volume of water in the PCR reaction mix was adjusted to 19.6 μL.

Following PCR, 5 μL of sample was taken for analysis on an agarose gel. Reactions for which bands were visualized on the gel were then subjected to further PCR in the presence of Taq polymerase (Invitrogen) using the following conditions:

Added directly to the remaining 45 μL of PCR reaction were 2 μL $H_2O$, 0.5 μL Taq, 0.2 μL dNTPs at 2.5 mM each, and 1.5 μL×50 mM $MgCl_2$ for a total of 50 μL (or alternatively, 1 μL of 10×Taq buffer was used in place of $MgCl_2$ while adjusting the $H_2O$ to maintain 50 μL final volume). PCR cycling was run as follows: 1 cycle of 95° C.×2 min., followed by 2 cycles of 95° C.×30 sec, 55° C. for 30 sec, 72° C. for 45 sec, followed by 1 cycle of 72° C. for 1 min.

Reactions for which bands were either not visualized on the gel or were otherwise judged to be too weak to continue, were supplemented with 1 μL Pfx buffer, 3.7 μL $H_2O$, and 0.3 μL Pfx polymerase and subjected to 1 cycle of 95° C.×2 min, followed by 10 cycles of 95° C.×30 sec, 55° C. for 30 sec, 68° C. for 45 sec, followed by 1 cycle of 68° C. for 1 min.

PCR reactions for which bands were visible following analysis on an agarose gel were cloned using a TOPO® cloning kit from Invitrogen following the manufacturer's suggested protocol. In brief, 44 PCR reaction was added to 1 μL salt solution (provided in the TOPO® kit) plus 1 μL TOPO® cloning vector. Following a 20 min. incubation at room temp., 1 or 2 μL were used to transform 100 μL XL1 blue as per protocol.

Reading frames from templates whose sequences were of further interest were recovered as follows: heavy chain templates were recovered by digesting the TOPO® clones with SgrAI and NheI, which are both present in all of the original heavy chain sequences. The resulting approximately 500 bp fragments, which contain the entire variable region including all of CDR3, were cloned into the cognate sites of an expression vector already comprising the heavy chain constant region to generate an intact, contiguous heavy chain open reading frame. One version of this vector also contains the transmembrane domain and cytoplasmic tail from the murine H2kk gene as an in-frame fusion with the IgG1 constant region to permit retention of the final IgG molecule on the cell surface, as described in Example 3. The alternative version of the expression vector has the transmembrane deleted to enable direct secretion of the antibodies of interest.

Similarly, light chain templates of interest were removed from their TOPO® cloning vectors using SbfI and MunI for kappa or SbfI and AclI for lambda, all of which sites are present in the original sequences. The resulting 350-400 bp fragments, which contain the entire light chain variable region including CDR3, were cloned into the cognate sites of the expression vector to generate an intact, contiguous light chain open reading frame.

The results demonstrated that in approximately 23% of the sequenced clones, there was at least one mutation within the CDR of the light chain resulting in the mutation of Glycine 31 to Aspartate (G31D). Based on the crystal structure of HyHEL 10 bound to HEL (Pons et al., (1999) Protein Science 8:958-68), this mutation would be predicted to result in the formation of an additional hydrogen bonding interaction during antigen binding, which clearly accounts for the increase in binding observed in the presence of 500 pM HEL in FIG. 46, and Biacore measurements. Importantly, the type of mutations observed (FIGS. 48A and B) followed the predicted pattern of mutations for SHM mediated mutation (as shown on FIG. 35), and did not result in widespread non-specific mutation of the entire coding regions of the heavy and light chains. These results, therefore, demonstrate the ability of the system to provide good affinity discrimination, as well as selection of improved variants of the antibodies, and binding proteins of the present invention, and the ability to provide for both sustained and pulsed hypermutation directed to specific regions of interest within one or more target proteins. Furthermore, a handful of additional mutations were identified that, when recombined into a single antibody construct improved upon the affinity of the wild-type protein, from 30 pM to better than 4 pM (FIG. 48C). This example demonstrates how a single sequence or library under selective pressure and in the presence of SHM can quickly generate higher affinity mutants, and how this flow of mutational events can be predicted exactly by the computational algorithms outlined above.

The data presented herein demonstrate that the disclosed systems and seed polynucleotides for somatic hypermutation are capable of high level targeted mutagenesis of a target protein of interest. Importantly, the system is capable of iterative rounds of mutagenesis and selection enabling the directed evolution of favorable mutations while reducing the accumulation of neutral and harmful mutations, both within the protein of interest, and within the expression system.

Example 14

Engineering Enhanced Mutants of AID

Activation induced cytidine deaminase (AID) is the primary enzyme responsible for initiating somatic hypermutation (SHM), class switch recombination (CSR) and gene conversion (GC) events during affinity maturation by the immune system. The enzyme has been especially well conserved during evolution, with the human, rat, cow, mouse and chicken orthologs exhibiting 94.4%, 93.9%, 93.9%, 92.4% and 89.4% identity to the canine (dog) amino acid sequence, respectively.

AID contains several predicted protein-protein interaction domains, post-translational modification sites and subcellular targeting motifs, one of which is a nuclear export signal (NES) that is localized in the carboxy terminal amino acids of the enzyme. The question as to whether or not a nuclear localization signal (NLS) is present within AID remains controversial with some groups claiming such a signal exists (Ito et al., PNAS 2004 Feb. 17; 101(7):1975-80) while others maintain that no functional NLS is present (Brar et al., J. Biol. Chem. 2004 Jun. 8; 279(25):26395-401; McBride et al., J. Exp. Med. 2004 May 3; 199(9):1235-44).

Native AID is found primarily in the cytoplasmic compartment of cells, as demonstrated by cell fractionation, western blotting and immunohistochemistry. Removal or disabling of the NES tends to permit higher steady-state resident concentrations of AID in the nucleus, higher levels of SHM, but also impaired or absent CSR (Brar et al, Id.; Durandy et al., Hum. Mutat. 2006 December; 27(12):1185-91; Ito et al, Id.; McBride et al, Id.).

Example 2 above describes the design and construction of an SHM resistant form of AID (SEQ ID No. 428) comprising a mutation in the NES (L198A) designed to disable nuclear export thereby promoting nuclear retention. To further enhance nuclear localization and, thus, the mutator activity of AID, further engineered versions of the enzyme were created by inserting the strong nuclear localization signal (NLS; PKKKRKV; SEQ ID NO: 439) derived from the SV40 T antigen (Kalderon et al, (1984). Cell 39, 499-509) near the amino terminus. To track AID expression, a FLAG epitope tag was also inserted to create (SEQ ID No. 429) which contains both a strong NLS and the mutant NES sequence.

Additional engineered versions of AID were also created by further modifying the C-terminal NES to reduce nuclear export. These constructs were prepared with and without the SV40 T antigen NLS.

In the first pair of NES mutants, polynucleotide sequences of SEQ ID No. 428 (without NLS) and SEQ ID No. 429 (with NLS) were modified such that amino acid residues L181, L183, L189, L196 and L198 encoded by the polynucleotide sequences were mutated to Alanine resulting in polynucleotide sequences of SEQ ID No. 431 (without NLS) and SEQ ID No. 433 (with NLS), respectively, and amino acid sequences of SEQ. ID. No. 432 (without NLS) and SEQ ID No. 434 (with NLS), respectively.

Muteins were generated by PCR, and then treated with Dpn1 to remove parental DNA.

To generate the alanine containing muteins, the following oligos were used:

```
                                      (SEQ ID NO: 440)
CAGCTCAGGAGAATCCTCGCCCCCGCTTATGAGGTCGACGACCTC
and

                                      (SEQ ID NO: 441)
GAGGTCGTCGACCTCATAAGCGGGGGCGAGGATTCTCCTGAGCTG.
```

Two separate PCR reactions were set up using vectors containing polynucleotide sequences set forth as SEQ ID No. 428 or SEQ ID No. 429 as template DNA, using Pfu Taq polymerase (Invitrogen) with the manufacturers kit buffers and 2.5 uM of each deoxynucleotide (Roche). PCR was performed with the following cycle conditions: 1 cycle of 95° C. for 3 min, followed by 20 cycles of [95° C. for 45 sec, 55° C. for 45 sec, 68° C. for 17 min], followed by 1 cycle of 68° C. for 5 min. After completion, 5 μl of the PCR reaction was run on a 1% agarose gel to confirm a successful reaction. The PCR reaction mix was then treated with Dpn1 (New England Biolabs) for at least 4 hrs at 37° C. to remove the parental DNA.

Five (5) μL of the Dpn1-treated PCR reaction was added to 100 μL of XL1-Blue super competent cells (Invitrogen) and transformed per the manufacturer's suggested protocol. Following sequence verification, the resulting DNA (which contained 2 of the 4 desired mutations; i.e., 181 and 183), was used as a template with oligos CCGCTTATGAGGTCGACGACGCCAGAGATGCCTTCCGGACCG (SEQ ID NO: 442) and AGGGTCCGGAAGGCATCTCTGGCGTCGTCGACCTCATAAGCGG (SEQ ID NO: 443) in the same protocols listed above to introduce the third of four mutations (i.e., 189). Finally, oligos CCAGAGATGCCTTCCGGACCGCCGGGGCTTGATGTACAATC (SEQ ID NO: 444) and GATTGTACATCAAGCCCCGGCGGTCCGGAAGGCATCTCTGG (SEQ ID NO: 445) were used to incorporate the fourth and final mutation (i.e., 196).

The final set of alanine-containing mutein products were digested using Sac1 and BsrG1 and ligated into vector backbones cut with the cognate restriction enzymes to generate SEQ. ID. No. 431 (without NLS) and SEQ. ID. No. 433 (with NLS), respectively.

In a second pair of muteins: polynucleotide sequences of SEQ. ID. No. 428 (without NLS) and SEQ. ID. No. 429 (with NLS) were modified such that amino acid residues Asp187, Asp188 and Asp191 encoded by the polynucleotide sequences were mutated to Glutamate and amino acid residue Thr195 encoded by the polynucleotide sequences was mutated to Isoluecine, thereby creating polynucleotide sequences SEQ ID No. 435 (without NLS) and SEQ ID No. 437 (with NLS), respectively, and amino acid sequences of SEQ ID No. 436 (without NLS) and SEQ. ID. No. 438 (with NLS), respectively.

The same set of procedures described above with respect to the alanine muteins was repeated to generate the glutamate containing muteins of AID SEQ ID No. 435 and SEQ ID No. 437, except that the following oligos: TCCTCCCCCTCTATGAGGTCGAAGAACTCAGAGAAGCCTTCCGGACCCTCGGGGC (SEQ ID NO: 446) and GCCCCGAGGGTCCGGAAGGCTTCTCTGAGTTCTTCGACCTCATAGAGGGGGAGGA (SEQ ID NO: 447) were used in place of the first pair of oligos, and the following oligos: AACTCAGAGAAGCCTTCCGGATCCTCGGGGCTTGATGTACAAT (SEQ ID NO: 448) and ATTGTACATCAAGCCCCGAGGATCCGGAAGGCTTCTCTGAGTT (SEQ ID NO: 449) were used in lieu of the second pair of oligos (no third PCR reaction was needed in this case). Products were treated as described above to generate SEQ ID No. 435 (without NLS) and SEQ ID No. 437 (with NLS).

Results and Discussion.

The six resulting AID constructs were subsequently tested for activity in a green fluorescent protein (GFP) reversion assay, and for frequency of mutations on an immunoglobulin IgG heavy chain (HC) template.

To perform the GFP reversion assay, the TAC codon for tyrosine 82 was altered to a TAG stop codon (GFP*). GFP* was cloned into an Anaptys episomal expression vector and stably transfected into HEK 293 (note: this cell line expresses EBNA1 from an integrated copy of the gene). Each AID construct in turn was transfected into the stably transfected GFP* cell line, and cells were placed under selection (blasticidin for GFP* and hygromycin for each of the AID constructs) by day 2 post transfection. Reversion of the stop codon back to tyrosine caused the episome-harboring cell to fluoresce green. The frequency of GFP reversion was measured by fluorescence-activated cell sorter (FACS) analysis at 3, 6, and 10 days post selection.

TABLE 16

Functional competence of AID muteins as gauged by FACS analysis of GFP revertant cells gated on days 3, 6, and 10.
Table 16

| Vector(s)/AID variants | % gated day 3 | % gated day 6 | % gated day 10 |
|---|---|---|---|
| GFP* alone | 0.04% | 0.02% | 0.01% |
| GFP* + expression of (SEQ ID No. 428) | 0.44% | 0.35% | 0.39% |
| GFP* + expression of (SEQ ID No. 429) | 0.31% | 0.37% | 0.19% |
| GFP* + expression of (SEQ ID No. 431) | 0.19% | 0.26% | 0.21% |
| GFP* + expression of (SEQ ID No. 433) | 0.36% | 0.35% | 0.32% |
| GFP* + expression of (SEQ ID No. 435) | 0.37% | 0.30% | 0.41% |
| GFP* + expression of (SEQ ID No. 437) | 0.18% | 0.26% | 0.21% |

The results indicate that co-transfection with each of the six AID constructs consistently yielded GFP revertants significantly above background, indicating that all 6 muteins of AID are functional.

Because the GFP reversion assay requires both the initial activity of AID and subsequent action by error prone polymerase in order to generate a positive, reverted cell, the results can provide a qualitative yes/no for function. In order to determine actual reversion rates, a more precise template mutagenesis experiment was also conducted. Thus, in addition to the GFP reversion assay, 2 of the AID constructs (SEQ ID No. 428; containing the L198A mutation in the NES) and SEQ ID No. 429, (containing the L198A NES mutation and the SV40 NLS)) were tested for their ability to induce mutations in the HC of HyHEL10 IgG (Pons et al, (1999) Protein Science 8:958-68; Smith-Gill et al. (1984) J. Immunology 132:963). Episomal expression constructs (as described previously) encoding the HC of HyHEL10, an N31G mutein of the HyHEL10 light chain (LC), and either an expression vector containing SEQ ID. No. 428 or the same vector backbone containing SEQ ID. No. 429, were co-transfected into HEK 293 cells. Antibiotic selective pressure was added to the transfected cell population (i.e., blasticidin, puromycin and hygromycin for HC, LC and AID, respectively), and cells were harvested following 2 months of culture. A total of 83 IgG HC templates were sequenced from cells transfected with an expression vector comprising SEQ ID No. 428, and 61 templates were sequences from cells transfected with an expression vector comprising SEQ ID No. 429. The percentage of mutations per template vs. form of AID is shown in Table 17, below. The mutation frequency calculated from the sequencing data is 1 mutation per 1438 bp generated by SEQ ID No. 428, and 1 mutation per 1059 bp generated by SEQ ID No. 429.

TABLE 17

Percentage of HyHEL10 IgG templates identified with mutations observed after co-expression of AID muteins SEQ ID No. 428 or SEQ ID No. 430
Table 17

| # Mutations per heavy chain template | SEQ ID. No. 428 | SEQ ID. No. 430 |
|---|---|---|
| 0 | 71% | 72% |
| 1 | 26% | 20% |
| 2 | 2.4% | 6.8% |
| 3 | 0 | 1.6% |
| 4 | 0 | 1.6% |

The results indicate that the version of AID that contains the NLS (SEQ ID No. 429) induced a greater number of mutations in the HyHEL10 HC IgG template (1 per 1059 bp vs 1 per 1438 for the non-NLS containing homolog), and similarly resulted in a greater number of templates containing multiple mutations (10% of templates by AID+NLS vs 2.4% for AID-NLS).

Sequences

Cold canine AID: nuclear export signal was abrogated by altering the unmodified CTT (Leu198) codon to GCT (ala, shown underlined below).

```
                                                                  (SEQ ID NO: 428)
ATGGACTCTCTCCTCATGAAGCAGAGAAAGTTTCTCTACCACTTCAAGAACGTCAGATGGGCCAAGGGGAGACATGAGACC

TATCTCTGTTACGTCGTCAAGAGGAGAGACTCAGCCACCTCTTTCTCCCTCGACTTTGGGCATCTCCGGAACAAGTCTGGG

TGTCATGTCGAACTCCTCTTCCTCCGCTATATCTCAGACTGGGACCTCGACCCCGGGAGATGCTATAGAGTCACTTGGTTT

ACCTCTTGGTCCCCCTGTTATGACTGCGCCAGACATGTCGCCGACTTCCTCAGGGGGTATCCCAATCTCTCCCTCCGCATA

TTCGCCGCCCGACTCTATTTTTGTGAGGACAGGAAAGCCGAGCCCGAGGGGCTCAGGAGACTCCACCGGGCCGGGGTCCAG

ATCGCCATCATGACATTTAAGGACTATTTCTATTGTTGGAATACATTTGTCGAGAATCGGGAGAAGACTTTCAAAGCCTGG

GAGGGGCTCCATGAGAACTCTGTCAGACTCTCTAGGCAGCTCAGGAGAATCCTCCTCCCCCTCTATGAGGTCGACGACCTC

AGAGATGCCTTCCGGACCCTCGGGGCTTGA
```

Features of the polynucleotide sequences (or amino acid sequences) are in 5' to 3' (or N- to C-terminal where appropriate) as follows:

SacI restriction site used for cloning, boxed letters; Kozak consensus, underlined; ATG start codon (bold capital letters); FLAG epitope tag (single underline); NLS (double-underline); cold canine AID; TGA stop codon (bold capital letters); BsrGI and AscI restriction sites used for cloning (boxed letters). * indicates stop codon in protein sequence.

Flag-NLS-AID.

gagctcctaaccaccATGgactacaaagatgacgatgataaaggtccaaagaagaagagaaaggtagactctctcctcatgaagcagagaaagtttctctacc
cacttcaagaacgtcagatgggccaaggggagacatgagacctatctctgttacgtcgtcaagaggagagactcagccacctctttctccctcgactttggg
atctccggaacaagtctgggtgtcatgtcgaactcctcttcctccgctatatctcagactgggacctcgaccccgggagatgctatagagtcacttggttt
acctcttggtcccccctgttatgactgcgccagacatgtcgccgacttcctcaggggggtatcccaatctctccctccgcatattcgccgcccgactctatttt
tgtgaggacaggaaagccgagcccgaggggctcaggagactccaccgggccggggtccagatcgccatcatgacatttaaggactatttctattgttggaat
acatttgtcgagaatcgggagaagactttcaaagcctgggaggggctccatgagaactctgtcagactctctaggcagctcaggagaatcctcctcccccctc
tatgaggtcgacgacctcagagatgccttccggaccctcggggctTGAtgtacaatccgcgtgagacgatcggcgcgcc
(SEQ ID. No. 429)

MDYKDDDDKGPKKKRKVDSLLMKQRKFLYHFKNVRWAKGRHETYLCYVVKRRDSATSFSLDFGHL
RNKSGCHVELLFLRYISDWDLDPGRCYRVTWFTSWSPCYDCARHVADFLRGYPNLSLRIFAARLYFCEDRKAE
PEGLRRLHRAGVQIAIMTFKDYFYCWNTFVENREKTFKAWEGLHENSVRLSRQLRRILLPLYEVDDLRDAFRTL
GA* (SEQ ID. No. 430)

The 4 underlined-and-capitalized GCC codons (ala) were changed from the original sequence (CTC encoding Leu) by site directed mutagenesis.

(SEQ ID. No. 431)

gagctcctaaccaccATGgactctctcctcatgaagcagagaaagttt
ctctaccacttcaagaacgtcagatgggccaaggggagacatgagacc
tatctctgttacgtcgtcaagaggagagactcagccacctctttctcc
ctcgactttgggcatctccggaacaagtctgggtgtcatgtcgaactc
ctcttcctccgctatatctcagactgggacctcgaccccgggagatgc
tatagagtcacttggtttacctcttggtcccccctgttatgactgcgcc
agacatgtcgccgacttcctcaggggggtatcccaatctctccctccgc
atattcgccgcccgactctattttttgtgaggacaggaaagccgagccc
gaggggctcaggagactccaccgggccggggtccagatcgccatcatg
acatttaaggactatttctattgttggaatacatttgtcgagaatcgg -continued gagaagactttcaaagcctgggaggggctccatgagaactctgtcaga
ctctctaggcagctcaggagaatcctcGCCcccGCCtatgaggtcgac
gacGCCagagatgccttccggaccGCCggggctTGAtgtaca.

(SEQ ID. No. 432)

MDSLLMKQRKFLYHFKNVRWAKGRHETYLCYVVKRRDSATSFSLDFGH
LRNKSGCHVELLFLRYISDWDLDPGRCYRVTWFTSWSPCYDCARHVAD
FLRGYPNLSLRIFAARLYFCEDRKAEPEGLRRLHRAGVQIAIMTFKDY
FYCWNTFVENREKTFKAWEGLHENSVRLSRQLRRILAPAYEVDDARDA
FRTAGA*.

The 4 underlined-and-capitalized GCC codons (ala) were changed from the original sequence (CTC encoding Leu) by site directed mutagenesis. Boxes and underlines are as described above.

gagctcctaaccaccATGgactacaaagatgacgatgataaaggtccaaagaagaagagaaaggtagactctctcctcatgaagcagagaaagtttctctacc
acttcaagaacgtcagatgggccaaggggagacatgagacctatctctgttacgtcgtcaagaggagagactcagccacctctttctccctcgactttgggcatctccggaacaa
gtctgggtgtcatgtcgaactcctcttcctccgctatatctcagactgggacctcgaccccgggagatgctatagagtcacttggtttacctcttggtcccccctgttatgactgcgcca
gacatgtcgccgacttcctcaggggggtatcccaatctctccctccgcatattcgccgcccgactctattttttgtgaggacaggaaagccgagcccgaggggctcaggagactcc
accgggccggggtccagatcgccatcatgacatttaaggactatttctattgttggaatacatttgtcgagaatcgggagaagactttcaaagcctgggaggggctccatgagaac
tctgtcagactctctaggcagctcaggagaatcctcGCCcccGCCtatgaggtcgacgacGCCagagatgccttccggaccGCCggggctTGAtgtaca (SEQ ID. No. 433)

MDYKDDDDKGPKKKRKVDSLLMKQRKFLYHFKNVRWAKGRHETYLCYVVKRRDSATSFSLDFGHL
RNKSGCHVELLFLRYISDWDLDPGRCYRVTWFTSWSPCYDCARHVADFLRGYPNLSLRIFAARLYFCEDRKAE
PEGLRRLHRAGVQIAIMTFKDYFYCWNTFVENREKTFKAWEGLHENSVRLSRQLRRILAPAYEVDDARDAFRT
AGA* (SEQ ID. No. 434)

The 3 underlined-and-capitalized GAA codons (Glu) were changed from the original sequence (Aspartate encoding codons). One additional mutation, T1951, (ACC to ATC) was also generated.

(SEQ ID. No. 435)

gagctcctaaccaccATGgactctctcctcatgaagcagagaaagtt
tctctaccacttcaagaacgtcagatgggccaaggggagacatgaga
cctatctctgttacgtcgtcaagaggagagactcagccacctctttc
tccctcgactttgggcatctccggaacaagtctgggtgtcatgtcga
actcctcttcctccgctatatctcagactgggacctcgaccccggga
gatgctatagagtcacttggtttacctcttggtcccccctgttatgac
tgcgccagacatgtcgccgacttcctcaggggtatcccaatctctc
cctccgcatattcgccgcccgactctatttttgtgaggacaggaaag
ccgagcccgaggggctcaggagactccaccgggccggggtccagatc
gccatcatgacatttaaggactatttctattgttggaatacatttgt
cgagaatcgggagaagactttcaaagcctgggaggggctccatgaga
actctgtcagactctctaggcagctcaggagaatcctcctcccccctc
tatgaggtcGAAGAActcagaGAAgccttccggATCctcggggctTG
Atgtaca (SEQ ID. No. 436)

MDSLLMKQRKFLYHFKNVRWAKGRHETYLCYVVKRRDSATSFSLDFG
HLRNKSGCHVELLFLRYISDWDLDPGRCYRVTWFTSWSPCYDCARHV
ADFLRGYPNLSLRIFAARLYFCEDRKAEPEGLRRLHRAGVQIAIMTF
KDYFYCWNTFVENREKTFKAWEGLHENSVRLSRQLRRILLPLYEVEE
LREAFRILGA*

The 3 underlined-and-capitalized GAA codons (Glu) were changed from the original sequence (Aspartate encoding codons). One additional mutation, T1951 (ACC to ATC) was also generated. Boxes and underlines are as described above.

gagctcctaaccaccATGgactacaaagatgacgatgataaaggtccaaagaagaagagaaaggtagactctctcctcatgaagcagagaaagtttctctacc acttcaagaacgtcagatgggccaaggggagacatgagacctatctgttacgtcgtcaagaggagagactcagccacctctttctccctcgactttgggcatctccggaacaa gtctgggtgtcatgtcgaactcctcttcctccgctatatctcagactgggacctcgaccccgggagatgctatagagtcacttggtttacctcttggtccccctgttatgactgcgcca gacatgtcgccgacttcctcaggggtatcccaatctctccctccgcatattcgccgcccgactctatttttgtgaggacaggaaagccgagcccgaggggctcaggagactcc accgggccggggtccagatcgccatcatgacatttaaggactatttctattgttggaatacatttgtcgagaatcgggagaagactttcaaagcctgggaggggctccatgagaac tctgtcagactctctaggcagctcaggagaatcctcctcccccctctatgaggtcGAAGAActcagaGAAgccttccggATCctcggggctTGAtgtaca (SEQ ID. No. 437)

MDYKDDDDKGPKKKRKVDSLLMKQRKFLYHFKNVRWAKGRHETYLCYVVKRRDSATSFSLDFGHL

RNKSGCHVELLFLRYISDWDLDPGRCYRVTWFTSWSPCYDCARHVADFLRGYPNLSLRIFAARLYFCEDRKAE

PEGLRRLHRAGVQIAIMTFKDYFYCWNTFVENREKTFKAWEGLHENSVRLSRQLRRILLPLYEVEELREAFRILG

A (SEQ ID. No. 438)

Example 15

Discovery and Optimization NGF Antibodies

Nerve growth factor (NGF) has been shown to be a critical survival and maintenance factor in the development of peripheral sympathetic and embryonic sensory neurons and of basal forebrain cholinergic neurons (Smeyne, et al., Nature 368:246-249 (1994); Crowley, et al., Cell 76:1001-1011 (1994)).

NGF activity is mediated through two different membrane-bound receptors, the TrkA tyrosine kinase receptor and the p75 receptor, which are structurally related to other members of the tumor necrosis factor receptor family (Chao, et al., Science 232:518-521 (1986)). NGF receptors have been found on a variety of cell types outside of the nervous system. For example, TrkA has been found on human monocytes, T- and B-lymphocytes and mast cells.

A direct relationship between increased NGF levels and a variety of inflammatory conditions has been established in human patients as well as in several animal models. These include systemic lupus erythematosus (Bracci-Laudiero, et al., Neuroreport 4:563-565 (1993)), multiple sclerosis (Bracci-Laudiero, et al., Neurosci. Left. 147:9-12 (1992)), psoriasis (Raychaudhuri, et al., Acta Derm. l'enereol. 78:84-86 (1998)), arthritis (Falcimi, et al., Ann. Rheum. Dis. 55:745-748 (1996)), interstitial cystitis (Okragly, et al., J. Urology 161:438-441 (1991)) and asthma (Braun, et al., Eur. J Immunol. 28:3240-3251 (1998)).

Primary sympathetic neurons are also known to respond to NGF and to also be involved in pain signaling (Aley, et al., Neuroscience 71:1083-1090 (1996)). Removing sympathetic innervation modifies the hyperalgesia normally seen in response to treatment with NGF (Woolf, et al., J. Neurosci. 16:2716-2723 (1996)).

The use of anti-NGF antibody to treat chronic pain has been described United States Patent Application Nos. 20040219144, 20040228862, 20040237124, 20040253244, 20050074821, 20050265994, 20060088884 and 20060147450.

1. Generation of Reagents

Preparation of Cell Surface Expressed Libraries

The preparation and cell banking of a HEK-293 cell line expressing a library of membrane-bound human antibody genes is described in Examples 5-8. This cell line also comprises an AID expression vector as described in Example 3, which is capable of constitutive AID expression. A HEK-293 cell line expressing AID, but not the antibody library was used as a negative control for the selections.

2. Selection of Specific Binding Members

For the first two rounds of selection using intact human NGF protein, 200 microliters of cells were incubated with approximately $1\times10^7$ fully-saturated human NGF-conjugated Spherotech avidin purple (Spherotech, Lake Forest, Ill.) beads for 30 minutes at 4° C.

Prior to incubation with NGF bound beads, the cells were collected, washed with an equal volume of PBS solution, pH 7.2 and resuspended in ice-cold PBS solution, pH 7.2 containing 1% (weight/volume) BSA at a final cell concentration of $5\times10^7$ cells/mL.

NGF-conjugated beads were prepared by incubation of the biotinylated protein with the streptavidin beads for 30 minutes at room temperature with slow tilt rotation as described previously. After coupling, the microparticles were washed and resuspended to a final microparticle concentration of $1\times10^9$ microparticles/ml. Prior to coupling to beads, NGF was biotinylated using sulfosuccinimidyl-6-(biotinamido)-6-hexanamidohexanoate (biotin reagent; Pierce product number 21338, Pierce, Rockford, Ill. 61105).

After incubation, the cell: bead mixture was washed once with ice-cold PBS solution, pH 7.2 containing 1% (weight/volume) BSA and resuspended in 200 microliters of ice-cold PBS solution, pH 7.2 containing 1% (weight/volume) BSA containing a 1:200 dilution of anti-IgG antibodies, as described previously. The cells were incubated at 4° C. for 30 minutes and then washed once with ice-cold PBS solution, pH 7.2 containing 1% (weight/volume) BSA and resuspended in 500 microliters of sterile ice-cold PBS solution, pH 7.2 containing 1% (weight/volume) BSA plus 2 nanograms/milliliter DAPI (Sigma-Aldrich Corp). Live IgG-positive cells that bound NGF-conjugated beads (excitation with a 25 mW 561 nm laser, collection through 620/40 and 750LP filters, respectively) were isolated by fluorescence activated cell sorting using a Cytopiea Influx Cell Sorter at a flow rate of approximately 10,000 events/second. In the first round of selection, the entire population of cells which bound to human NGF were isolated plated in a 6-well microtiter dish and allowed to expand for approximately 2 weeks to a population of approximately $1\times10^7$ cells before the next sort FIG. 49 (Panel A). The second round of sorting resulted in a significantly enriched population of NGF binding cells, and the most fluorescent cells were taken and allowed to expand as described above (Panel B of FIG. 49). Controls for these experiments are shown in the smaller insert panels. Samples of the cells from round 2 can be processed to determine the sequences of the variable domains and to characterize diversity of selected heavy and light chains, as described previously.

For the third round of selections with NGF protein, 200 microliters of the selected cells that bound to NGF from round 2 were incubated with approximately 50 nmolar biotinylated human NGF. The cell mixture was washed once with ice-cold PBS solution, pH 7.2 containing 1% (weight/volume) BSA followed by incubation with a 1:200 dilution of 1 mg/mL PE-conjugated streptavidin at 4° C. for 30 minutes. The cells were washed once with ice-cold PBS solution, pH 7.2 containing 1% (weight/volume) BSA and incubated with goat anti human IgG-FITC (Sigma-Aldrich Corp., St. Louis, Mo.) at a 1:500 dilution (2 μL). Samples were vortexed and incubated 4° C. for 30 minutes. The cells were then once with ice-cold PBS solution, pH 7.2 containing 1% (weight/volume) BSA and resuspended in 500 microliters of sterile ice-cold PBS solution, pH 7.2, containing 1% (weight/volume) BSA plus 2 nanograms/milliliter DAPI (Sigma-Aldrich Corp). Live IgG-positive cells that were positive for phycoerythrin (excitation with the 25 mW 561 nm laser, collection through 579/34) were isolated by fluorescence activated cell sorting using a Cytopeia Influx Cell Sorter at a flow rate of approximately 10,000 events/second. Subpopulations of cells that bound to human NGF are shown in FIG. 49 (Panel C) Sorted cells with the highest fluorescence intensity were plated in a 6-well microtiter dish to expand for approximately 2 weeks to a population of approximately $1\times10^7$ cells before the next sort.

For the fourth round of selection, cells were selected using 20 nM biotinylated human NGF, using the same procedures and incubations, as described above. The results of the FACS sorts are shown in FIG. 49 (Panel D).

For the fifth round of selection, cells were selected using 20 nM biotinylated human NGF using the same FACS procedures and incubations, as described above. The results of the FACS are shown in FIG. 49 (Panel E) and the results demonstrate a significant enrichment in binding compared to control incubations (insert panels in FIG. 49). In Panel E of FIG. 49, it is clear that selections using intact NGF protein show a finger of cells in the FACS scattergram exhibiting discrete binding. Selected subpopulations of cells were plated in a 6-well microtiter dish to expand for approximately 2 weeks to a population of approximately $1\times10^7$ cells before the next sort.

Samples of the cells from round 5 were processed to determine the sequences of the variable domains compared to round 2 results. As discussed previously, the sequences of the variable domains and new mutations introduced into the antibody via somatic hypermutation can be analyzed to determine their distribution within the clones analyzed, and specifically their location within the coding region of the heavy and light chains. Mutations can be rated based on their position within the heavy light chains; for example mutations within the CDRs can be rated highly, while those in frameworks regions and/or the constant domains can be rated less favorably. Key mutations that occur between different antibody families may be recombined between families to rapidly generate hybrid antibodies that exhibit favorable increases in affinity or selectivity that represent the sum of all, or a sub set of all, mutations observed. Conversely, multiply redundant clonal families can be consolidated to eliminate redundant diversity while maximizing useful diversity and eliminating non productive evolutionary paths.

3. Clonal Analysis

For each cell clone, the sequencing template is prepared either via PCR or episomal rescue, as described above in Example 13.

4. Functional Analysis

Heavy and light chains of interest after sequence analysis may be produced in a secreted form for further functional analysis as described below. In the case of heavy chains obtained from the surface displayed libraries, these are processed as described in Example 13, (i.e., by digestion with XhoI, followed by religation) to remove the transmembrane domain, enabling direct secretion of the antibody in to the media. Purified antibodies may be tested in any of the functional assays below to further characterize antibody activity.

A number of assays can be developed to help reveal prospective functional activity of isolated antibodies or within antibody pools as described below:

5. Affinity Analysis

A heavy and light chain pair of interest after sequence analysis from Round 5 were produced in a secreted form for further functional analysis as described above. The conditioned media containing the antibody in question was purified by Protein G affinity chromatography, and dialyzed into running buffer appropriate for the Biacore affinity experiments, typically phosphate saline buffer (PBS) pH 7.4.

Affinity analysis of the Round 5 anti-NGF lead antibody was performed on a Biacore series T-100 surface plasmon resonance instrument with the following experimental conditions. A CM5 Biacore chip was conditioned with Protein G to create a broad-spectrum anti-human IgG capture surface. A series of NGF ligand concentrations were passed over the chip surface on which either 500 RU of anti-NGF antibody had been captured, or no anti-NGF antibody had been captured (control surface). The rate of concentration-dependent association and dissociation of the analyte, NGF, was monitored as a function of time on the capture cell relative to the control flow cell. Results of these experiments can be seen in FIG. 50, which demonstrate a concentration-dependent association and dissociation of NGF to the antibody in question.

A kinetic multivariate analysis of these binding data shown in FIG. 50 predict a dissociation constant for binding of NGF to the anti-NGF antibody of Kd=670 nM. The off-rate ($k_d$) is predicted to be 0.367 ($s^{-1}$), with an association rate of $k_{on}$=5.5×$10^5$ ($s^{-1}M^{-1}$). These data demonstrate that we have isolated an anti-NGF antibody that binds to NGF with nM affinity using the protocols described above.

Example 16

Creation and Testing of Synthetic SHM Resistant and SHM Susceptible Genes

A. Polynucleotide Design

The starting sequence for unmodified Teal Fluorescent Protein (TFP) is shown in FIG. 51, together with the initial analysis of hot spot and cold spot frequency.

1. Hot TFP

As described for Example 1, sequence optimization is completed using the computer program SHMredesign, based on the hot spot and cold spot motifs listed in Table 7; the resulting hot and cold versions of TFP are shown in FIGS. 52 and 53, respectively.

Optimization of the TFP sequence to make the sequence more susceptible to somatic hypermutation resulted in an increase of about 170% in number of hot spots (an increase of 28), and reduced the number of cold spots by about 26% (a decrease of 27). Overall the frequency of hot spots increased to an average density of about 10 hot spots per 100 nucleotides from an initial density of about 6 hot spots per 100 nucleotides, and the overall frequency of cold spots decreased from about 15 cold spots per 100 nucleotides in the unmodified gene to about 11 cold spots per 100 nucleotides in the SHM susceptible form.

2. Cold TFP

Optimization of the TFP sequence to make the sequence more resistant to somatic hypermutation resulted in an increase of 120% in number of cold spots (an increase of 21), and reduced the number of hot spots by about 10% (a decrease of 4). Overall the frequency of cold spots increased to an average density of about 18 cold spots per 100 nucleotides from an initial density of about 15 cold spots per 100 nucleotides, and the overall frequency of hot spots decreased from about 6 hot spots per 100 nucleotides, in the unmodified gene to about 5 hot spots per 100 nucleotides in the SHM resistant form.

B. Cloning and Analysis

After final review to ensure that the synthetic polynucleotide sequence is free of extraneous restriction sites, the complete polynucleotide sequence is synthesized (DNA 2.0, Menlo Park, Calif.), cloned into one of DNA2.0's cloning vectors as describe herein, sequenced to confirm correct synthesis and tested for activity as described below.

Hek 293 cells are transfected with the expression vectors (AB102 and 136 as described above) containing either hot or cold versions of TFP driven for expression by an identical CMV promoter. Selection for stable expression began 3 days post transfection. Prior to FACS analysis, cells are harvested by trypsinization, ished twice in PBS containing 1% w/v BSA, and re-suspended in 200 μl PBS/1% BSA containing 2 ng/ml DAPI. Cells are analyzed in the Cytopeia Influx with 200 mW 488 nm and 50 mW 403 nm laser excitation. Up to one million cells per sample are acquired. DAPI fluorescence is measured through a 460/50 bandpass filter. GFP fluorescence is measured through a 528/38 bandpass filter. Percent GFP expression is reported in Table 18 as percentage of DAPI excluding live cells with no detectable GFP fluorescence above cellular background.

TABLE 18

Expression analysis of "hot" and "cold" versions of TFP

| Construct | % TFP Expressing cells | TFP Fluorescence | Control Fluorescence | Fold over control |
|---|---|---|---|---|
| Hot TFP (SHM susceptible) | 63.74 | 189.33 | 20.61 | 9 |
| Cold TFP (SHM resistant) | 66.92 | 429.72 | 19.93 | 22 |
| Hot TFP (SHM susceptible) | 48.39 | 183.21 | 20.09 | 9 |
| Cold TFP (SHM resistant) | 51.20 | 656.06 | 20.26 | 32 |

These results show good expression above background of both hot and cold versions of TFP. In this case, making the sequence "cold" produced the surprising result that relative expression of the protein is improved. Such improved expression provides an additional benefit to the SHM resistant synthetic genes.

To determine the relative stability/susceptibility of each construct to somatic hypermutation, stable cell lines of each transfected cell population are created, and tested to determine the relative speed by which they accumulate SHM mediated mutations. Because the majority of these mutations result in a loss of function, relative mutagenesis load are conveniently measured as a loss of fluorescence via FACS as described herein.

Episomal expression constructs carrying either a SHM optimized coding sequence for hot TFP or cold TFP were individually stably co-transfected with AID into HEK 293 cells and allowed to expand and grow for 3 weeks (the cold canine AID used in these experiments contains the NES-inactivating L198A mutation; SEQ ID NO: 428). Cell stocks were then frozen, and one vial each of hot TFP and cold TPF were thawed, grown in culture for 4 days, and then pulsed with supplemental AID by transiently transfecting the 4 day post-thaw culturing with an additional aliquot of the original AID expression construct (termed "AID pulsing"). Cells were harvested by trypsinization nine days following the AID pulse, pelleted at 1150×g for 5 min., and frozen for later use.

Cell pellets were subsequently thawed and TFP ORFs were recovered by PCR using oligonucleotide (oligo) primers GTGGGAGGTCTATATAAGCAGAGC (SEQ ID NO: 456) and GATCGTCTCACGCGGATTGTAC (SEQ ID NO: 457). The former oligo amplifies from near the 3' end of the CMV promoter used for driving expression of TFP mRNA, which lies 142 nt 5' to the TFP start codon, and the latter oligo matches sequences ending 1 nt 3' to the TFP stop codon.

Each PCR reaction (total volume of 50 μL) was run 35 cycles under the following conditions: 95° C. for 5 min, 35 cycles of (95° C. for 30 sec, 55° C. for 30 sec, 68° C. for 45 sec), followed by 1 min at 68° C. before cooling to 4° C. PCR amplified products were cloned into the TOPO® TA cloning vector (Invitrogen, Carlsbad, Calif.), and inserts were sequenced. A total of 166 hot and 111 cold TFP ORFs were rescued, sequenced and compared the resulting spectrum of mutations. Global statistics for the mutations observed in the two sets of sequences are shown in Table 19.

TABLE 19

| Mutation metrics for cold- and hot-TFP | | | | | |
|---|---|---|---|---|---|
| template | # ORFs sequenced | # mutations | total # nt sequenced | kb per mutation | templates per mutation |
| coldTFP | 111 | 18 | 61050 | 3391 | 6.1 |
| hotTFP | 166 | 100 | 88500 | 885 | 1.6 |

The mutation frequency is approximately 3.8-fold greater in the TFP template version with maximized hotspots vs. the cold TFP sequence with minimized hotspots. The data demonstrates that SHM optimization of polynucleotide sequences can be used to either increase or decrease the frequency of mutations experienced by a polynucleotide encoding a protein of interest.

FIG. 53D shows the mutations for a representative segment of the hot and cold TFP constructs. The central row shows the amino acid sequence of TFP (residues 59 thru 87) in single letter format, and the "hot" and "cold" starting nucleic acid sequences encoding the two constructs are shown above (hot) and below (cold) the amino acid sequence. Mutations observed in the hot sequence are aligned and stacked top of the gene sequences, while mutations in the cold TFP sequence are shown below. The results illustrate how "silent" changes to the coding sequences generate dramatic changes in observed AID-mediated SHM rates, demonstrating that engineered sequences can be effectively optimized to create fast or slow rates of SHM.

FIG. 53E shows that the spectrum of mutations generated by AID in the present in vitro tissue culture system mirror those observed in other studies and those seen during in vivo affinity maturation. FIG. 53E shows the mutations generated in the present study (Box (i) upper left, n=118), and compares them with mutations observed by Zan et al. (box (ii) upper right, n=702), Wilson et al. (lower left, n=25000; box (iii)), and a larger analysis of IGHV chains that have undergone affinity maturation (lower right, n=101,926; box (iv)). The Y-axis in each chart indicates the starting nucleotide, the X-axis indicates the end nucleotide, and the number in each square indicates the percentage (%) of time that nucleotide transition is observed. In the present study, the frequency of mutation transitions and transversions was similar to those seen in other data sets. Mutations of C to T and G to A are the direct result of AID activity on cytidines and account for 48% of all mutation events. In addition, mutations at bases A and T account for ~30% of mutation events (i.e., slightly less than frequencies observed in other datasets).

FIG. 53F shows that mutation events are distributed throughout the SHM optimized nucleotide sequence of the hot TFP gene, with a maximum instantaneous rate of about 0.08 events per 1000 nucleotides per generation centered around 300 nucleotides from the beginning of the open reading frame. Stable transfection and selection of a gene with AID (for 30 days) produces a maximum rate of mutation of 1 event per 480 nucleotides. As a result, genes may contain zero, one, two or more mutations per gene. The distribution of SHM-mediated events observed in hot TFP sequenced genes can be seen in FIG. 53G, compared to the significantly reduced pattern of mutations seen in cold TFP (FIG. 53H).

Thus the present study demonstrates that the creation of non-synonymous versions of genes such as Teal-fluorescent protein (TFP) that do not normally undergo somatic hypermutation can be used to target such genes for high rates of somatic hypermutation. Additionally, the creation of SHM resistant genes (while encoding for the same amino acids) can lead to proteins that have a reduced number of somatic hypermutation hot-spots and, thus, experience a dramatically reduced level of AID mediated hypermutation. In each instance of SHM optimization, mammalian codon usage and other factors effecting gene expression levels were considered in generating the engineered sequences, leading to proteins that also exhibit reasonable levels of translation and expression. The results, therefore, demonstrate that the present methods of SHM optimization (i) can be successfully used to target the activity of AID to specific regions of an expressed gene; (ii) can be used to speed or slow the rate of SHM, (iii) demonstrate that the spectrum of mutations generated by AID using this methodology is equivalent to that observed in vivo; (iv) and demonstrate that SHM optimization can be successfully performed on a gene of interest to either positively or negatively impact its rate of AID-mediated SHM without significantly negatively impacting its expression.

While preferred embodiments of the present invention have been shown and described herein, such embodiments are provided by way of example only. It should be understood that various alternatives to the embodiments of the invention described herein may be employed in practicing the invention. It is intended that the following claims define the scope of the invention and that methods and structures within the scope of these claims and their equivalents be covered thereby.

GENERAL REFERENCES

1. Wang et al. Evolution of new non-antibody proteins via iterative somatic hypermutation. Proc Natl Acad Sci USA. 2004 Nov. 30; 101(48):16745-16749.
2. Yelamos, et al, Targeting of non-Ig sequences in place of V segment by somatic hypermutation. Nature 1995; 376: 225-229.
3. Zheng, et al., Intricate targeting of immunoglobulin somatic hypermutation maximizes the efficiency of affinity maturation. J Exp Med. 2005 May 2; 201(9):1467-1478.
4. Ruckerl et al., Episomal vectors to monitor and induce somatic hypermutation in human Burkitt-Lymphoma cell lines. Mol. Immunol 2006 April; 43(10): 1645-1652.
5. Bachl et al., Increased transcription levels induce higher mutation rates in a hypermutating cell line. J. Immunol 2001 Apr. 15; 166(8):5051-5057.
6. Cumbers et al., Generation and iterative affinity maturation of antibodies in vitro using hypermutating B-cell lines. Nat Biotechnol. 2002 November; 20(11): 1129-1134.
7. Neuberger, et al. Somatic hypermutation at A.T pairs: polymerase error versus dUTP incorporation. Nat Rev Immunol 2005 February; 5(2): 171-178. Review.
8. Wang, et al. Genome-wide somatic hypermutation. Proc Natl Acad Sci USA. 2004 May 11; 101(19):7352-7356.
9. Wang and Wabl. Hypermutation rate normalized by chronological time. J Immunol 2005 May 1; 174(9):5650-5654.
10. Martin et al. Somatic hypermutation of the AID transgene in B and non-B cells. Proc Natl Acad Sci USA. 2002 Sep. 17; 99(19): 12304-12308.
11. Shinkura R, et al. Separate domains of AID are required for somatic hypermutation and class-switch recombination. Nat Immunol 2004 July; 5(7):707-712.
12. Zhang (Scharff) et al., Clonal instability of V region hypermutation in the Ramos Burkitt's lymphoma cell line. Int Immunol 2001 September; 13(9): 1175-1184.
13. Ruckerl and Bachl. Activation induced cytidine deaminase fails to induce a mutator phenotype in the human pre-B cell line Nalm6. Eur. J. Immunol. 2005; 35: 290-298.

14. Rogozin and Diaz. Cutting edge: DGYW/WRCH is a better predictor of mutability at G:C bases in Ig hypermutation than the widely accepted RGYW/WRCY motif and probably reflects a two-step activation-induced cytidine deaminase-triggered process. J. Immunol, 2004, 172: 3382-3384.

15. Martin et al. Activation-induced cytidine deaminase turns on somatic hypermutation in hybridomas. Nature. 2002 Feb. 14; 415(6873): 802-806.

16. U.S. Pat. No. 6,815,194

17. U.S. Pat. No. 5,885,827

18. Coker et al., (2006) Genetic and In vitro assays of DNA deamination Methods Enzymology 408 156-170

20. Conticello et al., (2005) Evolution of the AID/APOBEC family of polynucleotide (deoxy)cytidine deaminases. Mol. Biol. Evol. 22 (2) 367-377

21. Odegard et al., (2006) Targeting of somatic hypermutation Nature Rev. Imm. 6 573-583

22. Shen et al. (2006) Somatic hypermutation and class switch recombination in Msh6−/−Ung−/− double-knock out mice. J. Imm. 177 5386-5392

23. Neuberger et al. (2005) Somatic hypermutation at A.T pairs: polymerase error versus dUTP incorporation. Nat. Rev. Immunol 5(2) 171-8

24. Rogozin et al. (2004) Cutting Edge: DGYW/WRCH is a better predictor of mutability at G:C bases in Ig hypermutation than the widely accepted RGYW/WRCY motif and probably reflects a two step activation induced cytidine deaminase triggered process. J. Imm. 172 3382-3384

25. Wilson et al. (2005) MSH2-MSH6 stimulates DNA polymerase eta, suggesting a role for A:T mutations in antibody genes. J. Exp. Med. 201 (4) 637-645

26. Santa-Marta et al. (2006) HIV-1 vif protein blocks the cytidine deaminase activity of B-cell specific AID in the *E. coli* by a similar mechanism of action. Mol. Imm. 44 583-590

27. Zan et al. (2005) The translesion DNA polymerase theta play a dominant role in immunoglobulin gene somatic hypermutation. EMBO J. 24 3757-3769

28. Watanebe et al. (2004) Rad18 guides pol cta to replication stalling sites through physical interaction and PCNA monoubiquitination. EMBO J. 23 3886-3896

29. Besmer et al., (2006) The transcription elongation complex directs activation induced cytidine deaminase mediated DNA deamination. Mol. Cell. Biol. (2006) 26 (11) 4378-4385.

30. Steele et al. (2006) Computational analyses show A to G mutations correlate with nascent mRNA hairpins at somatic hypermutation hotspots. DNA Repair doi: 10.1016/j.dnarep.2006.06.002

31. Odegard et al. (2005) Histone modifications associated with somatic hypermutation Immunity 23 101-110

32. Komori et al. (2006) biased dA/dT somatic hypermutation as regulated by the heavy chain intronic iEu enhancer and 3' E alpha enhancers in human lymphoblastoid B cells. Mol. Imm. 43 1817-1826

33. Rada et al., (2001) The intrinsic hypermutability of antibody heavy and light chain genes decays exponentially. EMBO J. 20 4570-4576

34. Larijani et al. (2006) Mol. Cell. Biol. Doi:10.1128/MCB.00824-06.

35. Larijani et al., (2005) Methylation protects cytidines from AID-mediated deamination. Mol. Immunol 42(5) 599-604

36. Poltoratsky et al., (2006) Down regulation of DNA polymerase beta accompanies somatic hypermutation in human BL2 cell lines. DNA Repair. 2006 doi:10.1016/j.dnarep.2006.10.003

37. Hirt, (1967) Selective extraction of polyoma DNA from infected mouse cell cultures. J. Mol. Biol. 26:365-369.

38. Kapoor and Frappier, (2005) Methods for measuring the replication and segregation of Epstein-Barr virus-based plasmids. Methods Mol Biol. 292:247-66.

39. Wade-Martins et al., (1999) Long-term stability of large insert genomic DNA episomal shuttle vectors in human cells. Nuc Acids Res 27:1674-1682

40. Qiagen, Inc. alkaline lysis procedure, see www1.qiagen.com/literature/handbooks/PDF/PlasmidDNAPurification/PLS_QP_Miniprep/1034641_HB-_QIAprep__112005.pdf 41. Yates et al., (1984) A cis-acting element from the Epstein-Barr viral genome that permits stable replication of recombinant plasmids in latently infected cells. PNAS 81; 3806-3810.

42. Baker, (2005) The selectivity of beta-adrenoceptor antagonists at the human beta1, beta2 and beta3 adrenoceptors. Br J Pharmacol. February; 144(3):317-22.

43. Fitzgerald et al., (1998) Pharmacological and biochemical characterization of a recombinant human galanin GALR1 receptor: agonist character of chimeric galanin peptides. J Pharmacol Exp Ther. 1998 November; 287(2): 448-56.

44. Ghosh et al., (2006) Design, synthesis, and progress toward optimization of potent small molecule antagonists of CC chemokine receptor 8 (CCR8). J Med Chem. May 4; 49(9):2669-72.

45. Gillian R. et al., (2004) Quantitative Assays of Chemotaxis and Chemokinesis for Human Neural Cells. ASSAY and Drug Development Technologies. 2(5): 465-472.

46. Hintermann et al., (2005) Integrin Alpha6-Beta4-erbB2 Complex Inhibits Haptotaxis by Up-regulating E-cadherin Cell-Cell Junctions in Keratinocytes. J. Biol. Chem. 280 (9): 8004-8015.

47. Iwatsubo et al., (2003) J. Cardiovasc Pharmacol. January; 41 Suppl 1:S53-56.

48. Gearhart and Wood, (2001) Emerging links between hypermutation of antibody genes and DNA polymerases. Nature Rev. Immunol 1: 187-192.

49. Kawamura et al., (2004) DNA polymerase theta is preferentially expressed in lymphoid tissues and upregulated in human cancers. Int. J. Cancer 109(1):9-16.

50. Zan et al., (2005) The translesion DNA polymerase theta plays a dominant role in immunoglobulin gene somatic hypermutation. EMBO Journal 24, 3757-3769.

51. Zeng et al., (2001) DNA polymerase eta is an A-T mutator in somatic hypermutation of immunoglobulin variable genes. Nat. Immunol 2(6):537-41.

52. Habel et al. (2004) Maintenance of Epstein-Barr virus-derived episomal vectors in the murine Sp2/0 myeloma cell line is dependent upon exogenous expression of human EBP2. Biochem Cell Biol. 82(3):375-80.

53. Kapoor et al. (2001) Reconstitution of Epstein-Barr virus-based plasmid partitioning in budding yeast. EMBO J. 20(1-2):222-30.

What is claimed is:

1. A method for preparing a humanized antibody having a desired property, which method comprises:

(a) contacting one or more host cells that express or can be induced to express Activation Induced Cytidine Deaminase (AID) with:

(1) a first nucleic acid sequence which encodes one or more human antibody heavy chain protein scaffolds, wherein each heavy chain protein scaffold encodes all of a complementarity determining region 1 (CDR1) and all of a complementarity determining region 2 (CDR2) from the human antibody, (2) a first library of nucleic acid sequences, wherein each nucleic acid sequence of the library encodes all of a complementarity determining region 3 (CDR3) from a non-human antibody heavy chain protein, and wherein the first nucleic acid sequence of (i) and the first library of (ii) are operably linked in a first expression vector to produce a library of humanized antibody heavy chain protein-encoding polynucleotides comprising the CDR1 and CDR2 of the first nucleic acid sequence and the CDR3 of the first library, (3) a second nucleic acid sequence which encodes one or more human antibody light chain protein scaffolds, wherein each light chain protein scaffold encodes all of a CDR1 and all of a CDR2 from the human antibody, and (4) a second library of nucleic acid sequences, wherein each nucleic acid sequence of the library encodes all of a CDR3 from a non-human antibody light chain protein, and wherein the second nucleic acid sequence of (iii) and the second library of (iv) are operably linked in a second expression vector to produce a library of humanized antibody light chain protein-encoding polynucleotides comprising the CDR1 and CDR2 of the second nucleic acid sequence and the CDR3 of the second library, (b) whereupon AID expression in the one or more host cells induces one or more mutations in the nucleic acid sequences of the library of humanized antibody heavy chain protein-encoding polynucleotides produced in (a) (2) and one or more mutations in the nucleic acid sequences of the library of humanized antibody light chain protein-encoding polynucleotides produced in (a) (4), whereupon a humanized antibody having a desired property is produced by the one or more host cells, and (c) identifying or isolating the humanized antibody having the desired property.

2. The method of claim 1, wherein the first library of nucleic acid sequences has been synthetically produced.

3. The method of claim 1, wherein the second library of nucleic acid sequences has been synthetically produced.

4. The method of claim 1, wherein the one or more host cells are one or more eukaryotic cells or one or more prokaryotic cells.

5. The method of claim 1, wherein one or more of the first or second nucleic acid sequences, or the nucleic acid sequences of the first and second libraries has been modified as compared to a corresponding wild-type nucleic sequence to increase or decrease the density of somatic hypermutation (SHM) cold spots and/or SHM hot spots so as to increase or decrease the susceptibility of the nucleic acid sequence to SHM.

6. The method of claim 1, which optionally comprises establishing and culturing clonal colonies of the one or more host cells which produces a humanized antibody having the desired property.

7. The method of claim 1, wherein the human antibody is a monoclonal antibody.

8. The method of claim 1, wherein the non-human antibody is a monoclonal antibody.

9. The method of claim 1, wherein the non-human antibody is a mouse antibody.

10. The method of claim 1, wherein the first and second expression vectors are the same.

* * * * *

UNITED STATES PATENT AND TRADEMARK OFFICE

CERTIFICATE OF CORRECTION

PATENT NO. : 8,685,897 B2
APPLICATION NO. : 13/109106
DATED : April 1, 2014
INVENTOR(S) : Bowers et al.

It is certified that error appears in the above-identified patent and that said Letters Patent is hereby corrected as shown below:

On the title page, under "Assignee," item (73) should read as follows:

"AnaptysBio, Inc., San Diego, CA (US)".

In the Claims

Claim 1, Col. 467, lines 35-36, "the first nucleic acid sequence of (i) and the first library of (ii) are operably linked" should read --the first nucleic acid sequence of (1) and the first library of (2) are operably linked--.

Claim 1, Col. 467, lines 48-49, "and wherein the second nucleic acid sequence of (iii) and the second library of (iv) are operably linked" should read --and wherein the second nucleic acid sequence of (3) and the second library of (4) are operably linked--.

Signed and Sealed this
Second Day of September, 2014

Michelle K. Lee
*Deputy Director of the United States Patent and Trademark Office*

SEQUENCE LISTING

<160> NUMBER OF SEQ ID NOS: 475

<210> SEQ ID NO 1
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 1 tacagctat 9

<210> SEQ ID NO 2
<211> LENGTH: 133
<212> TYPE: PRT
<213> ORGANISM: Aspergillus terreus
<220> FEATURE:
<221> NAME/KEY: MOD_RES
<222> LOCATION: (133)..(133)
<223> OTHER INFORMATION: Variable amino acid

<400> SEQUENCE: 2

```
Met Ala Lys Pro Leu Ser Gln Glu Glu Ser Thr Leu Ile Glu Arg Ala
1               5                   10                  15

Thr Ala Thr Ile Asn Ser Ile Pro Ile Ser Glu Asp Tyr Ser Val Ala
            20                  25                  30

Ser Ala Ala Leu Ser Ser Asp Gly Arg Ile Phe Thr Gly Val Asn Val
        35                  40                  45

Tyr His Phe Thr Gly Gly Pro Cys Ala Glu Leu Val Val Leu Gly Thr
    50                  55                  60

Ala Ala Ala Ala Ala Ala Gly Asn Leu Thr Cys Ile Val Ala Ile Gly
65                  70                  75                  80

Asn Glu Asn Arg Gly Ile Leu Ser Pro Cys Gly Arg Cys Arg Gln Val
                85                  90                  95

Leu Leu Asp Leu His Pro Gly Ile Lys Ala Ile Val Lys Asp Ser Asp
            100                 105                 110

Gly Gln Pro Thr Ala Val Gly Ile Arg Glu Leu Leu Pro Ser Gly Tyr
        115                 120                 125

Val Trp Glu Gly Xaa
    130
```

<210> SEQ ID NO 3
<211> LENGTH: 399
<212> TYPE: DNA
<213> ORGANISM: Aspergillus terreus

<400> SEQUENCE: 3

```
atggccaagc ctttgtctca agaagaatcc accctcattg aaagagcaac ggctacaatc      60

aacagcatcc ccatctctga agactacagc gtcgccagcg cagctctctc tagcgacggc     120

cgcatcttca ctggtgtcaa tgtatatcat tttactgggg gaccttgcgc agaactcgtg     180

gtgctgggca ctgctgctgc tgcggcagct ggcaacctga cttgtatcgt cgcgatcgga     240

aatgagaaca ggggcatctt gagcccctgc ggacggtgcc gacaggttct tctcgatctg     300

catcctggga tcaaagccat agtgaaggac agtgatggac agccgacggc agttgggatt     360

cgtgaattgc tgccctctgg ttatgtgtgg gagggctaa                            399
```

<210> SEQ ID NO 4
<211> LENGTH: 399

<212> TYPE: DNA
<213> ORGANISM: Artificial Sequence
<220> FEATURE:
<223> OTHER INFORMATION: Synthetic construct

<400> SEQUENCE: 4
atggccaagc ccctctctca agaggagtcc accctcattg agagagccac tgccacaatc 60
aactccatcc ccatctctga ggactactcc gtcgcctccg ccgccctctc gtcagacggg 120
agaatcttca ctggggtcaa tgtctatcat tttactgggg ggccctgtgc cgagctcgtc 180
gtcctcggga cagccgccgc cgccgccgcc gggaacctca cttgtatcgt cgccataggg 240
aatgagaaca gggggatcct ctccccctgc gggagatgcc gacaggtcct cctcgacctc 300
caccccggga tcaaagccat agtcaaggac tcagacgggc agcccacagc cgtcgggatt 360
cgagagctcc tcccctctgg gtatgtctgg gaggggtaa 399

<210> SEQ ID NO 5
<211> LENGTH: 399
<212> TYPE: DNA
<213> ORGANISM: Artificial Sequence
<220> FEATURE:
<223> OTHER INFORMATION: Synthetic construct

<400> SEQUENCE: 5
atggctaaac ctcttagcca ggaagaaagt accttgattg aacgtgcaac tgctacaatc 60
aacagcatac ccatatctga agactactct gttgccagtg cagctttaag ttcagacggt 120
aggattttta caggtgtgaa tgtttaccac tttactgggg gaccttgtgc agagttggta 180
gtactaggta cagctgcagc tgcagcagct ggcaacctaa cctgtattgt agcaatcggt 240
aatgaaaaca ggggcatact aagcccctgc ggtagatgca ggcaagtact gttagatctg 300
catcctggca tcaaagcaat agttaaggac agtgatgggc agccaactgc agttggtatt 360
agggaactac tgccctctgg ttatgtatgg gagggctaa 399

<210> SEQ ID NO 6
<211> LENGTH: 198
<212> TYPE: PRT
<213> ORGANISM: Homo sapiens

<400> SEQUENCE: 6

Met Asp Ser Leu Leu Met Asn Arg Arg Lys Phe Leu Tyr Gln Phe Lys
1               5                   10                  15

Asn Val Arg Trp Ala Lys Gly Arg Arg Glu Thr Tyr Leu Cys Tyr Val
            20                  25                  30

Val Lys Arg Arg Asp Ser Ala Thr Ser Phe Ser Leu Asp Phe Gly Tyr
        35                  40                  45

Leu Arg Asn Lys Asn Gly Cys His Val Glu Leu Leu Phe Leu Arg Tyr
    50                  55                  60

Ile Ser Asp Trp Asp Leu Asp Pro Gly Arg Cys Tyr Arg Val Thr Trp
65                  70                  75                  80

Phe Thr Ser Trp Ser Pro Cys Tyr Asp Cys Ala Arg His Val Ala Asp
                85                  90                  95

Phe Leu Arg Gly Asn Pro Asn Leu Ser Leu Arg Ile Phe Thr Ala Arg
            100                 105                 110

Leu Tyr Phe Cys Glu Asp Arg Lys Ala Glu Pro Glu Gly Leu Arg Arg
        115                 120                 125

Leu His Arg Ala Gly Val Gln Ile Val Ile Met Thr Phe Lys Asp Tyr
    130                 135                 140

```
Phe Tyr Cys Trp Asn Thr Phe Val Glu Asn His Glu Arg Thr Phe Lys
145                 150                 155                 160

Ala Trp Glu Gly Leu His Glu Asn Ser Val Arg Leu Ser Arg Gln Leu
                165                 170                 175

Arg Arg Ile Leu Leu Pro Leu Tyr Glu Val Asp Asp Leu Arg Asp Ala
            180                 185                 190

Phe Arg Thr Leu Gly Leu
        195


<210> SEQ ID NO 7
<211> LENGTH: 198
<212> TYPE: PRT
<213> ORGANISM: Mus musculus

<400> SEQUENCE: 7

Met Asp Ser Leu Leu Met Lys Gln Lys Lys Phe Leu Tyr His Phe Lys
1               5                   10                  15

Asn Val Arg Trp Ala Lys Gly Arg His Glu Thr Tyr Leu Cys Tyr Val
            20                  25                  30

Val Lys Arg Arg Asp Ser Ala Thr Ser Phe Ser Leu Asp Phe Gly Tyr
        35                  40                  45

Leu Arg Asn Lys Ser Gly Cys His Val Glu Leu Leu Phe Leu Arg Tyr
    50                  55                  60

Ile Ser Asp Trp Asp Leu Asp Pro Gly Arg Cys Tyr Arg Val Thr Trp
65                  70                  75                  80

Phe Thr Ser Trp Ser Pro Cys Tyr Asp Cys Ala Arg His Val Ala Glu
                85                  90                  95

Phe Leu Arg Trp Asn Pro Asn Leu Ser Leu Arg Ile Phe Thr Ala Arg
            100                 105                 110

Leu Tyr Phe Cys Glu Asp Arg Lys Ala Glu Pro Glu Gly Leu Arg Arg
        115                 120                 125

Leu His Arg Ala Gly Val Gln Ile Gly Ile Met Thr Phe Lys Asp Tyr
    130                 135                 140

Phe Tyr Cys Trp Asn Thr Phe Val Glu Asn Arg Glu Arg Thr Phe Lys
145                 150                 155                 160

Ala Trp Glu Gly Leu His Glu Asn Ser Val Arg Leu Ser Arg Gln Leu
                165                 170                 175

Arg Arg Ile Leu Leu Pro Leu Tyr Glu Val Asp Asp Leu Arg Asp Ala
            180                 185                 190

Phe Arg Met Leu Gly Leu
        195


<210> SEQ ID NO 8
<211> LENGTH: 198
<212> TYPE: PRT
<213> ORGANISM: Canis familiaris

<400> SEQUENCE: 8

Met Asp Ser Leu Leu Met Lys Gln Lys Lys Phe Leu Tyr His Phe Lys
1               5                   10                  15

Asn Val Arg Trp Ala Lys Gly Arg His Glu Thr Tyr Leu Cys Tyr Val
            20                  25                  30

Val Lys Arg Arg Asp Ser Ala Thr Ser Phe Ser Leu Asp Phe Gly Tyr
        35                  40                  45

Leu Arg Asn Lys Ser Gly Cys His Val Glu Leu Leu Phe Leu Arg Tyr
    50                  55                  60

Ile Ser Asp Trp Asp Leu Asp Pro Gly Arg Cys Tyr Arg Val Thr Trp
```

65 70 75 80

Phe Thr Ser Trp Ser Pro Cys Tyr Asp Cys Ala Arg His Val Ala Asp
85 90 95

Phe Leu Arg Gly Tyr Pro Asn Leu Ser Leu Arg Ile Phe Ala Ala Arg
100 105 110

Leu Tyr Phe Cys Glu Asp Arg Lys Ala Glu Pro Glu Gly Leu Arg Arg
115 120 125

Leu His Arg Ala Gly Val Gln Ile Ala Ile Met Thr Phe Lys Asp Tyr
130 135 140

Phe Tyr Cys Trp Asn Thr Phe Val Glu Asn Arg Glu Arg Thr Phe Lys
145 150 155 160

Ala Trp Glu Gly Leu His Glu Asn Ser Val Arg Leu Ser Arg Gln Leu
165 170 175

Arg Arg Ile Leu Leu Pro Leu Tyr Glu Val Asp Asp Leu Arg Asp Ala
180 185 190

Phe Arg Thr Leu Gly Leu
195

<210> SEQ ID NO 9
<211> LENGTH: 198
<212> TYPE: PRT
<213> ORGANISM: Rattus norvegicus

<400> SEQUENCE: 9

Met Asp Ser Leu Leu Met Lys Gln Lys Lys Phe Leu Tyr His Phe Lys
1 5 10 15

Asn Val Arg Trp Ala Lys Gly Arg His Glu Thr Tyr Leu Cys Tyr Val
20 25 30

Val Lys Arg Arg Asp Ser Ala Thr Ser Phe Ser Leu Asp Phe Gly Tyr
35 40 45

Leu Arg Asn Lys Ser Gly Cys His Val Glu Leu Leu Phe Leu Arg Tyr
50 55 60

Ile Ser Asp Trp Asp Leu Asp Pro Gly Arg Cys Tyr Arg Val Thr Trp
65 70 75 80

Phe Thr Ser Trp Ser Pro Cys Tyr Asp Cys Ala Arg His Val Ala Glu
85 90 95

Phe Leu Arg Trp Asn Pro Asn Leu Ser Leu Arg Ile Phe Thr Ala Arg
100 105 110

Leu Tyr Phe Cys Glu Asp Arg Lys Ala Glu Pro Glu Gly Leu Arg Arg
115 120 125

Leu His Arg Ala Gly Val Gln Ile Gly Ile Met Thr Phe Lys Asp Tyr
130 135 140

Phe Tyr Cys Trp Asn Thr Phe Val Glu Asn His Glu Arg Thr Phe Lys
145 150 155 160

Ala Trp Glu Gly Leu His Glu Asn Ser Val Arg Leu Ser Arg Gln Leu
165 170 175

Arg Arg Ile Leu Leu Pro Leu Tyr Glu Val Asp Asp Leu Arg Asp Ala
180 185 190

Phe Arg Ile Leu Gly Leu
195

<210> SEQ ID NO 10
<211> LENGTH: 198
<212> TYPE: PRT
<213> ORGANISM: Pan troglodytes

<400> SEQUENCE: 10

-continued

Met Asp Ser Leu Leu Met Asn Arg Arg Lys Phe Leu Tyr Gln Phe Lys
1 5 10 15

Asn Val Arg Trp Ala Lys Gly Arg Arg Glu Thr Tyr Leu Cys Tyr Val
20 25 30

Val Lys Arg Arg Asp Ser Ala Thr Ser Phe Ser Leu Asp Phe Gly Tyr
35 40 45

Leu Arg Asn Lys Asn Gly Cys His Val Glu Leu Leu Phe Leu Arg Tyr
50 55 60

Ile Ser Asp Trp Asp Leu Asp Pro Gly Arg Cys Tyr Arg Val Thr Trp
65 70 75 80

Phe Thr Ser Trp Ser Pro Cys Tyr Asp Cys Ala Arg His Val Ala Asp
85 90 95

Phe Leu Arg Gly Asn Pro Asn Leu Ser Leu Arg Ile Phe Thr Ala Arg
100 105 110

Leu Tyr Phe Cys Glu Asp Arg Lys Ala Glu Pro Glu Gly Leu Arg Arg
115 120 125

Leu His Arg Ala Gly Val Gln Ile Ala Ile Met Thr Phe Lys Asp Tyr
130 135 140

Phe Tyr Cys Trp Asn Thr Phe Val Glu Asn His Glu Arg Thr Phe Lys
145 150 155 160

Ala Trp Glu Gly Leu His Glu Asn Ser Val Arg Leu Ser Arg Gln Leu
165 170 175

Arg Arg Ile Leu Leu Pro Leu Tyr Glu Val Asp Asp Leu Arg Asp Ala
180 185 190

Phe Arg Thr Leu Gly Leu
195

<210> SEQ ID NO 11
<211> LENGTH: 198
<212> TYPE: PRT
<213> ORGANISM: Canis sp.

<400> SEQUENCE: 11

Met Asp Ser Leu Leu Met Lys Gln Arg Lys Phe Leu Tyr His Phe Lys
1 5 10 15

Asn Val Arg Trp Ala Lys Gly Arg His Glu Thr Tyr Leu Cys Tyr Val
20 25 30

Val Lys Arg Arg Asp Ser Ala Thr Ser Phe Ser Leu Asp Phe Gly His
35 40 45

Leu Arg Asn Lys Ser Gly Cys His Val Glu Leu Leu Phe Leu Arg Tyr
50 55 60

Ile Ser Asp Trp Asp Leu Asp Pro Gly Arg Cys Tyr Arg Val Thr Trp
65 70 75 80

Phe Thr Ser Trp Ser Pro Cys Tyr Asp Cys Ala Arg His Val Ala Asp
85 90 95

Phe Leu Arg Gly Tyr Pro Asn Leu Ser Leu Arg Ile Phe Ala Ala Arg
100 105 110

Leu Tyr Phe Cys Glu Asp Arg Lys Ala Glu Pro Glu Gly Leu Arg Arg
115 120 125

Leu His Arg Ala Gly Val Gln Ile Ala Ile Met Thr Phe Lys Asp Tyr
130 135 140

Phe Tyr Cys Trp Asn Thr Phe Val Glu Asn Arg Glu Lys Thr Phe Lys
145 150 155 160

Ala Trp Glu Gly Leu His Glu Asn Ser Val Arg Leu Ser Arg Gln Leu
165 170 175

```
Arg Arg Ile Leu Leu Pro Leu Tyr Glu Val Asp Asp Leu Arg Asp Ala
            180                 185                 190

Phe Arg Thr Leu Gly Leu
        195
```

<210> SEQ ID NO 12
<211> LENGTH: 594
<212> TYPE: DNA
<213> ORGANISM: Canis sp.

<400> SEQUENCE: 12

```
atggacagtt tactgatgaa acagcgcaaa ttcttatatc actttaagaa cgtccgctgg      60

gccaaaggta gacatgagac ctacctgtgt tatgttgtga agaggcggga tagtgcaaca     120

tctttttccc tggacttcgg ccacctccgt aataagtccg ggtgccacgt ggaactgctg     180

ttcttgcgtt atattagcga ctgggacctg gacccagggc ggtgttatcg ggtgacttgg     240

tttacctctt ggtccccctg ctatgattgt gcacgccatg tggctgattt tcttcgcggc     300

tatccaaatc taagtctacg tatctttgca gcacggttat acttttgtga ggatcgcaag     360

gcagagcccg agggtctgcg gcgcctacat agggctgggg tccagatcgc tattatgacc     420

ttcaaggatt acttttattg ctggaataca tttgtcgaga acagggagaa aaccttcaag     480

gcctgggagg gcctgcatga aaactccgtg agactgagca gacaactgcg aagaatcctg     540

ttgcctctgt atgaggtcga cgacctaagg gacgctttcc gcaccctagg ctta           594
```

<210> SEQ ID NO 13
<211> LENGTH: 594
<212> TYPE: DNA
<213> ORGANISM: Artificial Sequence
<220> FEATURE:
<223> OTHER INFORMATION: Synthetic construct

<400> SEQUENCE: 13

```
atggacagtt tactgatgaa acagcgcaag ttcctgtacc actttaagaa tgttcggtgg      60

gcaaaaggta ggcatgaaac ctacctgtgt tatgtagtta aaaggcggga tagtgcaaca     120

agctttagct tggacttcgg gcaccttcgt aacaaaagcg gctgccatgt tgaactgctg     180

ttcttgaggt acattagcga ctgggacctg gacccaggta gatgctaccg agtaacttgg     240

tttactagtt ggagcccatg ctatgattgt gcaaggcatg tagcagattt tcttcgcggc     300

tatccaaacc taagccttag aatctttgca gcaaggttgt acttttgtga ggatcgcaag     360

gcagagcccg aggggctacg ccggctgcat agggctggag tacaaatagc tattatgacc     420

ttcaaggatt acttttactg ttggaataca tttgttgaga acagggagaa aaccttcaaa     480

gcctgggagg gtttgcatga aaactcagta aggttaagca ggcaactgcg aagaatacta     540

ctacctctgt atgaggttga cgacctaagg gatgccttcc gtaccctagg ctta           594
```

<210> SEQ ID NO 14
<211> LENGTH: 594
<212> TYPE: DNA
<213> ORGANISM: Artificial Sequence
<220> FEATURE:
<223> OTHER INFORMATION: Synthetic construct

<400> SEQUENCE: 14

```
atggactccc tcctcatgaa acagaggaag tttctctacc atttcaaaaa tgtcaggtgg      60

gccaagggga gacatgagac ttatctctgt tatgtcgtca agagacggga ctcagccacg     120

agtttctccc tcgactttgg gcatctcaga aacaagtcgg ggtgccatgt cgagctcctc     180
```

ttcctcagat acatctcaga ctgggacctc gaccccggga ggtgctatag agtcacctgg 240
tttacctcct ggtccccctg ctacgactgt gcccgacatg tcgccgactt cctcaggggg 300
taccccaatc tctccctcag aatattcgcc gccagactct atttctgtga ggacaggaag 360
gccgagcccg aggggctcag gagactccac agggccgggg tccagatcgc cattatgaca 420
ttcaaagact acttctactg ctggaacaca tttgtcgaga atagggagaa gacttttaag 480
gcctgggagg ggctccatga gaattcggtc agactctctc gccaactcag gagaattctc 540
ctccccctct atgaggtcga cgacctcagg gacgccttca ggaccctcgg gctc 594

<210> SEQ ID NO 15
<211> LENGTH: 597
<212> TYPE: DNA
<213> ORGANISM: Canis familiaris

<400> SEQUENCE: 15
atggacagcc tcctgatgaa gcagaggaag tttctttacc atttcaagaa tgtccgctgg 60
gcgaagggtc gccatgagac ttacttgtgc tacgtggtga agcggcggga tagtgccacc 120
tccttttctc tggactttgg tcaccttcga aacaagtcgg gctgccacgt ggagctgctc 180
ttcctccgct acatctccga ctgggacctg gaccccggcc ggtgctaccg cgtcacctgg 240
ttcacgtcct ggagcccctg ctacgactgc gcgcggcacg tggcggactt cctgcgcggg 300
taccccaacc tcagcctcag gatcttcgcc gcgcgcctct acttctgcga ggaccgcaag 360
gcggagcccg aggggctgcg gcggctgcac cgggcgggcg tccagatcgc catcatgacc 420
ttcaaggatt atttttattg ctggaatact tttgtggaaa atcgtgaaaa aactttcaaa 480
gcctgggagg ggttgcacga aaattccgtt cgactatcca gacagcttcg acgcattctt 540
ttgcccctgt atgaggttga tgacttacga gatgcatttc gtactttggg actttga 597

<210> SEQ ID NO 16
<211> LENGTH: 597
<212> TYPE: DNA
<213> ORGANISM: Artificial Sequence
<220> FEATURE:
<223> OTHER INFORMATION: Synthetic construct

<400> SEQUENCE: 16
atggacagcc tcctgatgaa gcagaggaag tttctttacc atttcaagaa tgtccgctgg 60
gccaagggga gacatgagac ttacttgtgc tatgtggtca agagaaggga tagtgccacc 120
tccttttctc tggactttgg tcacttgagg aataagtcgg gctgtcatgt cgagctgctc 180
ttcctccgct acatctccga ctgggacctg gaccccggga gatgctatag agtcacctgg 240
ttcacgtcct ggagcccctg ctacgactgc gccagacatg tcgccgactt cctgaggggg 300
tatcccaacc tcagcctcag gatcttcgcc gcccgtctct acttctgcga ggaccgtaag 360
gccgagcccg aggggctgag gagactccac agggccggag tccagatcgc catcatgacc 420
ttcaaggatt atttttattg ctggaatact tttgtggaga atagggaaaa aactttcaaa 480
gcctgggagg ggctccatga gaattctgtc agactcagta gacagctcag gagaattctt 540
ttgcccctgt atgaggttga tgaccttaga gacgcattta ggacactggg actttga 597

<210> SEQ ID NO 17
<211> LENGTH: 597
<212> TYPE: DNA
<213> ORGANISM: Homo sapiens

<400> SEQUENCE: 17

-continued atggacagcc tcttgatgaa ccggaggaag tttctttacc aattcaaaaa tgtccgctgg 60
gctaagggtc gccgtgagac ctacctgtgc tacgtagtga agaggcgtga cagtgctaca 120
tccttttcac tggactttgg ttatcttcgc aataagaacg gctgccacgt ggaattgctc 180
ttcctccgct acatctcgga ctgggaccta gaccctggcc gctgctaccg cgtcacctgg 240
ttcacctcct ggagcccctg ctacgactgt gcccgacatg tggccgactt tctgcgaggg 300
aaccccaacc tcagtctgag gatcttcacc gcgcgcctct acttctgtga ggaccgcaag 360
gctgagcccg aggggctgcg gcggctgcac cgcgccgggg tgcaaatagc catcatgacc 420
ttcaaagatt atttttactg ctggaatact tttgtagaaa accatgaaag aactttcaaa 480
gcctgggaag ggctgcatga aaattcagtt cgtctctcca gacagcttcg acgcatcctt 540
ttgcccctgt atgaggttga tgacttacga gacgcatttc gtactttggg actttga 597

<210> SEQ ID NO 18
<211> LENGTH: 597
<212> TYPE: DNA
<213> ORGANISM: Mus musculus

<400> SEQUENCE: 18
atggacagcc ttctgatgaa gcaaaagaag tttctttacc atttcaaaaa tgtccgctgg 60
gccaagggac gccatgagac ctacctctgc tacgtggtga agaggagaga tagtgccacc 120
tcctgctcac tggacttcgg ccaccttcgc aacaagtctg gctgccacgt ggaattgttg 180
ttcctacgct acatctcaga ctgggacctg gacccgggcc ggtgttaccg cgtcacctgg 240
ttcacctcct ggagcccgtg ctatgactgt gcccggcacg tggctgagtt tctgagatgg 300
aaccctaacc tcagcctgag gattttcacc gcgcgcctct acttctgtga agaccgcaag 360
gctgagcctg aggggctgcg gagactgcac cgcgctgggg tccagatcgg gatcatgacc 420
ttcaaagact atttttactg ctggaataca tttgtagaaa atcgtgaaag aactttcaaa 480
gcctgggaag ggctacatga aaattctgtc cggctaacca gacaacttcg acgcatcctt 540
ttgcccttgt acgaagtcga tgacttgcga gatgcatttc gtatgttggg attttga 597

<210> SEQ ID NO 19
<211> LENGTH: 6
<212> TYPE: DNA
<213> ORGANISM: Artificial Sequence
<220> FEATURE:
<223> OTHER INFORMATION: Synthetic oligonucleotide

<400> SEQUENCE: 19 agctac 6

<210> SEQ ID NO 20
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 20 gtcgtcgtc 9

<210> SEQ ID NO 21
<211> LENGTH: 142
<212> TYPE: DNA
<213> ORGANISM: Artificial Sequence
<220> FEATURE:
<223> OTHER INFORMATION: Synthetic oligonucleotide

<400> SEQUENCE: 21
acggccgtgt attactgtgc gagagtcgtc gtcagctaca gctacgtcgt cgtcgctgaa 60
tacttccagc actggggcca gggcaccctg gtcaccgtct cctcagcctc caccaagggc 120
ccatcggtct tcccgctagc ac 142

<210> SEQ ID NO 22
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 22
gtcgtcgtcc agctacagct agtcgtcgtc 30

<210> SEQ ID NO 23
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 23
gtcgtcgtca cagctacagc tgtcgtcgtc 30

<210> SEQ ID NO 24
<211> LENGTH: 47
<212> TYPE: PRT
<213> ORGANISM: Artificial Sequence
<220> FEATURE:
<223> OTHER INFORMATION: Synthetic peptide

<400> SEQUENCE: 24

Thr Ala Val Tyr Tyr Cys Ala Arg Val Val Val Ser Tyr Ser Tyr Val
1 5 10 15

Val Val Ala Glu Tyr Phe Gln His Trp Gly Gln Gly Thr Leu Val Thr
20 25 30

Val Ser Ser Ala Ser Thr Lys Gly Pro Ser Val Phe Pro Leu Ala
35 40 45

<210> SEQ ID NO 25
<211> LENGTH: 10
<212> TYPE: PRT
<213> ORGANISM: Artificial Sequence
<220> FEATURE:
<223> OTHER INFORMATION: Synthetic peptide

<400> SEQUENCE: 25

Val Val Val Gln Leu Gln Leu Val Val Val
1 5 10

<210> SEQ ID NO 26
<211> LENGTH: 10
<212> TYPE: PRT
<213> ORGANISM: Artificial Sequence
<220> FEATURE:
<223> OTHER INFORMATION: Synthetic peptide

<400> SEQUENCE: 26

Val Val Val Thr Ala Thr Ala Val Val Val
1 5 10

<210> SEQ ID NO 27

<211> LENGTH: 34
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Dhb
<220> FEATURE:
<221> NAME/KEY: MOD_RES
<222> LOCATION: (5)..(5)
<223> OTHER INFORMATION: Dha
<220> FEATURE:
<221> NAME/KEY: MOD_RES
<222> LOCATION: (8)..(8)
<223> OTHER INFORMATION: Abu
<220> FEATURE:
<221> NAME/KEY: MOD_RES
<222> LOCATION: (13)..(13)
<223> OTHER INFORMATION: Abu
<220> FEATURE:
<221> NAME/KEY: MOD_RES
<222> LOCATION: (23)..(23)
<223> OTHER INFORMATION: Abu
<220> FEATURE:
<221> NAME/KEY: MOD_RES
<222> LOCATION: (25)..(25)
<223> OTHER INFORMATION: Abu
<220> FEATURE:
<221> NAME/KEY: MOD_RES
<222> LOCATION: (33)..(33)
<223> OTHER INFORMATION: Dha

<400> SEQUENCE: 27

```
Ile Xaa Ala Ile Xaa Leu Ala Xaa Pro Gly Ala Lys Xaa Gly Ala Leu
1               5                   10                  15

Met Gly Ala Asn Met Lys Xaa Ala Xaa Ala Asn Ala Ser Ile His Val
            20                  25                  30

Xaa Lys
```

<210> SEQ ID NO 28
<211> LENGTH: 34
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Dhb
<220> FEATURE:
<221> NAME/KEY: MOD_RES
<222> LOCATION: (5)..(5)
<223> OTHER INFORMATION: Dha
<220> FEATURE:
<221> NAME/KEY: MOD_RES
<222> LOCATION: (8)..(8)
<223> OTHER INFORMATION: Abu
<220> FEATURE:
<221> NAME/KEY: MOD_RES
<222> LOCATION: (13)..(13)
<223> OTHER INFORMATION: Abu
<220> FEATURE:
<221> NAME/KEY: MOD_RES
<222> LOCATION: (19)..(19)
<223> OTHER INFORMATION: Abu
<220> FEATURE:
<221> NAME/KEY: MOD_RES
<222> LOCATION: (23)..(23)
<223> OTHER INFORMATION: Abu
<220> FEATURE:
<221> NAME/KEY: MOD_RES
<222> LOCATION: (25)..(25)
<223> OTHER INFORMATION: Abu
<220> FEATURE:

<221> NAME/KEY: MOD_RES
<222> LOCATION: (33)..(33)
<223> OTHER INFORMATION: Dha

<400> SEQUENCE: 28

Ile Xaa Ala Ile Xaa Leu Ala Xaa Pro Gly Ala Lys Xaa Gly Ala Leu
1 5 10 15

Met Gly Xaa Asn Met Lys Xaa Ala Xaa Ala Asn Ala Ser Ile His Val
20 25 30

Xaa Lys

<210> SEQ ID NO 29
<211> LENGTH: 34
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Dhb
<220> FEATURE:
<221> NAME/KEY: MOD_RES
<222> LOCATION: (3)..(3)
<223> OTHER INFORMATION: Dha
<220> FEATURE:
<221> NAME/KEY: MOD_RES
<222> LOCATION: (5)..(5)
<223> OTHER INFORMATION: Dha
<220> FEATURE:
<221> NAME/KEY: MOD_RES
<222> LOCATION: (8)..(8)
<223> OTHER INFORMATION: Dhb
<220> FEATURE:
<221> NAME/KEY: MOD_RES
<222> LOCATION: (13)..(13)
<223> OTHER INFORMATION: Dhb
<220> FEATURE:
<221> NAME/KEY: MOD_RES
<222> LOCATION: (23)..(23)
<223> OTHER INFORMATION: Dhb
<220> FEATURE:
<221> NAME/KEY: MOD_RES
<222> LOCATION: (25)..(25)
<223> OTHER INFORMATION: Dhb
<220> FEATURE:
<221> NAME/KEY: MOD_RES
<222> LOCATION: (33)..(33)
<223> OTHER INFORMATION: Dha

<400> SEQUENCE: 29

Ile Xaa Xaa Ile Xaa Leu Cys Xaa Pro Gly Cys Lys Xaa Gly Ala Leu
1 5 10 15

Met Gly Cys Asn Met Lys Xaa Ala Xaa Cys Asn Cys Ser Ile His Val
20 25 30

Xaa Lys

<210> SEQ ID NO 30
<211> LENGTH: 34
<212> TYPE: PRT
<213> ORGANISM: Artificial Sequence
<220> FEATURE:
<223> OTHER INFORMATION: Synthetic peptide

<400> SEQUENCE: 30

Ile Thr Ser Ile Ser Leu Cys Thr Pro Gly Cys Lys Thr Gly Ala Leu
1 5 10 15

Met Gly Cys Asn Met Lys Thr Ala Thr Cys Asn Cys Ser Ile His Val
20 25 30

Ser Lys

<210> SEQ ID NO 31
<211> LENGTH: 2979
<212> TYPE: DNA
<213> ORGANISM: Unknown
<220> FEATURE:
<223> OTHER INFORMATION: NisB sequence

<400> SEQUENCE: 31
atgattaagt catcatttaa agctcagcct ttcctcgtgc gaaataccat cctgtcccct 60
aatgataaaa ggtccttcac agagtacact caggtgatcg agacggtatc aaagaataag 120
gtctttcttg aacagctgct gctcgccaac cccaaattat acaacgttat gcagaagtat 180
aatgctggct tgctgaaaaa aaagcgcgtt aaaaaattgt tcgaatctat atacaagtat 240
tacaagcgtt cttacctgcg gagcaccccg tttggcttgt tttctgaaac ctcgatcggc 300
gtattctcaa agtcatctca gtataaactg atggggaaga ccaccaaagg tatccgcctg 360
gacacccaat ggctgatcag gctggtgcat aagatggagg tcgatttctc taaaaagcta 420
agcttcacgc gtaataatgc caactataaa ttcggcgaca gggtgtttca ggtctacacc 480
atcaacagca gcgagcttga ggaggtgaat atcaaataca ctaacgtgta tcagatcatt 540
tcagagttct gtgaaaatga ctaccagaaa tacgaagaca tttgcgaaac tgtgactctg 600
tgctacgggg acgaatacag agaactgtca gagcagtact taggctcgct gattgtgaac 660
cattatctga tctctaacct tcagaaagac ctgctttcag atttctcgtg ggacacattc 720
ctcactaagg tcgaggctat cgatgaggat aagaagtata taatcccccct gaagaaggtg 780 cagaaattca ttcaggagta ctccgagatt gaaatcggcg aaggcattga aaaattgaag 840
gagatttacc aagaaatgtc tcagatttta gaaaacgata actatattca gatagacctg 900
ataagcgatt ccgaaatcaa ctttgacgta aagcaaaagc aacagctgga gcaccttgcc 960
gaatttctcg ggaacaccac caagtccgtg agaaggacct atcttgatga ttataaggac 1020
aaatttatcg aaaaatacgg tgtcgatcag gaagtccaga ttaccgagct tttgatagt 1080 actttcggca ttggcgcgcc ttataattac aaccatcctc gcaatgactt ttacgagagt 1140
gaaccttcta ctctttacta ctccgaggaa gagagggaaa agtacctgtc catgtacgtg 1200
gaagcagtga aaaatcacaa tgtgattaat ttggatgatc tggagtctca ctatcagaag 1260
atggacttag agaaaaagag cgaattgcag ggtctggaac tgttcctaaa cctcgcaaag 1320
gagtacgaga aagatatttt tattctgggc gatatagtgg gcaataacaa cctgggcggc 1380
gctagcggtc gttttagcgc cctaagcccc gagctgacta gctatcacag aaccatcgtc 1440
gactccgtgg agagagagaa cgagaataag gagataacaa gctgcgaaat tgtgttcctg 1500
cctgagaaca ttaggcacgc caacgtgatg catacaagca tcatgcggcg gaaagtcctt 1560
ccattcttca cttccacctc acacaatgag gtgcagctaa ccaacatcta catcggcatc 1620
gacgaaaagg agaaatttta tgccagagac atctccaccc aagaagtgct gaagttttat 1680
atcacctcta tgtataacaa gacactattc agtaacgaac tcagatttct ttacgagata 1740
tctttagacg acaagttcgg aaatctaccc tgggagctga tatacagaga cttcgattac 1800
attccacgcc tggtgtttga tgagattgtg ataagcccag ccaagtggaa aatctggggg 1860
cgagacgtga acaataaaat gacgattcgg gagttgattc agtcaaagga aatacctaag 1920
gaattttaca ttgtgaatgg ggacaacaaa gtgtatttga gtcaggaaaa cccgctcgac 1980
atggaaatcc tggaaagtgc cattaagaag tcatctaaga gaaaggattt catcgaactg 2040

```
caggagtact ttgaggatga gaacatcatc aataagggtc agaaaggcag ggttgctgac   2100

gtggtcgtgc ccttcattcg aacacgagca ctgggcaacg aggggcgcgc ctttatcagg   2160

gagaagcgtg tgtcagtcga gcgccgcgag aaactgccct ttaatgagtg gctatatttg   2220

aagttgtaca tctctattaa taggcagaat gaatttttac tgagttacct tccagacata   2280

cagaagattg ttgccaacct gggcgggaag ttgtttttttc tcagatatac agatccgaag   2340

ccacatatac ggctgcgcat caagtgctcc gatctctttc tggcctatgg atcaatactg   2400

gaaatcctga agaggtctca gaaaaatcgt atcatgtcta catttgatat ttccatttat   2460

gaccaggagg tcgaaagata cggtggcttc gacactcttg aactgtccga agctattttt   2520

tgtgctgact ccaaaattat acctaactta ttgactctga tcaaggacac aaataatgac   2580

tggaaggtcg acgatgtctc catactggtc aactaccttt atttgaagtg tttctttcaa   2640

aacgacaaca aaaaaatcct caattttctg aacctggtgt ctcccaagaa ggtcaaggag   2700

aacgtaaacg aaaagatcga gcactacctg aagttgctca aggtggataa tctgggagac   2760

cagatctttt atgacaaaaa cttcaaggaa ctgaagcatg caatcaagaa tctctttctc   2820

aaaatgattg cccaggattt tgagctccag aaagtgtatt cgatcattga cagtatcatc   2880

cacgtgcata ataaccgctt gataggcatc gaaagggata aggagaagct gatctattac   2940

acgctccagc gcctgtttgt ctctgaggag tacatgaag                          2979
```

<210> SEQ ID NO 32
<211> LENGTH: 2979
<212> TYPE: DNA
<213> ORGANISM: Artificial Sequence
<220> FEATURE:
<223> OTHER INFORMATION: Synthetic construct

<400> SEQUENCE: 32

```
atgattaagt cctctttcaa agcccagccc ttcctcgtcc gaaatactat tctctccccc     60

aatgacaaga ggagcttcac agagtacact caagtcatcg agacagtctc aaagaataag    120

gtcttcctcg agcagctcct cctcgccaac cccaaactct ataatgtcat gcagaagtat    180

aatgccgggc tcctcaaaaa aaagagggtc aagaagctct tcgagagcat atacaagtat    240

tacaagaggt cttacctcag gtcgaccccc tttgggctct tctccgagac gagcatcggg    300

gtcttctcca agtcctccca atataaactc atggggaaga ccaccaaggg gattagactc    360

gacacccagt ggctcataag actcgtccat aaaatggagg tcgacttctc taaaaagctc    420

tcttttaccc gaaataatgc caactataaa tttggggaca gggtctttca ggtctacacc    480

atcaactcct ctgagctcga ggaggtcaat atcaaataca ctaatgtcta tcagatcatc    540

tctgagttct gtgagaatga ctaccagaaa tatgaggaca tttgcgagac ggtcactctc    600

tgttatgggg acgagtatag ggagctctct gagcaatatc tcgggtctct cattgtcaat    660

cactatctca tctctaacct ccagaaggac ctcctctctg acttctcgtg ggacacattc    720

ctcactaagg tcgaggccat cgacgaggac aaaaaatata taatcccccct caagaaggtc    780

cagaagttca ttcaggagta ctccgagatt gagatagggg aggggattga gaaactcaaa    840

gagatttacc aggagatgtc tcagatcctc gagaatgaca attatattca gatagacctc    900

atctctgact cggagataaa ctttgacgtc aagcaaaagc agcaactcga gcatctcgcc    960

gagtttctcg ggaacaccac caagagtgtc aggaggacct atctcgacga ctataaggac   1020

aaattcatcg agaaatacgg ggtcgaccaa gaggtccaga ttaccgagct ctttgactct   1080

accttcggga ttggggcccc ctacaattac aaccaccccc ggaatgactt ttacgagtct   1140
```

-continued gagccctcca ccctctacta ctccgaggag gagagggaga aatacctctc catgtatgtc 1200
gaggccgtca aaaatcacaa tgtcataaat ctcgacgacc tcgagtctca ctatcagaag 1260
atggacctcg agaaaaagag cgagctccag gggctcgagc tcttcctcaa tctcgccaag 1320
gagtacgaga aagacatttt catcctcggg gacatagtcg ggaataataa cctcgggggg 1380
gcctcgggga gattctctgc cctctccccc gagctcacct cctatcacag gaccatagtc 1440
gactcagtcg agagagagaa cgagaataag gagatcacct catgcgagat agtcttcctc 1500
cccgagaaca ttagacatgc caatgtcatg catacctcca taatgagacg caaggtcctc 1560
cccttcttta cctccacctc ccacaatgag gtccaactca ccaacatcta catagggatc 1620
gacgagaagg agaaatttta tgccagagac atctccaccc aagaggtcct caagttttat 1680
atcacctcta tgtataacaa gaccctcttc tccaatgagc tcaggttcct ctacgagatc 1740
tccctcgacg acaagttcgg gaatctcccc tgggagctca tatacagaga ctttgactac 1800
atccccagac tcgtctttga cgagattgtc atctccccccg ccaagtggaa aatctggggg 1860
agagacgtca acaataaaat gacgattcgg gagctcattc agtcaaagga gatccccaag 1920
gagttttata tagtcaatgg ggacaacaaa gtctatctct cccaggagaa tcccctcgac 1980
atggagatcc tcgagagtgc cattaagaag tcctcaaaga gaaaagactt tatcgagctc 2040
caagagtact ttgaggacga gaacatcatc aataaggggc agaaggggag agtcgccgac 2100
gtcgtcgtcc ccttcattcg gacgagggcc ctcgggaacg aggggagggc cttcatcagg 2160
gagaagaggg tctcagtcga gaggagagag aagctcccct ttaatgagtg gctctacctc 2220
aagctctaca tctctattaa tagacagaat gagtttctcc tctcttatct ccccgacata 2280
cagaaaattg tcgccaacct cgggggggaaa ctctttttc tcagatatac agaccccaag 2340
ccccacataa gactccgcat caagtgctcg gacctcttcc tcgcctatgg gtctattctc 2400
gagatcctca agaggtctca gaaaaatcgt atcatgtcta cttttgacat ctccatatat 2460
gaccaggagg tcgagagata cgggggggttt gacaccctcg agctctctga ggccattttc 2520
tgtgccgact ccaaaatcat ccccaatctc ctcactctca tcaaggacac aaataatgac 2580
tggaaggtcg acgacgtctc cattctcgtc aattacctct atctcaagtg tttctttcaa 2640
aacgacaaca aaaaaatcct caattttctc aatctcgtct cccccaagaa ggtcaaggag 2700
aacgtcaacg agaagatcga gcactatctc aaactcctca aggtcgacaa cctcggggac 2760
caaatctttt atgacaaaaa cttcaaagag ctcaaacatg ccatcaagaa tctctttctc 2820
aaaatgattg cccaagactt tgagctccaa aaagtctatt cgatcattga ctccataatc 2880
cacgtccata ataaccgtct cattgggatt gagagggaca aggagaagct catctattac 2940
actctccaga gactctttgt ctctgaggag tacatgaag 2979

<210> SEQ ID NO 33
<211> LENGTH: 2046
<212> TYPE: DNA
<213> ORGANISM: Unknown
<220> FEATURE:
<223> OTHER INFORMATION: NisP sequence

<400> SEQUENCE: 33
atgaagaaga tcctcggatt tctattcatc gtgtgttctc tgggcctgtc cgctaccgtg 60
catggcgaaa caactaattc ccagcaactt ctgtccaaca acatcaacac agagcttata 120
aatcacaatt ctaatgcaat tctctccagt actgaggggt cgaccaccga ctcaatcaat 180
ctcggcgcac agagtcccgc tgtaaagtcc actacacgta cggagctcga tgtaaccggg 240

-continued

```
gccgcgaaga ctctcctcca gacatcagct gtgcagaagg aaatgaaagt ctcgttacaa    300

gagacccagg tgtccagtga attttccaag cgcgattcag tgaccaataa agaggcagtt    360

cccgtgagca aggatgaact gctggagcag tccgaggtgg ttgtgagtac cagttctatc    420

cagaaaaata agattctcga caacaagaag aaaagagcaa acttcgtcac aagctcccca    480

ctaatcaaag agaaaccaag caactctaaa gatgcctctg ggtcattgga caactctgcc    540

agtcctcttt cgtataggaa ggctaaggag gtggtctccc ttcggcagcc cctaaagaac    600

cagaaagttg aagctcagcc tcttctgatc tcgaattctt cggaaaagaa ggcctcagtg    660

tacactaatt cccacgactt ttgggattac caatgggata tgaagtatgt cactaacaac    720

ggcgagagct atgccctgta ccaacccagt aagaaaatca gtgtggggat aatcgattct    780

ggtattatgg aggagcaccc cgacctgtct aactccttag gcaactattt taagaacctg    840

gtgcctaagg gtggatttga taacgaggag ccagacgaaa cgggtaatcc cagcgatatc    900

gtggacaaaa tgggccacgg gactgaagtt gctgggcaga tcaccgccaa cggtaacatt    960

ctgggtgtgg cccccggtat cactgtgaat atttatcgag ttttcgggga aaacctcagc   1020

aagagtgaat gggtcgcgcg tgcaatcagg agggcagcgg atgacggcaa caaagtgatc   1080

aatatctctg cggggcaata tctcatgatc tccggctcat acgacgacgg cacgaatgac   1140

tatcaggaat acctgaacta caagtctgcg atcaattatg ctacagccaa gggatccatt   1200

gtagtcgcgg cactgggcaa cgactcccta aacattcagg acaatcagac gatgattaac   1260

ttcctcaaac ggttcaggag tattaaggtc cccggtaaag tcgtcgatgc cccctcagtg   1320

ttcgaggacg tcattgccgt cgggggcatt gatggttatg gtaatataag tgattttagt   1380

aacatcggcg ctgacgcaat atacgcaccg gccggcacca ctgccaactt caagaagtac   1440

ggccaggaca aatttgtctc tcagggctac tacctaaagg actggctgtt tacaaccgcc   1500

aatactggct ggtatcaata cgtgtatggc aacagctttg cgactcctaa agttagcggt   1560

gccctcgcac ttgtcgttga caaatacggc attaagaatc ccaatcagct taagcggttt   1620

ctcctgatga acagtcctga agttaacggc aatcgcgttt taaatattgt ggacctgctc   1680

aatggtaaaa acaaggcctt cagcctcgac acggacaaag gacaggacga tgctataaat   1740

cataagtcta tggaaaacct taaggagtca agagatacca tgaaacagga acaggacaaa   1800

gagatacagc ggaataccaa taacaacttc agcataaaga acgacttcca caatatcagc   1860

aaagaggtta tcagtgtaga ctacaatatc aaccagaaaa tggccaataa taggaacagc   1920

cgcggtgctg tttctgtccg gtcccaggag atcctgccag tgaccggcga cggcgaagac   1980

ttcctgcctg ctctggggat cgtgtgcatc tccattctcg gtatcttgaa aagaaagaca   2040

aaaaac                                                              2046
```

<210> SEQ ID NO 34
<211> LENGTH: 2046
<212> TYPE: DNA
<213> ORGANISM: Artificial Sequence
<220> FEATURE:
<223> OTHER INFORMATION: Synthetic construct

<400> SEQUENCE: 34

```
atgaagaaga ttctcgggtt tctctttatc gtctgctccc tcgggctctc ggccactgtc     60

catggggaga cgactaattc ccagcagctc ctctcaaaca acatcaacac tgagctcata    120

aatcacaatt ctaatgccat tctctcctct acagaggggt cgacgacaga ctcaatcaat    180

ctcggggccc agtcccccgc cgtcaagtcg accacaagga ctgagctcga cgtcacgggg    240
```

-continued

```
gccgccaaga ctctcctcca gacctctgcc gtccaaaagg agatgaaagt ctctctccaa    300

gagactcaag tctcctctga gttctccaag agggactctg tcaccaataa ggaggccgtc    360

cccgtctcaa aggacgagct cctcgagcag tccgaggtcg tcgtctccac ctcctcaatc    420

cagaaaaata agattctcga caacaagaag aagagggcca acttcgtcac ctcctccccc    480

ctcatcaaag agaagccctc aaactcaaag gacgcctctg gggtcattga caactctgcc    540

tccccccctct catataggaa ggccaaggag gtcgtctctc tccgccagcc cctcaagaac    600

caaaaagtcg aggcccagcc cctcctcatc tcgaattcct ccgagaagaa ggcctcagtc    660

tacaccaatt cccacgactt ttgggactat cagtgggaca tgaagtatgt cactaacaac    720

ggggagagct atgccctcta tcagccctcc aaaaaaatct cagtcgggat aatcgactct    780

gggataatgg aggagcaccc cgacctctct aactctctcg ggaattattt taagaacctc    840

gtccccaagg gggggtttga caacgaggag cccgacgaga cagggaatcc ctccgacata    900

gtcgacaaaa tggggcacgg gacagaggtc gccgggcaga tcaccgccaa cgggaatatc    960

ctcggggtcg cccccgggat tacagtcaat atctatcgag tctttgggga gaatctctca   1020

aagagtgagt gggtcgcccg ggccatcagg agggccgccg acgacgggaa caaagtcatc   1080

aatatctccg ccgggcaata tctcatgatc tcggggtcat acgacgacgg gacaaatgac   1140

tatcaggagt atctcaatta caagtcggcc atcaattatg ccactgccaa ggggtccatt   1200

gtcgtcgccg ccctcgggaa cgactctctc aatattcagg acaatcagac gatgattaac   1260

ttcctcaaga gatttaggag tattaaggtc cccgggaaag tcgtcgacgc cccctctgtc   1320

tttgaggacg tcattgccgt cggggggatt gacgggtatg ggaatatctc agacttctca   1380

aacattgggg ccgacgccat atacgccccc gccgggacga cagccaactt caagaaatac   1440

gggcaggaca aatttgtctc tcaggggtac tatctcaagg actggctctt tacgacagcc   1500

aatactgggt ggtatcaata cgtctatggg aactcgtttg ccaccccccaa ggtctcgggg   1560

gccctcgccc tcgtcgtcga caaatacggg ataaagaatc ccaatcagct caagagattt   1620

ctcctcatga attcccccga ggtcaacggg aatagagtcc tcaatattgt cgacctcctc   1680

aacgggaaaa acaaggcctt ctctctcgac acggacaagg ggcaagacga cgccataaat   1740

cataagtcta tggagaatct caaggagtca agggacacca tgaaacaaga gcaggacaaa   1800

gagatacaga ggaacaccaa taacaacttc tccatcaaga acgacttcca caatatctca   1860

aaagaggtca tctctgtcga ctacaatatc aaccagaaaa tggccaataa taggaactcc   1920

cggggggccg tctctgtccg gtcccaggag atcctccccg tcacagggga cggggaggac   1980

ttcctccccg ccctcgggat cgtctgtatc tccatactcg ggatcctcaa gagaaagaca   2040

aaaaac                                                               2046
```

```
<210> SEQ ID NO 35
<211> LENGTH: 1800
<212> TYPE: DNA
<213> ORGANISM: Unknown
<220> FEATURE:
<223> OTHER INFORMATION: NisT sequence

<400> SEQUENCE: 35

atggacgagg taaaagagtt tacgagcaag cagttcttct atacactgct aacgctccca     60

tcaactctga aactgatctt tcagctggaa aagaggtacg ccatttatct gattgtgctt    120

aacgctataa ccgccttcgt cccgctggca tccctcttta tctatcagga cctgattaac    180

agtgtgctgg gctctggtcg ccatcttata aatattatca tcatatactt cattgtgcag    240
```

-continued

```
gtgattacta ccgtgttggg ccagttagag tcctacgtat cgggcaaatt tgacatgcgg    300
ctcagctatt caatcaatat gcggcttatg aggacgacgt ctagcctgga attatccgac    360
tacgaacagg ctgatatgta caatatcata gagaaagtga cccaggattc cacctacaag    420
cctttccagt tattcaatgc catcattgtc gagttgtcat catttatctc tttgctgtca    480
agtcttttct tcataggcac gtggaacatt ggagtggcca tcctgttgct gattgtccct    540
gttttgtcac tagttctttt cctcagggtg gggcaactgg aattcctcat tcagtggcaa    600
agagcatcat cggagcgaga aacctggtac atcgtttacc tgctgactca tgatttcagc    660
ttcaaggaga tcaaactgaa taacatcagt aactatttta tccacaagtt tggcaaactt    720
aagaaagggt tcatcaacca ggatttggct atcgctcgga agaagacata ttttaatatc    780
tttcttgatt tcattttaaa cctaatcaat attctgacca tcttcgccat gattctctct    840
gttcgggcag gtaagcttct gattggcaat ctcgtgtctc tcattcaggc catatcaaaa    900
attaatacat attctcagac catgatccag aacatctaca ttatctacaa cacctcattg    960
tttatggagc aactgttcga gtttcttaag agagaatcag tagttcataa gaagattgag   1020
gacaccgaaa tttgcaatca gcacatcggc actgtgaagg ttatcaacct gtcatatgta   1080
tatcctaact ctaatgcctt cgcactcaaa aatatcaatc tgagcttcga aaaaggggaa   1140
ctgactgcca tcgtcggtaa aaatggctcc ggcaaatcta cacttgtaaa aataattagc   1200
ggcctgtatc agcccaccat gggcataatc cagtacgaca agatgcgctc ctccctcatg   1260
ccagaggaat tctatcagaa gaacatctcc gtcctgtttc aggattttgt caaatacgaa   1320
ctcactattc gggagaatat aggcctatcg gaccttagtt cacagtggga ggatgagaag   1380
ataatcaagg tactcgataa tctggggctc gactttttga agaccaataa ccaatacgtc   1440
ctggatacac agctgggaaa ctggttccag gaaggccacc agctgagtgg cggtcagtgg   1500
cagaagattg ctctcgccag gacatttttt aaaaaggcct caatctacat tcttgacgag   1560
ccaagcgctg ccctggaccc cgtggcggag aaagaaattt ttgactattt tgtcgccctg   1620
agcgagaaca acatctctat attcatctct catagcctga atgctgctcg taaggccaac   1680
aagatcgtcg tgatgaagga tggacaggtt gaggacgtcg ggagccatga cgtgcttctt   1740
agacggtgcc agtactatca ggagctgtat tacagcgagc agtatgaaga taatgatgag   1800
```

<210> SEQ ID NO 36
<211> LENGTH: 1800
<212> TYPE: DNA
<213> ORGANISM: Artificial Sequence
<220> FEATURE:
<223> OTHER INFORMATION: Synthetic construct

<400> SEQUENCE: 36

```
atggacgagg tcaaagagtt tacgagcaag cagttcttct atactctcct cactctcccc     60
tcaactctca agctcatctt ccagctcgag aagagatacg ccatttatct cattgtcctc    120
aacgccatca ctgccttcgt ccccctcgcc tctctcttta tctatcagga cctcattaac    180
tctgtcctcg ggtcggggag acatctcata aacattatca tcatatactt catagtccaa    240
gtcattacta cagtcctcgg gcagctcgag tcctatgtct ctgggaagtt tgacatgaga    300
ctctcttact caatcaatat gagactcatg aggacgacct cctccctcga gctctctgac    360
tacgagcaag ccgacatgta caatatcata gagaaggtca cccaagactc cacctataag    420
cccttccagc tcttcaatgc catcattgtc gagctctcct ctttcatctc tctcctctcc    480
tccctcttct tcatcgggac ttggaacata ggggtcgcca tcctcctcct catagtcccc    540
```

-continued

```
gtcctctccc tcgtcctctt cctcagagtc gggcagctcg agttcctcat tcagtggcag    600

agggcctcgt ctgagagaga gacctggtat atagtctatc tcctcactca tgacttctca    660

ttcaaggaga tcaagctcaa taatatctca aactatttta tccacaagtt tgggaaactc    720

aagaaggggt tcatcaacca ggacctcgcc atcgcccgga agaagacata ttttaatatc    780

ttcctcgact tcatcctcaa cctcataaac atcctcacca tcttcgccat gattctctct    840

gtcagagccg ggaagctcct catcgggaat ctcgtctctc tcattcaggc catctccaaa    900

attaatacat attctcagac catgatccag aacatctaca ttatctacaa cacctctctc    960

tttatggagc aactcttcga gttcctcaag agagagtcag tcgtccataa aaagattgag   1020

gacactgaga tttgcaatca gcacatcggg acagtcaaag tcatcaatct ctcatatgtc   1080

taccccaact ctaatgcctt cgccctcaaa aatataaatc tctcttttga gaagggggag   1140

ctcactgcca tcgtcgggaa aaacgggagt gggaagtcca ctctcgtcaa aataatctcg   1200

gggctctatc agcccaccat ggggatcatc cagtacgaca agatgaggtc ctccctcatg   1260

cccgaggagt tctatcagaa gaacatctcc gtcctcttcc aggacttcgt caaatatgag   1320

ctcactattc gggagaatat tggctctcg gacctctcct ctcagtggga ggacgagaag   1380

ataatcaagg tcctcgacaa tctcgggctc gacttcctca agaccaataa ccaatacgtc   1440

ctcgacaccc agctcgggaa ctggtttcag gaggggcacc agctctctgg ggggcagtgg   1500

cagaaaattg ccctcgccag gacatttttt aaaaaggcct caatctacat tctcgacgag   1560

ccctcagccg ccctcgaccc cgtcgccgag aaagagatat tcgactattt tgtcgccctc   1620

tcagagaaca acatctctat attcatctct cactctctca atgccgcccg aaaggccaac   1680

aagatcgtcg tcatgaaaga cgggcaagtc gaggacgtcg ggagccatga cgtcctcctc   1740

agacggtgcc agtactatca ggagctctat tactccgagc agtatgagga caatgacgag   1800
```

<210> SEQ ID NO 37
<211> LENGTH: 171
<212> TYPE: DNA
<213> ORGANISM: Unknown
<220> FEATURE:
<223> OTHER INFORMATION: NisA sequence

<400> SEQUENCE: 37

```
atgtctacta aagacttcaa cctggacctc gtgagtgtga gcaaaaagga ttccggggct     60

agcccaagga taacctccat ttctctgtgt acacctggat gcaaaactgg ggccctcatg    120

gggtgtaata tgaagacggc gacatgccat tgttccatcc acgtttccaa g             171
```

<210> SEQ ID NO 38
<211> LENGTH: 171
<212> TYPE: DNA
<213> ORGANISM: Artificial Sequence
<220> FEATURE:
<223> OTHER INFORMATION: Synthetic construct

<400> SEQUENCE: 38

```
atgtctacta aagacttcaa tctcgacctc gtctcagtct ccaaaaagga ctcgggggcc     60

tcccccagaa taaccagcat aagcctgtgt acacctggct gtaaaactgg ggctctcatg    120

ggctgtaaca tgaagacagc cacatgccat tgtagtatac atgtctccaa g             171
```

<210> SEQ ID NO 39
<211> LENGTH: 1254
<212> TYPE: DNA
<213> ORGANISM: Unknown
<220> FEATURE:

<223> OTHER INFORMATION: NisC sequence

<400> SEQUENCE: 39
atgcgcatca tgatgaataa gaagaatatt aaaaggaatg tggaaaagat tatcgctcag 60
tgggacgaga ggactcggaa gaacaaagag aactttgact tcggggagct gactctctct 120
accggccttc ctggtattat cttaatgctg gcagagctga aaaataaaga taacagtaag 180
atttaccaaa agaagatcga taactatata gagtacattg tttcgaaact gtcaacctac 240
ggtctcttaa ccggcagtct ctattccggg gccgcgggca tagccttaag cattctgcac 300
ctgcgcgagg atgacgaaaa gtataaaaat ctcttagact ctctaaaccg gtacatcgag 360
tatttcgtga gggaaaagat tgagggcttt aatctggaga atatcacccc ccccgattac 420
gatgtcatcg agggcctcag cggtatcctt tcctacctgt tgctgataaa tgatgaacag 480
tatgatgatc tgaagatttt gatcatcaac ttcttgtcaa atttaactaa agagaacaat 540
ggtctcattt ctttgtacat caagagcgag aatcagatgt cccagtcaga gtccgaaatg 600
taccctcttg ggtgtctgaa catgggtctc gcccacggac tggccggagt gggctgcata 660
ctggcttacg cccatatcaa agggtacagt aatgaggcct ctctatccgc actgcagaaa 720
atcatcttta tttacgagaa gttcgagttg gagcgaaaaa aacagttcct gtggaaagat 780
ggcctggtgg ctgacgaact caaaaaggag aaggtcatca gggaggcctc ttttattaga 840
gacgcgtggt gctatggggg ccctggtatt tctctcctct acctatacgg tgggttagcc 900
ctggacaacg actactttgt tgataaagcc gagaaaatcc ttgaatcagc catgcagcgc 960
aaattgggaa tcgatagtta tatgatctgc catggataca gtggcctaat cgagatatgc 1020
agtctattta agcggctgct gaatacaaag aaattcgata gttacatgga ggagttcaat 1080
gtcaatagcg aacagatcct ggaagaatac ggggatgaga gtgggaccgg attcctggag 1140
ggcatctccg gctgtatcct ggtcttaagt aagttcgaat actccatcaa ctttacatac 1200
tggcggcagg ccttgctact tttcgacgat tttctcaagg gagggaagag gaaa 1254

<210> SEQ ID NO 40
<211> LENGTH: 1254
<212> TYPE: DNA
<213> ORGANISM: Artificial Sequence
<220> FEATURE:
<223> OTHER INFORMATION: Synthetic construct

<400> SEQUENCE: 40
atgagaataa tgatgaataa gaagaatatt aagaggaatg tcgagaagat tatcgcccag 60
tgggacgaga ggactcggaa gaacaaagag aactttgact tcggggagct cactctgagt 120
accggtctcc ccgggattat cctcatgctc gccgagctca agaataaaga caactcaaaa 180
atttaccaaa agaagatcga caactatata gagtacatcg tctctaagct ctctacctat 240
gggctcctca cggggtcttt gtactcgggg gccgccggga tagccctctc aatactccat 300
ctccgagagg acgacgagaa atacaaaaat ctcctcgact ctctcaaccg gtacatcgag 360
tatttcgtca gggagaagat tgaggggttc aatctcgaga atatcacccc ccccgactat 420
gatgtaattg agggactctc agggatactc tcatatctcc tcctcatcaa tgacgagcag 480
tatgacgacc tcaagattct catcatcaac tttctctcca atctcactaa agagaataat 540
gggctcatct ccctctacat caagagcgag aatcagatgt cccagtcaga gtctgagatg 600
taccccctcg ggtgtctcaa tatggggctg gctcatggtc tcgccggggt cgggtgcatc 660
ctcgcctacg cccatataaa ggggtactcc aacgaggcct ccctctcggc cctccagaag 720
atcatcttta tttacgagaa gttcgagctc gagagaaaaa aacagttcct ctggaaagat 780
ggtttggtcg ccgacgagct caagaaggag aaggtcatca gggaggcctc ttttattaga 840
gatgcctggt gctatggggg gcccgggatc tctctcctct acctctatgg ggggctcgcc 900
ctcgacaacg actattttgt cgacaaggcc gagaagatcc tcgagagcgc catgcagagg 960
aaactgggta tagatagtta catgatttgc catggttaca gtgggctcat agagatatgc 1020
tccctcttca agagactcct caacacaaag aaatttgact cgtacatgga ggagttcaat 1080
gtcaattcgg agcagatcct cgaggagtac ggggacgagt cggggacagg gtttctcgag 1140
gggatctcgg ggtgcatcct cgtcctctcc aagtttgagt actccatcaa ctttacatac 1200
tggagacagg ccctcctcct cttcgacgac ttcctcaagg gggggaagag gaaa 1254

<210> SEQ ID NO 41
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 41 atcggcggc 9

<210> SEQ ID NO 42
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 42 gccgccgat 9

<210> SEQ ID NO 43
<211> LENGTH: 32
<212> TYPE: PRT
<213> ORGANISM: Artificial Sequence
<220> FEATURE:
<223> OTHER INFORMATION: Synthetic peptide

<400> SEQUENCE: 43

Lys Leu Arg Ser Phe Val Cys Glu Val Cys Thr Arg Ala Phe Ala Arg
1 5 10 15

Gln Glu His Leu Lys Arg His Tyr Arg Ser His Ser Gly Asn Leu Gly
20 25 30

<210> SEQ ID NO 44
<211> LENGTH: 6
<212> TYPE: DNA
<213> ORGANISM: Artificial Sequence
<220> FEATURE:
<223> OTHER INFORMATION: Synthetic oligonucleotide

<400> SEQUENCE: 44 gtatgc 6

<210> SEQ ID NO 45
<211> LENGTH: 6
<212> TYPE: DNA
<213> ORGANISM: Artificial Sequence
<220> FEATURE:
<223> OTHER INFORMATION: Synthetic oligonucleotide

<400> SEQUENCE: 45 gtatgt 6

<210> SEQ ID NO 46
<211> LENGTH: 6
<212> TYPE: DNA
<213> ORGANISM: Artificial Sequence
<220> FEATURE:
<223> OTHER INFORMATION: Synthetic oligonucleotide

<400> SEQUENCE: 46 gtctgc 6

<210> SEQ ID NO 47
<211> LENGTH: 6
<212> TYPE: DNA
<213> ORGANISM: Artificial Sequence
<220> FEATURE:
<223> OTHER INFORMATION: Synthetic oligonucleotide

<400> SEQUENCE: 47 gtctgt 6

<210> SEQ ID NO 48
<211> LENGTH: 6
<212> TYPE: DNA
<213> ORGANISM: Artificial Sequence
<220> FEATURE:
<223> OTHER INFORMATION: Synthetic oligonucleotide

<400> SEQUENCE: 48 gtgtgc 6

<210> SEQ ID NO 49
<211> LENGTH: 6
<212> TYPE: DNA
<213> ORGANISM: Artificial Sequence
<220> FEATURE:
<223> OTHER INFORMATION: Synthetic oligonucleotide

<400> SEQUENCE: 49 gtgtgt 6

<210> SEQ ID NO 50
<211> LENGTH: 6
<212> TYPE: DNA
<213> ORGANISM: Artificial Sequence
<220> FEATURE:
<223> OTHER INFORMATION: Synthetic oligonucleotide

<400> SEQUENCE: 50 gtttgc 6

<210> SEQ ID NO 51
<211> LENGTH: 6
<212> TYPE: DNA
<213> ORGANISM: Artificial Sequence
<220> FEATURE:
<223> OTHER INFORMATION: Synthetic oligonucleotide

<400> SEQUENCE: 51 gtttgt 6

<210> SEQ ID NO 52
<211> LENGTH: 6
<212> TYPE: DNA
<213> ORGANISM: Artificial Sequence
<220> FEATURE:

-continued

<223> OTHER INFORMATION: Synthetic oligonucleotide

<400> SEQUENCE: 52 gaacac 6

<210> SEQ ID NO 53
<211> LENGTH: 6
<212> TYPE: DNA
<213> ORGANISM: Artificial Sequence
<220> FEATURE:
<223> OTHER INFORMATION: Synthetic oligonucleotide

<400> SEQUENCE: 53 gaacat 6

<210> SEQ ID NO 54
<211> LENGTH: 6
<212> TYPE: DNA
<213> ORGANISM: Artificial Sequence
<220> FEATURE:
<223> OTHER INFORMATION: Synthetic oligonucleotide

<400> SEQUENCE: 54 gagcac 6

<210> SEQ ID NO 55
<211> LENGTH: 6
<212> TYPE: DNA
<213> ORGANISM: Artificial Sequence
<220> FEATURE:
<223> OTHER INFORMATION: Synthetic oligonucleotide

<400> SEQUENCE: 55 gagcat 6

<210> SEQ ID NO 56
<211> LENGTH: 20
<212> TYPE: PRT
<213> ORGANISM: Artificial Sequence
<220> FEATURE:
<223> OTHER INFORMATION: Synthetic peptide

<400> SEQUENCE: 56

Ser Leu Ser Cys Arg Ala Ser Gln Ser Ile Gly Asp Asn Leu His Trp
1 5 10 15

Tyr Gln Gln Lys
20

<210> SEQ ID NO 57
<211> LENGTH: 20
<212> TYPE: PRT
<213> ORGANISM: Artificial Sequence
<220> FEATURE:
<223> OTHER INFORMATION: Synthetic peptide

<400> SEQUENCE: 57

Ser Leu Ser Cys Arg Ala Ser Gln Ser Ile Gly Asn Asn Leu His Trp
1 5 10 15

Tyr Gln Gln Lys
20

<210> SEQ ID NO 58
<211> LENGTH: 20
<212> TYPE: PRT
<213> ORGANISM: Artificial Sequence
<220> FEATURE:

<223> OTHER INFORMATION: Synthetic peptide

<400> SEQUENCE: 58

Ser Leu Ser Cys Arg Ala Ser Gln Ser Ile Gly Gly Asn Leu His Trp
1 5 10 15

Tyr Gln Gln Lys
20

<210> SEQ ID NO 59
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 59
ccaaagtatt ggcgataacc 20

<210> SEQ ID NO 60
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 60
ccaaagtatt ggcaataacc 20

<210> SEQ ID NO 61
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 61
ccaaagtatt ggcggtaacc 20

<210> SEQ ID NO 62
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(5)
<223> OTHER INFORMATION: Ser, Tyr or Asn

<400> SEQUENCE: 62

Xaa Xaa Xaa Xaa Xaa
1 5

<210> SEQ ID NO 63
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(6)
<223> OTHER INFORMATION: Ser, Tyr or Asn

<400> SEQUENCE: 63

Xaa Xaa Xaa Xaa Xaa Xaa
1 5

<210> SEQ ID NO 64
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(7)
<223> OTHER INFORMATION: Ser, Tyr or Asn

<400> SEQUENCE: 64

Xaa Xaa Xaa Xaa Xaa Xaa Xaa
1               5

<210> SEQ ID NO 65
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(8)
<223> OTHER INFORMATION: Ser, Tyr or Asn

<400> SEQUENCE: 65

Xaa Xaa Xaa Xaa Xaa Xaa Xaa Xaa
1               5

<210> SEQ ID NO 66
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(9)
<223> OTHER INFORMATION: Ser, Tyr or Asn

<400> SEQUENCE: 66

Xaa Xaa Xaa Xaa Xaa Xaa Xaa Xaa Xaa
1               5

<210> SEQ ID NO 67
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(10)
<223> OTHER INFORMATION: Ser, Tyr or Asn

<400> SEQUENCE: 67

Xaa Xaa Xaa Xaa Xaa Xaa Xaa Xaa Xaa Xaa
1               5                   10

<210> SEQ ID NO 68
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 68 agtcgactt                                                                9

-continued

<210> SEQ ID NO 69
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 69 agtcgactg 9

<210> SEQ ID NO 70
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 70 agtcgatta 9

<210> SEQ ID NO 71
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 71 agtcgacta 9

<210> SEQ ID NO 72
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 72 agtcgactc 9

<210> SEQ ID NO 73
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 73 agtcgattg 9

<210> SEQ ID NO 74
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 74 agtaggctt 9

<210> SEQ ID NO 75
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 75 agtaggctg 9

<210> SEQ ID NO 76
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 76 agtaggtta 9

<210> SEQ ID NO 77
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 77 agtaggcta 9

<210> SEQ ID NO 78
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 78 agtaggctc 9

<210> SEQ ID NO 79
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 79 agtaggttg 9

<210> SEQ ID NO 80
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 80 agtcgtctt 9

<210> SEQ ID NO 81
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 81 agtcgtctg 9

<210> SEQ ID NO 82
<211> LENGTH: 9
<212> TYPE: DNA

<213> ORGANISM: Artificial Sequence
<220> FEATURE:
<223> OTHER INFORMATION: Synthetic oligonucleotide

<400> SEQUENCE: 82 agtcgttta 9

<210> SEQ ID NO 83
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 83 agtcgtcta 9

<210> SEQ ID NO 84
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 84 agtcgtctc 9

<210> SEQ ID NO 85
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 85 agtcgtttg 9

<210> SEQ ID NO 86
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 86 agtagactt 9

<210> SEQ ID NO 87
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 87 agtagactg 9

<210> SEQ ID NO 88
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 88 agtagatta 9

<210> SEQ ID NO 89
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 89 agtagacta 9

<210> SEQ ID NO 90
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 90 agtagactc 9

<210> SEQ ID NO 91
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 91 agtagattg 9

<210> SEQ ID NO 92
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 92 agtcggctt 9

<210> SEQ ID NO 93
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 93 agtcggctg 9

<210> SEQ ID NO 94
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 94 agtcggtta 9

<210> SEQ ID NO 95
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 95 agtcggcta 9

<210> SEQ ID NO 96
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 96 agtcggctc 9

<210> SEQ ID NO 97
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 97 agtcggttg 9

<210> SEQ ID NO 98
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 98 agtcgcctt 9

<210> SEQ ID NO 99
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 99 agtcgcctg 9

<210> SEQ ID NO 100
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 100 agtcgctta 9

<210> SEQ ID NO 101
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 101 agtcgccta 9

<210> SEQ ID NO 102
<211> LENGTH: 9
<212> TYPE: DNA

<213> ORGANISM: Artificial Sequence
<220> FEATURE:
<223> OTHER INFORMATION: Synthetic oligonucleotide

<400> SEQUENCE: 102 agtcgcctc 9

<210> SEQ ID NO 103
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 103 agtcgcttg 9

<210> SEQ ID NO 104
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 104 tcacgactt 9

<210> SEQ ID NO 105
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 105 tcacgactg 9

<210> SEQ ID NO 106
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 106 tcacgatta 9

<210> SEQ ID NO 107
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 107 tcacgacta 9

<210> SEQ ID NO 108
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 108 tcacgactc 9

<210> SEQ ID NO 109
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 109 tcacgattg 9

<210> SEQ ID NO 110
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 110 tcaaggctt 9

<210> SEQ ID NO 111
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 111 tcaaggctg 9

<210> SEQ ID NO 112
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 112 tcaaggtta 9

<210> SEQ ID NO 113
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 113 tcaaggcta 9

<210> SEQ ID NO 114
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 114 tcaaggctc 9

<210> SEQ ID NO 115
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 115 tcaaggttg 9

<210> SEQ ID NO 116
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 116 tcacgtctt 9

<210> SEQ ID NO 117
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 117 tcacgtctg 9

<210> SEQ ID NO 118
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 118 tcacgttta 9

<210> SEQ ID NO 119
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 119 tcacgtcta 9

<210> SEQ ID NO 120
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 120 tcacgtctc 9

<210> SEQ ID NO 121
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 121 tcacgtttg 9

<210> SEQ ID NO 122
<211> LENGTH: 9
<212> TYPE: DNA

<213> ORGANISM: Artificial Sequence
<220> FEATURE:
<223> OTHER INFORMATION: Synthetic oligonucleotide

<400> SEQUENCE: 122 tcaagactt 9

<210> SEQ ID NO 123
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 123 tcaagactg 9

<210> SEQ ID NO 124
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 124 tcaagatta 9

<210> SEQ ID NO 125
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 125 tcaagacta 9

<210> SEQ ID NO 126
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 126 tcaagactc 9

<210> SEQ ID NO 127
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 127 tcaagattg 9

<210> SEQ ID NO 128
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 128 tcacggctt 9

<210> SEQ ID NO 129
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 129 tcacggctg 9

<210> SEQ ID NO 130
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 130 tcacggtta 9

<210> SEQ ID NO 131
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 131 tcacggcta 9

<210> SEQ ID NO 132
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 132 tcacggctc 9

<210> SEQ ID NO 133
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 133 tcacggttg 9

<210> SEQ ID NO 134
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 134 tcacgcctt 9

<210> SEQ ID NO 135
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 135 tcacgcctg 9

<210> SEQ ID NO 136
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 136 tcacgctta 9

<210> SEQ ID NO 137
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 137 tcacgccta 9

<210> SEQ ID NO 138
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 138 tcacgcctc 9

<210> SEQ ID NO 139
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 139 tcacgcttg 9

<210> SEQ ID NO 140
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 140 agccgactt 9

<210> SEQ ID NO 141
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 141 agccgactg 9

<210> SEQ ID NO 142
<211> LENGTH: 9
<212> TYPE: DNA

<213> ORGANISM: Artificial Sequence
<220> FEATURE:
<223> OTHER INFORMATION: Synthetic oligonucleotide

<400> SEQUENCE: 142 agccgatta 9

<210> SEQ ID NO 143
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 143 agccgacta 9

<210> SEQ ID NO 144
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 144 agccgactc 9

<210> SEQ ID NO 145
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 145 agccgattg 9

<210> SEQ ID NO 146
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 146 agcaggctt 9

<210> SEQ ID NO 147
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 147 agcaggctg 9

<210> SEQ ID NO 148
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 148 agcaggtta 9

<210> SEQ ID NO 149
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 149 agcaggcta 9

<210> SEQ ID NO 150
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 150 agcaggctc 9

<210> SEQ ID NO 151
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 151 agcaggttg 9

<210> SEQ ID NO 152
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 152 agccgtctt 9

<210> SEQ ID NO 153
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 153 agccgtctg 9

<210> SEQ ID NO 154
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 154 agccgttta 9

<210> SEQ ID NO 155
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 155 agccgtcta 9

<210> SEQ ID NO 156
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 156 agccgtctc 9

<210> SEQ ID NO 157
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 157 agccgtttg 9

<210> SEQ ID NO 158
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 158 agcagactt 9

<210> SEQ ID NO 159
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 159 agcagactg 9

<210> SEQ ID NO 160
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 160 agcagatta 9

<210> SEQ ID NO 161
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 161 agcagacta 9

<210> SEQ ID NO 162
<211> LENGTH: 9
<212> TYPE: DNA

<213> ORGANISM: Artificial Sequence
<220> FEATURE:
<223> OTHER INFORMATION: Synthetic oligonucleotide

<400> SEQUENCE: 162 agcagactc 9

<210> SEQ ID NO 163
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 163 agcagattg 9

<210> SEQ ID NO 164
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 164 agccggctt 9

<210> SEQ ID NO 165
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 165 agccggctg 9

<210> SEQ ID NO 166
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 166 agccggtta 9

<210> SEQ ID NO 167
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 167 agccggcta 9

<210> SEQ ID NO 168
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 168 agccggctc 9

<210> SEQ ID NO 169
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 169 agccggttg 9

<210> SEQ ID NO 170
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 170 agccgcctt 9

<210> SEQ ID NO 171
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 171 agccgcctg 9

<210> SEQ ID NO 172
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 172 agccgctta 9

<210> SEQ ID NO 173
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 173 agccgccta 9

<210> SEQ ID NO 174
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 174 agccgcctc 9

<210> SEQ ID NO 175
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 175 agccgcttg 9

<210> SEQ ID NO 176
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 176 tcgcgactt 9

<210> SEQ ID NO 177
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 177 tcgcgactg 9

<210> SEQ ID NO 178
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 178 tcgcgatta 9

<210> SEQ ID NO 179
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 179 tcgcgacta 9

<210> SEQ ID NO 180
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 180 tcgcgactc 9

<210> SEQ ID NO 181
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 181 tcgcgattg 9

<210> SEQ ID NO 182
<211> LENGTH: 9
<212> TYPE: DNA

<213> ORGANISM: Artificial Sequence
<220> FEATURE:
<223> OTHER INFORMATION: Synthetic oligonucleotide

<400> SEQUENCE: 182 tcgaggctt 9

<210> SEQ ID NO 183
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 183 tcgaggctg 9

<210> SEQ ID NO 184
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 184 tcgaggtta 9

<210> SEQ ID NO 185
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 185 tcgaggcta 9

<210> SEQ ID NO 186
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 186 tcgaggctc 9

<210> SEQ ID NO 187
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 187 tcgaggttg 9

<210> SEQ ID NO 188
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 188 tcgcgtctt 9

<210> SEQ ID NO 189
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 189 tcgcgtctg 9

<210> SEQ ID NO 190
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 190 tcgcgttta 9

<210> SEQ ID NO 191
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 191 tcgcgtcta 9

<210> SEQ ID NO 192
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 192 tcgcgtctc 9

<210> SEQ ID NO 193
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 193 tcgcgtttg 9

<210> SEQ ID NO 194
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 194 tcgagactt 9

<210> SEQ ID NO 195
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 195 tcgagactg 9

<210> SEQ ID NO 196
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 196 tcgagatta 9

<210> SEQ ID NO 197
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 197 tcgagacta 9

<210> SEQ ID NO 198
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 198 tcgagactc 9

<210> SEQ ID NO 199
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 199 tcgagattg 9

<210> SEQ ID NO 200
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 200 tcgcggctt 9

<210> SEQ ID NO 201
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 201 tcgcggctg 9

<210> SEQ ID NO 202
<211> LENGTH: 9
<212> TYPE: DNA

<213> ORGANISM: Artificial Sequence
<220> FEATURE:
<223> OTHER INFORMATION: Synthetic oligonucleotide

<400> SEQUENCE: 202 tcgcggtta 9

<210> SEQ ID NO 203
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 203 tcgcggcta 9

<210> SEQ ID NO 204
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 204 tcgcggctc 9

<210> SEQ ID NO 205
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 205 tcgcggttg 9

<210> SEQ ID NO 206
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 206 tcgcgcctt 9

<210> SEQ ID NO 207
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 207 tcgcgcctg 9

<210> SEQ ID NO 208
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 208 tcgcgctta 9

<210> SEQ ID NO 209
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 209 tcgcgccta 9

<210> SEQ ID NO 210
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 210 tcgcgcctc 9

<210> SEQ ID NO 211
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 211 tcgcgcttg 9

<210> SEQ ID NO 212
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 212 tcccgactt 9

<210> SEQ ID NO 213
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 213 tcccgactg 9

<210> SEQ ID NO 214
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 214 tcccgatta 9

<210> SEQ ID NO 215
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 215 tcccgacta 9

<210> SEQ ID NO 216
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 216 tcccgactc 9

<210> SEQ ID NO 217
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 217 tcccgattg 9

<210> SEQ ID NO 218
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 218 tccaggctt 9

<210> SEQ ID NO 219
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 219 tccaggctg 9

<210> SEQ ID NO 220
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 220 tccaggtta 9

<210> SEQ ID NO 221
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 221 tccaggcta 9

<210> SEQ ID NO 222
<211> LENGTH: 9
<212> TYPE: DNA

<213> ORGANISM: Artificial Sequence
<220> FEATURE:
<223> OTHER INFORMATION: Synthetic oligonucleotide

<400> SEQUENCE: 222 tccaggctc 9

<210> SEQ ID NO 223
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 223 tccaggttg 9

<210> SEQ ID NO 224
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 224 tcccgtctt 9

<210> SEQ ID NO 225
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 225 tcccgtctg 9

<210> SEQ ID NO 226
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 226 tcccgttta 9

<210> SEQ ID NO 227
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 227 tcccgtcta 9

<210> SEQ ID NO 228
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 228 tcccgtctc 9

<210> SEQ ID NO 229
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 229 tcccgtttg 9

<210> SEQ ID NO 230
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 230 tccagactt 9

<210> SEQ ID NO 231
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 231 tccagactg 9

<210> SEQ ID NO 232
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 232 tccagatta 9

<210> SEQ ID NO 233
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 233 tccagacta 9

<210> SEQ ID NO 234
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 234 tccagactc 9

<210> SEQ ID NO 235
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 235 tccagattg 9

<210> SEQ ID NO 236
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 236 tcccggctt 9

<210> SEQ ID NO 237
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 237 tcccggctg 9

<210> SEQ ID NO 238
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 238 tcccggtta 9

<210> SEQ ID NO 239
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 239 tcccggcta 9

<210> SEQ ID NO 240
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 240 tcccggctc 9

<210> SEQ ID NO 241
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 241 tcccggttg 9

<210> SEQ ID NO 242
<211> LENGTH: 9
<212> TYPE: DNA

<213> ORGANISM: Artificial Sequence
<220> FEATURE:
<223> OTHER INFORMATION: Synthetic oligonucleotide

<400> SEQUENCE: 242 tcccgcctt 9

<210> SEQ ID NO 243
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 243 tcccgcctg 9

<210> SEQ ID NO 244
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 244 tcccgctta 9

<210> SEQ ID NO 245
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 245 tcccgccta 9

<210> SEQ ID NO 246
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 246 tcccgcctc 9

<210> SEQ ID NO 247
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 247 tcccgcttg 9

<210> SEQ ID NO 248
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 248 tctcgactt 9

<210> SEQ ID NO 249
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 249 tctcgactg 9

<210> SEQ ID NO 250
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 250 tctcgatta 9

<210> SEQ ID NO 251
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 251 tctcgacta 9

<210> SEQ ID NO 252
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 252 tctcgactc 9

<210> SEQ ID NO 253
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 253 tctcgattg 9

<210> SEQ ID NO 254
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 254 tctaggctt 9

<210> SEQ ID NO 255
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 255 tctaggctg 9

<210> SEQ ID NO 256
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 256 tctaggtta 9

<210> SEQ ID NO 257
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 257 tctaggcta 9

<210> SEQ ID NO 258
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 258 tctaggctc 9

<210> SEQ ID NO 259
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 259 tctaggttg 9

<210> SEQ ID NO 260
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 260 tctcgtctt 9

<210> SEQ ID NO 261
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 261 tctcgtctg 9

<210> SEQ ID NO 262
<211> LENGTH: 9
<212> TYPE: DNA

<213> ORGANISM: Artificial Sequence
<220> FEATURE:
<223> OTHER INFORMATION: Synthetic oligonucleotide

<400> SEQUENCE: 262 tctcgttta 9

<210> SEQ ID NO 263
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 263 tctcgtcta 9

<210> SEQ ID NO 264
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 264 tctcgtctc 9

<210> SEQ ID NO 265
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 265 tctcgtttg 9

<210> SEQ ID NO 266
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 266 tctagactt 9

<210> SEQ ID NO 267
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 267 tctagactg 9

<210> SEQ ID NO 268
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 268 tctagatta 9

-continued

<210> SEQ ID NO 269
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 269 tctagacta 9

<210> SEQ ID NO 270
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 270 tctagactc 9

<210> SEQ ID NO 271
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 271 tctagattg 9

<210> SEQ ID NO 272
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 272 tctcggctt 9

<210> SEQ ID NO 273
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 273 tctcggctg 9

<210> SEQ ID NO 274
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 274 tctcggtta 9

<210> SEQ ID NO 275
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 275 tctcggcta 9

<210> SEQ ID NO 276
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 276 tctcggctc 9

<210> SEQ ID NO 277
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 277 tctcggttg 9

<210> SEQ ID NO 278
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 278 tctcgcctt 9

<210> SEQ ID NO 279
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 279 tctcgcctg 9

<210> SEQ ID NO 280
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 280 tctcgctta 9

<210> SEQ ID NO 281
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 281 tctcgccta 9

<210> SEQ ID NO 282
<211> LENGTH: 9
<212> TYPE: DNA

<213> ORGANISM: Artificial Sequence
<220> FEATURE:
<223> OTHER INFORMATION: Synthetic oligonucleotide

<400> SEQUENCE: 282 tctcgcctc 9

<210> SEQ ID NO 283
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 283 tctcgcttg 9

<210> SEQ ID NO 284
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 284 agtaggctt 9

<210> SEQ ID NO 285
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 285 agtaggctg 9

<210> SEQ ID NO 286
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 286 agtaggtta 9

<210> SEQ ID NO 287
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 287 agtaggcta 9

<210> SEQ ID NO 288
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 288 agcaggctt 9

<210> SEQ ID NO 289
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 289 agcaggctg 9

<210> SEQ ID NO 290
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 290 agcaggtta 9

<210> SEQ ID NO 291
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 291 agcaggcta 9

<210> SEQ ID NO 292
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 292 agcaggttg 9

<210> SEQ ID NO 293
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 293 agtaggttg 9

<210> SEQ ID NO 294
<211> LENGTH: 6
<212> TYPE: DNA
<213> ORGANISM: Artificial Sequence
<220> FEATURE:
<223> OTHER INFORMATION: Synthetic oligonucleotide

<400> SEQUENCE: 294 agctac 6

<210> SEQ ID NO 295
<211> LENGTH: 6
<212> TYPE: DNA
<213> ORGANISM: Artificial Sequence
<220> FEATURE:
<223> OTHER INFORMATION: Synthetic oligonucleotide

<400> SEQUENCE: 295 agcagc 6

<210> SEQ ID NO 296
<211> LENGTH: 6
<212> TYPE: DNA
<213> ORGANISM: Artificial Sequence
<220> FEATURE:
<223> OTHER INFORMATION: Synthetic oligonucleotide

<400> SEQUENCE: 296 tacagc 6

<210> SEQ ID NO 297
<211> LENGTH: 6
<212> TYPE: DNA
<213> ORGANISM: Artificial Sequence
<220> FEATURE:
<223> OTHER INFORMATION: Synthetic oligonucleotide

<400> SEQUENCE: 297 tactac 6

<210> SEQ ID NO 298
<211> LENGTH: 6
<212> TYPE: DNA
<213> ORGANISM: Artificial Sequence
<220> FEATURE:
<223> OTHER INFORMATION: Synthetic oligonucleotide

<400> SEQUENCE: 298 aactac 6

<210> SEQ ID NO 299
<211> LENGTH: 6
<212> TYPE: DNA
<213> ORGANISM: Artificial Sequence
<220> FEATURE:
<223> OTHER INFORMATION: Synthetic oligonucleotide

<400> SEQUENCE: 299 aacaac 6

<210> SEQ ID NO 300
<211> LENGTH: 6
<212> TYPE: DNA
<213> ORGANISM: Artificial Sequence
<220> FEATURE:
<223> OTHER INFORMATION: Synthetic oligonucleotide

<400> SEQUENCE: 300 tactac 6

<210> SEQ ID NO 301
<211> LENGTH: 6
<212> TYPE: DNA
<213> ORGANISM: Artificial Sequence
<220> FEATURE:
<223> OTHER INFORMATION: Synthetic oligonucleotide

<400> SEQUENCE: 301 tacaac 6

<210> SEQ ID NO 302
<211> LENGTH: 399
<212> TYPE: DNA

<213> ORGANISM: Artificial Sequence
<220> FEATURE:
<223> OTHER INFORMATION: Synthetic construct

<400> SEQUENCE: 302
atggccaagc ctttgtctca agaagaatcc accctcattg aaagagcaac ggctacaatc 60
aacagcatcc ccatctctga agactacagc gtcgccagcg cagctctctc tagcgacggc 120
cgcatcttca ctggtgtcaa tgtatatcat tttactgggg gaccttgcgc agaactcgtg 180
gtgctgggca ctgctgctgc tgcggcagct ggcaacctga cttgtatcgt cgcgatcgga 240
aatgagaaca ggggcatctt gagcccctgc ggacggtgcc gacaggttct tctcgatctg 300
catcctggga tcaaagccat agtgaaggac agtgatggac agccgacggc agttgggatt 360
cgtgaattgc tgccctctgg ttatgtgtgg gagggctaa 399

<210> SEQ ID NO 303
<211> LENGTH: 399
<212> TYPE: DNA
<213> ORGANISM: Artificial Sequence
<220> FEATURE:
<223> OTHER INFORMATION: Synthetic construct

<400> SEQUENCE: 303
atggccaagc ctttgtctca agaagaatcc accctcattg aaagagcaac ggctacaatc 60
aacagcatcc ccatctctga agactacagc gtcgccagcg cagctctctc tagcgacggc 120
cgcatcttca ctggtgtcaa tgtatatcat tttactgggg gaccttgcgc agaactcgtg 180
gtgctgggca ctgctgctgc tgcggcagct ggcaacctga cttgtatcgt cgcgatcgga 240
aatgagaaca ggggcatctt gagcccctgc ggacggtgcc gacaggttct tctcgatctg 300
catcctggga tcaaagccat agtgaaggac agtgatggac agccgacggc agttgggatt 360
cgtgaattgc tgccctctgg ttatgtgtgg gagggctaa 399

<210> SEQ ID NO 304
<211> LENGTH: 691
<212> TYPE: DNA
<213> ORGANISM: Artificial Sequence
<220> FEATURE:
<223> OTHER INFORMATION: Synthetic construct

<400> SEQUENCE: 304
agcttggccc attgcatacg ttgtatccat atcataatat ctacatttat attggctcat 60
gtccaacatt accgccatgt tgacattgat tattgactag ttattaatag taatcaatta 120
cggggtcatt agttcatagc ccatatatgg agttccgcgt tacataactt acggtaaatg 180
gcccgcctgg ctgaccgccc aacgaccccc gcccattgac gtcaataatg acgtatgttc 240
ccatagtaac gccaataggg actttccatt gacgtcaatg ggtggagtat ttacggtaaa 300
ctgcccactt ggcagtacat caagtgtatc atatgccaag tacgccccct attgacgtca 360
atgacggtaa atggcccgcc tggcattatg cccagtacat gaccttatgg gactttccta 420
cttggcagta catctacgta ttagtcatcg ctattaccat ggtgatgcgg ttttggcagt 480
acatcaatgg gcgtggatag cggtttgact cacggggatt tccaagtctc caccccattg 540
acgtcaatgg gagtttgttt tggcaccaaa atcaacggga ctttccaaaa tgtcgtaaca 600
actccgcccc attgacgcaa atgggcggta ggcgtgtacg gtgggaggtc tatataagca 660
gagctggttt agtgaaccgt cagatcgcct a 691

<210> SEQ ID NO 305

-continued

<211> LENGTH: 85
<212> TYPE: DNA
<213> ORGANISM: Artificial Sequence
<220> FEATURE:
<223> OTHER INFORMATION: Synthetic oligonucleotide

<400> SEQUENCE: 305
ttccctgcag gattgtttaa acaccagatc tgcttgaatc cgcggataag aggactagta 60
ttcgtctcac tagggagagc tccta 85

<210> SEQ ID NO 306
<211> LENGTH: 617
<212> TYPE: DNA
<213> ORGANISM: Artificial Sequence
<220> FEATURE:
<223> OTHER INFORMATION: Synthetic construct

<400> SEQUENCE: 306
tgtacaatcc gcgtgagacg atcggcgcgc ccgcccctct ccctcccccc cccctaacgt 60
tactggccga agccgcttgg aataaggccg gtgtgcgttt gtctatatgt tattttccac 120
catattgccg tcttttggca atgtgagggc ccggaaacct ggccctgtct tcttgacgag 180
cattcctagg ggtctttccc ctctcgccaa aggaatgcaa ggtctgttga atgtcgtgaa 240
ggaagcagtt cctctggaag cttcttgaag acaaacaacg tctgtagcga ccctttgcag 300
gcagcggaac cccccacctg gcgacaggtg cctctgcggc caaaagccac gtgtataaga 360
tacacctgca aaggcggcac aaccccagtg ccacgttgtg agttggatag ttgtggaaag 420
agtcaaatgg ctctcctcaa gcgtattcaa caaggggctg aaggatgccc agaaggtacc 480
ccattgtatg ggatctgatc tggggcctcg gtgcacatgc tttacatgtg tttagtcgag 540
gttaaaaaaa cgtctaggcc ccccgaacca cggggacgtg gttttccttt gaaaaacacg 600
atgataatat ggccggc 617

<210> SEQ ID NO 307
<211> LENGTH: 6
<212> TYPE: DNA
<213> ORGANISM: Artificial Sequence
<220> FEATURE:
<223> OTHER INFORMATION: Synthetic oligonucleotide

<400> SEQUENCE: 307 tctaga 6

<210> SEQ ID NO 308
<211> LENGTH: 405
<212> TYPE: DNA
<213> ORGANISM: Artificial Sequence
<220> FEATURE:
<223> OTHER INFORMATION: Synthetic construct

<400> SEQUENCE: 308
atggccaagc ctttgtctca agaagaatcc accctcattg aaagggccac tgctacaatc 60
aacagcatcc ccatctctga agactactct gtcgccagcg cagctctctc ctctgacggg 120
agaatcttca ctggtgtcaa tgtatatcat tttactgggg gaccttgcgc agagcttgtg 180
gtcctgggga ctgctgctgc tgctgcagcc ggaaacctga cttgtatcgt cgccataggg 240
aatgagaaca gaggcatctt gagcccctgt gggagatgca gacaagtcct cctggacctc 300
catcctggga tcaaagccat agtgaaggac agtgatggac agcccacagc cgttgggatc 360
agggagttgc tgccatctgg ttatgtgtgg gagggctaat ctaga 405

<210> SEQ ID NO 309
<211> LENGTH: 1032
<212> TYPE: DNA
<213> ORGANISM: Artificial Sequence
<220> FEATURE:
<223> OTHER INFORMATION: Synthetic construct

<400> SEQUENCE: 309
atgaaaaagc ctgaactgac tgccacctct gttgagaagt ttttaataga gaagtttgac 60
tctgtgtcag acctcatgca gctttctgag ggagaggagt ctagagcctt tagctttgat 120
gtggggggga gaggctatgt cctgagagtc aatagctgtg cagatggttt ctacaaagat 180
aggtatgtct atagacattt tgcatccgcc gccctcccca ttccagaggt ccttgacatt 240
ggggaattct cagagagcct gacctattgc atttcccgga gagcccaggg tgtgactctt 300
caagacctgc ctgagacaga actccctgca gtgctccagc ccgtcgccga ggccatggat 360
gcaatcgccg ccgcagacct cagccagacc tcggggtttg ggccctttgg cccccagggg 420
ataggccaat acactacatg gagagatttc atatgcgcta ttgctgaccc ccatgtgtat 480
cactggcaaa ctgtgatgga cgacacagtc tcagcctctg tcgcacaagc cctggacgag 540
ctgatgcttt gggccgagga ctgcccagag gtcagacatc tcgtccatgc cgactttggg 600
tcaaacaatg tcctgacgga caatgggaga atcactgctg tcattgactg gagcgaggcc 660
atgtttgggg actcccaata cgaggtcgcc aacatcttct tctggagacc ctggttggct 720
tgtatggagc agcagacccg ttactttgag aggaggcatc cagagctcgc tgggagccct 780
agattgaggg cctatatgct caggataggg cttgaccaac tctatcagag cttggttgac 840
ggcaattttg atgacgcagc ttgggctcag ggagatgcg acgccatagt gaggagtggg 900
gccgggactg tcgggagaac tcagatcgcc aggaggtcag ctgccgtctg gactgacggc 960
tgtgtagaag tcttagccga ctctgggaac aggagaccca gcactcgtcc agaggccaag 1020
gaatgatcta ga 1032

<210> SEQ ID NO 310
<211> LENGTH: 610
<212> TYPE: DNA
<213> ORGANISM: Unknown
<220> FEATURE:
<223> OTHER INFORMATION: Pur sequence

<400> SEQUENCE: 310
caccatgacc gagtacaagc ccacggtgcg cctcgccacc cgcgacgacg tcccccgggc 60
cgttcgcacc ctcgccgccg cgttcgccga ctaccccgcc acgcgccaca ccgtggaccc 120
ggacaggcac atcgagcggg tcaccgagct gcaagaactc ttcctcacgc gcgtcgggct 180
cgacatcggc aaggtgtggg tcgcggacga cggcgccgct gtggcggtct ggaccacgcc 240
ggagagcgtc gaagcggggg cggtgttcgc cgagatcggc ccgcgcatgg ccgagttgag 300
cggttcccgg ctggccgcgc agcaacagat ggaaggcctc ctggcgccgc accggcccaa 360
ggagcccgcg tggttcctgg ctaccgtcgg agtctcgccc gaccaccagg gcaagggtct 420
gggcagcgcc gtcgtgctcc ccggagtgga ggctgccgag cgtgccgggg tgcccgcctt 480
cctcgagacc tccgcgcccc gcaacctccc cttctacgag cggctcggct tcaccgtcac 540
cgccgacgtc gaggtgcccg aaggaccgcg cacctggtgc atgacccgca agcccggtgc 600
ctgatctaga 610

<210> SEQ ID NO 311

| | | |
|---|---|---|
| <211> LENGTH: 700 | | |
| <212> TYPE: DNA | | |
| <213> ORGANISM: Artificial Sequence | | |
| <220> FEATURE: | | |
| <223> OTHER INFORMATION: Synthetic construct | | |

<400> SEQUENCE: 311

| | | | | | |
|---|---|---|---|---|---|
| ggatctttgt | gaaggaacct | tacttctgtg | gtgtgacata | attggacaaa | ctacctacag | 60 |
| agatttaaag | ctctaaggta | aatataaaat | ttttaagtgt | ataatgtgtt | aaactactga | 120 |
| ttctaattgt | tgtggtattt | tagattccaa | cctatggaac | ttatgaatgg | gagcagtggt | 180 |
| ggaatgcctt | taatgaggaa | aacctgtttt | gctcagaaga | aatgccatct | agtgatgatg | 240 |
| aggctactgc | tgactctcaa | cattctactc | ctccaaaaaa | gaagagaaag | gtagaagacc | 300 |
| ccaaggactt | tccttcagaa | ttggtaagtt | ttttgagtca | tgctgtgttt | agtaatagaa | 360 |
| ctcttgcttg | ctttgctatt | tacaccacaa | aggaaaaagc | tgcactgcta | tacaagaaaa | 420 |
| ttatggaaaa | atatttgatg | tatagtgcct | tgactagaga | tcataatcag | ccataccaca | 480 |
| tttgtagagg | ttttacttgc | tttaaaaaac | ctcccacacc | tccccctgaa | cctgaaacat | 540 |
| aaaatgaatg | caattgttgt | tgttaacttg | tttattgcag | cttataatgg | ttacaaataa | 600 |
| agcaatagca | tcacaaattt | cacaaataaa | gcatttttat | cactgcattc | tagttgtggt | 660 |
| ttgtccaaac | tcatcaatgt | atcttatcat | gtctggatcc | | | 700 |

| | | |
|---|---|---|
| <210> SEQ ID NO 312 | | |
| <211> LENGTH: 2026 | | |
| <212> TYPE: DNA | | |
| <213> ORGANISM: Artificial Sequence | | |
| <220> FEATURE: | | |
| <223> OTHER INFORMATION: Synthetic construct | | |

<400> SEQUENCE: 312

| | | | | | |
|---|---|---|---|---|---|
| actgtcttct | ttatcatgca | actcgtagga | caggtgccct | ggccgggtcc | gcaggaaaag | 60 |
| gacaagcagc | gaaaattcac | gcccccttgg | gaggtggcgg | catatgcaaa | ggatagcact | 120 |
| cccactctac | tactgggtat | catatgctga | ctgtatatgc | atgaggatag | catatgctac | 180 |
| ccggatacag | attaggatag | catatactac | ccagatatag | attaggatag | catatgctac | 240 |
| ccagatatag | attaggatag | cctatgctac | ccagatataa | attaggatag | catatactac | 300 |
| ccagatatag | attaggatag | catatgctac | ccagatatag | attaggatag | cctatgctac | 360 |
| ccagatatag | attaggatag | catatgctac | ccagatatag | attaggatag | catatgctat | 420 |
| ccagatattt | gggtagtata | tgctacccag | atataaatta | ggatagcata | tactacccta | 480 |
| atctctatta | ggatagcata | tgctacccgg | atacagatta | ggatagcata | tactacccag | 540 |
| atatagatta | ggatagcata | tgctacccag | atatagatta | ggatagccta | tgctacccag | 600 |
| atataaatta | ggatagcata | tactacccag | atatagatta | ggatagcata | tgctacccag | 660 |
| atatagatta | ggatagccta | tgctacccag | atatagatta | ggatagcata | tgctatccag | 720 |
| atatttgggt | agtatatgct | acccatggca | acattagccc | accgtgctct | cagcgacctc | 780 |
| gtgaatatga | ggaccaacaa | ccctgtgctt | ggcgctcagg | cgcaagtgtg | tgtaatttgt | 840 |
| cctccagatc | gcagcaatcg | cgcccctatc | ttggcccgcc | cacctactta | tgcaggtatt | 900 |
| cccgggggtg | ccattagtgg | ttttgtgggc | aagtggtttg | accgcagtgg | ttagcggggt | 960 |
| tacaatcagc | caagttatta | cacccttatt | ttacagtcca | aaaccgcagg | cggcgtgtg | 1020 |
| ggggctgacg | cgtgccatca | ctccacaatt | tcaagagaaa | gagtggccac | ttgtctttgt | 1080 |
| ttatgggccc | cattggcgtg | gagccccgtt | taattttcgg | gggtgttaga | gacaaccagt | 1140 |

ggagtccgct gctgtcggcg tccactctct ttccccttgt tacaaataga gtgtaacaac 1200
atggttcacc tgtcttggtc cctgcctggg acacatctta ataaccccag tatcatattg 1260
cactaggatt atgtgttgcc catagccata aattcgtgtg agatggacat ccagtcttta 1320
cggcttgtcc ccaccccatg gatttctatt gttaaagata ttcagaatgt ttcattccta 1380
cactaggatt tattgcccaa ggggtttgtg agggttatat tggtgtcata gcacaatgcc 1440
accactgaac ccatcgtcca aattttattc tggatgcgtc acctgaaacc ttgttttcga 1500
gcacctcaca tacaccttac tgttcacaac tcagcagtta ttctattagc taaacgaagg 1560
agaatgaaga agcaggcgaa gattcaggag agttcactgc ccgctccttg atcttcagcc 1620
actgcccttg tgactaaaat ggttcactac cctcgtggaa tcctgacccc atgtaaataa 1680
aaccgtgaca gctcatgggg tgggagatat cgctgttcct taggaccctt ttactaaccc 1740
taattcgata gcatatgctt cccgttgggt aacatatgct attgaattag ggttagtctg 1800
gatagtatat actactaccc gggaagcata tgctacccgt ttagggttaa caagggggcc 1860
ttataaacac tattgctaat gccctcttga gggtccgctt atcggtagct acacaggccc 1920
ctctgattga cgttggtgta gcctcccgta gtcttcctgg gcccctggga ggtacatgtc 1980
ccccagcatt ggtgtaagag cttcagccaa gagttacaca taaagg 2026

<210> SEQ ID NO 313
<211> LENGTH: 1015
<212> TYPE: DNA
<213> ORGANISM: Artificial Sequence
<220> FEATURE:
<223> OTHER INFORMATION: Synthetic construct

<400> SEQUENCE: 313
aaaaggggcc cgagcttaag actggccgtc gttttacaac acagaaagag tttgtagaaa 60
cgcaaaaagg ccatccgtca ggggccttct gcttagtttg atgcctggca gttccctact 120
ctcgccttcc gcttcctcgc tcactgactc gctgcgctcg gtcgttcggc tgcggcgagc 180
ggtatcagct cactcaaagg cggtaatacg gttatccaca gaatcagggg ataacgcagg 240
aaagaacatg tgagcaaaag gccagcaaaa ggccaggaac cgtaaaaagg ccgcgttgct 300
ggcgtttttc cataggctcc gcccccctga cgagcatcac aaaaatcgac gctcaagtca 360
gaggtggcga aacccgacag gactataaag ataccaggcg tttccccctg gaagctccct 420
cgtgcgctct cctgttccga ccctgccgct taccggatac ctgtccgcct ttctcccttc 480
gggaagcgtg gcgctttctc atagctcacg ctgtaggtat ctcagttcgg tgtaggtcgt 540
tcgctccaag ctgggctgtg tgcacgaacc ccccgttcag cccgaccgct gcgccttatc 600
cggtaactat cgtcttgagt ccaacccggt aagacacgac ttatcgccac tggcagcagc 660
cactggtaac aggattagca gagcgaggta tgtaggcggt gctacagagt tcttgaagtg 720
gtggcctaac tacggctaca ctagaagaac agtatttggt atctgcgctc tgctgaagcc 780
agttaccttc ggaaaaagag ttggtagctc ttgatccggc aaacaaacca ccgctggtag 840
cggtggtttt tttgtttgca agcagcagat tacgcgcaga aaaaaaggat ctcaagaaga 900
tcctttgatc ttttctacgg ggtctgacgc tcagtggaac gacgcgcgcg taactcacgt 960
taagggattt tggtcatgag cttgcgccgt cccgtcaagt cagcgtaatg ctctg 1015

<210> SEQ ID NO 314
<211> LENGTH: 1078
<212> TYPE: DNA
<213> ORGANISM: Artificial Sequence
<220> FEATURE:

<223> OTHER INFORMATION: Synthetic construct

<400> SEQUENCE: 314
cttaccaatg cttaatcagt gaggcaccta tctcagcgat ctgtctattt cgttcatcca 60
tagttgcctg actccccgtc gtgtagataa ctacgatacg ggagggctta ccatctggcc 120
ccagcgctgc gatgataccg cgagaaccac gctcaccggc tccggattta tcagcaataa 180
accagccagc cggaagggcc gagcgcagaa gtggtcctgc aactttatcc gcctccatcc 240
agtctattaa ttgttgccgg gaagctagag taagtagttc gccagttaat agtttgcgca 300
acgttgttgc catcgctaca ggcatcgtgg tgtcacgctc gtcgtttggt atggcttcat 360
tcagctccgg ttcccaacga tcaaggcgag ttacatgatc ccccatgttg tgcaaaaaag 420
cggttagctc cttcggtcct ccgatcgttg tcagaagtaa gttggccgca gtgttatcac 480
tcatggttat ggcagcactg cataattctc ttactgtcat gccatccgta agatgctttt 540
ctgtgactgg tgagtactca accaagtcat tctgagaata gtgtatgcgg cgaccgagtt 600
gctcttgccc ggcgtcaata cgggataata ccgcgccaca tagcagaact ttaaaagtgc 660
tcatcattgg aaaacgttct tcggggcgaa aactctcaag gatcttaccg ctgttgagat 720
ccagttcgat gtaacccact cgtgcaccca actgatcttc agcatctttt actttcacca 780
gcgtttctgg gtgagcaaaa acaggaaggc aaaatgccgc aaaaaaggga ataagggcga 840
cacggaaatg ttgaatactc atattcttcc tttttcaata ttattgaagc atttatcagg 900
gttattgtct catgagcgga tacatatttg aatgtattta gaaaaataaa caaatagggg 960
tcagtgttac aaccaattaa ccaattctga acattatcgc gagcccattt atacctgaat 1020
atggctcata acaccccttg cagtgcgact aacggcatga agctcgtcgg ggcgtacg 1078

<210> SEQ ID NO 315
<211> LENGTH: 1228
<212> TYPE: DNA
<213> ORGANISM: Artificial Sequence
<220> FEATURE:
<223> OTHER INFORMATION: Synthetic construct

<400> SEQUENCE: 315
cttagaaaaa ctcatcgagc atcaaatgaa actgcaattt attcatatca ggattatcaa 60
taccatattt ttgaaaaagc cgtttctgta atgaaggaga aaactcaccg aggcagttcc 120
ataggatggc aagatcctgg tatcggtctg cgattccgac tcgtccaaca tcaatacaac 180
ctattaattt cccctcgtca aaaataaggt tatcaagtga gaaatcacca tgagtgacga 240
ctgaatccgg tgagaatggc aaaagtttat gcatttcttt ccagacttgt tcaacaggcc 300
agccattacg ctcgtcatca aaatcactcg catcaaccaa accgttattc attcgtgatt 360
gcgcctgagc gaggcgaaat acgcgatcgc tgttaaaagg acaattacaa acaggaatcg 420
agtgcaaccg gcgcaggaac actgccagcg catcaacaat attttcacct gaatcaggat 480
attcttctaa tacctggaac gctgtttttc cggggatcgc agtggtgagt aaccatgcat 540
catcaggagt acggataaaa tgcttgatgg tcggaagtgg cataaattcc gtcagccagt 600
ttagtctgac catctcatct gtaacatcat tggcaacgct acctttgcca tgtttcagaa 660
acaactctgg cgcatcgggc ttcccataca agcgatagat tgtcgcacct gattgcccga 720
cattatcgcg agcccattta tacccatata aatcagcatc catgttggaa tttaatcgcg 780
gcctcgacgt ttcccgttga atatggctca tattcttcct tttcaatat tattgaagca 840
tttatcaggg ttattgtctc atgagcggat acatatttga atgtatttag aaaaataaac 900
aaataggggt cagtgttaca accaattaac caattctgaa cattatcgcg agcccattta 960
tacctgaata tggctcataa caccccttgc agtgcgacta acggcatgaa gctcgtcggg 1020
gaaataatga ttttattttg actgatagtg acctgttcgt tgcaacaaat tgataagcaa 1080
tgctttctta taatgccaac tttgtacaag aaagctgggt ttttttttta gcctgctttt 1140
ttgtacaaag ttggcattat aaaaaagcat tgctcatcaa tttgttgcaa cgaacaggtc 1200
actatcagtc aaaataaaat cattattt 1228

<210> SEQ ID NO 316
<211> LENGTH: 291
<212> TYPE: DNA
<213> ORGANISM: Homo sapiens

<400> SEQUENCE: 316
cgtacgtact cctgcttgct gatccacatc tgctggaagg tggacagcga ggccaggatg 60
gagccgccga tccacacgga gtacttgcgc tcaggaggag caatgaagct tatctgagga 120
gggaagggga caggcagtga ggaccctgga tgtgacagct ccaagcttcc acacaccaca 180
ggaccccaca gccgacctgc ccaggtcagc tcaggcagga aagacaccca ccttgatctt 240
cattgtgctg ggtgccaggg cagtgatctc cttctgcatc ctgtcatcga t 291

<210> SEQ ID NO 317
<211> LENGTH: 288
<212> TYPE: DNA
<213> ORGANISM: Homo sapiens

<400> SEQUENCE: 317
cgtacgaggt gaggctgcag ttccatgatg tgtccggcga catcttccac cagcagtgca 60
agcgcaacga gctggtgatc cgcgtgcagc ccaacgaggc cgtgtaccag agaaggagca 120
gtgtggaggg tgggcggcct gggcccgggg gactccacat ggtggcaggc agtggcatca 180
gcaagacact ctctccctca cagaacgtga agctccctga cgcctacgag cgcctcatcc 240
tggacgtctt ctgcgggagc cagatgcact tcgtgcgcag gaatcgat 288

<210> SEQ ID NO 318
<211> LENGTH: 374
<212> TYPE: DNA
<213> ORGANISM: Artificial Sequence
<220> FEATURE:
<223> OTHER INFORMATION: Synthetic construct

<400> SEQUENCE: 318
ttcgaagctg tggaatgtgt gtcagttagg gtgtggaaag tccccaggct ccccagcagg 60
cagaagtatg caaagcatgc atctcaatta gtcagcaacc aggtgtggaa agtccccagg 120
ctccccagca ggcagaagta tgcaaagcat gcatctcaat tagtcagcaa ccatagtccc 180
gcccctaact ccgcccatcc cgcccctaac tccgcccagt tccgcccatt ctccgcccca 240
tggctgacta attttttta tttatgcaga ggccgaggcc gcctcggcct ctgagctatt 300
ccagaagtag tgaggaggct tttttggagg cctaggcttt tgcaaaaagc tctgacccct 360
cacaaggagc cggc 374

<210> SEQ ID NO 319
<211> LENGTH: 25
<212> TYPE: DNA
<213> ORGANISM: Artificial Sequence
<220> FEATURE:
<223> OTHER INFORMATION: Synthetic oligonucleotide
<220> FEATURE:

<221> NAME/KEY: modified_base
<222> LOCATION: (7)..(19)
<223> OTHER INFORMATION: a, c, g, t, unknown or other

<400> SEQUENCE: 319
caggtgnnnn nnnnnnnnnc aggtg 25

<210> SEQ ID NO 320
<211> LENGTH: 6
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (3)..(4)
<223> OTHER INFORMATION: a, c, g, t, unknown or other

<400> SEQUENCE: 320 canntg 6

<210> SEQ ID NO 321
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 321
gtagtcgaat tcccacatgt cttacatggt atatg 35

<210> SEQ ID NO 322
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 322
gactacgaat tctcctgagg acacagtgat ag 32

<210> SEQ ID NO 323
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 323
gtagtcgcgg ccgcctagtt cctagctact tcttta 36

<210> SEQ ID NO 324
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 324
aattcaggtg ctggggtagg gagcaggtgc tacactgcag accaggtgct gc 52

<210> SEQ ID NO 325
<211> LENGTH: 52
<212> TYPE: DNA
<213> ORGANISM: Artificial Sequence
<220> FEATURE:
<223> OTHER INFORMATION: Synthetic oligonucleotide -continued

<400> SEQUENCE: 325
ggccgcagca cctggtctgc agtgtagcac ctgctcccta ccccagcacc tg 52

<210> SEQ ID NO 326
<211> LENGTH: 767
<212> TYPE: DNA
<213> ORGANISM: Mus sp.

<400> SEQUENCE: 326
ccagcttagg ctacacagag aaactatcta aaaaataatt actaactact taataggaga 60
ttggatgtta agatctggtc actaagaggc agaattgaga ttcgaagcca gtattttcta 120
cctggtatgt tttaaattgc agtaaggatc taagtgtaga tatataataa taagattcta 180
ttgatctctg caacaacaga gagtgttaga tttgtttgga aaaaaatatt atcagccaac 240
atcttctacc atttcagtat agcacagagt acccacccat atctccccac ccatccccca 300
taccagactg gttattgatt ttcatggtga ctggcctgag aagattaaaa aaagtaatgc 360
taccttattg ggagtgtccc atggaccaag atagcaactg tcatagctac cgtcacactg 420
ctttgatcaa gaagaccctt tgaggaactg aaaacagaac cttaggcaca tctgttgctt 480
tcgctcccat cctcctccaa cagcctgggt ggtgcactcc acaccctttc aagtttccaa 540
agcctcatac acctgctccc taccccagca cctggccaag gctgtatcca gcactgggat 600
gaaaatgata ccccacctcc atcttgtttg atattactct atctcaagcc ccaggttagt 660
ccccagtccc aatgcttttg cacagtcaaa actcaacttg gaataatcag tatccttgaa 720
gagttctgat atggtcactg ggcccatata ccatgtaaga catgtgg 767

<210> SEQ ID NO 327
<211> LENGTH: 1251
<212> TYPE: DNA
<213> ORGANISM: Artificial Sequence
<220> FEATURE:
<223> OTHER INFORMATION: Synthetic construct

<400> SEQUENCE: 327
tcctgaggac acagtgatag gaacagagcc actaatctga agagaacaga gatgtgacag 60
actacactaa tgtgagaaaa acaaggaaag ggtgacttat tggagatttc agaaataaaa 120
tgcatttatt attatattcc cttattttaa ttttctatta gggaattaga aagggcataa 180
actgctttat ccagtgttat attaaaagct taatgtatat aatcttttag aggtaaaatc 240
tacagccagc aaaagtcatg gtaaatattc tttgactgaa ctctcactaa actcctctaa 300
attatatgtc atattaactg gttaaattaa tataaatttg tgacatgacc ttaactggtt 360
aggtaggata tttttcttca tgcaaaaata tgactaataa taatttagca caaaaatatt 420
tcccaatact ttaattctgt gatagaaaaa tgtttaactc agctactata atcccataat 480
tttgaaaact atttattagc ttttgtgttt gacccttccc tagccaaagg caactattta 540
aggacccttt aaaactcttg aaactacttt agagtcatta agttatttaa ccacttttaa 600
ttactttaaa atgatgtcaa ttccctttta actattaatt tattttaagg ggggaaaggc 660
tgctcataat tctattgttt ttcttggtaa agaactctca gttttcgttt ttactacctc 720
tgtcacccaa gagttggcat ctcaacagag gggactttcc gagaggccat ctggcagttg 780
cttaagatca gaagtgaagt ctgccagttc ctcccaggca ggtggcccag attacagttg 840
acctgttctg gtgtggctaa aaattgtccc atgtggttac aaaccattag accagggtct 900
gatgaattgc tcagaatatt tctggacacc caaatacaga ccctggctta aggccctgtc 960

```
catacagtag gtttagcttg gctacaccaa aggaagccat acagaggcta ataccagagt   1020

attcttggaa gagacaggag aaaatgaaag ccagtttctg ctcttacctt atgtgcttgt   1080

gttcagactc ccaaacatca ggagtgtcag ataaactggt ctgaatctct gtctgaagca   1140

tggaactgaa aagaatgtag tttcagggaa gaaaggcaat agaaggaagc ctgagaatat   1200

cttcaaaggg tcagactcaa tttactttct aaagaagtag ctaggaacta g            1251


<210> SEQ ID NO 328
<211> LENGTH: 121
<212> TYPE: PRT
<213> ORGANISM: Homo sapiens

<400> SEQUENCE: 328

Met Ser Val Ser Phe Leu Ile Phe Leu Pro Val Leu Gly Leu Pro Trp
1               5                   10                  15

Gly Val Leu Ser Gln Val Gln Leu Gln Gln Ser Gly Pro Gly Leu Val
            20                  25                  30

Lys Pro Ser Gln Thr Leu Ser Leu Thr Cys Ala Ile Ser Gly Asp Ser
        35                  40                  45

Val Ser Ser Asn Ser Ala Ala Trp Asn Trp Ile Arg Gln Ser Pro Ser
    50                  55                  60

Arg Gly Leu Glu Trp Leu Gly Arg Thr Tyr Tyr Arg Ser Lys Trp Tyr
65                  70                  75                  80

Asn Asp Tyr Ala Val Ser Val Lys Ser Arg Ile Thr Ile Asn Pro Asp
                85                  90                  95

Thr Ser Lys Asn Gln Phe Ser Leu Gln Leu Asn Ser Val Thr Pro Glu
            100                 105                 110

Asp Thr Ala Val Tyr Tyr Cys Ala Arg
        115                 120


<210> SEQ ID NO 329
<211> LENGTH: 111
<212> TYPE: PRT
<213> ORGANISM: Homo sapiens

<400> SEQUENCE: 329

Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
        35                  40                  45

Ser Gly Tyr Tyr Trp Ser Trp Ile Arg Gln Pro Pro Gly Lys Gly Leu
    50                  55                  60

Glu Trp Ile Gly Glu Ile Asn His Ser Gly Ser Thr Asn Tyr Asn Pro
65                  70                  75                  80

Ser Leu Lys Ser Arg Val Thr Ile Ser Val Asp Thr Ser Lys Asn Gln
                85                  90                  95

Phe Ser Leu Lys Leu Ser Ser Val Thr Ala Ala Asp Thr Ala Val
            100                 105                 110


<210> SEQ ID NO 330
<211> LENGTH: 111
<212> TYPE: PRT
<213> ORGANISM: Homo sapiens

<400> SEQUENCE: 330

Met Lys His Leu Trp Phe Phe Leu Leu Leu Val Ala Ala Pro Arg Trp
```

-continued

```
1               5                   10                  15

Val Leu Ser Gln Val Gln Leu Gln Glu Ser Gly Pro Gly Leu Val Lys
            20                  25                  30

Pro Ser Glu Thr Leu Ser Leu Thr Cys Thr Val Ser Gly Gly Ser Ile
        35                  40                  45

Ser Ser Tyr Tyr Trp Ser Trp Ile Arg Gln Pro Pro Gly Lys Gly Leu
    50                  55                  60

Glu Trp Ile Gly Tyr Ile Tyr Tyr Ser Gly Ser Thr Asn Tyr Asn Pro
65                  70                  75                  80

Ser Leu Lys Ser Arg Val Thr Ile Ser Val Asp Thr Ser Lys Asn Gln
                85                  90                  95

Phe Ser Leu Lys Leu Ser Ser Val Thr Ala Ala Asp Thr Ala Val
            100                 105                 110


<210> SEQ ID NO 331
<211> LENGTH: 112
<212> TYPE: PRT
<213> ORGANISM: Homo sapiens

<400> SEQUENCE: 331

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Ser Tyr Ala Met His Trp Val Arg Gln Ala Pro Gly Lys Gly Leu
    50                  55                  60

Glu Trp Val Ala Val Ile Ser Tyr Asp Gly Ser Asn Lys Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110


<210> SEQ ID NO 332
<211> LENGTH: 112
<212> TYPE: PRT
<213> ORGANISM: Homo sapiens

<400> SEQUENCE: 332

Met Glu Leu Gly Leu Ser Trp Val Phe Leu Val Ala Ile Leu Glu Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Trp Met Ser Trp Val Arg Gln Ala Pro Gly Lys Gly Leu
    50                  55                  60

Glu Trp Val Ala Asn Ile Lys Gln Asp Gly Ser Glu Lys Tyr Tyr Val
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110


<210> SEQ ID NO 333
```

<211> LENGTH: 112
<212> TYPE: PRT
<213> ORGANISM: Homo sapiens

<400> SEQUENCE: 333

```
Met Glu Phe Gly Leu Ser Trp Leu Phe Leu Val Ala Lys Ile Lys Gly
1               5                   10                  15

Val Gln Cys Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Ala Met Ser Trp Val Arg Gln Ala Pro Gly Lys Gly Leu
    50                  55                  60

Glu Trp Val Ser Ala Ile Ser Gly Ser Gly Gly Ser Thr Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110
```

<210> SEQ ID NO 334
<211> LENGTH: 112
<212> TYPE: PRT
<213> ORGANISM: Homo sapiens

<400> SEQUENCE: 334

```
Met Gly Ser Thr Ala Ile Leu Ala Leu Leu Leu Ala Val Leu Gln Gly
1               5                   10                  15

Val Cys Ser Glu Val Gln Leu Val Gln Ser Gly Ala Glu Val Lys Lys
            20                  25                  30

Pro Gly Glu Ser Leu Lys Ile Ser Cys Lys Gly Ser Gly Tyr Ser Phe
        35                  40                  45

Thr Ser Tyr Trp Ile Gly Trp Val Arg Gln Met Pro Gly Lys Gly Leu
    50                  55                  60

Glu Trp Met Gly Ile Ile Tyr Pro Gly Asp Ser Asp Thr Arg Tyr Ser
65                  70                  75                  80

Pro Ser Phe Gln Gly Gln Val Thr Ile Ser Ala Asp Lys Ser Ile Ser
                85                  90                  95

Thr Ala Tyr Leu Gln Trp Ser Ser Leu Lys Ala Ser Asp Thr Ala Val
            100                 105                 110
```

<210> SEQ ID NO 335
<211> LENGTH: 112
<212> TYPE: PRT
<213> ORGANISM: Homo sapiens

<400> SEQUENCE: 335

```
Met Asp Trp Thr Trp Arg Ile Leu Phe Leu Val Ala Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Gly Tyr Tyr Met His Trp Val Arg Gln Ala Pro Gly Gln Gly Leu
    50                  55                  60

Glu Trp Met Gly Arg Ile Asn Pro Asn Ser Gly Gly Thr Asn Tyr Ala
65                  70                  75                  80

Gln Lys Phe Gln Gly Arg Val Thr Ser Thr Arg Asp Thr Ser Ile Ser
```

```
                85                  90                  95

Thr Ala Tyr Met Glu Leu Ser Arg Leu Arg Ser Asp Asp Thr Ala Val
            100                 105                 110


<210> SEQ ID NO 336
<211> LENGTH: 112
<212> TYPE: PRT
<213> ORGANISM: Homo sapiens

<400> SEQUENCE: 336

Met Asp Trp Thr Trp Arg Phe Leu Phe Val Val Ala Ala Ala Thr Gly
1               5                   10                  15

Val Gln Ser Gln Val Gln Leu Val Gln Ser Gly Ala Glu Val Lys Lys
            20                  25                  30

Pro Gly Ser Ser Val Lys Val Ser Cys Lys Ala Ser Gly Gly Thr Phe
        35                  40                  45

Ser Ser Tyr Ala Ile Ser Trp Val Arg Gln Ala Pro Gly Gln Gly Leu
    50                  55                  60

Glu Trp Met Gly Gly Ile Ile Pro Ile Phe Gly Thr Ala Asn Tyr Ala
65                  70                  75                  80

Gln Lys Phe Gln Gly Arg Val Thr Ile Thr Ala Asp Glu Ser Thr Ser
                85                  90                  95

Thr Ala Tyr Met Glu Leu Ser Ser Leu Arg Ser Glu Asp Thr Ala Val
            100                 105                 110


<210> SEQ ID NO 337
<211> LENGTH: 111
<212> TYPE: PRT
<213> ORGANISM: Homo sapiens

<400> SEQUENCE: 337

Met Arg Leu Pro Ala Gln Leu Leu Gly Leu Leu Met Leu Trp Val Pro
1               5                   10                  15

Gly Ser Ser Gly Asp Val Val Met Thr Gln Ser Pro Leu Ser Leu Pro
            20                  25                  30

Val Thr Leu Gly Gln Pro Ala Ser Ile Ser Cys Arg Ser Ser Gln Ser
        35                  40                  45

Leu Val Tyr Ser Asp Gly Asn Thr Tyr Leu Asn Trp Phe Gln Gln Arg
    50                  55                  60

Pro Gly Gln Ser Pro Arg Arg Leu Ile Tyr Lys Val Ser Asn Trp Asp
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Ala Val Tyr
            100                 105                 110


<210> SEQ ID NO 338
<211> LENGTH: 112
<212> TYPE: PRT
<213> ORGANISM: Homo sapiens

<400> SEQUENCE: 338

Met Val Leu Gln Thr Gln Val Phe Ile Ser Leu Leu Leu Trp Ile Ser
1               5                   10                  15

Gly Ala Tyr Gly Asp Ile Val Met Thr Gln Ser Pro Asp Ser Leu Ala
            20                  25                  30

Val Ser Leu Gly Glu Arg Ala Thr Ile Asn Cys Lys Ser Ser Gln Ser
        35                  40                  45
```

```
Val Leu Tyr Ser Ser Asn Asn Lys Asn Tyr Leu Ala Trp Tyr Gln Gln
    50                  55                  60

Lys Pro Gly Gln Pro Pro Lys Leu Leu Ile Tyr Trp Ala Ser Thr Arg
65                  70                  75                  80

Glu Ser Gly Val Pro Asp Arg Phe Ser Gly Ser Gly Ser Gly Thr Asp
                85                  90                  95

Phe Thr Leu Thr Ile Ser Ser Leu Gln Ala Glu Asp Val Ala Val Tyr
            100                 105                 110


<210> SEQ ID NO 339
<211> LENGTH: 108
<212> TYPE: PRT
<213> ORGANISM: Homo sapiens

<400> SEQUENCE: 339

Met Asp Met Arg Val Pro Ala Gln Leu Leu Gly Leu Leu Gln Leu Trp
1               5                   10                  15

Leu Ser Gly Ala Arg Cys Asp Ile Gln Met Thr Gln Ser Pro Ser Ser
            20                  25                  30

Leu Ser Ala Ser Val Gly Asp Arg Val Thr Ile Thr Cys Gln Ala Ser
        35                  40                  45

Gln Asp Ile Ser Asn Tyr Leu Asn Trp Tyr Gln Gln Lys Pro Gly Lys
    50                  55                  60

Ala Pro Lys Leu Leu Ile Tyr Asp Ala Ser Asn Leu Glu Thr Gly Val
65                  70                  75                  80

Pro Ser Arg Phe Ser Gly Ser Gly Ser Gly Thr Asp Phe Thr Phe Thr
                85                  90                  95

Ile Ser Ser Leu Gln Pro Glu Asp Ile Ala Val Tyr
            100                 105


<210> SEQ ID NO 340
<211> LENGTH: 108
<212> TYPE: PRT
<213> ORGANISM: Homo sapiens

<400> SEQUENCE: 340

Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Ser Ile Ser Ser Tyr Leu Asn Trp Tyr Gln Gln Lys Pro Gly Lys
    50                  55                  60

Ala Pro Lys Leu Leu Ile Tyr Ala Ala Ser Ser Leu Gln Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Val Tyr
            100                 105


<210> SEQ ID NO 341
<211> LENGTH: 107
<212> TYPE: PRT
<213> ORGANISM: Homo sapiens

<400> SEQUENCE: 341

Met Glu Thr Pro Ala Gln Leu Leu Phe Leu Leu Leu Leu Trp Leu Pro
1               5                   10                  15
```

```
Asp Thr Thr Gly Glu Ile Val Leu Thr Gln Ser Pro Gly Thr Leu Ser
            20                  25                  30

Leu Ser Pro Gly Glu Arg Ala Thr Leu Ser Cys Arg Ala Ser Gln Ser
        35                  40                  45

Val Ser Ser Ser Tyr Leu Ala Trp Tyr Gln Gln Lys Pro Gly Gln Ala
    50                  55                  60

Pro Arg Leu Leu Ile Tyr Gly Ala Ser Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr
            100                 105


<210> SEQ ID NO 342
<211> LENGTH: 105
<212> TYPE: PRT
<213> ORGANISM: Homo sapiens

<400> SEQUENCE: 342

Met Ala Trp Thr Pro Leu Phe Leu Phe Leu Leu Thr Cys Cys Pro Gly
1               5                   10                  15

Ser Asn Ser Gln Thr Val Val Thr Gln Glu Pro Ser Leu Thr Val Ser
            20                  25                  30

Pro Gly Gly Thr Val Thr Leu Thr Cys Ala Ser Ser Thr Gly Ala Val
        35                  40                  45

Thr Ser Gly Tyr Tyr Pro Asn Trp Phe Gln Gln Lys Pro Gly Gln Ala
    50                  55                  60

Pro Arg Ala Leu Ile Tyr Ser Thr Ser Asn Lys His Ser Trp Thr Pro
65                  70                  75                  80

Ala Arg Phe Ser Gly Ser Leu Leu Gly Gly Lys Ala Ala Leu Thr Leu
                85                  90                  95

Ser Gly Val Gln Pro Glu Asp Glu Ala
            100                 105


<210> SEQ ID NO 343
<211> LENGTH: 105
<212> TYPE: PRT
<213> ORGANISM: Homo sapiens

<400> SEQUENCE: 343

Met Ala Trp Ser Pro Leu Leu Leu Thr Leu Leu Ala His Cys Thr Gly
1               5                   10                  15

Ser Trp Ala Gln Ser Val Leu Thr Gln Pro Pro Ser Val Ser Gly Ala
            20                  25                  30

Pro Gly Gln Arg Val Thr Ile Ser Cys Thr Gly Ser Ser Ser Asn Ile
        35                  40                  45

Gly Ala Gly Tyr Asp Val His Trp Tyr Gln Gln Leu Pro Gly Thr Ala
    50                  55                  60

Pro Lys Leu Leu Ile Tyr Gly Asn Ser Asn Arg Pro Ser Gly Val Pro
65                  70                  75                  80

Asp Arg Phe Ser Gly Ser Lys Ser Gly Thr Ser Ala Ser Leu Ala Ile
                85                  90                  95

Thr Gly Leu Gln Ala Glu Asp Glu Ala
            100                 105


<210> SEQ ID NO 344
<211> LENGTH: 105
```

<212> TYPE: PRT
<213> ORGANISM: Homo sapiens

<400> SEQUENCE: 344

Met Ala Trp Ser Pro Leu Leu Leu Thr Leu Leu Ala His Cys Thr Gly
1 5 10 15

Ser Trp Ala Gln Ser Ala Leu Thr Gln Pro Arg Ser Val Ser Gly Ser
20 25 30

Pro Gly Gln Ser Val Thr Ile Ser Cys Thr Gly Thr Ser Ser Asp Val
35 40 45

Gly Gly Tyr Asn Tyr Val Ser Trp Tyr Gln Gln His Pro Gly Lys Ala
50 55 60

Pro Lys Leu Met Ile Tyr Asp Val Ser Lys Arg Pro Ser Gly Val Pro
65 70 75 80

Asp Arg Phe Ser Gly Ser Lys Ser Gly Asn Thr Ala Ser Leu Thr Ile
85 90 95

Ser Gly Leu Gln Ala Glu Asp Glu Ala
100 105

<210> SEQ ID NO 345
<211> LENGTH: 102
<212> TYPE: PRT
<213> ORGANISM: Homo sapiens

<400> SEQUENCE: 345

Met Ala Trp Thr Val Leu Leu Leu Gly Leu Leu Ser His Cys Thr Gly
1 5 10 15

Ser Val Thr Ser Tyr Val Leu Thr Gln Pro Pro Ser Val Ser Val Ala
20 25 30

Pro Gly Lys Thr Ala Arg Ile Thr Cys Gly Gly Asn Asn Ile Gly Ser
35 40 45

Lys Ser Val His Trp Tyr Gln Gln Lys Pro Gly Gln Ala Pro Val Leu
50 55 60

Val Ile Tyr Tyr Asp Ser Asp Arg Pro Ser Gly Ile Pro Glu Arg Phe
65 70 75 80

Ser Gly Ser Asn Ser Gly Asn Thr Ala Thr Leu Thr Ile Ser Arg Val
85 90 95

Glu Ala Glu Asp Glu Ala
100

<210> SEQ ID NO 346
<211> LENGTH: 320
<212> TYPE: PRT
<213> ORGANISM: Homo sapiens

<400> SEQUENCE: 346

Leu Ala Pro Ser Ser Lys Ser Thr Ser Gly Gly Thr Ala Ala Leu Gly
1 5 10 15

Cys Leu Val Lys Asp Tyr Phe Pro Glu Pro Val Thr Val Ser Trp Asn
20 25 30

Ser Gly Ala Leu Thr Ser Gly Val His Thr Phe Pro Ala Val Leu Gln
35 40 45

Ser Ser Gly Leu Tyr Ser Leu Ser Ser Val Val Thr Val Pro Ser Ser
50 55 60

Ser Leu Gly Thr Gln Thr Tyr Ile Cys Asn Val Asn His Lys Pro Ser
65 70 75 80

Asn Thr Lys Val Asp Lys Lys Val Glu Pro Lys Ser Cys Asp Lys Thr
85 90 95

His Thr Cys Pro Pro Cys Pro Ala Pro Glu Leu Leu Gly Gly Pro Ser
100 105 110

Val Phe Leu Phe Pro Pro Lys Pro Lys Asp Thr Leu Met Ile Ser Arg
115 120 125

Thr Pro Glu Val Thr Cys Val Val Val Asp Val Ser His Glu Asp Pro
130 135 140

Glu Val Lys Phe Asn Trp Tyr Val Asp Gly Val Glu Val His Asn Ala
145 150 155 160

Lys Thr Lys Pro Arg Glu Glu Gln Tyr Asn Ser Thr Tyr Arg Val Val
165 170 175

Ser Val Leu Thr Val Leu His Gln Asp Trp Leu Asn Gly Lys Glu Tyr
180 185 190

Lys Cys Lys Val Ser Asn Lys Ala Leu Pro Ala Pro Ile Glu Lys Thr
195 200 205

Ile Ser Lys Ala Lys Gly Gln Pro Arg Glu Pro Gln Val Tyr Thr Leu
210 215 220

Pro Pro Ser Arg Asp Glu Leu Thr Lys Asn Gln Val Ser Leu Thr Cys
225 230 235 240

Leu Val Lys Gly Phe Tyr Pro Ser Asp Ile Ala Val Glu Trp Glu Ser
245 250 255

Asn Gly Gln Pro Glu Asn Asn Tyr Lys Thr Thr Pro Pro Val Leu Asp
260 265 270

Ser Asp Gly Ser Phe Phe Leu Tyr Ser Lys Leu Thr Val Asp Lys Ser
275 280 285

Arg Trp Gln Gln Gly Asn Val Phe Ser Cys Ser Val Met His Glu Ala
290 295 300

Leu His Asn His Tyr Thr Gln Lys Ser Leu Ser Leu Ser Pro Gly Lys
305 310 315 320

<210> SEQ ID NO 347
<211> LENGTH: 91
<212> TYPE: PRT
<213> ORGANISM: Homo sapiens

<400> SEQUENCE: 347

Gln Leu Lys Ser Gly Thr Ala Ser Val Val Cys Leu Leu Asn Asn Phe
1 5 10 15

Tyr Pro Arg Glu Ala Lys Val Gln Trp Lys Val Asp Asn Ala Leu Gln
20 25 30

Ser Gly Asn Ser Gln Glu Ser Val Thr Glu Gln Asp Ser Lys Asp Ser
35 40 45

Thr Tyr Ser Leu Ser Ser Thr Leu Thr Leu Ser Lys Ala Asp Tyr Glu
50 55 60

Lys His Lys Val Tyr Ala Cys Glu Val Thr His Gln Gly Leu Ser Ser
65 70 75 80

Pro Val Thr Lys Ser Phe Asn Arg Gly Glu Cys
85 90

<210> SEQ ID NO 348
<211> LENGTH: 97
<212> TYPE: PRT
<213> ORGANISM: Homo sapiens

<400> SEQUENCE: 348

Thr Leu Phe Pro Pro Ser Ser Glu Glu Leu Gln Ala Asn Lys Ala Thr
1 5 10 15

```
Leu Val Cys Leu Ile Ser Asp Phe Tyr Pro Gly Ala Val Thr Val Ala
            20                  25                  30

Trp Lys Ala Asp Ser Ser Pro Val Lys Ala Gly Val Glu Thr Thr Thr
        35                  40                  45

Pro Ser Lys Gln Ser Asn Asn Lys Tyr Ala Ala Ser Ser Tyr Leu Ser
    50                  55                  60

Leu Thr Pro Glu Gln Trp Lys Ser His Lys Ser Tyr Ser Cys Gln Val
65                  70                  75                  80

Thr His Glu Gly Ser Thr Val Glu Lys Thr Val Ala Pro Thr Glu Cys
                85                  90                  95

Ser


<210> SEQ ID NO 349
<211> LENGTH: 75
<212> TYPE: PRT
<213> ORGANISM: Homo sapiens

<400> SEQUENCE: 349

Leu Glu Pro Pro Pro Ser Thr Val Ser Asn Met Ala Thr Val Ala Val
1               5                   10                  15

Leu Val Val Leu Gly Ala Ala Ile Val Thr Gly Ala Val Val Ala Phe
            20                  25                  30

Val Met Lys Met Arg Arg Arg Asn Thr Gly Gly Lys Gly Gly Asp Tyr
        35                  40                  45

Ala Leu Ala Pro Gly Ser Gln Thr Ser Asp Leu Ser Leu Pro Asp Cys
    50                  55                  60

Lys Val Met Val His Asp Pro His Ser Leu Ala
65                  70                  75


<210> SEQ ID NO 350
<211> LENGTH: 6
<212> TYPE: DNA
<213> ORGANISM: Artificial Sequence
<220> FEATURE:
<223> OTHER INFORMATION: Synthetic oligonucleotide

<400> SEQUENCE: 350

aacgtt                                                                  6


<210> SEQ ID NO 351
<211> LENGTH: 8
<212> TYPE: DNA
<213> ORGANISM: Artificial Sequence
<220> FEATURE:
<223> OTHER INFORMATION: Synthetic oligonucleotide

<400> SEQUENCE: 351

ggcgcgcc                                                                8


<210> SEQ ID NO 352
<211> LENGTH: 6
<212> TYPE: DNA
<213> ORGANISM: Artificial Sequence
<220> FEATURE:
<223> OTHER INFORMATION: Synthetic oligonucleotide

<400> SEQUENCE: 352

gaagac                                                                  6


<210> SEQ ID NO 353
<211> LENGTH: 6
<212> TYPE: DNA
```

<213> ORGANISM: Artificial Sequence
<220> FEATURE:
<223> OTHER INFORMATION: Synthetic oligonucleotide

<400> SEQUENCE: 353 gtcttc 6

<210> SEQ ID NO 354
<211> LENGTH: 6
<212> TYPE: DNA
<213> ORGANISM: Artificial Sequence
<220> FEATURE:
<223> OTHER INFORMATION: Synthetic oligonucleotide

<400> SEQUENCE: 354 cgtctc 6

<210> SEQ ID NO 355
<211> LENGTH: 6
<212> TYPE: DNA
<213> ORGANISM: Artificial Sequence
<220> FEATURE:
<223> OTHER INFORMATION: Synthetic oligonucleotide

<400> SEQUENCE: 355 gagacg 6

<210> SEQ ID NO 356
<211> LENGTH: 6
<212> TYPE: DNA
<213> ORGANISM: Artificial Sequence
<220> FEATURE:
<223> OTHER INFORMATION: Synthetic oligonucleotide

<400> SEQUENCE: 356 cggccg 6

<210> SEQ ID NO 357
<211> LENGTH: 8
<212> TYPE: DNA
<213> ORGANISM: Artificial Sequence
<220> FEATURE:
<223> OTHER INFORMATION: Synthetic oligonucleotide

<400> SEQUENCE: 357 ggccggcc 8

<210> SEQ ID NO 358
<211> LENGTH: 6
<212> TYPE: DNA
<213> ORGANISM: Artificial Sequence
<220> FEATURE:
<223> OTHER INFORMATION: Synthetic oligonucleotide

<400> SEQUENCE: 358 caattg 6

<210> SEQ ID NO 359
<211> LENGTH: 6
<212> TYPE: DNA
<213> ORGANISM: Artificial Sequence
<220> FEATURE:
<223> OTHER INFORMATION: Synthetic oligonucleotide

<400> SEQUENCE: 359 gctagc 6

<210> SEQ ID NO 360
<211> LENGTH: 8
<212> TYPE: DNA
<213> ORGANISM: Artificial Sequence
<220> FEATURE:
<223> OTHER INFORMATION: Synthetic oligonucleotide

<400> SEQUENCE: 360 cctgcagg 8

<210> SEQ ID NO 361
<211> LENGTH: 8
<212> TYPE: DNA
<213> ORGANISM: Artificial Sequence
<220> FEATURE:
<223> OTHER INFORMATION: Synthetic oligonucleotide

<400> SEQUENCE: 361 crccggyg 8

<210> SEQ ID NO 362
<211> LENGTH: 1570
<212> TYPE: DNA
<213> ORGANISM: Artificial Sequence
<220> FEATURE:
<223> OTHER INFORMATION: Synthetic construct

<400> SEQUENCE: 362
caccggtgcc accatggact ggacctggag gatcctcttc ttggtggcag cagccacagg 60
agcccactcc caggttcagc tggtgcagtc tggggctgag gtgaagaagc ctggggcctc 120
agtgaaggtc tcctgcaagg cttctggata caccttcacc ggctactata tgcactgggt 180
tcgacaggcc cctggacaag ggcttgagtg gatgggacgg atcaacccta acagtggtgg 240
cacaaactat gcacagaagt ttcagggcag agttaccagt accagggaca cgtccatcag 300
cacagcctac atggaactaa gcaggctgag atcagacgac acggccgtgt attactgtgc 360
agagctagca ccctcctcca agagcacctc tgggggcaca gcggccctgg gctgcctggt 420
caaggactac ttccccgaac ctgtgacggt gtcgtggaac tcaggcgccc tgaccagcgg 480
cgtgcacacc ttcccggctg tcctacagtc ctcaggactc tactccctca gcagcgtggt 540
gacagtgccc tccagcagct tgggcaccca gacctacatc tgcaacgtga atcacaagcc 600
cagcaacacc aaggtggaca agaaagttga gcccaaatct tgtgacaaaa ctcacacatg 660
cccaccgtgc ccagcacctg aactcctggg gggaccgtca gtcttcctct tcccccccaaa 720 acccaaggac accctcatga tctcccggac ccctgaggtc acatgcgtgg tggtggacgt 780
gagccacgag gaccctgagg tcaagttcaa ctggtacgtg gacggcgtgg aggtgcataa 840
tgccaagaca aagccgcggg aggagcagta caacagcacg taccgggtgg tcagcgtcct 900
caccgtcctg caccaggact ggctgaatgg caaggagtac aagtgcaagg tctccaacaa 960
agccctccca gcccccatcg agaaaaccat ctccaaagcc aaagggcagc cccgagaacc 1020
acaggtgtac accctgcccc catcccggga tgagctgacc aagaaccagg tcagcctgac 1080
ctgcctggtc aaaggcttct atcccagcga catcgccgtg gagtgggaga gcaatgggca 1140
gccggagaac aactacaaga ccacgcctcc cgtgctggac tccgacggct ccttcttcct 1200
ctacagcaag ctcaccgtgg acaagagcag gtggcagcag gggaacgtct tctcatgctc 1260
cgtgatgcat gaggctctgc acaaccacta cacgcagaag agcctctccc tgtctccggg 1320
taaactcgag cctcctccat ccactgtctc caacatggcg accgttgctg ttctggttgt 1380
ccttggagct gcaatagtca ctggagctgt ggtggctttt gtgatgaaga tgagaaggag 1440
aaacacaggt ggaaaaggag gggactatgc tctggctcca ggctcccaga cctctgatct 1500
gtctctccca gattgtaaag tgatggttca tgaccctcat tctctagcgt gaggccggcc 1560
aaggcgcgcc 1570

<210> SEQ ID NO 363
<211> LENGTH: 347
<212> TYPE: DNA
<213> ORGANISM: Artificial Sequence
<220> FEATURE:
<223> OTHER INFORMATION: Synthetic construct

<400> SEQUENCE: 363
caccggtgcc accatggact ggacctggag gttcctcttt gtggtggcag cagctacagg 60
tgtccagtcc caggtgcagc tggttcagtc tggggctgag gtgaagaagc ctgggtcctc 120
ggtgaaggtc tcctgcaagg cttctggagg caccttcagc agctatgcta tcagctgggt 180
gcgacaggcc cctggacaag ggcttgagtg gatgggaggg atcatcccta tctttggtac 240
agcaaactac gcacagaagt tccagggcag agtcacgatt accgctgacg aatccacgag 300
cacagcctac atggaactaa gcagcctgag atcagaggac acggccg 347

<210> SEQ ID NO 364
<211> LENGTH: 347
<212> TYPE: DNA
<213> ORGANISM: Artificial Sequence
<220> FEATURE:
<223> OTHER INFORMATION: Synthetic construct

<400> SEQUENCE: 364
caccggtgcc accatggaat tgggactaag ctgggttttc cttgttgcta ttttagaagg 60
tgtccagtgt gaggtgcagc tggtggagtc tgggggaggc ttggtccagc ctggggggtc 120
cctgagactc tcctgtgcag cctctggatt cacctttagt agctattgga tgagctgggt 180
ccgccaggct ccagggaagg ggctggagtg ggtggccaac ataaagcaag atggaagtga 240
gaaatactat gtggactctg tgaagggccg attcaccatc tccagagaca acgccaagaa 300
ctcactgtat ctgcaaatga acagcctgag agccgaggac acggccg 347

<210> SEQ ID NO 365
<211> LENGTH: 347
<212> TYPE: DNA
<213> ORGANISM: Artificial Sequence
<220> FEATURE:
<223> OTHER INFORMATION: Synthetic construct

<400> SEQUENCE: 365
caccggtgcc accatggagt ttgggctgag ctggcttttt cttgtggcta ttttaaaagg 60
tgtccagtgt gaggtgcagc tgttggagtc tgggggaggc ttggtacagc ctggggggtc 120
cctgagactc tcctgtgcag cctctggatt cacctttagc agctatgcca tgagctgggt 180
ccgccaggct ccagggaagg ggctggagtg ggtctcagct attagtggta gtggtggtag 240
cacatactac gcagactccg tgaagggccg gttcaccatc tccagagaca attccaagaa 300
cacgctgtat ctgcaaatga acagcctgag agccgaggac acggccg 347

<210> SEQ ID NO 366
<211> LENGTH: 347
<212> TYPE: DNA
<213> ORGANISM: Artificial Sequence
<220> FEATURE:

<223> OTHER INFORMATION: Synthetic construct

<400> SEQUENCE: 366
caccggtgcc accatggagt ttggactaag ctgggttttc ctcgttgctc ttttaagagg 60
tgtccagtgt caggtgcagc tggtggagtc tgggggaggc gtggtccagc ctgggaggtc 120
cctgagactc tcctgtgcag cgtctggatt caccttcagt agctatgcta tgcactgggt 180
ccgccaggct ccaggcaagg ggctggagtg ggtggcagtt atatcatatg atggaagcaa 240
taaatactac gcagactccg tgaagggccg attcaccatc tccagagaca attccaagaa 300
cacgctgtat ctgcaaatga acagcctgag agctgaggac acggccg 347

<210> SEQ ID NO 367
<211> LENGTH: 344
<212> TYPE: DNA
<213> ORGANISM: Artificial Sequence
<220> FEATURE:
<223> OTHER INFORMATION: Synthetic construct

<400> SEQUENCE: 367
caccggtgcc accatgaaac acctgtggtt cttcctcctc ctggtggcag ctcccagatg 60
ggtcctgtcc caggtgcagc tacaacagtg gggcgcagga ctgttgaagc cttcggagac 120
cctgtccctc acctgcgctg tctatggtgg gtccttcagt ggttactact ggagctggat 180
ccgccagccc ccagggaagg ggctggagtg gattggggaa atcaatcata gtggaagcac 240
caactacaac ccgtccctca agagtcgagt caccatatca gtagacacgt ccaagaacca 300
gttctccctg aagctgagtt ctgtgaccgc tgcggacacg gccg 344

<210> SEQ ID NO 368
<211> LENGTH: 344
<212> TYPE: DNA
<213> ORGANISM: Artificial Sequence
<220> FEATURE:
<223> OTHER INFORMATION: Synthetic construct

<400> SEQUENCE: 368
caccggtgcc accatgaaac atctgtggtt cttccttctc ctggtggcag ctcccagatg 60
ggtcctgtcc caggtgcagc tgcaggagtc gggcccagga ctggtgaagc cttcggagac 120
cctgtccctc acctgcactg tctctggtgg ctccatcagt agttactact ggagctggat 180
ccggcagccc ccagggaagg gactggagtg gattgggtat atctattaca gtgggagcac 240
caactacaac ccctccctca agagtcgagt caccatatca gtagacacgt ccaagaacca 300
gttctccctg aagctgagtt ctgtgaccgc tgcggacacg gccg 344

<210> SEQ ID NO 369
<211> LENGTH: 347
<212> TYPE: DNA
<213> ORGANISM: Artificial Sequence
<220> FEATURE:
<223> OTHER INFORMATION: Synthetic construct

<400> SEQUENCE: 369
caccggtgcc accatggggt caaccgccat cctcgccctc ctcctggctg ttctccaagg 60
agtctgttcc gaggtgcagc tggttcagtc tggagcagag gtgaaaaagc ccggggagtc 120
tctgaaaatc tcctgtaagg gttctggata cagctttacc agctactgga tcggctgggt 180
gcgccagatg cccgggaaag gcctggagtg gatggggatc atctatcctg gtgactctga 240
taccagatac agcccgtcct tccaaggcca agttaccatc tcagccgaca agtccatcag 300
caccgcctac ctgcagtgga gcagcctgaa ggcctcggac acggccg 347

<210> SEQ ID NO 370
<211> LENGTH: 359
<212> TYPE: DNA
<213> ORGANISM: Artificial Sequence
<220> FEATURE:
<223> OTHER INFORMATION: Synthetic construct

<400> SEQUENCE: 370
caccggtgcc accatgtctg tctccttcct catcttcctg cccgtgctgg gcctcccatg 60
gggtgtcctg tcacaggtac agctgcagca gtcaggtcca ggactggtga agccctcgca 120
gaccctctca ctcacctgtg ccatctccgg ggacagtgtc tctagcaaca gtgctgcttg 180
gaactggatc aggcagtccc catcgagagg ccttgagtgg ctgggaagga catactacag 240
gtccaagtgg tataatgatt atgcagtatc tgtgaaaagt cgaataacca tcaacccaga 300
cacatccaag aaccagttct ccctgcagct gaactctgtg actcccgagg acacggccg 359

<210> SEQ ID NO 371
<211> LENGTH: 650
<212> TYPE: DNA
<213> ORGANISM: Artificial Sequence
<220> FEATURE:
<223> OTHER INFORMATION: Synthetic construct

<400> SEQUENCE: 371
cctgcaggcc accatggtgt tgcagaccca ggtcttcatt tctctgttgc tctggatctc 60
tggtgcctac ggggacatcg tgatgaccca gtctccagac tccctggctg tgtctctggg 120
cgagagggcc accatcaact gcaagtccag ccagagtgtt ttatacagct ccaacaataa 180
gaactactta gcttggtacc agcagaaacc aggacagcct cctaagctgc tcatttactg 240
ggcatctacc cgggaatccg gggtccctga ccgattcagt ggcagcgggt ctgggacaga 300
tttcactctc accatcagca gcctacaggc tgaagatgtg gcagtgtatt agagacgtgt 360
atttaccaat tgaaatctgg aactgcctct gttgtgtgcc tgctgaataa cttctatccc 420
agagaggcca aagtacagtg gaaggtggat aacgccctcc aatcgggtaa ctcccaggag 480
agtgtcacag agcaggacag caaggacagc acctacagcc tcagcagcac cctgacgctg 540
agcaaagcag actacgagaa acacaaagtc tacgcctgcg aagtcaccca tcagggcctc 600
agctcgcccg tcacaaagag cttcaacagg ggagagtgtt gaggcgcgcc 650

<210> SEQ ID NO 372
<211> LENGTH: 342
<212> TYPE: DNA
<213> ORGANISM: Artificial Sequence
<220> FEATURE:
<223> OTHER INFORMATION: Synthetic construct

<400> SEQUENCE: 372
cctgcaggcc accatggaaa ccccagcgca gcttctcttc ctcctgctac tctggctccc 60
agataccacc ggagaaattg tgttgacgca gtctccaggc accctgtctt tgtctccagg 120
ggaaagagcc accctctctt gcagggccag tcagagtgtt agcagcagct acttagcctg 180
gtaccagcag aaacctggcc aggctcccag gctcctcatc tatggtgcat ccagcagggc 240
cactggcatc ccagacaggt tcagtggtag tgggtctggg acagacttca ctctcaccat 300
cagcagactg gagcctgaag attttgcagt gtattagaga cg 342

<210> SEQ ID NO 373

<211> LENGTH: 354
<212> TYPE: DNA
<213> ORGANISM: Artificial Sequence
<220> FEATURE:
<223> OTHER INFORMATION: Synthetic construct

<400> SEQUENCE: 373
cctgcaggcc accatgaggc tccctgccca gctcctgggg ctgctaatgc tctgggtccc 60
aggatccagt ggggatgttg tgatgactca gtctccactc tccctgcccg tcacccttgg 120
acagccggcc tccatctctt gcaggtctag tcaaagcctc gtatacagtg atggaaacac 180
ctacttgaat tggtttcagc agaggccagg ccaatctcca aggcgcctaa tttataaggt 240
ttctaactgg gactctgggg tcccagacag attcagcggt agtgggtcag gcactgattt 300
cacactgaaa atcagcaggg tggaggctga ggatgttgca gtgtattaga gacg 354

<210> SEQ ID NO 374
<211> LENGTH: 345
<212> TYPE: DNA
<213> ORGANISM: Artificial Sequence
<220> FEATURE:
<223> OTHER INFORMATION: Synthetic construct

<400> SEQUENCE: 374
cctgcaggcc accatggaca tgagggtccc cgcccagctc ctggggctcc tgctactctg 60
gctccgaggt gccagatgtg acatccagat gacccagtct ccatcctccc tgtctgcatc 120
tgtaggagac agagtcacca tcacttgccg ggcaagtcag agcattagca gctatttaaa 180
ttggtatcag cagaaaccag ggaaagcccc taagctcctg atctatgctg catccagttt 240
gcaaagtggg gtcccatcaa ggttcagtgg tagtggatct gggacagatt tcactctcac 300
catcagcagt ctgcaacctg aagattttgc agtgtattag agacg 345

<210> SEQ ID NO 375
<211> LENGTH: 345
<212> TYPE: DNA
<213> ORGANISM: Artificial Sequence
<220> FEATURE:
<223> OTHER INFORMATION: Synthetic construct

<400> SEQUENCE: 375
cctgcaggcc accatggaca tgagggtccc tgcccagctc ctggggctcc tgcagctctg 60
gctctcaggt gccagatgtg acatccagat gacccagtct ccatcctccc tgtctgcatc 120
tgtaggagac agagtcacca tcacttgcca ggcgagtcag gacattagca actatttaaa 180
ttggtatcag cagaaaccag ggaaagcccc taagctcctg atctacgatg catccaattt 240
ggaaacaggg gtcccatcaa ggttcagtgg aagtggatct gggacagatt ttactttcac 300
catcagcagc ctgcagcctg aagatattgc agtgtattag agacg 345

<210> SEQ ID NO 376
<211> LENGTH: 639
<212> TYPE: DNA
<213> ORGANISM: Artificial Sequence
<220> FEATURE:
<223> OTHER INFORMATION: Synthetic construct

<400> SEQUENCE: 376
cctgcaggcc accatggcct ggtctcctct cctcctcact ctcctcgctc actgcacagg 60
gtcctgggcc cagtctgtgc tgacgcagcc gccctcagtg tctggggccc cagggcagag 120
agttaccatc tcctgcactg ggagcagctc caacatcggg gcaggttatg atgtacactg 180

-continued gtaccagcag cttccaggaa cagcccccaa actcctcatc tatggtaaca gcaatcggcc 240
ctcaggggtc cctgaccgat tctctggctc caagtctggc acctcagcct ccctggccat 300
cactgggctc caggctgaag acgaggctga ttattaaacg ttgttcccac cctcctctga 360
ggagcttcaa gccaacaagg ccacactggt gtgtctcata agtgacttct acccgggagc 420
cgtgacagtt gcctggaagg cagatagcag ccccgtcaag gcgggggtgg agaccaccac 480
accctccaaa caaagcaaca acaagtacgc ggccagcagc tacctgagcc tgacgcctga 540
gcagtggaag tcccacaaaa gctacagctg ccaggtcacg catgaaggga gcaccgtgga 600
gaagacagtt gcccctacgg aatgttcatg aggcgcgcc 639

<210> SEQ ID NO 377
<211> LENGTH: 328
<212> TYPE: DNA
<213> ORGANISM: Artificial Sequence
<220> FEATURE:
<223> OTHER INFORMATION: Synthetic construct

<400> SEQUENCE: 377
cctgcaggcc accatggcct ggtctcctct cctcctcact ctcctcgctc actgcacagg 60
gtcctgggcc cagtctgccc tgactcagcc tcgctcagtg tccgggtctc ctggacagtc 120
agtcaccatc tcctgcactg gaaccagcag tgatgttggt ggttataact atgtctcctg 180
gtaccaacag cacccaggca aagcccccaa actcatgatt tatgatgtca gtaagcggcc 240
ctcaggggtc cctgatcgct tctctggctc caagtctggc aacacggcct ccctgaccat 300
ctctgggctc caggctgaag acgaggct 328

<210> SEQ ID NO 378
<211> LENGTH: 319
<212> TYPE: DNA
<213> ORGANISM: Artificial Sequence
<220> FEATURE:
<223> OTHER INFORMATION: Synthetic construct

<400> SEQUENCE: 378
cctgcaggcc accatggcct ggaccgttct cctcctcggc ctcctctctc actgcacagg 60
ctctgtgacc tcctatgtgc tgactcagcc accctcagtg tcagtggccc caggaaagac 120
ggccaggatt acctgtgggg gaaacaacat tggaagtaaa agtgtgcact ggtaccagca 180
gaagccaggc caggcccctg tgctggtcat ctattatgat agcgaccggc cctcagggat 240
ccctgagcga ttctctggct ccaactctgg gaacacggcc accctgacca tcagcagggt 300
cgaagccgaa gacgaggct 319

<210> SEQ ID NO 379
<211> LENGTH: 328
<212> TYPE: DNA
<213> ORGANISM: Artificial Sequence
<220> FEATURE:
<223> OTHER INFORMATION: Synthetic construct

<400> SEQUENCE: 379
cctgcaggcc accatggcct ggactcctct ctttctgttc ctcctcactt gctgcccagg 60
gtccaattct cagactgtgg tgactcagga gccctcactg actgtgtccc caggagggac 120
agtcactctc acctgtgctt ccagcactgg agcagtcacc agtggttact atccaaactg 180
gttccagcag aaacctggac aagcacccag ggcactgatt tatagtacaa gcaacaaaca 240
ctcctggacc cctgcccggt tctcaggctc cctccttggg ggcaaagctg ccctgacact 300
gtcaggtgtg cagcctgaag acgaggct 328

<210> SEQ ID NO 380
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 380
ggaatccggc cgtgtattac tgtgcaaga 29

<210> SEQ ID NO 381
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 381
ggaatccggc cgtgtattac tgtgcgaaa 29

<210> SEQ ID NO 382
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 382
ggaatccggc cgtgtattac tgtgcgaga 29

<210> SEQ ID NO 383
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 383
ggaatccggc cgtatattac tgtgcgaaa 29

<210> SEQ ID NO 384
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 384
ggaatcggct agcgggaaga cggatgggcc cttg 34

<210> SEQ ID NO 385
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 385
ggaatcggct agcgggaaga ccgatgggcc cttg 34

<210> SEQ ID NO 386
<211> LENGTH: 33
<212> TYPE: DNA
<213> ORGANISM: Artificial Sequence
<220> FEATURE:

<223> OTHER INFORMATION: Synthetic oligonucleotide

<400> SEQUENCE: 386
ggaatcggct agcgggaaaa gggttggggc gga 33

<210> SEQ ID NO 387
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 387
gaagtagtcc ctgaccaggc 20

<210> SEQ ID NO 388
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 388
aagtcctgtg cgaggcagc 19

<210> SEQ ID NO 389
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 389
ggaatccgtc tcgtattact gtcagcaata ttatag 36

<210> SEQ ID NO 390
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 390
ggaatccgtc tcgtattact gtcagcagta tggtag 36

<210> SEQ ID NO 391
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 391
ggaatccgtc tcgtattact gcatgcaagg tacaca 36

<210> SEQ ID NO 392
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 392
ggaatccgtc tcgtattact gtcaacagag ttacag 36

<210> SEQ ID NO 393

<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 393
ggaatccgtc tcgtattact gtcaacagta tgataa 36

<210> SEQ ID NO 394
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 394
ggaatccaat tgctcatcag atggcgggaa g 31

<210> SEQ ID NO 395
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 395
ggcctctctg ggatagaag 19

<210> SEQ ID NO 396
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 396
ggaatcgaag acgaggctga ttattactgc cagtcct 37

<210> SEQ ID NO 397
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 397
ggaatcgaag acgaggctga ttattactgc tgctcat 37

<210> SEQ ID NO 398
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 398
ggaatcgaag acgaggctga ctattactgt caggtgt 37

<210> SEQ ID NO 399
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 399
ggaatcgaag acgaggctga gtattactgc ctgctct 37

<210> SEQ ID NO 400
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 400
ggaatcaacg ttaccgtggg gttggccttg 30

<210> SEQ ID NO 401
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 401
ggaatcaacg ttaccgaggg ggcagccttg 30

<210> SEQ ID NO 402
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 402
ggaatcaacg ttaccgatgg ggcagccttg 30

<210> SEQ ID NO 403
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 403
gctcccgggt agaagtcac 19

<210> SEQ ID NO 404
<211> LENGTH: 6
<212> TYPE: DNA
<213> ORGANISM: Artificial Sequence
<220> FEATURE:
<223> OTHER INFORMATION: Synthetic oligonucleotide

<400> SEQUENCE: 404 agctac 6

<210> SEQ ID NO 405
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 405 gtcgtcgtc 9

<210> SEQ ID NO 406
<211> LENGTH: 30
<212> TYPE: DNA
<213> ORGANISM: Artificial Sequence
<220> FEATURE:

<223> OTHER INFORMATION: Synthetic oligonucleotide

<400> SEQUENCE: 406
gtcgtcgtca gctacagcta cgtcgtcgtc 30

<210> SEQ ID NO 407
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 407
gtcgtcgtcc agctacagct agtcgtcgtc 30

<210> SEQ ID NO 408
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 408
gtcgtcgtca cagctacagc tgtcgtcgtc 30

<210> SEQ ID NO 409
<211> LENGTH: 1419
<212> TYPE: DNA
<213> ORGANISM: Artificial Sequence
<220> FEATURE:
<223> OTHER INFORMATION: Synthetic construct

<400> SEQUENCE: 409
atgaaacacc tgtggttctt cctcctcctg gtggcagctc ccagatgggt cctgtcccag 60
gtgcagctac aacagtgggg cgcaggactg ttgaagcctt cggagaccct gtccctcacc 120
tgcgctgtct atggtgggtc cttcagtggt tactactgga gctggatccg ccagccccca 180
gggaaggggc tggagtggat tggggaaatc aatcatagtg gaagcaccaa ctacaacccg 240
tccctcaaga gtcgagtcac catatcagta gacacgtcca agaaccagtt ctccctgaag 300
ctgagctctg tgaccgccgc ggacacggcc gtgtattact gtgcgagagt cgtcgtcagc 360
tacagctacg tcgtcgtcgc tgaatacttc cagcactggg gccagggcac cctggtcacc 420
gtctcctcag cctccaccaa gggcccatcg gtcttccccc tagcaccctc ctccaagagc 480
acctctgggg gcacagcggc cctgggctgc ctggtcaagg actacttccc cgaaccggtg 540
acggtgtcgt ggaactcagg cgccctgacc agcggcgtgc acaccttccc ggctgtcctt 600
cagtcctcag gactctactc cctcagcagc gtggtgaccg tgccctccag cagcttgggc 660
acccagacct acatctgcaa cgtgaatcac aagcccagca acaccaaggt ggacaagaaa 720
gttgagccca aatcttgtga caaaactcac acatgcccac cgtgcccagc acctgaactc 780
ctggggggac cgtcagtctt cctcttcccc ccaaaaccca aggacaccct catgatctcc 840
cggacccctg aggtcacatg cgtggtggtg gacgtgagcc acgaagaccc tgaggtcaag 900
ttcaactggt acgtggacgg cgtggaggtg cataatgcca agacaaagcc gcgggaggag 960
cagtacaaca gcacgtaccg ggtggtcagc gtcctcaccg tcctgcacca ggactggctg 1020
aatggcaagg agtacaagtg caaggtctcc aacaaagccc tcccagcccc catcgagaaa 1080
accatctcca aagccaaagg gcagccccga gaaccacagg tgtacaccct gcccccatcc 1140
cgggatgagc tgaccaagaa ccaggtcagc ctgacctgcc tggtcaaagg cttctatccc 1200
agcgacatcg ccgtggagtg ggagagcaat gggcagccgg agaacaacta caagaccacg 1260
cctcccgtgc tggactccga cggctccttc ttcctataca gcaagctcac cgtggacaag 1320
agcaggtggc agcaggggaa cgtcttctca tgctccgtga tgcatgaggc tctgcacaac 1380
cactacacgc agaagagcct ctccctgtct ccgggtaaa 1419

<210> SEQ ID NO 410
<211> LENGTH: 144
<212> TYPE: DNA
<213> ORGANISM: Artificial Sequence
<220> FEATURE:
<223> OTHER INFORMATION: Synthetic oligonucleotide

<400> SEQUENCE: 410
acacggccgt gtattactgt gcgagagtcg tcgtcagcta cagctacgtc gtcgtcgctg 60
aatacttcca gcactggggc cagggcaccc tggtcaccgt ctcctcagcc tccaccaagg 120
gcccatcggt cttcccgcta gcac 144

<210> SEQ ID NO 411
<211> LENGTH: 144
<212> TYPE: DNA
<213> ORGANISM: Artificial Sequence
<220> FEATURE:
<223> OTHER INFORMATION: Synthetic oligonucleotide

<400> SEQUENCE: 411
acacggccgt gtattactgt gcgagagtcg tcgtccagct acagctagtc gtcgtcgctg 60
aatacttcca gcactggggc cagggcaccc tggtcaccgt ctcctcagcc tccaccaagg 120
gcccatcggt cttcccgcta gcac 144

<210> SEQ ID NO 412
<211> LENGTH: 144
<212> TYPE: DNA
<213> ORGANISM: Artificial Sequence
<220> FEATURE:
<223> OTHER INFORMATION: Synthetic oligonucleotide

<400> SEQUENCE: 412
acacggccgt gtattactgt gcgagagtcg tcgtcacagc tacagctgtc gtcgtcgctg 60
aatacttcca gcactggggc cagggcaccc tggtcaccgt ctcctcagcc tccaccaagg 120
gcccatcggt cttcccgcta gcac 144

<210> SEQ ID NO 413
<211> LENGTH: 57
<212> TYPE: PRT
<213> ORGANISM: Lactococcus lactis

<400> SEQUENCE: 413

Met Ser Thr Lys Asp Phe Asn Leu Asp Leu Val Ser Val Ser Lys Lys
1               5                   10                  15

Asp Ser Gly Ala Ser Pro Arg Ile Thr Ser Ile Ser Leu Cys Thr Pro
            20                  25                  30

Gly Cys Lys Thr Gly Ala Leu Met Gly Cys Asn Met Lys Thr Ala Thr
        35                  40                  45

Cys His Cys Ser Ile His Val Ser Lys
    50                  55

<210> SEQ ID NO 414
<211> LENGTH: 417
<212> TYPE: PRT

<213> ORGANISM: Lactococcus lactis

<400> SEQUENCE: 414

```
Met Arg Ile Met Met Asn Lys Lys Asn Ile Lys Arg Asn Val Glu Lys
1               5                   10                  15

Ile Ile Ala Gln Trp Asp Glu Arg Thr Arg Lys Asn Lys Glu Asn Phe
            20                  25                  30

Asp Phe Gly Glu Leu Thr Leu Ser Thr Gly Leu Pro Gly Ile Ile Leu
        35                  40                  45

Met Leu Ala Glu Leu Lys Asn Lys Asp Asn Ser Lys Ile Tyr Gln Lys
    50                  55                  60

Lys Ile Asp Asn Tyr Ile Glu Tyr Ile Val Ser Lys Leu Ser Thr Tyr
65                  70                  75                  80

Gly Leu Leu Thr Gly Ser Leu Tyr Ser Gly Ala Ala Gly Ile Ala Leu
                85                  90                  95

Ser Ile Leu His Leu Arg Glu Asp Asp Glu Lys Tyr Lys Asn Leu Leu
            100                 105                 110

Asp Ser Leu Asn Arg Tyr Ile Glu Tyr Phe Val Arg Glu Lys Ile Glu
        115                 120                 125

Gly Phe Asn Leu Glu Asn Ile Thr Pro Pro Asp Tyr Asp Val Ile Glu
    130                 135                 140

Gly Leu Ser Gly Ile Leu Ser Tyr Leu Leu Leu Ile Asn Asp Glu Gln
145                 150                 155                 160

Tyr Asp Asp Leu Lys Ile Leu Ile Ile Asn Phe Leu Ser Asn Leu Thr
                165                 170                 175

Lys Glu Asn Asn Gly Leu Ile Ser Leu Tyr Ile Lys Ser Glu Asn Gln
            180                 185                 190

Met Ser Gln Ser Glu Ser Glu Met Tyr Pro Leu Gly Cys Leu Asn Met
        195                 200                 205

Gly Leu Ala His Gly Leu Ala Gly Val Gly Cys Ile Leu Ala Tyr Ala
    210                 215                 220

His Ile Lys Gly Tyr Ser Asn Glu Ala Ser Leu Ser Ala Leu Gln Lys
225                 230                 235                 240

Ile Ile Phe Ile Tyr Glu Lys Phe Glu Leu Glu Arg Lys Lys Gln Phe
                245                 250                 255

Leu Trp Lys Asp Gly Leu Val Ala Asp Glu Leu Lys Lys Glu Lys Val
            260                 265                 270

Ile Arg Glu Ala Ser Phe Ile Arg Asp Ala Trp Cys Tyr Gly Gly Pro
        275                 280                 285

Gly Ile Ser Leu Leu Tyr Leu Tyr Gly Gly Leu Ala Leu Asp Asn Asp
    290                 295                 300

Tyr Phe Val Asp Lys Ala Glu Lys Ile Leu Glu Ser Ala Met Gln Arg
305                 310                 315                 320

Lys Leu Gly Ile Asp Ser Tyr Met Ile Cys His Gly Tyr Ser Gly Leu
                325                 330                 335

Ile Glu Ile Cys Ser Leu Phe Lys Arg Leu Leu Asn Thr Lys Lys Phe
            340                 345                 350

Asp Ser Tyr Met Glu Glu Phe Asn Val Asn Ser Glu Gln Ile Leu Glu
        355                 360                 365

Glu Tyr Gly Asp Glu Ser Gly Thr Gly Phe Leu Glu Gly Ile Ser Gly
    370                 375                 380

Cys Ile Leu Val Leu Ser Lys Phe Glu Tyr Ser Ile Asn Phe Thr Tyr
385                 390                 395                 400

Trp Arg Gln Ala Leu Leu Leu Phe Asp Asp Phe Leu Lys Gly Gly Lys
```

405 410 415

Arg

<210> SEQ ID NO 415
<211> LENGTH: 993
<212> TYPE: PRT
<213> ORGANISM: Lactococcus lactis

<400> SEQUENCE: 415

Met Ile Lys Ser Ser Phe Lys Ala Gln Pro Phe Leu Val Arg Asn Thr
1 5 10 15

Ile Leu Ser Pro Asn Asp Lys Arg Ser Phe Thr Glu Tyr Thr Gln Val
20 25 30

Ile Glu Thr Val Ser Lys Asn Lys Val Phe Leu Glu Gln Leu Leu Leu
35 40 45

Ala Asn Pro Lys Leu Tyr Asn Val Met Gln Lys Tyr Asn Ala Gly Leu
50 55 60

Leu Lys Lys Lys Arg Val Lys Lys Leu Phe Glu Ser Ile Tyr Lys Tyr
65 70 75 80

Tyr Lys Arg Ser Tyr Leu Arg Ser Thr Pro Phe Gly Leu Phe Ser Glu
85 90 95

Thr Ser Ile Gly Val Phe Ser Lys Ser Ser Gln Tyr Lys Leu Met Gly
100 105 110

Lys Thr Thr Lys Gly Ile Arg Leu Asp Thr Gln Trp Leu Ile Arg Leu
115 120 125

Val His Lys Met Glu Val Asp Phe Ser Lys Lys Leu Ser Phe Thr Arg
130 135 140

Asn Asn Ala Asn Tyr Lys Phe Gly Asp Arg Val Phe Gln Val Tyr Thr
145 150 155 160

Ile Asn Ser Ser Glu Leu Glu Glu Val Asn Ile Lys Tyr Thr Asn Val
165 170 175

Tyr Gln Ile Ile Ser Glu Phe Cys Glu Asn Asp Tyr Gln Lys Tyr Glu
180 185 190

Asp Ile Cys Glu Thr Val Thr Leu Cys Tyr Gly Asp Glu Tyr Arg Glu
195 200 205

Leu Ser Glu Gln Tyr Leu Gly Ser Leu Ile Val Asn His Tyr Leu Ile
210 215 220

Ser Asn Leu Gln Lys Asp Leu Leu Ser Asp Phe Ser Trp Asp Thr Phe
225 230 235 240

Leu Thr Lys Val Glu Ala Ile Asp Glu Asp Lys Lys Tyr Ile Ile Pro
245 250 255

Leu Lys Lys Val Gln Lys Phe Ile Gln Glu Tyr Ser Glu Ile Glu Ile
260 265 270

Gly Glu Gly Ile Glu Lys Leu Lys Glu Ile Tyr Gln Glu Met Ser Gln
275 280 285

Ile Leu Glu Asn Asp Asn Tyr Ile Gln Ile Asp Leu Ile Ser Asp Ser
290 295 300

Glu Ile Asn Phe Asp Val Lys Gln Lys Gln Gln Leu Glu His Leu Ala
305 310 315 320

Glu Phe Leu Gly Asn Thr Thr Lys Ser Val Arg Arg Thr Tyr Leu Asp
325 330 335

Asp Tyr Lys Asp Lys Phe Ile Glu Lys Tyr Gly Val Asp Gln Glu Val
340 345 350

Gln Ile Thr Glu Leu Phe Asp Ser Thr Phe Gly Ile Gly Ala Pro Tyr
355 360 365

```
Asn Tyr Asn His Pro Arg Asn Asp Phe Tyr Glu Ser Glu Pro Ser Thr
    370                 375                 380

Leu Tyr Tyr Ser Glu Glu Glu Arg Glu Lys Tyr Leu Ser Met Tyr Val
385                 390                 395                 400

Glu Ala Val Lys Asn His Asn Val Ile Asn Leu Asp Asp Leu Glu Ser
                405                 410                 415

His Tyr Gln Lys Met Asp Leu Glu Lys Lys Ser Glu Leu Gln Gly Leu
            420                 425                 430

Glu Leu Phe Leu Asn Leu Ala Lys Glu Tyr Glu Lys Asp Ile Phe Ile
        435                 440                 445

Leu Gly Asp Ile Val Gly Asn Asn Asn Leu Gly Gly Ala Ser Gly Arg
    450                 455                 460

Phe Ser Ala Leu Ser Pro Glu Leu Thr Ser Tyr His Arg Thr Ile Val
465                 470                 475                 480

Asp Ser Val Glu Arg Glu Asn Glu Asn Lys Glu Ile Thr Ser Cys Glu
                485                 490                 495

Ile Val Phe Leu Pro Glu Asn Ile Arg His Ala Asn Val Met His Thr
            500                 505                 510

Ser Ile Met Arg Arg Lys Val Leu Pro Phe Phe Thr Ser Thr Ser His
        515                 520                 525

Asn Glu Val Gln Leu Thr Asn Ile Tyr Ile Gly Ile Asp Glu Lys Glu
    530                 535                 540

Lys Phe Tyr Ala Arg Asp Ile Ser Thr Gln Glu Val Leu Lys Phe Tyr
545                 550                 555                 560

Ile Thr Ser Met Tyr Asn Lys Thr Leu Phe Ser Asn Glu Leu Arg Phe
                565                 570                 575

Leu Tyr Glu Ile Ser Leu Asp Asp Lys Phe Gly Asn Leu Pro Trp Glu
            580                 585                 590

Leu Ile Tyr Arg Asp Phe Asp Tyr Ile Pro Arg Leu Val Phe Asp Glu
        595                 600                 605

Ile Val Ile Ser Pro Ala Lys Trp Lys Ile Trp Gly Arg Asp Val Asn
    610                 615                 620

Asn Lys Met Thr Ile Arg Glu Leu Ile Gln Ser Lys Glu Ile Pro Lys
625                 630                 635                 640

Glu Phe Tyr Ile Val Asn Gly Asp Asn Lys Val Tyr Leu Ser Gln Glu
                645                 650                 655

Asn Pro Leu Asp Met Glu Ile Leu Glu Ser Ala Ile Lys Lys Ser Ser
            660                 665                 670

Lys Arg Lys Asp Phe Ile Glu Leu Gln Glu Tyr Phe Glu Asp Glu Asn
        675                 680                 685

Ile Ile Asn Lys Gly Gln Lys Gly Arg Val Ala Asp Val Val Val Pro
    690                 695                 700

Phe Ile Arg Thr Arg Ala Leu Gly Asn Glu Gly Arg Ala Phe Ile Arg
705                 710                 715                 720

Glu Lys Arg Val Ser Val Glu Arg Arg Glu Lys Leu Pro Phe Asn Glu
                725                 730                 735

Trp Leu Tyr Leu Lys Leu Tyr Ile Ser Ile Asn Arg Gln Asn Glu Phe
            740                 745                 750

Leu Leu Ser Tyr Leu Pro Asp Ile Gln Lys Ile Val Ala Asn Leu Gly
        755                 760                 765

Gly Lys Leu Phe Phe Leu Arg Tyr Thr Asp Pro Lys Pro His Ile Arg
    770                 775                 780

Leu Arg Ile Lys Cys Ser Asp Leu Phe Leu Ala Tyr Gly Ser Ile Leu
```

```
785                 790                 795                 800

Glu Ile Leu Lys Arg Ser Gln Lys Asn Arg Ile Met Ser Thr Phe Asp
                805                 810                 815

Ile Ser Ile Tyr Asp Gln Glu Val Glu Arg Tyr Gly Gly Phe Asp Thr
            820                 825                 830

Leu Glu Leu Ser Glu Ala Ile Phe Cys Ala Asp Ser Lys Ile Ile Pro
        835                 840                 845

Asn Leu Leu Thr Leu Ile Lys Asp Thr Asn Asn Asp Trp Lys Val Asp
    850                 855                 860

Asp Val Ser Ile Leu Val Asn Tyr Leu Tyr Leu Lys Cys Phe Phe Gln
865                 870                 875                 880

Asn Asp Asn Lys Lys Ile Leu Asn Phe Leu Asn Leu Val Ser Pro Lys
                885                 890                 895

Lys Val Lys Glu Asn Val Asn Glu Lys Ile Glu His Tyr Leu Lys Leu
            900                 905                 910

Leu Lys Val Asp Asn Leu Gly Asp Gln Ile Phe Tyr Asp Lys Asn Phe
        915                 920                 925

Lys Glu Leu Lys His Ala Ile Lys Asn Leu Phe Leu Lys Met Ile Ala
    930                 935                 940

Gln Asp Phe Glu Leu Gln Lys Val Tyr Ser Ile Ile Asp Ser Ile Ile
945                 950                 955                 960

His Val His Asn Asn Arg Leu Ile Gly Ile Glu Arg Asp Lys Glu Lys
                965                 970                 975

Leu Ile Tyr Tyr Thr Leu Gln Arg Leu Phe Val Ser Glu Glu Tyr Met
            980                 985                 990

Lys


<210> SEQ ID NO 416
<211> LENGTH: 682
<212> TYPE: PRT
<213> ORGANISM: Lactococcus lactis

<400> SEQUENCE: 416

Met Lys Lys Ile Leu Gly Phe Leu Phe Ile Val Cys Ser Leu Gly Leu
1               5                   10                  15

Ser Ala Thr Val His Gly Glu Thr Thr Asn Ser Gln Gln Leu Leu Ser
            20                  25                  30

Asn Asn Ile Asn Thr Glu Leu Ile Asn His Asn Ser Asn Ala Ile Leu
        35                  40                  45

Ser Ser Thr Glu Gly Ser Thr Thr Asp Ser Ile Asn Leu Gly Ala Gln
    50                  55                  60

Ser Pro Ala Val Lys Ser Thr Thr Arg Thr Glu Leu Asp Val Thr Gly
65                  70                  75                  80

Ala Ala Lys Thr Leu Leu Gln Thr Ser Ala Val Gln Lys Glu Met Lys
                85                  90                  95

Val Ser Leu Gln Glu Thr Gln Val Ser Ser Glu Phe Ser Lys Arg Asp
            100                 105                 110

Ser Val Thr Asn Lys Glu Ala Val Pro Val Ser Lys Asp Glu Leu Leu
        115                 120                 125

Glu Gln Ser Glu Val Val Val Ser Thr Ser Ser Ile Gln Lys Asn Lys
    130                 135                 140

Ile Leu Asp Asn Lys Lys Lys Arg Ala Asn Phe Val Thr Ser Ser Pro
145                 150                 155                 160

Leu Ile Lys Glu Lys Pro Ser Asn Ser Lys Asp Ala Ser Gly Val Ile
                165                 170                 175
```

-continued

```
Asp Asn Ser Ala Ser Pro Leu Ser Tyr Arg Lys Ala Lys Glu Val Val
            180                 185                 190

Ser Leu Arg Gln Pro Leu Lys Asn Gln Lys Val Glu Ala Gln Pro Leu
        195                 200                 205

Leu Ile Ser Asn Ser Ser Glu Lys Lys Ala Ser Val Tyr Thr Asn Ser
    210                 215                 220

His Asp Phe Trp Asp Tyr Gln Trp Asp Met Lys Tyr Val Thr Asn Asn
225                 230                 235                 240

Gly Glu Ser Tyr Ala Leu Tyr Gln Pro Ser Lys Lys Ile Ser Val Gly
                245                 250                 255

Ile Ile Asp Ser Gly Ile Met Glu Glu His Pro Asp Leu Ser Asn Ser
            260                 265                 270

Leu Gly Asn Tyr Phe Lys Asn Leu Val Pro Lys Gly Gly Phe Asp Asn
        275                 280                 285

Glu Glu Pro Asp Glu Thr Gly Asn Pro Ser Asp Ile Val Asp Lys Met
    290                 295                 300

Gly His Gly Thr Glu Val Ala Gly Gln Ile Thr Ala Asn Gly Asn Ile
305                 310                 315                 320

Leu Gly Val Ala Pro Gly Ile Thr Val Asn Ile Tyr Arg Val Phe Gly
                325                 330                 335

Glu Asn Leu Ser Lys Ser Glu Trp Val Ala Arg Ala Ile Arg Arg Ala
            340                 345                 350

Ala Asp Asp Gly Asn Lys Val Ile Asn Ile Ser Ala Gly Gln Tyr Leu
        355                 360                 365

Met Ile Ser Gly Ser Tyr Asp Asp Gly Thr Asn Asp Tyr Gln Glu Tyr
    370                 375                 380

Leu Asn Tyr Lys Ser Ala Ile Asn Tyr Ala Thr Ala Lys Gly Ser Ile
385                 390                 395                 400

Val Val Ala Ala Leu Gly Asn Asp Ser Leu Asn Ile Gln Asp Asn Gln
                405                 410                 415

Thr Met Ile Asn Phe Leu Lys Arg Phe Arg Ser Ile Lys Val Pro Gly
            420                 425                 430

Lys Val Val Asp Ala Pro Ser Val Phe Glu Asp Val Ile Ala Val Gly
        435                 440                 445

Gly Ile Asp Gly Tyr Gly Asn Ile Ser Asp Phe Ser Asn Ile Gly Ala
    450                 455                 460

Asp Ala Ile Tyr Ala Pro Ala Gly Thr Thr Ala Asn Phe Lys Lys Tyr
465                 470                 475                 480

Gly Gln Asp Lys Phe Val Ser Gln Gly Tyr Tyr Leu Lys Asp Trp Leu
                485                 490                 495

Phe Thr Thr Ala Asn Thr Gly Trp Tyr Gln Tyr Val Tyr Gly Asn Ser
            500                 505                 510

Phe Ala Thr Pro Lys Val Ser Gly Ala Leu Ala Leu Val Val Asp Lys
        515                 520                 525

Tyr Gly Ile Lys Asn Pro Asn Gln Leu Lys Arg Phe Leu Leu Met Asn
    530                 535                 540

Ser Pro Glu Val Asn Gly Asn Arg Val Leu Asn Ile Val Asp Leu Leu
545                 550                 555                 560

Asn Gly Lys Asn Lys Ala Phe Ser Leu Asp Thr Asp Lys Gly Gln Asp
                565                 570                 575

Asp Ala Ile Asn His Lys Ser Met Glu Asn Leu Lys Glu Ser Arg Asp
            580                 585                 590

Thr Met Lys Gln Glu Gln Asp Lys Glu Ile Gln Arg Asn Thr Asn Asn
```

-continued

```
        595                 600                 605

Asn Phe Ser Ile Lys Asn Asp Phe His Asn Ile Ser Lys Glu Val Ile
    610                 615                 620

Ser Val Asp Tyr Asn Ile Asn Gln Lys Met Ala Asn Asn Arg Asn Ser
625                 630                 635                 640

Arg Gly Ala Val Ser Val Arg Ser Gln Glu Ile Leu Pro Val Thr Gly
                645                 650                 655

Asp Gly Glu Asp Phe Leu Pro Ala Leu Gly Ile Val Cys Ile Ser Ile
            660                 665                 670

Leu Gly Ile Leu Lys Arg Lys Thr Lys Asn
        675                 680


<210> SEQ ID NO 417
<211> LENGTH: 600
<212> TYPE: PRT
<213> ORGANISM: Lactococcus lactis

<400> SEQUENCE: 417

Met Asp Glu Val Lys Glu Phe Thr Ser Lys Gln Phe Phe Tyr Thr Leu
1               5                   10                  15

Leu Thr Leu Pro Ser Thr Leu Lys Leu Ile Phe Gln Leu Glu Lys Arg
            20                  25                  30

Tyr Ala Ile Tyr Leu Ile Val Leu Asn Ala Ile Thr Ala Phe Val Pro
        35                  40                  45

Leu Ala Ser Leu Phe Ile Tyr Gln Asp Leu Ile Asn Ser Val Leu Gly
    50                  55                  60

Ser Gly Arg His Leu Ile Asn Ile Ile Ile Ile Tyr Phe Ile Val Gln
65                  70                  75                  80

Val Ile Thr Thr Val Leu Gly Gln Leu Glu Ser Tyr Val Ser Gly Lys
                85                  90                  95

Phe Asp Met Arg Leu Ser Tyr Ser Ile Asn Met Arg Leu Met Arg Thr
            100                 105                 110

Thr Ser Ser Leu Glu Leu Ser Asp Tyr Glu Gln Ala Asp Met Tyr Asn
        115                 120                 125

Ile Ile Glu Lys Val Thr Gln Asp Ser Thr Tyr Lys Pro Phe Gln Leu
    130                 135                 140

Phe Asn Ala Ile Ile Val Glu Leu Ser Ser Phe Ile Ser Leu Leu Ser
145                 150                 155                 160

Ser Leu Phe Phe Ile Gly Thr Trp Asn Ile Gly Val Ala Ile Leu Leu
                165                 170                 175

Leu Ile Val Pro Val Leu Ser Leu Val Leu Phe Leu Arg Val Gly Gln
            180                 185                 190

Leu Glu Phe Leu Ile Gln Trp Gln Arg Ala Ser Ser Glu Arg Glu Thr
        195                 200                 205

Trp Tyr Ile Val Tyr Leu Leu Thr His Asp Phe Ser Phe Lys Glu Ile
    210                 215                 220

Lys Leu Asn Asn Ile Ser Asn Tyr Phe Ile His Lys Phe Gly Lys Leu
225                 230                 235                 240

Lys Lys Gly Phe Ile Asn Gln Asp Leu Ala Ile Ala Arg Lys Lys Thr
                245                 250                 255

Tyr Phe Asn Ile Phe Leu Asp Phe Ile Leu Asn Leu Ile Asn Ile Leu
            260                 265                 270

Thr Ile Phe Ala Met Ile Leu Ser Val Arg Ala Gly Lys Leu Leu Ile
        275                 280                 285

Gly Asn Leu Val Ser Leu Ile Gln Ala Ile Ser Lys Ile Asn Thr Tyr
```

```
    290                 295                 300

Ser Gln Thr Met Ile Gln Asn Ile Tyr Ile Ile Tyr Asn Thr Ser Leu
305                 310                 315                 320

Phe Met Glu Gln Leu Phe Glu Phe Leu Lys Arg Glu Ser Val Val His
                325                 330                 335

Lys Lys Ile Glu Asp Thr Glu Ile Cys Asn Gln His Ile Gly Thr Val
            340                 345                 350

Lys Val Ile Asn Leu Ser Tyr Val Tyr Pro Asn Ser Asn Ala Phe Ala
        355                 360                 365

Leu Lys Asn Ile Asn Leu Ser Phe Glu Lys Gly Glu Leu Thr Ala Ile
    370                 375                 380

Val Gly Lys Asn Gly Ser Gly Lys Ser Thr Leu Val Lys Ile Ile Ser
385                 390                 395                 400

Gly Leu Tyr Gln Pro Thr Met Gly Ile Ile Gln Tyr Asp Lys Met Arg
                405                 410                 415

Ser Ser Leu Met Pro Glu Glu Phe Tyr Gln Lys Asn Ile Ser Val Leu
            420                 425                 430

Phe Gln Asp Phe Val Lys Tyr Glu Leu Thr Ile Arg Glu Asn Ile Gly
        435                 440                 445

Leu Ser Asp Leu Ser Ser Gln Trp Glu Asp Glu Lys Ile Ile Lys Val
    450                 455                 460

Leu Asp Asn Leu Gly Leu Asp Phe Leu Lys Thr Asn Asn Gln Tyr Val
465                 470                 475                 480

Leu Asp Thr Gln Leu Gly Asn Trp Phe Gln Glu Gly His Gln Leu Ser
                485                 490                 495

Gly Gly Gln Trp Gln Lys Ile Ala Leu Ala Arg Thr Phe Phe Lys Lys
            500                 505                 510

Ala Ser Ile Tyr Ile Leu Asp Glu Pro Ser Ala Ala Leu Asp Pro Val
        515                 520                 525

Ala Glu Lys Glu Ile Phe Asp Tyr Phe Val Ala Leu Ser Glu Asn Asn
    530                 535                 540

Ile Ser Ile Phe Ile Ser His Ser Leu Asn Ala Ala Arg Lys Ala Asn
545                 550                 555                 560

Lys Ile Val Val Met Lys Asp Gly Gln Val Glu Asp Val Gly Ser His
                565                 570                 575

Asp Val Leu Leu Arg Arg Cys Gln Tyr Tyr Gln Glu Leu Tyr Tyr Ser
            580                 585                 590

Glu Gln Tyr Glu Asp Asn Asp Glu
        595                 600
```

<210> SEQ ID NO 418
<211> LENGTH: 15
<212> TYPE: PRT
<213> ORGANISM: Artificial Sequence
<220> FEATURE:
<223> OTHER INFORMATION: Synthetic peptide

<400> SEQUENCE: 418

```
Asn Phe Asp Phe Gly Glu Leu Thr Leu Ser Thr Gly Leu Pro Gly
1               5                   10                  15
```

<210> SEQ ID NO 419
<211> LENGTH: 6
<212> TYPE: DNA
<213> ORGANISM: Artificial Sequence
<220> FEATURE:
<223> OTHER INFORMATION: Synthetic oligonucleotide

<400> SEQUENCE: 419 gagcac 6

<210> SEQ ID NO 420
<211> LENGTH: 1683
<212> TYPE: DNA
<213> ORGANISM: Artificial Sequence
<220> FEATURE:
<223> OTHER INFORMATION: Synthetic construct

<400> SEQUENCE: 420
agatctgctt gaatccgcgg ataagaggac tagtattcgt ctcactaggg agagctcacc 60
accatgaaca agttgctgtg ctgcgcgctc gtgtttctgg acatctccat taagtggacc 120
acccaggacg tgcagcttca ggagtcagga cctagcctcg tgaaaccttc tcagactctg 180
tccctcacct gttctgtcac tggcgactcc atcaccagtg attactggag ctggatccgg 240
aaattcccag ggaatagact tgagtacatg ggtacgtaa gctacagtgg tagcacttac 300
tacaatccat ctctcaaaag tcgaatctcc atcacccgag acacatccaa gaaccagtac 360
tacctggatt tgaattctgt gactactgag gacacagcca catattactg tgcaaactgg 420
gacggtgatt actggggcca agggactctg gtcactgtct ctgcagccaa aacgacaccc 480
ccatctgtct atccactggc ccctggatct gctgcccaaa ctaactccat ggtgaccctg 540
ggatgcctgg tcaagggcta tttccctgag ccagtgacag tgacctggaa ctctggatcc 600
ctgtccagcg gtgtgcacac cttcccagct gtcctgcagt ctgacctcta cactctgagc 660
agctcagtga ctgtcccctc cagccctcgg cccagcgaga ccgtcacctg caacgttgcc 720
cacccggcca gcagcaccaa ggtggacaag aaaattgtgc ccagggattg tggttgtaag 780
ccttgcatat gtacagtccc agaagtatca tctgtcttca tcttcccccc aaagcccaag 840
gatgtgctca ccattactct gactcctaag gtcacgtgtg ttgtggtaga catcagcaag 900
gatgatcccg aggtccagtt cagctggttt gtagatgatg tggaggtgca cacagctcag 960
acgcaacccc gggaggagca gttcaacagc actttccgct cagtcagtga acttcccatc 1020
atgcaccagg actggctcaa tggcaaggag ttcaaatgca gggtcaacag tgcagctttc 1080
cctgccccca tcgagaaaac catctccaaa accaaaggca gaccgaaggc tccacaggtg 1140
tacaccattc cacctcccaa ggagcagatg gccaaggata aagtcagtct gacctgcatg 1200
ataacagact tcttccctga agacattact gtggagtggc agtggaatgg gcagccagcg 1260
gagaactaca agaacactca gcccatcatg aacacgaatg gctcttactt cgtctacagc 1320
aagctcaatg tgcagaagag caactgggag gcaggaaata ctttcacctg ctctgtgtta 1380
catgagggcc tgcacaacca ccatactgag aagagcctct cccactctcc tggtaaactc 1440
gagcctcctc catccactgt ctccaacatg gcgaccgttg ctgttctggt tgtccttgga 1500
gctgcaatag tcactggagc tgtggtggct tttgtgatga agatgagaag gagaaacaca 1560
ggtggaaaag gaggggacta tgctctggct ccaggctccc agacctctga tctgtctctc 1620
ccagattgta aagtgatggt tcatgaccct cattctctag cgtgaggccg gccaaggcgc 1680
gcc 1683

<210> SEQ ID NO 421
<211> LENGTH: 533
<212> TYPE: PRT
<213> ORGANISM: Artificial Sequence
<220> FEATURE:
<223> OTHER INFORMATION: Synthetic construct

<400> SEQUENCE: 421

```
Met Asn Lys Leu Leu Cys Cys Ala Leu Val Phe Leu Asp Ile Ser Ile
1               5                   10                  15

Lys Trp Thr Thr Gln Asp Val Gln Leu Gln Glu Ser Gly Pro Ser Leu
            20                  25                  30

Val Lys Pro Ser Gln Thr Leu Ser Leu Thr Cys Ser Val Thr Gly Asp
        35                  40                  45

Ser Ile Thr Ser Asp Tyr Trp Ser Trp Ile Arg Lys Phe Pro Gly Asn
    50                  55                  60

Arg Leu Glu Tyr Met Gly Tyr Val Ser Tyr Ser Gly Ser Thr Tyr Tyr
65                  70                  75                  80

Asn Pro Ser Leu Lys Ser Arg Ile Ser Ile Thr Arg Asp Thr Ser Lys
                85                  90                  95

Asn Gln Tyr Tyr Leu Asp Leu Asn Ser Val Thr Thr Glu Asp Thr Ala
            100                 105                 110

Thr Tyr Tyr Cys Ala Asn Trp Asp Gly Asp Tyr Trp Gly Gln Gly Thr
        115                 120                 125

Leu Val Thr Val Ser Ala Ala Lys Thr Thr Pro Pro Ser Val Tyr Pro
    130                 135                 140

Leu Ala Pro Gly Ser Ala Ala Gln Thr Asn Ser Met Val Thr Leu Gly
145                 150                 155                 160

Cys Leu Val Lys Gly Tyr Phe Pro Glu Pro Val Thr Val Thr Trp Asn
                165                 170                 175

Ser Gly Ser Leu Ser Ser Gly Val His Thr Phe Pro Ala Val Leu Gln
            180                 185                 190

Ser Asp Leu Tyr Thr Leu Ser Ser Ser Val Thr Val Pro Ser Ser Pro
        195                 200                 205

Arg Pro Ser Glu Thr Val Thr Cys Asn Val Ala His Pro Ala Ser Ser
    210                 215                 220

Thr Lys Val Asp Lys Lys Ile Val Pro Arg Asp Cys Gly Cys Lys Pro
225                 230                 235                 240

Cys Ile Cys Thr Val Pro Glu Val Ser Ser Val Phe Ile Phe Pro Pro
                245                 250                 255

Lys Pro Lys Asp Val Leu Thr Ile Thr Leu Thr Pro Lys Val Thr Cys
            260                 265                 270

Val Val Val Asp Ile Ser Lys Asp Asp Pro Glu Val Gln Phe Ser Trp
        275                 280                 285

Phe Val Asp Asp Val Glu Val His Thr Ala Gln Thr Gln Pro Arg Glu
    290                 295                 300

Glu Gln Phe Asn Ser Thr Phe Arg Ser Val Ser Glu Leu Pro Ile Met
305                 310                 315                 320

His Gln Asp Trp Leu Asn Gly Lys Glu Phe Lys Cys Arg Val Asn Ser
                325                 330                 335

Ala Ala Phe Pro Ala Pro Ile Glu Lys Thr Ile Ser Lys Thr Lys Gly
            340                 345                 350

Arg Pro Lys Ala Pro Gln Val Tyr Thr Ile Pro Pro Pro Lys Glu Gln
        355                 360                 365

Met Ala Lys Asp Lys Val Ser Leu Thr Cys Met Ile Thr Asp Phe Phe
    370                 375                 380

Pro Glu Asp Ile Thr Val Glu Trp Gln Trp Asn Gly Gln Pro Ala Glu
385                 390                 395                 400

Asn Tyr Lys Asn Thr Gln Pro Ile Met Asn Thr Asn Gly Ser Tyr Phe
                405                 410                 415
```

```
Val Tyr Ser Lys Leu Asn Val Gln Lys Ser Asn Trp Glu Ala Gly Asn
            420                 425                 430

Thr Phe Thr Cys Ser Val Leu His Glu Gly Leu His Asn His His Thr
        435                 440                 445

Glu Lys Ser Leu Ser His Ser Pro Gly Lys Leu Glu Pro Pro Pro Ser
    450                 455                 460

Thr Val Ser Asn Met Ala Thr Val Ala Val Leu Val Val Leu Gly Ala
465                 470                 475                 480

Ala Ile Val Thr Gly Ala Val Val Ala Phe Val Met Lys Met Arg Arg
                485                 490                 495

Arg Asn Thr Gly Gly Lys Gly Gly Asp Tyr Ala Leu Ala Pro Gly Ser
            500                 505                 510

Gln Thr Ser Asp Leu Ser Leu Pro Asp Cys Lys Val Met Val His Asp
        515                 520                 525

Pro His Ser Leu Ala
    530


<210> SEQ ID NO 422
<211> LENGTH: 235
<212> TYPE: PRT
<213> ORGANISM: Artificial Sequence
<220> FEATURE:
<223> OTHER INFORMATION: Synthetic construct

<400> SEQUENCE: 422

Met Asn Lys Leu Leu Cys Cys Ala Leu Val Phe Leu Asp Ile Ser Ile
1               5                   10                  15

Lys Trp Thr Thr Gln Asp Ile Val Leu Thr Gln Ser Pro Ala Thr Leu
            20                  25                  30

Ser Val Thr Pro Gly Asn Ser Val Ser Leu Ser Cys Arg Ala Ser Gln
        35                  40                  45

Ser Ile Gly Asn Asn Leu His Trp Tyr Gln Gln Lys Ser His Glu Ser
    50                  55                  60

Pro Arg Leu Leu Ile Lys Tyr Ala Ser Gln Ser Ile Ser Gly Ile Pro
65                  70                  75                  80

Ser Arg Phe Ser Gly Ser Gly Ser Gly Thr Asp Phe Thr Leu Ser Ile
                85                  90                  95

Asn Ser Val Glu Thr Glu Asp Phe Gly Met Tyr Phe Cys Gln Gln Ser
            100                 105                 110

Asn Ser Trp Pro Tyr Thr Phe Gly Gly Gly Thr Lys Leu Glu Ile Lys
        115                 120                 125

Arg Ala Asp Ala Ala Pro Thr Val Ser Ile Phe Pro Pro Ser Ser Glu
    130                 135                 140

Gln Leu Thr Ser Gly Gly Ala Ser Val Val Cys Phe Leu Asn Asn Phe
145                 150                 155                 160

Tyr Pro Lys Asp Ile Asn Val Lys Trp Lys Ile Asp Gly Ser Glu Arg
                165                 170                 175

Gln Asn Gly Val Leu Asn Ser Trp Thr Asp Gln Asp Ser Lys Asp Ser
            180                 185                 190

Thr Tyr Ser Met Ser Ser Thr Leu Thr Leu Thr Lys Asp Glu Tyr Glu
        195                 200                 205

Arg His Asn Ser Tyr Thr Cys Glu Ala Thr His Lys Thr Ser Thr Ser
    210                 215                 220

Pro Ile Val Lys Ser Phe Asn Arg Asn Glu Cys
225                 230                 235
```

<210> SEQ ID NO 423
<211> LENGTH: 728
<212> TYPE: DNA
<213> ORGANISM: Artificial Sequence
<220> FEATURE:
<223> OTHER INFORMATION: Synthetic construct

<400> SEQUENCE: 423
gagctcacca caatgaacaa gttgctgtgc tgcgcgctcg tgtttctgga catctccatt 60
aagtggacca cccaggatat tgtgctaact cagtctccag ccaccctgtc tgtgactcca 120
ggaaatagcg tcagtctttc ctgcagggcc agccaaagta ttggcaacaa cctacactgg 180
tatcaacaaa aatcacatga gtctccaagg cttctcatca agtatgcttc ccagtccatc 240
tctgggatcc cctccaggtt cagtggcagt ggatcaggga cagatttcac tctcagtatc 300
aacagtgtgg agactgaaga ttttggaatg tatttctgtc aacagagtaa cagctggcct 360
tacacgttcg gaggggggac caagctggaa ataaaacggg ctgatgctgc accaactgta 420
tccatcttcc caccatccag tgagcagtta acatctggag gtgcctcagt cgtgtgcttc 480
ttgaacaact tctaccccaa agacatcaat gtcaagtgga agattgatgg cagtgaacga 540
caaaatggcg tcctgaacag ttggactgat caggacagca aagacagcac ctacagcatg 600
agcagcaccc tcacgttgac caaggacgag tatgaacgac ataacagcta tacctgtgag 660
gccactcaca agacatcaac ttcacccatt gtcaagagct tcaacaggaa tgagtgttga 720
ggcgcgcc 728

<210> SEQ ID NO 424
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 424
gtgggaggtc tatataagca gagc 24

<210> SEQ ID NO 425
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 425
cagaggtgct cttggaggag ggt 23

<210> SEQ ID NO 426
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 426
acacaacaga ggcagttcca gatt 24

<210> SEQ ID NO 427
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 427
agtgtggcct tgttggcttg aa 22

<210> SEQ ID NO 428
<211> LENGTH: 597
<212> TYPE: DNA
<213> ORGANISM: Artificial Sequence
<220> FEATURE:
<223> OTHER INFORMATION: Synthetic construct

<400> SEQUENCE: 428
atggactctc tcctcatgaa gcagagaaag tttctctacc acttcaagaa cgtcagatgg 60
gccaagggga gacatgagac ctatctctgt tacgtcgtca agaggagaga ctcagccacc 120
tctttctccc tcgactttgg gcatctccgg aacaagtctg ggtgtcatgt cgaactcctc 180
ttcctccgct atatctcaga ctgggacctc gaccccggga gatgctatag agtcacttgg 240
tttacctctt ggtcccctg ttatgactgc gccagacatg tcgccgactt cctcaggggg 300
tatcccaatc tctccctccg catattcgcc gcccgactct atttttgtga ggacaggaaa 360
gccgagcccg aggggctcag gagactccac cgggccgggg tccagatcgc catcatgaca 420
tttaaggact atttctattg ttggaataca tttgtcgaga atcgggagaa gactttcaaa 480
gcctgggagg ggctccatga gaactctgtc agactctcta ggcagctcag gagaatcctc 540
ctccccctct atgaggtcga cgacctcaga gatgccttcc ggaccctcgg ggcttga 597

<210> SEQ ID NO 429
<211> LENGTH: 691
<212> TYPE: DNA
<213> ORGANISM: Artificial Sequence
<220> FEATURE:
<223> OTHER INFORMATION: Synthetic construct

<400> SEQUENCE: 429
gagctcctaa ccaccatgga ctacaaagat gacgatgata aaggtccaaa gaagaagaga 60
aaggtagact ctctcctcat gaagcagaga aagtttctct accacttcaa gaacgtcaga 120
tgggccaagg ggagacatga gacctatctc tgttacgtcg tcaagaggag agactcagcc 180
acctctttct ccctcgactt tgggcatctc cggaacaagt ctgggtgtca tgtcgaactc 240
ctcttcctcc gctatatctc agactgggac ctcgaccccg ggagatgcta tagagtcact 300
tggtttacct cttggtcccc ctgttatgac tgcgccagac atgtcgccga cttcctcagg 360
gggtatccca atctctccct ccgcatattc gccgcccgac tctatttttg tgaggacagg 420
aaagccgagc ccgaggggct caggagactc caccgggccg gggtccagat cgccatcatg 480
acatttaagg actatttcta ttgttggaat acatttgtcg agaatcggga gaagactttc 540
aaagcctggg aggggctcca tgagaactct gtcagactct ctaggcagct caggagaatc 600
ctcctccccc tctatgaggt cgacgacctc agagatgcct tccggaccct cggggcttga 660
tgtacaatcc gcgtgagacg atcggcgcgc c 691

<210> SEQ ID NO 430
<211> LENGTH: 214
<212> TYPE: PRT
<213> ORGANISM: Artificial Sequence
<220> FEATURE:
<223> OTHER INFORMATION: Synthetic construct

<400> SEQUENCE: 430

Met Asp Tyr Lys Asp Asp Asp Asp Lys Gly Pro Lys Lys Lys Arg Lys
1 5 10 15

```
Val Asp Ser Leu Leu Met Lys Gln Arg Lys Phe Leu Tyr His Phe Lys
            20                  25                  30

Asn Val Arg Trp Ala Lys Gly Arg His Glu Thr Tyr Leu Cys Tyr Val
        35                  40                  45

Val Lys Arg Arg Asp Ser Ala Thr Ser Phe Ser Leu Asp Phe Gly His
    50                  55                  60

Leu Arg Asn Lys Ser Gly Cys His Val Glu Leu Leu Phe Leu Arg Tyr
65                  70                  75                  80

Ile Ser Asp Trp Asp Leu Asp Pro Gly Arg Cys Tyr Arg Val Thr Trp
                85                  90                  95

Phe Thr Ser Trp Ser Pro Cys Tyr Asp Cys Ala Arg His Val Ala Asp
            100                 105                 110

Phe Leu Arg Gly Tyr Pro Asn Leu Ser Leu Arg Ile Phe Ala Ala Arg
        115                 120                 125

Leu Tyr Phe Cys Glu Asp Arg Lys Ala Glu Pro Glu Gly Leu Arg Arg
    130                 135                 140

Leu His Arg Ala Gly Val Gln Ile Ala Ile Met Thr Phe Lys Asp Tyr
145                 150                 155                 160

Phe Tyr Cys Trp Asn Thr Phe Val Glu Asn Arg Glu Lys Thr Phe Lys
                165                 170                 175

Ala Trp Glu Gly Leu His Glu Asn Ser Val Arg Leu Ser Arg Gln Leu
            180                 185                 190

Arg Arg Ile Leu Leu Pro Leu Tyr Glu Val Asp Asp Leu Arg Asp Ala
        195                 200                 205

Phe Arg Thr Leu Gly Ala
    210
```

<210> SEQ ID NO 431
<211> LENGTH: 618
<212> TYPE: DNA
<213> ORGANISM: Artificial Sequence
<220> FEATURE:
<223> OTHER INFORMATION: Synthetic construct

<400> SEQUENCE: 431

```
gagctcctaa ccaccatgga ctctctcctc atgaagcaga gaaagtttct ctaccacttc      60

aagaacgtca gatgggccaa ggggagacat gagacctatc tctgttacgt cgtcaagagg     120

agagactcag ccacctcttt ctccctcgac tttgggcatc tccggaacaa gtctgggtgt     180

catgtcgaac tcctcttcct ccgctatatc tcagactggg acctcgaccc cgggagatgc     240

tatagagtca cttggtttac ctcttggtcc ccctgttatg actgcgccag acatgtcgcc     300

gacttcctca gggggtatcc caatctctcc ctccgcatat tcgccgcccg actctatttt     360

tgtgaggaca ggaaagccga gcccgagggg ctcaggagac tccaccgggc cggggtccag     420

atcgccatca tgacatttaa ggactatttc tattgttgga atacatttgt cgagaatcgg     480

gagaagactt tcaaagcctg ggagggggctc catgagaact ctgtcagact ctctaggcag     540

ctcaggagaa tcctcgcccc cgcctatgag gtcgacgacg ccagagatgc cttccggacc     600

gccggggctt gatgtaca                                                   618
```

<210> SEQ ID NO 432
<211> LENGTH: 198
<212> TYPE: PRT
<213> ORGANISM: Artificial Sequence
<220> FEATURE:
<223> OTHER INFORMATION: Synthetic construct

<400> SEQUENCE: 432

```
Met Asp Ser Leu Leu Met Lys Gln Arg Lys Phe Leu Tyr His Phe Lys
1               5                   10                  15

Asn Val Arg Trp Ala Lys Gly Arg His Glu Thr Tyr Leu Cys Tyr Val
            20                  25                  30

Val Lys Arg Arg Asp Ser Ala Thr Ser Phe Ser Leu Asp Phe Gly His
        35                  40                  45

Leu Arg Asn Lys Ser Gly Cys His Val Glu Leu Leu Phe Leu Arg Tyr
    50                  55                  60

Ile Ser Asp Trp Asp Leu Asp Pro Gly Arg Cys Tyr Arg Val Thr Trp
65                  70                  75                  80

Phe Thr Ser Trp Ser Pro Cys Tyr Asp Cys Ala Arg His Val Ala Asp
                85                  90                  95

Phe Leu Arg Gly Tyr Pro Asn Leu Ser Leu Arg Ile Phe Ala Ala Arg
            100                 105                 110

Leu Tyr Phe Cys Glu Asp Arg Lys Ala Glu Pro Glu Gly Leu Arg Arg
        115                 120                 125

Leu His Arg Ala Gly Val Gln Ile Ala Ile Met Thr Phe Lys Asp Tyr
    130                 135                 140

Phe Tyr Cys Trp Asn Thr Phe Val Glu Asn Arg Glu Lys Thr Phe Lys
145                 150                 155                 160

Ala Trp Glu Gly Leu His Glu Asn Ser Val Arg Leu Ser Arg Gln Leu
                165                 170                 175

Arg Arg Ile Leu Ala Pro Ala Tyr Glu Val Asp Asp Ala Arg Asp Ala
            180                 185                 190

Phe Arg Thr Ala Gly Ala
        195
```

<210> SEQ ID NO 433
<211> LENGTH: 666
<212> TYPE: DNA
<213> ORGANISM: Artificial Sequence
<220> FEATURE:
<223> OTHER INFORMATION: Synthetic construct

<400> SEQUENCE: 433

```
gagctcctaa ccaccatgga ctacaaagat gacgatgata aaggtccaaa gaagaagaga      60

aaggtagact ctctcctcat gaagcagaga aagtttctct accacttcaa gaacgtcaga     120

tgggccaagg ggagacatga gacctatctc tgttacgtcg tcaagaggag agactcagcc     180

acctctttct ccctcgactt tgggcatctc cggaacaagt ctgggtgtca tgtcgaactc     240

ctcttcctcc gctatatctc agactgggac ctcgaccccg ggagatgcta tagagtcact     300

tggtttacct cttggtcccc ctgttatgac tgcgccagac atgtcgccga cttcctcagg     360

gggtatccca atctctccct ccgcatattc gccgcccgac tctatttttg tgaggacagg     420

aaagccgagc ccgaggggct caggagactc caccgggccg gggtccagat cgccatcatg     480

acatttaagg actatttcta ttgttggaat acatttgtcg agaatcggga gaagactttc     540

aaagcctggg aggggctcca tgagaactct gtcagactct ctaggcagct caggagaatc     600

ctcgcccccg cctatgaggt cgacgacgcc agagatgcct tccggaccgc cggggcttga     660

tgtaca                                                                666
```

<210> SEQ ID NO 434
<211> LENGTH: 214
<212> TYPE: PRT
<213> ORGANISM: Artificial Sequence
<220> FEATURE:

<223> OTHER INFORMATION: Synthetic construct

<400> SEQUENCE: 434

```
Met Asp Tyr Lys Asp Asp Asp Asp Lys Gly Pro Lys Lys Lys Arg Lys
1               5                   10                  15

Val Asp Ser Leu Leu Met Lys Gln Arg Lys Phe Leu Tyr His Phe Lys
            20                  25                  30

Asn Val Arg Trp Ala Lys Gly Arg His Glu Thr Tyr Leu Cys Tyr Val
        35                  40                  45

Val Lys Arg Arg Asp Ser Ala Thr Ser Phe Ser Leu Asp Phe Gly His
    50                  55                  60

Leu Arg Asn Lys Ser Gly Cys His Val Glu Leu Leu Phe Leu Arg Tyr
65                  70                  75                  80

Ile Ser Asp Trp Asp Leu Asp Pro Gly Arg Cys Tyr Arg Val Thr Trp
                85                  90                  95

Phe Thr Ser Trp Ser Pro Cys Tyr Asp Cys Ala Arg His Val Ala Asp
            100                 105                 110

Phe Leu Arg Gly Tyr Pro Asn Leu Ser Leu Arg Ile Phe Ala Ala Arg
        115                 120                 125

Leu Tyr Phe Cys Glu Asp Arg Lys Ala Glu Pro Glu Gly Leu Arg Arg
    130                 135                 140

Leu His Arg Ala Gly Val Gln Ile Ala Ile Met Thr Phe Lys Asp Tyr
145                 150                 155                 160

Phe Tyr Cys Trp Asn Thr Phe Val Glu Asn Arg Glu Lys Thr Phe Lys
                165                 170                 175

Ala Trp Glu Gly Leu His Glu Asn Ser Val Arg Leu Ser Arg Gln Leu
            180                 185                 190

Arg Arg Ile Leu Ala Pro Ala Tyr Glu Val Asp Asp Ala Arg Asp Ala
        195                 200                 205

Phe Arg Thr Ala Gly Ala
    210
```

<210> SEQ ID NO 435
<211> LENGTH: 618
<212> TYPE: DNA
<213> ORGANISM: Artificial Sequence
<220> FEATURE:
<223> OTHER INFORMATION: Synthetic construct

<400> SEQUENCE: 435

```
gagctcctaa ccaccatgga ctctctcctc atgaagcaga gaaagtttct ctaccacttc     60

aagaacgtca gatgggccaa ggggagacat gagacctatc tctgttacgt cgtcaagagg    120

agagactcag ccacctcttt ctccctcgac tttgggcatc tccggaacaa gtctgggtgt    180

catgtcgaac tcctcttcct ccgctatatc tcagactggg acctcgaccc cgggagatgc    240

tatagagtca cttggtttac ctcttggtcc ccctgttatg actgcgccag acatgtcgcc    300

gacttcctca gggggtatcc caatctctcc ctccgcatat tcgccgcccg actctatttt    360

tgtgaggaca ggaaagccga gcccgagggg ctcaggagac tccaccgggc cggggtccag    420

atcgccatca tgacatttaa ggactatttc tattgttgga atacatttgt cgagaatcgg    480

gagaagactt tcaaagcctg ggaggggctc catgagaact ctgtcagact ctctaggcag    540

ctcaggagaa tcctcctccc cctctatgag gtcgaagaac tcagagaagc cttccggatc    600

ctcggggctt gatgtaca                                                  618
```

<210> SEQ ID NO 436

<211> LENGTH: 198
<212> TYPE: PRT
<213> ORGANISM: Artificial Sequence
<220> FEATURE:
<223> OTHER INFORMATION: Synthetic construct

<400> SEQUENCE: 436

Met Asp Ser Leu Leu Met Lys Gln Arg Lys Phe Leu Tyr His Phe Lys
1 5 10 15

Asn Val Arg Trp Ala Lys Gly Arg His Glu Thr Tyr Leu Cys Tyr Val
20 25 30

Val Lys Arg Arg Asp Ser Ala Thr Ser Phe Ser Leu Asp Phe Gly His
35 40 45

Leu Arg Asn Lys Ser Gly Cys His Val Glu Leu Leu Phe Leu Arg Tyr
50 55 60

Ile Ser Asp Trp Asp Leu Asp Pro Gly Arg Cys Tyr Arg Val Thr Trp
65 70 75 80

Phe Thr Ser Trp Ser Pro Cys Tyr Asp Cys Ala Arg His Val Ala Asp
85 90 95

Phe Leu Arg Gly Tyr Pro Asn Leu Ser Leu Arg Ile Phe Ala Ala Arg
100 105 110

Leu Tyr Phe Cys Glu Asp Arg Lys Ala Glu Pro Glu Gly Leu Arg Arg
115 120 125

Leu His Arg Ala Gly Val Gln Ile Ala Ile Met Thr Phe Lys Asp Tyr
130 135 140

Phe Tyr Cys Trp Asn Thr Phe Val Glu Asn Arg Glu Lys Thr Phe Lys
145 150 155 160

Ala Trp Glu Gly Leu His Glu Asn Ser Val Arg Leu Ser Arg Gln Leu
165 170 175

Arg Arg Ile Leu Leu Pro Leu Tyr Glu Val Glu Glu Leu Arg Glu Ala
180 185 190

Phe Arg Ile Leu Gly Ala
195

<210> SEQ ID NO 437
<211> LENGTH: 666
<212> TYPE: DNA
<213> ORGANISM: Artificial Sequence
<220> FEATURE:
<223> OTHER INFORMATION: Synthetic construct

<400> SEQUENCE: 437
gagctcctaa ccaccatgga ctacaaagat gacgatgata aaggtccaaa gaagaagaga 60
aaggtagact ctctcctcat gaagcagaga aagtttctct accacttcaa gaacgtcaga 120
tgggccaagg ggagacatga gacctatctc tgttacgtcg tcaagaggag agactcagcc 180
acctctttct ccctcgactt tgggcatctc cggaacaagt ctgggtgtca tgtcgaactc 240
ctcttcctcc gctatatctc agactgggac ctcgaccccg ggagatgcta tagagtcact 300
tggtttacct cttggtcccc ctgttatgac tgcgccagac atgtcgccga cttcctcagg 360
gggtatccca atctctccct ccgcatattc gccgcccgac tctatttttg tgaggacagg 420
aaagccgagc ccgaggggct caggagactc caccgggccg gggtccagat cgccatcatg 480
acatttaagg actatttcta ttgttggaat acatttgtcg agaatcggga gaagactttc 540
aaagcctggg aggggctcca tgagaactct gtcagactct ctaggcagct caggagaatc 600
ctcctccccc tctatgaggt cgaagaactc agagaagcct tccggatcct cggggcttga 660
tgtaca 666

<210> SEQ ID NO 438
<211> LENGTH: 214
<212> TYPE: PRT
<213> ORGANISM: Artificial Sequence
<220> FEATURE:
<223> OTHER INFORMATION: Synthetic construct

<400> SEQUENCE: 438

```
Met Asp Tyr Lys Asp Asp Asp Asp Lys Gly Pro Lys Lys Lys Arg Lys
1               5                   10                  15

Val Asp Ser Leu Leu Met Lys Gln Arg Lys Phe Leu Tyr His Phe Lys
            20                  25                  30

Asn Val Arg Trp Ala Lys Gly Arg His Glu Thr Tyr Leu Cys Tyr Val
        35                  40                  45

Val Lys Arg Arg Asp Ser Ala Thr Ser Phe Ser Leu Asp Phe Gly His
    50                  55                  60

Leu Arg Asn Lys Ser Gly Cys His Val Glu Leu Leu Phe Leu Arg Tyr
65                  70                  75                  80

Ile Ser Asp Trp Asp Leu Asp Pro Gly Arg Cys Tyr Arg Val Thr Trp
                85                  90                  95

Phe Thr Ser Trp Ser Pro Cys Tyr Asp Cys Ala Arg His Val Ala Asp
            100                 105                 110

Phe Leu Arg Gly Tyr Pro Asn Leu Ser Leu Arg Ile Phe Ala Ala Arg
        115                 120                 125

Leu Tyr Phe Cys Glu Asp Arg Lys Ala Glu Pro Glu Gly Leu Arg Arg
    130                 135                 140

Leu His Arg Ala Gly Val Gln Ile Ala Ile Met Thr Phe Lys Asp Tyr
145                 150                 155                 160

Phe Tyr Cys Trp Asn Thr Phe Val Glu Asn Arg Glu Lys Thr Phe Lys
                165                 170                 175

Ala Trp Glu Gly Leu His Glu Asn Ser Val Arg Leu Ser Arg Gln Leu
            180                 185                 190

Arg Arg Ile Leu Leu Pro Leu Tyr Glu Val Glu Glu Leu Arg Glu Ala
        195                 200                 205

Phe Arg Ile Leu Gly Ala
    210
```

<210> SEQ ID NO 439
<211> LENGTH: 7
<212> TYPE: PRT
<213> ORGANISM: Artificial Sequence
<220> FEATURE:
<223> OTHER INFORMATION: Synthetic peptide

<400> SEQUENCE: 439

```
Pro Lys Lys Lys Arg Lys Val
1               5
```

<210> SEQ ID NO 440
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 440

```
cagctcagga gaatcctcgc ccccgcttat gaggtcgacg acctc                     45
```

<210> SEQ ID NO 441

<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 441
gaggtcgtcg acctcataag cgggggcgag gattctcctg agctg 45

<210> SEQ ID NO 442
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 442
ccgcttatga ggtcgacgac gccagagatg ccttccggac cg 42

<210> SEQ ID NO 443
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 443
agggtccgga aggcatctct ggcgtcgtcg acctcataag cgg 43

<210> SEQ ID NO 444
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 444
ccagagatgc cttccggacc gccggggctt gatgtacaat c 41

<210> SEQ ID NO 445
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 445
gattgtacat caagccccgg cggtccggaa ggcatctctg g 41

<210> SEQ ID NO 446
<211> LENGTH: 55
<212> TYPE: DNA
<213> ORGANISM: Artificial Sequence
<220> FEATURE:
<223> OTHER INFORMATION: Synthetic oligonucleotide

<400> SEQUENCE: 446
tcctccccct ctatgaggtc gaagaactca gagaagcctt ccggaccctc ggggc 55

<210> SEQ ID NO 447
<211> LENGTH: 55
<212> TYPE: DNA
<213> ORGANISM: Artificial Sequence
<220> FEATURE:
<223> OTHER INFORMATION: Synthetic oligonucleotide

<400> SEQUENCE: 447
gccccgaggg tccggaaggc ttctctgagt tcttcgacct catagagggg gagga 55

<210> SEQ ID NO 448
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 448
aactcagaga agccttccgg atcctcgggg cttgatgtac aat 43

<210> SEQ ID NO 449
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 449
attgtacatc aagccccgag gatccggaag gcttctctga gtt 43

<210> SEQ ID NO 450
<211> LENGTH: 16
<212> TYPE: PRT
<213> ORGANISM: Artificial Sequence
<220> FEATURE:
<223> OTHER INFORMATION: Synthetic peptide

<400> SEQUENCE: 450

Lys Arg Pro Ala Ala Thr Lys Lys Ala Gly Gln Ala Lys Lys Lys Lys
1 5 10 15

<210> SEQ ID NO 451
<211> LENGTH: 1291
<212> TYPE: DNA
<213> ORGANISM: Artificial Sequence
<220> FEATURE:
<223> OTHER INFORMATION: Synthetic construct

<400> SEQUENCE: 451
gctagcaccc tcctccaaga gcacctctgg gggcacagcg gccctgggct gcctggtcaa 60
ggactacttc cccgaacctg tgacggtgtc gtggaactca ggcgccctga ccagcggcgt 120
gcacaccttc ccggctgtcc tacagtcctc aggactctac tccctcagca gcgtggtgac 180
agtgccctcc agcagcttgg gcacccagac ctacatctgc aacgtgaatc acaagcccag 240
caacaccaag gtggacaaga aagttgagcc caaatcttgt gacaaaactc acacatgccc 300
accgtgccca gcacctgaac tcctgggggg accgtcagtc ttcctcttcc ccccaaaacc 360
caaggacacc ctcatgatct cccggacccc tgaggtcaca tgcgtggtgg tggacgtgag 420
ccacgaggac cctgaggtca agttcaactg gtacgtggac ggcgtggagg tgcataatgc 480
caagacaaag ccgcgggagg agcagtacaa cagcacgtac cgggtggtca gcgtcctcac 540
cgtcctgcac caggactggc tgaatggcaa ggagtacaag tgcaaggtct ccaacaaagc 600
cctcccagcc cccatcgaga aaaccatctc caaagccaaa gggcagcccc gagaaccaca 660
ggtgtacacc ctgcccccat cccgggatga gctgaccaag aaccaggtca gcctgacctg 720
cctggtcaaa ggcttctatc ccagcgacat cgccgtggag tgggagagca atgggcagcc 780
ggagaacaac tacaagacca cgcctcccgt gctggactcc gacggctcct tcttcctcta 840
cagcaagctc accgtggaca agagcaggtg gcagcagggg aacgtcttct catgctccgt 900
gatgcatgag gctctgcaca accactacac gcagaagagc ctctccctgt ctccgggtaa 960

```
actcgagata acttcgtata gcatacatta tacgaagtta tctcctcctc catccactgt   1020

ctccaacatg gcgaccgttg ctgttctggt tgtccttgga gctgcaatag tcactggagc   1080

tgtggtggct tttgtgatga agatgagaag gagaaacaca ggtggaaaag gaggggacta   1140

tgctctggct ccaggctccc agacctctga tctgtctctc ccagattgta aagtgatggt   1200

tcatgaccct cattctctag cgtgactcga gtgaataact tcgtataatg tatgctatac   1260

gaagttatgg ccggccagaa ttcggcgcgc c                                  1291


<210> SEQ ID NO 452
<211> LENGTH: 354
<212> TYPE: PRT
<213> ORGANISM: Artificial Sequence
<220> FEATURE:
<223> OTHER INFORMATION: Synthetic construct

<400> SEQUENCE: 452

Leu Ala Pro Ser Ser Lys Ser Thr Ser Gly Gly Thr Ala Ala Leu Gly
1               5                   10                  15

Cys Leu Val Lys Asp Tyr Phe Pro Glu Pro Val Thr Val Ser Trp Asn
            20                  25                  30

Ser Gly Ala Leu Thr Ser Gly Val His Thr Phe Pro Ala Val Leu Gln
        35                  40                  45

Ser Ser Gly Leu Tyr Ser Leu Ser Ser Val Val Thr Val Pro Ser Ser
    50                  55                  60

Ser Leu Gly Thr Gln Thr Tyr Ile Cys Asn Val Asn His Lys Pro Ser
65                  70                  75                  80

Asn Thr Lys Val Asp Lys Lys Val Glu Pro Lys Ser Cys Asp Lys Thr
                85                  90                  95

His Thr Cys Pro Pro Cys Pro Ala Pro Glu Leu Leu Gly Gly Pro Ser
            100                 105                 110

Val Phe Leu Phe Pro Pro Lys Pro Lys Asp Thr Leu Met Ile Ser Arg
        115                 120                 125

Thr Pro Glu Val Thr Cys Val Val Val Asp Val Ser His Glu Asp Pro
    130                 135                 140

Glu Val Lys Phe Asn Trp Tyr Val Asp Gly Val Glu Val His Asn Ala
145                 150                 155                 160

Lys Thr Lys Pro Arg Glu Glu Gln Tyr Asn Ser Thr Tyr Arg Val Val
                165                 170                 175

Ser Val Leu Thr Val Leu His Gln Asp Trp Leu Asn Gly Lys Glu Tyr
            180                 185                 190

Lys Cys Lys Val Ser Asn Lys Ala Leu Pro Ala Pro Ile Glu Lys Thr
        195                 200                 205

Ile Ser Lys Ala Lys Gly Gln Pro Arg Glu Pro Gln Val Tyr Thr Leu
    210                 215                 220

Pro Pro Ser Arg Asp Glu Leu Thr Lys Asn Gln Val Ser Leu Thr Cys
225                 230                 235                 240

Leu Val Lys Gly Phe Tyr Pro Ser Asp Ile Ala Val Glu Trp Glu Ser
                245                 250                 255

Asn Gly Gln Pro Glu Asn Asn Tyr Lys Thr Thr Pro Pro Val Leu Asp
            260                 265                 270

Ser Asp Gly Ser Phe Phe Leu Tyr Ser Lys Leu Thr Val Asp Lys Ser
        275                 280                 285

Arg Trp Gln Gln Gly Asn Val Phe Ser Cys Ser Val Met His Glu Ala
    290                 295                 300
```

```
Leu His Asn His Tyr Thr Gln Lys Ser Leu Ser Leu Ser Pro Gly Lys
305                 310                 315                 320

Leu Glu Ile Thr Ser Tyr Ser Ile His Tyr Thr Lys Leu Ser Pro Pro
                325                 330                 335

Pro Ser Thr Val Ser Asn Met Ala Thr Val Ala Val Leu Val Val Leu
            340                 345                 350

Gly Ala


<210> SEQ ID NO 453
<211> LENGTH: 343
<212> TYPE: PRT
<213> ORGANISM: Enterobacteria phage P1

<400> SEQUENCE: 453

Met Ser Asn Leu Leu Thr Val His Gln Asn Leu Pro Ala Leu Pro Val
1               5                   10                  15

Asp Ala Thr Ser Asp Glu Val Arg Lys Asn Leu Met Asp Met Phe Arg
            20                  25                  30

Asp Arg Gln Ala Phe Ser Glu His Thr Trp Lys Met Leu Leu Ser Val
        35                  40                  45

Cys Arg Ser Trp Ala Ala Trp Cys Lys Leu Asn Asn Arg Lys Trp Phe
    50                  55                  60

Pro Ala Glu Pro Glu Asp Val Arg Asp Tyr Leu Leu Tyr Leu Gln Ala
65                  70                  75                  80

Arg Gly Leu Ala Val Lys Thr Ile Gln Gln His Leu Gly Gln Leu Asn
                85                  90                  95

Met Leu His Arg Arg Ser Gly Leu Pro Arg Pro Ser Asp Ser Asn Ala
            100                 105                 110

Val Ser Leu Val Met Arg Arg Ile Arg Lys Glu Asn Val Asp Ala Gly
        115                 120                 125

Glu Arg Ala Lys Gln Ala Leu Ala Phe Glu Arg Thr Asp Phe Asp Gln
    130                 135                 140

Val Arg Ser Leu Met Glu Asn Ser Asp Arg Cys Gln Asp Ile Arg Asn
145                 150                 155                 160

Leu Ala Phe Leu Gly Ile Ala Tyr Asn Thr Leu Leu Arg Ile Ala Glu
                165                 170                 175

Ile Ala Arg Ile Arg Val Lys Asp Ile Ser Arg Thr Asp Gly Gly Arg
            180                 185                 190

Met Leu Ile His Ile Gly Arg Thr Lys Thr Leu Val Ser Thr Ala Gly
        195                 200                 205

Val Glu Lys Ala Leu Ser Leu Gly Val Thr Lys Leu Val Glu Arg Trp
    210                 215                 220

Ile Ser Val Ser Gly Val Ala Asp Asp Pro Asn Asn Tyr Leu Phe Cys
225                 230                 235                 240

Arg Val Arg Lys Asn Gly Val Ala Ala Pro Ser Ala Thr Ser Gln Leu
                245                 250                 255

Ser Thr Arg Ala Leu Glu Gly Ile Phe Glu Ala Thr His Arg Leu Ile
            260                 265                 270

Tyr Gly Ala Lys Asp Asp Ser Gly Gln Arg Tyr Leu Ala Trp Ser Gly
        275                 280                 285

His Ser Ala Arg Val Gly Ala Ala Arg Asp Met Ala Arg Ala Gly Val
    290                 295                 300

Ser Ile Pro Glu Ile Met Gln Ala Gly Gly Trp Thr Asn Val Asn Ile
305                 310                 315                 320

Val Met Asn Tyr Ile Arg Asn Leu Asp Ser Glu Thr Gly Ala Met Val
```

```
                325                 330                 335

Arg Leu Leu Glu Asp Gly Asp
            340


<210> SEQ ID NO 454
<211> LENGTH: 1032
<212> TYPE: DNA
<213> ORGANISM: Enterobacteria phage P1

<400> SEQUENCE: 454

atgtccaatt tactgaccgt acaccaaaat ttgcctgcat taccggtcga tgcaacgagt      60

gatgaggttc gcaagaacct gatggacatg ttcagggatc gccaggcgtt ttctgagcat     120

acctggaaaa tgcttctgtc cgtttgccgg tcgtgggcgg catggtgcaa gttgaataac     180

cggaaatggt ttcccgcaga acctgaagat gttcgcgatt atcttctata tcttcaggcg     240

cgcggtctgg cagtaaaaac tatccagcaa catttgggcc agctaaacat gcttcatcgt     300

cggtccgggc tgccacgacc aagtgacagc aatgctgttt cactggttat gcggcggatc     360

cgaaaagaaa acgttgatgc cggtgaacgt gcaaaacagg ctctagcgtt cgaacgcact     420

gatttcgacc aggttcgttc actcatggaa aatagcgatc gctgccagga tatacgtaat     480

ctggcatttc tggggattgc ttataacacc ctgttacgta tagccgaaat tgccaggatc     540

agggttaaag atatctcacg tactgacggt gggagaatgt taatccatat tggcagaacg     600

aaaacgctgg ttagcaccgc aggtgtagag aaggcactta gcctgggggt aactaaactg     660

gtcgagcgat ggatttccgt ctctggtgta gctgatgatc cgaataacta cctgttttgc     720

cgggtcagaa aaaatggtgt tgccgcgcca tctgccacca gccagctatc aactcgcgcc     780

ctggaaggga tttttgaagc aactcatcga ttgatttacg gcgctaagga tgactctggt     840

cagagatacc tggcctggtc tggacacagt gcccgtgtcg gagccgcgcg agatatggcc     900

cgcgctggag tttcaatacc ggagatcatg caagctggtg gctggaccaa tgtaaatatt     960

gtcatgaact atatccgtaa cctggatagt gaaacagggg caatggtgcg cctgctggaa    1020

gatggcgatt ag                                                        1032


<210> SEQ ID NO 455
<211> LENGTH: 1221
<212> TYPE: DNA
<213> ORGANISM: Artificial Sequence
<220> FEATURE:
<223> OTHER INFORMATION: Synthetic construct

<400> SEQUENCE: 455

gctagcaccc tcctccaaga gcacctctgg gggcacagcg gccctgggct gcctggtcaa      60

ggactacttc cccgaacctg tgacggtgtc gtggaactca ggcgccctga ccagcggcgt     120

gcacaccttc ccggctgtcc tacagtcctc aggactctac tccctcagca gcgtggtgac     180

agtgccctcc agcagcttgg gcacccagac ctacatctgc aacgtgaatc acaagcccag     240

caacaccaag gtggacaaga aagttgagcc caaatcttgt gacaaaactc acacatgccc     300

accgtgccca gcacctgaac tcctgggggg accgtcagtc ttcctcttcc ccccaaaacc     360

caaggacacc ctcatgatct cccggacccc tgaggtcaca tgcgtggtgg tggacgtgag     420

ccacgaggac cctgaggtca agttcaactg gtacgtggac ggcgtggagg tgcataatgc     480

caagacaaag ccgcgggagg agcagtacaa cagcacgtac cgggtggtca gcgtcctcac     540

cgtcctgcac caggactggc tgaatggcaa ggagtacaag tgcaaggtct ccaacaaagc     600

cctcccagcc cccatcgaga aaaccatctc caaagccaaa gggcagcccc gagaaccaca     660
```

ggtgtacacc ctgcccccat cccgggatga gctgaccaag aaccaggtca gcctgacctg 720
cctggtcaaa ggcttctatc ccagcgacat cgccgtggag tgggagagca atgggcagcc 780
ggagaacaac tacaagacca cgcctcccgt gctggactcc gacggctcct tcttcctcta 840
cagcaagctc accgtggaca agagcaggtg gcagcagggg aacgtcttct catgctccgt 900
gatgcatgag gctctgcaca accactacac gcagaagagc ctctccctgt ctccgggtaa 960
actcgagcct cctccatcca ctgtctccaa catggcgacc gttgctgttc tggttgtcct 1020
tggagctgca atagtcactg gagctgtggt ggcttttgtg atgaagatga gaaggagaaa 1080
cacaggtgga aaaggagggg actatgctct ggctccaggc tcccagacct ctgatctgtc 1140
tctcccagat tgtaaagtga tggttcatga ccctcattct ctagcgtgac tcgagtgagg 1200
ccggccagaa ttcggcgcgc c 1221

<210> SEQ ID NO 456
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 456
gtgggaggtc tatataagca gagc 24

<210> SEQ ID NO 457
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 457
gatcgtctca cgcggattgt ac 22

<210> SEQ ID NO 458
<211> LENGTH: 703
<212> TYPE: DNA
<213> ORGANISM: Unknown
<220> FEATURE:
<223> OTHER INFORMATION: Teal Fluorescent Protein sequence

<400> SEQUENCE: 458
atggtctcta agggcgaaga gaccactatg ggcgtgatca agcccgacat gaaaattaaa 60
ctgaagatgg aaggtaacgt gaacggccac gcctttgtga tagagggcga gggggaaggg 120
aaaccatcga tggtaccaat acaatcaatc tggaggtgaa ggaaggtgct ccccttccct 180
tttcctacga catcctgaca acagcttttg cctatggtaa ccgggccttc accaagtacc 240
cggacgacat ccccaattac tcaagcagtc attcccggag ggtatagtt gggaacgcac 300 tatgaccttc gaggataagg ggattgtcaa ggtcaagagc gacataagca tggaggaaga 360
ttcgtttatc tatgagatac acctgaaggg tgaaatttcc cccccaacgg ccccgttatg 420
cagaaaaaga ccaccgggtg ggacgcctcc acggagcgaa tgtacgtccg cgatggggtg 480
ctcaagggcg acgtaaaaca caaactgctg ctggaaggcg gcgggcccac cgtgttgact 540
tcaagacgat ttatcgtgcc aagaaggccg tcaaacttcc cgactaccac ttcgtagatc 600
acagaatcga gatactcaac catgacaagg attacaacaa ggtgaccgtc tatgagagcc 660
cgtggctaga aactccaccg atgggatgga cgagttatat aaa 703

-continued

<210> SEQ ID NO 459
<211> LENGTH: 703
<212> TYPE: DNA
<213> ORGANISM: Artificial Sequence
<220> FEATURE:
<223> OTHER INFORMATION: Synthetic construct

<400> SEQUENCE: 459
atggtttcca aaggggagga aacaacaatg ggtgttataa aaccggacat gaagattaag 60
ctgaaaatgg aaggcaatgt taatgggcat gcttttgtga tagaggggga aggtgagggt 120
aagccctcga tggtacaaac actatcaacc tagaggtgaa ggaaggtgca ccgctgccat 180
tttcctatga tatcctcacc actgcctttg catacggcaa cagggccttt accaagtacc 240
ctgatgacat tcccaactac tcaagcagag ttttcctgag ggtatagct gggagagaac 300 catgacgttt gaggataaag ggattgttaa ggtcaagtct gacatcagca tggaagagga 360
tagctttata tacgaaatcc acctgaaggg ggaaatttcc ctcctaacgg ccctgtgatg 420
cagaaaaaaa ctaccggttg ggatgccagt acagaacgaa tgtatgtacg tgacggagta 480
ctcaaaggcg atgtaaagca taaactgctg cttgaaggtg ggggccccat agagttgact 540
ttaagacaat ttatagggcc aaaaaagctg taaaattgcc cgactaccat tttgtagatc 600
atcggatcga aattcttaac catgacaagg actataacaa agtgactgta tatgagagtc 660
agttgctcgc aacagtactg atggaatgga tgaattgtac aag 703

<210> SEQ ID NO 460
<211> LENGTH: 703
<212> TYPE: DNA
<213> ORGANISM: Artificial Sequence
<220> FEATURE:
<223> OTHER INFORMATION: Synthetic construct

<400> SEQUENCE: 460
atggtctcta agggagaaga gaccactatg ggagtcatca agcccgacat gaaaattaaa 60
ctgaagatgg aaggtaatgt caatggccac gcctttgtga tagagggaga gggggaaggg 120
aaaccattga tgggaccaat acaatcaatc tggaggtgaa ggaaggtgct ccccttccct 180
tttcctacga catcctgaca acagcttttg cctatgggaa cagggccttc accaagtacc 240
ccgacgacat ccccaattac tcaagcagtc cttccccgag ggtatagtt gggaaaggac 300 tatgaccttt gaggacaagg ggattgtcaa ggtcaagagc gacataagca tggaggaaga 360
ctcttttatc tatgagatac acctgaaggg tgaaatttcc cccccaatgg gcccgttatg 420
cagaaaaaga ccaccgggtg ggacgcctcc acggagagaa tgtacgtcag ggacggggtg 480
ctcaagggag atgtcaaaca caaactgctg ctggaaggtg gggggcccac agagtcgact 540
tcaagacgat ttatagagcc aagaaggccg tcaaactccc agactaccac tttgtggacc 600
acagaatcga gatactcaac catgacaagg attacaacaa ggtgaccgtc tatgagagcc 660
cgtggctaga aactccactg acgggatgga cgagttatat aaa 703

<210> SEQ ID NO 461
<211> LENGTH: 34
<212> TYPE: PRT
<213> ORGANISM: Artificial Sequence
<220> FEATURE:
<223> OTHER INFORMATION: Synthetic peptide

<400> SEQUENCE: 461

Ala Phe Ala Tyr Gly Asn Arg Ala Phe Thr Lys Tyr Pro Asp Asp Ile
1 5 10 15

```
Pro Asn Tyr Phe Lys Gln Ser Phe Pro Glu Gly Tyr Ser Trp Glu Arg
            20                  25                  30

Thr Met


<210> SEQ ID NO 462
<211> LENGTH: 102
<212> TYPE: DNA
<213> ORGANISM: Artificial Sequence
<220> FEATURE:
<223> OTHER INFORMATION: Synthetic oligonucleotide

<400> SEQUENCE: 462

gcctttryat atgrtrayag asytttyaca aagtaycctg atgacatacc taaytacttc     60

aarbagagct tccccrargg ttayagttgg gagyrtacya tg                       102


<210> SEQ ID NO 463
<211> LENGTH: 102
<212> TYPE: DNA
<213> ORGANISM: Artificial Sequence
<220> FEATURE:
<223> OTHER INFORMATION: Synthetic oligonucleotide

<400> SEQUENCE: 463

gccttcgcct atgggaayag ggccttcacc aratatcccg acgacatccc caactacttt     60

aracagtctt tccctgrggg rtactcctgg gagaggacta tg                       102


<210> SEQ ID NO 464
<211> LENGTH: 5
<212> TYPE: PRT
<213> ORGANISM: Artificial Sequence
<220> FEATURE:
<223> OTHER INFORMATION: Synthetic peptide

<400> SEQUENCE: 464

Lys Ile Pro Ile Lys
1               5


<210> SEQ ID NO 465
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 465

ggcaacaacc ta                                                         12


<210> SEQ ID NO 466
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 466

ggagctaacc ta                                                         12


<210> SEQ ID NO 467
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 467
```

ggcggtaacc ta 12

<210> SEQ ID NO 468
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 468
ggcagcaacc ta 12

<210> SEQ ID NO 469
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 469
ggcaacagcc ta 12

<210> SEQ ID NO 470
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 470
ggcaacggtc ta 12

<210> SEQ ID NO 471
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 471
ggcagcagcc ta 12

<210> SEQ ID NO 472
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 472
ggcaacaact ta 12

<210> SEQ ID NO 473
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 473
ggcgataacc ta 12

<210> SEQ ID NO 474
<211> LENGTH: 32
<212> TYPE: DNA
<213> ORGANISM: Artificial Sequence
<220> FEATURE:

-continued

```
<223> OTHER INFORMATION: Synthetic oligonucleotide

<400> SEQUENCE: 474

gactacctcg agccagctta ggctacacag ag                          32


<210> SEQ ID NO 475
<211> LENGTH: 4
<212> TYPE: PRT
<213> ORGANISM: Artificial Sequence
<220> FEATURE:
<223> OTHER INFORMATION: Synthetic peptide

<400> SEQUENCE: 475

Cys Cys His His
1
```